(12) United States Patent
Collini et al.

(10) Patent No.: US 7,576,215 B2
(45) Date of Patent: Aug. 18, 2009

(54) QUINOLINES AND PHARMACEUTICAL COMPOSITIONS THEREOF

(75) Inventors: Michael D. Collini, Clifton Heights, PA (US); Robert R. Singhaus, Jr., Pottstown, PA (US); Baihua Hu, Audubon, PA (US); James W. Jetter, Norristown, PA (US); Robert L. Morris, Wayne, PA (US); David H. Kaufman, Schwenksville, PA (US); Christopher P. Miller, Wayne, PA (US); John W. Ullrich, Exton, PA (US); Rayomand J. Unwalla, Eagleville, PA (US); Jay E. Wrobel, Lawrence, NJ (US); Elaine Quinet, Berwyn, PA (US); Ponnal Nambi, Berwyn, PA (US); Ronald C. Bernotas, Royersford, PA (US); Merle Elloso, Devon, PA (US)

(73) Assignee: Wyeth, Madison, NJ (US)

( * ) Notice: Subject to any disclaimer, the term of this patent is extended or adjusted under 35 U.S.C. 154(b) by 535 days.

(21) Appl. No.: 11/010,236

(22) Filed: Dec. 10, 2004

(65) Prior Publication Data

US 2005/0131014 A1  Jun. 16, 2005

Related U.S. Application Data

(60) Provisional application No. 60/529,009, filed on Dec. 12, 2003, provisional application No. 60/600,296, filed on Aug. 10, 2004.

(51) Int. Cl.
*C07D 215/38* (2006.01)

(52) U.S. Cl. .................. 546/156; 546/153; 546/157; 546/167

(58) Field of Classification Search .................. 546/153, 546/156, 157, 167; 514/312, 313
See application file for complete search history.

(56) References Cited

U.S. PATENT DOCUMENTS

| | | | |
|---|---|---|---|
| 4,375,544 A | 3/1983 | Meth-Cohn et al. | |
| 4,407,803 A | 10/1983 | Haviv et al. | |
| 4,761,419 A | 8/1988 | Picard et al. | |
| 5,183,825 A | 2/1993 | Kees | |
| 5,593,992 A | 1/1997 | Adams et al. | |
| 5,753,675 A | 5/1998 | Wattanasin | |
| 5,817,674 A | 10/1998 | Clemence et al. | |
| 5,837,719 A | 11/1998 | de Laszlo et al. | |
| 6,004,979 A | 12/1999 | Clemence et al. | |
| 6,172,084 B1 | 1/2001 | Cuny et al. | |
| 6,495,562 B1 | 12/2002 | Bruncko et al. | |
| 6,538,022 B1 | 3/2003 | Pollesello et al. | |

FOREIGN PATENT DOCUMENTS

| | | |
|---|---|---|
| DE | 3905908 | 9/1990 |
| DE | 3927369 | 2/1991 |
| DE | 3935139 | 4/1991 |
| DE | 3935491 | 5/1991 |
| DE | 4139751 | 6/1993 |
| DE | 4243279 | 6/1994 |
| DE | 19532714 | 3/1997 |
| DE | 19709125 | 9/1998 |
| EP | 157362 | 10/1985 |
| EP | 0 304 063 | 8/1988 |
| EP | 529450 | 3/1990 |
| EP | 372657 | 6/1990 |
| EP | 387610 | 9/1990 |
| EP | 399291 | 11/1990 |
| EP | 414076 | 2/1991 |
| EP | 414078 | 2/1991 |
| EP | 418071 | 3/1991 |
| EP | 466452 | 1/1992 |
| EP | 0498723 | 8/1992 |
| EP | 498723 | * 8/1992 |
| EP | 499926 | 8/1992 |
| EP | 509359 | 10/1992 |
| EP | 535548 | 4/1993 |
| EP | 545170 | 6/1993 |
| EP | 545171 | 6/1993 |
| EP | 570112 | 11/1993 |
| EP | 582908 | 2/1994 |
| EP | 0628550 | 6/1994 |
| EP | 675111 | 10/1995 |
| EP | 720987 | 7/1996 |
| EP | 720988 | 7/1996 |
| EP | 808627 | 11/1997 |
| EP | 808628 | 11/1997 |
| EP | 812841 | 12/1997 |
| EP | 1106612 | 6/2001 |
| EP | 1270535 | 1/2003 |

(Continued)

OTHER PUBLICATIONS

Clemence, abstract only CA118:22153, abstract only of EP 498722, Aug. 1992.*

Cao G. et al. "Antidiabetic Action of a Liver X Receptor Agonist Mediated By Inhibition of Hepatic Gluconeogenesis," *J. Biol. Chem.* (2003) 278(2)1131-1136.

Collins J.L. et al., "Identification of a nonsteroidal liver X receptor agonist through parallel array synthesis of tertiary," *J. Med. Chem.* (2000) 45:1963-1966.

(Continued)

*Primary Examiner*—D. Margaret Seaman
(74) *Attorney, Agent, or Firm*—Fish & Richardson P.C.

(57) ABSTRACT

This invention provides compounds of formula I

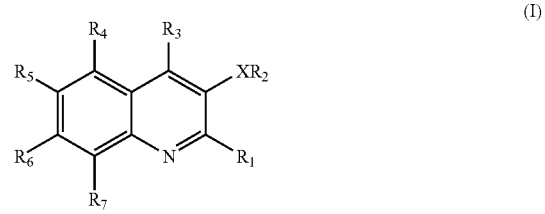

that are useful in the treatment or inhibition of LXR mediated diseases.

9 Claims, No Drawings

FOREIGN PATENT DOCUMENTS

| | | |
|---|---|---|
| FR | 2827599 | 1/2003 |
| JP | 4-182469 | 6/1992 |
| JP | 05-043589 | 2/1993 |
| JP | 5-130897 | 5/1993 |
| JP | 95-128327 | 8/1993 |
| JP | 06092939 | 4/1994 |
| JP | 6-92939 | 5/1994 |
| JP | 07-010870 | 1/1995 |
| JP | 07089957 | 4/1995 |
| JP | 10067658 | 10/1998 |
| JP | 2002-371078 | 12/2002 |
| WO | WO 91/09017 | 6/1991 |
| WO | WO 93/07124 | 9/1992 |
| WO | WO 02/090375 | 11/1992 |
| WO | WO 92/19614 | 11/1992 |
| WO | WO 93/14081 | 7/1993 |
| WO | WO 95/07922 | 3/1995 |
| WO | WO 95/10505 | 4/1995 |
| WO | WO 96/01830 | 1/1996 |
| WO | WO 96/06840 | 3/1996 |
| WO | WO 97/34893 | 9/1997 |
| WO | WO 97/44036 | 11/1997 |
| WO | WO 98/14430 | 4/1998 |
| WO | WO 98/20007 | 5/1998 |
| WO | WO 98/34115 | 8/1998 |
| WO | WO 99/01130 | 1/1999 |
| WO | WO 99/31086 | 6/1999 |
| WO | WO 00/12497 | 3/2000 |
| WO | WO 00/13681 | 3/2000 |
| WO | WO 00/13682 | 3/2000 |
| WO | WO 00/31063 | 6/2000 |
| WO | WO 00/42026 | 7/2000 |
| WO | WO 00/54759 | 9/2000 |
| WO | WO 01/41704 | 6/2001 |
| WO | WO 01/55140 | 8/2001 |
| WO | WO 01/56552 | 8/2001 |
| WO | WO 01/62234 | 8/2001 |
| WO | WO 01/64197 | 9/2001 |
| WO | WO 01/64199 | 9/2001 |
| WO | WO 01/64217 | 9/2001 |
| WO | WO 01/64218 | 9/2001 |
| WO | WO 01/64226 | 9/2001 |
| WO | WO 01/64246 | 9/2001 |
| WO | WO 01/64252 | 9/2001 |
| WO | WO 01/70227 | 9/2001 |
| WO | WO 01/70228 | 9/2001 |
| WO | WO 01/70698 | 9/2001 |
| WO | WO 01/82917 | 11/2001 |
| WO | WO 02/12191 | 2/2002 |
| WO | WO 02/26713 | 4/2002 |
| WO | WO 02/30407 | 4/2002 |
| WO | WO 02/30426 | 4/2002 |
| WO | WO 02/43733 | 6/2002 |
| WO | WO 02/085364 | 10/2002 |
| WO | WO 02/096397 | 12/2002 |
| WO | WO 03/013523 | 2/2003 |
| WO | WO 03/024441 | 3/2003 |
| WO | WO 03/031408 | 4/2003 |
| WO | WO 03/082198 | 10/2003 |

OTHER PUBLICATIONS

Joseph S.B. et al., "Reciprocal regulation of inflammation and lipid metabolism by liver X receptors," *Nat Med.* (2003) 9(2):213-9.

Joseph S.B. et al., "LXRs: new therapeutic targets in atherosclerosis?," *Current Opinion in Pharmacology* (2003) 3:192-197.

Green, T.W. et al., "Productive Groups in Organic Synthesis," $3^{rd}$ Edition, New York: John Wiley & Sons (1999).

Schultz, J.R. et al., "Role of LXRs in control of lipogenesis," *Genes & Development* (2000) 14(22):2831-2838.

Smith, Michael B. and March, Joseph, March's Advanced Organic Chemistry: Reactions, Mechanisms, and Structure, $5^{th}$ Edition, New York: John Wiley & Sons (2001).

Sun Y. et al. "Expression of liver X receptor target genes decreases cellular amyloid β peptide secretion*," *J. Biol. Chem.* (2003) 278(30):27688-27694.

Ohnmacht, Jr. et al., "Antimalarials. 5. .α.-Dibutylaminomethyl- and .alpha.-(2-piperidyl)-3-quinolinemethanols," *Journal of Medicinal Chemistry* (1971) 14(1):17-24.

Gallagher et al., "Regulation of stress-induced cytokine production by pyridinylimidazoles; inhibition of CSBP kinase," *Bioorganic & Medicinal Chemistry* (1997) 5(1):49-64.

Akeson et al., "Suppression of interleukin-1β and LDL scavenger receptor expression in macrophages by a selective protein kinase C inhibitor," *Journal of Lipid Research* (1991) 32(10):1699-1707.

Joseph et al., "Synthetic LXR ligand inhibits the development of atherosclerosis in mice," *PNAS* (2002) 99(11):7604-7609.

Partial International Search Report dated Jun. 3, 2005 for International Application No. PCT/US2004/041399.

Spencer, T., et al., "Pharmacophore analysis of the nuclear oxysterol receptor LXR alpha," *J. of Med. Chem* (2001) 44(6):886-97.

Janowski, B., et al., "Structural requirements of ligands for the oxysterol liver X receptors LXR alpha and LXR beta," *Proceedings of the National Academy of Sciences of the United States of America* (1999) 96:266-71.

International Search report mailed Sep. 19, 2005 from International Application No. PCT/US2004/041399.

* cited by examiner

QUINOLINES AND PHARMACEUTICAL COMPOSITIONS THEREOF

CROSS REFERENCE TO RELATED APPLICATIONS

This application claims priority benefit of U.S. Provisional Application Ser. No. 60/529,009 filed Dec. 12, 2003, and U.S. Provisional Application Ser. No. 60/600,296 filed Aug. 10, 2004, each of which is incorporated by reference herein in its entirety.

BACKGROUND OF THE INVENTION

This invention provides quinolines that are useful in the treatment or inhibition of LXR mediated diseases.

Atherosclerosis, a complex disease of lipid disorder and inflammation, is the leading cause of death in developed countries. A number of independent risk factors have been identified and the most notable are high levels of serum LDL cholesterol and low HDL cholesterol. Although some of the most effective therapies such as statins have been shown to lower LDL cholesterol significantly (20-60%), still most patients experience adverse coronary events. Also, statins have their own undesirable side effect profile (myotoxicity) which prevent many patients from taking them. Therefore, additional therapeutic strategies to not only decrease LDL cholesterol but also increase HDL cholesterol are critically needed. An important reason to increase HDL cholesterol is to increase cholesterol transport from peripheral tissues to liver for metabolism and excretion. This function of transporting cholesterol from periphery to liver is called reverse cholesterol transport and HDL plays a major role in this pathway. In addition, HDL has been suggested to inhibit the oxidation of LDL cholesterol, reduce the inflammatory response of endothelial cells, inhibit the coagulation pathway and promote the availability of nitric oxide. The key transporter involved in HDL production and reverse cholesterol transport is ABCA1. Therefore, upregulation of ABCA1 results in increased reverse cholesterol transport as well as inhibition of cholesterol absorption in the gut.

LXRs (Liver X receptors), originally identified from liver as orphan receptors, are members of the nuclear hormone receptor super family and are involved in the regulation of cholesterol and lipid metabolism. They are ligand-activated transcription factors and bind to DNA as obligate heterodimers with retinoid X receptors. While LXRα is restricted to certain tissues such as liver, kidney, adipose tissue, intestine and macrophages, LXRβ displays a ubiquitous tissue distribution pattern. Activation of LXRs by oxysterols (endogenous ligands) in macrophages results in the expression of several genes involved in lipid metabolism and reverse cholesterol transport including ABCA1, ABCG1 and ApoE. Studies have been conducted in LXRα k/o, LXRβ k/o and double k/o mice to determine the physiological role of LXRs in lipid homeostasis and atherosclerosis. The data indicate that in double k/o mice on normal chow diet, increased cholesterol accumulation was observed in macrophages (foam cells) of spleen, lung and arterial wall. This was associated with reduced serum HDL cholesterol and increased LDL cholesterol despite normal total cholesterol levels. While LXRα k/o mice did not show significant changes in hepatic gene expression, LXRβ k/o mice showed 58% decrease in hepatic ABCA1 expression and 208% increase in SREBP1c expression suggesting that LXRβ may be involved in the regulation of liver SREBP1c expression. Agonists of LXRα or β are very effective in upregulating ABCA1 expression (desirable effect) in macrophages. The biological activities of several agonists have been shown in two atherosclerotic mouse models (ApoE k/o and LDLR k/o). Treatment of these mice with agonists for 12 weeks resulted in significant inhibition of atherosclerotic lesions. While these two compounds had variable effects on serum cholesterol and lipoprotein levels, both compounds caused a significant increase in serum HDL cholesterol and triglyceride levels. These in vivo data agree well with the in vitro data obtained for the compounds in macrophages.

In addition to the lipid and triglyceride effects described above, a very recent communication in Nature Medicine (9: 213-219, 2003) presents convincing data that activation of LXRs results in the inhibition of inflammation and proinflammatory gene expression in three different models of inflammation (LPS-induced sepsis, acute contact dermatitis of the ear and chronic atherosclerotic inflammation of the artery wall). These data suggest that LXR modulators can mediate two-pronged effect (removal of cholesterol from the macrophages and inhibition of vascular inflammation) resulting in the inhibition of atherosclerotic lesion.

DESCRIPTION OF THE INVENTION

This invention provides compounds of formula 1, having the structure

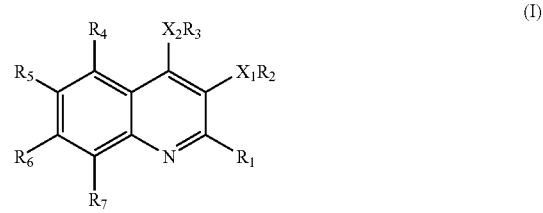

(I)

wherein:
$R_1$ is —H or $C_1$ to $C_3$ alkyl;
$X_1$ is a bond, $C_1$ to $C_5$ alkyl, —C(O)—, —C(=$CR_8R_9$)—, —O—, —S(O)$_t$—, —$NR_8$—, —$CR_8R_9$—, —$CHR_{23}$, —$CR_8(OR_9)$—, —$C(OR_8)_2$—, —$CR_8(OC(O)R^9)$—, —C=$NOR_9$—, —$C(O)NR_8$—, —$CH_2O$—, —$CH_2S$—, —$CH_2NR_8$—, —$OCH_2$—, —$SCH_2$—, —$NR_8CH_2$—, or

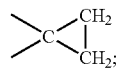

$R_2$ is H, $C_1$ to $C_6$ alkyl, $C_2$ to $C_6$ alkenyl, $C_2$ to $C_6$ alkynyl, $C_3$ to $C_6$ cycloalkyl, —$CH_2OH$, $C_7$ to $C_{11}$ arylalkyl, phenyl, naphthyl, $C_1$ to $C_3$ perfluoroalkyl, CN, C(O)$NH_2$, $CO_2R_{12}$ or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR_8R_9$, —CN, —OH, and $C_1$ to $C_3$ alkyl substituted with 1 to 5 fluorines, or
$R_2$ is a heterocycle selected from the group consisting of pyridine, thiophene, benzisoxazole, benzothiophene, oxadiazole, pyrrole, pyrazole, imidazole and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —$NO_2$, —$NR_8R_9$, —CN, and $C_1$ to $C_3$ alkyl substituted with 1 to 5 fluorines;

$X_2$ is a bond or —$CH_2$—;

$R_3$ is phenyl, naphthyl, or phenyl or naphthyl substituted by one to four groups independently selected from $C_1$ to $C_3$ alkyl, hydroxy, phenyl, acyl, halogen, —$NH_2$, —CN, —$NO_2$, $C_1$ to $C_3$ alkoxy, $C_1$ to $C_3$ perfluoroalkyl, $C_1$ to $C_3$ alkyl substituted with 1 to 5 fluorines, $NR_{14}R_{15}$, —C(O)$R_{10}$, —C(O)$NR_{10}R_{11}$, —C(O)$NR_{11}$A, —C≡$CR_8$, —CH═$CHR_8$, —WA, —C≡CA, —CH═CHA, —WYA, —$WYNR_{11}$—A, —$WYR_{10}$, —WY($CH_2$)$_j$A, —$WCHR_{11}$, ($CH_2$)$_j$A, —W($CH_2$)$_j$A, —W($CH_2$)$_j R_{10}$, —$CHR_{11}$W($CH_2$)$_j R_{10}$, —$CHR_{11}$W($CH_2$)$_j$A, —$CHR_{11}NR_{12}$YA, —$CHR_{11}NR_{12}YR_{10}$, pyrrole, —W($CH_2$)$_j$A($CH_2$)$_k$D($CH_2$)$_p$Z, —W($CR_{18}R_{19}$)A($CH_2$)$_k$D($CH_2$)$_p$Z, —($CH_2$)$_j$WA($CH_2$)$_k$D($CH_2$)$_p$Z, —CH═CHA($CH_2$)$_k$D($CH_2$)$_p$Z, —C≡CA($CH_2$)$_k$D($CH_2$)$_p$Z, —W($CH_2$)$_j$C≡CA($CH_2$)$_k$D($CH_2$)$_p$Z, and —W($CH_2$)$_j$Z, or $R_3$ is a heterocycle selected from pyridine, pyrimidine, thiophene, furan, benzothiophene, indole, benzofuran, benzimidazole, benzothiazole, benzoxazole, and quinoline each of which may be optionally substituted with one to three groups independently selected from $C_1$ to $C_3$ alkyl, $C_1$ to $C_3$ alkoxy, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R_{10}$, —C(O)$NR_{10}R_{11}$, —C(O)$NR_{11}$A, —C≡$CR_8$, —CH═$CHR_8$, —WA, —C≡CA, —CH═CHA, —WYA, —$WYR_{10}$, —WY($CH_2$)$_j$A, —W($CH_2$)$_j$A, —W($CH_2$)$_j R_{10}$, —$CHR_{11}$W($CH_2$)$_j R_{10}$, —$CHR_{11}$W($CH_2$)$_j$A, —$CHR_{11}NR_{12}$YA, —$CHR_{11}NR_{12}YR_{10}$, —$WCHR_{11}$ ($CH_2$)$_j$A, —W($CH_2$)$_j$A($CH_2$)$_k$D($CH_2$)$_p$Z, —W($CR_{18}R_{19}$)A($CH_2$)$_k$D($CH_2$)$_p$Z, —($CH_2$)$_j$WA($CH_2$)$_k$D($CH_2$)$_p$Z, —CH═CHA($CH_2$)$_k$D($CH_2$)$_p$Z, —C≡CA($CH_2$)$_k$D($CH_2$)$_p$Z, —W($CH_2$)$_j$C≡CA($CH_2$)$_k$D($CH_2$)$_p$Z, and —W($CH_2$)$_j$Z;

W is a bond, —O—, —S—, —S(O)—, —S(O)$_2$—, —$NR_{11}$—, or —N(COR$_{12}$)—;

Y is —CO—, —S(O)$_2$—, —CONR$_{13}$, —CONR$_{13}$CO—, —CONR$_{13}$SO$_2$—, —C(NCN)—, —CSNR$_{13}$—,C(NH)NR$_{13}$, or —C(O)O—;

j is 0 to 3;
k is 0 to 3;
t is 0 to 2;
D is a bond, —CH═CH—, —C≡, —C(O)—, —C≡C—, phenyl, —O—, —NH—, —S—, —CHR$_{14}$—, —CR$_{14}$R$_{15}$—, —OCHR$_{14}$—, —OCR$_{14}$R$_{15}$—, or —CH(OH)CH(OH)—;

p is 0 to 6;

Z is —CO$_2$R$_{11}$, —CONR$_{10}$R$_{11}$, —C(═NR$_{10}$)NR$_{11}$R$_{12}$, —CONH$_2$NH$_2$, —CN, —CH$_2$OH, —NR$_{16}$R$_{17}$, phenyl, CONHCH(R$_{20}$)COR$_{12}$, phthalimide, pyrrolidine-2,5-dione, thiazolidine-2,4-dione, tetrazolyl, pyrrole, indole, oxazole, 2-thioxo-1,3-thiazolidin-4-one, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —CO$_2$CH$_3$, —CO$_2$H, —COCH$_3$, —CONH$_2$ and —CN; wherein said $C_1$ to $C_7$ amines are optionally substituted with one to two substituents independently selected from the group consisting of —OH, halogen, —OCH$_3$, and —C≡CH; wherein said phenyl is optionally substituted with CO$_2$R$_{11}$, wherein said $C_3$ to $C_7$ cyclic amines are optionally substituted with one or two substituents independently selected from the group consisting of —OH —CH$_2$OH, —CH$_2$OCH$_3$, —CO$_2$CH$_3$, and —CONH$_2$, and wherein said oxazole is optionally substituted with CH$_2$CO$_2$R$_{11}$;

A is phenyl, naphthyl, tetrahydronaphthyl, indan, or biphenyl, each of which may be optionally substituted by one to four groups independently selected from halogen, $C_1$ to $C_3$ alkyl, $C_2$ to $C_4$ alkenyl, $C_2$ to $C_4$ alkynyl, acyl, hydroxy, halogen, —CN, —NO$_2$, —CO$_2$R$_{11}$, —CH$_2$CO$_2$R$_{11}$, phenyl, $C_1$ to $C_3$ perfluoroalkoxy, $C_1$ to $C_3$ perfluoroalkyl, —NR$_{10}$R$_{11}$, —CH$_2$NR$_{10}$R$_{11}$, —SR$_{11}$, $C_1$ to $C_6$ alkyl substituted with 1 to 5 fluorines, $C_1$ to $C_3$ alkyl substituted with 1 to 2 —OH groups, $C_1$ to $C_6$ alkoxy optionally substituted with 1 to 5 fluorines, or phenoxy optionally substituted with 1 to 2 CF$_3$ groups; or A is a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole, benzo[1,2,5]-oxadiazole, isochromen-1-one, benzothiophene, benzofuran, 2,3-dihydrobenzo[1,4]-dioxine, bithienyl, quinazolin-2,4-[1,3H]dione, and 3-H-isobenzofuran-1-one, each of which may be optionally substituted by one to three groups independently selected from halogen, $C_1$ to $C_3$ alkyl, acyl, hydroxy, —CN, —NO$_2$, $C_1$ to $C_3$ perfluoroalkyl, —NR$_{10}$R$_{11}$, —CH$_2$NR$_{10}$R$_{11}$, —SR$_{11}$, $C_1$ to $C_6$ alkyl substituted with 1 to 5 fluorines, and $C_1$ to $C_3$ alkoxy optionally substituted with 1 to 5 fluorines;

$R_4$, $R_5$, and $R_6$ are each, independently, —H or —F;

$R_7$ is hydrogen, $C_1$ to $C_4$ alkyl, $C_1$ to $C_4$ perfluoroalkyl, halogen, —NO$_2$ or —CN, phenyl or phenyl substituted with one or two group independently selected from halogen, $C_1$ to $C_2$ alkyl and OH;

provided that if $R_7$ is hydrogen, then $R_3$ is selected from:
(a) phenyl substituted by —W(CH$_2$)$_j$A(CH$_2$)$_k$D(CH$_2$)$_p$Z, —W(CR$_{18}$R$_{19}$)A(CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z, wherein the phenyl moiety is further optionally substituted with one or two groups independently selected from $C_1$ to $C_2$ alkyl, $C_1$ to $C_2$ perfluoroalkyl, halogen, and CN; and
(b) a heterocycle selected from pyridine, pyrimidine, thiophene, and furan, each of which is substituted by one of —W(CH$_2$)$_j$A(CH$_2$)$_k$D(CH$_2$)$_p$Z, —W(CR$_{18}$R$_{19}$)A(CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z;

further provided that if $X_1$ $R_2$ forms hydrogen, then $R_3$ is selected from:
(a) phenyl substituted by —W(CH$_2$)$_j$A(CH$_2$)$_k$D(CH$_2$)$_p$Z, —W(CR$_{18}$R$_{19}$)A(CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z, wherein the phenyl moiety is further optionally substituted with one or two groups independently selected from $C_1$ to $C_2$ alkyl, $C_1$ to $C_2$ perfluoroalkyl, halogen, and CN; and
(b) a heterocycle selected from pyridine, pyrimidine, thiophene, and furan, each of which is substituted by one of —W(CH$_2$)$_j$A(CH$_2$)$_k$D(CH$_2$)$_p$Z, —W(CR$_{18}$R$_{19}$)A(CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z;

further provided that $R_3$ and $R_7$ cannot both be hydrogen;

each $R_8$ is independently —H, or $C_1$ to $C_3$ alkyl;
each $R_9$ is independently —H, or $C_1$ to $C_3$ alkyl;
each $R_{10}$ is independently —H, —OH, $C_1$ to $C_3$ alkoxy, $C_1$ to $C_7$ alkyl, $C_3$ to $C_7$ alkenyl, $C_3$ to $C_7$ alkynyl, $C_3$ to $C_7$ cycloalkyl, —CH$_2$CH$_2$OCH$_3$, 2-methyl-tetrahydrofuran, 2-methyl-tetrahydro-pyran, 4-methyl-piperidine, morpholine, pyrrolidine, or phenyl optionally substituted with one or two $C_1$ to $C_3$ alkoxy groups, wherein said $C_1$ to $C_7$ alkyl is optionally substituted with 1, 2 or 3 groups independently selected from $C_1$ to $C_3$ alkoxy, $C_1$ to $C_3$ thioalkoxy and CN;

each $R_{11}$ is independently —H, $C_1$ to $C_3$ alkyl or $R_{22}$;
or $R_{10}$ and $R_{11}$, when attached to the same atom, together with said atom form:
a 5 to 7 membered saturated ring, optionally substituted by 1 to 2 groups independently selected from $C_1$ to $C_3$ alkyl, OH and $C_1$-$C_3$ alkoxy, or
a 5 to 7 membered ring containing 1 or 2 heteroatoms, optionally substituted by 1 to 2 groups independently selected from $C_1$ to $C_3$ alkyl, OH and $C_1$-$C_3$ alkoxy;

each $R_{12}$ is independently —H, or $C_1$ to $C_3$ alkyl;
each $R_{13}$ is independently —H, or $C_1$ to $C_3$ alkyl;
each $R_{14}$ and $R_{15}$ is, independently, $C_1$ to $C_7$ alkyl, $C_3$ to $C_8$ cycloalkyl, $C_2$ to $C_7$ alkenyl, $C_2$ to $C_7$ alkynyl, —OH, —F, $C_7$ to $C_{14}$ arylalkyl, where said arylalkyl is optionally substituted with 1 to 3 groups independently selected from $NO_2$, $C_1$ to $C_6$ alkyl, $C_1$ to $C_3$ perhaloalkyl, halogen, $CH_2CO_2R_{11}$, phenyl and $C_1$ to $C_3$ alkoxy, or $R_{14}$ and $R_{15}$ together with the atom to which they are attached can form a 3 to 7 membered saturated ring;

each $R_{16}$ and $R_{17}$ is, independently, hydrogen, $C_1$ to $C_3$ alkyl, $C_1$ to $C_3$ alkenyl, $C_1$ to $C_3$ alkynyl, phenyl, benzyl or $C_3$ to $C_8$ cycloalkyl, wherein said $C_1$ to $C_3$ alkyl is optionally substituted with one OH group, and wherein said benzyl is optionally substituted with 1 to 3 groups independently selected from $C_1$ to $C_3$ alkyl and $C_1$ to $C_3$ alkoxy; or $R_{16}$ and $R_{17}$, together with the atom to which they are attached, can form a 3 to 8 membered heterocycle which is optionally substituted with one or two substituents independently selected from the group consisting of $C_1$ to $C_3$ alkyl, —OH, $CH_2OH$, —$CH_2OCH_3$, —$CO_2CH_3$, and —$CONH_2$;

each $R_{18}$ and $R_{19}$ is, independently, $C_1$ to $C_3$ alkyl;
each $R_{20}$ is independently H, phenyl, or the side chain of a naturally occurring alpha amino acid;
each $R_{22}$ is independently arylalkyl optionally substituted with $CH_2CO_2H$; and
each $R_{23}$ is phenyl;

or a pharmaceutically acceptable salt thereof, which are useful in the treatment or inhibition of LXR mediated diseases.

In particular, the compounds of this invention are useful in the treatment and inhibition of atherosclerosis and atherosclerotic lesions, lowering LDL cholesterol levels, increasing HDL cholesterol levels, increasing reverse cholesterol transport, inhibiting cholesterol absorption, treatment or inhibition of Alzheimer's disease, type I diabetes, type II diabetes, multiple sclerosis, rheumatoid arthritis, acute coronary syndrome, restenosis, inflammatory bowel disease (IBD), Crohn's disease, endometriosis, celiac, and thyroiditis.

The present compounds are also useful for the treatment of TH-1 mediated diseases, particularly in mammals. Accordingly, in some embodiemtns, the present invention provides methods of treating a Th1-mediated disease in a mammal in need thereof, which comprises providing to said mammal an effective amount of a compound as disclosed herein. Non-limiting examples of Th1-mediated diseases to which the methods of the invention are amenable include multiple sclerosis, rheumatoid arthritis, autoimmune thyroid disease, inflammatory bowel disease, Crohn's disease and atherosclerosis.

The present compounds are further useful for suppression of lymphocyte function or activation in a mammal. Thus, in a further aspect, the invention provides methods for suppressing lymphocyte function or activation in a mammal in need thereof, which comprises providing to said mammal an effective amount of a compound of a compound as described herein. In some embodiments, the lymphocyte function that is suppressed is lymphokine production.

The present compounds find further use in the suppression of macrophage function or activation in a mammal. Thus, in a further aspect, the invention provides methods for suppressing macrophage function or activation in a mammal in need thereof, which comprises providing to said mammal an effective amount of a compound as described herein.

In a further aspect, the present compounds find further use in suppressing cytokine production in a mammal. Accordingly, the present invention further provides methods of suppressing cytokine production in a mammal in need thereof, which comprises providing to said mammal an effective amount of a compound as described herein.

In a further aspect, the present invention provides methods of treating a Th1-mediated disease in a mammal in need thereof, which comprises providing to said mammal an effective amount of a compound selected from compounds III, IV, and V:

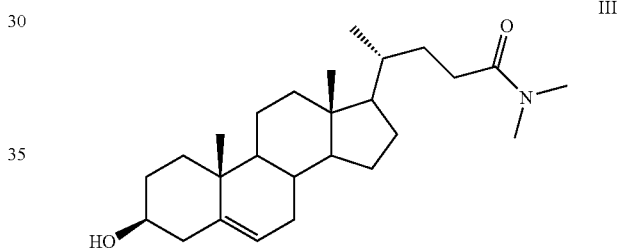

III

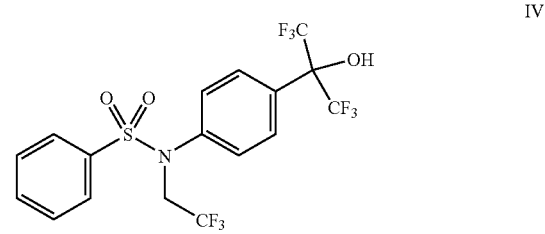

IV

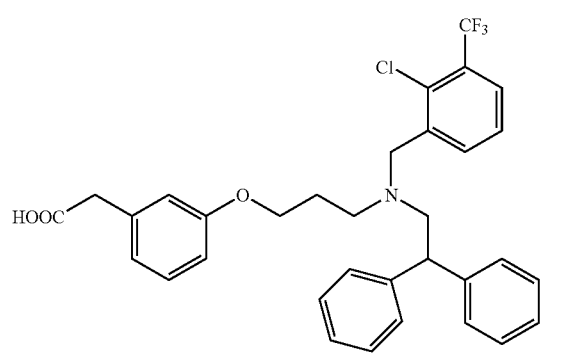

V

In a further aspect, the invention provides methods of suppressing lymphocyte function or activation in a mammal in need thereof, which comprises providing to said mammal an effective amount of a compound selected from compounds III, IV, and V as described above. In some such embodiments, the lymphocyte function is lymphokine production.

In a further aspect, the invention provides methods of suppressing cytokine production in a mammal in need thereof, which comprises providing to said mammal an effective amount of a compound selected from compounds III, IV, and V, as described above.

In a further aspect, the invention provides methods of suppressing macrophage function or activation in a mammal in need thereof, which comprises providing to said mammal an effective amount of a compound selected from compounds III, IV, and V, as described above.

Pharmaceutically acceptable salts of the compounds of Formula (I) with an acidic moiety can be formed from organic and inorganic bases. Suitable salts with bases are, for example, and not by way of limitation, metal salts, such as alkali metal or alkaline earth metal salts, for example sodium, potassium, or magnesium salts; or salts with ammonia or an organic amine, such as morpholine, thiomorpholine, piperidine, pyrrolidine, a mono-, di- or tri-lower alkylamine, for example ethyl-tert-butyl-, diethyl-, diisopropyl-, triethyl-, tributyl- or dimethylpropylamine, or a mono-, di-, or trihydroxy lower alkylamine, for example mono-, di- or triethanolamine. Internal salts may furthermore be formed. Similarly, when a compound of the present invention contains a basic moiety, salts can be formed from organic and inorganic acids. For example salts can be formed from acetic, propionic, lactic, citric, tartaric, succinic, fumaric, maleic, malonic, mandelic, malic, phthalic, hydrochloric, hydrobromic, phosphoric, nitric, sulfuric, methanesulfonic, napthalenesulfonic, benzenesulfonic, toluenesulfonic, camphorsulfonic, and similarly known pharmaceutically acceptable acids.

Preferred compounds of this invention include compounds of formula I having the structure:

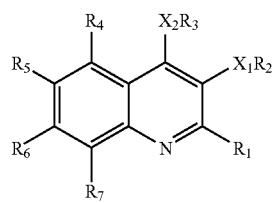

(I)

wherein the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $X_1$, $X_2$, W, Y, and A are each defined below, independently or any combination thereof:

R, is —H;

$X_1$ is a bond, —C(O)—, —O—, —S(O)$_t$—, —NR$_8$—, or —CR$_8$R$_9$—;

$R_2$ is $C_1$ to $C_6$ alkyl, $CF_3$, CN, phenyl, or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —NO$_2$, —NR$_8$R$_9$, —CN, —OH, and $C_1$ to $C_3$ alkyl substituted with 1 to 5 fluorines, or $R_2$ is a heterocycle selected from the group consisting of pyridine, thiophene, benzisoxazole, benzothiophen, oxadiazole, pyrrole, pryrazole, imidazole and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —NO$_2$, —NR$_8$R$_9$, —CN, and $C_1$ to $C_3$ alkyl substituted with 1 to 5 fluorines;

$X_2$ is a bond or —CH$_2$—;

$R_3$ is phenyl, naphthyl, or phenyl or naphthyl substituted by one to four groups independently selected from $C_1$ to $C_3$ alkyl, hydroxy, phenyl, acyl, halogen, —NH$_2$, —CN, —NO$_2$, $C_1$ to $C_3$ perfluoroalkyl, $C_1$ to $C_3$ alkyl substituted with 1 to 5 fluorines, —C(O)R$_{10}$, —C(O)NR$_{10}$R$_{11}$, —C(O)NR$_{11}$A, —C≡CR$_8$, —CH═CHR$_8$, —WA, —C≡CA, —CH═CHA, —WYA, —WYR$_{10}$, —WY(CH$_2$)$_j$A, —WCHR$_{11}$(CH$_2$)$_j$A, —W(CH$_2$)$_j$A, —W(CH$_2$)$_j$R$_{10}$, —CHR$_{11}$W(CH$_2$)$_j$R$_{10}$, —CHR$_{11}$W(CH$_2$)$_j$A, CHR$_{11}$NR$_{12}$YA, —CHR$_{11}$NR$_{12}$YR$_{10}$, and pyrrole; or $R_3$ is a heterocycle selected from pyridine, pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$ alkyl, hydroxy, phenyl, acyl, halogen, —NH$_2$, —CN, —NO$_2$, $C_1$ to $C_3$ perfluoroalkyl, $C_1$ to $C_3$ alkyl substituted with 1 to 5 fluorines, —C(O)R$_{10}$, —C(O)NR$_{10}$R$_{11}$, —C(O)NR$_{11}$A, —C≡CR$_8$, —CH═CHR$_8$, —WA, —C≡CA, —CH═CHA, —WYA, —WYR$_{10}$, —WY(CH$_2$)$_j$A, —W(CH$_2$)$_j$A, —W(CH$_2$)$_j$R$_{10}$, —CHR$_{11}$W(CH$_2$)$_j$R$_{10}$, —CHR$_{11}$W(CH$_2$)$_j$A, —CHR$_{11}$NR$_{12}$YA, and —CHR$_{11}$NR$_{12}$YR$_{10}$;

W is a bond, —O—, —S—, —S(O)—, —S(O)$_2$—, —NR$_{11}$—, or —N(COR$_{12}$)—;

Y is —CO—, —S(O)$_2$—, —CONR$_{13}$, —CONR$_{13}$CO—, —CONR$_{13}$SO$_2$—, —C(NCN)—, —CSNR$_{13}$, —C(NH)NR$_{13}$, or —C(O)O—;

j is 0 to 3;

t is 0 to 2;

A is phenyl, naphthyl, tetrahydronaphthyl, or phenyl substituted by one to four groups independently selected from halogen, $C_1$ to $C_3$ alkyl, $C_2$ to $C_4$ alkenyl, $C_2$ to $C_4$ alkynyl, acyl, $C_1$ to $C_3$ alkoxy, hydroxy, halogen, —CN, —NO$_2$, —CO$_2$R$_{11}$, —CH$_2$CO$_2$R$_{11}$, phenyl, phenoxy, $C_1$ to $C_3$ perfluoroalkoxy, $C_1$ to $C_3$ perfluoroalkyl, —NR$_{10}$R$_{11}$, —CH$_2$NR$_{10}$R$_{11}$, —SR$_{11}$, $C_1$ to $C_3$ alkyl substituted with 1 to 5 fluorines, $C_1$ to $C_6$ alkyl substituted with 1 to 2 —OH groups, and $C_1$ to $C_6$ alkoxy optionally substituted with 1 to 5 fluorines, or A is a heterocycle selected from pyrrole, pyridine, pyrimidine, thiophene, furan, quinoline, oxazole, thiazole, imidazole, isoxazole, indole, benzo[1,3]-dioxole, benzo[1,2,5]-oxadiazole, isochromen-1-one, and 3-H-isobenzofuran-1-one, each of which may be optionally substituted by one to three groups independently selected from halogen, $C_1$ to $C_3$ alkyl, acyl, $C_1$ to $C_3$ alkoxy, hydroxy, halogen, —CN, —NO$_2$, $C_1$ to $C_3$ perfluoroalkyl, —NR$_{10}$R$_{11}$, —CH$_2$NR$_{10}$R$_{11}$, —SR$_{11}$, $C_1$ to $C_6$ alkyl substituted with 1 to 5 fluorines;

$R_4$, $R_5$, $R_6$ are each, independently, —H;

$R_7$ is $C_1$ to $C_4$ alkyl, $C_1$ to $C_4$ perfluoroalkyl, or halogen;

each $R_8$ is independently —H, or $C_1$ to $C_2$ alkyl;

each $R_9$ is independently —H, or $C_1$ to $C_2$ alkyl;

each $R_{10}$ is independently —H, $C_1$ to $C_7$ alkyl, $C_2$ to $C_7$ alkenyl, or $C_3$ to $C_7$ cycloalkyl;

each $R_{11}$ is independently —H, or $C_1$ to $C_3$ alkyl;

each $R_{12}$ is independently —H, or $C_1$ to $C_3$ alkyl; and each $R_{13}$ is independently —H, or $C_1$ to $C_3$ alkyl;

or a pharmaceutically acceptable salt thereof.

More preferred compounds of this invention include compounds of formula I having the structure

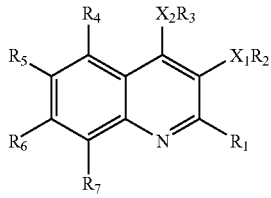

(I)

wherein:

$X_1$ is a bond, —C(O)—, or —$CR_8R_9$—;

$R_2$ is phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR_8R_9$, —CN, —OH, and $C_1$ to $C_3$ alkyl substituted with 1 to 5 fluorines, or $R_2$ is a heterocycle selected from the group consisting of pyridine, thiophene, and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —$NO_2$, —$NR_8R_9$, CN, and $C_1$ to $C_3$ alkyl substituted with 1 to 5 fluorines, $X_2$ is a bond $R_3$ is phenyl substituted independently by one to four groups independently selected from hydroxy, halogen, $C_1$ to $C_3$ perfluoroalkyl, $C_1$ to $C_3$ alkyl substituted with 1 to 5 fluorines, —C≡$CR_8$, —CH=$CHR_8$, —WA, —C≡CA, —WYA, —WY$(CH_2)_j$A, —W$(CH_2)_j$A, —$WCHR_{11}$$(CH_2)_j$A, and —$CHR_{11}$W$(CH_2)_j$A; and wherein the remaining constituent variables are as defined immediately above; or a pharmaceutically acceptable salt thereof.

Another preferred embodiment includes those compounds of formula I having structure:

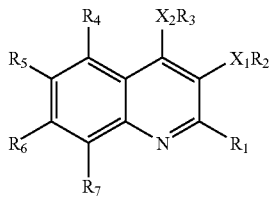

(I)

wherein:

$R_1$ is H;

$X_1$ is a bond, —C(O)—, —O—, —S(O)$_t$—, —$NR_8$—, —$CR_8R_9$—, or —$CR_8(OR_9)$—;

$R_2$ is $C_1$ to $C_6$ alkyl, $C_2$ to $C_6$ alkenyl, $C_2$ to $C_6$ alkynyl, $C_3$ to $C_8$ cycloalkyl, —$CH_2OH$, $CF_3$, CN, phenyl, or phenyl substituted by one to four groups independently selected from $C_1$ to $C_3$ alkyl, $C_1$ to $C_3$ alkoxy, $C_1$ to $C_2$ perfluoroalkyl, halogen, —$NO_2$, —$NR_8R_9$, —CN, and $C_1$ to $C_2$ alkyl substituted with 1 to 3 fluorines, or $R_2$ is a heterocycle selected from pyridine, thiophene, and furan, each of which may be optionally substituted with one to three groups independently selected from $C_1$ to $C_3$ alkyl, $C_1$ to $C_3$ alkoxy, $C_1$ to $C_2$ perfluoroalkyl, halogen, —$NO_2$, —$NR_8R_9$, —CN, and $C_1$ to $C_2$ alkyl substituted with 1 to 3 fluorines;

$X_2$ is a bond or —$CH_2$—;

$R_3$ is phenyl substituted by —W$(CH_2)_j$A$(CH_2)_k$D$(CH_2)_p$Z, —W$(CR_{18}R_{19})$A$(CH_2)_k$D$(CH_2)_p$Z, —$(CH_2)_j$WA$(CH_2)_k$D$(CH_2)_p$Z, —CH=CHA$(CH_2)_k$D$(CH_2)_p$Z, —C≡CA$(CH_2)_k$D$(CH_2)_p$Z, or W$(CH_2)_j$C≡CA$(CH_2)_k$D$(CH_2)_p$Z, and further optionally substituted with one or two groups independently selected from $C_1$ to $C_2$ alkyl, $C_1$ to $C_2$ perfluoroalkyl, halogen, and —CN, or $R_3$ is a heterocycle selected from pyridine, pyrimidine, thiophene, and furan, each of which is optionally substituted by —W$(CH_2)_j$A$(CH_2)_k$D$(CH_2)_p$Z, —W$(CR_{18}R_{19})$A$(CH_2)_k$D$(CH_2)_p$Z, —$(CH_2)_j$WA$(CH_2)_k$D$(CH_2)_p$Z, —CH=CHA$(CH_2)_k$D$(CH_2)_p$Z, —C≡CA$(CH_2)_k$D$(CH_2)_p$Z, or —W$(CH_2)_j$C≡CA$(CH_2)_k$D$(CH_2)_p$Z;

W is a bond, —O—, —S—, —S(O)—, —S(O)$_2$—, —$NR_{11}$—, or —N(COR$_{12}$)—;

j is 0 to 3;

k is 0 to 3;

t is 0 to 2;

D is a bond, —CH=CH—, —C≡C—, phenyl, —O—, —NH—, —S—, —$CHR_{14}$—, —$CR_{14}R_{15}$—, —$OCHR_{14}$—, —$OCR_{14}R_{15}$—, or —CH(OH)CH(OH)—;

p is 0 to 6,

Z is —$CO_2R_{11}$, —$CONR_{10}R_{11}$, —C(=$NR_{10}$)$NR_{11}R_{12}$, —$CONH_2NH_2$, —CN, —$CH_2OH$, —$NR_{16}R_{17}$, CON-HCH($R_{20}$)COR$_{12}$, phthalimide, pyrrolidine-2,5-dione, thiazolidine-2,4-dione, tetrazolyl, pyrrole, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —$CO_2CH_3$, —$CO_2H$, —$COCH_3$ and —CN; wherein said $C_1$ to $C_7$ amines are optionally substituted with one to two substituents independently selected from the group consisting of —OH, halogen, —$OCH_3$, and —C≡CH; and wherein said $C_3$ to $C_7$ cyclic amines are optionally substituted with one or two substituents independently selected from the group consisting of —OH—$CH_2OH$, —$CH_2OCH_3$, —$CO_2CH_3$, and —$CONH_2$;

A is phenyl, or phenyl substituted by one to four groups independently selected from halogen, acyl, $C_1$ to $C_3$ alkyl, $C_1$ to $C_3$ alkoxy, hydroxy, halogen, —CN, —$NO_2$, $C_1$ to $C_3$ perfluoroalkyl, —$NR_{10}R_{11}$, —$CH_2NR_{10}R_{11}$, —$SR_{11}$, and $C_1$ to $C_2$ alkyl substituted with 1 to 3 fluorines; or A is a heterocycle selected from pyrrole, pyridine, pyrimidine, thiophene, indole, oxazole, and furan, each of which may be optionally substituted by one to three groups independently selected from halogen, acyl, $C_1$ to $C_3$ alkyl, $C_1$ to $C_3$ alkoxy, hydroxy, —CN, —$NO_2$, $C_1$ to $C_3$ perfluoroalkyl, —$NR_{10}R_{11}$, —$CH_2NR_{10}R_{11}$, —$SR_{11}$, and $C_1$ to $C_2$ alkyl substituted with 1 to 3 fluorines;

$R_4$, $R_5$, $R_6$ are —H;

$R_7$ is —H, $C_1$ to $C_4$ alkyl, $C_1$ to $C_4$ perfluoroalkyl, or halogen;

each $R_8$ is independently —H, or $C_1$ to $C_2$ alkyl;

each $R_9$ is independently —H, or $C_1$ to $C_2$ alkyl;

each $R_{10}$ is independently —H, or $C_1$ to $C_3$ alkyl;

each $R_{11}$ is independently —H, or $C_1$ to $C_3$ alkyl;

or $R_{10}$ and $R_{11}$, when attached to the same atom, together with said atom form:

a 5 to 7 membered saturated ring, optionally substituted by 1 to 2 groups independently selected from $C_1$ to $C_3$ alkyl, OH and $C_1$-$C_3$ alkoxy; or a 5 to 7 membered ring containing 1 or 2 heteroatoms, optionally substituted by 1 to 2 groups independently selected from $C_1$ to $C_3$ alkyl, OH and $C_1$-$C_3$ alkoxy;

each $R_{12}$ is independently —H, or $C_1$ to $C_3$ alkyl;

each $R_{14}$, and $R_{15}$ is, independently, $C_1$ to $C_7$ alkyl, $C_3$ to $C_8$ cycloalkyl, $C_2$ to $C_7$ alkenyl, $C_2$ to $C_7$ alkynyl, —OH, —F, $C_7$ to $C_{14}$ arylalkyl, where said arylalkyl is optionally substituted with 1 to 3 groups independently selected from $NO_2$, $C_1$ to $C_6$ alkyl, C, to $C_3$ perhaloalkyl, halogen and $C_1$ to $C_3$ alkoxy, or $R_{14}$ and $R_{15}$ together with the atom to which they are attached can form a 3 to 7 membered saturated ring;

each $R_{16}$ and $R_{17}$ is, independently, hydrogen, $C_1$ to $C_3$ alkyl, $C_1$ to $C_3$ alkenyl, $C_1$ to $C_3$ alkynyl, or $C_3$ to $C_8$ cycloalkyl, wherein said $C_1$ to $C_3$ alkyl is optionally substituted with one OH group; or $R_{16}$ and $R_{17}$, together with the atom to which they are attached, can form a 3 to 8 membered heterocycle which is optionally substituted with one or two substituents independently selected from the group consisting of $C_1$ to $C_3$ alkyl, —OH, $CH_2OH$, —$CH_2OCH_3$, —$CO_2CH_3$, and —$CONH_2$;

each $R_{18}$ and $R_{19}$ is, independently $C_1$ to $C_3$ alkyl;

or a pharmaceutically acceptable salt thereof.

Another more preferred embodiment includes those compounds of formula I having the structure:

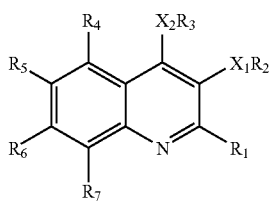
(I)

wherein:

$X_1$ is a bond, —C(O)—, or —$CR_8R_9$—;

$R_2$ is $C_1$ to $C_6$ alkyl, $CF_3$, CN, phenyl, or phenyl substituted by one to four groups independently selected from $C_1$ to $C_2$ perfluoroalkyl, halogen, and $C_1$ to $C_2$ alkyl substituted with 1 to 3 fluorines, or $R_2$ is a heterocycle selected from thiophene, and furan, each of which may be optionally substituted with one to three groups independently selected from $C_1$ to $C_2$ perfluoroalkyl, halogen, and $C_1$ to $C_2$ alkyl substituted with 1 to 3 fluorines;

$X_2$ is a bond $R_3$ is phenyl substituted by —W($CH_2$)$_j$A($CH_2$)$_k$D($CH_2$)$_p$Z, —W($CR_{18}R_{19}$)A($CH_2$)$_k$D($CH_2$)$_p$Z, —C≡CA($CH_2$)$_k$D($CH_2$)$_p$Z, or —($CH_2$)$_j$WA($CH_2$)$_k$D($CH_2$)$_p$Z, and further optionally substituted with one or two groups independently selected from $C_1$ to $C_2$ perfluoroalkyl, halogen, and —CN, or $R_3$ is a heterocycle selected from pyridine, pyrimidine, thiophene, and furan each of which is optionally substituted by —W($CH_2$)$_j$A($CH_2$)$_k$D($CH_2$)$_p$Z, —W($CR_{18}R_{19}$)A($CH_2$)$_k$D($CH_2$)$_p$Z, or —($CH_2$)$_j$WA($CH_2$)$_k$D($CH_2$)$_p$Z;

D is a bond, —O—, —NH—, —S—, —$CHR_{14}$—, —$CR_{14}R_{15}$—, —$OCHR_{14}$—, or —$OCR_{14}R_{15}$—;

Z is —$CO_2R_{11}$, —$CONR_{10}R_{11}$, —CN, —$CH_2OH$, or —$NR_{16}R_{17}$;

A is phenyl, or phenyl substituted by one to four groups independently selected from halogen, —CN, $C_1$ to $C_3$ perfluoroalkyl, and $C_1$ to $C_2$ alkyl substituted with 1 to 3 fluorines, or A is a heterocycle selected from pyrrole, pyridine, pyrimidine, and thiophene, each of which may be optionally substituted by one to three groups independently selected from halogen, —CN, $C_1$ to $C_3$ perfluoroalkyl, and $C_1$ to $C_2$ alkyl substituted with 1 to 3 fluorines;

wherein the remaining constituent variables are as defined immediately above;

or a pharmaceutically acceptable salt thereof.

This invention also provides processes for preparing compounds of formula I or a pharmaceutically acceptable salt thereof; whichs processes include one of the following:

a) reacting a compound of formula II

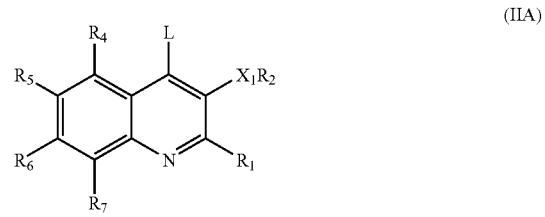
(IIA)

wherein L is Cl or triflate, $R_1$, $R_2$ and $R_{4-7}$ are as defined above, and $X_1$ is —CO—, with a boronic acid derivative of formula:

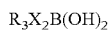
$R_3X_2B(OH)_2$ wherein $R_3$ and $X_2$ are as defined above, to give a compound of formula I wherein $X_1$ is —CO—;

or b) reacting a compound of formula

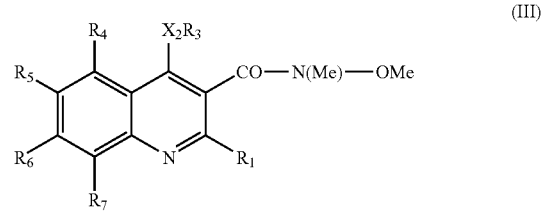
(III)

wherein $R_1$, $R_{3-7}$ and $X_2$ are as defined above, with a Grignard of formula:

$R_2MgBr$ wherein $R_2$ is as defiend above, to give a corresponding compound of formula (I) wherein $X_1$ is —CO—;

or c) cyclocondensing a compound of formula IV

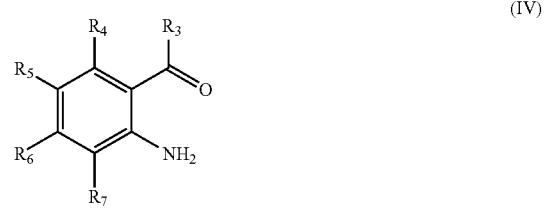
(IV)

wherein R$_{3-7}$ are as defined above, with a compound of formula

R$_2$X$_1$—CH$_2$—CHO wherein R$_2$ and X$_1$ are as defined above, to give a corresponding compound of formula

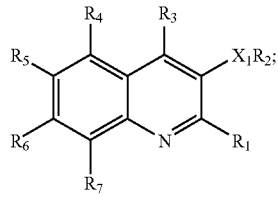

(Ia)

or d) reacting a compound of formula V

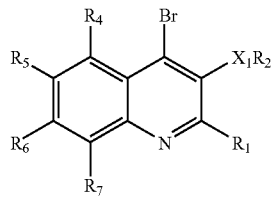

(V)

wherein R$_1$ and R$_{4-7}$ are as defined above, and X$_1$ is a bond, —S— or —O—, with a boronic acid derivative of formula:

R$_3$B(OH)$_2$ wherein R$_3$ is as defined above, to give a corresponding compound of formula I wherein X$_2$ is a bond.

or e) reacting a compound of formula

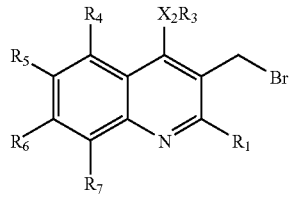

(VI)

wherein X$_2$, R$_1$ and R$_{3-7}$ are as defined above, with a boronic acid derivative of formula

R$_2$B(OH)$_2$ wherein R$_2$ is as defined herein, to give a corresponding compound of formula I wherein X, is —CH$_2$—;

or f) reacting a compound VI as defined above with pyrrole, pyrazole or imidazole to give a corresponding compound of formula I wherein R$_2$ is pyrrole, pyrazole or imidazole and X$_1$ is —CH$_2$—;

or g) reacting a compound of formula VI as defined above with an alcohol or phenol of of formula R$_2$O to give a corresponding compound of formula I wherein X$_1$ is —CH$_2$O—;

or h) cyclising a compound of formula

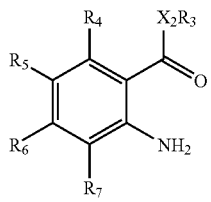

wherein X$_2$ and R$_{3-7}$ are as defined above, with a compound of formula

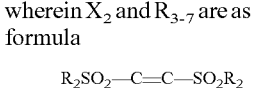

R$_2$SO$_2$—C≡C—SO$_2$R$_2$ wherein R$_2$ is as defined above, to give a corresponding compound of formula I wherein R$_1$ is H, X$_1$ is SO$_2$;

or i) reacting a compound of formula

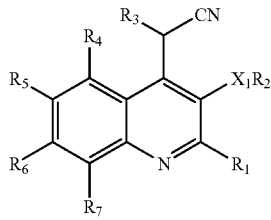

wherein R$_{1-7}$ and X, are as defined above, with HBr to give a corresponding compound of formula I wherein X$_2$ is —CH$_2$—.

Also if desired a basic compound of formula I may be converted to a pharmaceutically acid addition acceptable salt thereof or vice versa by the addition of base.

Additionally a compound of formula I having a reactive substituent group or site may be converted to a different compound of formula I.

As used herein, the term "alkyl" as a group or part of a group includes both branched and straight-chain saturated aliphatic hydrocarbon groups having the specified number of carbon atoms, e.g. methyl (Me), ethyl (Et), propyl (Pr), isopropyl (i-Pr), isobutyl (i-Bu), secbutyl (s-Bu), tertbutyl (t-Bu), isopentyl, isohexyl and the like, unless specified otherwise, akyl groups typically have 1-12 carbon atoms.

The term "cycloalkyl" is intended to have its normal meaning of a cyclic alkyl group, e.g., cyclopropyl, cyclobutyl, cyclopentyl, cyclohexyl, and the like.

As used herein the term "alkoxy" has its normal meaning of a group of formula —O-alkyl. As used herein, the term alkenyl is intended to denote alkyl groups that contain at least one double bond, including for example but not limited to vinyl, allyl, 2-methyl-allyl, 4-but-3-enyl, 4-hex-5-enyl, 3-methyl-but-2-enyl, cyclohex-2-enyl and the like.

As used herein, the term alkynyl is intended to denote alkyl groups that include at least one triple bond, including for example but not limited to but-1-yne, propyne, pent-2-yne, ethynyl-cyclohexyl and the like.

As used herein, the term halogen has its normal meaning of period seven elements, including F, Cl, Br and I.

As used herein the term aryl is intended to mean an aromatic hydrocarbon system, e.g., of 6-20 carbon atoms, for example phenyl, naphthyl, phenanthrenyl, anthracenyl, pyrenyl, and the like. Also included within the definition of aryl are such aromatic systems containing one or more further fused aromatic rings, for example fluorenyl groups.

As used herein, the term arylalkyl is intended to mean a group of formula—alkyl-aryl, alkyl-(aryl)$_2$, and alkyl-(aryl)$_3$, wherein aryl and alkyl have the definitions herein. Non-limiting examples of arylalkyl groups include benzyl, diphenylmethyl and triphenylmethyl.

As used herein, the term acyl is intended to mean an alkyl, aryl or arylalkyl group that is connected through a carbonyl group, for example and not limitation, groups of formula —C(=O)-alkyl, —C(=O)-aryl, and (i.e.—C(=O)-arylalkyl.

As used herein, the term "heterocycle" indicates a ring system containing at least one hetero (i.e., non-carbon) atom, e.g., 1-4 hetero atoms, which may be the same or different, for example O, N or S. Some preferred heterocycles include, without limitation, pyridine, thiophene, benzisoxazole, benzothiophen, oxadiazole, pyrrole, pryazole, and furan. Further non-limiting examples of heterocycle groups include radicals derived from imidazole, tetrazole, imidazolidine, isothiazole, isoxazole, oxathiazole, oxazole, oxazoline, pyrazolidine, pyrazoline, pyrrolidine, pyrroline, thiazoline, oxazine, piperazine, piperidine, pyran, pyrazine, pyridazine, pyrimidine, thiadizine, thiazine, benzodioxine, benzodioxole, benzofuran, chromene, cinnoline, indazole, indole, indoline, indolizine, isoindole, isoindoline, isoquinoline, naphthalene, naphthyridine, phthalazine, purine, quinazoline, quinoline, and quinolizine.

The term "bithienyl" is intended to mean a group of formula thiophene-thiophene, wherein the two thiophene moieties are connected through any atom thereof.

The term $C_1$ to $C_7$ amines is intended to mean aliphatic amines having from 1 to 7 carbon atoms. The term $C_3$ to $C_7$ cyclic amines is intended to mean saturated amines containing at least one ring, and from 3 to 7 carbon atoms.

The term "side chain of a naturally occurring alpha amino acid" is intended to denote the side chains of alanine, arginine, asparagines, aspartic acid, cysteine, glutamine, glutamic acid, histidine, isoleucine, leucine, lysine, methionine, phenylalanine, serine, threonine, tryptophan, tyrosine and valine, the side chain thereof being the portion designated "R" in the formula H$_2$N—CH(R)—COOH.

As used in accordance with this invention, the term "providing," with respect to providing a compound or substance covered by this invention, means either directly administering such a compound or substance, or administering a prodrug, derivative, or analog which will form the effective amount of the compound or substance within the body. This invention also covers providing the compounds of this invention to treat the disease states disclosed herein that the compounds are useful for treating.

The compounds of the present invention can contain an asymmetric atom, and some of the compounds can contain one or more asymmetric atoms or centers, which can thus give rise to optical isomers (enantiomers) and diastereomers. The present invention includes such optical isomers (enantiomers) and diastereomers (geometric isomers); as well as the racemic and resolved, enantiomerically pure R and S stereoisomers; as well as other mixtures of the R and S stereoisomers and pharmaceutically acceptable salts thereof. Optical isomers can be obtained in pure form by standard procedures known to those skilled in the art, and include, but are not limited to, diastereomeric salt formation, kinetic resolution, and asymmetric synthesis. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of formula (I) can be conveniently prepared by the procedures outlined in schemes below from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. Although not limited to any one of several sources, classic texts such as Smith, M. B.; March, J. *March's Advanced Organic Chemistry: Reactions, Mechanisms, and Structure,* 5$^{th}$ ed.; John Wiley & Sons: New York, 2001; and Greene, T. W.; Wuts, P. G. M. *Protective Groups in Organic Synthesis,* 3$^{rd}$ ed.; John Wiley & Sons: New York, 1999 are useful and recognized reference textbooks of organic synthesis known to those in the art.

According to Scheme 1, aniline (1) can be condensed with diethyl ethoxymethylenemalonate (2) to provide the compound of formula (3). The latter compound is cyclized thermally to provide the quinoline of formula (4). Conversion of the phenol of (4) to the chloride of formula (5) can be accomplished readily with chlorinating agents such as phosphorus oxychloride. Reaction of the ester moiety of (5) with an organolithium reagent (R$_2$Li) provides the compound of formula (6). Reaction of (6) with a boronic acid reagent of formula R$_3$X$_2$B(OH)$_2$ in the presence of a palladium catalyst provides the compound of formula (I), where X$_1$=CO.

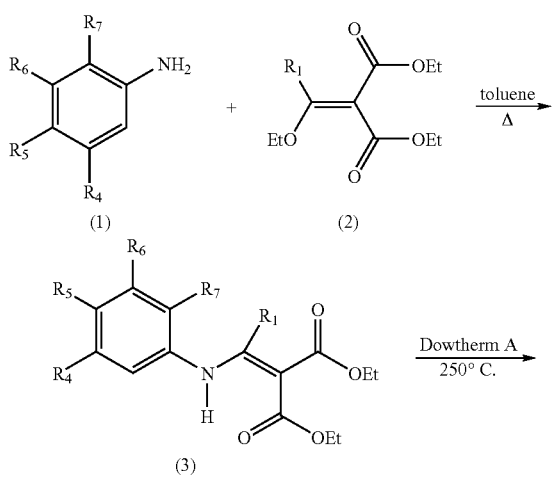

Scheme 1.

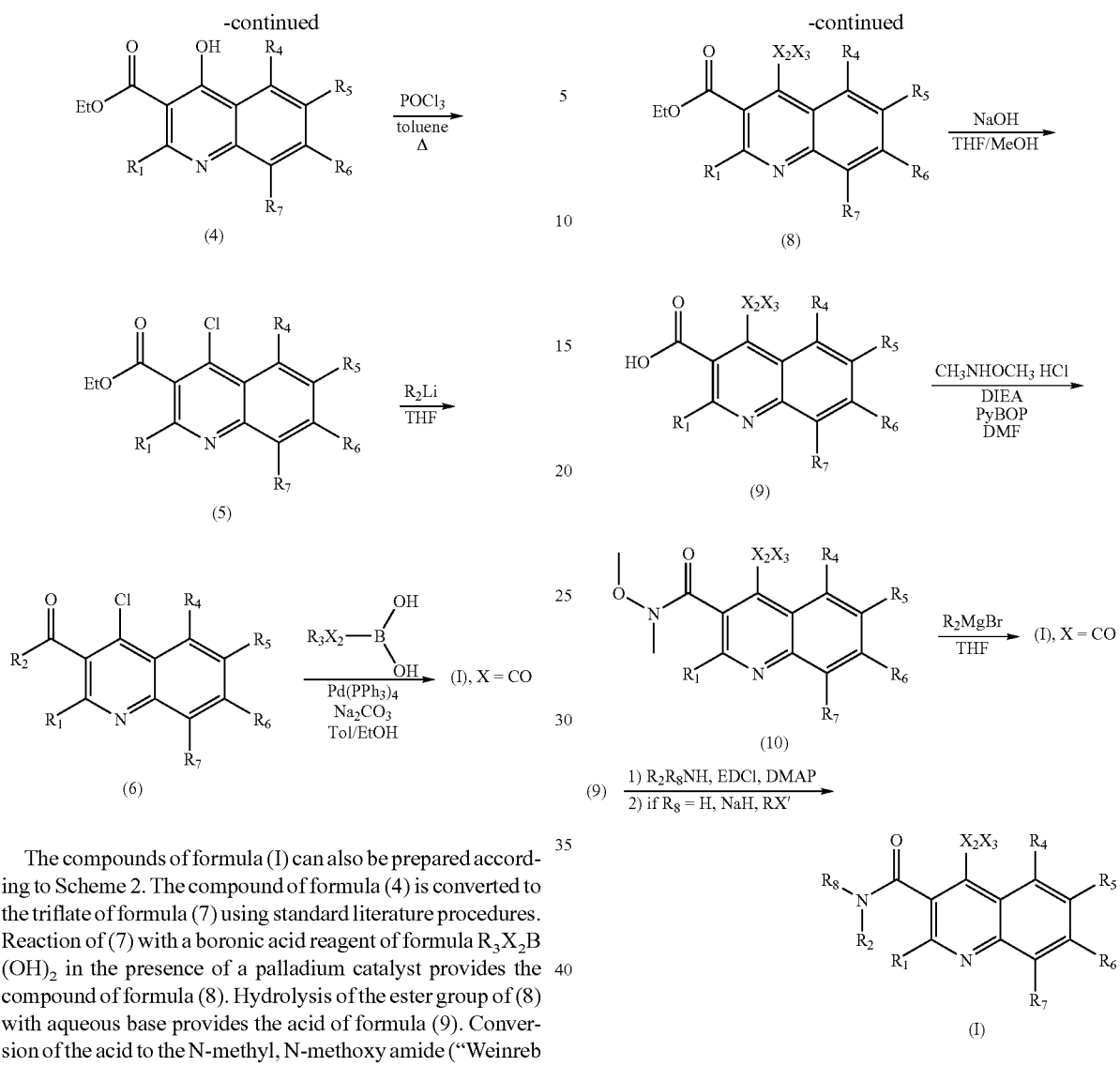

The compounds of formula (I) can also be prepared according to Scheme 2. The compound of formula (4) is converted to the triflate of formula (7) using standard literature procedures. Reaction of (7) with a boronic acid reagent of formula $R_3X_2B(OH)_2$ in the presence of a palladium catalyst provides the compound of formula (8). Hydrolysis of the ester group of (8) with aqueous base provides the acid of formula (9). Conversion of the acid to the N-methyl, N-methoxy amide ("Weinreb amide") of formula (10) occurs readily under standard amidation conditions. Reaction of the amide (10) with a Grignard reagent of formula $R_2MgBr$ occurs readily to provide the compound of formula (I), where $X_1$=CO. The carboxylic acid of formula (9) can also under go amidation to the compounds of formula (I) under standard amidation conditions Compounds of formula (I) can also be prepared according to Scheme 3. The ethoxy acrylic acid, ethyl ester of formula (11) is condensed with an aniline of formula (1) to provide the compound of formula (12). The latter compound is thermally cyclized to the quinoline of formula (13). Conversion to the chloride is effected with standard chlorinating agents such as $POCl_3$ the compound of formula (6). The compound of formula (6) is converted to the compound of formula (I) as outlined in Scheme 1.

Scheme 2.

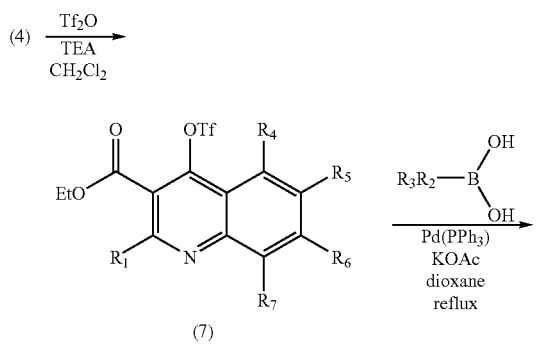

Scheme 3

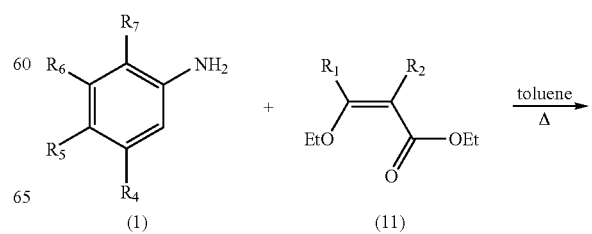

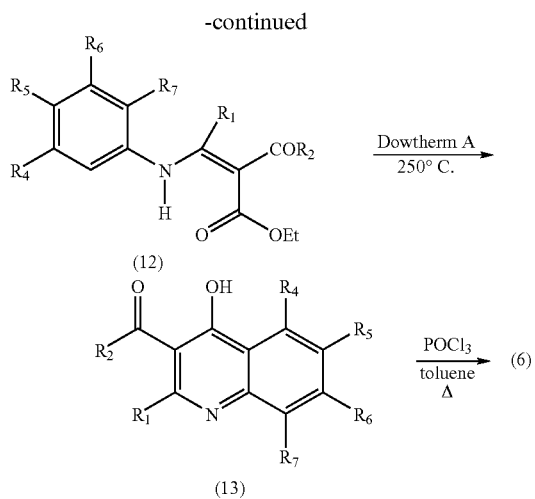

The compounds of formula (I) can also be prepared according to Scheme 4. The compound of formula (13) is converted to the triflate of formula (14) using standard literature procedures. Reaction of (14) with a boronic acid reagent of formula $R_3X_2B(OH)_2$ in the presence of a palladium catalyst provides the compound of formula (I), where $X_1$=CO.

Scheme 4

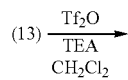

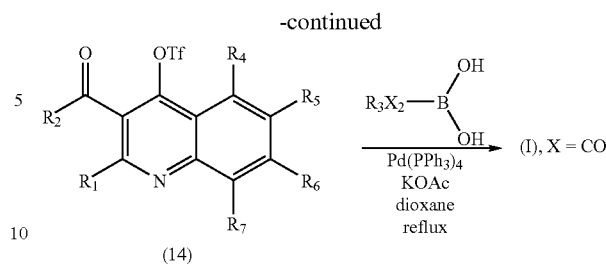

According to Scheme 5, the carbonyl group of the compounds of formula (I), where $X_1$=CO, can be readily converted to other moieties. Treatment of (I), where $X_1$=CO with hydrazine followed by potassium hydroxide provides the compound of formula (I), where $X_1$=$CH_2$. Reduction of (I), where $X_1$=CO with sodium borohydride provides the alcohol of formula (I), where $X_1$=CH(OH). Reaction of (I), where $X_1$=CO with a Grignard reagent of formula $R_8$MgBr provides the alcohol of formula (I), where $X_1$=$CR_8$(OH). Reaction of the compound of formula (I), where $X_1$=CO with hydroxylamine provides the oxime of formula (I), where $X_1$=CN(OH). Alkylation of the alcohols of formula (I), where $X_1$=CH(OH) or $CR_8$(OH) or the oxime of formula (I) using, for instance, sodium hydride followed by an alkylating agent of formula $R_9X'$ provides the ethers of formula (I), where $X_1$=CH(ORG) or $X_1$=$CR_8$($OR_9$) or the oxime ether of formula (I), where $X_1$=CN($OR_9$). Acylation of the alcohol of formula (I), where $X_1$=CH(OH) with an acid halide of formula $C_9$COCl provides the ester of formula (I), where $X_1$=CH($OCOR_9$).

Scheme 5.

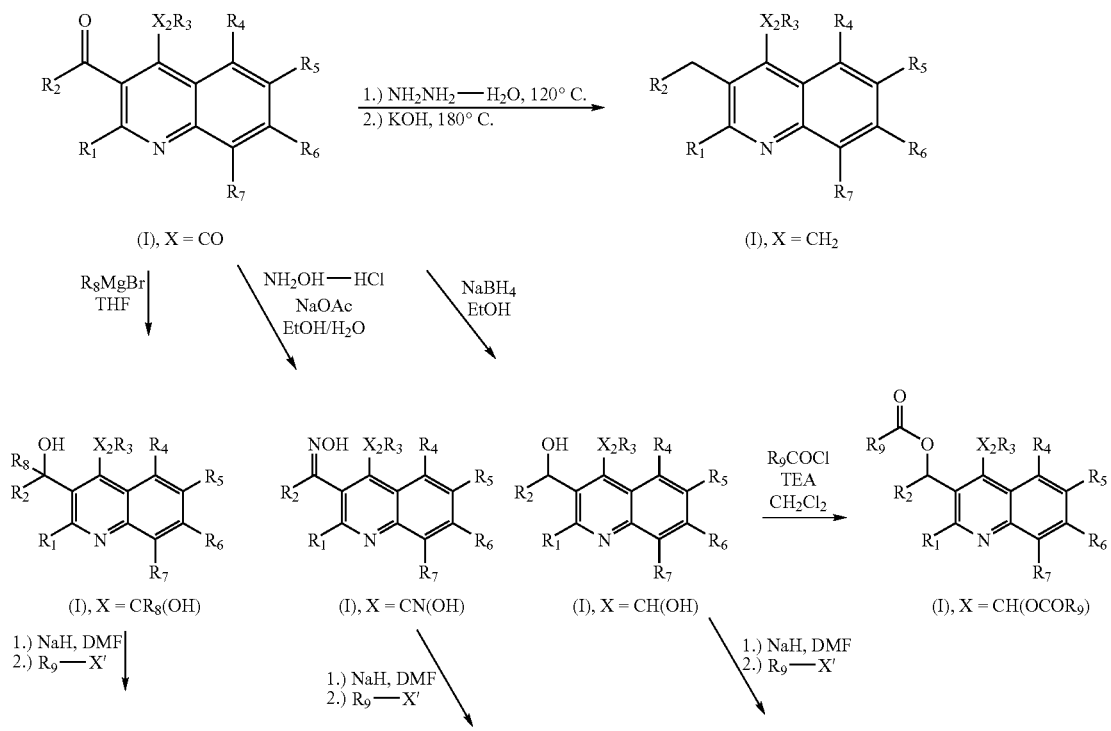

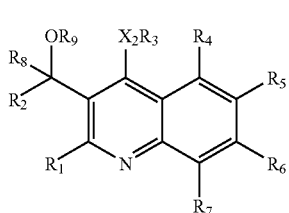

(I), X = CR8(OR9)

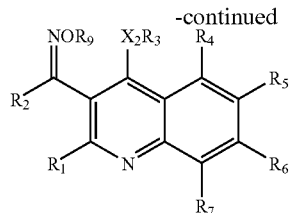

(I), X = CN(OR9)

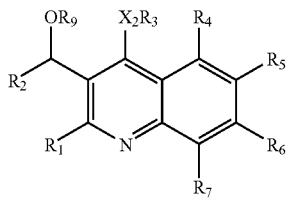

(I), X = CH(OR9)

According to Scheme 6, certain compounds of formula (I) prepared by Schemes 1-5, contain a $(CH_2)_jOH$ moiety on the phenyl ring that is attached to the 4-position of the quinoline ring system. Alkylation of this OH with an alkylating agent RX' using potassium, sodium or cesium carbonate as the base provides the alkylated compound of formula (I). Alternatively, if j is 1 or more and ROH is a phenol or substituted phenol, or j is 0 and ROH is an alcohol where the OH is connected to a sp3 hybridized carbon, then the alcohol of formula (I) and the ROH can be reacted with triphenylphosphine ($PPh_3$) and diisopropylazodicarboxylate (DIAD) to form the ether of formula (I). Alternatively, arylation of this OH, when j=0, with an aryl iodide, bromide or boronic acid using an appropriate copper catalyst, and a tertiary amine base if necessary provides the aryl ether of formula (I). If the R group of the compound of formula (I) contains a carboxylic acid ester moiety, this moiety can be transformed to the carboxylic acid upon treatment with aqueous lithium, sodium or potassium hydroxide in a suitable organic solvent. If the R group of the compound of formula (I) contains a $CH_2X'$ where X' is a halogen Br or Cl, then this group can be transformed to $CH_2CN$ upon treatment with sodium cyanide in a suitable organic solvent. If the R group of the compound of formula (I) contains a $CH_2CN$, then this group can be transformed to the tetrazole

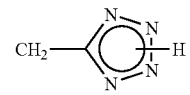

using standard conditions such as, sodium, in DMF at 125° C.

Scheme 6.

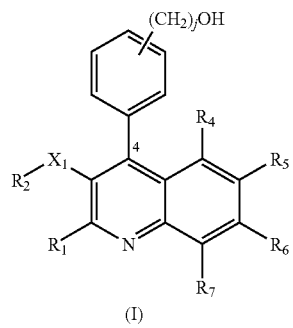

According to Scheme 7, certain compounds of formula (I) prepared by Schemes 1-5, contain a free $NH_2$ moiety on the phenyl ring that is attached to the 4-position of the quinoline ring system. Treatment of the free $NH_2$ compound of formula (I) with a sulfonyl chloride of formula $ClSO_2$-A provides the corresponding sulfonamide of formula (I). Treatment of the free $NH_2$ compound of formula (I) with an acid chloride of formula ClCO-A provides the amide of formula (I). Treatment of the free $NH_2$ compound of formula (I) with an isocyanate of formula A-CNCO provides the urea of formula (I).

Scheme 7.

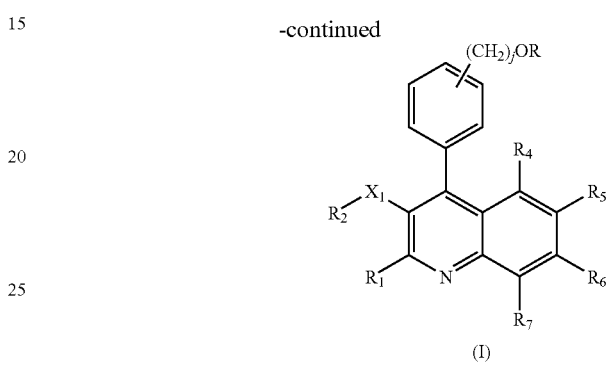

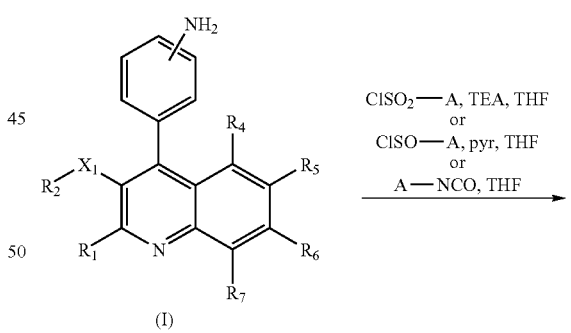

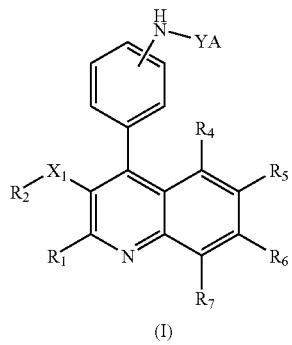

According to Scheme 8, certain compounds of formula (I) prepared by Scheme 1-5, contain a free NH$_2$ moiety on the phenyl ring that is attached to the 4-position of the quinoline ring system. Treatment of the free amine with an aldehyde (RCHO) and a reducing agent such as NaBH(OAc)$_3$, results in the secondary amine product of formula (I). The same product of formula (I) could also be obtained upon treating the starting primary amine with alkylating agent (RX') in the presence of a base. Treatment of the secondary amine with an aldehyde (R'CHO) and a reducing agent such as NaBH(OAc)$_3$, results in the tertiary amine product of formula (I). The same product of formula (I) could also be obtained upon treating the starting secondary amine with alkylating agent (R'X') in the presence of a base. Treatment of the NHR" of compound of formula (I) with a sulfonyl chloride of formula ClSO$_2$—R' provides the corresponding sulfonamide of formula (I). Treatment of the NHR" compound of formula (I) with an acid chloride of formula ClCO—R' provides the amide of formula (I). Treatment of the NHR" compound of formula (I) with an isocyanate of formula R'—CNCO provides the urea of formula (I). If the R group of the compound of formula (I) contains a carboxylic acid ester moiety this moiety can be transformed to the carboxylic acid upon treatment with aqueous lithium, sodium or potassium hydroxide in a suitable organic solvent. If the R group of the compound of formula (I) contains a CH$_2$X' where X' is a halogen Br or Cl, then this group can be transformed to CH$_2$CN upon treatment with sodium cyanide in a suitable organic solvent. If the R group of the compound of formula (I) contains a CH$_2$CN, then this group can be transformed to the tetrazole

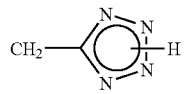

using standard conditions such as sodium in DMF at 125° C.

Scheme 8.

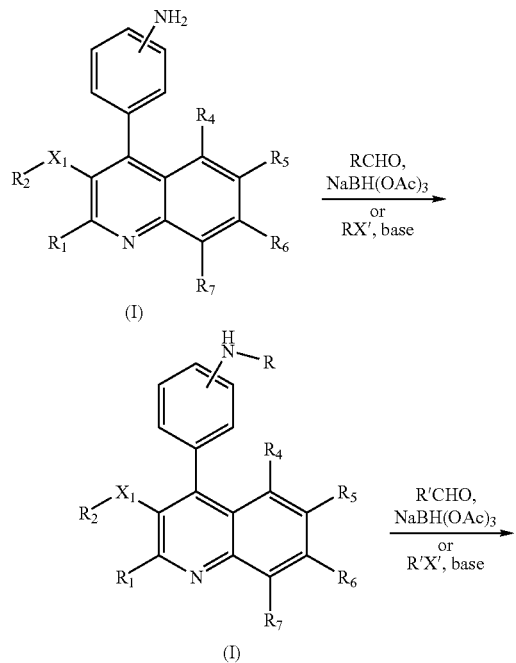

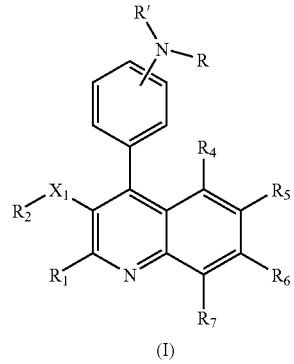

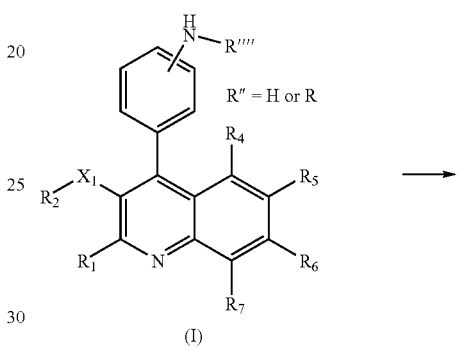

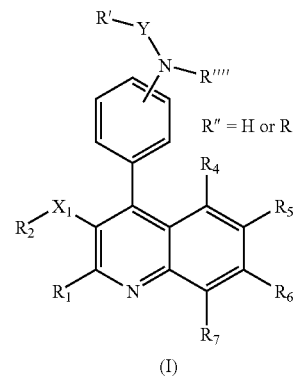

According to Scheme 9, the compounds of formula (I) where X$_1$=bond, or C$_1$ to C$_3$ alkyl can also be prepared. The compound of formula (18) is converted to the N-methyl, N-methoxy amide ("Weinreb amide") of formula (19) under standard amidation conditions. Reaction of the amide (19) with a lithio or Grignard reagent of formula R$_3$Li or R$_3$MgBr at low temperature provides the compound of formula (20). Alternatively, the compound of formula (16) is lithiated alpha to fluorine and then treated with an appropriately substituted aldehyde. The resulting alcohol (17) is converted to the ketone (20) under standard oxidation conditions. Conversion of (20) into the aniline is accomplished with ammonium hydroxide at elevated temperature. Substituted anilines of formula (21) undergo clean condensation, cyclization in acetic acid with a catalytic amount of sulfuric acid at elevated temperature to provide compounds of formula (I).

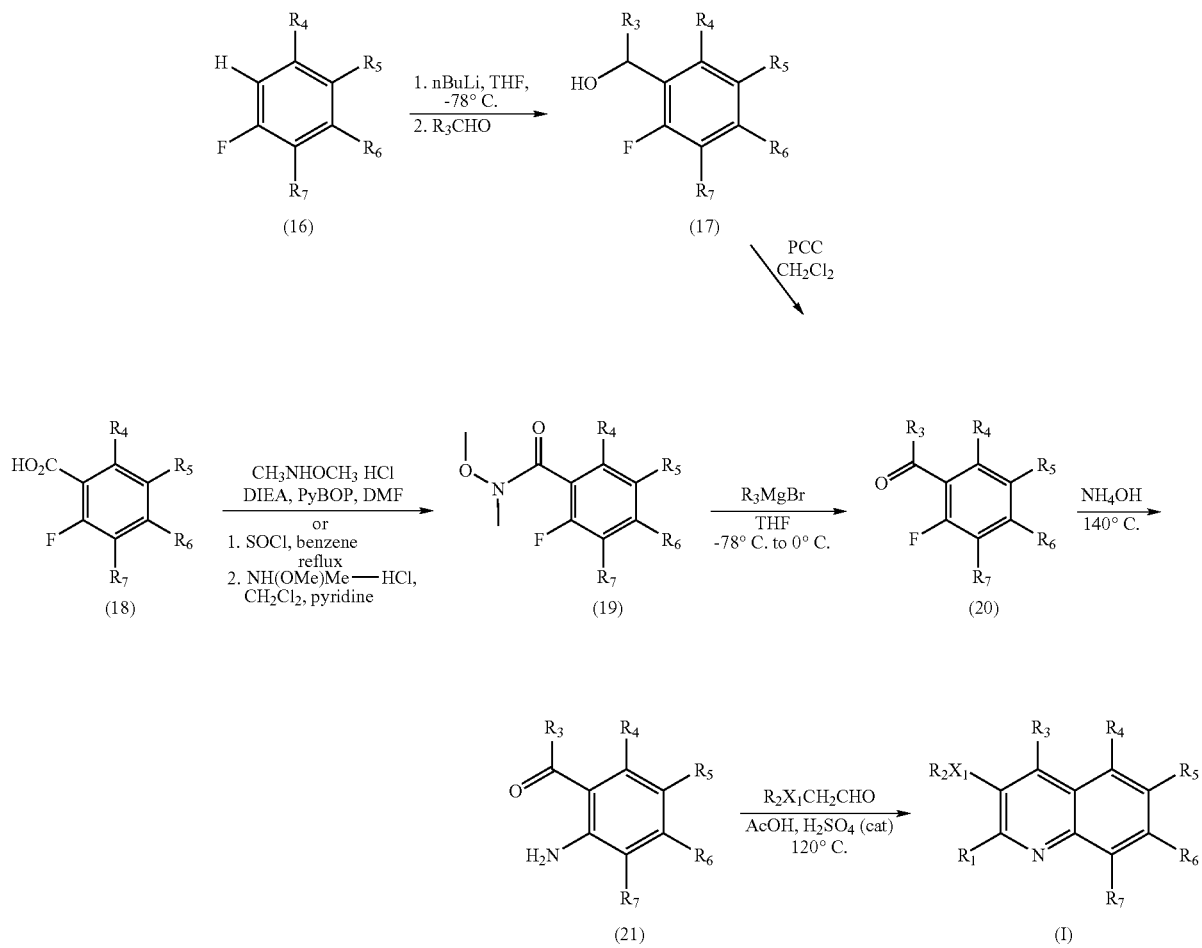
According to Scheme 10 the phenol group of the compound (22) can be readily alkylated to give the benzyl chloride (23), which can be further alkylated with either amines or pyrroles. The phenol group of the compound (22) can also be readily acylated with sulfonyl chloride, acyl chloride, and isocyanate.
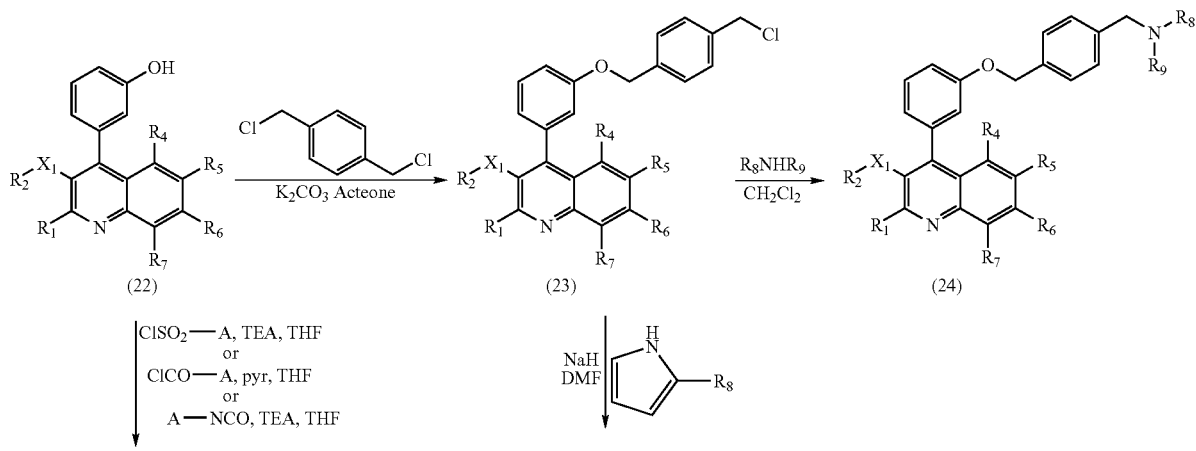

-continued

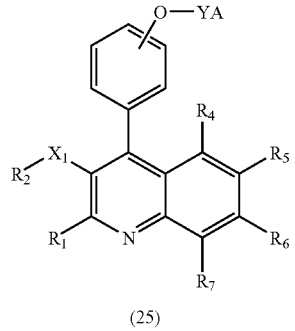
(25)

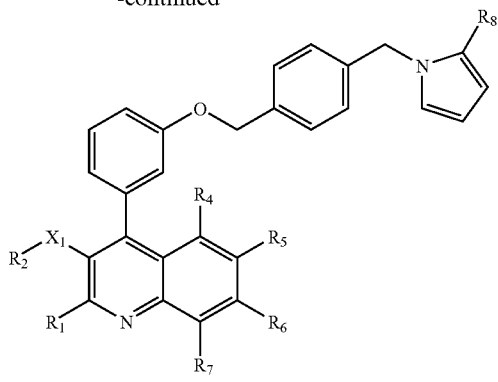
(26)

The compounds of formula (I) can also be prepared according to Scheme 11. Coupling of (27) with aryl iodine in the presence of a palladium catalyst provides the ester (28) which can be converted to the corresponding carboxylic acid (29) under a standard basic hydrolysis condition.

Scheme 11.

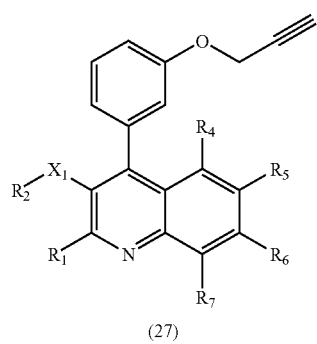
(27)

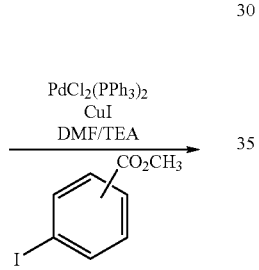

PdCl$_2$(PPh$_3$)$_2$
CuI
DMF/TEA

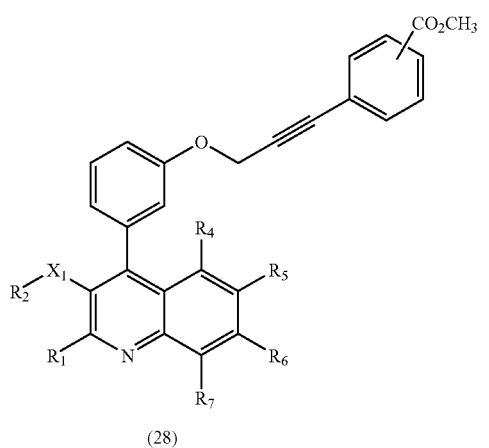
(28)

NaOH
THF/MeOH

-continued

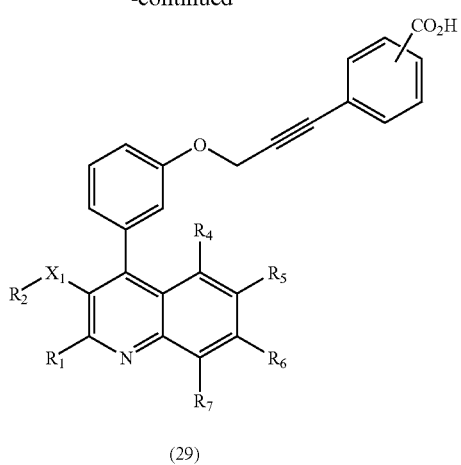
(29)

According to Scheme 12, reaction of aminophenyl (30) with an large excess of the cyclic acetal 2,5-dimethoxytetrahydrofuran gave pyrrole (31). This amine can also be arylated with boronic acid in the presence of a base, preferably 2,6-lutidine, an additive such as myristic acid, and Cu(OAc)$_2$ in an inert solvent such as toluene at room temperature.

Scheme 12.
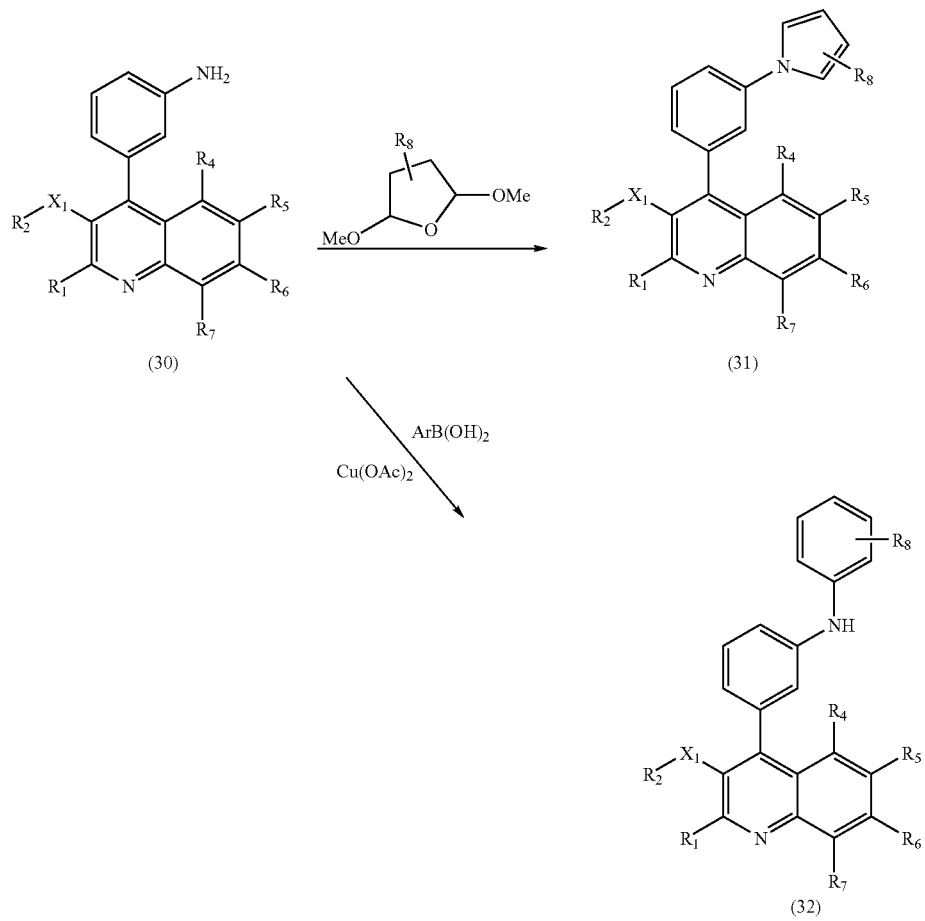
According to Scheme 13, treatment of the free $NH_2$ compound (30) with an isothiocyanate of formula ArNCS provides the thiourea of formula (33). Reaction of (33) with ammonium hydroxide in the presence of lead acetate provides the guanidine of formula (34). Reaction of the compound (33) with lead cyanamide provides the cyano guanidine (35).
Scheme 13.
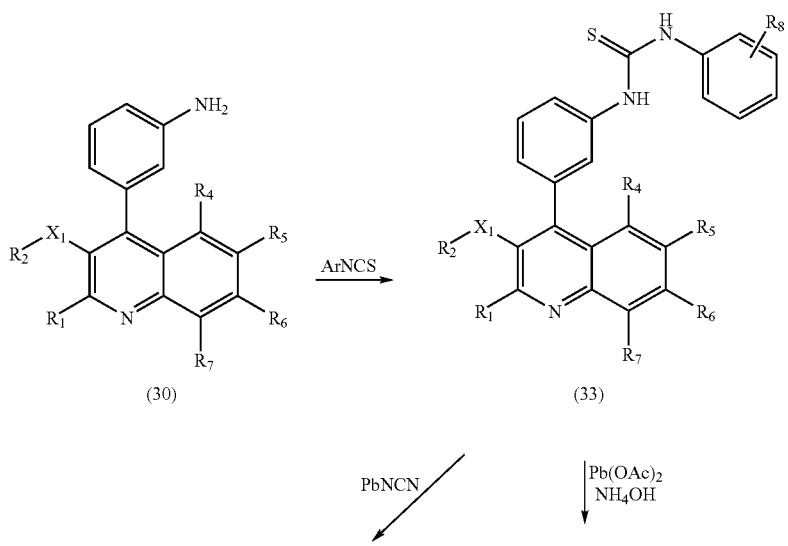

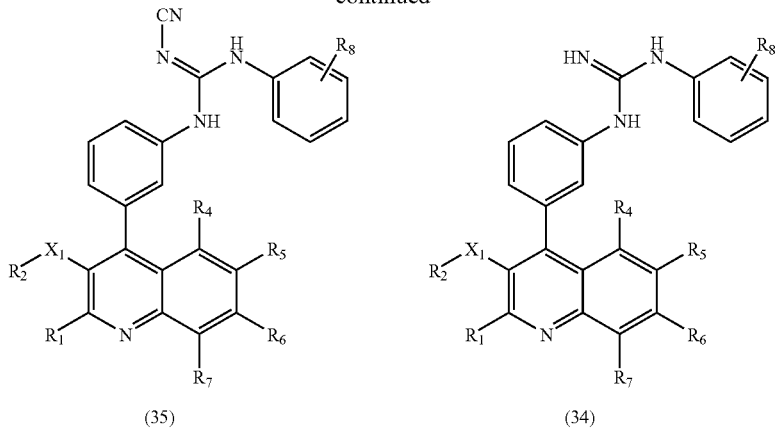

According to Scheme 14, the ester of formula (36) is converted to the phenyl acetamide (37) or Phenyl-acetic acid hydrazide (38) under standard conditions. Alkylation of this ester with an alkylating agent RX' using cesium carbonate as the base provides the mono or di-alkylated compound of formula (39). Alternatively, compound (39) can be prepared by mono or di-alkylation of the benzonitrile (40) followed by Ray (Ni) reduction and reductive amination as described in Scheme 8.

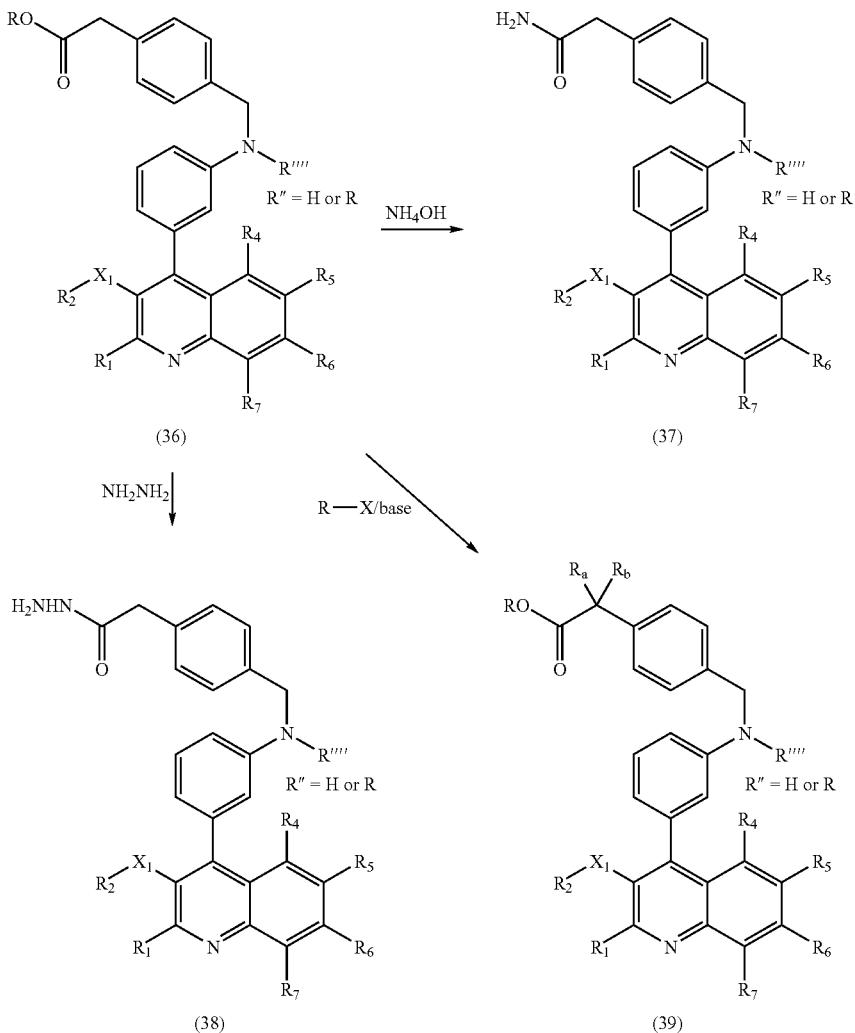

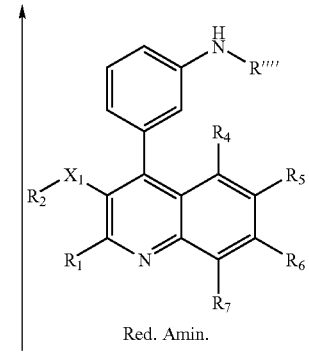

Red. Amin.

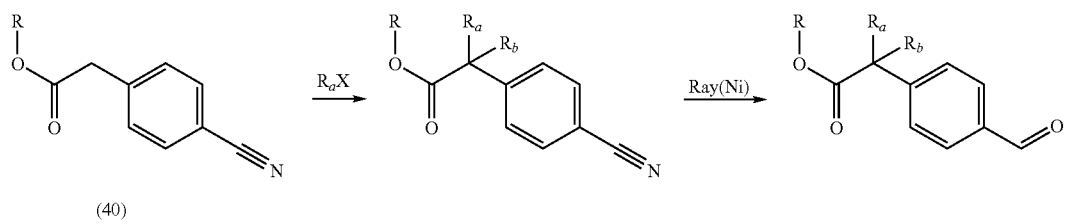

(40)

The compounds of formula (I) can also be prepared according to Scheme 15. The compound of formula (41) is converted to the hydroxyl compound (42) using standard reduction procedures. The compound of formula (41) can also be converted to the di-fluoro compound (44) by treatment of DAST. Reductive amination of aldehyde (42) or (45) with the amine (30) provides the compound of formula (43) or (46).

Scheme 15.

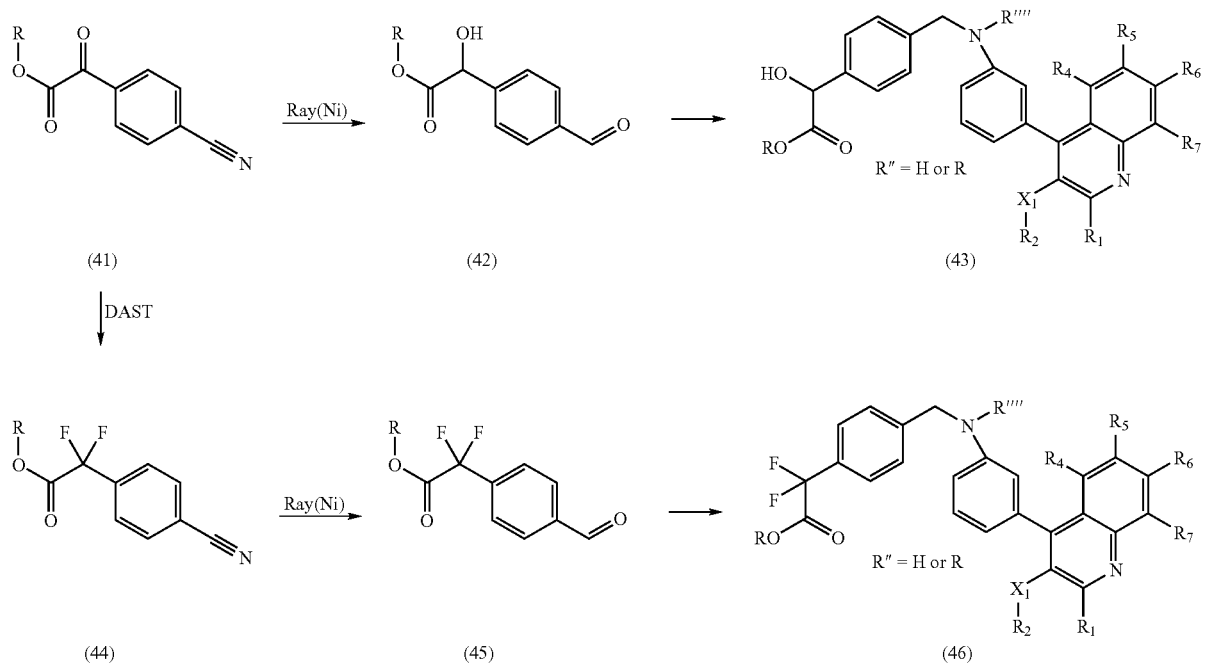

Compounds (47) can be prepared as shown in Scheme 16. The addition of a Grignard reagent to Weinreb amide (47) in THF produces ketones (I).

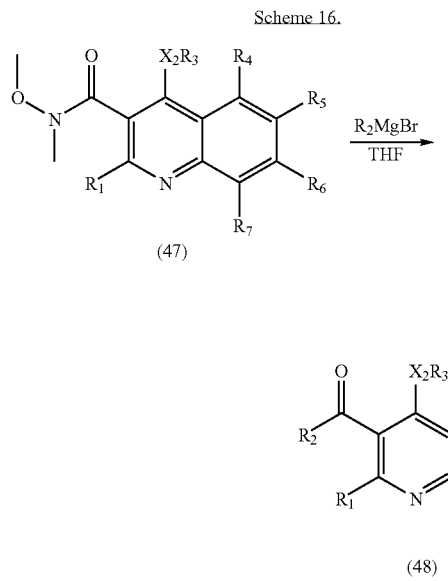

The carbonyl group of compound (48) can be modified as shown in Scheme 17. The reaction of (48) with trimethylorthoformate in MeOH with paratoluenesulfonic acid produces dimethoxy compounds (49). The reaction of (48) with a Grignard reagent produces (50) which can be converted to alkene (51) by refluxing in ethanolic HCl. Compound (52) can be produced via catalytic hydrogenation of (51).

Other modifications to the carbonyl of compound (48) can be made as shown in Scheme 18. Compound (48) can be converted to the hydrazone (53) by reaction with hydrazine in ethylene glycol. Compound (54) can be converted to the oxime (55) by treating with hydroxylamine in aqueous ethanol at reflux. Oxime (55) can be reacted with acetic anhydride to produce oxime acetate (56). The reaction of compound (56) with NaH in DMF produces benzisoxazole (57).

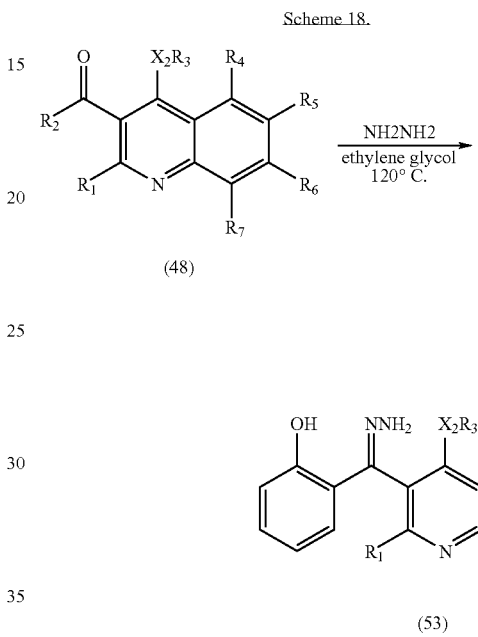

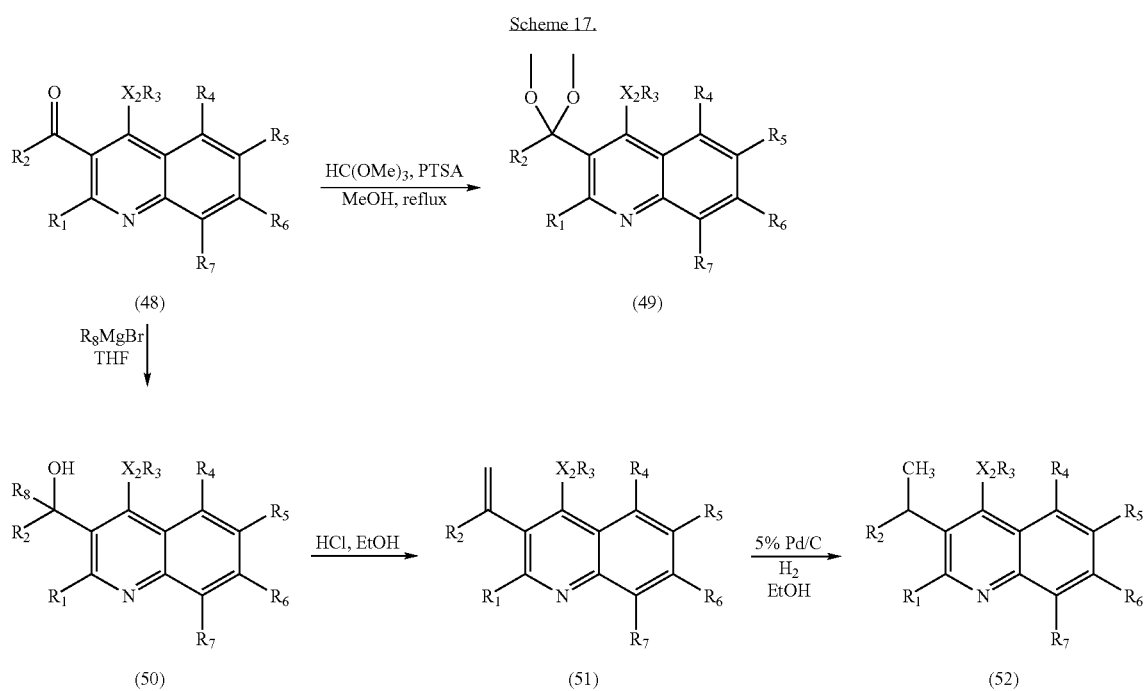

Scheme 19.

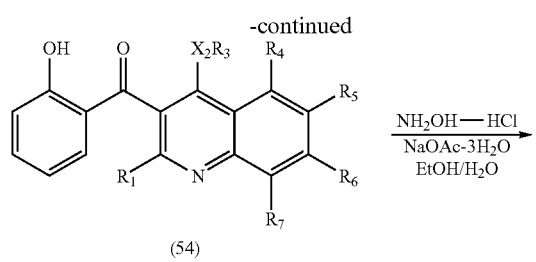

(54)

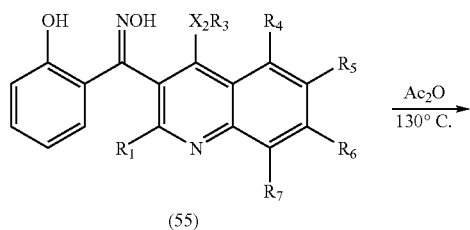

(55)

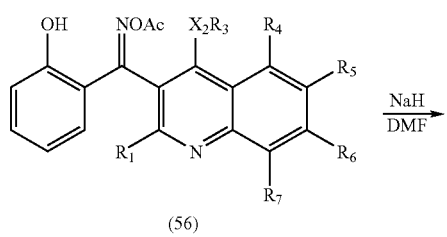

(56)

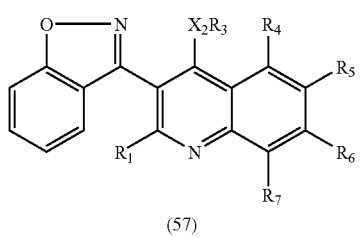

(57)

Compounds of formula (59) can be synthesized as shown in Scheme 19. The reaction of phenol (58) in CH$_2$Cl$_2$ with Cs$_2$CO$_3$ with an appropriate alkylating agent produces benzylated compounds (59).

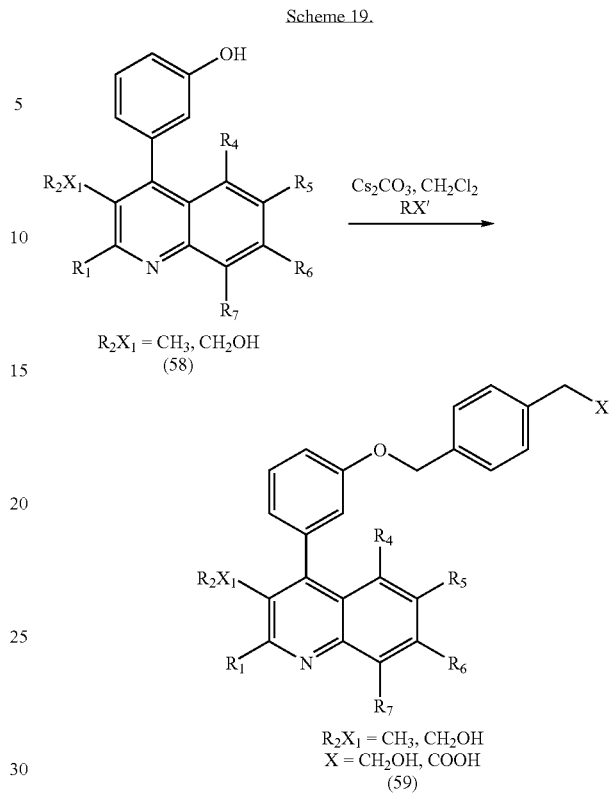

$R_2X_1 = CH_3, CH_2OH$
(58)

$R_2X_1 = CH_3, CH_2OH$
X = CH$_2$OH, COOH
(59)

Compound of formula (I) can also be prepared according to Scheme 20. The compound of formula (60) is converted to the decarboxylated product (61) with Dowtherm A at reflux. Bromination of (61) with bromine provides bromide of formula (62). Compounds of formula (63) where X=bond are prepared from bromide of formula (62) by coupling with a boronic acid reagent of formula ArB(OH)$_2$ in the presence of a palladium catalyst. Compounds of formula (63) where X=S or O can be prepared by aromatic substitution in the presence of the sodium thioaryloxide or potassium aryloxide. Conversion of the quinolin-4-ol (63) to the bromide of formula (64) can be accomplished readily with brominating agents such as phosphorus oxybromide. Compounds of formula (65) in which Y=H, OH, NH$_2$, or OMe and R'=Cl, or F are prepared as described in Scheme 6. Compounds of formula (65) where Y=NH$_2$ or OH and R'=H, Cl or F are alkylated with an alkylating agent RX' using potassium carbonate or the like as the base which provides the alkylated compound of formula (66).

Scheme 20.

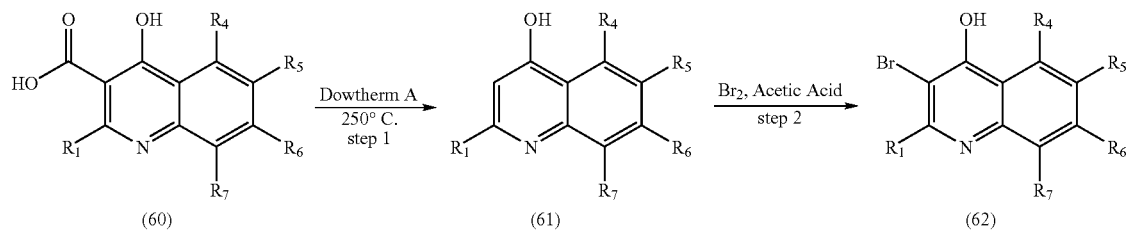

(60)    (61)    (62)

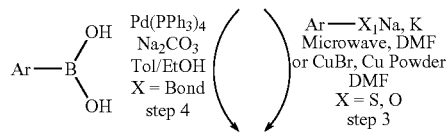

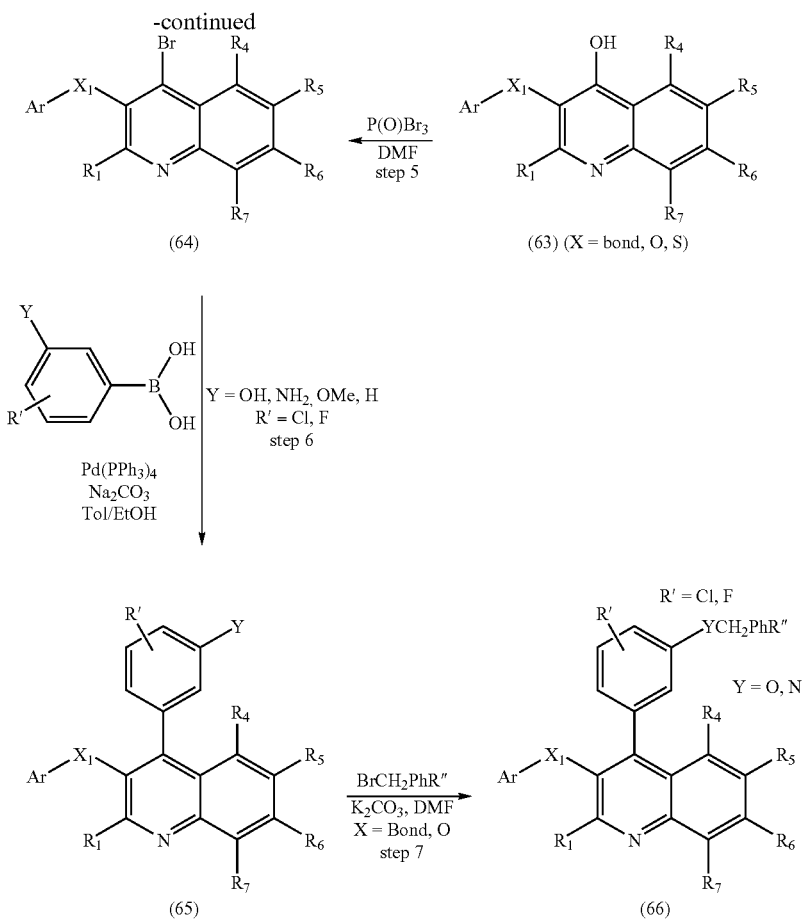

Compound of formula (I) can also be prepared according to Scheme 21. The compound (67) is converted to the alcohol (68) by reduction with lithium borohydride or other literature reducing agents. Reaction of (68) with phosphorous tribromide or other brominating agent provides bromides of (69). Compounds (70) are prepared from bromide (69) by coupling with a boronic acid reagent of formula $R_2B(OH)_2$ in the presence of a palladium catalyst. Compounds (71) exemplified by pyrrole, imidazole, and pyrazole are prepared by reacting bromides (69) with the appropriate heterocycle in the presence of a base such as sodium hydride. Compounds (72) are prepared by treating alcohols and phenols of formula $R_2OH$ with a base in the presence of a bromide (69).

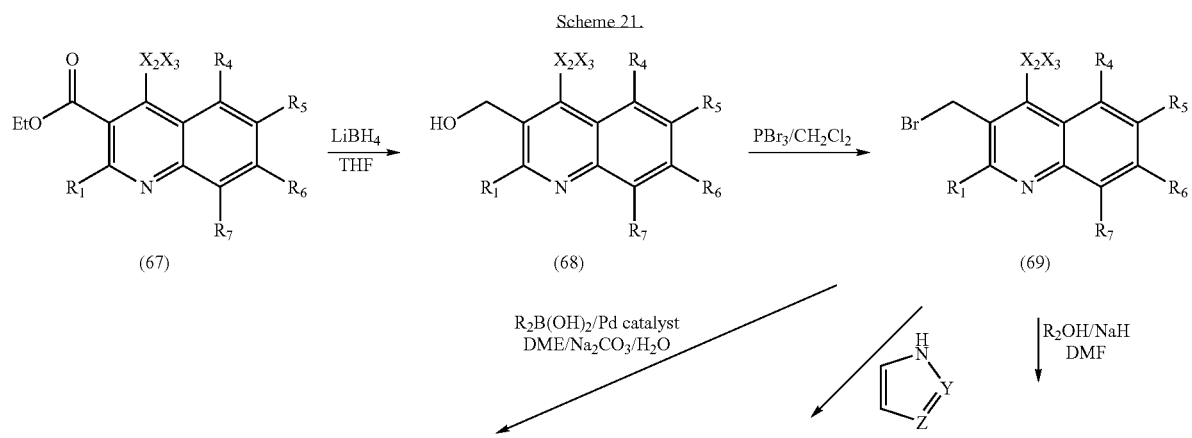

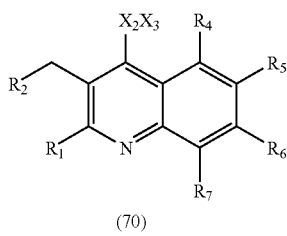
(70)

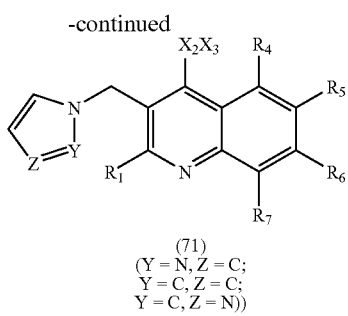
(71)
(Y = N, Z = C;
Y = C, Z = C;
Y = C, Z = N))

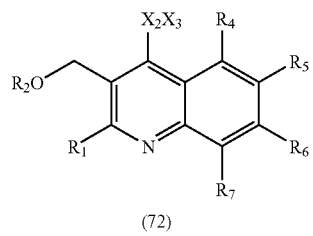
(72)

Compounds (74) can be prepared according to Scheme 22. The ester (67) is condensed with an N-hydroxy-amidine (73) in the presence of strong base such as sodium hydride and a solvent such as THF to provide the compound (74).

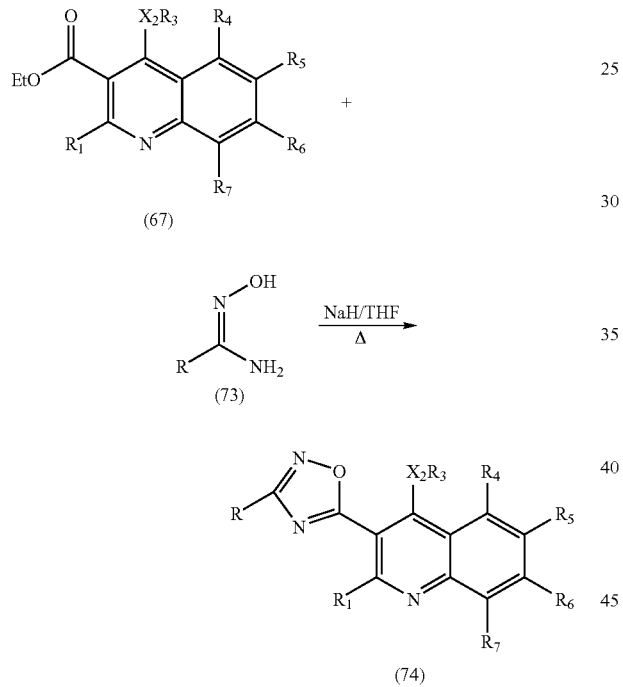

Compounds (77) can be prepared according to Scheme 23. The phenacylaniline (75), the preparation of which is described in Scheme 9, is treated with a 1,2-disulfonyl-alkene (76) in the presence of a base to provide a compound (77).

Scheme 23.

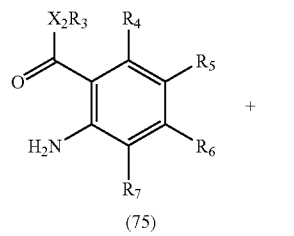
(75)

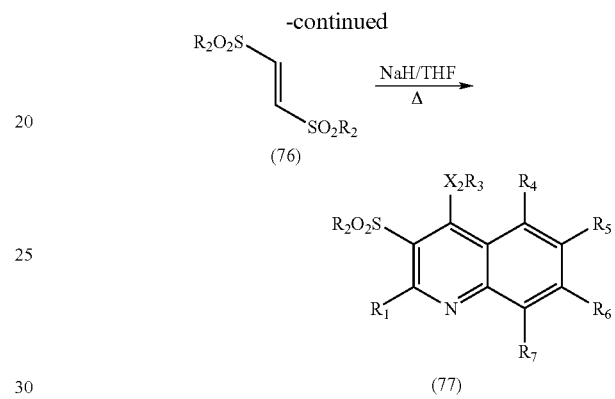
(77)

According to Scheme 24, certain compounds (79) are prepared by reaction of the aryl-halide (78) with a boronic acid reagent of formula $R_3B(OH)_2$ in the presence of a palladium catalyst.

If the R group of the compound (79) contains a carboxylic acid ester moiety, this moiety can be transformed to the carboxylic acid upon treatment with aqueous lithium, sodium or potassium hydroxide in a suitable organic solvent. If the R group of the compound (79) contains a $CH_2X'$ where $X'$ is a halogen Br or Cl, then this group can be transformed to $CH_2CN$ upon treatment with sodium cyanide in a suitable organic solvent. If the R group of the compound (79) contains a $CH_2CN$, then this group can be transformed to the tetrazole

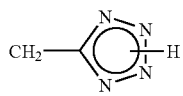

using standard conditions such as sodium in DMF at 125° C.

Scheme 24.

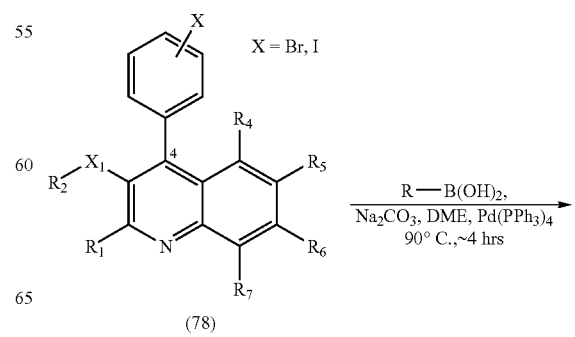
(78)

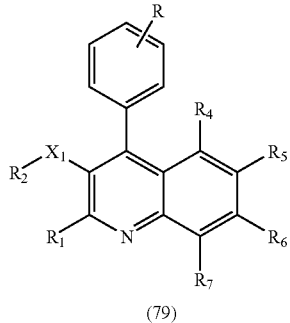

The compounds of formula (I) can also be prepared according to Scheme 25. Coupling an appropriate aryl bromide (80) in the presence of a palladium catalyst with trimethyl-tributylstannanylethynyl-silane followed by desilation provides the aryl-acetylene (81). The acetylene, (81) can be coupled with an appropriate aryl-halide (bromo or iodo) in the presence of a palladium catalyst to provide the diphenyl substituted acetylene (82). Modification of the acetylene linker is conveniently carried out using hydrogenation with heterogeneous catalysis to (83).

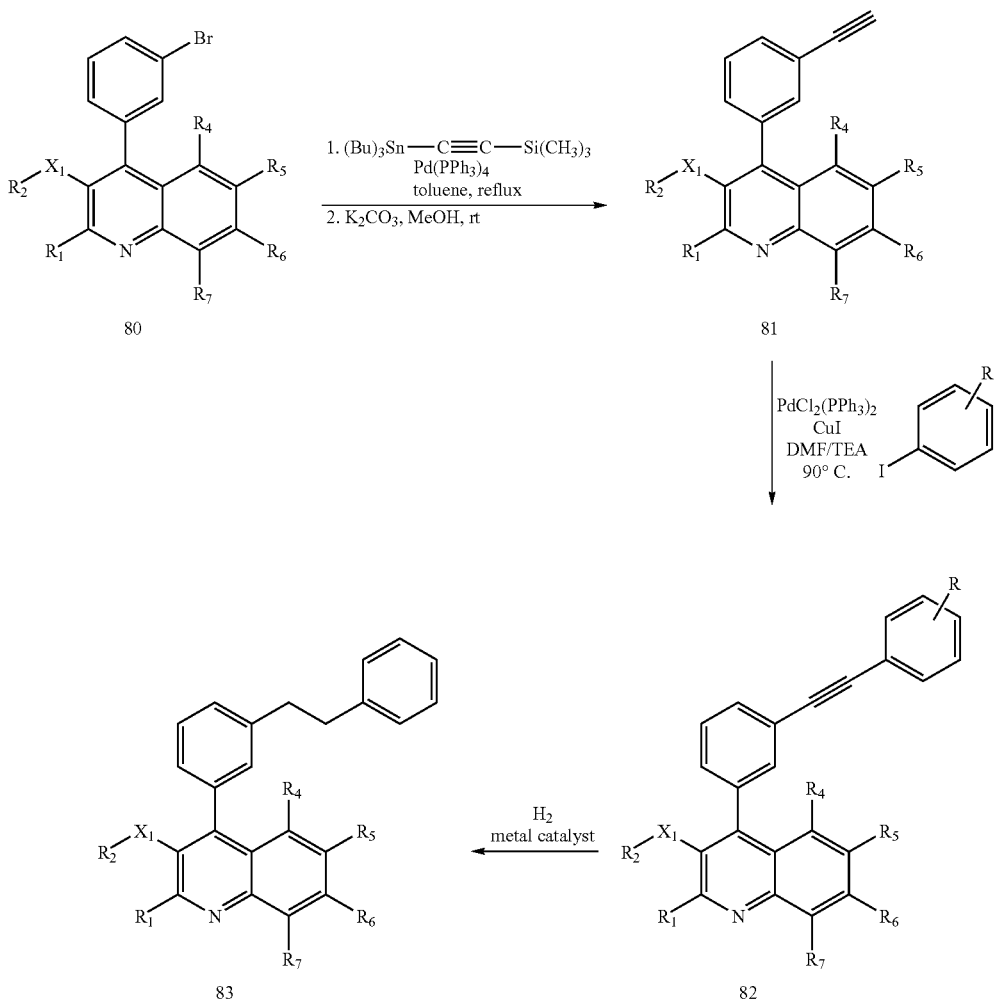

The compounds of formula (I) can also be prepared according to Scheme 26. Bromide 84 can be reacted with a 2-aryl or 2-heteroarylacetonitril of formula 85 in the presence of a base such as sodium hydride to afford compound 86. Compound 86 can be reacted with hydrobromic acid to remove the nitrile group and afford compound 87. Any substituents on the aryl or heteroaryl moiety of 87 can be further elaborated by any of the preceding procedures.

Scheme 26.

Representative compounds of this invention were evaluated in standard pharmacological test procedures which measured their affinity to bind to LXR and to upregulate the gene ABCA1, which causes cholesterol efflux from atherogenic cells, such as macrophages.

LXR activation is critical for maintaining cholesterol homeostasis, but its coincident regulation of fatty acid metabolism may lead to increased serum and hepatic triglyceride levels. Selective LXR modulators that activate cholesterol efflux with minimal impact on SREBP-1c expression and triglyceride synthesis in liver would be expected to reduce atherosclerotic risk with an improved therapeutic index and minimize the potential for deleterious effects on metabolic balance. A method is described herein for identifying selective LXR ligands with differential activity for regulating ABCA1 (ABCG1) vs. SREBP-1c.

Accordingly, LXR ligands were identified initially in cell-free LXR beta and LXR alpha competition binding assays. LXR ligands were further characterized by gene expression profiling for tissue selective gene regulation. Selective LXR modulators demonstrate agonist activity for ABCA1 transactivation but exhibit no effect or inhibition of SREBP-1c gene expression in differentiated THP-1 macrophages. Gene expression analysis in an antagonist mode was used to further delineate differential regulation of ABCA1 and SREBP-1c gene expression. In a competition assay with known potent synthetic LXR agonists, selective LXR ligands preferentially antagonize SREBP-1c activation (a marker for genes involved in cholesterol and fatty acid homeostasis) but have minimal or additive effects on ABCA1 gene expression or genes known to enhance HDL biogenesis. Cell type or tissue specificity may be further evaluated in additional cell lines, intestinal, CaCo2 or liver, HepG2 and Huh-7 cells where ABCA1 activity influences net cholesterol absorption and reverse cholesterol transport.

The test procedures performed, and results obtained are briefly described below.

Ligand-Binding Test Procedure for Human LXRβ.

Ligand-binding to the human LXRβ was demonstrated for representative compounds of this invention by the following procedure.

Materials and Methods:
Buffer: 100 mM KCl, 100 mM TRIS (pH 7.4 at +4° C.), 8.6% glycerol, 0.1 mM PMSF*, 2 mM MTG*, 0.2% CHAPS (* not used in wash buffer) Tracer: $^3$H T0901317
Receptor source: *E. coli* extracted from cells expressing biotinylated hLXRβ. Extract was made in a similar buffer as above, but with 50 mM TRIS.

Day 1
Washed streptavidin and coated flash plates with wash buffer.
Diluted receptor extract to give Bmax ~4000 cpm and add to the wells.
Wrapped the plates in aluminum foil and stored them at +4° C. over night.

Day 2
Made a dilution series in DMSO of the test ligands.
Made a 5 nM solution of the radioactive tracer in buffer.
Mixed 250 µl diluted tracer with 5 µl of the test ligand from each concentration of the dilution series.
Washed the receptor-coated flash plates.
Added 200 µl per well of the ligand/radiolabel mixture to the receptor-coated flash plates.
Wrapped the plates in aluminum foil and incubate at +4° C. over night.

Day 3
Aspirated wells, and washed the flashed plates. Sealed the plate.
Measured the remaining radioactivity in the plate.

Results:
Representative compounds of this invention had activity (IC50 values) in the LXRβ ligand binding assay in the range between 0.001 to 20 uM.

Quantitative Analysis of ABCA1 Gene Regulation in THP-1 Cells.

The compounds of formula (I) effect on the regulation of the ABCA1 gene was evaluated using the following procedure.

Materials and Methods
Cell culture: The THP-1 monocytic cell line (ATCC # TIB-202) was obtained from American Type Culture Collection (Manassas, Va.) and cultured in RPMI 1640 medium (Gibco, Carlsbad, Calif.) containing 10% FBS, 2 mM L-glutamine, and 55 uM beta-Mercaptoethanol (BME). Cells were plated in 96-well format at a density of $7.5 \times 10^4$ in complete medium containing 50-100 ng/ml phorbal 12,13-dibutyrate (Sigma, St. Louis, Mo.) for three days to induce differentiation into adherent macrophages. Differentiated THP-1 cells were treated with test compounds or ligands dissolved in DMSO (Sigma, D-8779) in culture medium lacking phorbal ester. Final concentrations of DMSO did not exceed 0.3% of the media volume. Dose response effects were measured in duplicate, in the range of 0.001 to 30 micromolar concentrations and treated cells were incubated for an additional 18 hrs prior to RNA isolation. Unstimulated cells treated with vehicle were included as negative controls on each plate. An LXR agonist reference, N-(2,2,2-Trifluoroethyl)-N-[4-(2,2,2-trifluoro-1-hydroxy-1-trifluoromethyl-ethyl)-phenyl]-benzenesulfonamide (Schultz, Joshua R., Genes & Development (2000), 14(22), 2831-2838), was dosed at 1.0 uM and served as a positive control. In antagonist mode, the compound under study is analyzed in the presence of 150 nM GW3965, trifluoromethyl-benzyl)-(2,2-diphenyl-ethyl)-amino]-propoxy]-phenyl)-acetic acid (Collins, J. L., J. Med. Chem. (2000), 45:1963-1966.). Results of antagonist analysis are expressed as % antagonism and IC50 (in µM).

RNA isolation and quantitation: Total cellular RNA was isolated from treated cells cultured in 96-well plates using PrepStation 6100 (Applied Biosystems, Foster City, Calif.), according to the manufacturer's recommendations. RNA was resuspended in ribonuclease-free water and stored at −70° C. prior to analysis. RNA concentrations were quantitated with RiboGreen test procedure, #R-11490 (Molecular Probes, Eugene, Oreg.).

Gene expression analysis: Gene-specific mRNA quantitation was performed by real-time PCR with the Perkin Elmer Corp. chemistry on an ABI Prism 7700 Sequence detection system (Applied Biosystems, Foster City, Calif.) according to the manufacturer's instructions. Samples (50-100 ng) of total RNA were assayed in duplicate or triplicate in 50 µl reactions using one-step RT-PCR and the standard curve method to estimate specific mRNA concentrations. Sequences of gene-specific primer and probe sets were designed with Primer Express Software (Applied Biosystems, Foster City, Calif.). The human ABCA1 primer and probe sequences are: forward, CMCATGMTGCCATTTTCCAA, reverse, ATAATC-CCCTGAACCCAAGGA, and probe, 6FAM-TAAAGC-CATGCCCTCTGCAGGAACA-TAMRA. RT and PCR reactions were performed according to PE Applied Biosystem's protocol for Taqman Gold RT-PCR or Qiagen's protocol for Quantitect probe RT-PCR. Relative levels of ABCA1 mRNA are normalized using GAPDH mRNA or 18S rRNA probe/primer sets purchased commercially (Applied Biosystems, Foster City, Calif.).

Statistics:

Mean, standard deviation and statistical significance of duplicate evaluations of RNA samples were assessed using ANOVA, one-way analysis of variance using SAS analysis.

Reagents:
GAPDH Probe and Primers—Taqman GAPDH Control Reagents 402869 or 4310884E
18S Ribosomal RNA—Taqman 18S Control Reagents 4308329
10 Pack Taqman PCR Core Reagent Kit 402930
Qiagen Quantitect probe RT-PCR 204443.

Results:

Representative compounds of this invention were shown to upregulate the transcription of the ABCA1 gene in THP-1 cells (EC50 value) in a range between 0.001 to 15 uM with efficacy values in the range of 20 to 250% when compared to the efficacy shown by 1.0 uM of the reference standard.

Quantitative Analysis of SREBP-1C Gene Regulation in THP-1 Cells.

The compounds of formula (II) effect on the regulation of the SREBP-1c gene was evaluated using the same procedure as described for ABCA1 however, a primer and probe set specific for human SREBP-1c was substituted in gene expression analysis. The human SREBP-1c primer and probe sequences are: forward, AGGGCGGGCGCAGAT, reverse, GGTTGTTGATAAGCTGMGCATGT, and probe, 6FAM-TCGAAAGTGCMTCCATGGCTCCG-TAMRA.

Based on the results obtained in the standard pharmacological test procedures, the compounds of this invention are useful in treating or inhibiting LXR mediated diseases. In particular, the compounds of this invention are useful in the treatment and inhibition of atherosclerosis and atherosclerotic lesions, lowering LDL cholesterol levels, increasing HDL cholesterol levels, increasing reverse cholesterol transport, inhibiting cholesterol absorption, treatment or inhibition of Alzheimer's disease, type I diabetes, type II diabetes, multiple sclerosis, rheumatoid arthritis, acute coronary syndrome, restenosis, inflammatory bowel disease (IBD), Crohn's disease, endometriosis, celiac, and thyroiditis.

Additionally, compounds of formula II having the structure,

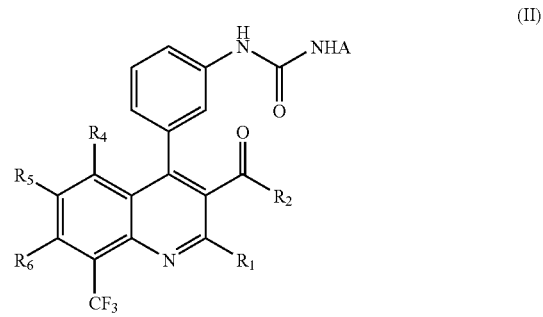

wherein
$R_1$ is —H or C1 to C3 alkyl;
$R_2$ is phenyl, or phenyl substituted independently by one or more of the groups independently selected from C1 to C3 alkyl, C1 to C3 alkoxy, C1 to C3 perfluoroalkyl, C1 to C3 alkyl substituted with 1 to 5 fluorines, halogen, —NO$_2$, —NR$_8$R$_9$, and —CN; or
A is phenyl, or phenyl substituted by one to four groups independently selected from halogen, C1 to C3 alkyl, acyl, C1 to C3 alkoxy, hydroxy, halogen, —CN, —NO$_2$, C1 to C3 perfluoroalkyl, and C1 to C3 alkyl substituted with 1 to 5 fluorines;
$R_8$ is —H, or C1 to C3 alkyl;
$R_9$ is —H, or C1 to C3 alkyl;
$R_4$, $R_5$, and $R_6$ are each independently —H or —F;

or a pharmaceutically acceptable salt thereof, are selective LXR modulators, as gene specific modulation in cell based assays showed agonist activity for ABCA1 and antagonist activity for SREBP-1c. In the agonist mode, selective LXR modulators exhibited≧20% efficacy for ABCA1 activation by LXR and little or no agonism for SREBP-1c (≦25% efficacy relative to reference). In the antagonist mode, selective compounds showed no antagonism of ABCA1 gene expression. There may be an additive effect on ABCA1 gene expression relative to reference ligands at their EC$_{50}$ concentration. In the antagonist mode, selective compounds inhibited agonist-mediated SREBP-1c gene expression in a dose dependent fashion.

It is understood that the effective dosage of the active compounds of this invention may vary depending upon the particular compound utilized, the mode of administration, the condition, and severity thereof, of the condition being treated, as well as the various physical factors related to the individual being treated. It is projected that compounds of this invention will be administered at an oral daily dosage of from about 0.05 mg to about 30 mg per kilogram of body weight, preferably administered in divided doses two to six times per day, or in a sustained release form, and may be adjusted to provide the optimal therapeutic result.

The compounds of this invention can be formulated neat or with a pharmaceutical carrier for administration, the proportion of which is determined by the solubility and chemical nature of the compound, chosen route of administration and standard pharmacological practice. The pharmaceutical carrier may be solid or liquid.

A solid carrier can include one or more substances which may also act as flavoring agents, sweetening agents, lubricants, solubilizers, suspending agents, fillers, glidants, compression aids, binders, or tablet-disintegrating agents; it can also be an encapsulating material. In powders, the carrier is a finely divided solid which is in admixture with the finely divided active ingredient.

Solid dosage unit forms or compositions such as tablets, troches, pills, capsules, powders, and the like, may contain a solid carrier binder such as gum tragacanth, acacia, corn starch or gelatin; excipients such as dicalcium phosphate; a disintegrating agent such as corn starch, potato starch, alginic acid; a lubricant such as magnesium stearate; and a sweetening agent such as sucrose, lactose, or saccharin. When a dosage unit form is a capsule, it may contain, in addition to materials of the above type, a liquid carrier such as a fatty oil. Various other materials may be present as coatings or to modify the physical form of the dosage unit. For instance, tablets may be coated with shellac, sugar or both.

Liquid carriers are used in preparing liquid dosage forms such as solutions, suspensions, dispersions, emulsions, syrups, elixirs and pressurized compositions. The active ingredient can be dissolved or suspended in a pharmaceutically acceptable liquid carrier such as water, an organic solvent, a mixture of both, or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmoregulators. Suitable examples of liquid carriers for oral and parenteral administration include water (partially containing additives as above, e.g. cellulose derivatives, preferably sodium carboxymethyl cellulose solution); alcohols, including monohydric alcohols such as ethanol and polyhydric alcohols such as glycols and their derivatives; lethicins, and oils such as fractionated coconut oil and arachis oil. For parenteral administration, the liquid carrier can also be an oily ester such as ethyl oleate and isopropyl myristate. Sterile liquid carriers are useful in sterile liquid form compositions for parenteral administration. The liquid carrier for pressurized compositions can be a halogenated hydrocarbon or other pharmaceutically acceptable propellant.

A liquid pharmaceutical composition such as a syrup or elixir may contain, in addition to one or more liquid carriers and the active ingredients, a sweetening agent such as sucrose, preservatives such as methyl and propyl parabens, a pharmaceutically acceptable dye or coloring agent, or a flavoring agent such as cherry or orange flavoring.

Liquid pharmaceutical compositions which are sterile solutions or suspensions can be administered intraocularly or parenterally, for example, by intramuscular, intraperitoneal or subcutaneous injection. Sterile solutions can also be administered intravenously. The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy injectability exists. It must be stable under the conditions of manufacture and storage and must be preserved against the contaminating action of microorganisms such as bacteria and fungi. The carrier can be a solvent or dispersion medium containing a liquid carrier, for example, water, ethanol, polyol (e.g. glycerol, propylene glycol and liquid polyethylene glycol), suitable mixtures thereof, and vegetable oils. The liquid carrier may be suitably mixed with a surfactant such as hydroxypropylcellulose.

The compounds of the present invention may also be administered rectally or vaginally in the form of a conventional suppository. For administration by intranasal or intrabronchial inhalation or insufflation, the compounds of this invention may be formulated into an aqueous or partially aqueous solution, which can then be utilized in the form of an aerosol. The compounds of this invention may be administered topically, or also transdermally through the use of a transdermal patch containing the active compound and a carrier that is inert to the active compound, which is non toxic to the skin, and allows delivery of the agent for systemic absorption into the blood stream via the skin. The carrier may take any number of forms such as creams and ointments, pastes, gels, and occlusive devices. The creams and ointments may be viscous liquid or semisolid emulsions of either the oil-in-water or water-in-oil type. Pastes comprised of absorptive powders dispersed in petroleum or hydrophilic petroleum containing the active ingredient may also be suitable. A variety of occlusive devices may be used to release the active ingredient into the blood stream such as a semipermeable membrane covering a reservoir containing the active ingredient with or without a carrier, or a matrix containing the active ingredient. Other occlusive devices are known in the literature.

The following describes the preparation of representative compounds of this invention. Compounds described as homogeneous were determined to be of 90% or greater purity (exclusive of enantiomers) by analytical reverse phase chromatographic analysis with 254 nM UV detection. Melting points are reported as uncorrected in degrees centigrade. The infrared data is reported as wave numbers at maximum absorption, $v_{max}$, in reciprocal centimeters, $cm^{-1}$. Mass spectral data is reported as the mass-to-charge ratio, m/z; and for high resolution mass spectral data, the calculated and experimentally found masses, $[M+H]^+$, for the neutral formulae M are reported. Nuclear magnetic resonance data is reported as δ in parts per million (ppm) downfield from the standard, tetramethylsilane; along with the solvent, nucleus, and field strength parameters. The spin-spin homonuclear coupling constants are reported as J values in hertz; and the multiplicities are reported as a: s, singlet; d, doublet; t, triplet; q, quartet; quintet; or br, broadened.

EXAMPLE 1

PHENYL[4-PHENYL-8-(TRIFLUOROMETHYL) QUINOLIN-3-YL]METHANONE

1) Preparation of Diethyl 2-({[2-(trifluoromethyl)phenyl]amino}methylene)malonate.

Diethyl ethoxymethylenemalonate (compound III, 50.4 mL, 249.3 mmol) and 2-(Trifluoromethyl)aniline (compound II, 31 mL, 249.3 mmol) was taken into toluene (250 mL) and refluxed overnight twice. Toluene was evaporated and the resulting liquid was taken into hexane and allowed to sit in a freezer for 1 hour. A white solid crashed out and was filtered and dried to yield 69.73 g (84.4%) of the title compound as white crystals. MS ESI (m/z) 332 ([M+H]$^+$); MS ESI (m/z) 330 ([M−H]$^−$); Anal Calcd. For $C_{15}H_{16}F_3NO_4$: C, 54.38; H, 4.87; N, 4.23. Found: C, 54.49; H, 4.68; N, 4.06.

2) Preparation of 4-Hydroxy-8-(trifluoromethyl)-3-quinolinecarboxylic acid ethyl ester.

Diethyl 2-({[2-(trifluoromethyl)phenyl]amino}methylene)malonate (compound of formula (IV)), 69.73 g, 210.5 mmol) was taken into Dowtherm A (350 mL) and brought to reflux (~250° C.) with the removal of ethanol that was formed during the reaction for 45 min. The reaction was allowed to cool to approximately 100° C. then carefully poured into hexane (1 L) and allowed to cool overnight. A white solid precipitated which was filtered and dried to afford the title compound as a white solid (55.04 g, 91.7%). MS ESI (m/z) 286 ([M+H]$^+$); MS ESI (m/z) 284 ([M−H]$^−$).

3) Preparation of 4-Chloro-8-(trifluoromethyl)-3-quinolinecarboxylic acid ethyl ester.

4-Hydroxy-8-(trifluoromethyl)-3-quinolinecarboxylic acid ethyl ester (compound of formula (V)), 11.27 g, 39.55 mmol) was taken into toluene (125 mL), then POCl$_3$ (7.4 mL, 79.08 mmol) was added and the mixture was refluxed for 1.5 hours. The reaction was carefully poured into ice-water with vigorous stirring, then added carefully added saturated NaHCO$_3$ until the solution was neutral. Dilute with ethyl acetate and separate the layers. The organic layer was dried over MgSO$_4$, filtered and concentrated. The resulting material was passed through a short silica gel plug using 10% ethyl acetate in hexane. Concentration and drying under high vacuum yielded 9.93 g of the title compound as a white solid.

4) Preparation of [4-Chloro-8-(trifluoromethyl)quinolin-3-yl](phenyl)methanone.

4-Chloro-8-(trifluoromethyl)-3-quinolinecarboxylic acid ethyl ester (compound of formula (VI)), 3.0 g, 9.87 mmol) was taken into THF (40 mL) and cooled to −78° C. Phenyllithium (6.6 mL, 11.85 mmol, 1.8 M solution in cyclohexane-ether 70:30) was added dropwise and stirred at −78° C. for 4 hours. The reaction was poured into water/saturated ammonium chloride solution and extracted with ethyl acetate. The combined organics was dried over MgSO$_4$ and concentrated. The material was purified via column chromatography using 5% ethyl actetate in hexane as the eluent to yield 1.7 g of material that was comprised of both the starting material and product. Therefore, this material was taken into hexane and heated, then added a minimal amount of ethyl acetate to dissolve the solid. The mixture was allowed to cool overnight where a solid precipitated. The solvent was decanted to leave 0.599 g of the title compound as a yellowish white solid. MS ESI (m/z) 336/338 ([M+H]$^+$); Anal. Calcd. For $C_{17}H_9ClF_3NO$: C, 60.82; H, 2.70; N, 4.17. Found: C, 60.48; H, 2.60; N, 4.02.

5) Preparation of Phenyl[4-phenyl-8-(trifluoromethyl)quinolin-3-yl]methanone.

[4-Chloro-8-(trifluoromethyl)quinolin-3-yl](phenyl)methanone (compound of formula (VII)), 0.050 g, 0.15 mmol) was taken into toluene/EtOH (3 mL/0.5 mL). Then phenylboronic acid (0.30 mmol) was added followed by 2 M Na$_2$CO$_3$ (0.25 mL, 0.5 mmol) and finally Pd(PPh$_3$)$_4$ (0.009 g, 0.0075 mmol). The reaction was heated at 90° C. for 4 hours. The solvent was removed and the resulting material was purified via column chromatography using 5% ethyl acetate in hexane to elute out 0.043 g of the title compound: MS (ESI) m/z 378 ([M+H]$^+$); Anal. Calcd for $C_{23}H_{14}F_3NO$: C, 73.21; H, 3.74; N, 3.71. Found: C, 72.16; H, 3.77; N, 3.69.

EXAMPLE 2

[4-(4-METHOXYPHENYL)-8-(TRIFLUOROMETHYL)QUINOLIN-3-YL](PHENYL) METHANONE

This compound was prepared according to the procedure of Example 1 step 5, substituting 4-methoxyphenylboronic acid for phenyl boronic acid. MS (ESI) m/z 408 ([M+H]$^+$).

EXAMPLE 3

[[4-(4-HYDROXYPHENYL)-8-(TRIFLUOROMETHYL)QUINOLIN-3-YL](PHENYL) METHANONE

This compound was prepared according to the procedure of Example 1 step 5, substituting 4-hydroxyphenylboronic acid for phenyl boronic acid. MS (ESI) m/z 394 ([M+H]$^+$); MS (ESI) m/z 392 ([M−H]$^−$); Anal. Calcd for $C_{23}H_{14}F_3NO_2$: C, 70.23; H, 3.59; N, 3.56. Found: C, 69.56; H, 3.74; N, 3.41.

EXAMPLE 4

[4-(4-METHYLPHENYL)-8-(TRIFLUOROMETHYL)QUINOLIN-3-YL](PHENYL)METHANONE

This compound was prepared according to the procedure of Example 1 step 5, substituting 4-methylphenylboronic acid for phenyl boronic acid MS (ESI) m/z 392 ([M+H]$^+$); Anal. Calcd for $C_{24}H_{16}F_3NO$: C, 73.65; H, 4.12; N, 3.58. Found: C, 72.83; H, 4.46; N, 3.45.

EXAMPLE 5

[4-(3,4-DIMETHOXYPHENYL)-8-(TRIFLUOROMETHYL)QUINOLIN-3-YL](PHENYL) METHANONE

This compound was prepared according to the procedure of Example 1 step 5, substituting 3,4-dimethoxyphenylboronic acid for phenyl boronic acid. MS (ESI) m/z 438 ([M+H]$^+$); Anal. Calcd for $C_{25}H_{18}F_3NO_3 \cdot 0.3H_2O$: C, 67.81; H, 4.23; N, 3.16. Found: C, 67.85; H, 4.20; N, 2.90.

EXAMPLE 6

[4-(2,6-DIMETHOXYPHENYL)-8-(TRIFLUOROMETHYL)QUINOLIN-3-YL](PHENYL) METHANONE

This compound was prepared according to the procedure of Example 1 step 5, substituting 2,3-dimethoxyphenylboronic acid for phenyl boronic acid MS (ESI) m/z 438 ([M+H]$^+$); Anal. Calcd for $C_{25}H_{18}F_3NO_3 \cdot 0.25H_2O$: C, 67.95; H, 4.22; N, 3.17. Found: C, 67.97; H, 3.98; N, 3.09.

EXAMPLE 7

1-{2-[3-BENZOYL-8-(TRIFLUOROMETHYL) QUINOLIN-4-YL]PHENYL}ETHANONE

This compound was prepared according to the procedure of Example 1 step 5, substituting 2-acetylphenylboronic acid for phenyl boronic acid. MS (ESI) m/z 420 ([M+H]$^+$); Anal.

Calcd for $C_{25}H_{16}F_3NO_2.0.2H_2O$: C, 70.99; H, 3.91; N, 3.31. Found: C, 70.89; H, 3.68; N, 3.25.

EXAMPLE 8

[4-(4-CHLOROPHENYL)-8-(TRIFLUOROMETHYL)QUINOLIN-3-YL](PHENYL) METHANONE

This compound was prepared according to the procedure of Example 1 step 5, substituting 4-chlorophenylboronic acid for phenyl boronic acid. MS (ESI) m/z 412/414 ([M+H]$^+$). $^1$H NMR (CDCl$_3$) δ 9.12 (s, 1H), 8.19 (d, J=7.36 Hz, 1H), 7.92 (d, J=8.45 Hz, 1H), 7.64 (m, 2H), 7.52 (d, J=7.74 Hz, 2H), 7.28 (m, 6H).

EXAMPLE 9

[4-(1,1'-BIPHENYL-4-YL)-8-(TRIFLUOROMETHYL)QUINOLIN-3-YL](PHENYL) METHANONE

This compound was prepared according to the procedure of Example 1 step 5, substituting 4-(phenyl)phenylboronic acid for phenyl boronic acid. MS (ESI) m/z 454 ([M+H]$^+$); Anal. Calcd for $C_{29}H_{18}F_3NO.0.65H_2O$: C, 74.88; H, 4.18; N, 3.01. Found: C, 74.82; H, 4.09; N, 2.88.

EXAMPLE 10

PHENYL{8-(TRIFLUOROMETHYL)-4-[3-(TRIFLUOROMETHYL)PHENYL]QUINOLIN-3-YL}METHANONE

This compound was prepared according to the procedure of Example 1 step 5, substituting 3-trifluoromethylphenylboronic acid for phenyl boronic acid MS (ESI) m/z 446 ([M+H]$^+$); Anal. Calcd for $C_{24}H_{13}F_6NO.0.3H_2O$: C, 63.95; H, 3.04; N, 3.11. Found: C, 63.96; H, 3.14; N, 2.68.

EXAMPLE 11

[4-PHENYL-8-(TRIFLUOROMETHYL)QUINOLIN-3-YL](PYRIDIN-2-YL)METHANONE

1) Preparation of (4-Chloro-8-trifluoromethyl-quinolin-3-yl)-pyridin-2-yl-methanone.

2-Bromopyridine (0.74 mL, 7.90 mmol) was taken into THF (30 mL) and cooled to −78° C. Then BuLi (4.8 mL, 7.90 mmol, 1.6 M solution in hexane) was added dropwise and then stirred for 30 minutes. Next, 4-Chloro-8-(trifluoromethyl)-3-quinolinecarboxylic acid ethyl ester (2.0 g, 6.58 mmol) in THF (10 mL) was added rapidly and stirred at −78° C. for 4 hours. The reaction was poured into water/saturated NH$_4$Cl solution and then extracted with ethyl acetate. The organic layer was dried over MgSO$_4$, filtered and concentrated. The resulting material was purified via column chromatography using 15% ethyl acetate in hexane as the eluent to yield 0.823 g of (4-chloro-8-trifluoromethyl-quinolin-3-yl)-pyridin-2-yl-methanone as a yellow solid.

2) Preparation of [4-phenyl-8-(trifluoromethyl)quinolin-3-yl](pyridin-2-yl)methanone.

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone. MS (ESI) m/z 379 ([M+H]$^+$); Anal. Calcd for $C_{22}H_{13}F_3N_2O.0.1H_2O$: C, 69.51; H, 3.50; N, 7.37. Found: C, 69.39; H, 3.27; N, 7.27.

EXAMPLE 12

[4-(4-METHYLPHENYL)-8-(TRIFLUOROMETHYL)QUINOLIN-3-YL](PYRIDIN-2-YL) METHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 4-methylphenylboronic acid in place of phenyl boronic acid. MS (ESI) m/z 393 ([M+H]$^+$); Anal. Calcd for $C_{23}H_{15}F_3N_2O.0.2H_2O$: C, 69.76; H, 3.92; N, 7.07. Found: C, 69.73; H, 3.79; N, 6.99.

EXAMPLE 13

[4-(1,1'-BIPHENYL-4-YL)-8-(TRIFLUOROMETHYL)QUINOLIN-3-YL](PYRIDIN-2-YL) METHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 4-(phenyl)phenylboronic acid in place of phenyl boronic acid. MS (ESI) m/z 455 ([M+H]$^+$); Anal. Calcd for $C_{28}H_{17}F_3N_2O$: C, 74.00; H, 3.77; N, 6.16. Found: C, 73.99; H, 3.81; N, 5.92.

EXAMPLE 14

PYRIDIN-2-YL{8-(TRIFLUOROMETHYL)-4-[3-(TRIFLUOROMETHYL)PHENYL]QUINOLIN-3-YL}METHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 3-trifluoromethylphenylboronic acid in place of phenyl boronic acid. MS (ESI) m/z 447 ([M+H]$^+$); Anal. Calcd for $C_{23}H_{12}F_6N_2O$: C, 61.89; H, 2.71; N, 6.28. Found: C, 61.70; H, 2.66; N, 6.14.

EXAMPLE 15

[4-(3,4-DIMETHOXYPHENYL)-8-(TRIFLUOROMETHYL)QUINOLIN-3-YL](PYRIDIN-2-YL) METHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 3,4-diphenthoxyphenylboronic acid in place of phenyl boronic acid. MS (ESI) m/z 439 ([M+H]$^+$); Anal. Calcd for $C_{24}H_{17}F_3N_2O_3.0.15H_2O$: C, 65.35; H, 3.95; N, 6.35. Found: C, 65.20; H, 3.79; N, 6.33.

EXAMPLE 16

[4-(4-CHLOROPHENYL)-8-(TRIFLUOROMETHYL)QUINOLIN-3-YL](PYRIDIN-2-YL) METHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 4-chlorophenylboronic acid in place of phenyl boronic acid; MS (ESI) m/z 413/415 ([M+H]+); Anal. Calcd for $C_{22}H_{12}ClF_3N_2O$: C, 64.01; H, 2.93; N, 6.79. Found: C, 63.66; H, 3.03; N, 6.60.

EXAMPLE 17

[4-(3,4-DICHLOROPHENYL)-8-(TRIFLUOROMETHYL)QUINOLIN-3-YL](PYRIDIN-2-YL)METHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 3,4-dichlorophenylboronic acid in place of phenyl boronic acid. MS (ESI) m/z 447/449/451 ([M+H]+); $^1$H NMR (CDCl$_3$) δ 9.22 (s, 1H), 8.52 (d, J=4.6 Hz, 1H), 8.18 (d, J=7.21 Hz, 1H), 7.96 (d, J=7.83 Hz, 1H), 7.84 (m, 2H), 7.61 (m, 1H), 7.42 (m, 3H), 7.13 (dd, J=8.25 and 1.97 Hz, 1H).

EXAMPLE 18

[4-(4-TERT-BUTYLPHENYL)-8-(TRIFLUOROMETHYL)QUINOLIN-3-YL](PYRIDIN-2-YL)METHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 4-t-butylphenylboronic acid in place of phenyl boronic acid. MS (ESI) m/z 435 ([M+H]+); Anal. Calcd for $C_{26}H_{21}F_3N_2O$: C, 71.88; H, 4.87; N, 6.45. Found: C, 71.51; H, 5.09; N, 6.22.

EXAMPLE 19

1-{2-[3-(PYRIDIN-2-YLCARBONYL)-8-(TRIFLUOROMETHYL)QUINOLIN-4-YL]PHENYL}ETHANONE

This compound was prepared using the procedure of Example 1, step 5 using (4-chloro-8-trifluoromethyl-quinolin-3-yl)-pyridin-2-yl-methanone in place of [4-chloro-8-(trifluoromethyl)quinolin-3-yl](phenyl)methanone and 2-acetylphenylboronic acid in place of phenyl boronic acid. MS (ESI) m/z 421 ([M+H]+); $^1$H NMR (CDCl$_3$) δ 9.24 (s, 1H), 8.63 (d, J=4.16 Hz, 1H), 8.13 (d, J=7.03 Hz, 1H), 7.93 (m, 2H), 7.81 (m, 1H), 7.51 (m, 5H), 7.18 (m, 1H), 2.41 (s, 3H).

EXAMPLE 20

(2-METHOXYPHENYL)[4-PHENYL-8-(TRIFLUOROMETHYL)QUINOLIN-3-YL]METHANONE

1) Preparation of Ethyl 8-(trifluoromethyl)-4-{[(trifluoromethyl)sulfonyl]oxy}quinoline-3-carboxylate.

4-Hydroxy-8-(trifluoromethyl)-3-quinolinecarboxylic acid ethyl ester (49.71 g, 174.3 mmol) was taken into CH$_2$Cl$_2$ (500 mL) then trifluoromethanesulfonic anhydride (54.1 g, 191.73 mmol) was added. Next, the mixture was cooled to 0° C. where triethylamine was added dropwise via an addition funnel. After triethylamine was added the reaction was allowed to stir for 30 minutes. The reaction was quenched with water and extracted with methylene chloride. The combined organics were washed with 5% HCl and brine. Then dried over magnesium sulfate and filtered through a short silica gel plug using methylene chloride as the eluent. Concentration afforded ethyl 8-(trifluoromethyl)-4-{[(trifluoromethyl)sulfonyl]oxy}quinoline-3-carboxylate as a tan solid (70.98 g, 97.6%). MS (ESI) m/z 418 ([M+H]+); Anal. Calcd for $C_{14}H_9F_6NO_5S$: C, 40.30; H, 2.17; N, 3.36. Found: C, 40.42; H, 1.97; N, 3.29.

2) Preparation of Ethyl 4-phenyl-8-(trifluoromethyl)quinoline-3-carboxylate.

Ethyl 8-(trifluoromethyl)-4-{[(trifluoromethyl)sulfonyl]oxy}quinoline-3-carboxylate (45.6 g, 109.3 mmol) was taken into dioxane (500 mL). Then phenylboronic acid (26.7 g, 218.6 mmol), K$_3$PO$_4$ (69.6 g, 327.9 mmol) and Pd(PPh$_3$)$_4$ (6.3 g, 5.5 mmol) was added and the reaction was brought to reflux for 1 hour. The reaction was filtered through Celite was still warm and concentrated. The resulting material was passed through a short silica gel plug and concentrated to yield the desired product as a brown viscous liquid (35.96 g). MS (ESI) m/z 346 ([M+H]+).

3) Preparation of 4-Phenyl-8-(trifluoromethyl)quinoline-3-carboxylic acid.

Ethyl 4-phenyl-8-(trifluoromethyl)quinoline-3-carboxylate (35.96 g, 104.14 mmol) was taken into THF/MeOH (300 mL of 1:1 mixture) along with 2 M NaOH (200 mL) and heated at 70° C. for 20 minutes. The organics were removed and the remaining aqueous layer was cooled to 0° C. and acidified with concentrated HCl. The mixture was concentrated and the resulting material was passed through a silica gel column using CH$_2$Cl$_2$, then 20% MeOH in CH$_2$Cl$_2$. The fractions were combined and the volume was reduced and then diluted to twice the volume with hexane and placed in a freezer overnight. A solid precipitated which was filtered and dried to yield the carboxylic acid as a brown solid (14.03 g). MS (ESI) m/z 318 ([M+H]+); MS (ESI) m/z 316 ([M−H]−).

4) Preparation of N-Methoxy-N-methyl-4-phenyl-8-(trifluoromethyl)quinoline-3-carboxamide.

4-Phenyl-8-(trifluoromethyl)quinoline-3-carboxylic acid (6.19 g, 19.51 mmol) was taken into DMF (75 mL) and cooled to 0° C. Then PyBOP (10.66 g, 20.49 mmol) was added followed by N,O-dimethylhydroxylamine hydrochloride (2.09 g, 21.46 mmol) and diisopropylethylamine (8.50 mL, 48.78 mmol). The reaction was stirred for 3 hours allowing to warm to room temperature during that time. The reaction was poured into water and extracted with ethyl acetate. The combined organics was washed with water, half-saturated brine and then dried over magnesium sulfate. Purification was carried out via column chromatography using 30% ethyl acetate in hexane as the eluent to yield the desired compound as a white solid (6.37 g, 90.6%). MS (ESI) m/z 361 ([M+H]+); Anal. Calcd for $C_{19}H_{15}F_3N_2O_2$·0.15H$_2$O: C, 62.86; H, 4.25; N, 7.72. Found: C, 62.89; H, 4.14; N, 7.55.

5) Preparation of (2-Methoxyphenyl)[4-phenyl-8-(trifluoromethyl)quinolin-3-yl]methanone. N-Methoxy-N-methyl-4-phenyl-8-(trifluoromethyl)quinoline-3-carboxamide (0.100 g, 0.278 mmol) was taken into THF (3 mL) and cooled to −78° C. where 2-methoxyphenylmagnesium bromide (0.833 mL, 0.833 mmol, 1.0 M solution in THF) was added and stirred for 10 minutes. Then the reaction was stirred for 1 hour at 0° C., then for 1 hour at room temperature (added an additional 0.5 mL of 2-methoxyphenylmagnesium bromide before room temperature reaction). The reaction was quenched with MeOH and 2 M HCl. The organics were removed and the resulting aqueous mixture was extracted with methylene chloride, dried over magnesium sulfate and concentrated. The resulting material was purified via column chromatography using 15% ethyl acetate in hexane as the eluent to afford 0.0315 g of the desired product. MS (ESI) m/z 408 ([M+H]$^+$); Anal. Calcd. for $C_{24}H_{16}F_3NO_2$: C, 70.76; H, 3.96; N, 3.44. Found: C, 70.76; H, 4.15; N, 3.22.

EXAMPLE 21

(2-METHYLPHENYL)[4-PHENYL-8-(TRIFLUOROMETHYL)QUINOLIN-3-YL]METHANONE

N-Methoxy-N-methyl-4-phenyl-8-(trifluoromethyl)quinoline-3-carboxamide (0.100 g, 0.278 mmol) was taken into THF (3 mL) and cooled to 0° C. where 2-methylphenylmagnesium bromide was added. The reaction was then allowed to stir at room temperature overnight. The reaction was quenched with MeOH and 2 M HCl and stirred for 5 minutes. The organics were removed and the resulting aqueous layer was extracted with methylene chloride, dried and concentrated. Column chromatography using 10% ethyl acetate in hexane afforded 0.057 g of the desired product as a white solid. MS (ESI) m/z 392 ([M+H]$^+$); Anal. Calcd. for $C_{24}H_{16}F_3NO$: C, 73.65; H, 4.12; N, 3.58. Found: C, 73.88; H, 3.87; N, 3.29.

EXAMPLE 22

(4-METHYLPHENYL)[4-PHENYL-8-(TRIFLUOROMETHYL)QUINOLIN-3-YL]METHANONE

This compound was prepared using the procedure of Example 21 substituting 4-methylphenylmagnesium bromide for 2-methylphenylmagnesium bromide. MS (ESI) m/z 392 ([M+H]$^+$); Anal. Calcd. for $C_{24}H_{16}F_3NO$: C, 73.65; H, 4.12; N, 3.58. Found: C, 73.52; H, 4.06; N, 3.32.

EXAMPLE 23

[4-PHENYL-8-(TRIFLUOROMETHYL)QUINOLIN-3-YL](PYRIDIN-3-YL)METHANONE

This compound was prepared using the procedure of Example 21 substituting 3-pyridylmagnesium bromide for 2-methylphenylmagnesium bromide. MS (ESI) m/z 379 ([M+H]$^+$); Anal. Calcd for $C_{22}H_{13}F_3N_2O$: C, 69.84; H, 3.46; N, 7.40. Found: C, 69.51; H, 3.52; N, 7.27.

EXAMPLE 24

(3-ETHYLPHENYL)[4-PHENYL-8-(TRIFLUOROMETHYL)QUINOLIN-3-YL]METHANONE

This compound was prepared using the procedure of Example 21 substituting 3-ethylphenylmagnesium bromide for 2-methylphenylmagnesium bromide. The HCl salt was further prepared using HCl in ether. MS (ESI) m/z 406 ([M+H]$^+$); $^1$H NMR (acetone-d$_6$) δ 9.23 (s, 1H), 8.40 (d, J=7.2 Hz, 1H), 8.12 (d, J=8.3 Hz, 1H), 7.88 (m, 1H), 7.53 (m, 2H), 7.39 (s, 6H), 7.29 (m, 1H), 2.60 (q, J=7.5 Hz, 2H), 1.14 (t, J=7.5 Hz, 3H).

EXAMPLE 25

[4-PHENYL-8-(TRIFLUOROMETHYL)QUINOLIN-3-YL](3-PROPYLPHENYL)METHANONE

This compound was prepared using the procedure of Example 21 substituting 3-propylphenylmagnesium bromide for 2-methylphenylmagnesium bromide. The HCl salt was further prepared using HCl in ether. MS (ESI) m/z 420 ([M+H]$^+$); Anal. Calcd for $C_{26}H_{20}F_3NO.HCl$ 1.6$H_2O$: C, 64.43; H, 5.03; N, 2.89. Found: C, 64.34; H, 4.67; N, 2.73.

EXAMPLE 26

(2,4-DIMETHYLPHENYL)[4-PHENYL-8-(TRIFLUOROMETHYL)QUINOLIN-3-YL]METHANONE

This compound was prepared using the procedure of Example 21 substituting 3,4-dimethylphenylmagnesium bromide for 2-methylphenylmagnesium bromide. MS (ESI) m/z 406 ([M+H]$^+$); Anal. Calcd. for $C_{25}H_{18}F_3NO$: C, 74.07; H, 4.48; N, 3.45. Found: C, 74.1; H, 4.65; N, 3.33.

EXAMPLE 27

(3-METHOXYPHENYL)[4-PHENYL-8-(TRIFLUOROMETHYL)QUINOLIN-3-YL]METHANONE

This compound was prepared using the procedure of Example 21 substituting 3-methoxyphenylmagnesium bromide for 2-methylphenylmagnesium bromide. MS (ESI) m/z 408 ([M+H]$^+$); Anal. Calcd for $C_{24}H_{16}F_3NO_2$: C, 70.76; H, 3.96; N, 3.44. Found: C, 70.70; H, 3.90; N, 3.27.

EXAMPLE 28

[4-PHENYL-8-(TRIFLUOROMETHYL)QUINOLIN-3-YL](THIEN-2-YL)METHANONE

This compound was prepared using the procedure of Example 21 substituting 2-thienylmagnesium bromide for 2-methylphenylmagnesium bromide.
MS (ESI) m/z 384 ([M+H]$^+$); Anal. Calcd for $C_{21}H_{12}F_3NOS$: C, 65.79; H, 3.15; N, 3.65. Found: C, 65.75; H, 2.94; N, 3.59.

EXAMPLE 29

[4-PHENYL-8-(TRIFLUOROMETHYL)QUINOLIN-3-YL](THIEN-3-YL)METHANONE

This compound was prepared using the procedure of Example 21 substituting 3-thienylmagnesium bromide for 2-methylphenylmagnesium bromide.
MS (ESI) m/z 384 ([M+H]$^+$); Anal. Calcd. for $C_{21}H_{12}F_3NOS$: C, 65.79; H, 3.15; N, 3.65. Found: C, 65.52; H, 3.01; N, 3.47.

EXAMPLE 30

(3-METHYLPHENYL)[4-PHENYL-8-(TRIFLUOROMETHYL)QUINOLIN-3-YL]METHANONE

3-Bromotoluene (0.078 mL, 0.64 mmol) was taken into THF (3 mL) and cooled to −78° C. Next, BuLi (0.32 mL of a 2.0 M Solution, 0.64 mmol) was added dropwise and then stirred for 30 minutes. Next, N-methoxy-N-methyl-4-phenyl-8-(trifluoromethyl)quinoline-3-carboxamide (0.231 g, 0.64 mmol) in THF (2 mL) was added quickly via syringe and allowed to stir overnight. MeOH and 2 N HCl were added and stirred for 5 minutes. Then the mixture was extracted with ethyl acetate and dried over magnesium sulfate and concentrated. The resulting material was purified via column chromatography using 10% ethyl acetate in hexane as the eluent to afford 0.060 g of desired product as an off white solid. MS (ESI) m/z 392 ([M+H]$^+$); Anal. Calcd. for $C_{24}H_{16}F_3NO$: C, 73.65; H, 4.12; N, 3.58. Found: C, 73.34; H, 4.08; N, 3.31.

EXAMPLE 31

3-BENZYL-4-PHENYL-8-(TRIFLUOROMETHYL) QUINOLINE

Phenyl[4-phenyl-8-(trifluoromethyl)quinolin-3-yl]methanone (Example 1, 0.244 g, 0.65 mmol) was taken into ethylene glycol (5 mL) along with hydrazine hydrate (0.3 mL) and heated at 120° C. for 2 hours. Next, a few pellets of KOH were added and reaction was heated at 180° C. for 4 hours. The reaction was allowed to cool to room temperature, where water was added and the mixture was extracted with ether and concentrated. The resulting material was purified via column chromatography using 5% ethyl acetate in hexane as the eluent to produce 0.128 g of desired product. MS (ESI) m/z 364 ([M+H]$^+$); $^1$H NMR (CDCl$_3$) δ 9.01 (s, 1H), 8.02 (d, J=7.2 Hz, 1H), 7.65 (d, J=7.6 Hz, 1H), 7.51 (m, 3H), 7.44 (m, 1H), 7.20 (m, 5H), 6.97 (m, 2H), 3.98 (s, 2H).

EXAMPLE 32

3-BENZYL-4-(4-METHOXYPHENYL)-8-(TRIFLUOROMETHYL)QUINOLINE

This compound was prepared using the procedure of Example 31 substituting [4-(4-methoxyphenyl)-8-(trifluoromethyl)quinolin-3-yl](phenyl)methanone of Example 2 for 2 phenyl[4-phenyl-8-(trifluoromethyl)quinolin-3-yl]methanone. The HCl salt was further prepared using HCl in ether. MS (ESI) m/z 394 ([M+H]$^+$); $^1$H NMR (acetone-d$_6$) δ 8.97 (s, 1H), 8.12 (d, J=7.2 Hz, 1H), 7.76 (d, J=8.4 Hz, 1H), 7.63 (m, 1H), 7.25 (m, 4H), 7.15 (m, 3H), 7.07 (d, J=7.5 Hz, 2H), 4.08 (s, 2H), 3.92 (s, 3H).

EXAMPLE 33

4-(4-TERT-BUTYLPHENYL)-3-(PYRIDIN-2-YL-METHYL)-8-(TRIFLUOROMETHYL)QUINOLINE

This compound was prepared using the procedure of Example 31 substituting [4-(4-tert-butylphenyl)-8-(trifluoromethyl)quinolin-3-yl](pyridin-2-yl)methanone. of Example 18 for 2 phenyl[4-phenyl-8-(trifluoromethyl)quinolin-3-yl]methanone. MS (ESI) m/z 421 ([M+H]$^+$); Anal. Calcd for $C_{26}H_{23}F_3N_2$: C, 74.27; H, 5.51; N, 6.66. Found: C, 73.94; H, 5.30; N, 6.53.

EXAMPLE 34

PHENYL[4-PHENYL-8-(TRIFLUOROMETHYL) QUINOLIN-3-YL]METHANOL

Phenyl[4-phenyl-8-(trifluoromethyl)quinolin-3-yl]methanone (Example 1, 0.200 g, 0.53 mmol) was taken into EtOH (5 mL) and cooled to 0° C. where was added NaBH$_4$ (0.020 g, 0.53 mmol). The ice bath was removed and the reaction was allowed to stir at room temperature overnight. The EtOH was removed and water was added to the resulting material, where it was extracted with methylene chloride, dried over sodium sulfate and concentrated. The product was purified via column chromatography using 15% ethyl acetate in hexane as the eluent to afford 0.194 g of desired product as a white solid. MS (ESI) m/z 380 ([M+H]$^+$); Anal. Calcd for $C_{23}H_{16}F_3NO$: C, 72.82; H, 4.25; N, 3.69. Found: C, 72.52; H, 4.20; N, 3.55.

EXAMPLE 35

3-[METHOXY(PHENYL)METHYL]-4-PHENYL-8-(TRIFLUOROMETHYL)QUINOLINE

Phenyl[4-phenyl-8-(trifluoromethyl)quinolin-3-yl]methanol (Example 34, 0.05 g, 0.132 mmol) was taken into DMF (3 mL). Next, NaH (0.011 g, 0.264 mmol, 60% dispersion) was added and stirred for 1 hour at room temperature. Next, iodomethane (0.04 ml, 0.66 mmol) was added and allowed to stir for 30 minutes. The reaction was quenched with water then extracted with ether. The combined organics were dried over magnesium sulfate and concentrated. The resulting material was purified via column chromatography using 5% ethyl acetate in hexane as the eluent to yield 0.039 g (75%) of desired product as a white solid. MS (ESI) m/z 394 ([M+H]$^+$); Anal. Calcd for $C_{24}H_{18}F_3NO$: C, 73.27; H, 4.61; N, 3.56. Found: C, 73.15; H, 4.16; N, 3.41.

EXAMPLE 36

PHENYL[4-PHENYL-8-(TRIFLUOROMETHYL) QUINOLIN-3-YL]METHYL ACETATE

Phenyl[4-phenyl-8-(trifluoromethyl)quinolin-3-yl]methanol (Example 34, 0.050 g, 0.132 mmol) was taken into CH$_2$Cl$_2$ (3 mL). Next, triethylamine (0.1 mL, 0.70 mmol) was added followed by acetyl chloride (0.05 mL, 0.70 mmol). The reaction was allowed to stir for 2 hours. The solvent was removed and the resulting material was taken up into an Ether/water/5% HCl solution. The layers were separated and the organic layer was washed once more with 5% HCl, dried over magnesium sulfate and concentrated. The product was purified via column chromatography using 7% ethyl acetate in hexane as the eluent to afford the product as a white solid (0.044 g, 79.4%). MS (ESI) m/z 422 ([M+H]$^+$); Anal. Calcd. for $C_{25}H_{18}F_3NO_2$: C, 71.25; H, 4.31; N, 3.32. Found: C, 71.15; H, 4.11; N, 3.21.

EXAMPLE 37

(E)-PHENYL[4-PHENYL-8-(TRIFLUOROMETHYL)QUINOLIN-3-YL]METHANONE OXIME

Phenyl[4-phenyl-8-(trifluoromethyl)quinolin-3-yl]methanone (Example 1, 0.128 g, 0.339 mmol) was taken into EtOH/H$_2$O (7 mL, 7:3 mixture) along with hydroxylamine hydrochloride (0.028 g, 0.407 mmol) and sodium acetate trihydrate (0.061 g, 0.447 mmol) and this mixture was refluxed for 1.5 hours. TLC and LC-MS showed no reaction. Therefore, excess quantities of hydroxylamine hydrochloride and sodium acetate trihydrate were added and refluxing was continued overnight. The reaction was concentrated and the resulting material was taken up into CH$_2$Cl$_2$/H$_2$O. The layers were separated and the aqueous layer was extracted with CH$_2$Cl$_2$. The combined organics were dried over sodium sulfate and concentrated. The product was purified via column chromatography using 15% ethyl acetate in hexane as the eluent to afford 0.100 g of desired product as a white solid. MS (ESI) m/z 393 ([M+H]$^+$);

MS (ESI) m/z 391 ([M–H]$^-$); Anal. Calcd. for $C_{23}H_{15}F_3N_2O$: C, 70.4; H, 3.85; N, 7.14. Found: C, 70.09; H, 3.65; N, 6.96.

EXAMPLE 38

(E)-PHENYL[4-PHENYL-8-(TRIFLUOROMETHYL)QUINOLIN-3-YL]METHANONE O-METHYLOXIME (E)-Phenyl[4-phenyl-8-(trifluoromethyl)quinolin-3-yl] methanone oxime (Example 37, 0.070 g, 0.18 mmol) was taken into DMF (3 mL). Then NaH (0.014 g, 0.36 mmol) was added and stirred for 20 minutes, followed by addition of iodomethane (0.05 mL, 0.72 mmol) and stirring over the weekend. The reaction was quenched with water and extracted with ether. The combined organics were washed with water and dried over magnesium sulfate and concentrated. The resulting material was purified via column chromatography using 5% ethyl acetate in hexane as the eluent to afford 0.063 g (86%) of desired product as a white solid. MS (ESI) m/z 407 ([M+H]$^+$); Anal. Calcd for $C_{24}H_{17}F_3N_2O$: C, 70.93; H, 4.22; N, 6.89. Found: C, 70.92; H, 4.19; N, 6.68.

EXAMPLE 39

1-PHENYL-1-[4-PHENYL-8-(TRIFLUOROMETHYL)QUINOLIN-3-YL]ETHANOL

Phenyl[4-phenyl-8-(trifluoromethyl)quinolin-3-yl]methanone (Example 1, 0.260 g, 0.688 mmol) was taken into THF (5 mL) and cooled to 0° C. Next, methylmagnesium bromide (0.45 mL of 3.0 M solution in Ether, 1.35 mmol) was added and the reaction was allowed to stir overnight allowing to warm to room temperature. TLC indicated the starting material was still present, therefore additional methylmagnesium bromide was added and the reaction was heated at 50° C. overnight. The reaction was allowed to cool and was quenched with saturated $NH_4Cl$ and extracted with $CH_2Cl_2$ dried over sodium sulfate and concentrated. The product was purified via column chromatography using 10% ethyl acetate in hexane as the eluent to afford 0.176 g (64.8%) of desired product. MS (ESI) m/z 394 ([M+H]$^+$); Anal. Calcd. for $C_{24}H_{18}F_3NO$ $0.5H_2O$: C, 71.63; H, 4.76; N, 3.48. Found: C, 71.45; H, 4.66; N, 3.09.

EXAMPLE 40

3-(1-METHOXY-1-PHENYLETHYL)-4-PHENYL-8-(TRIFLUOROMETHYL)QUINOLINE

1-Phenyl-1-[4-phenyl-8-(trifluoromethyl)quinolin-3-yl] ethanol (Example 39, 0.096 g, 0.243 mmol) was taken into DMF (3 mL) then NaH (0.020 g, 0.487 mmol) was added and stirred for 20 minutes. Lastly, iodomethane (0.08 mL, 1.22 mmol) was added and stirring was continued for 30 minutes. The reaction was quenched with water and extracted with ether. The combined organics were dried over magnesium sulfate and concentrated. The resulting material was purified via column chromatography using 5% ethyl acetate in hexane as the eluent. MS (ESI) m/z 408 ([M+H]$^+$); $^1$H NMR (CDCl$_3$) δ 9.59 (s, 1H), 8.01 (d, J=6.8 Hz, 1H), 7.31 (m, 3H), 7.12 (m, 5H), 7.0 (m, 2H), 6.74 (dd, J=7.5 and 1.2 Hz, 1H), 6.63 (dd, J=7.7 and 1.3 Hz, 1H), 3.06 (s, 3H), 1.8 (s, 3H).

EXAMPLE 41

(4-({4-[3-BENZOYL-8-(TRIFLUOROMETHYL)QUINOLIN-4-YL]PHENOXY}METHYL)BENZOIC ACID)

Preparation of (2-Benzoyl-3-(2-trifluoromethyl-phenylamino)-acrylic acid ethyl ester).

A mixture of 2-(trifluoromethyl)aniline(4.6 g, 28.8 mmol) and 2-benzoyl-3-ethoxy-acrylic acid ethyl ester 7.2 g, 28.8 mmol) in toluene (125 ml) was heated to reflux. After 18 hr, the reaction was cooled, concentrated and purified by column chromatography (eluent 10% EtOAc/hexane) to give 2-benzoyl-3-(2-trifluoromethyl-phenylamino)-acrylic acid ethyl ester (8.6 g, Yield=82%); MS (ESI) m/z 364(M+H)$^+$; Anal Calcd for $C_{19}H_{16}F_3NO_3$: C, 62.81; H, 4.44; N, 3.85. Found: C, 62.87; H, 4.21; N, 3.76.

Preparation of ((4-Hydroxy-8-trifluoromethyl-quinolin-3-yl)-phenyl-methanone).

A solution of 2-benzoyl-3-(2-trifluoromethyl-phenylamino)-acrylic acid ethyl ester(8.2 g, 22.4 mmol) in Dowtherm (120 ml) was heated to reflux. After 4 hr, the reaction was cooled and poured in hexane. The resulting solid was filtered and washed with hexane to give (4-hydroxy-8-trifluoromethyl-quinolin-3-yl)-phenyl-methanone (4.0 g, Yield=56%); MS (ESI) m/z 318(M+H)$^+$; Anal Calcd for $C_{17}H_{10}F_3NO_2$: C, 63.36; H, 3.18; N, 4.41. Found: C, 63.96; H, 3.14; N, 4.25.

Preparation of (3-Benzoyl-8-(trifluoromethyl)quinolin-4-yl trifluoromethanesulfonate).

A solution of (4-hydroxy-8-trifluoromethyl-quinolin-3-yl)-phenyl-methanone(1.2 g, 3.8 mmol), N-p-phenyltrifluoromethanesulfonimide(1.6 g, 4.5 mmol) and $K_2CO_3$ (2.0 g, 14.5 mmol) in DMF(20 ml) was stirred at rt. After 5 hr, the reaction was poured in water and extracted with ether. The ether was dried, concentrated to give a yellow solid which was triturated with MeOH, filtered to give a white solid (1.1 g, yield=65%); MS (ESI) m/z 450 (M+H)$^+$; Anal Calcd for $C_{18}H_9F_6NO_4S$: C, 48.12; H, 2.02; N, 3.12. Found: C, 48.06; H, 1.76; N, 2.99.

Preparation of ([4-(4-methoxyphenyl)-8-(trifluoromethyl)quinolin-3-yl(phenyl) methanone).

A solution of 3-benzoyl-8-(trifluoromethyl)quinolin-4-yl trifluoromethanesulfonate (1.8 g, 4 mmol), 4-methoxyphenylboronic acid(1.0 g, 6.5 mmol), and $K_3PO_4$(3.0 g) in dioxane (50 ml) was heated to reflux. After, 4 hr, the reaction was cooled, filtered, concentrated to give an oil which was purified by column chromatography (eluent 10% EtOAc/Hex) to give a white solid (1.3 g Yield=81%); MS (ESI) m/z 408 ([M+H]$^+$;

$^1$H NMR (DMSO) δ 9.10 (s, 1H), 8.32 (d, 1H, J=6.8 Hz), 8.01 (d, 1H, J=8.4 Hz), 7.78-7.74 (m, 1H), 7.66-7.63 (m, 2H), 7.56-7.52 (m, 1H), 7.38-7.35 (m, 2H), 7.26 (d, 2H, J=7.8 Hz), 6.94 (d, 2H, J=7.8 Hz), 3.88 (s, 3H);

Preparation of ([4-(4-Hydroxyphenyl)-8-(trifluoromethyl)quinolin-3-yl](phenyl) methanone).

A mixture of [4-(4-methoxyphenyl)-8-(trifluoromethyl)quinolin-3-yl](phenyl)methanone (1.3 g, 3.3 mmol) and pyridine HCl(10 g) was heated to 200° C. After 1 hr, the reaction was cooled and then diluted with 2N HCl. The acidic layer was extracted with EtOAc, dried and concentrated to give an oil which was triturated with 10% EtOAc/hexane to give a solid which was collected by filtration to give ([4-(4-hydroxyphenyl)-8-(trifluoromethyl)quinolin-3-yl](phenyl)methanone (0.80 g, Yield=68%); MS (ESI) m/z 394 ([M+H]$^+$); $^1$H NMR (DMSO) δ 9.72 (bs, 1H), 9.08 (s, 1H), 8.31 (d, 1H, J=6.8 Hz), 8.06 (d, 1H, J=8.6 Hz), 7.80-7.75 (m, 1H), 7.62-7.60 (m, 2H), 7.58-7.54 (m, 1H), 7.38-7.35 (m, 2H), 7.13 (d, 2H, J=7.8 Hz), 6.75 (d, 2H, J=7.8 Hz);

Preparation of (4-([4-[3-Benzoyl-8-(trifluoromethyl)quinolin-4-yl]phenoxy]methyl)benzoic Acid).

A solution of [4-(4-hydroxyphenyl)-8-(trifluoromethyl) quinolin-3-yl](phenyl) methanone (0.5 g, 1.3 mmol), methyl 4-bromomethylbenzoate(0.30 g, 1.3 mmol) and $K_2CO_3$ (0.42 g, 3 mmol) in acetone (20 ml) was heated to reflux. After 1 hr, the reaction was cooled, filtered and concentrated. The resulting oil was dissolved in THF/MeOH (20 ml) and treated with 2N NaOH (2 ml) and heated to reflux. After 1 hr, the reaction was cooled, poured into 2N HCl and extracted with EtOAc. The organic layer was dried, concentrated to give a solid which was triturated with 10% EtOAc/hexane, filtered to give the desired compound (0.32 g, Yield=47%); MS (ESI) m/z 528 ([M+H]$^+$); $^1$H NMR (DMSO) δ 12.98 (bs, 1H), 9.11 (s, 1H), 8.33 (d, 1H, J=6.8 Hz), 7.96-7.91 (m, 3H), 7.82-7.77 (m, 1H), 7.64-7.53 (m, 5H), 7.39-7.35 (m, 2H), 7.27 (d, 2H, J=7.8 Hz), 6.99 (d, 2H, J=7.8 Hz), 5.17 (s, 2H).

EXAMPLE 42

([4-(3-HYDROXYPHENYL)-8-(TRIFLUOROM-ETHYL)QUINOLIN-3-YL](PHENYL)METHA-NONE)

A solution of 3-benzoyl-8-(trifluoromethyl)quinolin-4-yl trifluoromethanesulfonate (1.6 g, 3.6 mmol), 3-hydroxyphenylboronic acid (0.60 g, 4.3 mmol), and K$_3$PO$_4$ (3.0 g) in dioxane (50 ml) was heated to reflux. After, 4 hr, the reaction was cooled, filtered, concentrated to give a solid which was triturated with 10% EtOAc/hexane to give a white solid (1.2 g Yield=86%); MS (ESI) m/z 394 ([M+H]$^+$; $^1$H NMR (DMSO) δ 9.54 (s, 1H), 9.11 (s, 1H), 8.339 (d, 1h, J=7.0 Hz), 8.01(d, 1H, J=8.0 Hz), 7.83-7.79 (m, 1H), 7.64-7.61 (m, 2h), 7.55-7.51 (m, 1H), 7.39 (t, 2H, J=7.8 Hz), 7.13 (t, 1H, =7.8 Hz), 6.72-6.68 (m, 3H); Anal. Calcd for C$_{23}$H$_{14}$F$_3$NO$_2$: C, 70.23; H, 3.59; N, 3.56. Found: C, 69.67; H, 3.43; N, 3.51.

EXAMPLE 43

([4-(3-METHOXYPHENYL)-8-(TRIFLUOROM-ETHYL)QUINOLIN-3-YL](PHENYL)METHA-NONE)

A solution of [4-(3-hydroxyphenyl)-8-(trifluoromethyl) quinolin-3-yl](phenyl)methanone (0.20 g, 0.58 mmol), iodomethane (Example 42, 0.14 g, 1.0 mmol) and K$_2$CO$_3$ (0.41 g, 3 mmol) in acetone (10 ml) was heated to reflux. After 2 hr, the reaction was cooled, filtered, concentrated to give an oil which was purified by column chromatography (eluent 10% EtOAc/hexane) to give a the desired product as a foam (0.10 g, Yield=48%); MS (ESI) m/z 408 ([M+H]$^+$)

EXAMPLES 44-55

The compounds of Examples 44-55 were prepared from [4-(3-hydroxyphenyl)-8-(trifluoromethyl)quinolin-3-yl] (phenyl)methanone (Example 42) using the procedure in Example 43 substituting Cs$_2$CO$_3$ for K$_2$CO$_3$, DMF for acetone, and the appropriate alkylating agent in place of iodomethane.

EXAMPLE 44

[4-[3-(BENZYLOXY)PHENYL]-8-(TRIFLUO-ROMETHYL)QUINOLIN-3-YL](PHENYL) METHANONE

From benzylbromide. MS (ESI) m/z 484 ([M+H]$^+$); HRMS: calcd for C$_{30}$H$_{20}$F$_3$NO$_2$, 483.1446; found (ESI_FT), 484.15164.

EXAMPLE 45

[4-{3-[(2-CHLOROBENZYL)OXY]PHENYL}-8-(TRIFLUOROMETHYL)QUINOLIN-3-YL](PHE-NYL)METHANONE

From 2-chlorobenzylbromide. MS (ESI_FT) m/z 518.11207 ([M+H]$^+$); MS (ESI_FT) m/z 518.11292 (CALC'D); HRMS: calcd for C$_{30}$H$_{19}$ClF$_3$NO$_2$, 517.1056; found (ESI_FT), 518.11207.

EXAMPLE 46

PHENYL[4-[3-(2-PHENYLETHOXY)PHENYL]-8-(TRIFLUOROMETHYL)QUINOLIN-3-YL] METHANONE

From 2-phenylbromoethane. HRMS: calcd for C$_{31}$H$_{22}$F$_3$NO$_2$, 497.1603; found (ESI_FT), 498.16655.

EXAMPLE 47

[4-{3-[(2-CHLORO-6-FLUOROBENZYL)OXY] PHENYL}-8-(TRIFLUOROMETHYL)QUINOLIN-3-YL](PHENYL)METHANONE

From 2-chloro-6-fluorobenzylbromide. MS (ESI) m/z 536/538 ([M+H]$^+$); HRMS: calcd for C$_{30}$H$_{18}$ClF$_4$NO$_2$, 535.0962; found (ESI_FT), 536.10194;

EXAMPLE 48

[4-{3-[(4-CHLOROBENZYL)OXY]PHENYL}-8-(TRIFLUOROMETHYL)QUINOLIN-3-YL](PHE-NYL)METHANONE

From 4-chlorobenzylbromide. MS (ESI) m/z 518/520 ([M+H]$^+$); HRMS: calcd for C$_{30}$H$_{19}$ClF$_3$NO$_2$, 517.1056; found (ESI_FT), 518.11102.

EXAMPLE 49

[4-{3-[(2-FLUOROBENZYL)OXY]PHENYL}-8-(TRIFLUOROMETHYL)QUINOLIN-3-YL](PHE-NYL)METHANONE

From 2-fluorobenzylbromide. MS (ESI) m/z 502 ([M+H]$^+$); HRMS: calcd for C$_{30}$H$_{19}$F$_4$NO$_2$, 501.1352; found (ESI_FT), 502.14127.

EXAMPLE 50

[4-{3-[(4-FLUOROBENZYL)OXY]PHENYL}-8-(TRIFLUOROMETHYL)QUINOLIN-3-YL](PHE-NYL)METHANONE

From 4-Fluorobenzylbromide. MS (ESI) m/z 502 ([M+H]$^+$); HRMS: calcd for C$_{30}$H$_{19}$F$_4$NO$_2$, 501.1352; found (ESI_FT), 502.1415.

EXAMPLE 51

[4-{3-[(2-CHLORO-4-FLUOROBENZYL)OXY]PHENYL}-8-(TRIFLUOROMETHYL)QUINOLIN-3-YL](PHENYL)METHANONE

From 2-chloro-4-fluorobenzylbromide. MS (ESI) m/z 536/538 ([M+H]$^+$); HRMS: calcd for $C_{30}H_{18}ClF_4NO_2$, 535.0962; found (ESI_FT), 536.1017.

EXAMPLE 52

PHENYL[4-{3-[(2,4,6-TRIFLUOROBENZYL)Oxy]PHENYL}-8-(TRIFLUOROMETHYL)QUINOLIN-3-YL]METHANONE

From 2, 4, 6-trifluorobenzylbromide. MS (ESI) m/z 538 ([M+H]$^+$); HRMS: calcd for $C_{30}H_{17}F_6NO_2$, 537.1163; found (ESI_FT), 538.12281.

EXAMPLE 53

[4-{3-[(2,4-DI FLUOROBENZYL)OXY]PHENYL}-8-(TRIFLUOROMETHYL)QUINOLIN-3-YL](PHENYL)METHANONE

From 2,4-difluorobenzylbromide. MS (ESI) m/z 520 ([M+H]$^+$); HRMS: calcd for $C_{30}H_{18}F_5NO_2$, 519.1258; found (ESI_FT), 520.13135.

EXAMPLE 54

[4-{3-[(3,4-DIFLUOROBENZYL)OXY]PHENYL}-8-(TRIFLUOROMETHYL)QUINOLIN-3-YL](PHENYL)METHANONE

From 2,4-difluorobenzylbromide. MS (ESI) m/z 520 ([M+H]$^+$); HRMS: calcd for $C_{30}H_{18}F_5NO_2$, 519.1258; found (ESI_FT), 520.13178.

EXAMPLE 55

([4-({3-[3-BENZOYL-8-(TRIFLUOROMETHYL)QUINOLIN-4-YL]PHENOXY}METHYL)PHENYL]ACETIC ACID

From 4-bromomethyl-phenylacetic acid. MS (ESI) m/z 542 ([M+H]$^+$); $^1$H NMR (DMSO) δ 12.34 (bs, 1H), 9.149s, 1H), 8.33 (d, 1H, J=6.7 Hz), 7.93 (d, 1H, J=8.5 Hz), 7.65-7.62 (m, 2H), 7.55-7.51 (m, 1H), 7.38-7.35 (m, 2H), 7.25-7.21 (m, 5H), 7.00-6.86 (m, 3H), 5.02-4.96 (m, 2H), 3.58 (s, 2H).

EXAMPLE 56

(4-({3-[3-BENZOYL-8-(TRIFLUOROMETHYL)QUINOLIN-4-YL]PHENOXY}METHYL)BENZOIC ACID)

A solution of 4-(3-hydroxyphenyl)-8-(trifluoromethyl)quinolin-3-yl](phenyl)methanone (Example 42, 1.0 g, 2.5 mmol), methyl 4-bromomethylbenzoate (0.57 g, 2.5 mmol) and $K_2CO_3$ (1.38 g, 10 mmol) in acetone (25 ml) was heated to reflux. After 2 hr, the reaction was cooled, filtered and concentrated. The resulting oil was taken up into THF/MeOH (20 ml) and 2N NaOH (2 ml) was added and the reaction was refluxed. After 2 hr, the reaction was cooled, poured into 2N HCl and extracted with EtOAc. The EtOAc was dried concentrated and the product was purified by column chromatography (eluent 40% EtOAc/hexane) to give the desired product as a foam (1.00 g, Yield=77%); MS (ESI) m/z 528 ([M+H]$^+$); $^1$H NMR (DMSO) δ 12.97 (s, 1H), 9.14 (s, 1H), 8.33 (d, 1H, J=6.6 Hz), 7.94-7.88 (m, 3H), 7.76 (t, 1H, J=8.0 Hz), 7.63 (d, 2H, J=7.1 Hz), 7.54-7.47 (m, 1H), 7.46 (d, 2H, J=8.5 Hz), 7.37-7.33 (m, 2H), 7.27 (t, 1H, J=7.8 Hz), 7.05-6.98 (m, 2H), 6.87 (m, 1H),

EXAMPLE 57

(3-({3-[3-BENZOYL-8-(TRIFLUOROMETHYL)QUINOLIN-4-YL]PHENOXY}METHYL)BENZOIC ACID

Prepared using the procedure in Example 56 except using methy 3-bromomethylbenzoate as the halide. MS (ESI) m/z 528 ([M+H]$^+$); $^1$H NMR (DMSO) δ 13.05 (s, 1H), 9.14 (s, 1H), 8.32 (d, 1H, J=6.8 Hz), 7.96-7.90 (m, 3H), 7.76 (t, 1H, J=7.8 Hz), 7.65-7.49 (m, 5H), 7.37 (t, 2H, J=7.5 Hz), 7.26 (t, 1H, J=8.0 Hz), 7.01-6.97 (m, 2H), 6.87-6.84 (m, 1H), 5.15-5.01 (m, 2H);

EXAMPLE 58

({3-[3-BENZOYL-8-(TRIFLUOROMETHYL)QUINOLIN-4-YL]PHENOXY}ACETIC ACID

Prepared using the procedure in Example 56 except using ethyl bromoacetate as the halide. MS (ESI) m/z 452 ([M+H]$^+$); $^1$H NMR (DMSO) δ 9.13 (s, 1H), 8.34 (d, 1H, J=7.9 Hz), 7.98 (d, 1H, J=8.5 Hz), 7.78 (t, 1H, J=8.0 Hz), 7.67 (d, 2H, J=7.0 Hz), 7.58-7.54 (m, 1H), 7.38-7.35 (m, 2H), 7.26 (t, 1H, J=8.0 Hz), 6.93-6.86 (m, 3H), 4.57 (s, 2H);

EXAMPLE 59

([4-PHENYL-6-FLUORO-8-(TRIFLUOROMETHYL)QUINOLIN-3-YL](PHENYL)METHANONE)

Preparation of 2-Benzoyl-3-(2-trifluoromethyl-4-fluorophenylamino)-acrylic acid ethyl ester A mixture of 4-fluoro-2-trifluoromethyl-aniline (5.0 g, 27.89 mmol) and 2-benzoyl-3-ethoxy-acrylic acid ethyl ester (6.9 g, 27.89 mmol) in toluene (125 mL) was heated at reflux. After 18 hr, the reaction was cooled, concentrated and purified by column chromatography (eluent 10% to 40% $Et_2O$/hexanes) to give 2-benzoyl-3-(2-trifluoromethyl-4-fluorophenylamino)-acrylic acid ethyl ester (6.6 g, 62%); MS (ESI) m/z 382 (M+H)$^+$; $^1$H NMR E:Z (mixture 1:1) (CDCl$_3$): δ 0.88 (t, J=5.38 Hz, 3H), 0.95 (t, J=5.38 Hz, 3H), 4.02 (q, J=5.38 Hz, 2H), 4.07 (t, J=5.38 Hz, 2H), 7.29-7.51 (m, 10H), 7.53-7.56 (dt, J=9.67, 1.54 Hz, 2H), 7.66-7.68 (dt, J=8.33, 1.41 Hz, 2H), 8.10-8.13 (d, J=12.68 Hz, 2H), 8.36-8.39 (d, J=12.43 Hz, 2H), 11.17-11.20 (d, J=12.68 Hz, 1H), 12.39-12.42 (d, J=12.43 Hz, 1H).

Preparation of 4-Hydroxy-6-fluoro-8-trifluoromethyl-quinolin-3-yl)-phenyl-methanone.

A solution of 2-benzoyl-3-(4-fluoro-2-trifluoromethyl-phenylamino)-acrylic acid ethyl ester(6.1 g, 16.0 mmol) in Dowtherm (75 mL) was heated to reflux. After 4 hr, the reaction was cooled and poured in hexane (150 mL). The resulting solid was filtered and washed with hexane, recrystalization (1:1 EtOAc/hexane) to give 4-hydroxy-6-fluoro-8-trifluoromethyl-quinolin-3-yl)-phenyl-methanone as a light yellow powder (2.8 g, 53%); MS (ESI) m/z 336 (M+H)+; 1H NMR (CDCl3): δ 6.99-7.7.02 (d, J=8.59 Hz, 1H), 7.33-7.36 (t, J=8.59 Hz, 1H), 7.79-7.81 (t, J=9.60 Hz, 1H), 7.61-7.67 (m, 2H), 7.96-7.98 (dd, J=8.32, 5.50 Hz, 1H), 9.14 (s, 1H), 14.16 (s, 1H).

Preparation of 3-Benzoyl-(4-fluoro-8-trifluoromethyl) quinolin-4-yl Trifluoromethanesulfonate.

A solution of (4-hydroxy-6-fluoro-8-trifluoromethyl-quinolin-3-yl)-phenyl-methanone (50 mg, 1.49 mmol) and triethylamine (310 mg, 3.07 mmol) in CH2Cl2 (15 mL) was stirred at 0° C. under calcium sulfate tube was added trifluoromethanesulfonic anhydride (505 mg, 1.79 mmol). After 1 hr, the reaction was poured into 2N HCl (25 mL) and extracted, washed with brine (15 mL), drying over MgSO4 and concentrated in vacuo to give 3-benzoyl-(4-fluoro-8-trifluoromethyl)quinolin-4-yl trifluoromethanesulfonate as an off white powder (510 mg, 71%); MS (ESI) m/z 468 (M+H)+; 1H NMR (CDCl3): δ 7.00-7.7.03 (d, J=8.59 Hz, 1H), 7.33-7.36 (t, J=8.59 Hz, 1H), 7.62-7.67 (m, 3H), 7.87-7.90 (d, J=8.32 Hz, 1H), 8.00-8.02 (dd, J=8.32, 5.50 Hz, 1H), 9.15 (s, 1H).

Preparation of ([4-Phenyl-6-fluoro-8-(trifluoromethyl) quinolin-3-yl](phenyl)methanone).

A solution of 3-benzoyl-6-fluoro-8-trifluoromethyl) quinolin-4-yl trifluoromethanesulfonate (510 g, 1.09 mmol), phenylboronic acid (166 mg, 1.36 mmol), K3PO4 (961 mg, 4.54 mmol), Pd(PPh3)4 (91 mg, 0.08 mmol) in dioxane (35 mL) was heated to reflux. After 3 hr, the reaction was cooled, filtered through celite, partitioned between 2N HCl (40 mL) and EtOAc (50 mL), dried over MgSO4 and concentrated in vacuo. Reverse Phase-HPLC afforded the title compound as a light yellow solid (138 mg, 32%); MS (ESI) m/z 396 (M+H)+; 1H NMR (CDCl3): δ 7.31-7.35 (m, 1H), 7.36-7.40 (m, 2H), 7.54-7.58 (dt, J=7.30, 2.99 Hz, 1H), 7.63-7.65 (d, J=7.15 Hz, 1H), 8.35-8.38 (dd, J=8.58 Hz, 1H), 9.14 (s, 1H).

EXAMPLE 60

[4-(3-AMINOPHENYL)-8-(TRIFLUOROMETHYL)QUINOLIN-3-YL](PHENYL)METHANONE

To a mixture of tetrakis(triphenylphosphine)palladium (0) (0.12, 0.1 mmol), 2N sodium carbonate (5 mL, 10 mmol), [4-chloro-8-(trifluoromethyl)quinolin-3-yl](phenyl)methanone (from Example 1, 0.67 g, 2.0 mmol) in 20 mL of toluene and 5 mL of ethanol was added 3-aminobenzeneboronic acid (0.62 g, 4.0 mmol). The reaction mixture was heated to 80° C. for 1 hour, diluted with ethyl acetate, washed with water and dried over MgSO4. Removal of solvent under reduced pressure gave a crude product that was purified by silica gel chromatography eluting with ethyl acetate/hexanes (5% to 50%) to give the title compound as a pale yellow solid; MS (EI) m/z 393.3 (M+H)+; 1H NMR (DMSO-d6): δ 5.21 (s, 2H), 6.39 (d, J=8.8 Hz, 1H), 6.47 (s, 1H), 6.48 (d, J=9.4 Hz, 1H), 6.95 (t, J=9.4 Hz, 1H), 7.39 (t, J=7.5 Hz, 2H), 7.56 (t, J=8.7 Hz, 1H), 7.63 (d, J=8.2 Hz, 2H), 7.80 (t, J=7.8 Hz, 1H), 8.10 (d, J=8.6 Hz, 1H), 8.31 (d, J=6.7 Hz, 1H), 9.08 (s, 1H).

EXAMPLE 61

4-[({3-[3-BENZOYL-8-(TRIFLUOROMETHYL)QUINOLIN-4-YL]PHENYL}AMINO)SULFONYL]BENZOIC ACID 4-(Chlorosulfonyl)benzoic acid (0.11 g, 0.5 mmol) in 5 mL of THF was added dropwise to a stirred solution of [4-(3-aminophenyl)-8-(trifluoromethyl)quinolin-3-yl](phenyl) methanone (0.098 g, 0.25 mmol) and triethylamine (0.4 mL, 0.29 mmol) in 5 mL of THF at room temperature. The reaction mixture was stirred overnight, diluted with ethyl acetate, washed with water, and concentrated. The residue was purified by semi-preparative HPLC (Column: Phenomenex C18 Luna 21.6 mm×60 mm, 50M; Solvent A: Water (0.1% TFA buffer); Solvent B: Acetonitrile (0.1% TFA buffer); Solvent Gradient: Time 0: 0% B; 10 min: 100% B; Hold 100% B 5 min. Flow Rate: 22.5 mL/min). The product was collected based on UV absorption and concentrated to give the title compound as a brown solid (0.075 g, 50%): MS (EI) m/z 601.1 (M+H)+; 1H NMR (DMSO-d6): δ 7.03 (d, J=7.7 Hz, 1H), 7.33 (t, J=8.0 Hz, 1H), 7.39 (t, J=7.8 Hz, 2H), 7.56 (t, J=7.4 Hz, 1H), 7.60-8.75 (m, 9H), 8.06 (d, J=8.6 Hz, 1H), 8.36 (d, J=7.3 Hz, 1H), 9.16 (s, 1H), 10.34 (s, 1H).

EXAMPLE 62

N-{3-[3-BENZOYL-8-(TRIFLUOROMETHYL)QUINOLIN-4-YL]PHENYL}BENZENESULFONAMIDE

The title compound was prepared from [4-(3-aminophenyl)-8-(trifluoromethyl)quinolin-3-yl](phenyl)methanone and benzenesulfonyl chloride following the procedure of Example 61 as an off-white solid: MS (EI) m/z 533.2 (M+H)+; 1H NMR (DMSO-d6): δ 6.95 (d, J=7.7 Hz, 1H), 7.03 (d, J=8.1 Hz, 1H), 7.05 (s, 1H), 7.20 (t, J=7.9 Hz, 1H), 7.35 (t, J=7.5 Hz, 2H), 7.50-7.70 (m, 9H), 7.76 (t, J=8.2 Hz, 1H), 8.33 (d, J=7.1 Hz, 1H), 9.11 (s, 1H), 10.38 (s, 1H).

EXAMPLE 63

N-{3-[3-BENZOYL-8-(TRIFLUOROMETHYL)QUINOLIN-4-YL]PHENYL}-4-(TRIFLUOROMETHYL)BENZENESULFONAMIDE

The title compound was prepared from [4-(3-aminophenyl)-8-(trifluoromethyl)quinolin-3-yl](phenyl)methanone and 4-(trifluoromethyl)benzenesulfonyl chloride following the procedure of Example 61 as an off-white solid: MS (EI) m/z 601.1 (M+H)+; 1H NMR (DMSO-d6): δ 7.00-7.10 (m, 3H), 7.24 (d, J=8.6 Hz, 1H), 7.33 (t, J=7.6 Hz, 2H), 7.50-7.60 (m, 3H), 7.70 (d, J=8.5 Hz, 1H), 7.75 (t, J=8.4 Hz, 1H), 7.87 (d, J=7.4 Hz, 2H), 7.96 (d, J=7.4 Hz, 2H), 8.34 (d, J=6.2 Hz, 1H), 9.11 (s, 1H), 10.65 (s, 1H).

EXAMPLE 64

N-[3-(3-BENZOYL-8-TRIFLUOROMETHYL-QUINOLIN-4-YL)-PHENYL]-BENZAMIDE

The title compound was prepared from [4-(3-aminophenyl)-8-(trifluoromethyl)quinolin-3-yl](phenyl)methanone and benzoyl chloride in substantially the same manner as described in Example 61 with one change: pyridine was used as a base instead of triethylamine; off-white solid: MS (EI) m/z 497.2 (M+H)+; 1H NMR (DMSO-d6): δ 7.03 (d, J=7.6 Hz, 1H), 7.33 (t, J=7.8 Hz, 1H), 7.39 (t, J=8.0 Hz, 2H), 7.50-7.95 (m, 10H), 8.05 (d, J=7.7 Hz, 1H), 8.36 (d, J=7.0 Hz, 1H), 9.16 (s, 1H), 10.33 (s, 1H).

EXAMPLE 65

1-[3-(3-BENZOYL-8-TRIFLUOROMETHYL-QUINOLIN-4-YL)-PHENYL]-3-PHENYL-UREA

The title compound was prepared from [4-(3-aminophenyl)-8-(trifluoromethyl)quinolin-3-yl](phenyl)methanone and phenyl isocyanate in substantially the same manner as described in Example 61 with one change: no triethylamine was used; off-white solid: MS (EI) m/z 512.2 (M+H)+; $^1$H NMR (DMSO-d$_6$): δ 6.90 (d, J=7.7 Hz, 1H), 6.96 (t, J=7.3 Hz, 1H), 7.20-7.30 (m, 3H), 7.35-7.47 (m, 6H), 7.57 (t, J=7.5 Hz, 1H), 7.66 (d, J=8.5 Hz, 2H), 7.83 (d, J=7.7 Hz, 1H), 8.35 (d, J=6.9 Hz, 1H), 8.66 (s, 1H), 8.74 (s, 1H), 9.14 (s, 1H).

EXAMPLE 66

{4-[({3-[3-BENZOYL-8-(TRIFLUOROMETHYL) QUINOLIN-4-YL]PHENYL}AMINO)METHYL] PHENYL}ACETIC ACID

[4-(3-Aminophenyl)-8-(trifluoromethyl)quinolin-3-yl] (phenyl)methanone (0.39 g, 1.0 mmol) and (4-formyl-phenyl)-acetic acid methyl ester (0.17 g, 0.96 mmol) were mixed in THF (15 mL) and then treated with NaBH(OAc)$_3$ (0.43 g, 2.0 mml) and acetic acid (0.5 mL). After stirring at 40° C. under a N$_2$ atmosphere for 2 h the mixture was quenched with water and then extracted with ethyl acetate. The organic residue was purified by silica gel chromatography using 5-50% EtOAc/hexanes as eluent to provide methyl {4-[({3-[3-benzoyl-8-(trifluoromethyl)quinolin-4-yl]phenyl}amino)methyl]phenyl}acetate as an orange solid (0.30 g, 54%): MS (EI) m/z 555.3 (M+H)+; $^1$H NMR (DMSO-d$_6$): δ 3.61 (s, 3H), 3.66 (s, 2H), 4.12 (d, J=6.0 Hz, 2H), 6.40 (d, J=6.8 Hz, 2H), 6.49 (d, J=6.8 Hz, 2H), 6.98 (t, J=7.7 Hz, 1H), 7.18-7.22 (m, 4H), 7.36 (t, J=7.5 Hz, 2H), 7.55 (t, J=7.4 Hz, 1H), 7.59 (d, J=9.0 Hz, 2H), 7.72 (t, J=8.6 Hz, 1H), 7.99 (d, J=8.5 Hz, 1H), 8.30 (d, J=7.3 Hz, 1H), 9.08 (s, 1H).

To a stirred solution of methyl {4-[({3-[3-benzoyl-8-(trifluoromethyl)quinolin-4-yl]phenyl}amino)methyl] phenyl}acetate (0.06 g, 0.11 mmol) in THF/methanol/water (2:1:1, 10 mL) was added lithium hydroxide monohydrate (0.06 g, 1.4 mmol). The reaction was stirred at 40° C. for 1 h. The reaction mixture was made acidic (pH 6) with glacial acetic acid, and the solid was collected and dried over P$_2$O$_5$ to give the title compound as an orange solid (0.05 g, 93%): MS (EI) m/z 541.3 (M+H)+; $^1$H NMR (DMSO-d$_6$): δ 3.53 (s, 2H), 4.12 (d, J=5.8 Hz, 2H), 6.35-6.55 (m, 4H), 6.97 (t, J=7.4 Hz, 1H), 7.15-7.22 (m, 4H), 7.36 (t, J=7.8 Hz, 2H), 7.55 (t, J=7.4 Hz, 1H), 7.61 (d, J=8.2 Hz, 2H), 7.72 (t, J=8.0 Hz, 1H), 7.98 (d, J=8.0 Hz, 1H), 8.29 (d, J=7.1 Hz, 1H), 9.08 (s, 1H).

EXAMPLE 67

(4-{[{3-[3-BENZOYL-8-(TRIFLUOROMETHYL) QUINOLIN-4-YL]PHENYL}(METHYL) AMINO] METHYL}PHENYL)ACETIC ACID

The title compound was prepared from methyl {4-[({3-[3-benzoyl-8-(trifluoromethyl)quinolin-4-yl]phenyl}amino) methyl]phenyl}acetate and 37% aqueous formaldehyde followed the procedures of Example 66 as an orange solid MS (EI) m/z 555.3 (M+H)+; $^1$H NMR (DMSO-d$_6$): δ 2.86 (s, 3H), 3.55 (s, 2H), 4.44 (s, 2H), 6.50 (d, J=7.5 Hz, 1H), 6.60-6.65 (m, 2H), 6.98 (d, J=8.1 Hz, 2H), 7.09 (t, J=7.9 Hz, 1H), 7.18 (d, J=8.0 Hz, 2H), 7.36 (t, J=7.4 Hz, 2H), 7.55 (t, J=6.2 Hz, 1H), 7.64 (d, J=7.0 Hz, 2H), 7.73 (t, J=7.8 Hz, 1H), 8.01 (d, J=7.7 Hz, 1H), 8.30 (d, J=7.0 Hz, 1H), 9.10 (s, 1H), 12.31 (br s, 1H).

EXAMPLE 68

([4-(3-HYDROXYMETHYL-PHENYL)-8-TRIFLUOROMETHYL-QUINOLIN-3-YL]-PHENYL-METHANONE)

A solution of (3-benzoyl-8-(trifluoromethyl)quinolin-4-yl trifluoromethanesulfonate). (3.0 g, 6.0 mmol), 3-hydroxymethylphenylboronic acid (1.5 g, 10 mmol), K$_3$PO$_4$ (3.0 g) and Pd(PPh$_3$)$_4$ (0.30 g) in dioxane (30 ml) was heated to reflux. After 3 hr, the reaction was cooled and poured into water. The aqueous layer was extracted with EtOAc, dried, concentrated to give an oil which was purified by column chromatography (eluent 30% EtOAc/Hexane) to give the title compound as a foam (2.6 g, 96%); MS (ESI) m/z 407([M+H]+); $^1$H NMR (DMSO) δ 9.149 (s, 1H), 8.33 (d, 1H, J=7.1 Hz), 7.96 (d, 1H), 7.8 Hz), 7.80 (t, 1H, J=7.4 Hz), 7.62 (d, 2H, H=7.1 Hz), 7.55 (t, 1H, J=7.5 Hz), 7.40-7.28 (m, 5H), 7.18-7.14 (m, 1H), 5.23 (t, 1H, J=5.6 Hz), 4.41 (d, 1H, J=5.6 Hz).

EXAMPLE 69

([4-({3-[3-BENZOYL-8-(TRIFLUOROMETHYL) QUINOLIN-4-YL]BENZYL}OXY)PHENYL]ACETIC ACID)

To a solution of [4-(3-hydroxymethyl-phenyl)-8-trifluoromethyl-quinolin-3-yl]-phenyl-methanone (0.20 g, 0.5 mmol), PPh$_3$ (0.2 g, 0.75 mmol) and methyl 4-hydroxyphenylacetate (0.13 g, 0.75 mmol) in THF (10 ml) was added DIAD (0.15 g, 0.75 mmol) drop wise. After 1 hr, the reaction was concentrated and purified by column chromatography (eluent 20% EtOAc/Hexane) to give a foam (0.14 g). The foam was dissolved in THF/MeOH (10 ml) and 1N NaOH (1 ml) and heated to reflux. After 1 hr, the reaction was cooled, poured into 1N HCl and extracted with EtOAc. The organic layer was dried and concentrated to the title compound as a foam (0.11 g, 41%); MS (ESI) m/z 542 ([M+H]+); $^1$H NMR (DMSO) δ 12.24 (s, 1H), 9.15 (s, 1H), 8.34 (d, 1H, J=6.7 Hz), 7.91 (d, 1H, J=7.2 Hz), 7.78 (t, 1H, J=7.6 Hz), 7.61 (d, 2H, J=8.2 Hz), 7.56-7.52 (m, 1H), 7.40-7.35 (m, 5H), 7.27-7.22 (m, 1H), 7.16 (d, 2H, J=8.2z), 6.85 (d, 2H, J=8.2 Hz), 5.04 (s, 2H), 3.47 (s, 2H).

EXAMPLE 70

([4-({3-[3-BENZOYL-8-(TRIFLUOROMETHYL) QUINOLIN-4-YL]PHENOXY}METHYL) PHENYL]ACETONITRILE)

A solution of [4-(3-hydroxyphenyl)-8-(trifluoromethyl) quinolin-3-yl](phenyl)methanone (1.5 g, 3.8 mmol), dichloro-p-xylene and K$_2$CO$_3$ in acetone (50 ml) was heated to reflux. After 18 hr, the reaction was cooled, filtered, concentrated and purified by column chromatography (eluent 20% EtOAc/Hexane) to give {4-[3-(4-chloromethyl-benzyloxy)-phenyl]-8-trifluoromethyl-quinolin-3-yl}-phenyl-methanone as a foam (1.1 g, 55%). This foam was dissolved in DMF and NaCN (0.16 g, 2.5 mmol) and NaI (0.075 g, 0.5 mmol) were added. The reaction was heated to 60° C. for 1 hr and then cooled. The solution was poured into water and extracted with EtOAc, which was dried and concentrated. The product was purified by column chromatography (eluent 20% EtOAc/Hexane) to give the title compound as a foam (0.80 g, 72%); MS (ESI) m/z 523 ([M+H]+); $^1$H NMR(DMSO) δ 9.14 (s, 1H), 8.33 (d, 1H, J=6.7 Hz), 7.93 (dd, 1H, J=8.5 Hz, 1.0 Hz), 7.78 (1, 1H, J=7.4 Hz), 7.64 (d, 2H, J=8.4 Hz), 7.57 (t, 1H, J=7.5 Hz), 7.40-7.35 (m, 6H), 7.26 (t, 1H, J=7.9 Hz), 6.99-6.94 (m, 2H), 6.84 (d, 1H, J=8.2 Hz), 5.10-4.97 (m, 2H), 4.05 (s, 2H).

EXAMPLE 71

(PHENYL[4-(3-{[4-(1H-TETRAZOL-5-YLMETHYL)BENZYL]OXY}PHENYL)-8-(TRIFLUOROMETHYL)QUINOLIN-3-YL]METHANONE)

A solution of ([4-({3-[3-benzoyl-8-(trifluoromethyl) quinolin-4-yl]phenoxy}methyl) phenyl]acetonitrile) (0.52 g, 1.0 mmol), sodium azide (0.33 g, 5.0 mmol) and NH$_4$Cl (0.27 g, 5 mmol) in DMF (30 ml) was heated to 125° C. After 48 hr, the reaction was cooled and poured into water. The aqueous layer was extracted with EtOAc, dried and concentrated. The product was purified by column chromatography (eluent 50% EtOAc/Hexane) to give the title compound as a foam (0.12 g, 22%); MS (ESI) m/z [M+H]+(566); $^1$H NMR (DMSO) δ 16.2 (s, 1H), 9.13 (s, 1H), 8.32 (d, 1H, J=6.7 Hz), 7.92 (d, 1H, J=8.4 Hz), 7.75 (t, 1H, J=7.8 Hz), 7.63 (d, 2H, J=8.4 Hz), 7.57-7.53 (m, 1H), 7.39-7.25 (m, 7H), 6.98-6.93 (m, 2H), 6.84 (d, 1H, J=8.2 Hz), 5.02-4.43 (m, 2H), 4.32 (s, 2H).

EXAMPLE 72

N, 4-DIPHENYL-8-(TRIFLUOROMETHYL) QUINOLINE-3-CARBOXAMIDE

To a solution of 4-phenyl-8-trifluoromethyl-quinoline-3-carboxylic acid (0.24 g, 0.757 mmole) in 15 mL DMF was added aniline (0.137 mL, 1.51 mmole), EDCI-HCl (0.218 g, 1.13 mmole), and DMAP (0.184 g, 1.51 mmole). After stirring at room temperature overnight, the solution was partitioned between ethyl acetate and water and the aqueous layer was extracted with ethyl acetate. The combined organic phases were washed with water, brine, and dried with magnesium sulfate. The organic phases were concentrated and the residue was loaded onto silica gel and chromatographed with hexanes:ethyl acetate (9:1) to afford 0.211 g (71%) of the title compound as a white solid: mp 207-208° C.; Calculated mass for C$_{23}$H$_{15}$N$_2$F$_3$O is 392.38, found by ESI MS, 393 (M+H)$^+$, found by HRMS (ESI), 393.12056 (M+H)$^+$; $^1$H NMR (DMSO-d$_6$) δ 10.40 (bs, 1H), 9.25 (bs, 1H), 8.31 (d, 1H, J=6.9 Hz), 7.90 (d, 1H, J=8.3 Hz), 7.77 (t, 1H, J=7.5 Hz), 7.47 (m, 7H), 7.28 (t, 2H, J=7.5 Hz), 7.06 (t, 1H, J=7.06 Hz). Anal. Calcd for C$_{23}$H$_{15}$N$_2$F$_3$O: C, 70.40; H, 3.85; N, 7.14. Found: C, 70.00; H, 3.61; N, 6.96.

EXAMPLE 73

4-({4-FLUORO-3-[3-PHENYL-8-(TRIFLUOROMETHYL)QUINOLIN-4-YL]PHENOXY}METHYL) PHENYL]ACETIC ACID

The title compound is prepared essentially as described in Example 400, supra, except using Ethyl [4-({4-fluoro-3-[3-phenyl-8-(trifluoromethyl)quinolin-4-yl]phenoxy}methyl) phenyl]acetate instead of 3-[3-phenyl-8-(trifluoromethyl) quinolin-4-yl]phenyl acetic acid ester to afford 0.100 g (96%) of the title compound as a white solid: mp 257° C.; Calculated mass for C$_3$,H$_{21}$NF$_4$O$_3$ is 531.51, found MS (ES) m/z 532.

EXAMPLE 74

N-{4-[3-BENZOYL-8-(TRIFLUOROMETHYL) QUINOLIN-4-YL]PHENYL}-N'-PHENYLUREA

The title compound was prepared from [4-(4-aminophenyl)-8-(trifluoromethyl)quinolin-3-yl](phenyl)methanone and phenyl isocyanate in substantially the same manner as described in Example 61 with one change: no triethylamine was used; off-white solid: MS (ES) m/z 510.2.

EXAMPLE 75

N-PHENYL-N'-{3-[3-PHENYL-8-(TRIFLUOROMETHYL)QUINOLIN-4-YL]PHENYL}UREA

The title compound was prepared from {3-[3-phenyl-8-(trifluoromethyl)quinolin-4-yl]phenyl}amine and phenyl isocyanate in substantially the same manner as described in Example 61 with one change: no triethylamine was used; off-white solid: mp 202-205° C.; MS (ES) m/z 481.8.

EXAMPLE 76

N-(2-CHLOROPHENYL)-N'-{3-[3-PHENYL-8-(TRIFLUOROMETHYL)QUINOLIN-4-YL] PHENYL}UREA

The title compound was prepared from {3-[3-phenyl-8-(trifluoromethyl)quinolin-4-yl]phenyl}amine and 2-chlorophenyl isocyanate in substantially the same manner as described in Example 61 with one change: no triethylamine was used; off-white solid: mp 192-195° C.; MS (ES) m/z 515.8.

EXAMPLE 77

N-(2-FLUOROPHENYL)-N'-{3-[3-PHENYL-8-(TRIFLUOROMETHYL)QUINOLIN-4-YL] PHENYL}UREA

The title compound was prepared from {3-[3-phenyl-8-(trifluoromethyl)quinolin-4-yl]phenyl}amine and 2-fluorophenyl isocyanate in substantially the same manner as described in Example 61 with one change: no triethylamine was used; off-white solid:

MS (ES) m/z 499.8.

EXAMPLE 78

[4-[3-({4-[(DIETHYLAMINO)METHYL] BENZYL}OXY) PHENYL]-8-(TRIFLUOROMETHYL)QUINOLIN-3-YL](PHENYL)METHANONE

Step 1: [4-(3-Hydroxyphenyl)-8-(trifluoromethyl)quinolin-3-yl](phenyl)methanone(2.5 g, 6.4 mmol), p-Dichloroxylene(5.6 g, 32 mmol), and K$_2$CO$_3$(2.6 g, 19 mmol) in Acetone (50 ml) was heated to reflux. After 3 hr, the reaction was cooled, filtered, and concentrated. The resulting oil was purified by column chromatography (eluent 15% EtOAc/Hex) to give {4-[3-(4-chloromethyl-benzyloxy)-phenyl]-8-trifluoromethyl-quinolin-3-yl}phenyl-methanone as a foam (2.7 g) MS m/z 532.

Step 2: A solution of {4-[3-(4-chloromethyl-benzyloxy)-phenyl]-8-trifluoromethyl-quinolin-3-yl}phenyl-methanone (011 g, 0.2 mmol) and diethylamine(0.3 g, 5.7 mmol) in CH$_2$Cl$_2$ (5 ml) was stirred at r.t. After 24 hr, the reaction was concentrated and purified by column chromatography (eluent 25% EtOAc/Hex) to give the title compound as a foam (0.10 g); MS m/z 569.

EXAMPLE 79

[4-[3-({4-[(DIMETHYLAMINO)METHYL] BENZYL}OXY)PHENYL]-8-(TRIFLUOROMETHYL)QUINOLIN-3-YL](PHENYL)METHANONE

Prepared using the procedure in Example 78 except using dimethylamine as the amine.

MS (ES) m/z 541.3.

EXAMPLE 80

[4-{3-[(4-{[(2-HYDROXYETHYL)(METHYL)AMINO]METHYL}BENZYL)OXY] PHENYL}-8-(TRIFLUOROMETHYL)QUINOLIN-3-YL](PHENYL)METHANONE

Prepared using the procedure in Example 78 except using N-Methylaminoethanol as the amine. MS (ES) m/z 571.3.

EXAMPLE 81

PHENYL[4-(3-{[4-(PYRROLIDIN-1-YLMETHYL)BENZYL]OXY}PHENYL)-8-(TRIFLUOROMETHYL)QUINOLIN-3-YL]METHANONE

Prepared using the procedure in Example 78 except using pyrollidine as the amine.
MS (ES) m/z 567.4.

EXAMPLE 82

PHENYL[4-(3-{[4-(PIPERIDIN-1-YLMETHYL)BENZYL]OXY}PHENYL)-8-(TRIFLUOROMETHYL) QUINOLIN-3-YL]METHANONE

Prepared using the procedure in Example 78 except using piperidine as the amine.
MS (ES) m/z 581.4.

EXAMPLE 83

[4-{3-[(4-{[ETHYL(METHYL)AMINO]METHYL}BENZYL)OXY] PHENYL}-8-(TRIFLUOROMETHYL) QUINOLIN-3-YL](PHENYL)METHANONE

Prepared using the procedure in Example 78 except using N-ethylmethylamine as the amine. MS (ES) m/z 555.4.

EXAMPLE 84

[4-[3-({4-[(METHYLAMINO)METHYL]BENZYL}OXY)PHENYL]-8-(TRIFLUOROMETHYL)QUINOLIN-3-YL](PHENYL)METHANONE

Prepared using the procedure in Example 78 except using methylamine as the amine. MS (ES) m/z 527.3.

EXAMPLE 85

[4-[3-({4-[(3-HYDROXYPIPERIDIN-1-YL)METHYL]BENZYL}OXY)PHENYL]-8-(TRIFLUOROMETHYL) QUINOLIN-3-YL](PHENYL)METHANONE

Prepared using the procedure in Example 78 except using 3-hydroxypiperidine as the amine. MS m/z 597.

EXAMPLE 86

[4-{3-[(4-{[METHYL(PROP-2-YNYL)AMINO]METHYL}BENZYL)OXY]PHENYL}-8-(TRIFLUOROMETHYL) QUINOLIN-3-YL](PHENYL)METHANONE

Prepared using the procedure in Example 78 except using N-methylpropargylamine as the amine. MS (ES) m/z 565.2.

EXAMPLE 87

[4-[3-({4-[(4-METHYLPIPERAZIN-1-YL)METHYL]BENZYL}OXY)PHENYL]-8-(TRIFLUOROMETHYL) QUINOLIN-3-YL](PHENYL)METHANONE

Prepared using the procedure in Example 78 except using N-methylpiperazine as the amine. MS m/z 596.

EXAMPLE 88

[4-[3-({4-[(3-HYDROXYPYRROLIDIN-1-YL)METHYL]BENZYL}OXY)PHENYL]-8-(TRIFLUOROMETHYL) QUINOLIN-3-YL](PHENYL)METHANONE

Prepared using the procedure in Example 78 except using 3-hydroxypyrollidine as the amine. MS (ESI) m/z 582.

EXAMPLE 89

[4-{3-[(4-{[2-(METHOXYMETHYL) PYRROLIDIN-1-YL]METHYL}BENZYL)OXY]PHENYL}-8-(TRIFLUOROMETHYL)QUINOLIN-3-YL](PHENYL)METHANONE

Prepared using the procedure in Example 78 except using 2-(methoxymethyl) pyrrolidine as the amine. MS (ES I) m/z 611.

EXAMPLE 90

[4-{3-[(4-{[2-(HYDROXYMETHYL)PYRROLIDIN-1-YL]METHYL}BENZYL)OXY]PHENYL}-8-(TRIFLUOROMETHYL)QUINOLIN-3-YL] (PHENYL)METHANONE

Prepared using the procedure in Example 78 except using 2-(hydroxymethyl) pyrrolidine as the amine. MS (ESI) m/z 597.

EXAMPLE 91

METHYL 1-[4-({3-[3-BENZOYL-8-(TRIFLUOROMETHYL)QUINOLIN-4-YL]PHENOXY}METHYL) BENZYL]PROLINATE

Prepared using the procedure in Example 78 except using proline methyl ester as the amine. MS (ES) m/z 625.4.

EXAMPLE 92

1-[4-({3-[3-BENZOYL-8-(TRIFLUOROMETHYL)QUINOLIN-4-YL]PHENOXY}METHYL) BENZYL]PROLINAMIDE

Prepared using the procedure in Example 78 except using pyrrolidine-2-carboxylic acid amide as the amine. MS (ES) m/z 610.3.

EXAMPLE 93

1-{1-[4-({3-[3-BENZOYL-8-(TRIFLUOROMETHYL)QUINOLIN-4-YL]PHENOXY}METHYL) BENZYL]-1H-PYRROL-2-YL}ETHANONE

1) [4-(3-Hydroxyphenyl)-8-(trifluoromethyl)quinolin-3-yl](phenyl)methanone: (2.5 g, 6.4 mmol), p-dichloroxylene (5.6 g, 32 mmol), and $K_2CO_3$ (2.6 g, 19 mmol) in acetone (50 ml) was heated to reflux. After 3 hr, the reaction was cooled, filtered, and concentrated. The resulting oil was purified by column chromatography (eluent 15% EtOAc/Hex) to give {4-[3-(4-chloromethyl-benzyloxy)-phenyl]-8-trifluoromethyl-quinolin-3-yl}phenyl-methanone as a foam (2.7 g). MS m/z 532.

2) 1-{1-[4-({3-[3-Benzoyl-8-(trifluoromethyl)quinolin-4-yl]phenoxy}methyl)benzyl]-1H-pyrrol-2-yl}ethanone: To a solution of 2-acetylpyrrole (0.065 g, 0.60 mmol) in DMF(4 ml) was added NaH (0.015 g, 0.60 mmol). After stirring the reaction for 10 min, 1-{1-[4-({3-[3-benzoyl-8-(trifluoromethyl)quinolin-4-yl]phenoxy}methyl)benzyl]-1H-pyrrol-2-yl}ethanone was added. The reaction was stirred at r.t. for 2 hr and then poured into water and extracted with EtOAc. The EtOAc was dried, concentrated and the product purified by column chromatography to give the title compound as a foam (0.095 g); MS (ES) m/z 605.3.

EXAMPLE 94

1-[4-({3-[3-BENZOYL-8-(TRIFLUOROMETHYL)QUINOLIN-4-YL]PHENOXY}METHYL)BENZYL]-1H-PYRROLE-2-CARBONITRILE

Prepared using the procedure in Example 93 except using 2-cyanopyrrole as the pyrrole. MS (ESI) m/z 588.

EXAMPLE 95

METHYL 1-[4-({3-[3-BENZOYL-8-(TRIFLUOROMETHYL)QUINOLIN-4-YL]PHENOXY}METHYL) BENZYL]-1H-PYRROLE-2-CARBOXYLATE

Prepared using the procedure in Example 93 except using 1H-pyrrole-2-carboxylic acid methyl ester as the pyrrole. MS (ESI) m/z 621.

EXAMPLE 96

1-[4-({3-[3-BENZOYL-8-(TRIFLUOROMETHYL)QUINOLIN-4-YL]PHENOXY}METHYL)BENZYL]-1H-PYRROLE-2-CARBOXYLIC ACID

Prepared by NaOH hydrolysis of methyl 1-[4-({3-[3-Benzoyl-8-(trifluoromethyl)quinolin-4-yl]phenoxy}methyl)benzyl]-1H-pyrrole-2-carboxylate; MS (ESI) m/z 607; MS (ESI) m/z 605.

EXAMPLE 97

1-[4-({3-[3-BENZOYL-8-(TRIFLUOROMETHYL)QUINOLIN-4-YL]PHENOXY}METHYL)BENZYL]PYRROLIDINE-2,5-DIONE

Prepared using the procedure in Example 93 except using succinimide instead of pyrrole. MS (ESI) m/z 595.

EXAMPLE 98

PHENYL[4-[3-(PROP-2-YNYLOXY)PHENYL]-8-(TRIFLUOROMETHYL)QUINOLIN-3-YL]METHANONE

The title compound was prepared from propargyl bromide followed the procedure of Example 43. MS (ESI) m/z 432.

EXAMPLE 99

[4-({3-[3-BENZYL-8-(TRIFLUOROMETHYL)QUINOLIN-4-YL]PHENOXY}METHYL)PHENYL]ACETIC ACID

Prepared using the procedure in Example 56 except using 3-[3-benzyl-8-(trifluoromethyl)quinolin-4-yl]phenol instead of 4-(3-hydroxyphenyl)-8-(trifluoromethyl) quinolin-3-yl] (phenyl)methanone and 4-bromomethyl-phenyl)-acetic acid ethyl ester as the halide. MS (ESI) m/z 528.

EXAMPLE 100

[3-({3-[3-BENZYL-8-(TRIFLUOROMETHYL)QUINOLIN-4-YL]PHENOXY}METHYL)PHENYL]ACETIC ACID

Prepared using the procedure in Example 56 except using 3-[3-benzyl-8-(trifluoromethyl)quinolin-4-yl]phenol instead of 4-(3-hydroxyphenyl)-8-(trifluoromethyl) quinolin-3-yl] (phenyl)methanone and 3-bromomethyl-phenyl)-acetic acid ethyl ester as the halide. MS (ES) m/z 526.

EXAMPLE 101

3-[4-({3-[3-BENZOYL-8-(TRIFLUOROMETHYL)QUINOLIN-4-YL]BENZYL}OXY)PHENYL]PROPANOIC ACID

This compound was made using the same procedure as example 69 but using 3-(4-Hydroxy-phenyl)-propionic acid methyl ester as the phenol; MS m/z 556.

EXAMPLE 102

3-[3-BENZOYL-8-(TRIFLUOROMETHYL)QUINOLIN-4-YL]PHENYL PHENYLCARBAMATE

A solution of [4-(3-hydroxyphenyl)-8-(trifluoromethyl)quinolin-3-yl](phenyl) methanone(Example 42) (0.20 g, 0.5 mmol), phenyl isocyanate(0.2 g, 1.7 mmol) and TEA(1 ml) in acetonitrile(5 ml) was stirred at r.t. After 20 hr the reaction was concentrated and the oil was purified by column chromatography (eluent 20% EtOAc/Hex) to give the title compound as a white foam (0.12 g); MS (ES) m/z 512.9.

EXAMPLE 103

4-(3-{3-[3-BENZOYL-8-(TRIFLUOROMETHYL)QUINOLIN-4-YL]PHENOXY}PROP-1-YNYL)BENZOIC ACID

A solution of phenyl[4-[3-(prop-2-ynyloxy)phenyl]-8-(trifluoromethyl)quinolin-3-yl]methanone (Example 21)(0.3 g, 0.7 mmol), methy 4-Iodobenzoate(0.22 g, 0.84 mmol), and $PdCl_2(PPh_3)_2$(0.05 g), and CuI(0.03 g) in $TEA/CH_3CN$ (10 ml) was stirred at r.t. After 2 hr, the reaction was poured into 2N HCl and extracted with EtOAc. The EtOAc was dried concentrated and purified by column chromatography to give an oil (0.28 g). This oil was dissolved in THF/MeOH(5 ml) and hydrolized with 1N NaOH (1 ml) to give the title compound as a foam (0.22 g); MS (ES) m/z 549.8.

EXAMPLE 104

3-(3-{3-[3-BENZOYL-8-(TRIFLUOROMETHYL) QUINOLIN-4-YL]PHENOXY}PROP-1-YNYL) BENZOIC ACID

Prepared as in Example 103 using methy 3-Iodobenzoate instead of methy 4-Iodobenzoate. MS (ES) m/z 549.8.

EXAMPLE 105

[4-({3-[3-[HYDROXY(PHENYL)METHYL]-8-(TRIFLUOROMETHYL)QUINOLIN-4-YL] PHENOXY}METHYL)PHENYL]ACETIC ACID

Prepared as in Example 34 using 4-({3-[3-benzoyl-8-(trifluoromethyl)quinolin-4-yl]phenoxy}methyl)phenyl]acetic acid (Example 55) instead of phenyl[4-phenyl-8-(trifluoromethyl)quinolin-3-yl]methanone; MS (ES) m/z 542.1.

EXAMPLE 106

{3-[3-BENZYL-8-(TRIFLUOROMETHYL) QUINOLIN-4-YL]PHENYL}METHANOL

This compound was prepared using the procedure of Example 1, step 5 using (3-benzyl-4-bromo-8-(trifluoromethyl)quinoline in place of [4-chloro-8-(trifluoromethyl)quinolin-3-yl](phenyl)methanone and 3-(hydroxymethyl)phenylboronic acid in place of phenyl boronic acid; MS (ES) m/z 392.5.

EXAMPLE 107

{4-[({3-[3-BENZOYL-8-(TRIFLUOROMETHYL) QUINOLIN-4-YL]PHENYL}AMINO)SULFONYL]PHENYL}ACETIC ACID

This title compound was prepared from (4-chlorosulfonyl-phenyl)-acetic acid according to the procedure of Example 61. MS (ESI) m/z 591; MS (ESI) m/z 589.

EXAMPLE 108

PHENYL[4-[3-(1H-PYRROL-1-YL)PHENYL]-8-(TRIFLUOROMETHYL)QUINOLIN-3-YL] METHANONE

A mixture of [4-(3-aminophenyl)-8-(trifluoromethyl) quinolin-3-yl](phenyl)methanone (0.04 g, 0.1 mmol) and 2,5-dimethoxytetrahydrofuran (0.08 g, 0.6 mmol) in 5 mL of acetic acid was heated at 80 for 1 h. Removal of solvent under reduced pressure gave a crude product that was purified by silica gel chromatography eluting with ethyl acetate/hexanes (5% to 30%) to give 30 mg (67%) of the title compound as an off-white solid. MS (ESI) m/z 443; HRMS: calcd for $C_{27}H_{17}F_3N_2O$, 442.1293; found (ESI, [M+H]$^+$), 443.1373.

EXAMPLE 109

(4-{[{3-[3-BENZOYL-8-(TRIFLUOROMETHYL) QUINOLIN-4-YL]PHENYL}(FORMYL)AMINO] METHYL}PHENYL)ACETIC ACID

A mixture of methyl {4-[({3-[3-benzoyl-8-(trifluoromethyl)quinolin-4-yl]phenyl}amino)methyl]phenyl}acetate (0.05 g, 0.09 mmol) in 5 mL of 96% of formic acid and 1 mL of acetic anhydride was heated under reflux for 1 h. Removal of solvent under reduced pressure gave a crude product that was used for the LiOH hydrolysis as described in Example 66. 35 Mg (68%) of the title compound was obtained as a pale yellow solid. MS (ESI) m/z 569; HRMS: calcd for $C_{33}H_{23}F_3N_2O_4$, 568.1610; found (ESI, [M−H]$^−$), 567.1543.

EXAMPLE 110

[4-(3-ANILINOPHENYL)-8-(TRIFLUOROMETHYL)QUINOLIN-3-YL] (PHENYL)METHANONE

Phenylboronic acid (0.12 g, 1.0 mmol), Cu(OAc)$_2$ (0.036 g, 0.2 mmol), and myristic acid (0.046 g, 0.2 mmol) were combined in a 100-mL round-bottom flask with a large stir bar. A rubber septum was attached, and dry toluene (2 mL), 2,6-lutidine (0.116 mL, 1.0 mmol), and {4-[({3-[3-benzoyl-8-(trifluoromethyl)quinolin-4-yl]phenyl}amino)methyl] phenyl}acetate (0.045 g, 0.09 mmol) were successively added. The resulting mixture was stirred at a high rate for 24 h, diluted with ethyl acetate (10 mL), filtered through a plug of silica gel, and then purified by semi-preparative HPLC (Column: Phenomenex C18 Luna 21.6 mm×60 mm, 5 μM; Solvent A: Water (0.1% TFA buffer); Solvent B: Acetonitrile (0.1% TFA buffer); Solvent Gradient: Time 0: 0% B; 10 min: 100% B; Hold 100% B 5 min. Flow Rate: 22.5 mL/min). The product was collected based on UV absorption and concentrated to give the title compound as a yellow solid (0.05 g, 94%). MS (ESI) m/z 469; MS (ESI) m/z 467; HRMS: calcd for $C_{29}H_{19}F_3N_2O$, 468.1449; found (ESI, [M−H]$^−$), 467.1362; Anal. Calcd for $C_{29}H_{19}F_3N_2O$: C, 74.35; H, 4.09; N, 5.98. Found: C, 74.27; H, 3.72; N, 5.82.

EXAMPLE 111

[4-[3-(BENZYLAMINO)PHENYL]-8-(TRIFLUOROMETHYL)QUINOLIN-3-YL](PHENYL) METHANONE

The title compound was prepared from benzaldehyde according to the procedure of Example 66. MS (ESI) m/z 483.

EXAMPLE 112

{3-[3-BENZYL-8-(TRIFLUOROMETHYL) QUINOLIN-4-YL]PHENYL}AMINE

The title compound was prepared from of [4-(3-aminophenyl)-8-(trifluoromethyl) quinolin-3-yl](phenyl)methanone according to the procedure of Example 31. MS (ESI) m/z 379.

EXAMPLE 113

2-{4-[({3-[3-BENZOYL-8-(TRIFLUOROMETHYL)QUINOLIN-4-YL]PHENYL}AMINO) METHYL]PHENYL}ACETAMIDE

A mixture of methyl {4-[({3-[3-benzoyl-8-(trifluoromethyl)quinolin-4-yl]phenyl}amino)methyl]phenyl}acetate (0.06 g, 0.11 mmol) in 25 mL of 28% of ammonium hydroxide and 5 mL of methanol was stirred at room temperature for 2 days. Removal of solvent under reduced pressure gave a crude product that was purified by semi-preparative HPLC. 15 Mg of the title compound was isolated (25%) as a pale yellow solid. MS (ESI) m/z 540.

EXAMPLE 114

{4-[({3-[3-BENZYL-8-(TRIFLUOROMETHYL)
QUINOLIN-4-YL]PHENYL}AMINO)METHYL]
PHENYL}ACETIC ACID

The title compound was prepared from {4-[({3-[3-benzoyl-8-(trifluoromethyl)quinolin-4-yl]phenyl}amino)methyl]phenyl}acetate according to the procedure of Example 31. MS (ESI) m/z 527.

EXAMPLE 115

[4-({3-[3-BENZOYL-8-(TRIFLUOROMETHYL)
QUINOLIN-4-YL]BENZYL}AMINO)PHENYL]
ACETIC ACID

The title compound was prepared from 3-[3-benzoyl-8-(trifluoromethyl)quinolin-4-yl]benzaldehyde and (4-aminophenyl)-acetic acid ethyl ester according to the procedure of Example 66. MS m/z 541.

EXAMPLE 116

3-[3-BENZOYL-8-(TRIFLUOROMETHYL)
QUINOLIN-4-YL]BENZALDEHYDE

The title compound was prepared from 3-formyl phenylboronic acid according to the procedure of Example 60. HRMS: calcd for $C_{24}H_{14}F_3NO_2$, 405.0977; found (ESI, [M+H]$^+$), 406.1042; Anal. Calcd for $C_{24}H_{14}F_3NO_2$: C, 71.11; H, 3.48; N, 3.46. Found: C, 71.23; H, 3.17; N, 3.28.

EXAMPLE 117

4-({3-[3-BENZOYL-8-(TRIFLUOROMETHYL)
QUINOLIN-4-YL]BENZYL}AMINO)BENZOIC
ACID

The title compound was prepared from 3-[3-benzoyl-8-(trifluoromethyl)quinolin-4-yl]benzaldehyde and 4-aminobenzoic acid ethyl ester according to the procedure of Example 66. MS m/z 527; MS m/z 525.

EXAMPLE 118

4-[({3-[3-BENZOYL-8-(TRIFLUOROMETHYL)
QUINOLIN-4-YL]BENZYL}AMINO)METHYL]
BENZOIC ACID

The title compound was prepared from 3-[3-benzoyl-8-(trifluoromethyl)quinolin-4-yl]benzaldehyde and 4-aminomethyl-benzoic acid ethyl ester according to the procedure of Example 66. MS m/z 541; MS m/z 539.

EXAMPLE 119

[3-({3-[3-BENZOYL-8-(TRIFLUOROMETHYL)
QUINOLIN-4-YL]BENZYL}AMINO)PHENYL]
ACETIC ACID

The title compound was prepared from 3-[3-benzoyl-8-(trifluoromethyl)quinolin-4-yl]benzaldehyde and (4-aminophenyl)-acetic acid according to the procedure of Example 66. HRMS: calcd for $C_{32}H_{23}F_3N_2O_3$, 540.1661; found (ESI, [M−H]$^−$), 539.1594.

EXAMPLE 120

METHYL (4-{[{3-[3-BENZOYL-8-(TRIFLUO-
ROMETHYL)QUINOLIN-4-YL]PHENYL}(ME-
THYL)AMINO]METHYL}PHENYL)ACETATE

The title compound was prepared from methyl {4-[({3-[3-benzoyl-8-(trifluoromethyl) quinolin-4-yl]phenyl}amino)methyl]phenyl}acetate and formaldehyde according to the procedure of step 1, Example 66. MS (ESI) m/z 569; HRMS: calcd for $C_{34}H_{27}F_3N_2O_3$, 568.1974; found (ESI, [M+H]$^+$), 569.2039; Anal. Calcd for $C_{34}H_{27}F_3N_2O_3$: C, 71.82; H, 4.79; N, 4.93. Found: C, 71.57; H, 4.64; N, 4.87.

EXAMPLE 121

4-[({3-[3-BENZOYL-8-(TRIFLUOROMETHYL)
QUINOLIN-4-YL]PHENYL}AMINO)METHYL]
BENZOIC ACID

The title compound was prepared from [4-(3-aminophenyl)-8-(trifluoromethyl)quinolin-3-yl](phenyl)methanone and 4-formyl-benzoic acid methyl ester according to the procedure of Example 66. MS (ESI) m/z 527.

EXAMPLE 122

3-[({3-[3-BENZOYL-8-(TRIFLUOROMETHYL)
QUINOLIN-4-YL]PHENYL}AMINO)METHYL]-
1H-INDOLE-6-CARBOXYLIC ACID

The title compound was prepared from [4-(3-aminophenyl)-8-(trifluoromethyl)quinolin-3-yl](phenyl)methanone and 3-formyl-1H-indole-6-carboxylic acid methyl ester according to the procedure of Example 66. MS (ESI) m/z 564.

EXAMPLE 123

[4-({[3-(3-BENZOYL-8-METHYLQUINOLIN-4-
YL)PHENYL]AMINO}METHYL)PHENYL]ACE-
TIC ACID

The title compound was prepared from [4-(3-amino-phenyl)-8-methyl-quinolin-3-yl]-phenyl-methanone and (4-formyl-phenyl)-acetic acid methyl ester according to the procedure of Example 66. MS (ESI) m/z 487; MS (ESI) m/z 485.

EXAMPLE 124

[4-(4-AMINOPHENYL)-8-(TRIFLUOROM-
ETHYL)QUINOLIN-3-YL](PHENYL)METHA-
NONE

The title compound was prepared from 4-aminophenylboronic acid according to the procedure of Example 60. HRMS: calcd for $C_{23}H_{15}F_3N_2O$, 392.1136; found (ESI, [M+H]$^+$), 393.1206.

EXAMPLE 125

2-{4-[({3-[3-BENZYL-8-(TRIFLUOROMETHYL)
QUINOLIN-4-YL]PHENYL}AMINO)METHYL]
PHENYL}ACETOHYDRAZIDE

The title compound was prepared from {4-[({3-[3-benzoyl-8-(trifluoromethyl)quinolin-4-yl]phenyl}amino)methyl]phenyl} acetic acid according to the procedure of Example 31. MS (ESI) m/z 541; HRMS: calcd for $C_{32}H_{27}F_3N_4O$, 540.2137; found (ESI, [M+H]$^+$), 541.2236.

EXAMPLE 126

{4-[({4-[3-BENZOYL-8-(TRIFLUOROMETHYL) QUINOLIN-4-YL]PHENYL}AMINO)METHYL] PHENYL}ACETIC ACID

The title compound was prepared from [4-(4-amino-phenyl)-8-methyl-quinolin-3-yl]-phenyl-methanone and (4-formyl-phenyl)-acetic acid methyl ester according to the procedure of Example 66. MS (ESI) m/z 541; MS (ESI) m/z 539.

EXAMPLE 127

N-{3-[3-BENZOYL-8-(TRIFLUOROMETHYL) QUINOLIN-4-YL]PHENYL}-N'-(2,4-DIFLUO-ROPHENYL)UREA

The title compound was prepared from 2,4-difluorophenyl isocyanate according to the procedure of Example 65. MS (ES) m/z 546.2.

EXAMPLE 128

N-{3-[3-BENZOYL-8-(TRIFLUOROMETHYL) QUINOLIN-4-YL]PHENYL}-N'-(2-FLUOROPHE-NYL)UREA

The title compound was prepared from 2-fluorophenyl isocyanate according to the procedure of Example 65. MS (ES) m/z 528.2.

EXAMPLE 129

N-{3-[3-BENZOYL-8-(TRIFLUOROMETHYL) QUINOLIN-4-YL]PHENYL}-N'-(4-FLUOROPHE-NYL)UREA

The title compound was prepared from 4-fluorophenyl isocyanate according to the procedure of Example 65. HRMS: calcd for $C_{30}H_{19}F_4N_3O_2$, 529.1413; found (ESI, [M+H]$^+$), 530.1506.

EXAMPLE 130

N-{3-[3-BENZOYL-8-(TRIFLUOROMETHYL) QUINOLIN-4-YL]PHENYL}-N'-(4-CYANOPHE-NYL)UREA

The title compound was prepared from 4-cyanofluorophenyl isocyanate according to the procedure of Example 65. MS (ES) m/z 535.2.

EXAMPLE 131

N-{3-[3-BENZOYL-8-(TRIFLUOROMETHYL) QUINOLIN-4-YL]PHENYL}-N'-[4-(METH-YLTHIO)PHENYL]UREA

The title compound was prepared from 4-methylthiophenyl isocyanate according to the procedure of Example 65. MS (ES) m/z 556.2.

EXAMPLE 132

N-{3-[3-BENZOYL-8-(TRIFLUOROMETHYL) QUINOLIN-4-YL]PHENYL}-N'-(2-METHYLPHE-NYL)UREA

The title compound was prepared from 2-methylphenyl isocyanate according to the procedure of Example 65. HRMS: calcd for $C_{31}H_{22}F_3N_3O_2$, 525.1664; found (ESI, [M+H]$^+$), 526.1735.

EXAMPLE 133

N-{3-[3-BENZOYL-8-(TRIFLUOROMETHYL) QUINOLIN-4-YL]PHENYL}-N'-(2,6-DICHLO-ROPHENYL)UREA

The title compound was prepared from 2,6-dichlorophenyl isocyanate according to the procedure of Example 65. HRMS: calcd for $C_{30}H_{18}Cl_2F_3N_3O_2$, 579.0728; found (ESI, [M+H]$^+$), 580.0793.

EXAMPLE 134

N-{3-[3-BENZOYL-8-(TRIFLUOROMETHYL) QUINOLIN-4-YL]PHENYL}-N'-(2,6-DIMETH-YLPHENYL) UREA

The title compound was prepared from 2,6-dimethylphenyl isocyanate according to the procedure of Example 65. HRMS: calcd for $C_{32}H_{24}F_3N_3O_2$, 539.1821; found (ESI, [M+H]$^+$), 540.1895.

EXAMPLE 135

N-{3-[3-BENZOYL-8-(TRIFLUOROMETHYL) QUINOLIN-4-YL]PHENYL}-N'-(3-METHOX-YPHENYL)UREA

The title compound was prepared from 3-methoxyphenyl isocyanate according to the procedure of Example 65. HRMS: calcd for $C_{31}H_{22}F_3N_3O_3$, 541.1613; found (ESI, [M+H]$^+$), 542.1719.

EXAMPLE 136

N-(3-Acetylphenyl)-N'-{3-[3-Benzoyl-8-(Trifluoromethyl)Quinolin-4-yl]Phenyl}Urea The title compound was prepared from 3-acetylphenyl isocyanate according to the procedure of Example 65. HRMS: calcd for $C_{32}H_{22}F_3N_3O_3$, 553.1613; found (ESI, [M+H]$^+$), 554.1678.

EXAMPLE 137

N-{3-[3-BENZOYL-8-(TRIFLUOROMETHYL) QUINOLIN-4-YL] PHENYL}-N'-[4-(DIMETHY-LAMINO)PHENYL]UREA

The title compound was prepared from 4-dimethylaminophenyl isocyanate according to the procedure of Example 65. HRMS: calcd for $C_{32}H_{25}F_3N_4O_2$ 554.5617; found (ESI, [M+H]$^+$), 555.2007.

EXAMPLE 138

N-{3-[3-BENZOYL-8-(TRIFLUOROMETHYL)QUINOLIN-4-YL]PHENYL}-N'-(4-NITROPHENYL)UREA

The title compound was prepared from 4-nitrophenylphenyl isocyanate according to the procedure of Example 65. HRMS: calcd for $C_{30}H_{19}F_3N_4O_4$, 556.1358; found (ESI, [M+H]$^+$), 557.1452.

EXAMPLE 139

N-{3-[3-BENZOYL-8-(TRIFLUOROMETHYL)QUINOLIN-4-YL]PHENYL}-N'-(4-PHENOXYPHENYL)UREA

The title compound was prepared from 4-phenoxyphenyl isocyanate according to the procedure of Example 65. HRMS: calcd for $C_{36}H_{24}F_3N_3O_3$, 603.1770; found (ESI, [M+H]$^+$), 604.1873.

EXAMPLE 140

N-{3-[3-BENZOYL-8-(TRIFLUOROMETHYL)QUINOLIN-4-YL]PHENYL}-N'-CYCLOHEXYLUREA

The title compound was prepared from cyclohexyl isocyanate according to the procedure of Example 65. MS (ES) m/z 516.2;

EXAMPLE 141

N-[({3-[3-BENZOYL-8-(TRIFLUOROMETHYL)QUINOLIN-4-YL]PHENYL}AMINO)CARBONYL]BENZAMIDE

The title compound was prepared from benzoyl isocyanate according to the procedure of Example 65. MS (ES) m/z 538.2.

EXAMPLE 142

N-[({3-[3-BENZOYL-8-(TRIFLUOROMETHYL)QUINOLIN-4-YL]PHENYL}AMINO)CARBONYL]BENZENESULFONAMIDE

The title compound was prepared from benzenesulfonyl isocyanate according to the procedure of Example 65. MS (ES) m/z 576.

EXAMPLE 143

N-{3-[3-BENZOYL-8-(TRIFLUOROMETHYL)QUINOLIN-4-YL]PHENYL}-N'-(3-FLUOROPHENYL)UREA

The title compound was prepared from 3-fluorophenyl isocyanate according to the procedure of Example 65. HRMS: calcd for $C_{30}H_{19}F_4N_3O_2$, 529.1413; found (ESI, [M+H]$^+$), 530.1515.

EXAMPLE 144

N-{3-[3-BENZOYL-8-(TRIFLUOROMETHYL)QUINOLIN-4-YL]PHENYL}-N'-BUTYLUREA

The title compound was prepared from n-butyl isocyanate according to the procedure of Example 65. MS (ES) m/z 490.3.

EXAMPLE 145

N-{3-[3-BENZOYL-8-(TRIFLUOROMETHYL)QUINOLIN-4-YL]PHENYL}-N'-BENZYLUREA

The title compound was prepared from benzyl isocyanate according to the procedure of Example 65. MS (ES) m/z 524.2.

EXAMPLE 146

N-ALLYL-N'-{3-[3-BENZOYL-8-(TRIFLUOROMETHYL)QUINOLIN-4-YL]PHENYL}UREA

The title compound was prepared from allyl isocyanate according to the procedure of Example 65. MS (ES) m/z 474.2.

EXAMPLE 147

N-{3-[3-BENZOYL-8-(TRIFLUOROMETHYL)QUINOLIN-4-YL]PHENYL}-N'-(4-FLUOROPHENYL) THIOUREA

The title compound was prepared from phenyl isothiocyanate according to the procedure of Example 65. MS (ES) m/z 544.2.

EXAMPLE 148

(4-{[({3-[3-BENZOYL-8-(TRIFLUOROMETHYL)QUINOLIN-4-YL]PHENYL}AMINO)CARBONYL]AMINO}PHENYL)ACETIC ACID

The title compound was prepared from (4-isocyanato-phenyl)-acetic acid ethyl ester according to the procedure of Example 65 followed by LiOH hydrolysis. HRMS: calcd for $C_{32}H_{22}F_3N_3O_4$, 569.1562; found (ESI, [M+H]$^+$), 570.1636.

EXAMPLE 149

(4-{[[3-(3-BENZOYL-8-METHYLQUINOLIN-4-YL)PHENYL](METHYL)AMINO]METHYL}PHENYL) ACETIC ACID

The title compound was prepared from (4-{[3-(3-benzoyl-8-methyl-quinolin-4-yl)-phenylamino]-methyl}-phenyl)-acetic acid methyl ester according to the procedure of Example 66. MS (ES) m/z 501.3.

EXAMPLE 150

{4-[3-(DIMETHYLAMINO)PHENYL]-8-METHYLQUINOLIN-3-YL}(PHENYL)METHANONE

The title compound was prepared from [4-(3-amino-phenyl)-8-methyl-quinolin-3-yl]-phenyl-methanone and formaldehyde according to the procedure of Example 66. MS (ES)

m/z 367.3; HRMS: calcd for $C_{25}H_{22}N_2O$, 366.1732; found (ESI, [M+H]$^+$), 367.1797; Anal. Calcd for $C_{25}H_{22}N_2O$: C, 81.94; H, 6.05; N, 7.64. Found: C, 81.71; H, 5.89; N, 7.56.

EXAMPLE 151

[4-({[3-(3-BENZYL-8-METHYLQUINOLIN-4-YL) PHENYL]AMINO}METHYL)PHENYL]ACETIC ACID

The title compound was prepared from [4-(3-amino-phenyl)-8-methyl-quinolin-3-yl]-phenyl-methanone and (4-formyl-phenyl)-acetic acid methyl ester according to the procedure of Example 66. MS (ES) m/z 473.3.

EXAMPLE 152

PHENYL[4-(3-{[(2-PHENYLETHYL)AMINO] METHYL}PHENYL)-8-(TRIFLUOROMETHYL) QUINOLIN-3-YL]METHANONE

The title compound was prepared from 3-[3-benzoyl-8-(trifluoromethyl)quinolin-4-yl]benzaldehyde and phenethylamine according to the procedure of Example 66. MS (ES) m/z 511.3.

EXAMPLE 153

PHENYL[4-(3-{[(PYRIDIN-4-YLMETHYL) AMINO]METHYL}PHENYL)-8-(TRIFLUOROMETHYL) QUINOLIN-3-YL]METHANONE

The title compound was prepared from 3-[3-benzoyl-8-(trifluoromethyl)quinolin-4-yl]benzaldehyde and 4-aminopyridine according to the procedure of Example 66. MS (ES) m/z 498.2.

EXAMPLE 154

[4-(3-{[(2-METHYLPHENYL)AMINO] METHYL}PHENYL)-8-(TRIFLUOROMETHYL) QUINOLIN-3-YL](PHENYL)METHANONE

The title compound was prepared from 3-[3-benzoyl-8-(trifluoromethyl)quinolin-4-yl]benzaldehyde and 2-methylaniline according to the procedure of Example 66. MS (ES) m/z 497.3.

EXAMPLE 155

PHENYL[4-(3-{[(TETRAHYDROFURAN-2-YLMETHYL)AMINO]METHYL}PHENYL)-8-(TRIFLUOROMETHYL) QUINOLIN-3-YL]METHANONE

The title compound was prepared from 3-[3-benzoyl-8-(trifluoromethyl)quinolin-4-yl]benzaldehyde and (tetrahydro-furan-2-yl)-methylamine according to the procedure of Example 66. MS (ES) m/z 491.2.

EXAMPLE 156

[4-(3-{[(2-METHOXYBENZYL)AMINO] METHYL}PHENYL)-8-(TRIFLUOROMETHYL) QUINOLIN-3-YL](PHENYL)METHANONE

The title compound was prepared from 3-[3-benzoyl-8-(trifluoromethyl)quinolin-4-yl]benzaldehyde and 2-methoxy-benzylamine according to the procedure of Example 66. MS (ES) m/z 527.2.

EXAMPLE 157

[4-(3-{[(4-METHOXYBENZYL)AMINO] METHYL}PHENYL)-8-(TRIFLUOROMETHYL) QUINOLIN-3-YL](PHENYL)METHANONE

The title compound was prepared from 3-[3-benzoyl-8-(trifluoromethyl)quinolin-4-yl]benzaldehyde and 4-methoxy-benzylamine according to the procedure of Example 66. MS (ES) m/z 527.2.

EXAMPLE 158

[4-[3-({[2-(METHYLTHIO)BENZYL] AMINO}METHYL)PHENYL]-8-(TRIFLUOROMETHYL)QUINOLIN-3-YL](PHENYL)METHANONE

The title compound was prepared from 3-[3-benzoyl-8-(trifluoromethyl)quinolin-4-yl]benzaldehyde and 2-methylthio benzylamine according to the procedure of Example 66. MS (ES) m/z 543.2.

EXAMPLE 159

(4-{[{3-[3-BENZYL-8-(TRIFLUOROMETHYL) QUINOLIN-4-YL]PHENYL}(METHYL)AMINO] METHYL}PHENYL)ACETIC ACID

The title compound was prepared from (4-{[3-(3-benzyl-8-trifluoromethyl-quinolin-4-yl)-phenylamino]-methyl}-phenyl)-acetic acid methyl ester and formaldehyde according to the procedure of Example 66. MS (ES) m/z 541.3.

EXAMPLE 160

PHENYL[4-(3-{[(2-PYRIDIN-2-YLETHYL) AMINO]METHYL}PHENYL)-8-(TRIFLUOROMETHYL) QUINOLIN-3-YL]METHANONE

The title compound was prepared from 3-[3-benzoyl-8-(trifluoromethyl)quinolin-4-yl]benzaldehyde and 2-pyridin-2-yl-ethylamine according to the procedure of Example 66. MS m/z 512.

EXAMPLE 161

[4-(3-{[(2-METHOXYETHYL)AMINO] METHYL}PHENYL)-8-(TRIFLUOROMETHYL) QUINOLIN-3-YL](PHENYL)METHANONE

The title compound was prepared from 3-[3-benzoyl-8-(trifluoromethyl)quinolin-4-yl]benzaldehyde and 2-methoxy-ethylamine according to the procedure of Example 66. MS m/z 465.

EXAMPLE 162

5-[({3-[3-BENZOYL-8-(TRIFLUOROMETHYL) QUINOLIN-4-YL]PHENYL}AMINO)METHYL]-2-HYDROXYBENZOIC ACID

The title compound was prepared from [4-(3-Aminophenyl)-8-(trifluoromethyl)quinolin-3-yl](phenyl)methanone and 4-formyl-2-hydroxy-benzoic acid according to the procedure of Example 66. MS (ESI) m/z 543.

EXAMPLE 163

{3-[({3-[3-BENZOYL-8-(TRIFLUOROMETHYL) QUINOLIN-4-YL]PHENYL}AMINO)METHYL] PHENOXY}ACETIC ACID

The title compound was prepared from [4-(3-aminophenyl)-8-(trifluoromethyl)quinolin-3-yl](phenyl)methanone and (3-formyl-phenoxy)-acetic acid according to the procedure of Example 66. MS (ESI) m/z 557.

EXAMPLE 164

{4-[({3-[3-BENZOYL-8-(TRIFLUOROMETHYL) QUINOLIN-4-YL]PHENYL}AMINO)METHYL] PHENOXY}ACETIC ACID

The title compound was prepared from [4-(3-aminophenyl)-8-(trifluoromethyl)quinolin-3-yl](phenyl)methanone and (4-formyl-phenoxy)-acetic acid according to the procedure of Example 66. MS (ESI) m/z 557.

EXAMPLE 165

(2E)-3-{4-[({3-[3-BENZOYL-8-(TRIFLUOROMETHYL)QUINOLIN-4-YL]PHENYL}AMINO) METHYL]PHENYL}ACRYLIC ACID

The title compound was prepared from [4-(3-aminophenyl)-8-(trifluoromethyl)quinolin-3-yl](phenyl)methanone and 3-(4-formyl-phenyl)-acrylic acid according to the procedure of Example 66. MS (ESI) m/z 553.

EXAMPLE 166

PHENYL[4-(3-{[(PIPERIDIN-4-YLMETHYL) AMINO]METHYL}PHENYL)-8-(TRIFLUOROMETHYL) QUINOLIN-3-YL]METHANONE

The title compound was prepared from 3-[3-benzoyl-8-(trifluoromethyl)quinolin-4-yl]benzaldehyde and C-piperidin-4-yl-methylamine according to the procedure of Example 66. MS (ESI) m/z 504.

EXAMPLE 167

{4-[({3-[3-[HYDROXY(PHENYL)METHYL]-8-(TRIFLUOROMETHYL)QUINOLIN-4-YL] PHENYL}AMINO) METHYL]PHENYL}ACETIC ACID

The title compound was prepared from (4-{[3-(3-benzoyl-8-trifluoromethyl-quinolin-4-yl)-phenylamino]-methyl}-phenyl)-acetic acid according to the procedure of Example 34. MS (ES) m/z 541.2.

EXAMPLE 168

ETHYL{4-[({3-[3-BENZOYL-8-(TRIFLUOROMETHYL)QUINOLIN-4-YL]PHENYL}AMINO) METHYL]PHENYL}(HYDROXY)ACETATE

Step 1: A mixture of (4-cyano-phenyl)-oxo-acetic acid ethyl ester 0.41 g, 2.0 mmol) in 25 mL of 90% formic acid and a large excess of Raney nickel (50% slurry in water) was refluxed for 1 hr. The solid was filtered off and the liquid was concentrated. The crude material was purified by silica gel chromatography (5~100% ethyl acetate/hexane) to give 0.35 g of (4-formyl-phenyl)-hydroxy-acetic acid ethyl ester as an oil.

Step 2: The title compound was prepared from [4-(3-amino-phenyl)-8-trifluoromethyl-quinolin-3-yl]-phenyl-methanone and (4-formyl-phenyl)-hydroxy-acetic acid ethyl ester according to the procedure of step 1, Example 66. MS (ES) m/z 585.3.

EXAMPLE 169

{4-[({3-[3-BENZOYL-8-(TRIFLUOROMETHYL) QUINOLIN-4-YL]PHENYL}AMINO)METHYL] PHENYL}(HYDROXY)ACETIC ACID

The title compound was prepared from ethyl {4-[({3-[3-benzoyl-8-(trifluoromethyl) quinolin-4-yl]phenyl}amino) methyl]phenyl}(hydroxy)acetate according to the procedure of step 2, Example 66. MS (ES) m/z 555.2.

EXAMPLE 170

ETHYL{4-[({3-[3-BENZOYL-8-(TRIFLUOROMETHYL)QUINOLIN-4-YL]PHENYL}AMINO) METHYL]PHENYL}(DIFLUORO)ACETATE

Step 1: A mixture of (4-cyano-phenyl)-oxo-acetic acid ethyl ester 1.0 g, 4.9 mmol) in 20 mL of dichloromethane and (diethylamino)sulfur trifluoride (DAST) (1.0 g, 6.2 mmol) was stirred at r.t. for 3 hrs. The mixture was poured into iced water and extracted with ethyl acetate. The organics were dried over $MgSO_4$ and concentrated to give crude (4-cyano-phenyl)-difluoro-acetic acid ethyl ester which was used for the reaction.

Step 2: Difluoro-(4-formyl-phenyl)-acetic acid ethyl ester was prepared from (4-cyano-phenyl)-difluoro-acetic acid ethyl ester by Raney nickel reduction.

Step 3: The title compound was prepared from [4-(3-amino-phenyl)-8-trifluoromethyl-quinolin-3-yl]-phenyl-methanone and difluoro-(4-formyl-phenyl)-acetic acid ethyl ester according to the procedure of step 1, Example 66. MS (ES) m/z 605.3.

EXAMPLE 171

{4-[({3-[3-BENZOYL-8-(TRIFLUOROMETHYL) QUINOLIN-4-YL]PHENYL}AMINO)METHYL] PHENYL}(DIFLUORO)ACETIC ACID

The title compound was prepared from ethyl {4-[({3-[3-benzoyl-8-(trifluoromethyl) quinolin-4-yl]phenyl}amino) methyl]phenyl}(difluoro)acetate according to the procedure of step 2, Example 66. MS (ES) m/z 575.2.

EXAMPLE 172

[4-({[3-(3-BENZOYL-8-CHLOROQUINOLIN-4-YL)PHENYL]AMINO}METHYL)PHENYL]ACETIC ACID

The title compound was prepared from [4-(3-amino-phenyl)-8-chloro-quinolin-3-yl]-phenyl-methanone and (4-formyl-phenyl)-acetic acid methyl ester according to the procedure of Example 66. MS (ESI) m/z 507.

EXAMPLE 173

[3-({[3-(3-BENZOYL-8-CHLOROQUINOLIN-4-YL)PHENYL]AMINO}METHYL)PHENYL]ACETIC ACID

The title compound was prepared from [4-(3-amino-phenyl)-8-chloro-quinolin-3-yl]-phenyl-methanone and (3-formyl-phenyl)-acetic acid methyl ester according to the procedure of Example 66. MS (ESI) m/z 507.

EXAMPLE 174

{3-[({3-[3-BENZYL-8-(TRIFLUOROMETHYL)QUINOLIN-4-YL]PHENYL}AMINO)METHYL]PHENYL}ACETIC ACID

The title compound was prepared from ethyl (3-{[3-(3-benzoyl-8-trifluoromethyl-quinolin-4-yl)-phenylamino]-methyl}-phenyl)-acetate according to the procedure of Example 31. MS (ESI) m/z 527; MS (ESI) m/z 525.

EXAMPLE 175

(3-{[(3-{8-CHLORO-3-[HYDROXY(PHENYL)METHYL]QUINOLIN-4-YL}PHENYL)AMINO]METHYL}PHENYL)ACETIC ACID

The title compound was prepared from [4-({[3-(3-benzoyl-8-chloroquinolin-4-yl)phenyl]amino}methyl)phenyl] acetic acid according to the procedure of Example 34. MS m/z 509.

EXAMPLE 176

(4-{[(3-{3-[HYDROXY(PHENYL)METHYL]-8-METHYLQUINOLIN-4-YL}PHENYL)AMINO]METHYL}PHENYL)ACETIC ACID

The title compound was prepared from (4-{[3-(3-benzoyl-8-methyl-quinolin-4-yl)-phenylamino]-methyl}-phenyl)-acetic acid according to the procedure of Example 34. MS m/z 489.

EXAMPLE 177

[4-({[3-(3-BENZYL-8-CHLOROQUINOLIN-4-YL)PHENYL]AMINO}METHYL)PHENYL]ACETIC ACID

The title compound was prepared from ethyl (3-{[3-(3-benzoyl-8-chloroquinolin-4-yl)-phenylamino]-methyl}-phenyl)-acetate according to the procedure of Example 31. MS (ESI) m/z 493.

EXAMPLE 178

2-{4-[({3-[3-BENZOYL-8-(TRIFLUOROMETHYL)QUINOLIN-4-YL]PHENYL}AMINO)METHYL]PHENYL}-2-METHYLPROPANOIC ACID

The title compound was prepared from [4-(3-amino-phenyl)-8-trifluoromethyl-quinolin-3-yl]-phenyl-methanone and 2-(4-formyl-phenyl)-2-methyl-propionic acid methyl ester according to the procedure of Example 66. MS m/z 569; MS m/z 567.

EXAMPLE 179

2-{4-[({3-[3-BENZYL-8-(TRIFLUOROMETHYL)QUINOLIN-4-YL]PHENYL}AMINO)METHYL]PHENYL}-2-METHYLPROPANOIC ACID

The title compound was prepared from [4-(3-amino-phenyl)-8-trifluoromethyl-quinolin-3-yl]-phenyl-methanone and 2-(4-formyl-phenyl)-propionic acid methyl ester according to the procedure of Example 66. HRMS: calcd for $C_{34}H_{29}F_3N_2O_2$, 554.2181; found (ESI, [M+H]$^+$), 555.2247.

EXAMPLE 180

2-{4-[({3-[3-BENZOYL-8-(TRIFLUOROMETHYL)QUINOLIN-4-YL]PHENYL}AMINO)METHYL]PHENYL}PROPANOIC ACID

The title compound was prepared from [4-(3-amino-phenyl)-8-trifluoromethyl-quinolin-3-yl]-phenyl-methanone and 2-(4-formyl-phenyl)-propionic acid methyl ester according to the procedure of Example 66. MS (ESI) m/z 555.

EXAMPLE 181

2-{4-[({3-[3-BENZYL-8-(TRIFLUOROMETHYL)QUINOLIN-4-YL]PHENYL}AMINO)METHYL]PHENYL}PROPANOIC ACID

The title compound was prepared from 2-{4-[({3-[3-benzoyl-8-(trifluoromethyl)quinolin-4-yl]phenyl}amino)methyl]phenyl}propanoic acid methyl eater according to the procedure of Example 31. MS (ESI) m/z 541.

EXAMPLE 182

N-[({3-[3-BENZOYL-8-(TRIFLUOROMETHYL)QUINOLIN-4-YL]PHENYL}AMINO)CARBONYL]-4-METHYLBENZENESULFONAMIDE

The title compound was prepared from 4-methyl-benzenesulfonyl isocyanate according to the procedure of Example 65. MS (ESI) m/z 590; MS (ESI) m/z 588.

EXAMPLE 183

N-[({3-[3-BENZOYL-8-(TRIFLUOROMETHYL)QUINOLIN-4-YL]PHENYL}AMINO)CARBONYL]-2-CHLOROBENZENESULFONAMIDE

The title compound was prepared from 2-chloro-benzenesulfonyl isocyanate according to the procedure of Example 65. MS (ESI) m/z 608.

EXAMPLE 184

N-[({3-[3-BENZOYL-8-(TRIFLUOROMETHYL)QUINOLIN-4-Yl]Phenyl}Amino)Carbonyl]-4-Fluorobenzenesulfonamide The title compound was prepared from 4-fluoro-benzenesulfonyl isocyanate according to the procedure of Example 65. MS (ESI) m/z 594.

EXAMPLE 185

N-[({3-[3-BENZOYL-8-(TRIFLUOROMETHYL)
QUINOLIN-4-YL]PHENYL}AMINO)CARBO-
NYL]-4-CHLOROBENZENESULFONAMIDE

The title compound was prepared from 4-chloro-benzene-sulfonyl isocyanate according to the procedure of Example 65. MS (ESI) m/z 610.

EXAMPLE 186

4-[4-({3-[3-BENZOYL-8-(TRIFLUOROMETHYL)
QUINOLIN-4-YL]BENZYL}AMINO)PHENYL]
BUTANOIC ACID

The title compound was prepared from 3-[3-benzoyl-8-(trifluoromethyl)quinolin-4-yl]benzaldehyde and 4-(4-amino-phenyl)-butyric acid according to the procedure of Example 66. MS (ES) m/z 567.0.

EXAMPLE 187

3-[4-({3-[3-BENZOYL-8-(TRIFLUOROMETHYL)
QUINOLIN-4-YL]BENZYL}AMINO)PHENYL]
PROPANOIC ACID

The title compound was prepared from 3-[3-benzoyl-8-(trifluoromethyl)quinolin-4-yl]benzaldehyde and 3-(4-amino-phenyl)-propionic acid. MS (ES) m/z 552.9.

EXAMPLE 188

N'-{3-[3-BENZOYL-8-(TRIFLUOROMETHYL)
QUINOLIN-4-YL]PHENYL}-N-METHYL-N-PHE-
NYLUREA

The title compound was prepared from N-methyl-N-phenylcarbamoyl chloride according to the procedure of Example 65. MS (ES) m/z 523.9.

EXAMPLE 189

N-{3-[3-BENZOYL-8-(TRIFLUOROMETHYL)
QUINOLIN-4-YL]PHENYL}-N-METHYL-N'-
PHENYLUREA

Step 1: A solution of [4-(3-amino-phenyl)-8-trifluoromethyl-quinolin-3-yl]-phenyl-methanone (100 mg) and dimethyl sulfate (150 mg) in ethanol was stirred at r.t. for 4 hrs. The solution was concentrated and purified by semi-HPLC to give [4-(3-methylamino-phenyl)-8-trifluoromethyl-quinolin-3-yl]-phenyl-methanone as a gum.

Step 2: The title compound was prepared from [4-(3-methylamino-phenyl)-8-trifluoromethyl-quinolin-3-yl]-phenyl-methanone and phenyl isocyanate according to the procedure of Example 65. MS (ES) m/z 524.0.

EXAMPLE 190

4'-[({3-[3-BENZOYL-8-(TRIFLUOROMETHYL)
QUINOLIN-4-YL]PHENYL}AMINO)METHYL]-
1,1'-BIPHENYL-2-CARBOXYLIC ACID

The title compound was prepared from [4-(3-amino-phenyl)-8-trifluoromethyl-quinolin-3-yl]-phenyl-methanone and (4'-formyl-biphenyl-2-yl)-acetic acid according to the procedure of Example 66. MS (ES) m/z 600.9.

EXAMPLE 191

{4'-[({3-[3-BENZOYL-8-(TRIFLUOROMETHYL)
QUINOLIN-4-YL]PHENYL}AMINO)METHYL]-
1,1'-BIPHENYL-4-YL}ACETIC ACID

The title compound was prepared from [4-(3-amino-phenyl)-8-trifluoromethyl-quinolin-3-yl]-phenyl-methanone and (4'-formyl-biphenyl-4-yl)-acetic acid according to the procedure of Example 66. MS (ES) m/z 617.2.

EXAMPLE 192

4'-[({3-[3-BENZOYL-8-(TRIFLUOROMETHYL)
QUINOLIN-4-YL]PHENYL}AMINO)METHYL]-
1,1'-BIPHENYL-4-CARBOXYLIC ACID

The title compound was prepared from [4-(3-amino-phenyl)-8-trifluoromethyl-quinolin-3-yl]-phenyl-methanone and 4'-formyl-biphenyl-4-carboxylic acid according to the procedure of Example 66. MS (ES) m/z 600.9.

EXAMPLE 193

4'-[({3-[3-BENZOYL-8-(TRIFLUOROMETHYL)
QUINOLIN-4-YL]PHENYL}AMINO)METHYL]-
1,1'-BIPHENYL-3-CARBOXYLIC ACID

The title compound was prepared from [4-(3-amino-phenyl)-8-trifluoromethyl-quinolin-3-yl]-phenyl-methanone and (4'-formyl-biphenyl-3-yl)-acetic acid according to the procedure of Example 66. MS (ES) m/z 600.9.

EXAMPLE 194

[4-{3-[(1,1'-BIPHENYL-4-YLMETHYL)AMINO]
PHENYL}-8-(Trifluoromethyl)Quinolin-3-Yl](Phe-
nyl)Methanone The title compound was prepared from [4-(3-amino-phenyl)-8-trifluoromethyl-quinolin-3-yl]-phenyl-methanone and biphenyl-4-carbaldehyde according to the procedure of Example 66. MS (ES) m/z 559.2.

EXAMPLE 195

N'-{3-[3-BENZOYL-8-(TRIFLUOROMETHYL)
QUINOLIN-4-YL]PHENYL}-N,N-DIETHY-
LUREA

The title compound was prepared from diethyl carbamoyl chloride according to the procedure of Example 65. MS (ES) m/z 489.9.

EXAMPLE 196

N-{3-[3-BENZOYL-8-(TRIFLUOROMETHYL)
QUINOLIN-4-Yl]Phenyl}Morpholine-4-Carboxam-
ide The title compound was prepared from 4-morpholinecarbamoyl chloride according to the procedure of Example 65. MS (ES) m/z 503.9; HRMS: calcd for $C_{28}H_{22}F_3N_3O_3$, 505.1613; found (ESI, [M+H]$^+$), 506.1691; Anal. Calcd for C$_{28}$H$_{22}$F$_3$N$_3$O$_3$: C, 66.53; H, 4.39; N, 8.31. Found: C, 66.29; H, 4.09; N, 7.99.

EXAMPLE 197

N-{3-[3-BENZOYL-8-(TRIFLUOROMETHYL) QUINOLIN-4-Yl]Phenyl}Pyrrolidine-1-Carboxamide The title compound was prepared from 1-pyrrolidinecarbamoyl chloride according to the procedure of Example 65. MS (ES) m/z 487.9.

EXAMPLE 198

N-{3-[3-BENZOYL-8-(TRIFLUOROMETHYL) QUINOLIN-4-YL]PHENYL}-N,N'-DIMETHYL-N'-PHENYLUREA

The title compound was prepared from N-methyl-N-phenylcarbamoyl chloride according to the procedure of Example 65. MS (ES) m/z 540.1.

EXAMPLE 199

4-{4-[({3-[3-BENZOYL-8-(TRIFLUOROMETHYL)QUINOLIN-4-Yl]Phenyl}Amino)Methyl]-3-Methoxyphenoxy}Butanoic Acid The title compound was prepared from [4-(3-amino-phenyl)-8-trifluoromethyl-quinolin-3-yl]-phenyl-methanone and 4-(4-formyl-3-methoxy-phenoxy)-butyric acid according to the procedure of Example 66. MS (ESI) m/z 613.

EXAMPLE 200

N-[4-({3-[3-BENZOYL-8-(TRIFLUOROMETHYL) QUINOLIN-4-YL]BENZYL}AMINO) BENZOYL]-BETA-ALANINE

The title compound was prepared from 3-[3-benzoyl-8-(trifluoromethyl)quinolin-4-yl]benzaldehyde and 3-(4-amino-benzoylamino)-propionic acid according to the procedure of Example 66. MS (ES) m/z 595.9.

EXAMPLE 201

3-[3-({3-[3-BENZOYL-8-(TRIFLUOROMETHYL) QUINOLIN-4-YL]BENZYL}AMINO)PHENYL] PROPANOIC ACID

The title compound was prepared from 3-[3-benzoyl-8-(trifluoromethyl)quinolin-4-yl]benzaldehyde and 3-(3-3mino-phenyl)-propionic acid according to the procedure of Example 66. HRMS: calcd for C$_{33}$H$_{25}$F$_3$N$_2$O$_3$, 554.1817; found (ESI, [M+H]$^+$), 555.1881.

EXAMPLE 202

PHENYL [({3-[3-BENZOYL-8-(TRIFLUOROMETHYL)QUINOLIN-4-YL]PHENYL}AMINO) CARBONYL]CARBAMATE

The title compound was prepared from phenyl isocyanatoformate according to the procedure of Example 65. MS (ESI) m/z 556.

EXAMPLE 203

3-[3-({3-[3-BENZYL-8-(TRIFLUOROMETHYL) QUINOLIN-4-YL]BENZYL}OXY)PHENYL]PROPANOIC ACID

The title compound was prepared from [3-(3-benzyl-8-trifluoromethyl-quinolin-4-yl)-phenyl]-methanol and 3-(3-hydroxy-phenyl)-propionic acid methyl ester according to the procedure of Example 69. MS (ESI) m/z 542.

EXAMPLE 204

N-{3-[3-BENZOYL-8-(TRIFLUOROMETHYL) QUINOLIN-4-YL]PHENYL}-N'-(2-CHLOROPHENYL)UREA

The title compound was prepared from 2-chlorophenyl isocyanate according to the procedure of Example 65. HRMS: calcd for C$_{30}$H$_{19}$ClF$_3$N$_3$O$_2$, 545.1118; found (ESI, [M+H]$^+$), 546.1206.

EXAMPLE 205

N-{3-[3-BENZOYL-8-(TRIFLUOROMETHYL) QUINOLIN-4-YL]PHENYL}-N'-(2-ETHYLPHENYL)UREA

The title compound was prepared from 2-ethylhenyl isocyanate according to the procedure of Example 65. HRMS: calcd for C$_{32}$H$_{24}$F$_3$N$_3$O$_2$, 539.1821; found (ESI, [M+H]$^+$), 540.1913.

EXAMPLE 206

N-{3-[3-BENZOYL-8-(TRIFLUOROMETHYL) QUINOLIN-4-YL]PHENYL}-N'-(2,3-DICHLOROPHENYL)UREA

The title compound was prepared from 2,3-dichlorophenyl isocyanate according to the procedure of Example 65. HRMS: calcd for C$_{30}$H$_{18}$Cl$_2$F$_3$N$_3$O$_2$, 579.0728; found (ESI, [M+H]$^+$), 580.0815.

EXAMPLE 207

N-{3-[3-BENZOYL-8-(TRIFLUOROMETHYL) QUINOLIN-4-YL]PHENYL}-N'-[2-(TRIFLUOROMETHYL) PHENYL]UREA

The title compound was prepared from 2-trifluoromethylphenyl isocyanate according to the procedure of Example 65. HRMS: calcd for C$_{31}$H$_{19}$F$_6$N$_3$O$_2$, 579.1381; found (ESI, [M+H]$^+$), 580.1436.

EXAMPLE 208

N-{3-[3-BENZOYL-8-(TRIFLUOROMETHYL) QUINOLIN-4-YL]PHENYL}-N'-[2-(TRIFLUOROMETHOXY)PHENYL]UREA

The title compound was prepared from 2-trifluoromethoxyphenyl isocyanate according to the procedure of Example 65. HRMS: calcd for C$_{31}$H$_{19}$F$_6$N$_3$O$_3$, 595.1331; found (ESI, [M+H]$^+$), 596.1426.

EXAMPLE 209

N-{3-[3-BENZOYL-8-(TRIFLUOROMETHYL) QUINOLIN-4-YL]PHENYL}-N'-(2-ISOPROPYLPHENYL)UREA

The title compound was prepared from 2-isopropylphenyl isocyanate according to the procedure of Example 65. HRMS: calcd for $C_{33}H_{26}F_3N_3O_2$, 553.1977; found (ESI, [M+H]$^+$), 554.2071.

EXAMPLE 210

N-{3-[3-BENZOYL-8-(TRIFLUOROMETHYL) QUINOLIN-4-YL]PHENYL}-N'-5,6,7,8-TETRAHYDRONAPHTHALEN-1-YLUREA

The title compound was prepared from 1-isocyanato-5,6,7,8-tetrahydronaphthalene according to the procedure of Example 65. MS (ESI) m/z 566.

EXAMPLE 211

(2S,3S)-3-{4-[({3-[3-BENZOYL-8-(TRIFLUOROMETHYL)QUINOLIN-4-YL] PHENYL}AMINO)METHYL]PHENYL}-3-HYDROXY-2-METHYLPROPANOIC ACID

The title compound was prepared from [4-(3-amino-phenyl)-8-trifluoromethyl-quinolin-3-yl]-phenyl-methanone and 3-(4-formyl-phenyl)-3-hydroxy-2-methyl-propionic acid according to the procedure of Example 66. MS (ES) m/z 583.0.

EXAMPLE 212

N-{3-[3-BENZOYL-8-(TRIFLUOROMETHYL) QUINOLIN-4-YL]PHENYL}-N'-(2-METHOXYPHENYL)UREA

The title compound was prepared from 2-methoxyphenyl isocyanate according to the procedure of Example 65. MS (ES) m/z 539.8.

EXAMPLE 213

N-{3-[3-BENZOYL-8-(TRIFLUOROMETHYL) QUINOLIN-4-YL]PHENYL}-N'-[2-FLUORO-3-(TRIFLUOROMETHYL) PHENYL]UREA

The title compound was prepared from 2-fluoro-3-trifluoromethyl-phenyl isocyanate according to the procedure of Example 65. MS (ESI) m/z 598.

EXAMPLE 214

3-[4-({3-[3-BENZYL-8-(TRIFLUOROMETHYL) QUINOLIN-4-YL]BENZYL}OXY)PHENYL] PROP-2-YNOIC ACID

The title compound was prepared from [3-(3-benzyl-8-trifluoromethyl-quinolin-4-yl)-phenyl]-methanol and (4-hydroxymethyl-phenyl)-propynoic acid methyl ester according to the procedure of Example 69. MS (ESI) m/z 538.

EXAMPLE 215

(5Z)-5-{4-[({3-[3-BENZOYL-8-(TRIFLUOROMETHYL)QUINOLIN-4-YL]PHENYL}AMINO) METHYL]BENZYLIDENE}-1,3-THIAZOLIDINE-2,4-DIONE

The title compound was prepared from [4-(3-amino-phenyl)-8-trifluoromethyl-quinolin-3-yl]-phenyl-methanone and 4-(2,4-dioxo-thiazolidin-5-ylidenemethyl)-benzaldehyde according to the procedure of Example 66. MS (ES) m/z 607.8.

EXAMPLE 216

2-[4-({[3-(3-BENZOYL-8-METHYLQUINOLIN-4-YL)PHENYL]AMINO}METHYL)PHENYL]-3-PHENYLPROPANOIC ACID

A mixture of (4-{[3-(3-benzoyl-8-methyl-quinolin-4-yl)-phenylamino]-methyl}-phenyl)-acetic acid (0.04 g, 0.08 mmol), benzyl bromide (0.12 g, 0.8 mmol), and cesium carbonate (0.33 g, 1 mmol) in 5 mL of DMF was stirred at room temperature for 2 h. The reaction was quenched with water and extracted with ethyl acetate. The combined organics were washed with water, dried over magnesium sulfate and concentrated. The crude ester was treated with LiOH followed by semi-preparative HPLC purification to give the title compound. MS (ESI) m/z 577.

EXAMPLE 217

N-{3-[3-BENZYL-8-(TRIFLUOROMETHYL) QUINOLIN-4-YL]PHENYL}-N'-(2-FLUOROPHENYL)UREA

The title compound was prepared from 3-(3-benzyl-8-trifluoromethyl-quinolin-4-yl)-phenylamine and 2-fluorophenyl isocyanate according to the procedure of Example 65. MS (ES) m/z 513.9.

EXAMPLE 218

N-{3-[3-BENZYL-8-(TRIFLUOROMETHYL) QUINOLIN-4-YL]PHENYL}-N'-(2-CHLOROPHENYL)UREA

The title compound was prepared from 3-(3-benzyl-8-trifluoromethyl-quinolin-4-yl)-phenylamine and 2-chlorophenyl isocyanate according to the procedure of Example 65. MS (ES) m/z 529.8.

EXAMPLE 219

N-{3-[3-BENZOYL-8-(TRIFLUOROMETHYL) QUINOLIN-4-YL] PHENYL}-N'-(2-BROMOPHENYL)UREA

The title compound was prepared from [4-(3-amino-phenyl)-8-trifluoromethyl-quinolin-3-yl]-phenyl-methanone and 2-bromophenyl isocyanate according to the procedure of Example 65. MS (ES) m/z 587.8.

EXAMPLE 220

N-{3-[3-BENZOYL-8-(TRIFLUOROMETHYL)QUINOLIN-4-YL]PHENYL}-N'-(2-IODOPHENYL)UREA

The title compound was prepared from [4-(3-amino-phenyl)-8-trifluoromethyl-quinolin-3-yl]-phenyl-methanone and 2-iodophenyl isocyanate according to the procedure of Example 65. MS (ES) m/z 635.7.

EXAMPLE 221

N-{3-[3-BENZOYL-8-(TRIFLUOROMETHYL)QUINOLIN-4-YL]PHENYL}-2-PHENYLACETAMIDE

The title compound was prepared from [4-(3-amino-phenyl)-8-trifluoromethyl-quinolin-3-yl]-phenyl-methanone and phenyl-acetyl chloride according to the procedure of Example 61. MS (ES) m/z 508.9.

EXAMPLE 222

N-{3-[3-BENZOYL-8-(TRIFLUOROMETHYL)QUINOLIN-4-YL]PHENYL}-2-(2-FLUOROPHENYL)ACETAMIDE

The title compound was prepared from [4-(3-amino-phenyl)-8-trifluoromethyl-quinolin-3-yl]-phenyl-methanone and 2-fluorophenyl-acetyl chloride according to the procedure of Example 61. MS (ES) m/z 526.8.

EXAMPLE 223

N-{3-[3-BENZOYL-8-(TRIFLUOROMETHYL)QUINOLIN-4-YL]PHENYL}-2-(2-CHLOROPHENYL)ACETAMIDE

The title compound was prepared from [4-(3-amino-phenyl)-8-trifluoromethyl-quinolin-3-yl]-phenyl-methanone and 2-chlorophenyl-acetyl chloride according to the procedure of Example 61. MS (ES) m/z 542.8.

EXAMPLE 224

ETHYL 4-{[({3-[3-BENZOYL-8-(TRIFLUOROMETHYL)QUINOLIN-4-YL]PHENYL}AMINO)CARBONYL]AMINO}BENZOATE

The title compound was prepared from [4-(3-amino-phenyl)-8-trifluoromethyl-quinolin-3-yl]-phenyl-methanone and 4-Isocyanato-benzoic acid ethyl ester according to the procedure of Example 65. HRMS: calcd for $C_{33}H_{24}F_3N_3O_4$, 583.1719; found (ESI, [M+H]$^+$), 584.1801.

EXAMPLE 225

4-{[({3-[3-BENZOYL-8-(TRIFLUOROMETHYL)QUINOLIN-4-YL]PHENYL}AMINO)CARBONYL]AMINO}BENZOIC ACID

The title compound was prepared from ethyl 4-{[({3-[3-benzoyl-8-(trifluoromethyl) quinolin-4-yl]phenyl}amino)carbonyl]amino}benzoate by hydrolysis with LiOH. HRMS: calcd for $C_{31}H_{20}F_3N_3O_4$, 555.1406; found (ESI, [M+H]$^+$), 556.1495.

EXAMPLE 226

N-{3-[3-BENZOYL-8-(TRIFLUOROMETHYL)QUINOLIN-4-YL]PHENYL}UREA

The title compound was prepared from [4-(3-amino-phenyl)-8-trifluoromethyl-quinolin-3-yl]-phenyl-methanone and trimethylsilyl isocyanate according to the procedure of Example 65. HRMS: calcd for $C_{24}H_{16}F_3N_3O_2$, 435.1195; found (ESI, [M+H]$^+$), 436.1258.

EXAMPLE 227

N-{3-[3-BENZOYL-8-(TRIFLUOROMETHYL)QUINOLIN-4-YL]PHENYL}-N'-(2,6-DIFLUOROPHENYL)UREA

The title compound was prepared from [4-(3-amino-phenyl)-8-trifluoromethyl-quinolin-3-yl]-phenyl-methanone and 2,6-difluorophenyl isocyanate according to the procedure of Example 65. HRMS: calcd for $C_{30}H_{18}F_5N_3O_2$, 547.1319; found (ESI, [M+H]$^+$), 548.1425.

EXAMPLE 228

5-{4-[({3-[3-BENZOYL-8-(TRIFLUOROMETHYL)QUINOLIN-4-YL]PHENYL}AMINO)METHYL]BENZYLIDENE}-2-THIOXO-1,3-THIAZOLIDIN-4-ONE

The title compound was prepared from [4-(3-amino-phenyl)-8-trifluoromethyl-quinolin-3-yl]-phenyl-methanone and 4-(4-oxo-2-thioxo-thiazolidin-5-ylidenemethyl)-benzaldehyde according to the procedure of Example 66. MS (ES) m/z 623.8.

EXAMPLE 229

5-{4-[({3-[3-BENZOYL-8-(TRIFLUOROMETHYL)QUINOLIN-4-YL]PHENYL}AMINO)METHYL]BENZYLIDENE}-3-METHYL-2-THIOXO-1,3-THIAZOLIDIN-4-ONE

The title compound was prepared from [4-(3-amino-phenyl)-8-trifluoromethyl-quinolin-3-yl]-phenyl-methanone and 4-(3-methyl-4-oxo-2-thioxo-thiazolidin-5-ylidenemethyl)-benzaldehyde according to the procedure of Example 66. MS (ES) m/z 637.9.

EXAMPLE 230

3-ALLYL-5-{4-[({3-[3-BENZOYL-8-(TRIFLUOROMETHYL)QUINOLIN-4-YL]PHENYL}AMINO)METHYL]BENZYLIDENE}-2-THIOXO-1,3-THIAZOLIDIN-4-ONE

The title compound was prepared from [4-(3-amino-phenyl)-8-trifluoromethyl-quinolin-3-yl]-phenyl-methanone and 4-(3-allyl-4-oxo-2-thioxo-thiazolidin-5-ylidenemethyl)-benzaldehyde according to the procedure of Example 66. MS (ES) m/z 663.8.

EXAMPLE 231

PHENYL N-{3-[3-BENZOYL-8-(TRIFLUOROMETHYL)QUINOLIN-4-YL]PHENYL}-N'-CYANOIMIDOCARBAMATE

A mixture of diphenyl cyanocarbonimidate (0.6 g, 2.52 mmol) and [4-(3-amino-phenyl)-8-trifluoromethyl-quinolin-3-yl]-phenyl-methanone (0.1 g, 0.26 mmol) in 30 mL of acetonitrile was refluxed for 3 days. Removal of solvent under reduced pressure gave a crude product that was purified by silica gel chromatography eluting with ethyl acetate/hexanes (5% to 30%) to give 65 mg (47%) of the title compound as an off-white solid. MS (ES) m/z 534.9.

EXAMPLE 232

N-{3-[3-BENZOYL-8-(TRIFLUOROMETHYL)QUINOLIN-4-YL]PHENYL}-N'-(2-NITROPHENYL)UREA

The title compound was prepared from [4-(3-amino-phenyl)-8-trifluoromethyl-quinolin-3-yl]-phenyl-methanone and 2-nitrophenyl isocyanate according to the procedure of Example 65. MS (ES) m/z 554.8.

EXAMPLE 233

N-(2-AMINOPHENYL)-N'-{3-[3-[HYDROXY(PHENYL)METHYL]-8-(TRIFLUOROMETHYL)QUINOLIN-4-YL]PHENYL}UREA

The title compound was prepared from N-{3-[3-benzoyl-8-(trifluoromethyl)quinolin-4-yl]phenyl}-N'-(2-nitrophenyl)urea by hydrogenation (Pd/C, 5 psi of $H_2$). MS (ES) m/z 526.9.

EXAMPLE 234

N-(2-AMINOPHENYL)-N'-{3-[3-BENZOYL-8-(TRIFLUOROMETHYL)QUINOLIN-4-YL]PHENYL}UREA

The title compound was prepared from N-{3-[3-benzoyl-8-(trifluoromethyl)quinolin-4-yl]phenyl}-N'-(2-nitrophenyl)urea by Zinin reduction ($Na_2S/NH_4Cl$). MS (ES) m/z 524.9.

EXAMPLE 235

N-{3-[3-BENZOYL-8-(TRIFLUOROMETHYL)QUINOLIN-4-YL]PHENYL}-N'-(2-CHLOROPHENYL) THIOUREA

The title compound was prepared from [4-(3-amino-phenyl)-8-trifluoromethyl-quinolin-3-yl]-phenyl-methanone and 2-chlorophenyl isothiocyanate according to the procedure of Example 65. MS (ES) m/z 559.8.

EXAMPLE 236

N-{3-[3-BENZOYL-8-(TRIFLUOROMETHYL)QUINOLIN-4-YL]PHENYL}-N'-(2-CHLOROPHENYL) GUANIDINE

A mixture of N-{3-[3-benzoyl-8-(trifluoromethyl)quinolin-4-yl]phenyl}-N'-(2-chlorophenyl)thiourea (0.07 g, 0.12 mmol), lead(IV) acetate (0.30 g, 0.68 mmol) in 10 mL of ethanol/28% ammonium hydroxide (1/1) was heated to reflux for 30 minutes. Removal of solvents under reduced pressure gave a crude product that was purified by preparative thin layer chromatography with ethyl acetate as the developing solvent to give 52 mg (71%) of the title compound as an off-white solid. MS (ES) m/z 542.8.

EXAMPLE 237

PHENYL[4-THIEN-2-YL-8-(TRIFLUOROMETHYL)QUINOLIN-3-YL]METHANONE

The title compound was prepared from 2-thiopnene boronic acid according to the procedure of Example 60. MS (ESI) m/z 384; HRMS: calcd for $C_{21}H_{12}F_3NOS$, 383.0592; found (ESI, [M+H]$^+$), 384.0645.

EXAMPLE 238

PHENYL[4-THIEN-3-YL-8-(TRIFLUOROMETHYL)QUINOLIN-3-YL]METHANONE

The title compound was prepared from 3-thiopnene boronic acid according to the procedure of Example 20. MS (ESI) m/z 384; HRMS: calcd for $C_{21}H_{12}F_3NOS$, 383.0592; found (ESI, [M+H]$^+$), 384.0634.

EXAMPLE 239

[4-(4-ETHYLPHENYL)-8-(TRIFLUOROMETHYL)QUINOLIN-3-Yl](PHENYL)METHANONE

The title compound was prepared from 4-ethylphenyl boronic acid according to the procedure of Example 20 step 2. MS (ESI) m/z 406; HRMS: calcd for $C_{25}H_{18}F_3NO$, 405.1340; found (ESI, [M+H]$^+$), 406.1382.

EXAMPLE 240

[4-(3-FLUOROPHENYL)-8-(TRIFLUOROMETHYL)QUINOLIN-3-YL](PHENYL)METHANONE

The title compound was prepared from 3-fluorophenyl boronic acid according to the procedure of Example 60. MS (ESI) m/z 396; HRMS: calcd for $C_{23}H_{13}F_4NO$, 395.0933; found (ESI, [M+H]$^+$), 396.098.

EXAMPLE 241

[4-(3-CHLORO-4-FLUOROPHENYL)-8-(TRIFLUOROMETHYL)QUINOLIN-3-YL](PHENYL)METHANONE

The title compound was prepared from 3-chloro-4-fluorophenyl boronic acid according to the procedure of Example 60. HRMS: calcd for $C_{23}H_{12}ClF_4NO$, 429.0544; found (ESI, [M+H]$^+$), 430.0606.

EXAMPLE 242

1-{3-[3-BENZOYL-8-(TRIFLUOROMETHYL)
QUINOLIN-4-YL]PHENYL}ETHANONE

The title compound was prepared from 3-ethanonephenyl boronic acid according to the procedure of Example 60. MS (ESI) m/z 420.

EXAMPLE 243

[4-[4-(DIMETHYLAMINO)PHENYL]-8-(TRIF-
LUOROMETHYL)QUINOLIN-3-YL](PHENYL)
METHANONE

The title compound was prepared from 4-dimethylaminophenyl boronic acid according to the procedure of Example 60. MS (ESI) m/z 421; HRMS: calcd for $C_{25}H_{19}F_3N_2O$, 420.1449; found (ESI, [M+H]$^+$), 421.1538.

EXAMPLE 244

[4-(3-METHYLPHENYL)-8-(TRIFLUOROM-
ETHYL)QUINOLIN-3-YL](PHENYL)METHA-
NONE

The title compound was prepared from 3-methylphenyl boronic acid according to the procedure of Example 60. HRMS: calcd for $C_{24}H_{16}F_3NO$, 391.1184; found (ESI, [M+H]$^+$), 392.127.

EXAMPLE 245

[4-[3-(DIMETHYLAMINO)PHENYL]-8-(TRIF-
LUOROMETHYL)QUINOLIN-3-YL](PHENYL)
METHANONE

The title compound was prepared from 3-dimethylaminophenyl boronic acid according to the procedure of Example 60. HRMS: calcd for $C_{25}H_{19}F_3N_2O$, 420.1449; found (ESI, [M+H]$^+$), 421.1524.

EXAMPLE 246

[4-(3,4-DIFLUOROPHENYL)-8-(TRIFLUOROM-
ETHYL)QUINOLIN-3-YL](PHENYL)METHA-
NONE

The title compound was prepared from 3,4-difluorophenyl boronic acid according to the procedure of Example 60. MS (ESI) m/z 414; HRMS: calcd for $C_{23}H_{12}F_5NO$, 413.0839; found (ESI, [M+H]$^+$), 414.0907.

EXAMPLE 247

[4-(3-NITROPHENYL)-8-(TRIFLUOROMETHYL)
QUINOLIN-3-YL](PHENYL)METHANONE

The title compound was prepared from 3-nitrophenyl boronic acid according to the procedure of Example 60. MS (ESI) m/z 423; HRMS: calcd for $C_{23}H_{13}F_3N_2O_3$, 422.0878; found (ESI, [M+H]$^+$), 423.0955.

EXAMPLE 248

[4-(3,5-DIFLUOROPHENYL)-8-(TRIFLUOROM-
ETHYL)QUINOLIN-3-YL](PHENYL)METHA-
NONE

To (4-chloro-8-trifluoromethyl-quinoline-3-yl)-phenyl-methanone (150 mg, 0.448 mmol), 3,5-difluorophenyl boronic acid (141 mg, 0.895 mmol), tetrakis(triphenylphosphine) palladium (52 mg, 0.045 mmol), sodium carbonate (50 mg, 1.41 mmol) in water (750 ml), glyme (2 ml), and ethanol (350 ml), was subjected to micro wave conditions (140° C., 300 watts, 300 sec.). The resulting dark red-brown mixture was filtered concentration in vacuo. Reverse phase gradient HPLC ($CH_3CN$, $H_2O$) afforded the title compound as a yellow powder (88 mg, 48%). MS (ESI) m/z 414; HRMS: calcd for $C_{23}H_{12}F_5NO$, 413.0839; found (ESI, [M+H]$^+$), 414.0911.

EXAMPLE 249

3-[3-BENZOYL-8-(TRIFLUOROMETHYL)
QUINOLIN-4-YL]BENZONITRILE

The title compound was prepared from 3-cyanophenyl boronic acid according to the procedure of Example 248. MS (ESI) m/z 403; HRMS: calcd for $C_{24}H_{13}F_3N_2O$, 402.0980; found (ESI, [M+H]$^+$), 403.1048.

EXAMPLE 250

4-[3-BENZOYL-8-(TRIFLUOROMETHYL)
QUINOLIN-4-YL]BENZONITRILE

The title compound was prepared from 4-cyanophenyl boronic acid according to the procedure of 248. MS (ESI) m/z 403; HRMS: calcd for $C_{24}H_{13}F_3N_2O$, 402.0980; found (ESI, [M+H]$^+$), 403.1046.

EXAMPLE 251

[4-(1-NAPHTHYL)-8-(TRIFLUOROMETHYL)
QUINOLIN-3-YL](PHENYL)METHANONE

The title compound was prepared from 1-naphthyl boronic acid according to the procedure of Example 248. MS (ESI) m/z 428; HRMS: calcd for $C_{27}H_{16}F_3NO$, 427.1184; found (ESI, [M+H]$^+$), 428.1255.

EXAMPLE 252

[4-(2-FURYL)-8-(TRIFLUOROMETHYL)QUINO-
LIN-3-YL](PHENYL)METHANONE

The title compound was prepared from 3-furyl boronic acid according to the procedure of Example 248. MS (ESI) m/z 368; HRMS: calcd for $C_{21}H_{12}F_3NO_2$, 367.0820; found (ESI, [M+H]$^+$), 368.0876.

EXAMPLE 253

[4-[3-(ETHYLSULFONYL)PHENYL]-8-(TRIF-
LUOROMETHYL)QUINOLIN-3-YL](PHENYL)
METHANONE

The title compound was prepared from 3-ethylsulfonylphenyl boronic acid according to the procedure of Example 248. MS (ESI) m/z 470; HRMS: calcd for $C_{25}H_{18}F_3NO_3S$, 469.0959; found (ESI, [M+H]$^+$), 470.1054.

EXAMPLE 254

PHENYL[4-PYRIDIN-3-YL-8-(TRIFLUOROM-
ETHYL)QUINOLIN-3-YL]METHANONE

The title compound was prepared from 4-pyridin-3-yl boronic acid according to the procedure of Example 248. MS (ESI) m/z 379; HRMS: calcd for $C_{22}H_{13}F_3N_2O$, 378.0980; found (ESI, [M+H]$^+$), 379.1046.

EXAMPLE 255

PHENYL[4-PYRIDIN-4-YL-8-(TRIFLUOROMETHYL)QUINOLIN-3-YL]METHANONE

The title compound was prepared from 4-pyridin-4-yl boronic acid according to the procedure of Example 248. MS (ESI) m/z 379; HRMS: calcd for $C_{22}H_{13}F_3N_2O$, 378.0980; found (ESI, [M+H]$^+$), 379.1044.

EXAMPLE 256

PHENYL[4-PYRIMIDIN-5-YL-8-(TRIFLUOROMETHYL)QUINOLIN-3-YL]METHANONE

The title compound was prepared from 4-pyridin-5-yl boronic acid according to the procedure of Example 248. MS (ESI) m/z 380; HRMS: calcd for $C_{21}H_{12}F_3N_3O$, 379.0932; found (ESI, [M+H]$^+$), 380.0999.

EXAMPLE 257

PHENYL[4-{3-[(THIEN-3-YLMETHYL)AMINO]PHENYL}-8-(TRIFLUOROMETHYL)QUINOLIN-3-YL]METHANONE

The title compound was prepared from thiophene-3-carbaldehyde according to the procedure of Example 66. MS (ESI) m/z 489; HRMS: calcd for $C_{28}H_{19}F_3N_2OS$, 488.1170; found (ESI, [M+H]$^+$), 489.1226.

EXAMPLE 258

PHENYL[4-{3-[(PYRIDIN-3-YLMETHYL)AMINO]PHENYL}-8-(TRIFLUOROMETHYL)QUINOLIN-3-YL]METHANONE

The title compound was prepared from pyridine-3-carbaldehyde according to the procedure of Example 66. MS (ESI) m/z 484; HRMS: calcd for $C_{29}H_{20}F_3N_3O$, 483.1558; found (ESI, [M+H]$^+$), 484.1611.

EXAMPLE 259

[4-(3-AMINOPHENYL)-8-METHYLQUINOLIN-3-YL](PHENYL)METHANONE

The title compound was prepared from 3-aminophenyl boronic acid according to the procedure of Example 60. MS (ESI) m/z 339; HRMS: calcd for $C_{23}H_{18}N_2O$, 338.1419; found (ESI, [M+H]$^+$), 339.1487.

EXAMPLE 260

PHENYL[4-{3-[(PYRIDIN-2-YLMETHYL)AMINO]PHENYL}-8-(TRIFLUOROMETHYL)QUINOLIN-3-YL]METHANONE

The title compound was prepared from pyridine-2-carbaldehyde according to the procedure of Example 66. MS (ES) m/z 484.2; HRMS: calcd for $C_{29}H_{20}F_3N_3O$, 483.1558; found (ESI, [M+H]$^+$), 484.1643.

EXAMPLE 261

PHENYL[4-{3-[(PYRIDIN-4-YLMETHYL)AMINO]PHENYL}-8-(TRIFLUOROMETHYL)QUINOLIN-3-YL]METHANONE

The title compound was prepared from pyridine-4-carbaldehyde according to the procedure of Example 66. MS (ES) m/z 482.2; HRMS: calcd for $C_{29}H_{20}F_3N_3O$, 483.1558; found (ESI, [M+H]$^+$), 484.1641.

EXAMPLE 262

[4-{3-[(2,5-DIFLUOROBENZYL)AMINO]PHENYL}-8-(TRIFLUOROMETHYL)QUINOLIN-3-YL](PHENYL) METHANONE

The title compound was prepared from 2,5-difluorophenyl carbaldehyde according to the procedure of Example 66. MS (ES) m/z 517.2; HRMS: calcd for $C_{30}H_{19}F_5N_2O$, 518.1418; found (ESI, [M+H]$^+$), 519.1492.

EXAMPLE 263

[4-{3-[(2-FLUOROBENZYL)AMINO]PHENYL}-8-(TRIFLUOROMETHYL)QUINOLIN-3-YL](PHENYL) METHANONE

The title compound was prepared from 2-fluorophenyl carbaldehyde according to the procedure of Example 66. MS (ES) m/z 499.2; HRMS: calcd for $C_{30}H_{20}F_4N_2O$, 500.1512; found (ESI, [M+H]$^+$), 501.1593.

EXAMPLE 264

[4-{3-[(2-FURYLMETHYL)AMINO]PHENYL}-8-(TRIFLUOROMETHYL)QUINOLIN-3-YL](PHENYL) METHANONE

The title compound was prepared from 2-furyl carbaldehyde according to the procedure of Example 66. MS (ES) m/z 473.2; HRMS: calcd for $C_{28}H_{19}F_3N_2O_2$, 472.1399; found (ESI, [M+H]$^+$), 473.1483.

EXAMPLE 265

[4-{3-[(2-FURYLMETHYL)(3-FURYLMETHYL)AMINO]PHENYL}-8-(TRIFLUOROMETHYL)QUINOLIN-3-YL](PHENYL)METHANONE

The title compound was prepared from 2-furyl carbaldehyde according to the procedure of Example 66. MS (ES) m/z 553.2; HRMS: calcd for $C_{33}H_{23}F_3N_2O_3$, 552.1661; found (ESI, [M+H]$^+$), 553.1754.

EXAMPLE 266

[4-{3-[(3-FLUOROBENZYL)AMINO]PHENYL}-8-(TRIFLUOROMETHYL)QUINOLIN-3-YL](PHENYL) METHANONE

The title compound was prepared from 3-fluorophenyl carbaldehyde according to the procedure of Example 66. MS (ES) m/z 501.2; HRMS: calcd for $C_{30}H_{20}F_4N_2O$, 500.1512; found (ESI, [M+H]$^+$), 501.1591.

EXAMPLE 267

[4-{3-[(2-CHLOROBENZYL)AMINO]PHENYL}-8-(TRIFLUOROMETHYL)QUINOLIN-3-YL](PHENYL) METHANONE

The title compound was prepared from 2-chlorophenyl carbaldehyde according to the procedure of Example 66. MS (ES) m/z 515.3; HRMS: calcd for $C_{30}H_{20}ClF_3N_2O$, 516.1216; found (ESI, [M+H]$^+$), 517.131.

EXAMPLE 268

PHENYL[4-{3-[(1,3-THIAZOL-2-YLMETHYL)AMINO]PHENYL}-8-(TRIFLUOROMETHYL)QUINOLIN-3-YL]METHANONE

The title compound was prepared from thiazole-2-carbaldehyde according to the procedure of Example 66. MS (ES) m/z 488.2; HRMS: calcd for $C_{27}H_{18}F_3N_3OS$, 489.1123; found (ESI, [M+H]$^+$), 490.1197.

EXAMPLE 269

[4-(3-AMINO-4-METHYLPHENYL)-8-(TRIFLUOROMETHYL)QUINOLIN-3-YL](PHENYL)METHANONE

The title compound was prepared from 3-amino-4-methylphenyl boronic acid according to the procedure of Example 60. MS (ES) m/z 407.2; HRMS: calcd for $C_{24}H_{17}F_3N_2O$, 406.1293; found (ESI, [M+H]$^+$), 407.1346.

EXAMPLE 270

ETHYL {3-[({3-[3-BENZOYL-8-(TRIFLUOROMETHYL)QUINOLIN-4-YL]PHENYL}AMINO)METHYL]PHENYL}ACETATE

The title compound was prepared from (3-formylphenyl) acetic acid ethyl ester according to the procedure of Example 66. MS (ES) m/z 567.3; HRMS: calcd for $C_{34}H_{27}F_3N_2O_3$, 568.1974; found (ESI, [M+H]$^+$), 569.2058.

EXAMPLE 271

{3-[({3-[3-BENZOYL-8-(TRIFLUOROMETHYL)QUINOLIN-4-YL]PHENYL}AMINO)METHYL]PHENYL}ACETIC ACID

The title compound was prepared from (3-formylphenyl) acetic acid ethyl ester according to the procedure of Example 66. MS (ESI) m/z 541; MS (ESI) m/z 539; HRMS: calcd for $C_{32}H_{23}F_3N_2O_3$, 540.1661; found (ESI, [M+H]$^+$), 541.1732.

EXAMPLE 272

[4-{3-[(3-NITROBENZYL)AMINO]PHENYL}-8-(TRIFLUOROMETHYL)QUINOLIN-3-YL](PHENYL) METHANONE

The title compound was prepared from 3-nitrophenylcarbaldehyde according to the procedure of Example 66. MS (ESI) m/z 528; HRMS: calcd for $C_{30}H_{20}F_3N_3O_3$, 527.1457; found (ESI, [M+H]$^+$), 528.1519.

EXAMPLE 273

[4-{3-[(3-METHYLBENZYL)AMINO]PHENYL}-8-(TRIFLUOROMETHYL)QUINOLIN-3-YL](PHENYL) METHANONE

The title compound was prepared from 3-methylphenylcarbaldehyde according to the procedure of Example 66. MS (ESI) m/z 497; MS (ESI) m/z 495; HRMS: calcd for $C_{31}H_{23}F_3N_2O$, 496.1762; found (ESI, [M+H]$^+$), 497.1817.

EXAMPLE 274

[4-(3-AMINOPHENYL)-8-CHLOROQUINOLIN-3-YL](PHENYL)METHANONE

The title compound was prepared from 3-aminophenyl boronic acid according to the procedure of Example 60. MS (ES) m/z 359.2; HRMS: calcd for $C_{22}H_{15}ClN_2O$, 358.0873; found (ESI, [M+H]$^+$), 359.0965.

EXAMPLE 275

[4-{3-[(4-ISOPROPYLBENZYL)AMINO]PHENYL}-8-(TRIFLUOROMETHYL)QUINOLIN-3-YL](PHENYL) METHANONE

The title compound was prepared from 4-isopropylphenylcarbaldehyde according to the procedure of Example 66. MS m/z 525; HRMS: calcd for $C_{33}H_{27}F_3N_2O$, 524.2075; found (ESI, [M+H]$^+$), 525.2142.

EXAMPLE 276

[4-(3-{[(5-CHLOROTHIEN-2-YL)METHYL]AMINO}PHENYL)-8-(TRIFLUOROMETHYL)QUINOLIN-3-YL](PHENYL)METHANONE

The title compound was prepared from 5-chloro-2-thiophenecarbaldehyde according to the procedure of Example 66. MS (ES) m/z 521.1; HRMS: calcd for $C_{28}H_{18}ClF_3N_2OS$, 522.0780; found (ESI, [M+H]$^+$), 523.0862.

EXAMPLE 277

[4-{3-[(2,4-DICHLOROBENZYL)AMINO]PHENYL}-8-(TRIFLUOROMETHYL)QUINOLIN-3-YL](PHENYL) METHANONE

The title compound was prepared from 2,4-dichlorophenylcarbaldehyde according to the procedure of Example 66. MS (ES) m/z 549.1; HRMS: calcd for $C_{30}H_{19}Cl_2F_3N_2O$, 550.0827; found (ESI, [M–H]$^-$), 549.0757.

EXAMPLE 278

PHENYL[4-{3-[(THIEN-2-YLMETHYL)AMINO]PHENYL}-8-(TRIFLUOROMETHYL)QUINOLIN-3-YL]METHANONE

The title compound was prepared from 2-thiophenecarbaldehyde according to the procedure of Example 66. MS (ES) m/z 489.2; HRMS: calcd for $C_{28}H_{19}F_3N_2OS$, 488.1170; found (ESI, [M+H]$^+$), 489.1266.

EXAMPLE 279

[4-(3-{[(4,5-DIMETHYL-2-FURYL)METHYL]AMINO}PHENYL)-8-(TRIFLUOROMETHYL)QUINOLIN-3-YL](PHENYL)METHANONE

The title compound was prepared from 4,5-dimethylfuryl-carbaldehyde according to the procedure of Example 66. MS (ES) m/z 501.2; HRMS: calcd for $C_{30}H_{23}F_3N_2O_2$, 500.1712; found (ESI, [M+H]$^+$), 501.1803.

EXAMPLE 280

[4-[3-(ETHYLAMINO)PHENYL]-8-(TRIFLUOROMETHYL)QUINOLIN-3-YL](PHENYL)METHANONE

The title compound was prepared from acetaldehyde according to the procedure of Example 66. MS (ESI) m/z 420; HRMS: calcd for $C_{25}H_{19}F_3N_2O$, 420.1449; found (ESI, [M+H]$^+$), 421.1521.

EXAMPLE 281

PHENYL[4-{3-[(3-PHENYLPROPYL)AMINO]PHENYL}-8-(TRIFLUOROMETHYL)QUINOLIN-3-YL]METHANONE

The title compound was prepared from 3-phenylpropylcarbaldehyde according to the procedure of Example 66. MS (ESI) m/z 511; HRMS: calcd for $C_{32}H_{25}F_3N_2O$, 510.1919; found (ESI, [M+H]$^+$), 511.1988.

EXAMPLE 282

PHENYL[4-{3-[(2-PHENYLETHYL)AMINO]PHENYL}-8-(TRIFLUOROMETHYL)QUINOLIN-3-YL]METHANONE

The title compound was prepared from phenethylcarbaldehyde according to the procedure of Example 66. MS (ESI) m/z 497; HRMS: calcd for $C_{31}H_{23}F_3N_2O$, 496.1762; found (ESI, [M+H]$^+$), 497.1835.

EXAMPLE 283

[4-{3-[(1H-IMIDAZOL-2-YLMETHYL)AMINO]PHENYL}-8-(TRIFLUOROMETHYL)QUINOLIN-3-YL](PHENYL)METHANONE

The title compound was prepared from 1H-imidazole-2-carbaldehyde according to the procedure of Example 66. MS (ESI) m/z 473; MS (ESI) m/z 471; HRMS: calcd for $C_{27}H_{19}F_3N_4O$, 472.1511; found (ESI, [M+H]$^+$), 473.1581.

EXAMPLE 284

[4-(3-{[(4-METHYL-1H-IMIDAZOL-5-YL)METHYL]AMINO}PHENYL)-8-(TRIFLUOROMETHYL) QUINOLIN-3-YL](PHENYL)METHANONE

The title compound was prepared from 5-methyl-3H-imidazole-5-carbaldehyde according to the procedure of Example 66. MS (ESI) m/z 486; HRMS: calcd for $C_{28}H_{21}F_3N_4O$, 487.496; found (ESI, [M+H]$^+$), 488.499.

EXAMPLE 285

PHENYL(8-(TRIFLUOROMETHYL)-4-{3-[(3-VINYLBENZYL)AMINO]PHENYL}QUINOLIN-3-YL) METHANONE

The title compound was prepared from 3-ethylenephenyl-carbaldehyde according to the procedure of Example 66. MS (ES) m/z 509.2; HRMS: calcd for $C_{32}H_{23}F_3N_2O$, 508.1762; found (ESI, [M+H]$^+$), 509.183.

EXAMPLE 286

PHENYL[8-(TRIFLUOROMETHYL)-4-(3-{[3-(TRIFLUOROMETHYL)BENZYL]AMINO}PHENYL)QUINOLIN-3-YL]METHANONE

The title compound was prepared from 3-trifluoromethylphenyl-carbaldehyde according to the procedure of Example 66. MS (ES) m/z 549.2; HRMS: calcd for $C_{31}H_{20}F_6N_2O$, 550.1480; found (ESI, [M+H]$^+$), 551.1533.

EXAMPLE 287

[4-{3-[(3-METHOXYBENZYL)AMINO]PHENYL}-8-(TRIFLUOROMETHYL)QUINOLIN-3-YL](PHENYL) METHANONE

The title compound was prepared from 3-methoxyphenyl-carbaldehyde according to the procedure of Example 66. MS (ES) m/z 513.2; HRMS: calcd for $C_{31}H_{23}F_3N_2O_2$, 512.1712; found (ESI, [M+H]$^+$), 513.1804.

EXAMPLE 288

[4-{3-[(3-CHLOROBENZYL)AMINO]PHENYL}-8-(TRIFLUOROMETHYL)QUINOLIN-3-YL](PHENYL) METHANONE

The title compound was prepared from 3-chlorophenyl-carbaldehyde according to the procedure of Example 66. MS (ES) m/z 517.1; HRMS: calcd for $C_{30}H_{20}ClF_3N_2O$, 516.1216; found (ESI, [M+H]$^+$), 517.1285.

EXAMPLE 289

[4-(3-{[4-(2-HYDROXYETHYL)BENZYL]AMINO}PHENYL)-8-(TRIFLUOROMETHYL)QUINOLIN-3-YL](PHENYL)METHANONE

The title compound was prepared from 4-(2-hydroxyethyl)-phenyl-carbaldehyde according to the procedure of Example 66. MS (ESI) m/z 527; HRMS: calcd for $C_{32}H_{25}F_3N_2O_2$, 526.1868; found (ESI, [M+H]$^+$), 527.1954.

EXAMPLE 290

[4-(3-AMINOPHENYL)-8-FLUOROQUINOLIN-3-YL](PHENYL)METHANONE

The title compound was prepared from 3-aminophenyl boronic acid according to the procedure of Example 60. HRMS: calcd for $C_{22}H_{15}FN_2O$, 342.1168; found (ESI, [M+H]$^+$), 343.1241.

EXAMPLE 291

[4-({[3-(3-BENZOYL-8-FLUOROQUINOLIN-4-YL)PHENYL]AMINO}METHYL)PHENYL]ACETIC ACID

The title compound was prepared from 4-formylbenzoic acid according to the procedure of Example 66. HRMS: calcd for $C_{31}H_{23}FN_2O_3$, 490.1693; found (ESI, [M+H]$^+$), 491.1758.

EXAMPLE 292

3-[({3-[3-BENZOYL-8-(TRIFLUOROMETHYL)QUINOLIN-4-YL]PHENYL}AMINO)METHYL]BENZONITRILE

The title compound was prepared from 3-formylbenzonitrile according to the procedure of Example 66. MS (ESI) m/z 508; HRMS: calcd for $C_{31}H_{20}F_3N_3O$, 507.1558; found (ESI, [M+H]$^+$), 508.163.

EXAMPLE 293

3-{4-[({3-[3-BENZOYL-8-(TRIFLUOROMETHYL)QUINOLIN-4-YL]PHENYL}AMINO)METHYL]PHENYL}PROPANOIC ACID

The title compound was prepared from 3-(4-formyl-phenyl)-propionic acid according to the procedure of Example 66. MS (ES) m/z 553.1; HRMS: calcd for $C_{33}H_{25}F_3N_2O_3$, 554.1817; found (ESI, [M+H]$^+$), 555.1888.

EXAMPLE 294

[4-({[3-(3-BENZOYLQUINOLIN-4-YL)PHENYL]AMINO}METHYL)PHENYL]ACETIC ACID

The title compound was prepared from 3-(4-formyl-phenyl)-acetic acid according to the procedure of Example 66. MS (ES) m/z 471.1; HRMS: calcd for $C_{31}H_{24}N_2O_3$, 472.1787; found (ESI, [M+H]$^+$), 473.1867.

EXAMPLE 295

[4-{3-[(4-HYDROXYBENZYL)AMINO]PHENYL}-8-(TRIFLUOROMETHYL)QUINOLIN-3-YL](PHENYL) METHANONE

The title compound was prepared from 4-hydroxybenzaldehyde according to the procedure of Example 66. MS (ES) m/z 497.1; HRMS: calcd for $C_{30}H_{21}F_3N_2O_2$, 498.1555; found (ESI, [M+H]$^+$), 499.1651.

EXAMPLE 296

[4-(3-{[4-(HYDROXYMETHYL)BENZYL]AMINO}PHENYL)-8-(TRIFLUOROMETHYL)QUINOLIN-3-YL](PHENYL)METHANONE

The title compound was prepared from 4-hydroxymethyl-benzaldehyde according to the procedure of Example 66. MS (ES) m/z 513.2; HRMS: calcd for $C_{31}H_{23}F_3N_2O_2$, 512.1712; found (ESI, [M+H]$^+$), 513.1772.

EXAMPLE 297

N-[3-(3-BENZOYL-8-CHLOROQUINOLIN-4-YL)PHENYL]-N'-(2,6-DICHLOROPHENYL)UREA

The title compound was prepared from 2,6-dichlorophenylisocyanate according to the procedure of Example 65. MS m/z 546; HRMS: calcd for $C_{29}H_{18}C_{13}N_3O_2$, 545.0465; found (ESI, [M+H]$^+$), 546.0533.

EXAMPLE 298

N-[3-(3-BENZOYL-8-CHLOROQUINOLIN-4-YL)PHENYL]-N'-PHENYLUREA

The title compound was prepared from phenylisocyanate according to the procedure of Example 65. MS m/z 478; HRMS: calcd for $C_{29}H_{20}ClN_3O_2$, 477.1244; found (ESI, [M+H]$^+$), 478.1312.

EXAMPLE 299

N-{3-[3-BENZYL-8-(TRIFLUOROMETHYL)QUINOLIN-4-YL]PHENYL}-N'-PHENYLUREA

The title compound was prepared from phenylisocyanate according to the procedure of Example 65. MS (ES) m/z 498.2; HRMS: calcd for $C_{30}H_{22}F_3N_3O$, 497.1715; found (ESI, [M+H]$^+$), 498.1775.

EXAMPLE 300

N-{3-[3-BENZYL-8-(TRIFLUOROMETHYL)QUINOLIN-4-YL]PHENYL}-N'-(2,6-DIMETHYLPHENYL)UREA

The title compound was prepared from 2,6-dimethylphenylisocyanate according to the procedure of Example 65. MS (ES) m/z 524.9; HRMS: calcd for $C_{32}H_{26}F_3N_3O$, 525.2028; found (ESI, [M+H]$^+$), 526.2091.

EXAMPLE 301

N-{3-[3-BENZYL-8-(TRIFLUOROMETHYL)QUINOLIN-4-YL]PHENYL}-N'-(2,6-DICHLOROPHENYL)UREA

The title compound was prepared from 2,6-dichlorophenylisocyanate according to the procedure of Example 65. MS (ES) m/z 563.8; HRMS: calcd for $C_{30}H_{20}Cl_2F_3N_3O$, 565.0935; found (ESI, [M+H]$^+$), 566.0988.

EXAMPLE 302

2-METHOXYPHENYL {3-[3-BENZOYL-8-(TRIFLUOROMETHYL)QUINOLIN-4-YL]PHENYL}CARBAMATE

The title compound was prepared from 2-methoxyphenyl-chloroformate according to the procedure of Example 65. MS (ES) m/z 543.1; HRMS: calcd for $C_{31}H_{21}F_3N_2O_4$, 542.1453; found (ESI, [M+H]$^+$), 543.1505.

EXAMPLE 303

4-METHOXYPHENYL {3-[3-BENZOYL-8-(TRIFLUOROMETHYL)QUINOLIN-4-YL]PHENYL}CARBAMATE

The title compound was prepared from 4-methoxyphenylchloroformate according to the procedure of Example 65. MS (ES) m/z 540.9; HRMS: calcd for $C_{31}H_{21}F_3N_2O_4$, 542.1453; found (ESI, [M+H]$^+$), 543.1536.

EXAMPLE 304

4-METHYLPHENYL {3-[3-BENZOYL-8-(TRIFLUOROMETHYL)QUINOLIN-4-YL]PHENYL}CARBAMATE

The title compound was prepared from 4-methylphenylchloroformate according to the procedure of Example 65. MS (ES) m/z 527.2; HRMS: calcd for $C_{31}H_{21}F_3N_2O_3$, 526.1504; found (ESI, [M+H]$^+$), 527.1578.

EXAMPLE 305

3-(TRIFLUOROMETHYL)PHENYL {3-[3-BENZOYL-8-(TRIFLUOROMETHYL)QUINOLIN-4-YL]PHENYL}CARBAMATE

The title compound was prepared from 3-trifluoromethylphenylchloroformate according to the procedure of Example 65. MS m/z 581; HRMS: calcd for $C_{31}H_{18}F_6N_2O_3$, 580.1222; found (ESI, [M+H]$^+$), 581.1281.

EXAMPLE 306

N-[3-(3-BENZOYL-8-CHLOROQUINOLIN-4-YL)PHENYL]-N'-(2,6-DIMETHYLPHENYL)UREA

The title compound was prepared from 2,6-dimethylphenylisocyanate according to the procedure of Example 65. MS (ES) m/z 506.1; HRMS: calcd for $C_{31}H_{24}ClN_3O_2$, 505.1557; found (ESI, [M+H]$^+$), 506.1624.

EXAMPLE 307

[8-CHLORO-4-(3-HYDROXYPHENYL)QUINOLIN-3-YL](PHENYL)METHANONE

The title compound was prepared from 3-hydroxyphenyl boronic acid according to the procedure of Example 60. MS (ESI) m/z 360; MS (ESI) m/z 358; HRMS: calcd for $C_{22}H_{14}ClNO_2$, 359.0713; found (ESI, [M+H]$^+$), 360.0776.

EXAMPLE 308

(8-CHLORO-4-{3-[(4-FLUOROBENZYL)OXY]PHENYL}QUINOLIN-3-YL)(PHENYL)METHANONE

The title compound was prepared from 4-fluorobenzylbromide according to the procedure of Example 43. MS (ESI) m/z 468; HRMS: calcd for $C_{29}H_{19}ClFNO_2$, 467.1088; found (ESI, [M+H]$^+$), 468.1151.

EXAMPLE 309

(8-CHLORO-4-{3-[(2-FLUOROBENZYL)OXY]PHENYL}QUINOLIN-3-YL)(PHENYL)METHANONE

The title compound was prepared from 2-fluorobenzylbromide according to the procedure of Example 43. MS (ESI) m/z 468; HRMS: calcd for $C_{29}H_{19}ClFNO_2$, 467.1088; found (ESI, [M+H]$^+$), 468.1159; Anal. Calcd for $C_{29}H_{19}ClFNO_2$: C, 74.44; H, 4.09; N, 2.99. Found: C, 74.25; H, 4.05; N, 2.69.

EXAMPLE 310

N-{3-[3-BENZOYL-8-(TRIFLUOROMETHYL)QUINOLIN-4-YL]PHENYL}-N'-(3-CHLORO-4-FLUOROPHENYL)UREA

The title compound was prepared from 3-chloro-4-fluorophenylisocyanate according to the procedure of Example 65. MS (ES) m/z 561.9; HRMS: calcd for $C_{30}H_{18}ClF_4N_3O_2$, 563.1024; found (ESI, [M+H]$^+$), 564.1091.

EXAMPLE 311

N-{3-[3-BENZOYL-8-(TRIFLUOROMETHYL)QUINOLIN-4-YL]PHENYL}-N'-(3,4-DIFLUOROPHENYL) UREA

The title compound was prepared from 3,4-difluorophenylisocyanate according to the procedure of Example 65. MS (ES) m/z 545.9; HRMS: calcd for $C_{30}H_{18}F_5N_3O_2$, 547.1319; found (ESI, [M+H]$^+$), 548.1396.

EXAMPLE 312

N-{3-[3-BENZOYL-8-(TRIFLUOROMETHYL)QUINOLIN-4-YL]PHENYL}-N'-(3,4,5-TRIMETHOXYPHENYL)UREA

The title compound was prepared from 3,4,5-trimethoxyphenylisocyanate according to the procedure of Example 65. MS (ES) m/z 600.0; HRMS: calcd for $C_{33}H_{26}F_3N_3O_5$, 601.1825; found (ESI, [M+H]$^+$), 602.1904.

EXAMPLE 313

N-{3-[3-BENZOYL-8-(TRIFLUOROMETHYL)QUINOLIN-4-YL]PHENYL}-N'-(2-PHENYLETHYL)UREA

The title compound was prepared from phenethylisocyanate according to the procedure of Example 65. MS (ES) m/z 538.0; HRMS: calcd for $C_{32}H_{24}F_3N_3O_2$, 539.1821; found (ESI, [M+H]$^+$), 540.1898.

EXAMPLE 314

N-{3-[3-BENZOYL-8-(TRIFLUOROMETHYL)QUINOLIN-4-YL]PHENYL}-N'-(2-THIEN-2-YL-ETHYL)UREA

The title compound was prepared from 2-(2-isocyantoethyl)-thiophene according to the procedure of Example 65. MS (ES) m/z 543.9; HRMS: calcd for $C_{30}H_{22}F_3N_3O_2S$, 545.1385; found (ESI, [M+H]$^+$), 546.1476.

EXAMPLE 315

N-{3-[3-BENZOYL-8-(TRIFLUOROMETHYL)
QUINOLIN-4-YL]PHENYL}-N'-(5-PHENYLTH-
IEN-2-YL)UREA

The title compound was prepared from 2-isocyanto-5-phenyl-thiophene according to the procedure of Example 65. MS (ES) m/z 591.9; HRMS: calcd for $C_{34}H_{22}F_3N_3O_2S$, 593.1385; found (ESI, [M+H]$^+$), 594.1453.

EXAMPLE 316

N-{3-[3-BENZOYL-8-(TRIFLUOROMETHYL)
QUINOLIN-4-YL]PHENYL}-N'-THIEN-3-
YLUREA

The title compound was prepared from 3-isocyantothiophene according to the procedure of Example 65. MS (ES) m/z 515.9; HRMS: calcd for $C_{28}H_{18}F_3N_3O_2S$, 517.1072; found (ESI, [M+H]$^+$), 518.1152.

EXAMPLE 317

N-{3-[3-BENZOYL-8-(TRIFLUOROMETHYL)
QUINOLIN-4-YL]PHENYL}-N'-THIEN-2-
YLUREA

The title compound was prepared from 2-isocyantothiophene according to the procedure of Example 65. MS (ES) m/z 515.9; HRMS: calcd for $C_{28}H_{18}F_3N_3O_2S$, 517.1072; found (ESI, [M+H]$^+$), 518.1161.

EXAMPLE 318

N-{3-[3-BENZOYL-8-(TRIFLUOROMETHYL)
QUINOLIN-4-YL]PHENYL}-N'-(3,5-DIMETHYL-
ISOXAZOL-4-YL)UREA

The title compound was prepared from 4-isocyanto-3,5-dimethylisoxazole according to the procedure of Example 65. MS (ES) m/z 529.0; HRMS: calcd for $C_{29}H_{21}F_3N_4O_3$, 530.1566; found (ESI, [M+H]$^+$), 531.1649.

EXAMPLE 319

N-{3-[3-BENZOYL-8-(TRIFLUOROMETHYL)
QUINOLIN-4-YL]PHENYL}-N'-(5-METHYL-3-
PHENYL ISOXAZOL-4-YL)UREA

The title compound was prepared from 4-isocyanto-5-methyl-3-phenylisoxazole according to the procedure of Example 65. MS (ES) m/z 591.0; HRMS: calcd for $C_{34}H_{23}F_3N_4O_3$, 592.1722; found (ESI, [M+H]$^+$), 593.1812.

EXAMPLE 320

N-2,1,3-BENZOTHIADIAZOL-4-YL-N'-{3-[3-
BENZOYL-8-(TRIFLUOROMETHYL)QUINO-
LIN-4-YL]PHENYL}UREA

The title compound was prepared from 4-isocyantobenzo[1,2,5]thiadiazole according to the procedure of Example 65. MS (ES) m/z 567.9; HRMS: calcd for $C_{30}H_{18}F_3N_5O_2S$, 569.1133; found (ESI, [M+H]$^+$), 570.1184.

EXAMPLE 321

[4-[(3-HYDROXYBENZYL)AMINO]-8-(TRIF-
LUOROMETHYL)QUINOLIN-3-YL](PHENYL)
METHANONE PHENYLISOXAZOL-4-YL)UREA

The title compound was prepared from (3-hydroxyphenyl)methyl boronic acid according to the procedure of Example 60. MS (ESI) m/z 423; HRMS: calcd for $C_{24}H_{17}F_3N_2O_2$, 422.1242; found (ESI, [M+H]$^+$), 423.132.

EXAMPLE 322

4-{[3-(3-BENZOYL-8-CHLOROQUINOLIN-4-YL)
PHENOXY]METHYL}BENZOIC ACID

The title compound was prepared from 4-bromomethylbenzoic acid ethyl ester according to the procedure of Example 43. MS (ES) m/z 494.1; HRMS: calcd for $C_{30}H_{20}ClNO_4$, 493.1081; found (ESI, [M+H]$^+$), 494.1151.

EXAMPLE 323

PHENYL {3-[3-BENZOYL-8-(TRIFLUOROM-
ETHYL)QUINOLIN-4-YL]
PHENYL}CARBAMATE

The title compound was prepared from phenylchloroformate according to the procedure of Example 65. MS (ES) m/z 513.0; HRMS: calcd for $C_{30}H_{19}F_3N_2O_3$, 512.1348; found (ESI, [M+H]$^+$), 513.1406.

EXAMPLE 324

3-{3-[({3-[3-BENZOYL-8-(TRIFLUOROM-
ETHYL)QUINOLIN-4YL]PHENYL}AMINO)ME-
THYL]PHENYL PROPANOIC ACID

The title compound was prepared from 3-(3-formylphenyl)-propionic acid ethyl ester according to the procedure of Example 66. MS (ES) m/z 552.9; HRMS: calcd for $C_{33}H_{25}F_3N_2O_3$, 554.1817; found (ESI, [M+H]$^+$), 555.1868.

EXAMPLE 325

3-{4-[({3-[3-BENZYL-8-(TRIFLUOROMETHYL)
QUINOLIN-4-YL]PHENYL}AMINO)METHYL]
PHENYL}PROPANOIC ACID

The title compound was prepared from 3-(4-formylphenyl)-propionic acid according to the procedure of Example 66. MS (ES) m/z 538.9; HRMS: calcd for $C_{33}H_{27}F_3N_2O_2$, 540.2025; found (ESI, [M+H]$^+$), 541.2115.

EXAMPLE 326

{4-[({3-[3-Benzoyl-8-(Trifluoromethyl)Quinolin-4-
YL]BENZYL}AMINO)METHYL]
PHENYL}ACETIC ACID The title compound was prepared from 4-formylphenyl acetic acid according to the procedure of Example 66. MS (ES) m/z 552.9; HRMS: calcd for $C_{33}H_{25}F_3N_2O_3$, 554.1817; found (ESI, [M+H]$^+$), 555.1894.

EXAMPLE 327

2-FURYL[4-PHENYL-8-(TRIFLUOROMETHYL)
QUINOLIN-3-YL]METHANONE

This compound is prepared according to the procedure of Example 21, substituting 2-furylmagnesium bromide for 2-methylphenylmagnesium bromide.
MS (ESI) m/z 368.

EXAMPLE 328

(4-BROMO-2-FURYL)[4-PHENYL-8-(TRIFLUO-
ROMETHYL)QUINOLIN-3-YL]METHANONE

This compound is prepared according to the procedure of Example 21, substituting 4-bromo-2-furylmagnesium bromide for 2-methylphenylmagnesium bromide. MS (ESI) m/z 446.

EXAMPLE 329

3-FURYL[4-PHENYL-8-(TRIFLUOROMETHYL)
QUINOLIN-3-YL]METHANONE

This compound is prepared according to the procedure of Example 21, substituting 3-furylmagnesium bromide for 2-methylphenylmagnesium bromide.
MS (ESI) m/z 368; HRMS: calcd for $C_{21}H_{12}F_3NO_2+H$, 368.08984; found (ESI, [M+H]$^+$), 368.0887.

EXAMPLE 330

(3-BROMO-2-FURYL)[4-PHENYL-8-(TRIFLUO-
ROMETHYL)QUINOLIN-3-YL]METHANONE

This compound is prepared according to the procedure of Example 21, substituting 3-bromo-2-furylmagnesium bromide for 2-methylphenylmagnesium bromide.
MS (ESI) m/z 446; HRMS: calcd for $C_{21}H_{11}BrF_3NO_2+H$, 446.00035; found (ESI, [M+H]$^+$), 445.9997.

EXAMPLE 331

(3-METHYLTHIEN-2-YL)[4-PHENYL-8-(TRIF-
LUOROMETHYL)QUINOLIN-3-YL]METHA-
NONE

This compound is prepared according to the procedure of Example 21, substituting 3-methyl-2-thienylmagnesium bromide for 2-methylphenylmagnesium bromide.
MS (ESI) m/z 398; HRMS: calcd for $C_{22}H_{14}F_3NOS+H$, 398.08264; found (ESI, [M+H]$^+$), 398.0811.

EXAMPLE 332

(4-ETHYLPHENYL)[4-PHENYL-8-(TRIFLUO-
ROMETHYL)QUINOLIN-3-YL]METHANONE

This compound is prepared according to the procedure of Example 21, substituting 4-ethylphenylmagnesium bromide for 2-methylphenylmagnesium bromide.
MS (ESI) m/z 406; HRMS: calcd for $C_{25}H_{18}F_3NO+H$, 406.14187; found (ESI, [M+H]$^+$), 406.1407.

EXAMPLE 333

(4-FLUOROPHENYL)[4-PHENYL-8-(TRIFLUO-
ROMETHYL)QUINOLIN-3-YL]METHANONE

This compound is prepared according to the procedure of Example 21, substituting 4-fluorophenylmagnesium bromide for 2-methylphenylmagnesium bromide.
MS (ESI) m/z 396; HRMS: calcd for $C_{23}H_{13}F_4NO+H$, 396.10115; found (ESI, [M+H]$^+$), 396.1012.

EXAMPLE 334

(4-CHLOROPHENYL)[4-PHENYL-8-(TRIFLUO-
ROMETHYL)QUINOLIN-3-YL]METHANONE

This compound is prepared according to the procedure of Example 21, substituting 4-chlorophenylmagnesium bromide for 2-methylphenylmagnesium bromide. MS m/z 412; HRMS: calcd for $C_{23}H_{13}ClF_3NO+H$, 412.07160; found (ESI, [M+H]$^+$), 412.0696.

EXAMPLE 335

BIS(4-CHLOROPHENYL)[4-PHENYL-8-(TRIF-
LUOROMETHYL)QUINOLIN-3-YL]METHANOL

This compound is prepared according to the procedure of Example 21, substituting excess 4-chlorophenylmagnesium bromide for 2-methylphenylmagnesium bromide. MS m/z 524; MS m/z 522; HRMS: calcd for $C_{29}H_{18}Cl_2F_3NO—H$, 522.06393; found (ESI, [M–H]$^-$), 522.0651.

EXAMPLE 336

(4-AMINOPHENYL)[4-PHENYL-8-(TRIFLUO-
ROMETHYL)QUINOLIN-3-Yl]METHANONE (4-Fluorophenyl)[4-phenyl-8-(trifluoromethyl)quinolin-3-yl]methanone (0.631 g, 1.60 mmol) and ammonium hydroxide (9 mL) are heated in a steel pressure vessel at 150° C. overnight. The cooled reaction is poured into water, extracted with methylene chloride, and concentrated in vacuo. The resulting solid into DMSO (2 mL) and ammonium hydroxide (8 mL) is heated in the steel bomb at 150° C. overnight and worked up as above. The product is purified by chromatography eluting with 30:70 ethyl acetate:hexane to yield the title compound as a solid (0.344 g). MS (ESI) m/z 393; HRMS: calcd for $C_{23}H_{15}F_3N_2O—H$, 391.10582; found (ESI, [M–H]$^-$), 391.1054.

EXAMPLE 337

(4-NITROPHENYL)[4-PHENYL-8-(TRIFLUO-
ROMETHYL)QUINOLIN-3-YL]METHANONE (4-Aminophenyl)[4-phenyl-8-(trifluoromethyl)quinolin-3-yl]methanone (0.050 g, 0.127 mmol) in AcOH (2 mL) is added slowly to a stirred solution of NaBO$_3$ 4H$_2$O (0.098 g, 0.637 mmol) in AcOH (3 mL) at 55° C. over 40 min. After 1 h, the reaction is cooled, poured into water and extracted with methylene chloride. The extracts are washed with saturated aq sodium bicarbonate, dried over MgSO$_4$ and concentrated. The residue is purified by chromatography eluting with 10:90 ethyl acetate:hexane to afford the title compound (0.0157 g). MS (ESI) m/z 423; HRMS: calcd for $C_{23}H_{13}F_3N_2O_3+H$, 423.09565; found (ESI, [M+H]$^+$), 423.0943.

EXAMPLE 338

[4-PHENYL-8-(TRIFLUOROMETHYL)QUINO-LIN-3-YL][4-(TRIFLUOROMETHYL)PHENYL]METHANONE

This compound is prepared according to the procedure of Example 21, substituting 4-trifluoromethylphenylmagnesium bromide for 2-methylphenylmagnesium bromide.
MS (ESI) m/z 446; HRMS: calcd for $C_{24}H_{13}F_6NO+H$, 446.09796; found (ESI, [M+H]$^+$), 446.0962.

EXAMPLE 339

(4-METHOXYPHENYL)[4-PHENYL-8-(TRIF-LUOROMETHYL)QUINOLIN-3-YL]METHA-NONE

This compound is prepared according to the procedure of Example 21, substituting 4-methoxyphenylmagnesium bromide for 2-methylphenylmagnesium bromide.
MS (ESI) m/z 408.1193; HRMS: calcd for $C_{24}H_{16}F_3NO_2$+H, 408.12114; found (ESI, [M+H]$^+$), 408.1193.

EXAMPLE 340

(4-BROMOPHENYL)[4-PHENYL-8-(TRIFLUO-ROMETHYL)QUINOLIN-3-YL]METHANONE (4-Aminophenyl)[4-phenyl-8-(trifluoromethyl)quinolin-3-yl]methanone (0.121 g, 0.31 mmol) in acetonitrile (5 mL) is added dropwise to a stirred solution of tert-butyl nitrite (0.055 mL, 0.46 mmol) and $CuBr_2$ (0.083 g, 0.372 mmol) in acetonitrile (5 mL) at 65° C. After 2 h, the reaction is poured into 2N aq HCl, extracted with methylene chloride, and the extracts washed once with 2N aq HCl. The extracts are dried over $MgSO_4$, concentrated in vacuo, and chromatographed eluting with 2.5:97.5 ethyl acetate:hexane to afford the title compound as a white solid (0.092 g). MS (ESI) m/z 456.0199; HRMS: calcd for $C_{23}H_{13}BrF_3NO+H$, 456.02108; found (ESI, [M+H]$^+$), 456.0199.

EXAMPLE 341

(4-HYDROXYPHENYL)[4-PHENYL-8-(TRIF-LUOROMETHYL)QUINOLIN-3-YL]METHA-NONE (4-Methoxyphenyl)[4-phenyl-8-(trifluoromethyl)quinolin-3-yl]methanone (0.174 g) and pyridine hydrochloride are heated at 200° C. for 2 h and then cooled. The resulting solid is taken into methylene chloride and 2N aq HCl. The layers are separated, the aqueous layer is extracted again, and the combined organics are washed with saturated sodium bicarbonate and dried over $MgSO_4$. The residue is chromatographed eluting with 25:75 ethyl acetate:hexane to afford the title compound as a white solid (0.132 g). MS (ES) m/z 392.1; HRMS: calcd for $C_{23}H_{14}F_3NO_2$—H, 392.08984; found (ESI, [M−H]$^−$), 392.0883.

EXAMPLE 342

[4-PHENYL-8-(TRIFLUOROMETHYL)QUINO-LIN-3-YL](4-VINYLPHENYL)METHANONE

This compound is prepared according to the procedure of Example 21, substituting 4-vinylphenylmagnesium bromide for 2-methylphenylmagnesium bromide MS (ES) m/z 404.2; HRMS: calcd for $C_{25}H_{16}F_3NO+H$, 404.12622; found (ESI, [M+H]$^+$), 404.1245.

EXAMPLE 343

(2-HYDROXYPHENYL)[4-PHENYL-8-(TRIF-LUOROMETHYL)QUINOLIN-3-YL]METHA-NONE (2-Methoxyphenyl)[4-phenyl-8-(trifluoromethyl)quinolin-3-yl]methanone (0.853 g, 2.09 mmol) and pyridine hydrochloride are heated at 200° C. for 4 h. The reaction is worked up and purified as in Example above except eluting with 10:90 ethyl acetate:hexane to afford the title product as white solid (0.669 g, 81%). MS (ESI) m/z 392.0901; HRMS: calcd for $C_{23}H_{14}F_3NO_2$—H, 392.08984; found (ESI, [M−H]$^−$), 392.0901.

EXAMPLE 344

1-[4-PHENYL-8-(TRIFLUOROMETHYL)QUINO-LIN-3-YL]PENTAN-1-ONE

This compound is prepared according to the procedure of Example 21, substituting butylmagnesium bromide for 2-methylphenylmagnesium bromide. HRMS: calcd for $C_{21}H_{18}F_3NO+H$, 358.14187; found (ESI, [M+H]$^+$), 358.141.

EXAMPLE 345

1-[4-PHENYL-8-(TRIFLUOROMETHYL)QUINO-LIN-3-YL]HEXAN-1-ONE

This compound is prepared according to the procedure of Example 21, substituting pentylmagnesium bromide for 2-methylphenylmagnesium bromide. HRMS: calcd for $C_{22}H_{20}F_3NO+H$, 372.15752; found (ESI, [M+H]$^+$), 372.1574.

EXAMPLE 346

CYCLOPROPYL[4-PHENYL-8-(TRIFLUOROM-ETHYL)QUINOLIN-3-YL]METHANONE

This compound is prepared according to the procedure of Example 21, substituting cyclopropylmagnesium bromide for 2-methylphenylmagnesium bromide. HRMS: calcd for $C_{20}H_{14}F_3NO+H$, 342.11057; found (ESI, [M+H]$^+$), 342.1118.

EXAMPLE 347

CYCLOPENTYL[4-PHENYL-8-(TRIFLUOROM-ETHYL)QUINOLIN-3-YL]METHANONE

This compound is prepared according to the procedure of Example 21, substituting cyclopentylmagnesium bromide for 2-methylphenylmagnesium bromide. HRMS: calcd for $C_{22}H_{18}F_3NO+H$, 370.14187; found (ESI, [M+H]$^+$), 370.141.

EXAMPLE 348

(3-FLUOROPHENYL)[4-PHENYL-8-(TRIFLUO-ROMETHYL)QUINOLIN-3-YL]METHANONE

This compound is prepared according to the procedure of Example 21, substituting 3-fluorophenylmagnesium bromide for 2-methylphenylmagnesium bromide. HRMS: calcd for $C_{23}H_{13}F_4NO+H$, 396.10115; found (ESI, [M+H]$^+$), 396.0993.

EXAMPLE 349

(3-CHLOROPHENYL)[4-PHENYL-8-(TRIFLUOROMETHYL)QUINOLIN-3-Yl]METHANONE

This compound is prepared according to the procedure of Example 21, substituting 3-chlorophenylmagnesium bromide for 2-methylphenylmagnesium bromide. HRMS: calcd for $C_{23}H_{13}ClF_3NO+H$, 412.07160; found (ESI, [M+H]$^+$), 412.0713.

EXAMPLE 350

(4-CHLORO-3-FLUOROPHENYL)[4-PHENYL-8-(TRIFLUOROMETHYL)QUINOLIN-3-Yl]METHANONE

This compound is prepared according to the procedure of Example 21, substituting 4-chloro-3-fluorophenylmagnesium bromide for 2-methylphenylmagnesium bromide. HRMS: calcd for $C_{23}H_{12}ClF_4NO+H$, 430.06218; found (ESI, [M+H]$^+$), 430.0606.

EXAMPLE 351

(3,4-DICHLOROPHENYL)[4-PHENYL-8-(TRIFLUOROMETHYL)QUINOLIN-3-YL]METHANONE

This compound is prepared according to the procedure of Example 21, substituting 3,4-dichlorophenylmagnesium bromide for 2-methylphenylmagnesium bromide. HRMS: calcd for $C_{23}H_{12}Cl_2F_3NO+H$, 446.03263; found (ESI, [M+H]$^+$), 446.0332.

EXAMPLE 352

(4-CHLORO-2-METHYLPHENYL)[4-PHENYL-8-(TRIFLUOROMETHYL)QUINOLIN-3-YL]METHANONE

This compound is prepared according to the procedure of Example 21, substituting 4-chloro-2-methylphenylmagnesium bromide for 2-methylphenylmagnesium bromide. HRMS: calcd for $C_{24}H_{15}ClF_3NO+H$, 426.08725; found (ESI, [M+H]$^+$), 426.0859.

EXAMPLE 353

(3-FLUORO-2-METHYLPHENYL)[4-PHENYL-8-(TRIFLUOROMETHYL)QUINOLIN-3-YL]METHANONE

This compound is prepared according to the procedure of Example 21, substituting 3-fluoro-2-methylphenylmagnesium bromide for 2-methylphenylmagnesium bromide. HRMS: calcd for $C_{24}H_{15}F_4NO+H$, 410.11680; found (ESI, [M+H]$^+$), 410.1158.

EXAMPLE 354

(3-FLUORO-4-METHYLPHENYL)[4-PHENYL-8-(TRIFLUOROMETHYL)QUINOLIN-3-YL]METHANONE

This compound is prepared according to the procedure of Example 21, substituting 3-fluoro-4-methylphenylmagnesium bromide for 2-methylphenylmagnesium bromide. HRMS: calcd for $C_{24}H_{15}F_4NO+H$, 410.11680; found (ESI, [M+H]$^+$), 410.117.

EXAMPLE 355

3-[DIMETHOXY(PHENYL)METHYL]-4-PHENYL-8-(TRIFLUOROMETHYL)QUINOLINE phenyl[4-phenyl-8-(trifluoromethyl)quinolin-3-yl]methanone (0.210 g, 0.56 mmol) in MeOH (5 mL) is refluxed with trimethylorthoformate (0.12 mL, 1.12 mmol) and para-toluenesulfonic acid (0.005 g). After 5 h, additional orthoformate (0.20 mL) is added. After 3 h more, more orthoformate (0.20 mL) is added. After refluxing overnight, the reaction is cooled and treated with NaOMe in methanol (0.5 mL). After 10 min of stirring, the reaction is concentrated and the residue chromatographed eluting with 5:95 ethyl acetate:hexanes to afford the title compound as a white solid (0.100 g). MS (ESI) m/z 424; HRMS: calcd for $C_{25}H_{20}F_3NO_2+H$, 424.15244; found (ESI, [M+H]$^+$), 424.1519.

EXAMPLE 356

4-PHENYL-3-(1-PHENYLVINYL)-8-(TRIFLUOROMETHYL)QUINOLINE 1-phenyl-1-[4-phenyl-8-(trifluoromethyl)quinolin-3-yl]ethanol (0.675 g, 1.72 mmol) in EtOH (13 mL) is refluxed with conc HCl (2.6 mL) for 2 h. The cooled reaction is poured into water and extracted with methylene chloride. The extract is washed with saturated aq sodium bicarbonate, dried (MgSO$_4$) and concentrated. The residue is chromatographed eluting with 5:95 ethyl acetate:hexane to afford the title compound as a yellow solid (0.546 g, 85%). MS (ESI) m/z 376; HRMS: calcd for $C_{24}H_{16}F_3N+H$, 376.13131; found (ESI, [M+H]$^+$), 376.1306.

EXAMPLE 357

4-PHENYL-3-(1-PHENYLETHYL)-8-(TRIFLUOROMETHYL)QUINOLINE 4-phenyl-3-(1-phenylvinyl)-8-(trifluoromethyl)quinoline (0.050 g, 0.133 mmol) and 5% Pd/C (0.010 g) in EtOH (7 mL) is hydrogenated on a Parr shaker (40 psi hydrogen) overnight. The reaction is filtered through Celite and concentrated. The product is chromatographed eluting with 2:98 ethyl acetate:hexanes to afford the title compound (0.051 g). MS (ESI) m/z 378; HRMS: calcd for $C_{24}H_{18}F_3N+H$, 378.14696; found (ESI, [M+H]$^+$), 378.1459.

EXAMPLE 358

(Z)-(2-HYDROXYPHENYL)[4-PHENYL-8-(TRIFLUOROMETHYL)QUINOLIN-3-YL]METHANONE HYDRAZONE (2-Hydroxyphenyl)[4-phenyl-8-(trifluoromethyl)quinolin-3-yl]methanone (0.05 g, 0.127 mmol) and 5% Pd/C (0.010 g) in ethylene glycol (3 mL) is heated at 120° C. for 0.5 h. The cooled reaction is treated with water and the product is extracted with methylene chloride. The dried extract (Na$_2$SO$_4$) and concentrated to afford the title compound (0.0318 g). MS (ESI) m/z 408.1312; HRMS: calcd for $C_{23}H_{16}F_3N_3O+H$, 408.13237; found (ESI, [M+H]$^+$), 408.1312.

EXAMPLE 359

3-(1,2-BENZISOXAZOL-3-YL)-4-PHENYL-8-(TRIFLUOROMETHYL)QUINOLINE (2-Hydroxyphenyl)[4-phenyl-8-(trifluoromethyl)quinolin-3-yl]methanone (0.079 g, 0.20 mmol), hydroxylamine hydrochloride (0.053 g, 0.762 mmol) and sodium acetate trihydrate (0.138 g, 1.02 mmol) is refluxed in EtOH/H$_2$O (5 mL of 7:3 mixture) for several hours. No reaction took place. The EtOH is removed and replaced with ethylene glycol along with more hydroxylamine hydrochloride and sodium acetate trihydrate and heated at 130° C. overnight. The reaction is poured into water and extracted with methylene chloride, dried (MgSO$_4$) and concentrated. The residue is chromatographed eluting with 15:85 ethyl acetate:hexanes to afford the oxime intermediate as a white solid (0.075 g, 91%). The intermediate (0.066 g, 0.161 mmol) and acetic anhydride (5 mL) are placed in an oil bath preheated to 130° C. for 1 min. The reaction is poured into water and extracted with ethyl acetate. The extracts are washed several times with saturated aq sodium bicarbonate, dried (MgSO$_4$) and concentrated to afford the oxime acetate intermediate (0.058 g) as a white foamy solid. The oxime acetate (0.058 g, 0.129 mmol) is dissolved in DMF (3 mL) and treated with NaH (0.015 g, 0.378 mmol, 60% dispersion in oil). The reaction is allowed to stir at room temperature for 1.5 h. The reaction is poured into water and extracted with ether. The extracts are washed with half-saturated brine, dried (MgSO$_4$), and concentrated in vacuo. The residue is chromatographed eluting with 10:90 ethyl acetate:hexane to afford the title compound (0.0128 g). HRMS: calcd for C$_{23}$H13F3N2O+H, 391.10582; found (ESI, [M+H]+), 391.1073.

EXAMPLE 360

3-(1-METHYL-1-PHENYLETHYL)-4-PHENYL-8-(TRIFLUOROMETHYL)QUINOLINE 3,3-Dimethyl-3-phenylpropionaldehyde (0.272 g, 1.67 mmol) and [2-amino-3-(trifluoromethyl)phenyl](phenyl)methanone (0.138 g, 0.52 mmol) are dissolved in AcOH (3 mL) and treated with 1:20H$_2$SO$_4$/AcOH solution (0.10 mL). The mixture is heated in a microwave at 175° C. for 15 min and a further 5 min at 200° C. The reaction is carefully poured into saturated aq sodium bicarbonate and extracted with ethyl acetate. The extracts are washed with saturated aq sodium bicarbonate and dried (MgSO$_4$). The product is chromatographed eluting with 5:95 ethyl acetate:hexane. The partially purified is further purified using Prep HPLC with a gradient of 10-100% acetonitrile/water to afford the title compound (0.069 g). HRMS: calcd for C$_{25}$H$_{20}$F$_3$N+H, 392.16261; found (ESI, [M+H]$^+$), 392.1637.

EXAMPLE 361

4-PHENYL-3-(1-PHENYLCYCLOPROPYL)-8-(TRIFLUOROMETHYL)QUINOLINE

Pyridinium chlorochromate (0.417 g, 1.94 mmol) in CH$_2$Cl$_2$ (3 mL) is treated with a mixture of 2-(1-phenylcyclopropyl)ethanol (0.157 g, 0.967 mmol) in CH$_2$Cl$_2$ (2 mL) for 2 h. The reaction is filtered through Celite, treated with AcOH (3 mL) and [2-amino-3-(trifluoromethyl)phenyl](phenyl)methanone (0.128 g, 0.484 mmol), and the methylene chloride is removed in vacuo. Then 1:20H$_2$SO$_4$:AcOH (0.1 mL) is added and the reaction is heated at 120° C. for 3.5 h. The cooled reaction is poured into saturated aq sodium bicarbonate and extracted with ethyl acetate. The extract is washed with saturated aq sodium bicarbonate and dried (MgSO$_4$). The residue is chromatographed eluting with 5:95 ethyl acetate:hexane and then prep HPLC with a gradient of 10-100% acetonitrile/water to afford the title compound (0.032 g). HRMS: calcd for C$_{25}$H$_{18}$F$_3$N+H, 390.14696; found (ESI, [M+H]$^+$), 390.1468.

EXAMPLE 362

(2-FLUOROPHENYL)[4-PHENYL-8-(TRIFLUOROMETHYL)QUINOLIN-3-Yl]METHANONE 3-(2-Fluorophenyl)-3-oxopropionaldehyde (0.451 g, 2.70 mmol) and [2-amino-3-(trifluoromethyl)phenyl](phenyl)methanone (0.119 g, 0.448 mmol) in AcOH (5 mL) is treated with 0.1 mL of 1:20H$_2$SO$_4$/AcOH solution and heated at reflux for 20 min. The cooled reaction is quenched with water and extracted with ethyl acetate twice. The combined organic layers are washed with saturated aq sodium bicarbonate and dried over MgSO$_4$. The product is purified by chromatography (5:95 ethyl acetate:hexane) to afford the title compound as a yellow solid (0.162 g, 91.5%). MS (ESI) m/z 396.1009; HRMS: calcd for C$_{23}$H$_{13}$F$_4$NO+H, 396.10115; found (ESI, [M+H]$^+$), 396.1009.

EXAMPLE 363

(2-BROMOPHENYL)[4-PHENYL-8-(TRIFLUOROMETHYL)QUINOLIN-3-YL]METHANONE

This compound is prepared according to the procedure above substituting 3-(2-bromophenyl)-3-oxopropionaldehyde for 3-(2-fluorophenyl)-3-oxopropionaldehyde. HRMS: calcd for C$_{23}$H13BrF3NO+H, 456.02108; found (ESI, [M+H]$^+$), 456.0229.

EXAMPLE 364

(2-CHLOROPHENYL)[4-PHENYL-8-(TRIFLUOROMETHYL)QUINOLIN-3-YL]METHANONE

This compound is prepared according to the procedure above substituting 3-(2-chlorophenyl)-3-oxopropionaldehyde for 3-(2-fluorophenyl)-3-oxopropionaldehyde. HRMS: calcd for C$_{23}$H$_{13}$ClF$_3$NO+H, 412.07160; found (ESI, [M+H]$^+$), 412.0703.

EXAMPLE 365

2-[4-({3-[3-METHYL-8-(TRIFLUOROMETHYL)QUINOLIN-4-YL]PHENOXY}METHYL)PHENYL]ETHANOL

To a stirred solution of 3-[3-Methyl-8-(trifluoromethyl)quinolin-4-yl]phenol (0.086 g, 0.28 mmol) and 2-(4-bromomethlyphenyl)ethanol (0.061 g, 0.28 mmol) in CH$_2$Cl$_2$ (5 mL) is added Cs$_2$CO$_3$ (0.365 g, 1.12 mmol). After 1.5 h, additional alkylating agent (0.015 g) is added and the reaction is stirred overnight. The reaction is neutralized with 2N aq HCl, extracted with ethyl acetate and dried (MgSO$_4$). Chromatography eluting with 5:95 ethyl acetate:hexane afforded the title compound (0.092 g, 75%).

HRMS: calcd for C$_{26}$H$_{22}$F$_3$NO$_2$+H, 438.16809; found (ESI, [M+H]$^+$), 438.167.

EXAMPLE 366

[4-({3-[3-METHYL-8-(TRIFLUOROMETHYL) QUINOLIN-4-YL]PHENOXY}METHYL)PHE- NYL]ACETIC ACID

3-[3-Methyl-8-(trifluoromethyl)quinolin-4-yl]phenol (1.13 g, 3.73 mmol) and 4-bromomethylphenylacetic acid (1.02 g, 4.47 mmol) in $CH_2Cl_2$ (60 mL) is treated with $Cs_2CO_3$ (4.86 g, 14.9 mmol) and the reaction is stirred overnight. The solvent is removed and the residue dissolved in THF and 2N aq NaOH. After heating at 70° C. for 1 h, the reaction is cooled and the layers separated. The aqueous layer is further extracted with ethyl acetate. The combined organics are dried ($Na_2SO_4$) and concentrated. The residue is chromatographed eluting with 20:80 ethyl acetate:hexane and then 5:95 methanol:methylene chloride to afford the title product.

HRMS: calcd for $C_{26}H_{20}F_3NO_3$+H, 452.14735; found (ESI, [M+H]$^+$), 452.1452.

EXAMPLE 367

[4-({3-[3-(HYDROXYMETHYL)-8-(TRIFLUO- ROMETHYL)QUINOLIN-4-YL] PHENOXY}METHYL)PHENYL]ACETIC ACID

4-Bromomethylphenylacetic acid (1.86 g, 8.13 mmol) is taken into $CH_2Cl_2$ (80 mL) and to this is added $Cs_2CO_3$ (9.63 g, 29.56 mmol) and the mixture is stirred for 1 hour. Next, 3-[3-(hydroxymethyl)-8-(trifluoromethyl)quinolin-4-yl] phenol (2.36 g, 7.39 mmol) is added and the reaction is stirred overnight. The reaction is not complete, therefore an additional 3 g of 4-bromomethylphenylacetic acid and 2 g of $Cs_2CO_3$ is added and stirring is continued for another overnight period. The reaction is neutralized with HCl and then the solvent is removed. The resulting material is taken up into THF/MeOH/2N NaOH and heated at 70° C. for 45 minutes. The reaction is neutralized with HCl then the organics are removed and the aqueous layer is extracted with ethyl acetate. The combined organics is washed with water and brine and finally dried over $Na_2SO_4$. The resulting material is purified via column chromatography using 50% ethyl acetate in hexanes as the eluent to yield a white solid, which still contained an impurity. This material is dissolved into ethyl acetate and washed with saturated sodium bicarbonate. The ethyl acetate layer is concentrated to yield the desired product. HRMS: calcd for $C_{26}H_{20}F_3NO_4$+H, 468.14227; found (ESI, [M+H]$^+$), 468.1428.

EXAMPLE 368

N-(4-METHYLPHENYL)-4-PHENYL-8-(TRIF- LUOROMETHYL)QUINOLINE-3-CARBOXAM- IDE

4-Phenyl-8-trifluoromethyl-quinoline-3-carboxylic acid (0.110 g, 0.347 mmol), whose preparation is described in Scheme 2, p-toluidine (0.074 mL, 0.693 mmol), EDCI-HCl (0.110 g, 0.520 mmol), and DMAP (0.084 g, 0.520 mmol). are dissolved in 1,2-dichloroethane (3 mL) in a 5 mL microwave tube. After stirring in the microwave reactor for 6 min at 70° C. the cooled solution is poured into 2 N aq HCl and extracted with methylene chloride, washed with water, brine, and dried with magnesium sulfate. The combined extracts are concentrated and the residue is chromatographed in 1:9 ethyl acetate:hexanes to afford the title amide as a white solid (0.078 g, 56%). mp 203-205° C.; MS (ES) m/z 405.2; HRMS: calcd for $C_{24}H_{17}N_2F_3O$+H, 407.13712; found (ESI, [M+H]$^+$), 407.1376.

EXAMPLE 369

ETHYL[4-({4-FLUORO-3-[3-PHENYL-8-(TRIF- LUOROMETHYL)QUINOLIN-4-YL] PHENOXY}METHYL)PHENYL]ACETATE

The title compound is prepared essentially as described in Example 396, supra, except using 4-(2-Fluoro-5-hydrox- yphenyl)-3-phenyl-8-(trifluoromethyl)quinoline instead of 3-[3-phenyl-8-(trifluoromethyl)quinolin-4-yl]phenol to afford 0.151 g (51%) of the title compound as a tan tacky solid: Calculated mass for $C_{33}H_{25}NF_4O_3$ is 559.56, found MS (ES) m/z 560; (M+H)$^+$.

EXAMPLE 370

N-(3-METHYLPHENYL)-4-PHENYL-8-(TRIF- LUOROMETHYL)QUINOLINE-3-CARBOXAM- IDE

The title compound is prepared essentially as described in Example 368, except using m-toluidine instead of p-toluidine to afford the title amide as a white solid (0.111 g, 62%). mp 182-184° C.; MS (ES) m/z 405.1; HRMS: calcd for $C_{24}H_{17}N_2F_3O$+H, 407.13712; found (ESI, [M+H]$^+$), 407.1385.

EXAMPLE 371

4-PHENYL-8-(TRIFLUOROMETHYL)-N-[3-(TRI- FLUOROMETHYL)PHENYL]QUINOLINE-3- CARBOXAMIDE

The title compound is prepared essentially as described in Example 368, except using 3-(trifluoromethyl)aniline instead of p-toluidine to afford the title amide as a tan solid (0.074 g, 60%). mp 155-157° C.; MS (ES) m/z 459.1; HRMS: calcd for $C_{24}H_{14}N_2F_6O$+H, 461.10886; found (ESI, [M+H]$^+$), 461.1096.

EXAMPLE 372

N-(4-CHLOROPHENYL)-4-PHENYL-8-(TRIF- LUOROMETHYL)QUINOLINE-3-CARBOXAM- IDE

The title compound is prepared essentially as described in Example 368, except using 4-chloroaniline instead of p-tolui- dine to afford the title amide as a tan solid (0.085 g, 62%). mp 153-155° C.; MS (ES) m/z 425.1; HRMS: calcd for $C_{23}H_{14}N_2F_3OCl$+H, 427.08250; found (ESI, [M+H]$^+$), 427.0819.

EXAMPLE 373

N-(3-CHLOROPHENYL)-4-PHENYL-8-(TRIF- LUOROMETHYL)QUINOLINE-3-CARBOXAM- IDE

The title compound is prepared essentially as described in Example 368, except using 3-chloroaniline instead of p-tolui- dine to afford the title amide as a white solid (0.086 g, 70%).

mp 159-161° C.; MS (ES) m/z 425.1; HRMS: calcd for $C_{23}H_{14}N_2F_3OCl+H$, 427.08250; found (ESI, [M+H]$^+$), 427.0826.

EXAMPLE 374

N-(2-CHLOROPHENYL)-4-PHENYL-8-(TRIFLUOROMETHYL)QUINOLINE-3-CARBOXAMIDE

The title compound is prepared essentially as described in Example 368, except using 2-chloroaniline instead of p-toluidine to afford the title amide as a white solid (0.011 g, 12%). mp 173-175° C.; MS (ES) m/z 425.2; HRMS: calcd for $C_{23}H_{14}N_2F_3OCl+H$, 427.08250; found (ESI, [M+H]$^+$), 427.0829.

EXAMPLE 375

N-(3-METHOXYPHENYL)-4-PHENYL-8-(TRIFLUOROMETHYL)QUINOLINE-3-CARBOXAMIDE

The title compound is prepared essentially as described in Example 368, except using m-anisidine instead of p-toluidine to afford the title amide as a tan solid (0.115 g, 80%). mp 141-434° C.; HRMS: calcd for $C_{23}H_{17}N_2F_3O_2+H$, 423.13204; found (ESI, [M+H]$^+$), 423.1315.

EXAMPLE 376

N-(4-FLUOROPHENYL)-4-PHENYL-8-(TRIFLUOROMETHYL)QUINOLINE-3-CARBOXAMIDE

The title compound is prepared essentially as described in Example 368, except using 4-fluoroaniline instead of p-toluidine to afford the title amide as a tan solid (0.120 g, 83%). mp 157-159° C.; MS (ES) m/z 409.2; HRMS: calcd for $C_{23}H_{14}N_2F_4O+H$, 411.11205; found (ESI, [M+H]$^+$), 411.1103.

EXAMPLE 377

N-(3-FLUOROPHENYL)-4-PHENYL-8-(TRIFLUOROMETHYL)QUINOLINE-3-CARBOXAMIDE

The title compound is prepared essentially as described in Example 368, except using 3-fluoroaniline instead of p-toluidine to afford the title amide as a tan solid (0.120 g, 86%). mp 171-173° C.; MS (ES) m/z 409.2; HRMS: calcd for $C_{23}H_{14}N_2F_4O+H$, 411.11205; found (ESI, [M+H]$^+$), 411.1108.

EXAMPLE 378

N-METHYL-N,4-DIPHENYL-8-(TRIFLUOROMETHYL)QUINOLINE-3-CARBOXAMIDE

To a solution of N,4-diphenyl-8-(trifluoromethyl)quinoline-3-carboxamide, (0.150 g, 0.382 mmol), whose preparation is described in Example 368, in DMF (20 mL) is added sodium hydride (0.010 g, 0.421 mmol). After stirring in an ice bath for 1 h, methyl iodide (0.027 mL, 0.421 mmol) is added drop wise and the reaction mixture is removed from the ice bath and stirred 2 h. The reaction mixture is partitioned between ethyl acetate and water and the aqueous layer is extracted with ethyl acetate. The combined extracts are washed with water, brine, and dried with magnesium sulfate. The extracts are concentrated and the residue is chromatographed with 1:4 ethyl acetate:hexanes to afford the title compound as a white solid (0.147 g, 96%). mp 188-190° C.; MS (ESI) m/z 407; HRMS: calcd for $C_{24}H_{17}N_2F_3O+H$, 407.13712; found (ESI, [M+H]$^+$), 407.1361.

EXAMPLE 379

N-METHYL-N-(3-METHYLPHENYL)-4-PHENYL-8-(TRIFLUOROMETHYL)QUINOLINE-3-CARBOXAMIDE

The title compound is prepared essentially as described in Example 378, except using N-(3-methylphenyl)-4-phenyl-8-(trifluoromethyl)quinoline-3-carboxamide instead of N,4-diphenyl-8-(trifluoromethyl)quinoline-3-carboxamide to afford the title amide as a tan solid (0.046 g, 83%). mp 174-176° C.; MS (ES) m/z 421.3; HRMS: calcd for $C_{25}H_{19}N_2F_3O+H$, 421.15277; found (ESI, [M+H]$^+$), 421.151.

EXAMPLE 380

N-METHYL-N-(4-METHYLPHENYL)-4-PHENYL-8-(TRIFLUOROMETHYL)QUINOLINE-3-CARBOXAMIDE

The title compound is prepared essentially as described in Example 378, except using N-(4-methylphenyl)-4-phenyl-8-(trifluoromethyl)quinoline-3-carboxamide instead of N,4-diphenyl-8-(trifluoromethyl)quinoline-3-carboxamide to afford the title amide as a white solid (0.046 g, 86%). mp 143-145° C.; MS (ES) m/z 421.3; HRMS: calcd for $C_{25}H_{19}N_2F_3O+H$, 421.15277; found (ESI, [M+H]$^+$), 421.1522.

EXAMPLE 381

N-METHYL-N-(2-METHYLPHENYL)-4-PHENYL-8-(TRIFLUOROMETHYL)QUINOLINE-3-CARBOXAMIDE

The title compound is prepared essentially as described in Example 378, except using N-(2-methylphenyl)-4-phenyl-8-(trifluoromethyl)quinoline-3-carboxamide instead of N,4-diphenyl-8-(trifluoromethyl)quinoline-3-carboxamide to afford the title amide as a tan solid (0.018 g, 23%). mp 144° C.; MS (ES) m/z 421.2; HRMS: calcd for $C_{25}H_{19}N_2F_3O+H$, 421.15277; found (ESI, [M+H]$^+$), 421.1508.

EXAMPLE 382

N-METHYL-4-PHENYL-8-(TRIFLUOROMETHYL)-N-[3-(TRIFLUOROMETHYL)PHENYL]QUINOLINE-3-CARBOXAMIDE

The title compound is prepared essentially as described in Example 378, except using N-(3-trifluoromethylphenyl)-4-phenyl-8-(trifluoromethyl)quinoline-3-carboxamide instead of N,4-diphenyl-8-(trifluoromethyl)quinoline-3-carboxamide to afford the amide as a white solid (0.028 g, 53%). mp 163-165° C.; MS (ES) m/z 475.2; HRMS: calcd for $C_{25}H_{16}N_2F_6O+H$, 475.12451; found (ESI, [M+H]$^+$), 475.1259.

EXAMPLE 383

N-(4-CHLOROPHENYL)-N-METHYL-4-PHENYL-8-(TRIFLUOROMETHYL)QUINOLINE-3-CARBOXAMIDE

The title compound is prepared essentially as described in Example 378, except using N-(4-chlorophenyl)-4-phenyl-8-(trifluoromethyl)quinoline-3-carboxamide instead of N,4-diphenyl-8-(trifluoromethyl)quinoline-3-carboxamide to afford the amide as a white solid (0.059 g, 73%). mp 177-179° C.; MS (ES) m/z 441.2; HRMS: calcd for $C_{24}H_{16}N_2F_3OCl+H$, 441.09815; found (ESI, [M+H]$^+$), 441.0965.

EXAMPLE 384

N-(3-CHLOROPHENYL)-N-METHYL-4-PHENYL-8-(TRIFLUOROMETHYL)QUINOLINE-3-CARBOXAMIDE

The title compound is prepared essentially as described in Example 378, except using N-(3-chlorophenyl)-4-phenyl-8-(trifluoromethyl)quinoline-3-carboxamide instead of N,4-diphenyl-8-(trifluoromethyl)quinoline-3-carboxamide to afford the amide as a white solid (0.057 g, 83%). mp: 211-213° C.; MS (ES) m/z 441.2; HRMS: calcd for $C_{24}H_{16}N_2F_3OCl+H$, 441.09815; found (ESI, [M+H]$^+$), 441.0973.

EXAMPLE 385

N-(4-ETHYLPHENYL)-N-METHYL-4-PHENYL-8-(TRIFLUOROMETHYL)QUINOLINE-3-CARBOXAMIDE

The title compound is prepared essentially as described in Example 378, except using N-(4-ethylphenyl)-4-phenyl-8-(trifluoromethyl)quinoline-3-carboxamide instead of N,4-diphenyl-8-(trifluoromethyl)quinoline-3-carboxamide to afford the amide as a tan solid (0.042 g, 63%). mp 136-138° C.; MS (ES) m/z 435.3; HRMS: calcd for $C_{26}H_{21}N_2F_3O+H$, 435.16842; found (ESI, [M+H]$^+$), 435.1691.

EXAMPLE 386

N-(3-ETHYLPHENYL)-N-METHYL-4-PHENYL-8-(TRIFLUOROMETHYL)QUINOLINE-3-CARBOXAMIDE

The title compound is prepared essentially as described in Example 378, except using N-(3-ethylphenyl)-4-phenyl-8-(trifluoromethyl)quinoline-3-carboxamide instead of N,4-diphenyl-8-(trifluoromethyl)quinoline-3-carboxamide to afford the amide as a white solid (0.062 g, 63%). mp 144-146° C.; MS (ES) m/z 435.3; HRMS: calcd for $C_{26}H_{21}N_2F_3O+H$, 435.16842; found (ESI, [M+H]$^+$), 435.1681.

EXAMPLE 387

N-(2-METHOXYPHENYL)-N-METHYL-4-PHENYL-8-(TRIFLUOROMETHYL)QUINOLINE-3-CARBOXAMIDE

The title compound is prepared essentially as described in Example 378, except using N-(2-methoxyphenyl)-4-phenyl-8-(trifluoromethyl)quinoline-3-carboxamide instead of N,4-diphenyl-8-(trifluoromethyl)quinoline-3-carboxamide to afford the amide as a tan solid (0.014 g, 33%). mp 138° C.; MS (ES) m/z 437.2; HRMS: calcd for $C_{25}H_{19}N_2F_3O_2+H$, 437.14769; found (ESI, [M+H]$^+$), 437.1498.

EXAMPLE 388

N-(4-FLUOROPHENYL)-N-METHYL-4-PHENYL-8-(TRIFLUOROMETHYL)QUINOLINE-3-CARBOXAMIDE

The title compound is prepared essentially as described in Example 378, except using N-(4-fluorophenyl)-4-phenyl-8-(trifluoromethyl)quinoline-3-carboxamide instead of N,4-diphenyl-8-(trifluoromethyl)quinoline-3-carboxamide to afford the amide as a tan solid (0.061 g, 73%). mp 138-140° C.; S (ES) m/z 425.2; HRMS: calcd for $C_{24}H_{16}N_2F_4O+H$, 425.12770; found (ESI, [M+H]$^+$), 425.1296.

EXAMPLE 389

N-(3-FLUOROPHENYL)-N-METHYL-4-PHENYL-8-(TRIFLUOROMETHYL)QUINOLINE-3-CARBOXAMIDE

The title compound is prepared essentially as described in Example 378, except using N-(3-fluorophenyl)-4-phenyl-8-(trifluoromethyl)quinoline-3-carboxamide instead of N,4-diphenyl-8-(trifluoromethyl)quinoline-3-carboxamide to afford the amide as a tan solid (0.066 g, 75%). mp 200-202° C.; MS (ES) m/z 425.2; HRMS: calcd for $C_{24}H_{16}N_2F_4O+H$, 425.12770; found (ESI, [M+H]$^+$), 425.1267.

EXAMPLE 390

3,4-DIPHENYL-8-(TRIFLUOROMETHYL)QUINOLINE

1) Preparation of 8-Trifluoromethyl-quinolin-4-ol 1 (CL-78142-2): 4-Hydroxy-8-trifluoromethyl-quinoline-3-carboxylic acid (17.07 g, 66.3 mmol) is heated at reflux in Dowtherm A (106 mL) for 3 h. Upon cooling, diethyl ether is added and the dark solution is stirred 1 h, suction filtered, and isolated solid air dried to afford the title compound as a white solid (10.01 g, 72%). mp 181-183° C.; MS (ESI) m/z 214; MS (ESI) m/z 212; HRMS: calcd for $C_{10}H_6NF_3O+H$, 214.04797; found (ESI_FT, [M+H]1+), 214.04703.

2) Preparation of 3-Bromo-8-(trifluoromethyl)quinolin-4-ol: 8-Trifluoromethyl-quinolin-4-ol (9.12 g, 42.8 mmol) is dissolved in acetic acid (300 mL). Bromine (2.20 mL 42.8 mmol) is dissolved in acetic acid (30 mL) and then added drop wise to the reaction over 20 min. After 0.5 h, the solution is poured into 500 mL of 2N NaOH and stirred. The white precipitate is filtered and dried in vacuo yielding the title compound as a white solid (10.3 g, 83%). mp 297-299° C.; MS (ESI) m/z 292; MS (ESI) m/z 290; HRMS: calcd for $C_{10}H_5BrNF_3O+H$, 291.95848; found (ESI_FT, [M+H]1+), 291.95847.

3) 3-Phenyl-8-(trifluoromethyl)quinolin-4-ol: A solution of 3-bromo-8-(trifluoromethyl)quinolin-4-ol (3.2 g, 10.95 mmol) and phenyl boronic acid (2.67 g, 21.91 mmol) in 2:1 toluene:methanol (120 mL) and sat aq NaHCO$_3$ (40 mL) is treated with Pd(PPh$_3$)$_4$ (760 mg) and heated at reflux overnight. The reaction is poured into water and extracted with ethyl acetate. The combined extracts are washed with 2N aq NaOH, water, brine, and dried with magnesium sulfate. The extracts are concentrated and the residue is chromatographed with 1:4 ethyl acetate:hexanes to afford the title compound as a yellow solid (6.4 g, 59%). mp 272-275° C.; MS (ESI) m/z 290; MS (ESI) m/z 288; HRMS: calcd for $C_{16}H_{10}NF_3O+H$, 290.07927; found (ESI_FT, [M+H]1+), 290.07816.

4) 4-Bromo-3-phenyl-8-(trifluoromethyl)quinoline: A stirred solution of 3-phenyl-8-(trifluoromethyl)quinolin-4-ol (0.162 g, 0.56 mmol) in DMF (5 mL) is treated with $P(O)Br_3$ (0.452 mg, 1.67 mmol) and heated at 90° C. After stirring 0.5 h, the solution is poured into 2N aq HCl and extracted with ethyl acetate. The combined extracts are washed with water, sat aq $NaHCO_3$, brine, dried over magnesium sulfate, and concentrated in vacuo to afford the title compound as a light orange solid (0.170 g, 86%). mp 75-77° C.; MS (ESI) m/z 352; HRMS: calcd for $C_{16}H_9NF_3Br+H$, 351.99487; found (ESI, [M+H]$^+$), 351.9948.

5) 3,4-Diphenyl-8-(trifluoromethyl)quinoline: The title compound is prepared essentially as described in step 3, except using 4-bromo-3-phenyl-8-(trifluoromethyl)quinoline instead of 3-bromo-8-(trifluoromethyl)quinolin-4-ol to afford the title compound as a white solid (0.171 g, 82%). mp 138-140° C.; MS (ESI) m/z 350; HRMS: calcd for $C_{22}H_{14}NF_3+H$, 350.11566; found (ESI, [M+H]$^+$), 350.1143.

EXAMPLE 391

3-[3-PHENYL-8-(TRIFLUOROMETHYL)QUINOLIN-4-YL]PHENOL

The title compound is prepared essentially as described in 390, except in Step 5 using 3-hydroxyphenyl boronic acid instead of phenyl boronic acid to afford the title compound as a tan solid (0.075 g, 60%). mp 123° C.; MS (ES) m/z 364.1; HRMS: calcd for $C_{22}H_{14}NF_3O$—H, 364.09492; found (ESI, [M–H]$^-$), 364.0936.

EXAMPLE 392

2-CHLORO-5-[3-PHENYL-8-(TRIFLUOROMETHYL)QUINOLIN-4-YL]PHENOL

The title compound is prepared essentially as described in 390, except in Step 5 using 2-chloro-3-hydroxy-phenyl boronic acid instead of phenyl boronic acid to afford the title compound as a white solid (0.031 g, 61%). mp 252° C.; MS (ES) m/z 397.8; HRMS: calcd for $C_{22}H_{13}NF_3OCl+H$, 400.07160; found (ESI, [M+H]$^+$), 400.0727.

EXAMPLE 393

4-(4-CHLORO-3-METHOXYPHENYL)-3-PHENYL-8-(TRIFLUOROMETHYL)QUINOLINE

The title compound is prepared essentially as described in Example 390, except in Step 5 using 2-chloro-3-methoxy phenyl boronic acid instead of phenyl boronic acid to afford the title compound as a white solid (0.031 g, 61%). mp 172-174° C.; MS (ES) m/z 414.1; HRMS: calcd for $C_{23}H_{15}NF_3OCl+H$, 414.08725; found (ESI, [M+H]$^+$), 414.0863.

EXAMPLE 394

4-(2-FLUORO-5-METHOXYPHENYL)-3-PHENYL-8-(TRIFLUOROMETHYL)QUINOLINE

The title compound is prepared essentially as described in Example 390, except in Step 5 using 4-fluoro-3-methoxy phenyl boronic acid instead of phenyl boronic acid to afford the title compound as a tacky solid (0.240 g, 65%). Calcd. mass for $C_{22}H_{15}NF_4O$ 397.37, found by MS (ES) m/z 397.9.

EXAMPLE 395

{3-[3-PHENYL-8-(TRIFLUOROMETHYL)QUINOLIN-4-YL]PHENYL}AMINE

The title compound is prepared essentially as described in Example 390, except in Step 5 using 3-amino phenyl boronic acid instead phenyl boronic acid to afford the title compound as a white solid (0.171 g, 69%). mp 163-165° C.; MS (ES) m/z 365.1; HRMS: calcd for $C_{22}H_{15}N_2F_3+H$, 365.12656; found (ESI, [M+H]$^+$), 365.1276.

EXAMPLE 396

ETHYL[4-({3-[3-PHENYL-8-(TRIFLUOROMETHYL)QUINOLIN-YL]PHENOXY}METHYL)PHENYL]ACETATE

To a solution of 3-[3-phenyl-8-(trifluoromethyl)quinolin-4-yl]phenol (0.178 g, 0.487 mmol), and potassium carbonate (0.134 g, 0.974 mmol), in DMF at 120° C. is added 4-bromomethylphenylacetic acid ethyl ester (0.334 g, 1.46 mmol), drop wise over 2 h. After an additional 2 h, the cooled reaction is poured into 2N aq HCl and extracted with ethyl acetate. The combined extracts are washed with sat aq $NaHCO_3$, water, brine, and dried with magnesium sulfate. The extracts are concentrated and the residue is chromatographed with 1:9 ethyl acetate:hexanes to afford the title compound as a syrup (0.051 g, 37%). MS m/z 542; HRMS: calcd for $C_{33}H_{26}NF_3O_3+H$, 542.19430; found (ESI, [M+H]$^+$), 542.194.

EXAMPLE 397

METHYL[4-({3-[3-PHENYL-8-(TRIFLUOROMETHYL)QUINOLIN-4-Yl]PHENOXY}METHYL)PHENYL]ACETATE

The title compound is prepared essentially as described in Example 396, except using 4-bromomethylphenylacetic acid methyl ester instead of 4-bromomethylphenylacetic acid ethyl ester to afford the title compound as a creamy tacky solid (0.066 g, 60%). Calcd mass for $C_{32}H_{24}NF_3O_3$ is 527.24, found MS (ES) m/z 528.2; (M+H)$^+$.

EXAMPLE 398

[4-({3-[3-PHENYL-8-(TRIFLUOROMETHYL)QUINOLIN-4-YL]PHENOXY}METHYL)PHENYL]ACETIC ACID

A solution of 3-[3-phenyl-8-(trifluoromethyl)quinolin-4-yl]phenyl acetic acid ethyl ester (0.051 g, 0.10 mmol), and 2N aq NaOH (0.100 mL, 0.20 mmol), in 1:1 ethanol:THF is refluxed at 120° C. for 1 h, cooled and poured into 2N aq HCl. The solution is extracted with ethyl acetate. The combined extracts are washed with sat aq $NaHCO_3$, water, brine, and dried with magnesium sulfate. The extracts are concentrated and the residue is chromatographed with 1:9 ethyl acetate:hexanes to afford the title compound as a colorless solid (0.045 g, 97%). mp 122° C.; MS (ES) m/z 514.2; HRMS: calcd $C_{31}H_{22}NF_3O_3+H$, 514.16300; found (ESI, [M+H]$^+$), 514.1629.

EXAMPLE 399

METHYL (2E)-3-[4-({3-[3-PHENYL-8-(TRIFLUO-ROMETHYL)QUINOLIN-4-YL]PHENOXY}METHYL)PHENYL]ACRYLATE

The title compound is prepared essentially as described in Example 396, except using 3-(4-bromomethyl-phenyl)-acrylic acid methyl ester instead of 4-bromomethylphenylacetic acid ethyl ester to afford the title compound as white solid (0.690 g, 96%). mp 91° C.; Calcd mass for $C_{32}H_{24}NF_3O_3$ is 539.55, found MS (ES) m/z 540.2.

EXAMPLE 400

2E)-3-[4-({3-[3-PHENYL-8-(TRIFLUOROMETHYL)QUINOLIN-4-YL]PHENOXY}METHYL)PHENYL]ACRYLIC ACID

The title compound is prepared essentially as described in Example 398, except using methyl(2E)-3-[4-({3-[3-phenyl-8-(trifluoromethyl)quinolin-4-yl]phenoxy}methyl) phenyl] acrylate instead of 3-[3-phenyl-8-(trifluoromethyl)quinolin-4-yl]phenyl acetic acid ethyl ester to afford the title compound as a white solid (0.167 g, 81%). mp 229° C.; Calcd mass for $C_{32}H_{22}NF_3O_3$ is 525.23, found MS (ES) m/z 523.8. ([M+H]−).

EXAMPLE 401

ETHYL(2E)-3-[4-({2-CHLORO-5-[3-PHENYL-8-(TRIFLUOROMETHYL)QUINOLIN-4-YL]PHENOXY}METHYL)PHENYL]ACETATE

The title compound is prepared essentially as described in Example 396, except 2-chloro-5-[3-phenyl-8-(trifluoromethyl)quinolin-4-yl]phenol instead of 3-[3-phenyl-8-(trifluoromethyl)quinolin-4-yl]phenol to afford 0.086 g (42%) of the title compound as a white solid; Calculated mass for $C_{33}H_{25}NF_3O_3Cl$ is 576.99, found MS (ES) m/z 576; (M+H)+.

EXAMPLE 402

4-({2-CHLORO-5-[3-PHENYL-8-(TRIFLUOROMETHYL)QUINOLIN-4-YL]PHENOXY}METHYL)PHENYL]ACETIC ACID

The title compound is prepared essentially as described in Example 398, except using ethyl 4-({2-chloro-5-[3-phenyl-8-(trifluoromethyl)quinolin-4-yl]phenoxy}methyl)phenyl] acetate instead of 3-[3-phenyl-8-(trifluoromethyl)quinolin-4-yl]phenyl acetic acid ethyl ester to afford the title compound as a white solid (0.031 g, 61%). mp 86° C.; Calcd mass for $C_{31}H_{21}NF_3O_3Cl$ is 547.96, found MS (ES) m/z 547.9.

EXAMPLE 403

METHYL (2E)-3-[4-({2-CHLORO-5-[3-PHENYL-8-(TRIFLUOROMETHYL)QUINOLIN-4-YL]PHENOXY}METHYL)PHENYL]ACRYLATE

The title compound is prepared essentially as described in 401, except 2-chloro-5-[3-phenyl-8-(trifluoromethyl)quinolin-4-yl]phenol instead of 3-[3-phenyl-8-(trifluoromethyl)quinolin-4-yl]phenol to afford 0.127 g (52%) of the title compound as a white solid: mp 149-151° C.; Calculated mass for $C_{33}H_{23}NF_3O_2Cl$ is 573.99, found MS (ES) m/z 573.9; (M+H)+.

EXAMPLE 404

(2E)-3-[4-({2-CHLORO-5-[3-PHENYL-8-(TRIFLUOROMETHYL)QUINOLIN-4-YL]PHENOXY}METHYL) PHENYL]ACRYLIC ACID

The title compound is prepared essentially as described in Example 398, except using methyl (2E)-3-[4-({2-chloro-5-[3-phenyl-8-(trifluoromethyl)quinolin-4-yl]phenoxy}methyl)phenyl]acrylate instead of 3-[3-phenyl-8-(trifluoromethyl)quinolin-4-yl]phenyl acetic acid ethyl ester to afford title compound as a white solid (0.097 g, 61%). mp 257° C.; Calcd mass for $C_{32}H_{21}NF_3O_3Cl$ is 559.97, found MS (ES) m/z 557.8.

EXAMPLE 405

ETHYL{4-[({3-[3-PHENYL-8-(TRIFLUOROMETHYL)QUINOLIN-4-YL]PHENYL}AMINO)METHYL]PHENYL}ACETATE

The title compound is prepared essentially as described in Example 396, except using {3-[3-Phenyl-8-(trifluoromethyl)quinolin-4-yl]phenyl}amine instead of 3-[3-phenyl-8-(trifluoromethyl)quinolin-4-yl]phenol to afford 0.127 g (52%) of the title compound as a yellow syrup: Calculated mass for $C_{33}H_{27}N_2F_3O_2$ is 540.57, found MS (ES) m/z 541.2; (M+H)+.

EXAMPLE 406

{4-[({3-[3-PHENYL-8-(TRIFLUOROMETHYL)QUINOLIN-4-YL]PHENYL}AMINO)METHYL]PHENYL} ACETIC ACID

The title compound is prepared essentially as described in Example 398, except using ethyl {4-[({3-[3-phenyl-8-(trifluoromethyl)quinolin-4-yl]phenyl}amino)methyl] phenyl}acetate instead 3-[3-phenyl-8-(trifluoromethyl) quinolin-4-yl]phenyl acetic acid ethyl ester to afford the title compound as a tan tacky solid (0.021 g, 31%). Calcd mass for $C_{31}H_{23}N_2F_3O_2$ is 512.53, found MS (ES) m/z 513.

EXAMPLE 407

3-PHENOXY-4-PHENYL-8-(TRIFLUOROMETHYL)QUINOLINE 1) 3-phenoxy-8-(trifluoromethyl)quinolin-4-ol: A solution of 3-bromo-8-(trifluoromethyl)quinolin-4-ol (1.28 g, 4.38 mmol), potassium phenoxide (4.24 g, 45.1 mmol), and copper powder (0.100 g, 1.61 mmol) in DMF (30 mL) is treated with CuBr (0.943 g, 6.57 mmol) and heated at reflux for 6 days. The cooled reaction is poured into 2N aq HCl and extracted with ethyl acetate. The combined extracts are washed with sat aq $NaHCO_3$, water, brine, and dried with magnesium sulfate. The extracts are concentrated and the residue is chromatographed with 1:9 ethyl acetate:hexanes to afford the title compound as a orange solid (0.471, 35%). mp 153-155° C.; Calcd mass for $C_{16}H_{10}NF_3O_2$ is 305.25, found by ESI MS, 306 (M+H)+.

2) 4-Bromo-3-phenoxy-8-(trifluoromethyl)quinoline: The title compound is prepared essentially as described in Example 392, step 4, except using 3-phenoxy-8-(trifluoromethyl)quinolin-4-ol instead of 3-phenyl-8-(trifluoromethyl)quinolin-4-ol to afford the title compound as a yellow solid (0.230 g, 80%). mp 122° C.; MS (ESI) m/z 368; HRMS: calcd for $C_{16}H_9NF_3OBr+H$, 367.98978; found (ESI, [M+H]$^+$), 367.9879.

3) 3-Phenoxy-4-phenyl-8-(trifluoromethyl)quinoline: The title compound is prepared essentially as described in Example 390 step 5, except using 4-bromo-3-phenoxy-8-(trifluoromethyl)quinoline instead of 4-bromo-3-phenyl-8-(trifluoromethyl)quinoline to afford the title compound as a tacky cream colored solid (0.075 g, 71%). MS (ESI) m/z 366; HRMS: calcd for $C_{22}H_{14}NF_3O+H$, 366.11057; found (ESI, [M+H]$^+$), 366.1085.

EXAMPLE 408

3-[3-PHENOXY-8-(TRIFLUOROMETHYL)QUINOLIN-4-YL]PHENOL

The title compound is prepared essentially as described in 407, except in step 3 using 3-hydroxy phenyl boronic acid instead of phenyl boronic acid to afford the title compound as a yellow syrup (0.066 g, 60%). Calcd mass for $C_{16}H_{10}NF_3O_2$ is 381.35, found MS (ES) m/z 380.0; (M+H)$^-$.

EXAMPLE 409

ETHYL [4-({3-[3-PHENOXY-8-(TRIFLUOROMETHYL)QUINOLIN-4-YL]PHENOXY}METHYL)PHENYL]ACETATE

The title compound is prepared essentially as described in Example 396, except using 3-[3-phenoxy-8-(trifluoromethyl)quinolin-4-yl]phenol instead of 3-[3-phenyl-8-(trifluoromethyl)quinolin-4-yl]phenol to afford the title compound as a tan syrup (0.066 g, 60%). Calcd mass for $C_{33}H_{26}NF_3O_4$ is 557.57, found MS (ES) m/z 557.9.

EXAMPLE 410

[4-({3-[3-PHENOXY-8-(TRIFLUOROMETHYL)QUINOLIN-4-YL]PHENOXY}METHYL)PHENYL]ACETIC ACID

The title compound is prepared essentially as described in Example 398, except using ethyl [4-({3-[3-phenoxy-8-(trifluoromethyl)quinolin-4-yl]phenoxy}methyl)phenyl]acetate instead of 3-[3-phenyl-8-(trifluoromethyl)quinolin-4-yl]phenyl acetic acid ethyl ester to afford the title compound as clear tacky solid (0.131 g, 61%). Calcd mass for $C_{31}H_{22}NF_3O_4$ is 529.52, found MS (ES) m/z 529.9.

EXAMPLE 411

4-PHENYL-3-(PHENYLTHIO)-8-(TRIFLUOROMETHYL)QUINOLINE 1) 3-(phenylthio)-8-(trifluoromethyl)quinolin-4-ol: A solution of 3-bromo-8-(trifluoromethyl)quinolin-4-ol (0.240 g, 0.830 mmol), sodium thiophenol (0.293 g, 45.1 mmol), is dissolved in DMF and heated in a microwave reactor for 10 min at 120° C. After which, the reaction is poured into water and extracted with ethyl acetate. The combined extracts are washed with sat aq NaHCO$_3$, water, brine, and dried with magnesium sulfate. The extracts are concentrated and the residue is chromatographed with 1:9 ethyl acetate:hexanes to afford the title compound as a white solid (0.151 g, 57%). mp 153-155° C.; MS (ESI) m/z 322; MS (ESI) m/z 320; HRMS: calcd for $C_{16}H_{10}NF_3OS+H$, 322.05134; found (ESI, [M+H]$^+$), 322.0486.

2) 4-Bromo-3-(phenylthio)-8-(trifluoromethyl)quinoline: The title compound is prepared essentially as described in Example 390, step 4, except using 3-(phenylthio)-8-(trifluoromethyl)quinolin-4-ol instead of 3-phenyl-8-(trifluoromethyl)quinolin-4-ol to afford the title compound as a white solid (0.230 g, 80%). mp 139-141° C.; MS (ESI) m/z 384; HRMS: calcd for $C_{16}H_9NF_3BrS+H$, 383.96694; found (ESI, [M+H]$^+$), 383.9657.

3) 4-Phenyl-3-(phenylthio)-8-(trifluoromethyl)quinoline: The title compound is prepared essentially as described in Example 390, step 5, except using 4-bromo-3-(phenylthio)-8-(trifluoromethyl)quinoline instead of 3-bromo-8-(trifluoromethyl)quinolin-4-ol to afford the title compound as a tacky solid (0.065 g, 44%). MS (ES) m/z 382.2; HRMS: calcd for $C_{22}H_{14}NF_3S+H$, 382.08773; found (ESI, [M+H]$^+$), 382.0864.

EXAMPLE 412

4-FLUORO-3-[3-PHENYL-8-(TRIFLUOROMETHYL)QUINOLIN-4-YL]PHENOL 4-(2-Fluoro-5-methoxyphenyl)-3-phenyl-8-(trifluoromethyl)quinoline (0.230 g, 0.578 mmol) was combined with pyridine-HCl (50 g) and raised to 200° C. in and oil bath for 2 hours. Upon cooling to a solid waxy solid, 2N HCl was added and the solid dissolved, poured into a separatory funnel and extracted with ethyl acetate. The combined organic phases were washed with sat. NaHCO$_3$, water, brine, and dried with magnesium sulfate to afford 0.142 g (65%) of the title compound as a tan solid: mp 85° C.; Calcd. mass for $C_{22}H_{13}NF_4O$ 383 found by MS (ES) m/z 393.9.

EXAMPLE 413

ETHYL [4-({4-FLUORO-3-[3-PHENYL-8-(TRIFLUOROMETHYL)QUINOLIN-4-YL]PHENOXY}METHYL) PHENYL]ACETATE

Arg 319 Et ester of Example 414.

EXAMPLE 414

[4-({4-FLUORO-3-[3-PHENYL-8-(TRIFLUOROMETHYL)QUINOLIN-4-YL]PHENOXY}METHYL)PHENYL]ACETIC ACID

Acid of Example 413.

EXAMPLE 415

3-(4-METHYLBENZYL)-4-PHENYL-8-(TRIFLUOROMETHYL)QUINOLINE

1) [4-phenyl-8-(trifluoromethyl)quinolin-3-yl]methanol: Ethyl 4-phenyl-8-(trifluoromethyl)quinoline-3-carboxylate (3.45 g, 10.0 mmol), was dissolved in THF (75 mL) and treated with 2.0 M LiBH$_4$ in THF (12.5 mL, 25.0 mmol) over 5 min at ambient temperature under nitrogen. After stirring 24 h, the reaction is quenched with methanol and stirred overnight. The reaction is concentrated in vacuo, treated with water, extracted with methylene chloride, dried over MgSO$_4$, and concentrated in vacuo. The residue is chromatographed with 40:60 ethyl acetate:hexane to afford the title compound as a solid (1.77 g). MS (ES) m/z 304.1; HRMS: calcd for $C_{17}H_{12}F_3NO$, 303.0871; found (ESI, [M+H]$^+$), 304.0934

2) 3-(Bromomethyl)-4-phenyl-8-(trifluoromethyl)quinoline: A stirred solution of [4-phenyl-8-(trifluoromethyl) quinolin-3-yl]methanol (1.76 g, 11.9 mmol) in dichloromethane (120 mL) is treated with 1.0 M PBr$_3$ in dichloromethane (13.1 mL, 13.1 mmol). After 3 h at ambient temperature, the reaction is treated with aq saturated NaHCO$_3$ (125 mL), the layers separated, and the aqueous extracted with dichloromethane. The organic extracts are dried with MgSO$_4$, concentrated, and the residue chromatographed with 20:80 ethyl acetate:hexane as eluent to afford the title compound as a foaming oil which is used quickly to minimize decomposition (2.11 g). MS (ES) m/z 366.0; HRMS: calcd for $C_{17}H_{11}BrF_3N$, 365.0027; found (ESI, [M+H]$^+$), 366.0091

3) 3-(4-Methylbenzyl)-4-phenyl-8-(trifluoromethyl) quinoline: A solution of 3-(bromomethyl)-4-phenyl-8-(trifluoromethyl)quinoline (128 mg, 0.35 mmol) and 4-MePhB (OH)$_2$ (72 mg, 0.525 mmol) in DME (3.0 mL) and 2.0 M Na$_2$CO$_3$ (0.6 mL) is treated with Pd(PPh$_3$)$_4$ (20 mg) and heated at 85° C. for 22 h. After an additional 24 h at ambient temperature, the reaction is treated with water (4 mL) and extracted with 1:4 ethyl acetate:hexanes (25 mL). The extract is dried with MgSO$_4$ and concentrated in vacuo. The residue is chromatographed with 15:85 ethyl acetate:hexane to afford the title compound as an oil. MS (ES) m/z 378.2; HRMS: calcd for $C_{24}H_{18}F_3N$, 377.1391; found (ESI, [M+H]$^+$), 378.1474;

EXAMPLE 416

3-(4-METHOXYBENZYL)-4-PHENYL-8-(TRIFLUOROMETHYL)QUINOLINE

The title compound is prepared essentially as described in Example 417, step 3, except using 4-methoxyphenylboronic acid instead of 4-methylphenylboronic acid.

MS m/z 410; HRMS: calcd for $C_{24}H_{18}F_3NO$, 393.1340; found (ESI, [M+H]$^+$), 394.1403;

EXAMPLE 417

3-(4-CHLOROBENZYL)-4-PHENYL-8-(TRIFLUOROMETHYL)QUINOLINE

The title compound is prepared essentially as described in Example 415, step 3, except using 4-chlorophenylboronic acid instead of 4-methylphenylboronic acid. MS (ES) m/z 398.2; HRMS: calcd for $C_{23}H_{15}ClF_3N$, 397.0845; found (ESI, [M+H]$^+$), 398.0916;

EXAMPLE 418

3-(3-CHLOROBENZYL)-4-PHENYL-8-(TRIFLUOROMETHYL)QUINOLINE

The title compound is prepared essentially as described in Example 415, step 3, except using 3-chlorophenylboronic acid instead of 4-methylphenylboronic acid. MS (ES) m/z 398.2; HRMS: calcd for $C_{23}H_{15}ClF_3N$, 397.0845; found (ESI, [M+H]$^+$), 398.0916;

EXAMPLE 419

3-(4-FLUOROBENZYL)-4-PHENYL-8-(TRIFLUOROMETHYL)QUINOLINE

The title compound is prepared essentially as described in Example 415, step 3, except using 4-fluorophenylboronic acid instead of 4-methylphenylboronic acid. MS (ES) m/z 382.2; HRMS: calcd for $C_{23}H_{15}F_4N$, 381.1141; found (ESI, [M+H]$^+$), 382.1211;

EXAMPLE 420

3-(3-FLUOROBENZYL)-4-PHENYL-8-(TRIFLUOROMETHYL)QUINOLINE

The title compound is prepared essentially as described in Example 415, step 3, except using 3-fluorophenylboronic acid instead of 4-methylphenylboronic acid. MS (ES) m/z 382.2; HRMS: calcd for $C_{23}H_{15}F_4N$, 381.1141; found (ESI, [M+H]$^+$), 382.1205;

EXAMPLE 421

3-(2-FLUOROBENZYL)-4-PHENYL-8-(TRIFLUOROMETHYL)QUINOLINE

The title compound is prepared essentially as described in Example 415, step 3, except using 2-fluorophenylboronic acid instead of 4-methylphenylboronic acid. MS (ES) m/z 382.2; HRMS: calcd for $C_{23}H_{15}F_4N$, 381.1141; found (ESI, [M+H]$^+$), 382.1233;

EXAMPLE 422

3-(3,5-DIFLUOROBENZYL)-4-PHENYL-8-(TRIFLUOROMETHYL)QUINOLINE

The title compound is prepared essentially as described in Example 415, step 3, except using 3,5-difluorophenylboronic acid instead of 4-methylphenylboronic acid. MS (ES) m/z 400.2; HRMS: calcd for $C_{23}H_{14}F_5N$, 399.1046; found (ESI, [M+H]$^+$), 400.1112;

EXAMPLE 423

3-{[4-PHENYL-8-(TRIFLUOROMETHYL)QUINOLIN-3-YL]METHYL}PHENOL

The title compound is prepared essentially as described in Example 415, step 3, except using 3-hydroxyphenylboronic acid instead of 4-methylphenylboronic acid.

MS (ES) m/z 378.2; HRMS: calcd for $C_{23}H_{16}F_3NO$, 379.1184; found (ESI, [M+H]$^+$), 380.1248;

EXAMPLE 424

3-(2-NAPHTHYLMETHYL)-4-PHENYL-8-(TRIFLUOROMETHYL)QUINOLINE

The title compound is prepared essentially as described in Example 415, step 3, except using 2-naphthylboronic acid instead of 4-methylphenylboronic acid. MS (ES) m/z 414.2; HRMS: calcd for $C_{27}H_{18}F_3N$, 413.1391; found (ESI, [M+H]$^+$), 414.1464;

EXAMPLE 425

4-{[4-PHENYL-8-(TRIFLUOROMETHYL) QUINOLIN-3-YL]METHYL}BENZONITRILE

The title compound is prepared essentially as described in Example 415, step 3, except using 4-cyanophenylboronic acid instead of 4-methylphenylboronic acid. MS (ES) m/z 387.1; HRMS: calcd for $C_{24}H_{15}F_3N_2$, 388.1187; found (ESI, [M+H]$^+$), 389.1261;

EXAMPLE 426

3-(1-BENZOTHIEN-2-YLMETHYL)-4-PHENYL-8-(TRIFLUOROMETHYL)QUINOLINE

The title compound is prepared essentially as described in Example 415, step 3, except using 2-benzothienylboronic acid instead of 4-methylphenylboronic acid. MS (ES) m/z 420.2; HRMS: calcd for $C_{25}H_{16}F_3NS$, 419.0956; found (ESI, [M+H]$^+$), 420.1031;

EXAMPLE 427

4-PHENYL-3-(THIEN-3-YLMETHYL)-8-(TRIFLUOROMETHYL)QUINOLINE

The title compound is prepared essentially as described in Example 415, step 3, except using 3-thienylboronic acid instead of 4-methylphenylboronic acid. MS (ES) m/z 370.1; HRMS: calcd for $C_{21}H_{14}F_3NS$, 369.0799; found (ESI, [M+H]$^+$), 370.0876;

EXAMPLE 428

3-(2-METHYLBENZYL)-4-PHENYL-8-(TRIFLUOROMETHYL)QUINOLINE

The title compound is prepared essentially as described in Example 415, step 3, except using 2-methylphenylboronic acid instead of 4-methylphenylboronic acid. HRMS: calcd for $C_{24}H_{18}F_3N$, 377.1391; found (ESI, [M+H]$^+$), 378.1469;

EXAMPLE 429

4-PHENYL-8-(TRIFLUOROMETHYL)-3-[4-(TRIFLUOROMETHYL)BENZYL]QUINOLINE

The title compound is prepared essentially as described in Example 415, step 3, except using 4-trifluoromethylphenylboronic acid instead of 4-methylphenylboronic acid. MS (ES) m/z 430.1; HRMS: calcd for $C_{24}H_{15}F_6N$, 431.1109; found (ESI, [M+H]$^+$), 432.1175;

EXAMPLE 430

3-(2-METHOXYBENZYL)-4-PHENYL-8-(TRIFLUOROMETHYL)QUINOLINE

The title compound is prepared essentially as described in Example 415, step 3, except using 2-methoxyphenylboronic acid instead of 4-methylphenylboronic acid. MS (ES) m/z 394.1; HRMS: calcd for $C_{24}H_{18}F_3NO$, 393.1340; found (ESI, [M+H]$^+$), 394.1414;

EXAMPLE 431

3-(2-CHLOROBENZYL)-4-PHENYL-8-(TRIFLUOROMETHYL)QUINOLINE

The title compound is prepared essentially as described in Example 415, step 3, except using 2-chlorophenylboronic acid instead of 4-methylphenylboronic acid. MS (ES) m/z 398.1; HRMS: calcd for $C_{23}H_{15}ClF_3N$, 397.0845; found (ESI, [M+H]$^+$), 398.0941;

EXAMPLE 432

3-(2,4-DIFLUOROBENZYL)-4-PHENYL-8-(TRIFLUOROMETHYL)QUINOLINE

The title compound is prepared essentially as described in Example 415, step 3, except using 2,4-difluorophenylboronic acid instead of 4-methylphenylboronic acid. MS (ES) m/z 400.1; HRMS: calcd for $C_{23}H_{14}F_5N$, 399.1046; found (ESI, [M+H]$^+$), 400.1107.

EXAMPLE 433

3-(PHENOXYMETHYL)-4-PHENYL-8-(TRIFLUOROMETHYL)QUINOLINE

A solution of phenol (235 mg, 5.0 mmol) in DMF (2.0 mL) is treated with NaH (60% in oil, 100 mg, 2.5 mmol) for 20 min and then treated with 3-(bromomethyl)-4-phenyl-8-(trifluoromethyl)quinoline (183 mg, 0.50 mmol) in DMF (1.0 mL). After 16 h, the reaction is treated with water and extracted with ether. The extract is dried with MgSO$_4$ and concentrated to an oil. Chromatography with 10:90 ethyl acetate:hexane affords the title compound as a white solid (114 mg, 62%). MS (ES) m/z 380.2; HRMS: calcd for $C_{23}H_{16}F_3NO$, 379.1184; found (ESI, [M+H]$^+$), 380.1246;

EXAMPLE 434

3-{[4-PHENYL-8-(TRIFLUOROMETHYL) QUINOLIN-3-YL]METHOXY}BENZONITRILE

Prepared as in Example 435 except using 3-cyanophenol as the reactant. MS (ES) m/z 405.1; HRMS: calcd for $C_{24}H_{15}F_3N_2O$, 404.1136; found (ESI, [M+H]$^+$), 405.1228;

EXAMPLE 435

3-[(4-CHLOROPHENOXY)METHYL]-4-PHENYL-8-(TRIFLUOROMETHYL)QUINOLINE

Prepared as in Example 435 except using 4-chlorophenol as the reactant. MS (ES) m/z 414.1; HRMS: calcd for $C_{23}H_{15}ClF_3NO$, 413.0794; found (ESI, [M+H]$^+$), 414.0858;

EXAMPLE 436

3-[(4-METHYLPHENOXY)METHYL]-4-PHENYL-8-(TRIFLUOROMETHYL)QUINOLINE

Prepared as in Example 435 except using 4-methylphenol as the reactant. MS (ES) m/z 394.1; HRMS: calcd for $C_{24}H_{18}F_3NO$, 393.1340; found (ESI, [M+H]$^+$), 394.142;

EXAMPLE 437

3-[(1-NAPHTHYLOXY)METHYL]-4-PHENYL-8-(TRIFLUOROMETHYL)QUINOLINE

Prepared as in Example 435 except using 1-naphthol as the reactant. MS (ES) m/z 430.2; HRMS: calcd for $C_{27}H_{18}F_3NO$, 429.1340; found (ESI, [M+H]$^+$), 430.1432;

EXAMPLE 438

3-[(2,4-DIMETHYLPHENOXY)METHYL]-4-PHENYL-8-(TRIFLUOROMETHYL)QUINOLINE

Prepared as in Example 433 except using 2,4-dimethylphenol as the reactant. MS (ES) m/z 408.2; HRMS: calcd for $C_{25}H_{20}F_3NO$, 407.1497; found (ESI, [M+H]$^+$), 408.1589;

EXAMPLE 439

3-[(4-METHOXYPHENOXY)METHYL]-4-PHENYL-8-(TRIFLUOROMETHYL)QUINOLINE

Prepared as in Example 433 except using 4-methoxyphenol as the reactant. MS (ES) m/z 410.2; HRMS: calcd for $C_{24}H_{18}F_3NO_2$, 409.1290; found (ESI, [M+H]$^+$), 410.1358.

EXAMPLE 440

3-[(CYCLOBUTYLOXY)METHYL]-4-PHENYL-8-(TRIFLUOROMETHYL)QUINOLINE

Prepared as in Example 433 except using cyclobutanol as the reactant. MS (ES) m/z 358.2; HRMS: calcd for $C_{21}H_{18}F_3NO$, 357.1340; found (ESI, [M+H]$^+$), 358.1401.

EXAMPLE 441

3-[(CYCLOPENTYLOXY)METHYL]-4-PHENYL-8-(TRIFLUOROMETHYL)QUINOLINE

Prepared as in Example 433 except using cyclopentanol as the reactant. MS (ES) m/z 372.2; HRMS: calcd for $C_{22}H_{20}F_3NO$, 371.1497; found (ESI, [M+H]$^+$), 372.1566;

EXAMPLE 442

4-PHENYL-3-[(2-PHENYLETHOXY)METHYL]-8-(TRIFLUOROMETHYL)QUINOLINE

Prepared as in Example 433 except using 2-phenyl-ethanol as the reactant. MS (ES) m/z 408.2; HRMS: calcd for $C_{25}H_{20}F_3NO$, 407.1497; found (ESI, [M+H]$^+$), 408.1555;

EXAMPLE 443

3-[(ALLYLOXY)METHYL]-4-PHENYL-8-(TRIFLUOROMETHYL)QUINOLINE

Prepared as in Example 433 except using allyl alcohol as the reactant. MS (ES) m/z 344.1; HRMS: calcd for $C_{20}H_{16}F_3NO$, 343.1184; found (ESI, [M+H]$^+$), 344.1268;

EXAMPLE 444

3-[(CYCLOHEXYLOXY)METHYL]-4-PHENYL-8-(TRIFLUOROMETHYL)QUINOLINE

Prepared as in Example 433 except using cyclohexanol as the reactant. MS m/z 386; HRMS: calcd for $C_{23}H_{22}F_3NO$, 385.1653; found (ESI, [M+H]$^+$), 386.1717;

EXAMPLE 445

3-(SEC-BUTOXYMETHYL)-4-PHENYL-8-(TRIFLUOROMETHYL)QUINOLINE

Prepared as in Example 433 except using sec-butyl alcohol as the reactant. MS (ES) m/z 360.2; HRMS: calcd for $C_{21}H_{20}F_3NO$, 359.1497; found (ESI, [M+H]$^+$), 360.1563;

EXAMPLE 446

3-{[(2-CHLOROBENZYL)OXY]METHYL}-4-PHENYL-8-(TRIFLUOROMETHYL)QUINOLINE

Prepared as in Example 433 except using 2-chlorobenzyl alcohol as the reactant. MS (ES) m/z 428.1; HRMS: calcd for $C_{24}H_{17}ClF_3NO$, 427.0951; found (ESI, [M+H]$^+$), 428.1013;

EXAMPLE 447

3-(ISOBUTOXYMETHYL)-4-PHENYL-8-(TRIFLUOROMETHYL)QUINOLINE

Prepared as in Example 433 except using isobutyl alcohol as the reactant. MS m/z 360; HRMS: calcd for $C_{21}H_{20}F_3NO$, 359.1497; found (ESI, [M+H]$^+$), 360.1566.

EXAMPLE 448

3-(ISOPROPOXYMETHYL)-4-PHENYL-8-(TRIFLUOROMETHYL)QUINOLINE

Prepared as in Example 433 except using 2-propanol as the reactant. MS (ES) m/z 346.1; HRMS: calcd for $C_{20}H_{18}F_3NO$, 345.1340; found (ESI, [M+H]$^+$), 346.1404.

EXAMPLE 449

3-(METHOXYMETHYL)$_4$-PHENYL-8-(TRIFLUOROMETHYL)QUINOLINE

Prepared as in Example 433 except using methanol as the reactant. MS (ES) m/z 318.2; HRMS: calcd for $C_{18}H_{14}F_3NO$, 317.1027; found (ESI, [M+H]$^+$), 318.1094.

EXAMPLE 450

3-(ETHOXYMETHYL)-4-PHENYL-8-(TRIFLUOROMETHYL)QUINOLINE

Prepared as in Example 433 except using ethanol as the reactant. MS (ES) m/z 332.1; HRMS: calcd for $C_{19}H_{16}F_3NO$, 331.1184; found (ESI, [M+H]$^+$), 332.1247.

EXAMPLE 451

4-PHENYL-3-(1H-PYRAZOL-1-YLMETHYL)-8-(TRIFLUOROMETHYL)QUINOLINE

A mixture of pyrazole (45 mg, 0.67 mmol) in DMF (2.0 mL) is treated with NaH (60% in oil, 27 mg, 0.67 mmol) is stirred 0.5 h, then treated with bromide (120 mg, 0.33 mmol) in DMF (1.0 mL). After stirring 6 d, the reaction is treated with water, extracted with ether, and the extracts dried with MgSO$_4$. The concentrated extract is chromatographed with 50:50 ethyl acetate:hexane to afford the title compound as a solid (79 mg). MS (ES) m/z 354.1; HRMS: calcd for $C_{20}H_{14}F_3N_3$, 353.1140; found (ESI, [M+H]$^+$), 354.1233.

EXAMPLE 452

4-PHENYL-3-(1H-PYRROL-1-YLMETHYL)-8-(TRIFLUOROMETHYL)QUINOLINE

Prepared as in Example 451 except using pyrrole in place of pyrazole. MS (ES) m/z 353.1; HRMS: calcd for $C_{21}H_{15}F_3N_2$, 352.1187; found (ESI, [M+H]$^+$), 353.1262.

EXAMPLE 453

3-(1H-IMIDAZOL-1-YLMETHYL)-4-PHENYL-8-(TRIFLUOROMETHYL)QUINOLINE

Prepared as in Example 451 except using imidazole in place of pyrazole. MS (ES) m/z 354.1; HRMS: calcd for $C_{20}H_{14}F_3N_3$, 353.1140; found (ESI, [M+H]$^+$), 354.1231.

EXAMPLE 454

3-(3-METHYL-1,2,4-OXADIAZOL-5-YL)-4-PHENYL-8-(TRIFLUOROMETHYL)QUINOLINE

A mixture of acetamidoxime (148 mg, 2.0 mmol) and powdered 4A molecular sieves (0.5 g) in THF (5 mL) is treated with 60% NaH in oil (80 mg, 2.0 mmol) for 15 min at ambient temperature. The reaction is treated with ethyl 4-phenyl-8-(trifluoromethyl)quinoline-3-carboxylate (173 mg, 0.50 mmol) and heated at reflux for 22 h. The reaction is cooled, concentrated, treated with water, and extracted with dichloromethane. The extracts are dried with MgSO$_4$, concentrated, and the residue chromatographed with 20:80 ethyl acetate:hexane to afford the title compound as an off-white solid (151 mg). MS (ES) m/z 356.1; HRMS: calcd for $C_{19}H_{12}F_3N_3O$, 355.0932; found (ESI, [M+H]$^+$), 356.1008.

EXAMPLE 455

4-PHENYL-3-(3-PHENYL-1,2,4-OXADIAZOL-5-YL)-8-(TRIFLUOROMETHYL)QUINOLINE

Prepared as in Example 454 except using PhC(NH$_2$)NOH. MS (ESI) m/z 418; HRMS: calcd for $C_{24}H_{14}F_3N_3O$, 417.1089; found (ESI, [M+H]$^+$), 418.1173.

EXAMPLE 456

4-PHENYL-3-(PHENYLSULFONYL)-8-(TRIFLUOROMETHYL)QUINOLINE

A stirred solution of aniline (265 mg, 1.00 mmol) prepared as in Example 75, Scheme 9, in DMF (4.0 mL) is treated with NaH (60% in oil, 44 mg, 1.10 mmol) at ambient temperature. After 3 min, PhSO$_2$CH=CHSO$_2$Ph (308 mg, 1.00 mmol) is added to the red solution. After stirring overnight, the reaction is treated with water and brine and extracted with CH$_2$Cl$_2$. The extract is concentrated in vacuo and the residue chromatographed eluting with 20:80, then 40:60, then 100:0 ethyl acetate:hexane mixtures. The title compound is isolated ($R_f$~0.25 in the initial system) as a pale yellow solid (100 mg). mp 149-151° C.; MS (ESI) m/z 414; HRMS: calcd for $C_{22}H_{14}F_3NO_2S$, 413.0697; found (ESI, [M+H]$^+$), 414.0755; Anal. Calcd for $C_{22}H_{14}F_3NO_2S$: C, 63.92; H, 3.41; N, 3.39. Found: C, 64.24; H, 3.30; N, 3.20.

EXAMPLE 457

3-(3-BENZYL-8-TRIFLUOROMETHYL-QUINOLIN-4-YL)-PHENOL 1) 2-Fluoro-N-methoxy-N-methyl-3-trifluoromethyl-benzamide: To a solution of 2-Fluoro-3-trifluoromethyl-benzoic acid, (15 g, 72 mmol) in 150 mL benzene at rt is added a solution of 10 mL (137 mmol) of SOCl$_2$ in 30 mL of CH$_2$Cl$_2$ drop wise over 30 min. The resulting solution is brought to reflux (pot: 85° C.) for ~6 hr. The vessel is cooled to rt and concentrated in vacuo, followed by 3×50 mL toluene azeotrope. The residue is taken up in CHCl$_3$ (250 mL) and 10 g (103 mmol) Weinreb reagent is added. The mixture is cooled to 0° C. and 16 mL pyridine is added via syringe in a slow stream. The vessel is allowed to warm to rt and stir at rt for 12 hr. The CHCl$_3$ is then stripped off and the residue taken up in CH$_2$Cl$_2$-Et$_2$O (1:1) 400 mL and washed with water, brine and then dried over Na$_2$SO$_4$, filtered and concentrated in vacuo to provide 17 g (95%) of the desired crude benzamide. This material is of sufficient purity for the next step.

2) (2-Fluoro-3-trifluoromethyl-phenyl)-(3-methoxy-phenyl)-methanone: 2-Fluoro-N-methoxy-N-methyl-3-trifluoromethyl-benzamide from step 1, is taken up in 150 mL THF and cooled to −78° C. A solution of 3-methoxy phenyl magnesium bromide in THF (1 M) (97 mL, 97 mmol) is added slowly (~1.5 hr) at −78° C. The vessel is then stirred for 1 hr at −78° C. and then brought to 0° C. and stirred for an additional 2 h. The reaction is quenched by pouring it into a ice cold 1 N HCl solution and extracting with EtOAc. The EtOAc layer is washed with water, brine and dried over Na$_2$SO$_4$, filtered and concentrated in vacuo to provide the desired crude ketone which is chromatographed with methylene chloride:hexane (90:10) to afford the title compound, 17.8 g (88%). MS (ES) m/z 299.1.

3) [2-amino-3-(trifluoromethyl)phenyl](3-methoxyphenyl)methanone: (2-Fluoro-3-trifluoromethyl-phenyl)-(3-methoxy-phenyl)-methanone, from step 2, (7 g, 23.5 mmol) is taken up in DME, (~50 mL) and 150 mL NH$_4$OH solution is added. The mixture is placed in a steel bomb and heated to 140° C. for ~6 hr. The vessel is then cooled in ice and carefully opened. The resulting mixture is concentrated and then extracted with EtOAc. The EtOAc layer is washed with water, brine and dried over Na$_2$SO$_4$, filtered and concentrated in vacuo to provide the desired aniline, which is purified by chromatography with methylene chloride:methaol (98:2) to afford the title compound, 4.8 g (70%). MS (ESI) m/z 296; HRMS: calcd for $C_{15}H_{12}F_3NO_2$+H+, 296.08929; found (ESI, [M+H]$^+$), 296.0887

4) [2-amino-3-(trifluoromethyl)phenyl](3-hydroxyphenyl)methanone: [2-amino-3-(trifluoromethyl)phenyl](3-methoxyphenyl)methanone, from step 3, (3 g, 10 mmol) and 40 g Py-HCl is placed into a RBF with a stir bar and lowered into a heating bath at 190-200° C. for 2-3 hr. The vessel is then cooled to RT and 1 N HCl is added to dissolve all solids. The mixture is extracted with EtOAc. The EtOAc layer is washed with water, brine and dried over Na$_2$SO$_4$, filtered and concentrated in vacuo to provide a semi-solid material. This material is repeatedly triturated with CH$_2$Cl$_2$. The methylene chloride is then concentrated providing the desired crude aniline. This material can be used crude however is purified by silica gel chromatography using methylene chloride and 1% methanol to give the title compound, 2.6 g, (91%): mp 106-107° C.; MS m/z 282; HRMS: calcd for $C_{14}H_{10}F_3NO_2$+, H+, 282.07364; found (ESI, [M+H]$^+$), 282.0729.

5) 3-(3-Benzyl-8-trifluoromethyl-quinolin-4-yl)-phenol: To a solution of [2-amino-3-(trifluoromethyl)phenyl](3-hydroxyphenyl)methanone from step 4, (3.0 g, 10.6 mmol) in AcOH (glacial, 20 mL) at rt is added 3-phenyl-propionaldehyde (2.1 g, 15.9 mmol) followed by 1.5 ml of a solution of

EXAMPLE 458

3-[3-(2-FLUOROPHENYL)-8-(TRIFLUOROMETHYL)QUINOLIN-4-YL]PHENOL

H$_2$SO$_4$ in AcOH (solution: 0.5 ml H$_2$SO$_4$ in 9.5 ml AcOH). The reaction mixture is then heated to 120° C. for approximately 3 hr. The vessel is cooled, the AcOH removed in vacuo and the residue taken up in EtOAc and washed with sat. NaHCO$_3$ solution. The EtOAc layer is dried over NaSO$_4$, filtered and concentrated giving an oily residue, which is purified by silica gel chromatography, CH$_2$Cl$_2$, MeOH (98:2) to afford the desired quinoline as a light yellow foam (2.8 g, 70%); MS (ES) m/z 378.2; HRMS: calcd for C$_{23}$H$_{16}$F$_3$NO+H+, 380.12567; found (ESI, [M+H]$^+$), 380.1257.

EXAMPLE 458

3-[3-(2-FLUOROPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (2-Fluoro-phenyl)-acetaldehyde following the procedure of Example 457: mp 186-187° C.; MS m/z 384, HRMS: calcd for C$_{22}$H$_{13}$F$_4$NO+H+, 384.10060; found (ESI, [M+H]$^+$), 384.1.

EXAMPLE 459

3-[3-(3-FLUOROPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (3-Fluoro-phenyl)-acetaldehyde following the procedure of Example 457: MS (ESI) m/z 384; HRMS: calcd for C$_{22}$H$_{13}$F$_4$NO+H+, 384.10060; found (ESI, [M+H]$^+$), 384.0992;

EXAMPLE 460

3-[3-(4-FLUOROPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (4-Fluoro-phenyl)-acetaldehyde following the procedure of Example 457: MS m/z 384; HRMS: calcd for C$_{22}$H$_{13}$F$_4$NO+H+, 384.10060; found (ESI, [M+H]$^+$), 384.0997.

EXAMPLE 461

3-[3-(2-METHOXYPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (2-Methoxy-phenyl)-acetaldehyde following the procedure of Example 457: MS (ESI) m/z 396; HRMS: calcd for C$_{23}$H$_{16}$F$_3$NO$_2$+H+, 396.12059; found (ESI, [M+H]$^+$), 396.1223.

EXAMPLE 462

3-[3-(3-METHOXYPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (3-Methoxy-phenyl)-acetaldehyde following the procedure of Example 457: MS (ES) m/z 394.0; HRMS: calcd for C$_{23}$H$_{16}$F$_3$NO$_2$+H+, 396.12059; found (ESI, [M+H]$^+$), 396.1196.

EXAMPLE 463

3-[3-(4-METHOXYPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (4-Methoxy-phenyl)-acetaldehyde following the procedure of Example 457: MS (ESI) m/z 396; HRMS: calcd for C$_{23}$H$_{16}$F$_3$NO$_2$+H+, 396.12059; found (ESI, [M+H]$^+$), 396.1195.

EXAMPLE 464

3-[3-(3-METHYLPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and m-Tolyl-acetaldehyde following the procedure of Example 457: MS (ES) m/z 378.0; HRMS: calcd for C$_{23}$H$_{16}$F$_3$NO+H+, 380.12567; found (ESI, [M+H]$^+$), 380.1263.

EXAMPLE 465

3-[3-MESITYL-8-(TRIFLUOROMETHYL)QUINOLIN-4-YL]PHENOL

The title compound was prepared from [2-amino-3-(trifluoromethyl)phenyl]-(3-hydroxy-phenyl)methanone and (2,4,6-Trimethyl-phenyl)-acetaldehyde following the procedure of Example 457: MS (ES) m/z 405.9; HRMS: calcd for C$_{25}$H$_{20}$F$_3$NO+H+, 408.15697; found (ESI, [M+H]$^+$), 408.1573.

EXAMPLE 466

3-[3-(2-METHYLPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and o-Tolyl-acetaldehyde following the procedure of Example 457: MS (ESI) m/z 380.126; HRMS: calcd for C$_{23}$H$_{16}$F$_3$NO+H+, 380.12567; found (ESI, [M+H]$^+$), 380.126.

EXAMPLE 467

3-{8-(TRIFLUOROMETHYL)-3-[2-(TRIFLUOROMETHYL)PHENYL]QUINOLIN-4-YL}PHENOL

The title compound was prepared from [2-amino-3-(trifluoromethyl)phenyl]-(3-hydroxy-phenyl)methanone and (2-Trifluoromethyl-phenyl)-acetaldehyde following the procedure of Example 457: MS (ES) m/z 431.9; HRMS: calcd for C$_{23}$H$_{13}$F$_6$NO+H+, 434.09741; found (ESI, [M+H]$^+$), 434.0961.

EXAMPLE 468

3-[3-(4-METHYLPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and p-Tolyl-acetaldehyde following the procedure of Example 457: MS (ESI) m/z 380; HRMS: calcd for C$_{23}$H$_{16}$F$_3$NO+H+, 380.12567; found (ESI, [M+H]$^+$), 380.1259.

EXAMPLE 469

3-[3-(2,5-DIMETHYLPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (2,5-Dimethyl-phenyl)-acetaldehyde following the procedure of Example 457: MS (ESI) m/z 394; HRMS: calcd for $C_{24}H_{18}F_3NO+H+$, 394.14132; found (ESI, [M+H]$^+$), 394.1402.

EXAMPLE 470

3-{8-(TRIFLUOROMETHYL)-3-[3-(TRIFLUOROMETHYL)PHENYL]QUINOLIN-4-Yl}PHENOL

The title compound was prepared from [2-amino-3-(trifluoromethyl)phenyl]-(3-hydroxy-phenyl)methanone and (3-Trifluoromethyl-phenyl)-acetaldehyde following the procedure of Example 457: HRMS: calcd for $C_{23}H_{13}F_6NO+H+$, 434.09741; found (ESI, [M+H]$^+$), 434.0993.

EXAMPLE 471

3-[3-(2-BROMOPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (2-Bromo-phenyl)-acetaldehyde following the procedure of Example 457: MS (ES) m/z 441.8; HRMS: calcd for $C_{22}H_{13}BrF_3NO+H+$, 444.02053; found (ESI, [M+H]$^+$), 444.0191.

EXAMPLE 472

3-[3-(3-BROMOPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (3-Bromo-phenyl)-acetaldehyde following the procedure of Example 457: MS (ES) m/z 441.8; HRMS: calcd for $C_{22}H_{13}BrF_3NO+H+$, 444.02053; found (ESI, [M+H]$^+$), 444.0206.

EXAMPLE 473

3-[3-(2-CHLOROPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (2-chloro-phenyl)-acetaldehyde following the procedure of Example 457: MS (ES) m/z 397.9; HRMS: calcd for $C_{22}H_{13}ClF_3NO+H+$, 400.07105; found (ESI, [M+H]$^+$), 400.0706.

EXAMPLE 474

3-[3-(3-CHLOROPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (3-chloro-phenyl)-acetaldehyde following the procedure of Example 457: MS (ES) m/z 397.9; HRMS: calcd for $C_{22}H_{13}ClF_3NO+H+$, 400.07105; found (ESI, [M+H]$^+$), 400.0697.

EXAMPLE 475

3-[3-(2,6-DICHLOROPHENYL)-8-(TRIFLUOROMETHYL)QUINOLIN-4-YL]PHENOL

The title compound was prepared from [2-amino-3-(trifluoromethyl)phenyl]-(3-hydroxy-phenyl)methanone and (2,6-dichloro-phenyl)-acetaldehyde following the procedure of Example 457: MS (ES) m/z 431.8; HRMS: calcd for $C_{22}H_{12}Cl_2F_3NO+H+$, 434.03208; found (ESI, [M+H]$^+$), 434.033.

EXAMPLE 476

3-[3-METHYL-8-(TRIFLUOROMETHYL)QUINOLIN-4-YL]PHENOL

The title compound was prepared from [2-amino-3-(trifluoromethyl)phenyl]-(3-hydroxy-phenyl)methanone and Propionaldehyde following the procedure of Example 457: MS (ES) m/z 304.28.

EXAMPLE 477

[2-METHYL-4-PHENYL-8-(TRIFLUOROMETHYL)QUINOLIN-3-YL](PHENYL)METHANONE 1) (2-Fluoro-3-trifluoromethyl-phenyl)-phenyl-methanone: The title compound was prepared from 2-Fluoro-N-methoxy-N-methyl-3-trifluoromethyl-benzamide and phenyl magnesium bromide following the procedure of Example 457, Step 2: MS (ES) m/z 268.2.

2) [2-amino-3-(trifluoromethyl)phenyl](phenyl)methanone: The title compound was prepared from (2-Fluoro-3-trifluoromethyl-phenyl)-phenyl-methanone following the procedure of Example 457, Step 3: MS (ESI) m/z 266; HRMS: calcd for $C_{14}H_{10}F_3NO+H+$, 266.07872; found (ESI, [M+H]$^+$), 266.0771

3) [2-methyl-4-phenyl-8-(trifluoromethyl)quinolin-3-yl](phenyl)methanone: The title compound was prepared from (2-Amino-3-trifluoromethyl-phenyl)-phenyl-methanone and 1-Phenyl-butane-1,3-dione following the procedure of Example 459, step 5: mp 175-177° C.; HRMS: calcd for $C_{24}H_{16}F_3NO+H+$, 392.12567; found (ESI, [M+H]$^+$), 392.1251.

EXAMPLE 478

[4-{3-[(2-NITROBENZYL)OXY]PHENYL}-8-(TRIFLUOROMETHYL)QUINOLIN-3-YL](PHENYL)-METHANONE

A solution of [4-(3-hydroxyphenyl)-8-(trifluoromethyl)quinolin-3-yl](phenyl)methanone (0.15 g, 0.38 mmol), 1-Bromomethyl-2-nitro-benzene (0.10 g, 0.46 mmol) and $CsCO_3$ (0.25 g, 0.76 mmol) in DMF (3 ml) was heated to 60° C. After 14 hr, the reaction was cooled, filtered and concentrated. The crude residue was purified by reverse phase HPLC to provide the desired compound (0.066 g, Yield=33%); MS (ESI) m/z 529;

EXAMPLE 479

[4-{3-[(3-NITROBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-3-nitro-benzene following the procedure of Example 478: MS (ESI) m/z 529.

EXAMPLE 480

[4-{3-[(4-NITROBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)Quinolin-3-yl](phenyl)methanone and 1-Bromomethyl-3-nitro-benzene following the procedure of Example 478: MS (ESI) m/z 529;

EXAMPLE 481

[4-{3-[(2-METHYLBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-2-methylbenzene following the procedure of Example 478: MS (ESI) m/z 498.

EXAMPLE 482

[4-{3-[(3-METHYLBENZYL)OXY]PHENYL}-8-(TRIFLUOROMETHYL)QUINOLIN-3-Yl](PHENYL)-METHANONE

The title compound was prepared from [4-(3-hydroxyphenyl)-8-(trifluoromethyl)quinolin-3-yl](phenyl)methanone and 1-Bromomethyl-3-methylbenzene following the procedure of Example 478: MS (ESI) m/z 498.

EXAMPLE 483

[4-{3-[(4-METHYLBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-4-methylbenzene following the procedure of Example 478: MS (ESI) m/z 498.

EXAMPLE 484

[4-{3-[(2-METHOXYBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-2-methoxybenzene following the procedure of Example 478: MS (ESI) m/z 514.

EXAMPLE 485

[4-{3-[(3-METHOXYBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-3-methoxy-benzene following the procedure of Example 478: MS (ESI) m/z 514.

EXAMPLE 486

[4-{3-[(4-METHOXYBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-4-methoxy-benzene following the procedure of Example 478: MS (ESI) m/z 514.

EXAMPLE 487

PHENYL[8-(TRIFLUOROMETHYL)-4-(3-{[2-(TRIFLUOROMETHYL) BENZYL]OXY}PHENYL)QUINOLIN-3-YL]METHANONE

The title compound was prepared from [4-(3-hydroxyphenyl)-8-(trifluoromethyl)quinolin-3-yl](phenyl)methanone and 1-Bromomethyl-2-trifluoromethyl-benzene following the procedure of Example 478: MS (ESI) m/z 552.

EXAMPLE 488

PHENYL[8-(TRIFLUOROMETHYL)-4-(3-{[3-(TRIFLUOROMETHYL)BENZYL]OXY}PHENYL)QUINOLIN-3-YL]-METHANONE

The title compound was prepared from [4-(3-hydroxyphenyl)-8-(trifluoromethyl)quinolin-3-yl](phenyl)methanone and 1-Bromomethyl-3-trifluoromethyl-benzene following the procedure of Example 478: MS (ESI) m/z 552.

EXAMPLE 489

[4-{3-[(4-TERT-BUTYLBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-4-tert-butyl-benzene following the procedure of Example 478: MS (ESI) m/z 540.

EXAMPLE 490

[4-{3-[(4-ISOPROPYLBENZYL)OXY]PHENYL}-8-(TRIFLUOROMETHYL)QUINOLIN-3-YL](PHENYL)-METHANONE

The title compound was prepared from [4-(3-hydroxyphenyl)-8-(trifluoromethyl)quinolin-3-yl](phenyl)methanone and 1-Bromomethyl-4-isopropylbenzene following the procedure of Example 478: MS (ESI) m/z 526;

EXAMPLE 491

[4-{3-[(4-CHLORO-2-FLUOROBENZYL)OXY]
PHENYL}-8-(TRIFLUOROMETHYL)QUINOLIN-
3-YL](PHENYL)-METHANONE

The title compound was prepared from [4-(3-hydroxyphenyl)-8-(trifluoromethyl)quinolin-3-yl](phenyl)methanone and 1-Bromomethyl-4-chloro-2-fluoro-benzene following the procedure of Example 478: MS (ESI) m/z 536.

EXAMPLE 492

[4-[3-(2-NAPHTHYLMETHOXY)PHENYL]-8-
(TRIFLUOROMETHYL)QUINOLIN-3-YL](PHE-
NYL)-METHANONE

The title compound was prepared from [4-(3-hydroxyphenyl)-8-(trifluoromethyl)quinolin-3-yl](phenyl)methanone and 2-Bromomethyl-naphthalene following the procedure of Example 478: MS (ESI) m/z 534.

EXAMPLE 493

PHENYL[4-[3-(PYRIDIN-2-YLMETHOXY)PHE-
NYL]-8-(TRIFLUOROMETHYL)QUINOLIN-3-
YL]-METHANONE

The title compound was prepared from [4-(3-hydroxyphenyl)-8-(trifluoromethyl)quinolin-3-yl](phenyl)methanone and 2-Bromomethyl-pyridine following the procedure of Example 478: MS (ESI) m/z 485.

EXAMPLE 494

PHENYL[4-[3-(PYRIDIN-4-YLMETHOXY)PHE-
NYL]-8-(TRIFLUOROMETHYL)QUINOLIN-3-
YL]-METHANONE

The title compound was prepared from [4-(3-hydroxyphenyl)-8-(trifluoromethyl)quinolin-3-yl](phenyl)methanone and 4-Bromomethyl-pyridine following the procedure of Example 478: MS (ESI) m/z 485.

EXAMPLE 495

[4-(3-ISOPROPOXYPHENYL)-8-(TRIFLUOROM-
ETHYL)QUINOLIN-3-YL](PHENYL)METHA-
NONE

The title compound was prepared from [4-(3-hydroxyphenyl)-8-(trifluoromethyl)quinolin-3-yl](phenyl)methanone and 2-Bromo-propane following the procedure of Example 478: MS (ESI) m/z 436.

EXAMPLE 496

[4-{3-[(4-METHYLPENT-3-ENYL)OXY]PHE-
NYL}-8-(TRIFLUOROMETHYL)QUINOLIN-3-
YL](PHENYL)METHANONE

The title compound was prepared from [4-(3-hydroxyphenyl)-8-(trifluoromethyl)quinolin-3-yl](phenyl)methanone and 5-Bromo-2-methyl-pent-2-ene following the procedure of Example 478: MS (ESI) m/z 476.

EXAMPLE 497

PHENYL[4-[3-(TETRAHYDRO-2H-PYRAN-2-
YLMETHOXY)PHENYL]-8-(TRIFLUOROM-
ETHYL)QUINOLIN-3-YL]METHANONE

The title compound was prepared from [4-(3-hydroxyphenyl)-8-(trifluoromethyl)quinolin-3-yl](phenyl)methanone and 2-Bromomethyl-tetrahydropyran following the procedure of Example 478: MS (ESI) m/z 492.

EXAMPLE 498

[4-{3-[(2,6-DICHLOROBENZYL)OXY]PHE-
NYL}-8-(TRIFLUOROMETHYL)QUINOLIN-3-
YL](PHENYL)METHANONE

The title compound was prepared from [4-(3-hydroxyphenyl)-8-(trifluoromethyl)quinolin-3-yl](phenyl)methanone and 2-Bromomethyl-1,3-dichlorobenzene following the procedure of Example 478: MS (ESI) m/z 552.

EXAMPLE 499

[4-{3-[(4-METHYLPENTYL)OXY]PHENYL}-8-
(TRIFLUOROMETHYL)QUINOLIN-3-YL](PHE-
NYL)-METHANONE

The title compound was prepared from [4-(3-hydroxyphenyl)-8-(trifluoromethyl)quinolin-3-yl](phenyl)methanone and 1-Bromo-4-methyl-pentane following the procedure of Example 478: MS (ES) m/z 478.3.

EXAMPLE 500

[4-[3-(CYCLOHEXYLMETHOXY)PHENYL]-8-
(TRIFLUOROMETHYL)QUINOLIN-3-YL](PHE-
NYL)-METHANONE

The title compound was prepared from [4-(3-hydroxyphenyl)-8-(trifluoromethyl)quinolin-3-yl](phenyl)methanone and Bromomethyl-cyclohexane following the procedure of Example 478: MS (ES) m/z 490.3.

EXAMPLE 501

[4-{3-[(6-CHLOROPYRIDIN-3-YL)METHOXY]
PHENYL}-8-(TRIFLUOROMETHYL)QUINOLIN-
3-YL](PHENYL)METHANONE

The title compound was prepared from [4-(3-hydroxyphenyl)-8-(trifluoromethyl)quinolin-3-yl](phenyl)methanone and 5-Bromomethyl-2-chloropyridine following the procedure of Example 478: MS (ES) m/z 519.1.

EXAMPLE 502

PHENYL[4-[3-(QUINOLIN-2-YLMETHOXY)
PHENYL]-8-(TRIFLUOROMETHYL)QUINOLIN-
3-YL]METHANONE

The title compound was prepared from [4-(3-hydroxyphenyl)-8-(trifluoromethyl)quinolin-3-yl](phenyl)methanone and 2-Bromomethyl-quinoline following the procedure of Example 478: MS (ES) m/z 535.3.

EXAMPLE 503

[4-{3-[(5-NITRO-2-FURYL)METHOXY]PHENYL}-8-(TRIFLUOROMETHYL)QUINOLIN-3-YL](PHENYL)METHANONE

The title compound was prepared from [4-(3-hydroxyphenyl)-8-(trifluoromethyl)quinolin-3-yl](phenyl)methanone and 2-Bromomethyl-5-nitro-furan following the procedure of Example 478: MS (ES) m/z 517.2.

EXAMPLE 504

[4-{3-[(2,6-DIFLUOROBENZYL)OXY]PHENYL}-8-(TRIFLUOROMETHYL)QUINOLIN-3-YL](PHENYL)METHANONE

The title compound was prepared from [4-(3-hydroxyphenyl)-8-(trifluoromethyl)quinolin-3-yl](phenyl)methanone and 2-Bromomethyl-1,3-difluorobenzene following the procedure of Example 478: MS (ESI) m/z 520.

EXAMPLE 505

[4-{3-[(4-BROMO-2-METHOXYBENZYL)OXY]PHENYL}-8-(TRIFLUOROMETHYL)QUINOLIN-3-YL](PHENYL)METHANONE

The title compound was prepared from [4-(3-hydroxyphenyl)-8-(trifluoromethyl)quinolin-3-yl](phenyl)methanone and 4-Bromo-1-bromomethyl-2-methoxy-benzene following the procedure of Example 478: MS (ES) m/z 592.1.

EXAMPLE 506

[4-{3-[(2,6-DIMETHYLBENZYL)OXY]PHENYL}-8-(TRIFLUOROMETHYL)QUINOLIN-3-YL](PHENYL)METHANONE

The title compound was prepared from [4-(3-hydroxyphenyl)-8-(trifluoromethyl)quinolin-3-yl](phenyl)methanone and 2-Bromomethyl-1,3-dimethylbenzene following the procedure of Example 478: MS (ESI) m/z 511.5.

EXAMPLE 507

METHYL-4-({3-[3-BENZOYL-8-(TRIFLUOROMETHYL)QUINOLIN-4-YL]PHENOXY}METHYL)-3-METHOXYBENZOATE

The title compound was prepared from [4-(3-hydroxyphenyl)-8-(trifluoromethyl)quinolin-3-yl](phenyl)methanone and 4-Bromomethyl-3-methoxy-benzoic acid methyl ester following the procedure of Example 478: mp 60-63° C.; MS (ES) m/z 571.9; HRMS: calcd for $C_{33}H_{24}F_3NO_5$+H+, 572.16793; found (ESI, [M+H]$^+$), 572.1708.

EXAMPLE 508

[4-[3-(1,3-BENZODIOXOL-5-YLMETHOXY)PHENYL]-8-(TRIFLUOROMETHYL)QUINOLIN-3-YL](PHENYL)METHANONE

The title compound was prepared from [4-(3-hydroxyphenyl)-8-(trifluoromethyl)quinolin-3-yl](phenyl)methanone and 5-Bromomethyl-benzo[1,3]dioxole following the procedure of Example 478: MS (ESI) m/z 528; HRMS: calcd for $C_{31}H_{20}F_3NO_4$+H+, 528.14172; found (ESI, [M+H]$^+$), 528.1435.

EXAMPLE 509

[4-[3-(2,1,3-BENZOXADIAZOL-5-YLMETHOXY)PHENYL]-8-(TRIFLUOROMETHYL)QUINOLIN-3-YL](PHENYL)METHANONE

The title compound was prepared from [4-(3-hydroxyphenyl)-8-(trifluoromethyl)quinolin-3-yl](phenyl)methanone and 5-Bromomethyl-benzo[1,2,5]oxadiazole following the procedure of Example 478: MS (ESI) m/z 526; MS (ESI) m/z 524; HRMS: calcd for $C_{30}H_{18}F_3N_3O_3$+H+, 526.13730; found (ESI, [M+H]$^+$), 526.1356.

EXAMPLE 510

4-({3-[3-BENZOYL-8-(TRIFLUOROMETHYL)QUINOLIN-4-YL]PHENOXY}METHYL)-1H-ISOCHROMEN-1-ONE

The title compound was prepared from [4-(3-hydroxyphenyl)-8-(trifluoromethyl)quinolin-3-yl](phenyl)methanone and 4-Bromomethyl-isochromen-1-one following the procedure of Example 478: MS (ESI) m/z 552; HRMS: calcd for $C_{33}H_{20}F_3NO_4$+H+, 552.14172; found (ESI, [M+H]$^+$), 552.1434.

EXAMPLE 511

3-{3-[3-BENZOYL-8-(TRIFLUOROMETHYL)QUINOLIN-4-YL]PHENOXY}-2-BENZOFURAN-1 (3H)-ONE

The title compound was prepared from [4-(3-hydroxyphenyl)-8-(trifluoromethyl)quinolin-3-yl](phenyl)methanone and 3-Bromo-3H-isobenzofuran-1-one following the procedure of Example 478: MS (ESI) m/z 526; HRMS: calcd for $C_{31}H_{18}F_3NO_4$+H+, 526.12607; found (ESI, [M+H]$^+$), 526.1287.

EXAMPLE 512

4-({3-[3-PHENYL-8-(TRIFLUOROMETHYL)QUINOLIN-4-YL]PHENOXY}METHYL)BENZOIC ACID

The title compound was prepared from [3-(3-Phenyl-8-trifluoromethyl-quinolin-4-yl)-phenol and 4-Bromomethyl-benzoic acid following the procedure of Example 1: mp 108-112° C.; MS m/z 500; HRMS: calcd for $C_{30}H_{20}F_3NO_3$+H+, 500.14680; found (ESI, [M+H]$^+$), 500.1461.

EXAMPLE 513

3-BENZYL-4-{3-[(2,6-DIMETHYLBENZYL)OXY]PHENYL}-8-(TRIFLUOROMETHYL)QUINOLINE

The title compound was prepared from 3-(3-Benzyl-8-trifluoromethyl-quinolin-4-yl)-phenol and 2-Bromomethyl-1,3-dimethyl-benzene following the procedure of Example 478: MS m/z 498; HRMS: calcd for $C_{32}H_{26}F_3NO$+H+, 498.20392; found (ESI, [M+H]$^+$), 498.2038.

EXAMPLE 514

4-({3-[3-BENZYL-8-(TRIFLUOROMETHYL) QUINOLIN-4-YL] PHENOXY}METHYL)-3-FLUOROBENZOIC ACID

The title compound was prepared from 3-(3-Benzyl-8-trifluoromethyl-quinolin-4-yl)-phenol and 4-Bromomethyl-3-fluoro-benzoic acid following the procedure of Example 478: MS m/z 532; MS m/z 530; HRMS: calcd for $C_{31}H_{21}F_4NO_3+H+$, 532.15303; found (ESI, [M+H]$^+$), 532.153;

EXAMPLE 515

4-({3-[3-BENZOYL-8-(TRIFLUOROMETHYL)QUINOLIN-4-YL]PHENOXY}METHYL)-3METHOXY-BENZOIC ACID

The title compound was prepared from [4-(3-hydroxyphenyl)-8-(trifluoromethyl)-quinolin-3-yl](phenyl)methanone and 4-Bromomethyl-3-methoxy-benzoic acid methyl ester following the procedure of Example 478 then hydrolysis using sodium hydroxide in THF:MeOH (1:2) at RT for 12 hr, the reaction mixture was acidified and concentrated. The crude residue was purified by reverse phase HPLC to provide the desired compound: mp 100-110° C.; MS (ES) m/z 555.8; HRMS: calcd for $C_{32}H_{22}F_3NO_5+H+$, 558.15228; found (ESI, [M+H]$^+$), 558.154.

EXAMPLE 516

3-BENZYL-4-[3-(4-METHOXYPHENOXY)PHENYL]-8-(TRIFLUOROMETHYL)QUINOLINE 1) (2-Fluoro-3-trifluoromethyl-phenyl)-[3-(4-methoxyphenoxy)-phenyl]-methanol: To a solution of 1-Fluoro-2-trifluoromethyl-benzene (0.39 ml, 0.003 mole) in 10 ml THF, cooled to −78° C., under nitrogen, was added 2.5M n-BuLi (1.5 ml, 0.0037 mole) dropwise over 3 minutes and then stirred 5 hr at −78° C. Then 3-(4-Methoxy-phenoxy)-benzaldehyde (0.78 ml, 0.0037 mole) in 1 ml THF was added over 3 minutes and the reaction allowed to warm to rt. A 1N HCl solution (15 ml) was added to the reaction and extracted with ethyl acetate. The organic layer was washed with brine, dried over magnesium sulfate and evaporated to dryness, giving 1.65 g of the title compound: MS (ES) m/z 375.1;

2) [2-fluoro-3-(trifluoromethyl)phenyl][3-(4-methoxyphenoxy)phenyl]methanone: To a suspension of pyridinium chlorochromate (19.7 g, 0.092 mole) in 400 ml dichloromethane is added a solution of (2-fluoro-3-trifluoromethylphenyl)-[3-(4-methoxyphenoxy)-phenyl]methanol (26.2 g, 0.061 mole) in 150 ml dichloromethane, dropwise over 20 minutes. This mixture was stirred at rt for 3.5 hr. The reaction was filtered, the filtrate was washed with 1N HCl (2×), brine and then dried over magnesium sulfate and evaporated to dryness to give 26.4 g of [2-fluoro-3-(trifluoromethyl)phenyl]-[3-(4-methoxyphenoxy)phenyl]methanone. This material was used in the subsequent step without further purification. The compound can be purified by reverse-phase HPLC: MS (ES) m/z 391.0; HRMS: calcd for $C_{21}H_{14}F_4O_3+H+$, 391.09518; found (ESI, [M+H]$^+$), 391.0938

3) [2-amino-3-(trifluoromethyl)phenyl][3-(4-methoxyphenoxy)phenyl]methanone: The title compound was prepared from (2-fluoro-3-trifluoromethylphenyl)-[3-(4-methoxy-phenoxy)-phenyl]methanone (0.64 g, 0.0015 mole) following the procedure of Example 457, Step 3: MS (ESI) m/z 388;

4) 3-benzyl-4-[3-(4-methoxyphenoxy)phenyl]-8-(trifluoromethyl)quinoline: The title compound was prepared from (2-amino-3-trifluoromethyl-phenyl)-[3-(4-methoxy-phenoxy)-phenyl]-methanone (0.41 g, 0.0011 mole) and hydrocinnamaldehyde (0.21 g, 0.0016 mole) following the procedure of, Example 457, Step 5. The crude product was purified by flash chromatography to give 0.33 g of 3-benzyl-4-[3-(4-methoxyphenoxy)phenyl]-8-(trifluoromethyl)quinoline: MS (ES) m/z 485.9.

EXAMPLE 517

4-{3-[3-BENZYL-8-(TRIFLUOROMETHYL)QUINOLIN-4-YL]PHENOXY}PHENOL

The title compound was prepared from 3-benzyl-4-[3-(4-methoxyphenoxy)phenyl]-8-(trifluoromethyl)quinoline (0.22 g, 0.00045 mole) following the procedure of Example 457, Step 4. The crude product was purified by flash chromatography to give the title compound: mp 55-60° C.; MS (ES) m/z 469.9; HRMS: calcd for $C_{29}H_{20}F_3NO_2+H+$, 472.15189; found (ESI, [M+H]$^+$), 472.153.

EXAMPLE 518

3-BENZYL-4-[3-(4-METHYLPHENOXY)PHENYL]-8-(TRIFLUOROMETHYL)QUINOLINE

The title compound was prepared from 1-Fluoro-2-trifluoromethyl-benzene and 3-p-Tolyloxy-benzaldehyde following the procedure of Example 516. The crude product was purified by flash chromatography to give the title compound: MS m/z 470.

EXAMPLE 519

3-{3-[3-BENZOYL-8-(TRIFLUOROMETHYL)QUINOLIN-4-YL]PHENOXY}BENZOIC ACID

To [4-(3-hydroxy-phenyl)-8-trifluoromethylquinolin-3-yl]-phenyl methanone (0.1 g, 0.00025 mole) and 3-carboxyphenyl boronic acid (0.12 g, 0.00072 mole) in 2 ml dichloromethane was added copper acetate (0.091 g, 0.0005 mole) and triethylamine (0.1 ml, 0.00072 mole). This mixture was stirred at room temperature overnight. The reaction was then filtered and the filtrate evaporated to dryness. The crude product was purified by flash chromatography to give 0.027 g of 3-[3-(3-benzoyl-8-trifluoromethyl-quinolin-4-yl)-phenoxy]-benzoic acid: MS: MS (ESI) m/z 514; MS (ESI) m/z 512.

EXAMPLE 520

[4-(3-PHENOXYPHENYL)-8-(TRIFLUOROMETHYL)QUINOLIN-3-YL](PHENYL)METHANONE

The title compound was prepared from [4-(3-hydroxyphenyl)-8-trifluoromethylquinolin-3-yl]-phenyl methanone and phenyl boronic acid, following the procedure of Example 519: MS (ESI) m/z 470.

EXAMPLE 521

4-{3-[3-BENZOYL-8-(TRIFLUOROMETHYL)QUINOLIN-4-YL]PHENOXY}BENZOIC ACID

The title compound was prepared from [4-(3-hydroxyphenyl)-8-trifluoromethylquinolin-3-yl]-phenyl methanone and 4-carboxyphenyl boronic acid, following the procedure of Example 519: MS (ESI) m/z 514; MS (ESI) m/z 512.

EXAMPLE 522

[4-{3-[(6-METHOXYPYRIDIN-3-YL)OXY]PHENYL}-8-(TRIFLUOROMETHYL)QUINOLIN-3-YL](PHENYL)-METHANONE

The title compound was prepared from [4-(3-hydroxyphenyl)-8-trifluoromethylquinolin-3-yl]-phenyl methanone and 2-Methoxy-5-pyridineboronic acid, following the procedure of Example 519: MS m/z 501.

EXAMPLE 523

[4-[3-(1H-INDOL-5-YLOXY) PHENYL]-8-(TRIFLUOROMETHYL)QUINOLIN-3-YL](PHENYL)METHANONE

The title compound was prepared from [4-(3-hydroxyphenyl)-8-trifluoromethylquinolin-3-yl]-phenyl methanone and 5-Indolylboronic acid, following the procedure of Example 519: MS m/z 509; MS m/z 507.

EXAMPLE 524

[4-[3-(1,3-BENZODIOXOL-5-YLOXY)PHENYL]-8-(TRIFLUOROMETHYL)QUINOLIN-3-YL](PHENYL)METHANONE

The title compound was prepared from [4-(3-hydroxyphenyl)-8-trifluoromethylquinolin-3-yl]-phenyl methanone and 3,4-(methylenedioxy) phenyl boronic acid, following the procedure of Example 519: MS m/z 514.

EXAMPLE 525

METHYL-4-[(4-{3-[3-BENZYL-8-(TRIFLUOROMETHYL)QUINOLIN-4-YL]PHENOXY}PHENOXY) METHYL]BENZOATE

The title compound was prepared from 4-{3-[3-benzyl-8-(trifluoromethyl)quinolin-4-yl]-phen-oxy}phenol (0.1 g, 0.0002 mole) and 4-Bromomethyl-benzoic acid methyl ester (0.057 g, 0.00024 mole) following the procedure of Example 478: MS (ESI) [M+H]$^+$, 620.0.

EXAMPLE 526

4-[(4-{3-[3-BENZYL-8-(TRIFLUOROMETHYL)QUINOLIN-4-YL]PHENOXY}PHENOXY)METHYL]BENZOIC ACID

The title compound was prepared from 4-{3-[3-benzyl-8-(trifluoromethyl)quinolin-4-yl]-phen-oxy}phenol (0.1 g, 0.0002 mole) and 4-Bromomethyl-benzoic acid methyl ester (0.057 g, 0.00024 mole) with subsequent hydrolysis following the procedure of Example 515: MS (ES) m/z 603.9; HRMS: calcd for $C_{37}H_{26}F_3NO_4$+H+, 606.18867; found (ESI, [M+H]$^+$), 606.1894.

EXAMPLE 527

METHYL-4-[(4-{3-[3-BENZYL-8-(TRIFLUOROMETHYL)QUINOLIN-4-YL]PHENOXY}PHENOXY)-ACETATE

The title compound was prepared from 4-{3-[3-benzyl-8-(trifluoromethyl)quinolin-4-yl]-phen-oxy}phenol and Bromo-acetic acid methyl ester following the procedure of Example 478: MS (ES) m/z 543.9.

EXAMPLE 528

(4-{3-[3-BENZYL-8-(TRIFLUOROMETHYL)QUINOLIN-4-YL]PHENOXY}PHENOXY)ACETIC ACID

The title compound was prepared from 4-{3-[3-benzyl-8-(trifluoromethyl)quinolin-4-yl]-phen-oxy}phenol and Bromo-acetic acid methyl ester with subsequent hydrolysis following the procedure of Example 515: MS (ES) m/z 527.9.

EXAMPLE 529

3-BENZYL-4-(3-BROMOPHENYL)-8-(TRIFLUOROMETHYL)QUINOLINE

The title compound was prepared from 1-Fluoro-2-trifluoromethyl-benzene and 3-bromo-benzaldehyde following the procedure of Example 516, Steps 1-4. The crude product was purified by flash chromatography to give the title compound: MS (ESI) m/z 442; HRMS: calcd for $C_{23}H_{15}BrF_3N$+H+, 442.04127; found (ESI, [M+H]$^+$), 442.0418.

EXAMPLE 530

3-{3'-[3-BENZYL-8-(TRIFLUOROMETHYL)QUINOLIN-4-YL]-1,1'-BIPHENYL-4-YL}PROPANOIC ACID

To a solution of 3-benzyl-4-(3-bromophenyl)-8-(trifluoromethyl)quinoline (0.30 g, 0.7 mmol), 4-(2-carboxyethyl)benzene boronic acid (0.15 g, 0.75 mmol) in 15 ml DME under a nitrogen atmosphere is added terakistriphenyl phosphine palladium (0.08 g, 0.07 mmol) followed by sodium carbonate (0.22 g, 2.04 mmol) dissolved in 5 ml water. The reaction mixture was heated to reflux for 12 hr. The reaction was cooled, poured into 1N HCl and extracted with EtOAc. The organic layer was dried and concentrated to provide the title compound as a tan solid (0.24 g, 70%): MS (ES) m/z 509.9; HRMS: calcd for $C_{32}H_{24}F_3NO_2$+H+, 512.18319; found (ESI, [M+H]$^+$), 512.1842;

EXAMPLE 531

{3-[3-BENZYL-8-(TRIFLUOROMETHYL)QUINOLIN-4-YL]PHENYL}(2,6-DIFLUOROBENZYL)AMINE

The title compound was prepared from {3-[3-benzyl-(trifluoromethyl)quinolin-4-yl]phenyl}amine and 2,6-difluorobenzaldehyde according to the procedure of step 1, Example 66. MS (ESI) m/z 505.

EXAMPLE 532

{3-[3-BENZYL-8-(TRIFLUOROMETHYL)QUINOLIN-4-YL]PHENYL}(3,3-DIFLUOROBENZYL)AMINE

The title compound was prepared from {3-[3-benzyl-8-(trifluoromethyl)quinolin-4-yl]phenyl}amine and 3,5-difluorobenzaldehyde according to the procedure of step 1, Example 66. MS (ESI) m/z 505.

EXAMPLE 533

{3-[3-BENZYL-8-(TRIFLUOROMETHYL) QUINOLIN-4-YL]PHENYL}(3,4-DICHLOROBENZYL)AMINE

The title compound was prepared from {3-[3-benzyl-8-(trifluoromethyl)quinolin-4-yl]phenyl}amine and 3,4-dichlorobenzaldehyde according to the procedure of step 1, Example 66. MS (ESI) m/z 537.

EXAMPLE 534

{3-[3-BENZYL-8-(TRIFLUOROMETHYL) QUINOLIN-4-YL]PHENYL}(2,3-DICHLOROBENZYL)AMINE

The title compound was prepared from {3-[3-benzyl-8-(trifluoromethyl)quinolin-4-yl]phenyl}amine and 2,3-dichlorobenzaldehyde according to the procedure of step 1, Example 66. MS (ESI) m/z 537.

EXAMPLE 535

{3-[3-BENZYL-8-(TRIFLUOROMETHYL) QUINOLIN-4-YL]PHENYL}(2,6-DICHLOROBENZYL)AMINE

The title compound was prepared from {3-[3-benzyl-8-(trifluoromethyl)quinolin-4-yl]phenyl}amine and 2,6-dichlorobenzaldehyde according to the procedure of step 1, Example 66. MS (ESI) m/z 537.

EXAMPLE 536

{3-[3-BENZYL-8-(TRIFLUOROMETHYL) QUINOLIN-4-YL]PHENYL}(5-CHLORO-2-NITROBENZYL)AMINE

The title compound was prepared from {3-[3-benzyl-8-(trifluoromethyl)quinolin-4-yl]phenyl}amine and 5-chloro-2-nitro-benzaldehyde according to the procedure of step 1, Example 66. MS (ESI) m/z 548.

EXAMPLE 537

{3-[3-BENZYL-8-(TRIFLUOROMETHYL) QUINOLIN-4-YL]PHENYL}[(4-BROMO-2-THIENYL)METHYL]AMINE

The title compound was prepared from {3-[3-benzyl-8-(trifluoromethyl)quinolin-4-yl]phenyl}amine and 4-bromo-2-formylthiophene according to the procedure of step 1, Example 66. MS (ESI) m/z 553.

EXAMPLE 538

{3-[3-BENZYL-8-(TRIFLUOROMETHYL) QUINOLIN-4-YL]PHENYL}(2,4-DICHLOROBENZYL)AMINE

The title compound was prepared from {3-[3-benzyl-8-(trifluoromethyl)quinolin-4-yl]phenyl}amine and 2,4-Dichlorobenzaldehyde according to the procedure of step 1, Example 66. MS (ESI) m/z 537.

EXAMPLE 539

{3-[3-BENZYL-8-(TRIFLUOROMETHYL) QUINOLIN-4-YL]PHENYL}(2-FLUOROBENZYL)AMINE

The title compound was prepared from {3-[3-benzyl-8-(trifluoromethyl)quinolin-4-yl]phenyl}amine and 2-fluorobenzaldehyde according to the procedure of step 1, Example 66. MS (ESI) m/z 487.

EXAMPLE 540

{3-[3-BENZYL-8-(TRIFLUOROMETHYL) QUINOLIN-4-YL]PHENYL}(2,3-DIFLUOROBENZYL)AMINE

The title compound was prepared from {3-[3-benzyl-8-(trifluoromethyl)quinolin-4-yl]phenyl}amine and 2,3-Difluorobenzaldehyde according to the procedure of step 1, Example 66. MS (ESI) m/z 505.

EXAMPLE 541

{3-[3-BENZYL-8-(TRIFLUOROMETHYL) QUINOLIN-4-YL]PHENYL}(2,3,6-TRICHLOROBENZYL)AMINE

The title compound was prepared from {3-[3-benzyl-8-(trifluoromethyl)quinolin-4-yl]phenyl}amine and 2,3,6-trichlorobenzaldehyde according to the procedure of step 1, Example 66. MS (ESI) m/z 571.

EXAMPLE 542

2-[({3-[3-BENZYL-8-(TRIFLUOROMETHYL) QUINOLIN-4-YL]PHENYL}AMINO)METHYL]-4-FLUOROPHENOL

The title compound was prepared from {3-[3-benzyl-8-(trifluoromethyl)quinolin-4-yl]phenyl}amine and 5-fluoro-2-hydroxybenzaldehyde according to the procedure of step 1, Example 66. MS (ESI) m/z 503; MS (ESI) m/z 501.

EXAMPLE 543

4-[({3-[3-BENZYL-8-(TRIFLUOROMETHYL) QUINOLIN-4-YL]PHENYL}AMINO)METHYL]-2-ETHOXYPHENOL

The title compound was prepared from {3-[3-benzyl-8-(trifluoromethyl)quinolin-4-yl]phenyl}amine and 5-ethoxy-4-hydroxybenzaldehyde according to the procedure of step 1, Example 66. MS (ESI) m/z 529; MS (ESI) m/z 527.

EXAMPLE 544

{3-[3-BENZYL-8-(TRIFLUOROMETHYL) QUINOLIN-4-YL]PHENYL}(2,3-DIHYDRO-1,4-BENZODIOXIN-6-YLMETHYL)AMINE

The title compound was prepared from {3-[3-benzyl-8-(trifluoromethyl)quinolin-4-yl]phenyl}amine and 1,4-benzodioxan-6-carboxaldehyde according to the procedure of step 1, Example 66. MS (ESI) m/z 527.

EXAMPLE 545

{3-[3-BENZYL-8-(TRIFLUOROMETHYL)
QUINOLIN-4-YL]PHENYL}(2-FLUORO-6-
METHOXYBENZYL)AMINE

The title compound was prepared from {3-[3-benzyl-8-(trifluoromethyl)quinolin-4-yl]phenyl}amine and 2-fluoro-6-methoxybenzaldehyde according to the procedure of step 1, Example 66. MS (ESI) m/z 517.

EXAMPLE 546

3-[({3-[3-BENZYL-8-(TRIFLUOROMETHYL)
QUINOLIN-4-YL]PHENYL}AMINO)METHYL]
BENZENE-1,2-DIOL

The title compound was prepared from {3-[3-benzyl-8-(trifluoromethyl)quinolin-4-yl]phenyl}amine and 2,3-dihydroxybenzaldehyde according to the procedure of step 1, Example 66. MS (ESI) m/z 501; MS (ESI) m/z 499.

EXAMPLE 547

2-[({3-[3-BENZYL-8-(TRIFLUOROMETHYL)
QUINOLIN-4-YL]PHENYL}AMINO)METHYL]-
6-FLUOROPHENOL

The title compound was prepared from {3-[3-benzyl-8-(trifluoromethyl)quinolin-4-yl]phenyl}amine and 3-fluoro-2-hydroxybenzaldehyde according to the procedure of step 1, Example 66. MS (ESI) m/z 503; MS (ESI) m/z 501.

EXAMPLE 548

2-[({3-[3-BENZYL-8-(TRIFLUOROMETHYL)
QUINOLIN-4-YL]PHENYL}AMINO)METHYL]-
6-ETHOXYPHENOL

The title compound was prepared from {3-[3-benzyl-8-(trifluoromethyl)quinolin-4-yl]phenyl}amine and 3-ethoxy-2-hydroxybenzaldehyde according to the procedure of step 1, Example 66. MS (ESI) m/z 529; MS (ESI) m/z 527.

EXAMPLE 549

{3-[3-BENZYL-8-(TRIFLUOROMETHYL)
QUINOLIN-4-YL]PHENYL}[(1-METHYL-1H-
INDOL-2-YL)METHYL]AMINE

The title compound was prepared from {3-[3-benzyl-8-(trifluoromethyl)quinolin-4-yl]phenyl}amine and 1-methylindole-2-carboxaldehyde according to the procedure of step 1, Example 66. MS (ESI) m/z 522.

EXAMPLE 550

N-[4-(BENZYLOXY)-3-METHOXYBENZYL]-3-
[3-BENZYL-8-(TRIFLUOROMETHYL)QUINO-
LIN-4-YL]ANILINE

The title compound was prepared from {3-[3-benzyl-8-(trifluoromethyl)quinolin-4-yl]phenyl}amine and 4-benzyloxy-3-methoxybenzaldehyde according to the procedure of step 1, Example 66. MS (ESI) m/z 605.

EXAMPLE 551

{3-[3-BENZYL-8-(TRIFLUOROMETHYL)
QUINOLIN-4-YL]PHENYL}[(6-BROMOPYRI-
DIN-3-YL)METHYL]AMINE

The title compound was prepared from {3-[3-benzyl-8-(trifluoromethyl)quinolin-4-yl]phenyl}amine and 6-bromopyridine-3-carbaldehyde according to the procedure of step 1, Example 66. MS (ESI) m/z 548.

EXAMPLE 552

{3-[3-BENZYL-8-(TRIFLUOROMETHYL)
QUINOLIN-4-YL]PHENYL}[(2-CHLOROQUINO-
LIN-3-YL)METHYL]AMINE

The title compound was prepared from {3-[3-benzyl-8-(trifluoromethyl)quinolin-4-yl]phenyl}amine and 2-chloroquinoline-3-carboxaldehyde to the procedure of step 1, Example 66. MS (ESI) m/z 554.

EXAMPLE 553

{3-[3-BENZYL-8-(TRIFLUOROMETHYL)
QUINOLIN-4-YL]PHENYL}[(6-METHOXYPYRI-
DIN-3-YL)METHYL]AMINE

The title compound was prepared from {3-[3-benzyl-8-(trifluoromethyl)quinolin-4-yl]phenyl}amine and 6-methoxypyridine-3-carbaldehyde to the procedure of step 1, Example 66. MS (ESI) m/z 500.

EXAMPLE 554

{3-[3-BENZYL-8-(TRIFLUOROMETHYL)
QUINOLIN-4-YL]PHENYL}[(6-CHLOROPYRI-
DIN-3-YL)METHYL]AMINE

The title compound was prepared from {3-[3-benzyl-8-(trifluoromethyl)quinolin-4-yl]phenyl}amine and 6-chloropyridine-3-carbaldehyde to the procedure of step 1, Example 66. MS (ESI) m/z 504.

EXAMPLE 555

{3-[3-BENZYL-8-(TRIFLUOROMETHYL)
QUINOLIN-4-YL]PHENYL}(2,3,4-TRI-
METHOXYBENZYL)AMINE

The title compound was prepared from {3-[3-benzyl-8-(trifluoromethyl)quinolin-4-yl]phenyl}amine and 2,3,4-trimethoxybenzaldehyde to the procedure of step 1, Example 66. MS (ESI) m/z 559.

EXAMPLE 556

{3-[3-BENZYL-8-(TRIFLUOROMETHYL)
QUINOLIN-4-YL]PHENYL}(1H-INDOL-5-YLM-
ETHYL)AMINE

The title compound was prepared from {3-[3-benzyl-8-(trifluoromethyl)quinolin-4-yl]phenyl}amine and 5-formylindole to the procedure of step 1, Example 66. MS (ESI) m/z 508.

EXAMPLE 557

{3-[3-BENZYL-8-(TRIFLUOROMETHYL) QUINOLIN-4-YL]PHENYL}(1H-INDOL-6-YLMETHYL)AMINE

The title compound was prepared from {3-[3-benzyl-8-(trifluoromethyl)quinolin-4-yl]phenyl}amine and 6-formylindole to the procedure of step 1, Example 66. MS (ESI) m/z 508.

EXAMPLE 558

{3-[3-BENZYL-8-(TRIFLUOROMETHYL) QUINOLIN-4-YL]PHENYL}[(1-ETHYL-1H-INDOL-6-YL)METHYL]AMINE

The title compound was prepared from {3-[3-benzyl-8-(trifluoromethyl)quinolin-4-yl]phenyl}amine and 6-formy-1-ethylindole to the procedure of step 1, Example 66. MS (ESI) m/z 536.

EXAMPLE 559

{3-[3-BENZYL-8-(TRIFLUOROMETHYL) QUINOLIN-4-YL]PHENYL}[(1-METHYL-1H-INDOL-5-YL)METHYL]AMINE

The title compound was prepared from {3-[3-benzyl-8-(trifluoromethyl)quinolin-4-yl]phenyl}amine and 5-formy-1-methylindole to the procedure of step 1, Example 66. MS (ES) m/z 522.3.

EXAMPLE 560

{3-[3-BENZYL-8-(TRIFLUOROMETHYL) QUINOLIN-4-YL]PHENYL}[(1-METHYL-1H-INDOL-7-YL)METHYL]AMINE

The title compound was prepared from {3-[3-benzyl-8-(trifluoromethyl)quinolin-4-yl]phenyl}amine and 7-formy-1-methylindole to the procedure of step 1, Example 66. MS (ES) m/z 522.3.

EXAMPLE 561

{3-[3-BENZYL-8-(TRIFLUOROMETHYL) QUINOLIN-4-YL]PHENYL}(1H-INDOL-7-YLMETHYL)AMINE

The title compound was prepared from {3-[3-benzyl-8-(trifluoromethyl)quinolin-4-yl]phenyl}amine and 7-formylindole to the procedure of step 1, Example 66. MS (ES) m/z 506.2.

EXAMPLE 562

{3-[3-BENZYL-8-(TRIFLUOROMETHYL) QUINOLIN-4-YL]PHENYL}(1H-INDOL-4-YLMETHYL)AMINE

The title compound was prepared from {3-[3-benzyl-8-(trifluoromethyl)quinolin-4-yl]phenyl}amine and 4-formylindole to the procedure of step 1, Example 66. MS (ES) m/z 506.2.

EXAMPLE 563

2-[4-({3-[3-BENZYL-8-(TRIFLUOROMETHYL) QUINOLIN-4-YL]PHENOXY}METHYL)PHENYL]-2-METHYLPROPANOIC ACID

Prepared using the procedure in Example 56 except using 3-[3-benzyl-8-(trifluoromethyl)quinolin-4-yl]phenol and 2-(4-Bromomethyl-phenyl)-2-methyl-propionic acid methyl ester as the halide. MS (ESI) m/z 556.

EXAMPLE 564

2-[4-({3-[3-BENZYL-8-(TRIFLUOROMETHYL) QUINOLIN-4-YL]PHENOXY}METHYL)PHENYL]PROPANOIC ACID

Prepared using the procedure in Example 56 except using 3-[3-benzyl-8-(trifluoromethyl)quinolin-4-yl]phenol and 2-(4-Bromomethyl-phenyl)-propionic acid ethyl ester as the halide. MS (ESI) m/z 542.

EXAMPLE 565

2-({3-[3-BENZYL-8-(TRIFLUOROMETHYL) QUINOLIN-4-YL]PHENOXY}METHYL) TEREPHTHALONITRILE

The title compound was prepared from 3-[3-benzyl-8-(trifluoromethyl)quinolin-4-yl]phenol and 2,5 dicyanobenzylbromide as in the procedure of Example 43. MS (ESI) m/z 520.

EXAMPLE 566

3-BENZYL-4-(3-{[5-CHLORO-2-(TRIFLUOROMETHYL)BENZYL]OXY}PHENYL)-8-(TRIFLUOROMETHYL)QUINOLINE

The title compound was prepared from 3-[3-benzyl-8-(trifluoromethyl)quinolin-4-yl]phenol and 5-chloro-2-trifluoromethylbenzyl bromide as in the procedure of Example 43. MS (ESI) m/z 572.

EXAMPLE 567

3-BENZYL-4-(3-{[5-FLUORO-2-(TRIFLUOROMETHYL)BENZYL]OXY}PHENYL)-8-(TRIFLUOROMETHYL)QUINOLINE

The title compound was prepared from 3-[3-benzyl-8-(trifluoromethyl)quinolin-4-yl]phenol and 5-fluoro-2-trifluoromethylbenzyl bromide as in the procedure of Example 43. MS (ESI) m/z 556.

EXAMPLE 568

[4-((1S)-1-{3-[3-BENZYL-8-(TRIFLUOROMETHYL)QUINOLIN-4-YL]PHENOXY}ETHYL) PHENYL]ACETIC ACID

The title compound was prepared using the procedure of example 69 using 3-[3-benzyl-8-(trifluoromethyl)quinolin-4-yl]phenol as the phenol and [4-(1-Hydroxy-ethyl)-phenyl]-acetic acid ethyl ester as the alcohol and isolated using chiral column chromatography. MS (ESI) m/z 540.

EXAMPLE 569

[4-((1R)-1-{3-[3-BENZYL-8-(TRIFLUOROM-ETHYL)QUINOLIN-4-YL]PHENOXY}ETHYL)PHENYL]ACETIC ACID

The title compound was prepared using the procedure of example 69 using 3-[3-benzyl-8-(trifluoromethyl)quinolin-4-yl]phenol as the phenol and [4-(1-Hydroxy-ethyl)-phenyl]-acetic acid ethyl ester as the alcohol and isolated using chiral column chromatography. MS (ESI) m/z 540.

EXAMPLE 570

5-({3-[3-BENZYL-8-(TRIFLUOROMETHYL)QUINOLIN-4-YL]BENZYL}OXY)-1H-INDOLE-2-CARBOXYLIC ACID

The title compound was prepared using the procedure of example 69 using 5-Hydroxy-1H-indole-2-carboxylic acid methyl ester as the phenol and [3-(3-Benzyl-8-trifluoromethyl-quinolin-4-yl)-phenyl]-methanol as the alcohol. MS (ESI) m/z 553.

EXAMPLE 571

N-{3-[3-(2-METHYLPHENYL)-8-(TRIFLUOROMETHYL)QUINOLIN-4-YL]PHENYL}-N'-PHENYLUREA

The title compound was prepared from {3-[3-(2-methylphenyl)-8 (trifluoromethyl)quinolin-4-yl]phenyl}amine and phenyl isocyanate in substantially the same manner as described in Example 65; off-white solid: mp 192-195° C.; MS (EI) m/z 498 (M+H)$^+$.

EXAMPLE 572

N-(2-CHLOROPHENYL)-N'-{3-[3-(2-METHYLPHENYL)-8-(TRIFLUOROMETHYL)QUINOLIN-4-YL]PHENYL}UREA

The title compound was prepared from {3-[3-(2-methylphenyl)-8-(trifluoromethyl)quinolin-4-yl]phenyl}amine and 2-chlorophenyl isocyanate in substantially the same manner as described in Example 65; off-white solid: mp 224-226° C.; MS (EI) m/z 532 (M+H)$^+$.

EXAMPLE 573

N-(2-FLUOROPHENYL)-N'-{3-[3-(2-METHYLPHENYL)-8-(TRIFLUOROMETHYL)QUINOLIN-4-YL]PHENYL}UREA

The title compound was prepared from {3-[3-(2-methylphenyl)-8 (trifluoromethyl)quinolin-4-yl]phenyl}amine and 2-fluorophenyl isocyanate in substantially the same manner as described in Example 65; off-white solid: mp 218-220° C.; MS (EI) m/z 516 (M+H)$^+$.

EXAMPLE 574

N-(2-CHLOROPHENYL)-N'-{3-[3-(2-TRIFLUOROMETHYLPHENYL)-8-(TRIFLUOROMETHYL)QUINOLIN-4-YL]PHENYL}UREA

The title compound was prepared from {3-[3-(2-trifluoromethylphenyl)-8-(trifluoromethyl)quinolin-4-yl]phenyl}amine and 2-chlorophenyl isocyanate in substantially the same manner as described in Example 65; off-white solid: mp 230-232° C.; MS (EI) m/z 587(M+H)$^+$.

EXAMPLE 575

[4-[3-(BENZYLTHIO)PHENYL]-8-(TRIFLUOROMETHYL)QUINOLIN-3-YL](PHENYL)METHANONE

This compound was prepared according to the procedure of Example 1 step 5, substituting [3-(benzylthio)phenyl]boronic acid for phenyl boronic acid. MS (ESI) m/z 500([M+H]$^+$).

EXAMPLE 576

3-[4-({3-[3-BENZYL-8-(TRIFLUOROMETHYL)QUINOLIN-4-YL]PHENYL}AMINO)PHENYL]PROPANOIC ACID

The title compound was prepared from {3-[3-benzyl-8-(trifluoromethyl)quinolin-4-yl]phenyl}amine and [4(2-ethoxycarbonylethyl)phenyl]boronic acid using the procedure of example 110 followed by hydrolysis with NaOH; MS (ESI) m/z 527([M+H]$^+$).

EXAMPLE 577

N-{3-[3-BENZOYL-8-(TRIFLUOROMETHYL)QUINOLIN-4-YL]PHENYL}-N'-(2-FLUOROPHENYL)THIOUREA

The title compound was prepared from [4-(3-amino-phenyl)-8-trifluoromethyl-quinolin-3-yl]-phenyl-methanone and 2-fluorophenyl isothiocyanate according to the procedure of Example 65. MS (ESI) m/z 546.

EXAMPLE 578

N-{3-[3-BENZOYL-8-(TRIFLUOROMETHYL)QUINOLIN-4-YL]PHENYL}-N'''-CYANO-N'-(2-FLUOROPHENYL)GUANIDINE

A mixture of N-{3-[3-benzoyl-8-(trifluoromethyl)quinolin-4-yl]phenyl}-N'-(2-fluorophenyl)thiourea (0.10 g, 0.18 mmol), PbNCN (0.50 g, 2.0 mmol) in 10 mL of acetonitrile/DME (1; 1) was heated to reflux for one hour. The solid was removed and the liquid was concentrated on vacuum. The crude material was purified by semi-preparative HPLC to give 11 mg of the title compound as an off-white solid. MS (ESI) m/z 554.

EXAMPLE 579

N-{3-[3-BENZOYL-8-(TRIFLUOROMETHYL)QUINOLIN-4-YL]PHENYL}-N'-(2-CHLOROPHENYL)-N'-CYANOGUANIDINE

The title compound was prepared from N-{3-[3-benzoyl-8-(trifluoromethyl)quinolin-4-yl]phenyl}-N'-(2-chlorophenyl)thiourea according to the procedure of Example 578. MS (ES) m/z 567.9.

EXAMPLE 580

N-{3-[3-BENZOYL-8-(TRIFLUOROMETHYL) QUINOLIN-4-YL]PHENYL}-N'-(2-FLUOROPHE-NYL)GUANIDINE

A mixture of N-{3-[3-benzoyl-8-(trifluoromethyl)quinolin-4-yl]phenyl}-N'-(2 fluorophenyl)thiourea (0.10 g, 0.18 mmol), lead acetate (0.50 g, 1.13 mmol) in 10 mL of ethanol/~30% ammonium hydroxide (1;1) was heated to reflux for one hour. The solid was removed and the liquid was concentrated on vacuum. The crude material was purified by semi-preparative HPLC to give 45 mg of the title compound as an off-white solid. MS (ESI) m/z 527.

EXAMPLE 581

N-{3-[3-BENZOYL-8-(TRIFLUOROMETHYL) QUINOLIN-4-YL]PHENYL}-N'-PHENYLTHIO-UREA

The title compound was prepared from [4-(3-amino-phenyl)-8-trifluoromethyl-quinolin 3-yl]-phenyl-methanone and phenyl isothiocyanate according to the procedure of Example 65. MS (ESI) m/z 526.

EXAMPLE 582

2-CHLOROPHENYL {3-[3-BENZOYL-8-(TRIFLUOROMETHYL)QUINOLIN-4-YL] PHENYL}CARBAMATE

The title compound was prepared from [4-(3-amino-phenyl)-8-trifluoromethyl-quinolin-3-yl]-phenyl-methanone and 2-chlorophenyl chloroformate according to the procedure of Example 65. MS (ES) m/z 546.9.

EXAMPLE 583

N-{3-[3-BENZOYL-8-(TRIFLUOROMETHYL) QUINOLIN-4-YL]PHENYL}-N'''-CYANO-N'-PHE-NYLGUANIDINE

The title compound was prepared from N-{3-[3-benzoyl-8-(trifluoromethyl)quinolin-4-yl]phenyl}-N'-phenylthiourea according to the procedure of Example 578. MS (ESI) m/z 534, 536.

EXAMPLE 584

{2-[4-({3-[3-BENZYL-8-(TRIFLUOROMETHYL) QUINOLIN-4-YL]BENZYL}OXY)PHENYL]-1,3-OXAZOL-4-YL}ACETIC ACID

The title compound was prepared from [4-(4-hydroxy-phenyl)-oxazol-2-yl]-acetic acid ethyl ester and [4-[3-(hydroxymethyl)phenyl]-8-(trifluoromethyl)quinolin-3 yl](phenyl)methanone according to the procedure of Example 69. MS (ESI) m/z 593, 595.

EXAMPLE 585

N-{3-[3-BENZOYL-8-(TRIFLUOROMETHYL) QUINOLIN-4-YL]BENZYL}-N'-(2-FLUOROPHE-NYL)UREA

Step 1: 4-[3-(2-Fluoro-phenyl)-ureidomethyl]-phenylboronic acid was prepared from 2-fluorophenyl isocyanate and 4-aminomethylphenylboronic acid HCL salt according to the procedure of Example 65.
Step 2: The title compound was prepared from 4-[3-(2-Fluoro-phenyl)-ureidomethyl]phenylboronic acid and [4-chloro-8-(trifluoromethyl)quinolin-3-yl](phenyl)methanone according to the procedure of Example 1. MS (ES) m/z 541.9.

EXAMPLE 586

4-(3-{[3-CYANO-8-(TRIFLUOROMETHYL) QUINOLIN-4-YL]AMINO}PHENYL)-8-(TRIF-LUOROMETHYL)QUINOLINE-3-CARBONI-TRILE

Step 1: 4-Chloro-8-(trifluoromethyl)quinoline-3-carbonitrile was prepared from 2-cyano-3-ethoxy-acrylic acid ethyl ester according to the procedure of Example 1.
Step 2: The title compound was prepared from 4-chloro-8-(trifluoromethyl)quinoline-3-carbonitrile and 3-aminophenylboronic acid according to the procedure of Example 1 as a side product. MS (ES) m/z 531.8.

EXAMPLE 587

4-(3-AMINOPHENYL)-8-(TRIFLUOROMETHYL) QUINOLINE-3-CARBONITRILE

The title compound was prepared from 4-chloro-8-(trifluoromethyl)quinoline-3-carbonitrile and 3-aminophenylboronic acid according to the procedure of Example 1.
MS (ES) m/z 314.0.

EXAMPLE 588

{4-[({3-[3-CYANO-8-(TRIFLUOROMETHYL) QUINOLIN-4-YL]PHENYL}AMINO)METHYL] PHENYL}ACETIC ACID

The title compound was prepared from 4-(3-aminophenyl)-8-(trifluoromethyl)quinoline-3-carbonitrile according to the procedure of Example 66.
MS (ES) m/z 459.9.

EXAMPLE 589

N-(2-CHLOROPHENYL)-N'-{3-[3-CYANO-8-(TRIFLUOROMETHYL)QUINOLIN-4-YL] PHENYL}UREA

The title compound was prepared from 4-(3-aminophenyl)-8(trifluoromethyl)quinoline-3-carbonitrile and 2-chlorophenyl isocyanate according to the procedure of Example 65. MS (ES) m/z 464.8.

EXAMPLE 590

4-(3-HYDROXYPHENYL)-8-(TRIFLUOROM-ETHYL)QUINOLINE-3-CARBONITRILE

The title compound was prepared from 4-chloro-8-(trifluoromethyl)quinoline-3-carbonitrile and 3-hydroxyphenylboronic acid according to the procedure of Example 1. HRMS: calcd for $C_{17}H_9F_3N_2O+H+$, 315.07397; found (ESI, [M+H]$^+$), 315.0752.

EXAMPLE 591

[4-({3-[3-CYANO-8-(TRIFLUOROMETHYL) QUINOLIN-4-YL]PHENOXY}METHYL)PHE-NYL]ACETIC ACID

The title compound was prepared from 4-(3-hydroxyphenyl)-8-(trifluoromethyl)quinoline-3-carbonitrile and 4-hydroxyphenyl acetic acid according to the procedure of Example 41. HRMS: calcd for $C_{26}H_{17}F_3N_2O_3+H+$, 463.12640; found (ESI, [M+H]$^+$), 463.1242.

EXAMPLE 592

{4-[({[4-({3-[3-CYANO-8-(TRIFLUOROMETHYL)QUINOLIN-4-YL]PHENOXY}METHYL)PHENYL]ACETYL}OXY)METHYL]PHENYL}ACETIC ACID

The title compound was prepared from 4-(3-hydroxyphenyl)-8-(trifluoromethyl)quinoline-3-carbonitrile and 4-hydroxyphenyl acetic acid according to the procedure of Example 41 as a di-alkylation product. HRMS: calcd for $C_{35}H_{25}F_3N_2O_5+H+$, 611.17883; found (ESI, [M+H]$^+$), 611.1773.

EXAMPLE 593

METHYL 2-{[({3-[3-BENZOYL-8-(TRIFLUOROMETHYL)QUINOLIN-4-YL]PHENYL}AMINO) CARBONYL]AMINO}BENZOATE

The title compound was prepared from [4-(3-amino-phenyl)-8-trifluoromethyl-quinolin-3-yl]-phenyl-methanone and methyl 2-isocyanatobenzoate according to the procedure of Example 65. MS (ES) m/z 567.9.

EXAMPLE 594

ETHYL 3-{[({3-[3-BENZOYL-8-(TRIFLUOROMETHYL)QUINOLIN-4-YL]PHENYL}AMINO)CARBONYL]AMINO}BENZOATE

The title compound was prepared from [4-(3-amino-phenyl)-8-trifluoromethyl-quinolin-3-yl]-phenyl-methanone and ethyl 3-isocyanatobenzoate according to the procedure of Example 65. MS (ES) m/z 581.9.

EXAMPLE 595

3-{3-[3-BENZOYL-8-(TRIFLUOROMETHYL)QUINOLIN-4-YL]PHENYL}QUINAZOLINE-2,4(1H,3H)-DIONE

The title compound was prepared from methyl 2-{[({3-[3-benzoyl-8-(trifluoromethyl)quinolin-4-yl]phenyl}amino)carbonyl]amino}benzoate and LiOH according to the procedure of Example 1. MS (ES) m/z 535.8.

EXAMPLE 596

3-{[({3-[3-BENZOYL-8-(TRIFLUOROMETHYL)QUINOLIN-4-YL]PHENYL}AMINO)CARBONYL]AMINO}BENZOIC ACID

The title compound was prepared from methyl 3-{[({3-[3-benzoyl-8-(trifluoromethyl)quinolin-4-yl]phenyl}amino)carbonyl]amino}benzoate and LiOH according to the procedure of Example 1. MS (ES) m/z 553.9.

EXAMPLE 597

4-(3-AMINOPHENYL)-8-(TRIFLUOROMETHYL)QUINOLINE-3-CARBOXAMIDE

A mixture of 4-(3-aminophenyl)-8-(trifluoromethyl)quinoline-3-carbonitrile (0.30 g, 0.96 mmol), 30% hydrogen peroxide (5 mL), NaOH (0.5 g, 12 mmol) and ethanol (15 mL) was heated to ~40° C. for 3 hours. The pH of the solution was adjusted to ~6 by diluted HCl. The reaction mixture was partitioned between ethyl acetate and water and the aqueous layer was extracted with ethyl acetate. The combined organic phases were washed with water, brine, and dried with magnesium sulfate. The organic phases were concentrated and the residue was loaded onto silica gel and chromatographed with hexanes:ethyl acetate (50% to 100%) to afford 0.13 g of the title compound as an off-white solid. MS (ESI) m/z 332;

EXAMPLE 598

{4-[({3-[3-(AMINOCARBONYL)-8-(TRIFLUOROMETHYL)QUINOLIN-4-YL]PHENYL}AMINO)METHYL]PHENYL}ACETIC ACID

The title compound was prepared from 4-(3-aminophenyl)-8-(trifluoromethyl)quinoline-3-carboxamide according to the procedure of Example 66. MS (ESI) m/z 478, 480.

EXAMPLE 599

[4-({3-[3-(AMINOCARBONYL)-8-(TRIFLUOROMETHYL)QUINOLIN-4-YL]PHENOXY}METHYL)PHENYL]ACETIC ACID

The title compound was prepared from 4-(3-hydroxyphenyl)-8-(trifluoromethyl)quinoline-3-carboxamide according to the procedure of Example 41.

MS (ESI) m/z 481.

EXAMPLE 600

{4-[({[4-({3-[3-(AMINOCARBONYL)-8-(TRIFLUOROMETHYL)QUINOLIN-4-YL]PHENOXY}METHYL)PHENYL]ACETYL}OXY)METHYL]PHENYL}ACETIC ACID

The title compound was prepared from 4-(3-hydroxyphenyl)-8-(trifluoromethyl)quinoline-3-carboxamide according to the procedure of Example 41 as a dialkylated product. MS (ESI) m/z 627, 629.

EXAMPLE 601

ETHYL 4-(3-HYDROXYPHENYL)-8-(TRIFLUOROMETHYL)QUINOLINE-3-CARBOXYLATE

The title compound was prepared from 4-chloro-8-trifluoromethyl-quinoline-3-carboxylic acid ethyl ester and 3-hydroxyphenylboronic acid according to the procedure of Example 1. MS (ES) m/z 359.9.

EXAMPLE 602

ETHYL 4-(3-AMINOPHENYL)-8-(TRIFLUOROMETHYL)QUINOLINE-3-CARBOXYLATE

The title compound was prepared from 4-chloro-8-trifluoromethyl-quinoline-3-carboxylic acid ethyl ester and 3-aminophenylboronic acid according to the procedure of Example 1. MS (ES) m/z 361.0;

EXAMPLE 603

ETHYL 4-[3-({[(2-CHLOROPHENYL)AMINO]
CARBONYL}AMINO)PHENYL]-8-(TRIFLUO-
ROMETHYL)QUINOLINE-3-CARBOXYLATE

The title compound was prepared from ethyl 4-(3-aminophenyl)-8-(trifluoromethyl)quinoline-3-carboxylate and 2-chlorophenyl isocyanate according to the procedure of Example 65. MS (ES) m/z 511.9.

EXAMPLE 604

4-{3-[(2-FLUOROBENZYL)OXY]PHENYL}-8-
(TRIFLUOROMETHYL)QUINOLINE-3-CAR-
BOXYLIC ACID

The title compound was prepared from ethyl 4-(3-hydroxyphenyl)-8-(trifluoromethyl)quinoline-3-carboxylate and 2-fluorobenzyl bromide according to the procedure of Example 41. MS (ES) m/z 439.9.

EXAMPLE 605

4-[3-({[(2-CHLOROPHENYL)AMINO]
CARBONYL}AMINO)PHENYL]-8-(TRIFLUO-
ROMETHYL) QUINOLINE-3-CARBOXYLIC
ACID

The title compound was prepared from ethyl 4-(3-aminophenyl)-8-(trifluoromethyl)quinoline-3-carboxylate and 2-chlorophenyl isocyanate according to the procedure of Example 65. MS (ES) m/z 483.9.

EXAMPLE 606

METHYL 2-[4-({3-[3-BENZOYL-8-(TRIFLUO-
ROMETHYL)QUINOLIN-4-YL]
PHENOXY}METHYL)PHENYL]-3-[4-(2-METH-
OXY-2-OXOETHYL)PHENYL]PROPANOATE

The title compound was prepared from [4-(3-hydroxyphenyl)-8-(trifluoromethyl)quinolin-3-yl](phenyl)methanone and (4-bromomethyl-phenyl)-acetic acid methyl ester according to the procedure of Example 41. MS (ESI) m/z 718; HRMS: calcd for $C_{43}H_{34}F_3NO_6$+H+, 718.24110; found (ESI, [M+H]$^+$), 718.2444.

EXAMPLE 607

2-[4-({3-[3-BENZOYL-8-(TRIFLUOROMETHYL)
QUINOLIN-4-YL]PHENOXY}METHYL)PHE-
NYL]-3-[4-(CARBOXYMETHYL)PHENYL]PRO-
PANOIC ACID

The title compound was prepared from methyl 2-[4-({3-[3-benzoyl-8-(trifluoromethyl)quinolin-4-yl]phenoxy}methyl)phenyl]-3-[4-(2-methoxy-2-oxoethyl)phenyl]propanoate by LiOH hydrolysis. MS (ES) m/z 688.0.

EXAMPLE 608

2-[4-({3-[3-BENZOYL-8-(TRIFLUOROMETHYL)
QUINOLIN-4-YL]PHENOXY}METHYL)PHE-
NYL]-2-PROP-2-YN-1-YLPENT-4-YNOIC ACID

The title compound was prepared from[4-({3-[3-benzoyl-8-(trifluoromethyl)quinolin-4-yl]phenoxy}methyl)phenyl] acetic acid methyl ester and propargyl bromide according to the procedure of Example 41. MS (ESI) m/z 618.

EXAMPLE 609

2-[4-({3-[3-BENZOYL-8-(TRIFLUOROMETHYL)
QUINOLIN-4-YL]PHENOXY}METHYL)PHE-
NYL]-3-(4-TERT-BUTYLPHENYL)PROPANOIC
ACID

The title compound was prepared from[4-({3-[3-benzoyl-8-(trifluoromethyl)quinolin-4-yl]phenoxy}methyl)phenyl] acetic acid methyl ester and 4-tert-butylbenzyl bromide according to the procedure of Example 41. MS (ES) m/z 688.1.

EXAMPLE 610

2-[4-({3-[3-BENZOYL-8-(TRIFLUOROMETHYL)
QUINOLIN-4-YL]PHENOXY}METHYL)PHE-
NYL]-3-(4-NITROPHENYL)PROPANOIC ACID

The title compound was prepared from[4-({3-[3-benzoyl-8-(trifluoromethyl)quinolin-4-yl]phenoxy}methyl)phenyl] acetic acid methyl ester and 4-nitrobenzyl bromide according to the procedure of Example 41. MS m/z 677;

EXAMPLE 611

2-[4-({3-[3-BENZOYL-8-(TRIFLUOROMETHYL)
QUINOLIN-4-YL]PHENOXY}METHYL)PHE-
NYL]-3-BIPHENYL-4-YLPROPANOIC ACID

The title compound was prepared from[4-({3-[3-benzoyl-8-(trifluoromethyl)quinolin-4-yl]phenoxy}methyl)phenyl] acetic acid methyl ester and 4-bromomethylbiphenyl according to the procedure of Example 41. MS m/z 708.

EXAMPLE 612

2-[4-({3-[3-BENZOYL-8-(TRIFLUOROMETHYL)
QUINOLIN-4-YL]PHENOXY}METHYL)PHE-
NYL]-3-PHENYLPROPANOIC ACID

The title compound was prepared from[4-({3-[3-benzoyl-8-(trifluoromethyl)quinolin-4-yl]phenoxy}methyl)phenyl] acetic acid methyl ester and benzyl bromide according to the procedure of Example 41. MS (ES) m/z 632.

EXAMPLE 613

2-[4-({3-[3-BENZOYL-8-(TRIFLUOROMETHYL)
QUINOLIN-4-YL]PHENOXY}METHYL)PHE-
NYL]-3,3-DIPHENYLPROPANOIC ACID

The title compound was prepared from[4-({3-[3-benzoyl-8-(trifluoromethyl)quinolin-4-yl]phenoxy}methyl)phenyl] acetic acid methyl ester and bromodiphenylmethane according to the procedure of Example 41. MS (ESI) m/z 708.

EXAMPLE 614

{4-[({3-[3-BENZYL-8-(TRIFLUOROMETHYL)
QUINOLIN-4-YL]PHENYL}THIO)METHYL]
PHENYL}ACETIC ACID

Step 1: 3-(4-Carboxymethyl-benzylsulfanyl)phenylboronic acid was prepared from 4-(bromomethyl)phenyl acetic acid and 3-mecaptophenylboronic acid according to the procedure of Example 41.

Step 2: The title compound was prepared from 3-(4-carboxymethyl-benzylsulfanyl)phenylboronic acid and [4-chloro-8-(trifluoromethyl)quinolin-3-yl](phenyl)methanone according to the procedure of Example 1. MS (ES) m/z 541.9.

EXAMPLE 615

{4-[({3-[3-BENZYL-8-(TRIFLUOROMETHYL)QUINOLIN-4-YL]PHENYL}SULFONYL)METHYL]PHENYL}ACETIC ACID

30% Hydrogen peroxide was added slowly to a stirred solution of {4-[({3-[3-benzyl-8-(trifluoromethyl)quinolin-4-yl]phenyl}thio)methyl]phenyl}acetic acid (70 mg) in 10 mL of acetic acid at 60° C. After being stirred at 60° C. for one hour the solution was poured into ice-water and the solid was collected to give the title compound as a white solid. HRMS: calcd for $C_{32}H_{24}F_3NO_4S$+H+, 576.14509; found (ESI, [M+H]$^+$), 576.1445.

EXAMPLE 616

{3-[3-BENZYL-8-(TRIFLUOROMETHYL)QUINOLIN-4-YL]PHENYL}(2,3-DIMETHOXYBENZYL)AMINE

The title compound was prepared from {3-[3-benzyl-8-(trifluoromethyl)quinolin-4-yl]phenyl}amine and 2,3-dimethoxy-benzaldehyde according to the procedure of Example 66. MS (ESI) m/z 529;

EXAMPLE 617

{3-[3-BENZYL-8-(TRIFLUOROMETHYL)QUINOLIN-4-YL]PHENYL}(2,5-DICHLOROBENZYL)AMINE

The title compound was prepared from {3-[3-benzyl-8-(trifluoromethyl)quinolin-4-yl]phenyl}amine and 2,4-dichloro-benzaldehyde according to the procedure of Example 66. MS (ESI) m/z 537.

EXAMPLE 618

{3-[3-BENZYL-8-(TRIFLUOROMETHYL)QUINOLIN-4-YL]PHENYL}(3-PHENOXYBENZYL)AMINE

The title compound was prepared from {3-[3-benzyl-8-(trifluoromethyl)quinolin-4-yl]phenyl}amine and 3-phenoxy-benzaldehyde according to the procedure of Example 66. MS (ES) m/z 561.1.

EXAMPLE 619

{3-[3-BENZYL-8-(TRIFLUOROMETHYL)QUINOLIN-4-YL]PHENYL}(2,5-DIMETHOXYBENZYL)AMINE

The title compound was prepared from {3-[3-benzyl-8-(trifluoromethyl)quinolin-4-yl]phenyl}amine and 2,5-dimethoxy-benzaldehyde according to the procedure of Example 66. MS (ES) m/z 529.1.

EXAMPLE 620

2-[({3-[3-BENZYL-8-(TRIFLUOROMETHYL)QUINOLIN-4-YL]PHENYL}AMINO)METHYL]-4-CHLOROPHENOL

The title compound was prepared from {3-[3-benzyl-8-(trifluoromethyl)quinolin-4-yl]phenyl}amine and 2-chloro-5-hydroxy-benzaldehyde according to the procedure of Example 66. MS (ES) m/z 517.0;

EXAMPLE 621

{3-[3-BENZYL-8-(TRIFLUOROMETHYL)QUINOLIN-4-YL]PHENYL}(3,4-DIMETHOXYBENZYL)AMINE

The title compound was prepared from {3-[3-benzyl-8-(trifluoromethyl)quinolin-4-yl]phenyl}amine and 3,4-dimethoxy-benzaldehyde according to the procedure of Example 66. MS (ES) m/z 529.1.

EXAMPLE 622

3-[({3-[3-BENZYL-8-(TRIFLUOROMETHYL)QUINOLIN-4-YL]PHENYL}AMINO)METHYL]-4-NITROPHENOL

The title compound was prepared from {3-[3-benzyl-8-(trifluoromethyl)quinolin-4-yl]phenyl}amine and 5-hydroxy-2-nitro-benzaldehyde according to the procedure of Example 66. MS (ES) m/z 528.0.

EXAMPLE 623

{3-[3-BENZYL-8-(TRIFLUOROMETHYL)QUINOLIN-4-YL]PHENYL}(4,5-DIMETHOXY-2-NITROBENZYL)AMINE

The title compound was prepared from {3-[3-benzyl-8-(trifluoromethyl)quinolin-4-yl]phenyl}amine and 4,5-dimethoxy-2-nitro-benzaldehyde according to the procedure of Example 66. MS (ES) m/z 574.1.

EXAMPLE 624

2-[({3-[3-BENZYL-8-(TRIFLUOROMETHYL)QUINOLIN-4-YL]PHENYL}AMINO)METHYL]-4-BROMOPHENOL

The title compound was prepared from {3-[3-benzyl-8-(trifluoromethyl)quinolin-4-yl]phenyl}amine and 5-bromo-2-hydroxy-benzaldehyde according to the procedure of Example 66. MS (ES) m/z 560.9.

EXAMPLE 625

2-[({3-[3-BENZYL-8-(TRIFLUOROMETHYL)QUINOLIN-4-YL]PHENYL}AMINO)METHYL]-5-METHOXYPHENOL

The title compound was prepared from {3-[3-benzyl-8-(trifluoromethyl)quinolin-4-yl]phenyl}amine and 2-hydroxy-4-methoxy-benzaldehyde according to the procedure of Example 66. MS (ESI) m/z 513.

EXAMPLE 626

{3-[3-BENZYL-8-(TRIFLUOROMETHYL)
QUINOLIN-4-YL]PHENYL}{[4-(DIMETHY-
LAMINO)-1-NAPHTHYL]METHYL}AMINE

The title compound was prepared from {3-[3-benzyl-8-(trifluoromethyl)quinolin-4-yl]phenyl}amine and 4-dimethylamino-naphthalene-1-carbaldehyde according to the procedure of Example 66. MS (ESI) m/z 562.

EXAMPLE 627

2-[({3-[3-BENZYL-8-(TRIFLUOROMETHYL)
QUINOLIN-4-YL]PHENYL}AMINO)METHYL]-
4-METHOXYPHENOL

The title compound was prepared from {3-[3-benzyl-8-(trifluoromethyl)quinolin-4-yl]phenyl}amine and 2-hydroxy-5-methoxy-benzaldehyde according to the procedure of Example 66. MS (ES) m/z 513.0.

EXAMPLE 628

4-[({3-[3-BENZYL-8-(TRIFLUOROMETHYL)
QUINOLIN-4-YL]PHENYL}AMINO)METHYL]
BENZENE-1,2-DIOL

The title compound was prepared from {3-[3-benzyl-8-(trifluoromethyl)quinolin-4-yl]phenyl}amine and 3,4-dihydroxy-benzaldehyde according to the procedure of Example 66. MS (ES) m/z 499.0.

EXAMPLE 629

2-[4-({3-[3-BENZOYL-8-(TRIFLUOROMETHYL)
QUINOLIN-4-YL]PHENOXY}METHYL)PHE-
NYL]PENT-4-ENOIC ACID

The title compound was prepared from[4-({3-[3-benzoyl-8-(trifluoromethyl)quinolin-4-yl]phenoxy}methyl)phenyl] acetic acid methyl ester and propargyl bromide according to the procedure of Example 41. MS (ESI) m/z 582.

EXAMPLE 630

2-[4-({3-[3-BENZOYL-8-(TRIFLUOROMETHYL)
QUINOLIN-4-YL]PHENOXY}METHYL)PHE-
NYL]HEX-4-YNOIC ACID

The title compound was prepared from[4-({3-[3-benzoyl-8-(trifluoromethyl)quinolin-4-yl]phenoxy}methyl)phenyl] acetic acid methyl ester and 1-bromo-but-2-yne according to the procedure of Example 41. MS (ESI) m/z 594; HRMS: calcd for $C_{36}H_{26}F_3NO_4$+H+, 594.18867; found (ESI, [M+H]$^+$), 594.1869;

EXAMPLE 631

2-[4-({3-[3-BENZOYL-8-(TRIFLUOROMETHYL)
QUINOLIN-4-YL]PHENOXY}METHYL)PHE-
NYL]HEPT-4-YNOIC ACID

The title compound was prepared from[4-({3-[3-benzoyl-8-(trifluoromethyl)quinolin-4-yl]phenoxy}methyl)phenyl] acetic acid methyl ester and 1-bromo-pent-2-yne according to the procedure of Example 41. MS (ESI) m/z 608. HRMS: calcd for $C_{37}H_{28}F_3NO_4$+H+, 608.20432; found (ESI, [M+H]$^+$), 608.2075;

EXAMPLE 632

2-[4-({3-[3-BENZOYL-8-(TRIFLUOROMETHYL)
QUINOLIN-4-YL]PHENOXY}METHYL)PHE-
NYL]-2-PENT-2-YN-1-YLHEPT-4-YNOIC ACID

The title compound was prepared from[4-({3-[3-benzoyl-8-(trifluoromethyl)quinolin-4-yl]phenoxy}methyl)phenyl] acetic acid methyl ester and 1-bromo-pent-2-yne according to the procedure of Example 41. HRMS: calcd for $C_{42}H_{34}F_3NO_4$+H+, 674.25127; found (ESI, [M+H]$^+$), 674.2532.

EXAMPLE 633

{3-[3-BENZYL-8-(TRIFLUOROMETHYL)
QUINOLIN-4-YL]PHENYL}(2-FLUORO-3-
METHOXYBENZYL)AMINE

The title compound was prepared from {3-[3-benzyl-8-(trifluoromethyl)quinolin-4-yl]phenyl}amine and 2-fluoro-3-methoxy-benzaldehyde according to the procedure of Example 66. MS (ESI) m/z 517.

EXAMPLE 634

{3-[3-BENZYL-8-(TRIFLUOROMETHYL)
QUINOLIN-4-YL]PHENYL}[3-(TRIFLUOROM-
ETHYL)BENZYL]AMINE

The title compound was prepared from {3-[3-benzyl-8-(trifluoromethyl)quinolin-4-yl]phenyl}amine and 3-trifluoromethyl-benzaldehyde according to the procedure of Example 66. MS (ESI) m/z 537.

EXAMPLE 635

{3-[3-BENZYL-8-(TRIFLUOROMETHYL)
QUINOLIN-4-YL]PHENYL}(5-FLUORO-2-
METHOXYBENZYL)AMINE

The title compound was prepared from {3-[3-benzyl-8-(trifluoromethyl)quinolin-4-yl]phenyl}amine and 5-fluoro-2-methoxy-benzaldehyde according to the procedure of Example 66. MS (ESI) m/z 517.

EXAMPLE 636

2-[({3-[3-BENZYL-8-(TRIFLUOROMETHYL)
QUINOLIN-4-YL]PHENYL}AMINO)METHYL]-
4-IODOPHENOL

The title compound was prepared from {3-[3-benzyl-8-(trifluoromethyl)quinolin-4-yl]phenyl}amine and 5-iodo-2-hydroxy-benzaldehyde according to the procedure of Example 66. MS (ESI) m/z 611.

EXAMPLE 637

{3-[3-BENZYL-8-(TRIFLUOROMETHYL)
QUINOLIN-4-YL]PHENYL}(3,4-DIETHOXY-
BENZYL)AMINE

The title compound was prepared from {3-[3-benzyl-8-(trifluoromethyl)quinolin-4-yl]phenyl}amine and 3,4-diethoxy-benzaldehyde according to the procedure of Example 66. MS (ESI) m/z 557.

EXAMPLE 638

N-[2-(BENZYLOXY)-3-METHOXYBENZYL]-3-[3-BENZYL-8-(TRIFLUOROMETHYL)QUINOLIN-4-YL]ANILINE

The title compound was prepared from {3-[3-benzyl-8-(trifluoromethyl)quinolin-4-yl]phenyl}amine and 2-benzyloxy-3-methoxy-benzaldehyde according to the procedure of Example 66. MS (ESI) m/z 605.

EXAMPLE 639

N,N-DIBENZYL-3-[3-BENZYL-8-(TRIFLUOROMETHYL)QUINOLIN-4-YL]ANILINE

The title compound was prepared from {3-[3-benzyl-8-(trifluoromethyl)quinolin-4-yl]phenyl}amine and benzaldehyde according to the procedure of Example 66. MS (ESI) m/z 559.

EXAMPLE 640

{3-[3-BENZYL-8-(TRIFLUOROMETHYL)QUINOLIN-4-YL]PHENYL}BIS(3-METHYLBENZYL)AMINE

The title compound was prepared from {3-[3-benzyl-8-(trifluoromethyl)quinolin-4-yl]phenyl}amine and 3-methyl-benzaldehyde according to the procedure of Example 66. MS (ESI) m/z 587.

EXAMPLE 641

{3-[3-BENZYL-8-(TRIFLUOROMETHYL)QUINOLIN-4-YL]PHENYL}BIS(2-ETHOXY-3-METHOXYBENZYL)AMINE

The title compound was prepared from {3-[3-benzyl-8-(trifluoromethyl)quinolin-4-yl]phenyl}amine and 2-ethoxy-3-methoxy-benzaldehyde according to the procedure of Example 66. MS (ESI) m/z 707.

EXAMPLE 642

N-BENZYL-3-[3-BENZYL-8-(TRIFLUOROMETHYL)QUINOLIN-4-YL]ANILINE

The title compound was prepared from {3-[3-benzyl-8-(trifluoromethyl)quinolin-4-yl]phenyl}amine and benzaldehyde according to the procedure of Example 66. MS (ESI) m/z 469.

EXAMPLE 643

{3-[3-BENZYL-8-(TRIFLUOROMETHYL)QUINOLIN-4-YL]PHENYL}(3-METHOXYBENZYL)AMINE

The title compound was prepared from {3-[3-benzyl-8-(trifluoromethyl)quinolin-4-yl]phenyl}amine and 3-methoxy-benzaldehyde according to the procedure of Example 66. MS (ESI) m/z 498.

EXAMPLE 644

{3-[3-BENZYL-8-(TRIFLUOROMETHYL)QUINOLIN-4-YL]PHENYL}(4-METHOXYBENZYL)AMINE

The title compound was prepared from {3-[3-benzyl-8-(trifluoromethyl)quinolin-4-yl]phenyl}amine and 4-methoxy-benzaldehyde according to the procedure of Example 66. MS (ESI) m/z 499.

EXAMPLE 645

{3-[3-BENZYL-8-(TRIFLUOROMETHYL)QUINOLIN-4-YL]PHENYL}(2-ETHOXY-3-METHOXYBENZYL)AMINE

The title compound was prepared from {3-[3-benzyl-8-(trifluoromethyl)quinolin-4-yl]phenyl}amine and 2-ethoxy-3-methoxy-benzaldehyde according to the procedure of Example 66. MS (ESI) m/z 543.

EXAMPLE 646

{3-[3-BENZYL-8-(TRIFLUOROMETHYL)QUINOLIN-4-YL]PHENYL}(3-CHLORO-4-FLUOROBENZYL)AMINE

The title compound was prepared from {3-[3-benzyl-8-(trifluoromethyl)quinolin-4-yl]phenyl}amine and 3-chloro-2-fluoro-benzaldehyde according to the procedure of Example 66. MS (ESI) m/z 521.

EXAMPLE 647

{3-[3-BENZYL-8-(TRIFLUOROMETHYL)QUINOLIN-4-YL]PHENYL}(3-CHLORO-4-METHOXYBENZYL)AMINE

The title compound was prepared from {3-[3-benzyl-8-(trifluoromethyl)quinolin-4-yl]phenyl}amine and 3-chloro-4-methoxy-benzaldehyde according to the procedure of Example 66. MS (ESI) m/z 533.

EXAMPLE 648

{3-[3-BENZYL-8-(TRIFLUOROMETHYL)QUINOLIN-4-YL]PHENYL}(3-CHLORO-2-FLUOROBENZYL)AMINE

The title compound was prepared from {3-[3-benzyl-8-(trifluoromethyl)quinolin-4-yl]phenyl}amine and 3-chloro-2-fluoro-benzaldehyde according to the procedure of Example 66. MS (ESI) m/z 521.

EXAMPLE 649

2-[({3-[3-BENZYL-8-(TRIFLUOROMETHYL)QUINOLIN-4-YL]PHENYL}AMINO)METHYL]-4-(TRIFLUOROMETHOXY)PHENOL

The title compound was prepared from {3-[3-benzyl-8-(trifluoromethyl)quinolin-4-yl]phenyl}amine and 2-hydroxy-3-trifluoromethyl-benzaldehyde according to the procedure of Example 66. MS (ESI) m/z 569;

EXAMPLE 650

{3-[3-BENZYL-8-(TRIFLUOROMETHYL)
QUINOLIN-4-YL]PHENYL}[5-CHLORO-2-(TRI-
FLUOROMETHYL)BENZYL]AMINE

The title compound was prepared from {3-[3-benzyl-8-(trifluoromethyl)quinolin-4-yl]phenyl}amine and 5-chloro-2-trifluoromethyl-benzaldehyde according to the procedure of Example 66. MS (ESI) m/z 571.

EXAMPLE 651

{3-[3-BENZYL-8-(TRIFLUOROMETHYL)
QUINOLIN-4-YL]PHENYL}[5-FLUORO-2-(TRIF-
LUOROMETHYL)BENZYL]AMINE

The title compound was prepared from {3-[3-benzyl-8-(trifluoromethyl)quinolin-4-yl]phenyl}amine and 5-fluoro-2-trifluoromethyl-benzaldehyde according to the procedure of Example 66. MS (ESI) m/z 555.

EXAMPLE 652

3-BENZYL-4-{3-[(2,5-DIMETHYLPHENOXY)
METHYL]PHENYL}-8-(TRIFLUOROMETHYL)
QUINOLINE

The title compound was prepared from {3-[3-benzyl-8-(trifluoromethyl)quinolin-4-yl]phenyl}methanol and 2,5-dimethylphenol according to the procedure of Example 69. MS (ESI) m/z 498.

EXAMPLE 653

3-BENZYL-4-(3-{[2-FLUORO-3-(TRIFLUOROM-
ETHYL)PHENOXY]METHYL}PHENYL)-8-(TRI-
FLUOROMETHYL)QUINOLINE

The title compound was prepared from {3-[3-benzyl-8-(trifluoromethyl)quinolin-4-yl]phenyl}methanol and 2-fluoro-3-trifluoromethylphenol according to the procedure of Example 69. MS (ESI) m/z 556.

EXAMPLE 654

3-BENZYL-4-{3-[(2,3-DIMETHYLPHENOXY)
METHYL]PHENYL}-8-(TRIFLUOROMETHYL)
QUINOLINE

The title compound was prepared from {3-[3-benzyl-8-(trifluoromethyl)quinolin-4-yl]phenyl}methanol and 2,3-dimethylphenol according to the procedure of Example 69. MS (ESI) m/z 498.

EXAMPLE 655

3-BENZYL-4-(3-{[2-CHLORO-3-(TRIFLUOROM-
ETHYL)PHENOXY]METHYL}PHENYL)-8-(TRI-
FLUOROMETHYL)QUINOLINE

The title compound was prepared from {3-[3-benzyl-8-(trifluoromethyl)quinolin-4-yl]phenyl}methanol and 2-chloro-3-trifluoromethylphenol according to the procedure of Example 69. MS (ESI) m/z 572.

EXAMPLE 656

3-BENZYL-4-{3-[(1-METHYL-1H-PYRROL-2-
YL)METHOXY]PHENYL}-8-(TRIFLUOROM-
ETHYL)QUINOLINE

The title compound was prepared from 3-[3-benzyl-8-(trifluoromethyl)quinolin-4-yl]phenol and (1-methyl-1H-pyrrol-2-yl)-methanol according to the procedure of Example 69. MS (ESI) m/z 473.

EXAMPLE 657

METHYL [5-({4-[3-BENZYL-8-(TRIFLUOROM-
ETHYL)QUINOLIN-4-YL]
PHENOXY}METHYL)-1-METHYL-1H-PYRROL-
2-YL]ACETATE

The title compound was prepared from 3-[3-benzyl-8-(trifluoromethyl)quinolin-4-yl]phenol and (5-hydroxymethyl-1-methyl-1H-pyrrol-2-yl)-acetic acid methyl ester according to the procedure of Example 69. MS (ESI) m/z 545.

EXAMPLE 658

{3-[3-BENZYL-8-(TRIFLUOROMETHYL)
QUINOLIN-4-YL]PHENYL}(2-THIENYLM-
ETHYL)AMINE

The title compound was prepared from {3-[3-benzyl-8-(trifluoromethyl)quinolin-4-yl]phenyl}amine and thiophene-2-carbaldehyde according to the procedure of Example 66. MS (ES) m/z 475.2.

EXAMPLE 659

{2-[({3-[3-BENZYL-8-(TRIFLUOROMETHYL)
QUINOLIN-4-YL]PHENYL}AMINO)METHYL]-
3-THIENYL}ACETIC ACID

The title compound was prepared from {3-[3-benzyl-8-(trifluoromethyl)quinolin-4-yl]phenyl}amine and (2-formyl-thiophen-3-yl)-acetic acid methyl ester according to the procedure of Example 66. MS (ES) m/z 531.1.

EXAMPLE 660

{5-[({3-[3-BENZYL-8-(TRIFLUOROMETHYL)
QUINOLIN-4-YL]PHENYL}AMINO)METHYL]-
2-THIENYL}ACETIC ACID

The title compound was prepared from {3-[3-benzyl-8-(trifluoromethyl)quinolin-4-yl]phenyl}amine and (5-formyl-thiophen-3-yl)-acetic acid methyl ester according to the procedure of Example 66. MS (ES) m/z 533.1.

EXAMPLE 661

(5Z)-5-{4-[({3-[3-BENZYL-8-(TRIFLUOROM-
ETHYL)QUINOLIN-4-YL]PHENYL}AMINO)
METHYL]BENZYLIDENE}-1,3-THIAZOLIDINE-
2,4-DIONE

The title compound was prepared from {3-[3-benzyl-8-(trifluoromethyl)quinolin-4-yl]phenyl}amine and 4-(2,4-dioxo-thiazolidin-5-ylidenemethyl)-benzaldehyde according to the procedure of Example 66. MS (ES) m/z 594.1.

EXAMPLE 662

(5Z)-5-{4-[({3-[3-BENZYL-8-(TRIFLUOROM-ETHYL)QUINOLIN-4-YL]PHENYL}AMINO)METHYL]BENZYLIDENE}-2-THIOXO-1,3-THIAZOLIDIN-4-ONE

The title compound was prepared from {3-[3-benzyl-8-(trifluoromethyl)quinolin-4-yl]phenyl}amine and 4-(4-oxo-2-thioxo-thiazolidin-5-ylidenemethyl)-benzaldehyde according to the procedure of Example 66. MS (ES) m/z 610.0.

EXAMPLE 663

5-{4-[({3-[3-BENZYL-8-(TRIFLUOROMETHYL)QUINOLIN-4-YL]PHENYL}AMINO)METHYL]BENZYL}-1,3-THIAZOLIDINE-2,4-DIONE

Treatment of (5Z)-5-{4-[({3-[3-benzyl-8-(trifluoromethyl)quinolin-4-yl]phenyl}amino)methyl]benzylidene}-1,3-thiazolidine-2,4-dione with LiBH$_4$ in pyridine gave the title compound. MS (ES) m/z 596.1 (M−1).

EXAMPLE 664

5-{4-[({3-[3-BENZYL-8-(TRIFLUOROMETHYL)QUINOLIN-4-YL]PHENYL}AMINO)METHYL]BENZYL}-2-THIOXO-1,3-THIAZOLIDIN-4-ONE

Treatment of (5Z)-5-{4-[({3-[3-benzyl-8-(trifluoromethyl)quinolin-4-yl]phenyl}amino) methyl]benzylidene}-2-thioxo-1,3-thiazolidin-4-one with LiBH$_4$ in pyridine gave the title compound. HRMS: calcd for $C_{34}H_{26}F_3N_3OS_2$+H+, 614.15421; found (ESI, [M+H]$^+$), 614.1539.

EXAMPLE 665

{3-[3-BENZYL-8-(TRIFLUOROMETHYL)QUINOLIN-4-YL]PHENYL}[(4-FLUOROBIPHE-NYL-3-YL)METHYL]AMINE

The title compound was prepared from {3-[3-benzyl-8-(trifluoromethyl)quinolin-4-yl]phenyl}amine and 4-fluoro-biphenyl-3-carbaldehyde according to the procedure of Example 66. MS (ES) m/z 563.0.

EXAMPLE 666

{3-[3-BENZYL-8-(TRIFLUOROMETHYL)QUINOLIN-4-YL]PHENYL}(2,2'-BITHIEN-5-YLMETHYL)AMINE

The title compound was prepared from {3-[3-benzyl-8-(trifluoromethyl)quinolin-4-yl]phenyl}amine and [2,2']bithiophenyl-5-carbaldehyde according to the procedure of Example 66. MS (ES) m/z 557.0.

EXAMPLE 667

{3-[3-BENZYL-8-(TRIFLUOROMETHYL)QUINOLIN-4-YL]PHENYL}[(3-FLUORO-4'-METHOXYBIPHENYL-4-YL)METHYL]AMINE

The title compound was prepared from {3-[3-benzyl-8-(trifluoromethyl)quinolin-4-yl]phenyl}amine and 3-fluoro-4'-methoxy-biphenyl-4-carbaldehyde according to the procedure of Example 66. MS (ESI) m/z 593.

EXAMPLE 668

3'-[({3-[3-BENZYL-8-(TRIFLUOROMETHYL)QUINOLIN-4-YL]PHENYL}AMINO)METHYL]-4'-FLUOROBIPHENYL-4-OL

The title compound was prepared from {3-[3-benzyl-8-(trifluoromethyl)quinolin-4-yl]phenyl}amine and 4-fluoro-4'-hydroxy-biphenyl-3-carbaldehyde according to the procedure of Example 66. MS (ESI) m/z 579.

EXAMPLE 669

{3-[3-BENZYL-8-(TRIFLUOROMETHYL)QUINOLIN-4-YL]PHENYL}(3-METHYLBEN-ZYL)AMINE

The title compound was prepared from {3-[3-benzyl-8-(trifluoromethyl)quinolin-4-yl]phenyl}amine and 3-methyl-benzaldehyde according to the procedure of Example 66. MS (ES) m/z 483.1.

EXAMPLE 670

{3-[3-BENZYL-8-(TRIFLUOROMETHYL)QUINOLIN-4-YL]PHENYL}(2,4-DIMETHYL-BENZYL)AMINE

The title compound was prepared from {3-[3-benzyl-8-(trifluoromethyl)quinolin-4-yl]phenyl}amine and 2,4-dimethyl-benzaldehyde according to the procedure of Example 66. MS (ESI) m/z 497.

EXAMPLE 671

N-[(1-ACETYL-1H-INDOL-3-YL)METHYL]-3-[3-BENZYL-8-(TRIFLUOROMETHYL)QUINOLIN-4-YL]ANILINE

The title compound was prepared from {3-[3-benzyl-8-(trifluoromethyl)quinolin-4-yl]phenyl}amine and 1-acetyl-1H-indole-3-carbaldehyde according to the procedure of Example 66. MS (ES) m/z 550.0.

EXAMPLE 672

N N-BIS[(1-ACETYL-1H-INDOL-3-YL)ME-THYL]-3-[3-BENZYL-8-(TRIFLUOROMETHYL)QUINOLIN-4-YL]ANILINE

The title compound was prepared from {3-[3-benzyl-8-(trifluoromethyl)quinolin-4-yl]phenyl}amine and 1-acetyl-1H-indole-3-carbaldehyde according to the procedure of Example 66. MS (ES) m/z 721.1.

EXAMPLE 673

3-BENZYL-4-{3-[(1-METHYL-1H-INDOL-3-YL)METHOXY]PHENYL}-8-(TRIFLUOROMETHYL)QUINOLINE

The title compound was prepared from 3-[3-benzyl-8-(trifluoromethyl)quinolin-4-yl]phenol and (1-methyl-1H-indol-3-yl)-methanol according to the procedure of Example 69. MS (ES) m/z 523.1.

EXAMPLE 674

{3-[3-BENZYL-8-(TRIFLUOROMETHYL) QUINOLIN-4-YL]PHENYL}[2-FLUORO-5-(1H-PYRROL-2-YL)BENZYL]AMINE

The title compound was prepared from {3-[3-benzyl-8-(trifluoromethyl)quinolin-4-yl]phenyl}amine and 2-(4-fluoro-3-formyl-phenyl)-pyrrole-1-carboxylic acid tert-butylamide according to the procedure of Example 66. MS (ES) m/z 552.0;

EXAMPLE 675

3-BENZYL-4-{3-[(1-METHYL-1H-INDOL-7-YL)METHOXY]PHENYL}-8-(TRIFLUOROMETHYL)QUINOLINE

The title compound was prepared from 3-[3-benzyl-8-(trifluoromethyl)quinolin-4-yl]phenol and (1-methyl-1H-indol-7-yl)-methanol according to the procedure of Example 69. MS (ES) m/z 523.6.

EXAMPLE 676

3-BENZYL-4-(3-ETHYNYL-PHENYL)-8-TRIFLUOROMETHYL-QUINOLINE

1) A solution of 3-benzyl-4-(3-bromo-phenyl)-8-trifluoromethyl-quinoline (1.0 g, 23 mmol) and trimethyl-tributylstannanylethynyl-silane (1.3 g, 34 mmol) in toluene (25 mL) is treated with Pd(PPh$_3$)$_4$ (270 mg) and heated at 120° C. for 3 h. The reaction is then cooled and concentrated in vacuo. The residue is chromatographed with 10:90 ethyl acetate:hexane to afford 3-benzyl-8-trifluoromethyl-4-(3-trimethylsilanylethynylphenyl)-quinoline as an oil. MS (ESI) m/z 460.0.

2) A solution of the above oil, 3-benzyl-8-trifluoromethyl-4-(3-trimethylsilanylethynylphenyl)-quinoline (730 mg, 1.6 mmol) and potassium carbonate (220 mg, 1.6 mmol) in methanol (30 mL) is stirred at ambient temperature for 3 h. The reaction mixture is stripped to dryness and the residue taken up in ethyl acetate and washed with 30 mL (1N HCl). The organic layer is dried and concentrated in vacuo to provide after chromatography 870 mg (80%) of the title compound: MS (ESI) m/z 388.

EXAMPLE 677

3-BENZYL-4-(3-PHENYLETHYNYL-PHENYL)-8-TRIFLUOROMETHYL-QUINOLINE

A solution of 3-benzyl-4-(3-ethynyl-phenyl)-8-trifluoromethyl-quinoline (80 mg, 0.2 mmol), iodobenzene 84 mg, 0.4 mmol), piperidine (80 mg, 0.9 mmol) in toluene (2.0 mL) is treated with Pd(Cl)$_2$(PPh$_3$)$_2$ (8.0 mg) and heated at 90° C. for 3 h. The reaction is then cooled and concentrated in vacuo. The residue is taken up in ethyl acetate and washed with 10 mL (1N HCl). The organic layer is dried and concentrated in vacuo to provide after chromatography 72 mg (75%) of the title compound. MS (ES) m/z 464.1.

EXAMPLE 678

[4-(2-{3-[3-BENZYL-8-(TRIFLUOROMETHYL)QUINOLIN-4-YL]PHENYL}ETHYL)PHENYL]ACETIC ACID

A solution of [4-({3-[3-benzyl-8-(trifluoromethyl)quinolin-4-yl]phenyl}ethynyl)-phenyl]acetic acid (50 mg, 0.09 mmol), in ethyl acetate:acetic acid (8:1, 4.0 mL) is treated with Pd/C (10%) (3 mg) and placed on a PARR hydrogenator under 40 psi H$_2$ The reaction filtered through celite and concentrated in vacuo. After chromatography (ethyl acetate:hexane, 33:70) the title saturated compound is obtained, 40 mg (80%). MS (ES) m/z 524.1.

Examples 679 to 694 were prepared using similar procedure to Example 676.

| Example | Name | MS |
|---|---|---|
| Example 679 | [4-({3-[3-benzyl-8-(trifluoromethyl)quinolin-4-yl]phenyl}ethynyl)phenyl]acetic acid | MS (ES) m/z 522.1; |
| Example 680 | ethyl 3-({3-[3-benzyl-8-(trifluoromethyl)quinolin-4-yl]phenyl}ethynyl)benzoate | MS (ES) m/z 536.2; |
| Example 681 | 3-({3-[3-benzyl-8-(trifluoromethyl)quinolin-4-yl]phenyl}ethynyl)benzoic acid | MS (ESI) m/z 506.1 (M + H)+ |
| Example 682 | methyl 4-({3-[3-benzyl-8-(trifluoromethyl)quinolin-4-yl]phenyl}ethynyl)benzoate | MS (ES) m/z 522.1; |
| Example 683 | 4-({3-[3-benzyl-8-(trifluoromethyl)quinolin-4-yl]phenyl}ethynyl)benzoic acid | MS (ES) m/z 506.2; |
| Example 684 | 3-[4-({3-[3-benzyl-8-(trifluoromethyl)quinolin-4-yl]phenyl}ethynyl)phenyl]propanoic acid | MS (ES) m/z 536.2; |
| Example 685 | methyl 3-[4-({3-[3-benzyl-8-(trifluoromethyl)quinolin-4-yl]phenyl}ethynyl)phenyl]propanoate | MS (ES) m/z 550.2; |
| Example 686 | [3-({3-[3-benzyl-8-(trifluoromethyl)quinolin-4-yl]phenyl}ethynyl)phenyl]acetic acid | MS (ES) m/z 522.1; |
| Example 687 | 3-[3-({3-[3-benzyl-8-(trifluoromethyl)quinolin-4-yl]phenyl}ethynyl)phenyl]propanoic acid | MS (ES) m/z 534.1; |
| Example 688 | methyl 3-[3-({3-[3-benzyl-8-(trifluoromethyl)quinolin-4-yl]phenyl}ethynyl)phenyl]propanoate | MS (ES) m/z 550.2; |
| Example 689 | 3-benzyl-4-{3-[(2-fluorophenyl)ethynyl]phenyl}-8-(trifluoromethyl)quinoline | MS (ESI) m/z 482; |
| Example 690 | 3-benzyl-4-{3-[(2-chlorophenyl)ethynyl]phenyl}-8-(trifluoromethyl)quinoline | MS (ESI) m/z 498; |
| Example 691 | 3-benzyl-4-{3-[(4-bromophenyl)ethynyl]phenyl}-8-(trifluoromethyl)quinoline | MS (ESI) m/z 542; |
| Example 692 | 3-benzyl-4-{3-[(2,5-dichlorophenyl)ethynyl]phenyl}-8-(trifluoromethyl)quinoline | MS (ESI) m/z 532; |
| Example 693 | 3-benzyl-4-{3-[(2,4-dichlorophenyl)ethynyl]phenyl}-8-(trifluoromethyl)quinoline | MS (ESI) m/z 523; |
| Example 694 | 3-benzyl-4-{3-[(3,4-dichlorophenyl)ethynyl]phenyl}-8-(trifluoromethyl)quinoline | MS (ESI) m/z 532; |

EXAMPLE 695

3-{[3-BENZYL-8-(TRIFLUOROMETHYL)QUINOLIN-4-YL]METHYL}PHENOL

1) A stirred mixture of 3-benzyl-4-bromo-8-(trifluoromethyl)quinoline (10.0 g, 27.31 mmol) and (3-methoxyphenyl)acetonitrile (5.57 mL, 40.96 mmol) in THF (100 mL) is treated with NaH (1.64 g, 41.0 mmol, 60% dispersion in oil). After 0.5 h at ambient temperature, the reaction is heated at 50° C. for 2 h. The cooled reaction is diluted with water, extracted with ethyl acetate, and the combined extracts are dried (MgSO$_4$) and concentrated. The residue is purified via column chromatography using 10:90 ethyl acetate:hexane as the eluent. The purified product is dissolved in a mixture of methylene chloride and hexane and concentrated until precipitation commences. After precipitation is complete, [3-benzyl-8-(trifluoromethyl)quinolin-4-yl](3-methoxyphenyl)acetonitrile is isolated as an off-white crystalline solid (5.18 g, 44%). HRMS: calcd for $C_{26}H_{19}F_3N_2O+H+$, 433.15222; found (ESI, [M+H]$^+$), 433.1528.

2) [3-Benzyl-8-(trifluoromethyl)quinolin-4-yl](3-methoxyphenyl)acetonitrile (5.14 g, 11.88 mmol) in 48% HBr (75 mL) is heated at 90° C. for 65 h. Cooled reaction is poured into concentrated ammonium hydroxide (50 mL) diluted with water and ice. The mixture is extracted with ethyl acetate and the combined extracts are dried (MgSO$_4$) and concentrated. The residue is purified via column chromatography using 15:85 ethyl acetate:hexane as the eluent to afford the title compound as a yellow powder (3.91 g, 84%). HRMS: calcd for $C_{24}H_{18}F_3NO+H+$, 394.14132; found (ESI, [M+H]$^+$), 394.1404.

EXAMPLE 696

METHYL 3-[(3-{[3-BENZYL-8-(TRIFLUOROMETHYL)QUINOLIN-4YL]METHYL}PHENOXY)METHYL]BENZOATE

3-{[3-Benzyl-8-(trifluoromethyl)quinolin-4-yl]methyl}phenol (0.100 g, 0.254 mmol), methyl 3-bromomethylbenzoate (0.058 g, 0.254 mmol) and Cs$_2$CO$_3$ (0.331 g, 1.02 mmol) in acetonitrile (4 mL) are stirred 18 h. The reaction is filtered and then purified using Prep HPLC (10 to 100% acetonitrile/water gradient) to afford 0.070 g of the title compound as a colorless oil. $^1$H NMR (CDCl$_3$) δ 8.96 (s, 1H), 8.12 (d, J=8.6 Hz, 1H), 8.02 (m, 2H), 7.97 (d, J=7.7 Hz, 1H), 7.5 (m, 2H), 7.42 (m, 1H), 7.18 (m, 6H), 6.80 (dd, J=8.2 and 2.0 Hz, 1H), 6.63 (d, J=7.7 Hz, 1H), 6.51 (s, 1H), 4.96 (s, 2H), 4.45 (s, 2H), 4.19 (s, 2H), 3.92 (s, 3H).

EXAMPLE 697

METHYL 4-[(3-{[3-BENZYL-8-(TRIFLUOROMETHYL)QUINOLIN-4YL]METHYL}PHENOXY)METHYL]BENZOATE

This compound is prepared according to the procedure of Example 696 using methyl 4-bromomethylbenzoate as the alkylating agent. $^1$H NMR (CDCl$_3$) δ 8.96 (s, 1H), 8.09 (d, J=7.9 Hz, 1H), 8.00 (m, 3H), 7.49 (m, 1H), 7.36 (d, J=8.4 Hz, 2H), 7.18 (m, 6H), 6.78 (dd, J=2.0, 8.2 Hz, 1H), 6.64 (dd, J=0.7, 7.7 Hz, 1H), 6.47 (s, 1H), 4.96 (s, 2H), 4.45 (s, 2H), 4.17 (s, 2H), 3.92 (s, 3H).

EXAMPLE 698

ETHYL {3-[(3-{[3-BENZYL-8-(TRIFLUOROMETHYL)QUINOLIN-4YL]METHYL}PHENOXY)METHYL]PHENYL}ACETATE

This compound is prepared according to the procedure of Example 696 using ethyl 3-bromomethylphenyl acetate as the alkylating agent. $^1$H NMR (CDCl$_3$) δ 8.96 (s, 1H), 8.13 (d, J=8.6 Hz, 1H), 8.02 (d, J=7.2 Hz, 1H), 7.51 (m, 1H), 7.23 (m, 8H), 7.10 (d, J=7.5 Hz, 2H), 6.80 (d, J=8.2 Hz, 1H), 6.61 (d, J=7.5 Hz, 1H), 6.53 (s, 1H), 4.91 (s, 2H), 4.45 (s, 2H), 4.19 (s, 2H), 4.14 (m, 2H), 3.6 (s, 2H), 1.24 (m, 3H).

EXAMPLE 699

METHYL {3-{3-[(3-{[3-BENZYL-8-(TRIFLUOROMETHYL)QUINOLIN-4YL]METHYL}PHENOXY)METHYL]PHENYL}PROPANOATE

This compound is prepared according to the procedure of Example 695 using methyl (3-bromomethylphenyl)propanoate as the alkylating agent. $^1$H NMR (CDCl$_3$): δ 8.96 (s, 1H), 8.13 (d, J=8.6 Hz, 1H), 8.02 (d, J=7.3 Hz, 1H), 7.50 (m, 1H), 7.18 (m, 10H), 6.80 (dd, J=2.3, 8.2 Hz, 1H), 6.61 (d, J=7.7 Hz, 1H), 6.53 (s, 1H), 4.89 (s, 2H), 4.45 (s, 2H), 4.19 (s, 2H), 3.65 (s, 3H), 2.94 (m, 2H), 2.60 (m, 2H).

EXAMPLE 700

METHYL {3-[(3-{[3-BENZYL-8-(TRIFLUOROMETHYL)QUINOLIN-4YL]METHYL}PHENOXY)METHYL]PHENOXY}ACETATE

The title compound is isolated as a colorless oil prepared according to the procedure of Example 696 except using methyl (3-bromomethylphenoxy)acetate as the alkylating agent. $^1$H NMR (CDCl$_3$): δ 8.96 (s, 1H), 8.11 (d, J=8.5 Hz, 1H), 8.02 (d, J=7.2 Hz, 1H), 7.51 (m, 1H), 7.18 (m, 7H), 6.90 (br s, 2H), 6.80 (m, 2H), 6.61 (d, J=7.7 Hz, 1H), 6.50 (s, 1H), 4.89 (s, 2H), 4.61 (s, 2H), 4.44 (s, 2H), 4.18 (s, 2H), 3.78 (s, 3H).

EXAMPLE 701

METHYL{4-[(3-{[3-BENZYL-8-(TRIFLUOROMETHYL)QUINOLIN-4-YL]METHYL}PHENOXY)METHYL]PHENOXY}ACETATE

This colorless oil is prepared according to the procedure of Example 696 using methyl (4-bromomethylphenoxy)acetate as the alkylating agent. $^1$H NMR (CDCl$_3$): δ 8.96 (s, 1H), 8.14 (d, J=8.6 Hz, 1H), 8.03 (d, J=7.3 Hz, 1H), 7.52 (m, 1H), 7.21 (m, 7H), 7.10 (d, J=7.3 Hz, 2H), 6.87 (d, J=8.6 Hz, 2H), 6.80 (dd, J=2.3, 8.2 Hz, 1H), 6.62 (d, J=7.7 Hz, 1H), 6.50 (s, 1H), 4.85 (s, 2H), 4.63 (s, 2H), 4.45 (s, 2H), 4.18 (s, 2H), 3.81 (s, 3H).

EXAMPLE 702

3-[(3-{([3-BENZYL-8-(TRIFLUOROMETHYL)QUINOLIN-4-YL]METHYL}PHENOXY)METHYL]BENZOIC ACID METHYL 3-[(3-{[3-BENZYL-8-(TRIFLUOROMETHYL)QUINOLIN-4 yl]methyl}phenoxy)methyl]benzoate and 1M aqueous LiOH in THF is stirred overnight. The reaction is acidified with dilute hydrochloric acid and extracted with ethyl acetate. The combined extracts are dried (Na$_2$SO$_4$) and concentrated to yield the title compound as a tan semi-solid. MS (ESI) m/z 528 ([M+H])$^+$; MS (ESI) m/z 526 ([M−H])$^−$.

EXAMPLE 703

4-[(3-{[3-BENZYL-8-(TRIFLUOROMETHYL) QUINOLIN-4-YL]METHYL}PHENOXY)ME-THYL]BENZOIC ACID

The yellow semi-solid product is formed analogously to the procedure of Example 702. MS (ESI) m/z 528 ([M+H])$^+$; MS (ESI) m/z 526 ([M−H])$^−$.

EXAMPLE 704

{3-[(3-{[3-BENZYL-8-(TRIFLUOROMETHYL) QUINOLIN-4-YL]METHYL}PHENOXY)ME-THYL]PHENYL}ACETIC ACID

The yellow oil product is prepared according to the procedure of Example 702. MS (ESI) m/z 542 ([M+H])$^+$; MS (ESI) m/z 540 ([M−H])$^−$.

EXAMPLE 705

3-{3-[(3-{[3-BENZYL-8-(TRIFLUOROMETHYL) QUINOLIN-4-YL]METHYL}PHENOXY)ME-THYL]PHENYL}PROPANOIC ACID

The yellow oil product is prepared according to the procedure of Example 702. MS (ESI) m/z 556 ([M+H])$^+$; MS (ESI) m/z 554 ([M−H])$^−$.

EXAMPLE 706

{3-[(3-{[3-BENZYL-8-(TRIFLUOROMETHYL) QUINOLIN-4-YL]METHYL}PHENOXY)ME-THYL]PHENOXY}ACETIC ACID

The yellow oil product is prepared according to the procedure of Example 702. MS (ESI) m/z 558 ([M+H])$^+$; MS (ESI) m/z 556 ([M−H])$^−$.

EXAMPLE 707

{4-[(3-{[3-BENZYL-8-(TRIFLUOROMETHYL) QUINOLIN-4-YL]METHYL}PHENOXY)ME-THYL]PHENOXY}ACETIC ACID

The yellow oil product is prepared according to the procedure of Example 702. MS (ESI) m/z 558 ([M+H])$^+$; MS (ESI) m/z 556 ([M−H])$^−$.

EXAMPLE 708

3-[3-(8-CHLORO-3-METHYLQUINOLIN-4-YL) PHENOXY]-N-ETHYLBENZAMIDE

To a stirred suspension of ethylamine hydrochloride (41 mg, 0.50 mmol) in toluene (2 mL) at ambient temperature under nitrogen is added 2.0M trimethylaluminum in toluene (0.25 mL, 0.50 mmol). After 0.5 h, methyl 3-[3-(8-chloro-3-methylquinolin-4-yl)phenoxy]benzoate (101 mg, 0.25 mmol) is added and the reaction heated at 60-65° C. for 16 h. The cooled reaction is treated with water (2 mL), then 2M aq HCl (1 mL) and extracted with dichloromethane (2×5 mL). The combined extracts are dried (MgSO4), concentrated in vacuo, and the resulting oil is chromatographed on silica gel using 50:50, then 75:25 ethyl acetate:hexane as eluent. The title compound is isolated as a glass (R$_f$~0.3 in first solvent system, 101 mg). MS (ES) m/z 417.2; HRMS: calcd for C25H21ClN2O2+H+, 417.13643; found (ESI, [M+H]+), 417.1357.

EXAMPLE 709

METHYL 3-{3-[3-BENZYL-8-(TRIFLUOROM-ETHYL)QUINOLIN-4-YL] PHENOXY}BENZOATE

A mixture of 3-[3-benzyl-8-(trifluoromethyl)quinolin-4-yl]phenol (2.65 g, 7.0 mmol), methyl 3-bromobenzoate (3.01 g, 14.0 mmol), CuO (1.01 g, 12.6 mol), and K$_2$CO$_3$ (1.93 g, 14.0 mmol) in dry pyridine (17.5 mL) are heated under nitrogen at 120° C. for 48 h. The cooled reaction is diluted with water (100 mL) and extracted with ether (2×100 mL). The dried (MgSO$_4$) extracts are concentrated to a dark oil which is chromatographed on silica gel using 20:80 ethyl acetate:hexane as eluent isolating the title compound as a colorless tacky solid (R$_f$~0.3, 1.53 g). MS (ESI) m/z 514; HRMS: calcd for C31H22F3NO3+H+, 514.16245; found (ESI, [M+H]+), 514.1638.

EXAMPLE 710

2-(3-{3-[3-BENZYL-8-(TRIFLUOROMETHYL) QUINOLIN-4-YL]PHENOXY}PHENYL)PRO-PAN-2-OL

To a stirred solution of methyl 3-{3-[3-benzyl-8-(trifluoromethyl)quinolin-4-yl]phenoxy}benzoate (128 mg, 0.25 mmol) in dry THF (2.5 mL) at 0° C. under nitrogen is treated with 3.0M MeMgBr in THF (0.50 mL, 1.50 mmol). The reaction is allowed to warm to ambient temperature over 2 h, then treated with 2M aq HCl (3 mL) followed by brine (5 mL) and extracted with ethyl acetate (2×15 mL). The combined extracts are dried (MgSO4), concentrated in vacuo, and the resulting oil is chromatographed on silica gel using 1:1 ethyl acetate:hexane as eluent to afford the title compound as a slightly tacky solid (R$_f$~0.5, 105 mg). mp<80° C. MS (ES) m/z 514.2; HRMS: calcd for C32H26F3NO2+H+, 514.19884; found (ESI, [M+H]+), 514.1963.

EXAMPLE 711

2-{4-[3-(3-PHENYL-8-TRIFLUOROMETHYL-QUINOLIN-4-YL)-PHENOXYMETHYL]-PHE-NYL}-ETHANOL

{4-[3-(3-Phenyl-8-trifluoromethyl-quinolin-4-yl)-phenoxymethyl]-phenyl}-acetic (0.051 g, 0.097 mmol) was dissolved into THF (3 mL) and stirred in an ice bath for 20 minutes. LAH (0.006 mg, 0.145 mmol) was added and the solution was stirred for an additional 60 minutes. The reaction was quenched with 2N HCl and extracted with ethyl acetate. The combined organics were dried over magnesium sulfate and concentrated. The resulting material was purified via column chromatography using 5% ethyl acetate in hexane as the eluent. mp 50° C.; MS (ES) m/z 500.1.

EXAMPLE 712

2-{4-[3-(3-PHENOXY-8-TRIFLUOROMETHYL-QUINOLIN-4-YL)-PHENOXYMETHYL]-PHE-NYL}-ETHANOL

The title compound was prepared from [{4-[3-(3-Phenoxy-8-trifluoromethyl-quinolin-4-yl)-phenoxymethyl]-phenyl}-acetic acid according to the procedure of Example 711. MS (ES) m/z 516.0.

EXAMPLE 713

3-{[3-(3-BENZYL-8-CHLOROQUINOLIN-4-YL)
PHENYL]AMINO}BENZAMIDE

3-{[3-(3-benzyl-8-chloroquinolin-4-yl)phenyl]
amino}benzoic acid was taken into benzene and to this was added thionyl chloride (2 eq.) and refluxed for 3 h. The solvent was removed and the resulting material was dried under high vacuum. The acid chloride was then taken up into THF, cooled to 0° C. and to this was added excess concentrated ammonium hydroxide and stirred overnight. The reaction was placed directly on Prep HPLC for purification using 10-100% acetonitrile in water as the eluent to yield the benzamide HRMS: calcd for C29H22ClN3O+H+, 464.15241; found (ESI, [M+H]+), 464.1544.

EXAMPLE 714

3-{[3-(3-BENZYL-8-CHLOROQUINOLIN-4-YL)
PHENYL]AMINO}-N-(2-HYDROXYETHYL)
BENZAMIDE

This compound was prepared via the procedure in Example 713 using ethanolamine in place of ammonium hydroxide. HRMS: calcd for C31H26ClN3O2+H+, 508.17863; found (ESI, [M+H]+), 508.1786.

EXAMPLE 715

3-{([3-(3-BENZYL-8-CHLOROQUINOLIN-4-YL)
PHENYL]AMINO}-N-METHYLBENZAMIDE

This compound was prepared via the procedure in Example 713 using methylamine in place of ammonium hydroxide. HRMS: calcd for C30H24ClN3O+H+, 478.16807; found (ESI, [M+H]+), 478.1703.

EXAMPLE 716

3-{[3-(3-BENZYL-8-CHLOROQUINOLIN-4-YL)
PHENYL]AMINO}-N-ETHYLBENZAMIDE

This compound was prepared via the procedure in Example 713 using ethylamine in place of ammonium hydroxide. HRMS: calcd for C31H26ClN3O+H+, 492.18371; found (ESI, [M+H]+), 492.1878.

EXAMPLE 717

3-{[3-(3-BENZYL-8-CHLOROQUINOLIN-4-YL)
PHENYL]AMINO}-N-CYCLOPROPYLBENZA-
MIDE

This compound was prepared via the procedure in Example 713 using cyclopropylamine in place of ammonium hydroxide. HRMS: calcd for C32H26ClN3O +H+, 504.18371; found (ESI, [M+H]+), 504.1826.

EXAMPLE 718

3-{[3-(3-BENZYL-8-CHLOROQUINOLIN-4-YL)
PHENYL]AMINO}-N-ISOPROPYLBENZAMIDE

This compound was prepared via the procedure in Example 713 using isopropylamine in place of ammonium hydroxide. HRMS: calcd for C32H28ClN3O+H+, 506.19937; found (ESI, [M+H]+), 506.2003.

EXAMPLE 719

3-{[3-(3-BENZYL-8-CHLOROQUINOLIN-4-YL)
PHENYL]AMINO}-N,N-DIETHYLBENZAMIDE

This compound was prepared via the procedure in Example 713 using diethylamine in place of ammonium hydroxide. HRMS: calcd for C33H30ClN3O+H+, 520.21502; found (ESI, [M+H]+), 520.2145.

EXAMPLE 720

[3-(3-BENZYL-8-CHLOROQUINOLIN-4-YL)
PHENYL][3-(PYRROLIDIN-1-YLCARBONYL)
PHENYL]AMINE

This compound was prepared via the procedure in Example 713 using pyrrolidine in place of ammonium hydroxide. HRMS: calcd for C33H28ClN3O+H+, 518.19937; found (ESI, [M+H]+), 518.2023.

EXAMPLE 721

[3-(3-BENZYL-8-CHLOROQUINOLIN-4-YL)
PHENYL][3-(PIPERIDIN-1-YLCARBONYL)PHE-
NYL]AMINE

This compound was prepared via the procedure in Example 713 using piperidine in place of ammonium hydroxide. HRMS: calcd for C34H30ClN3O+H+, 532.21502; found (ESI, [M+H]$^+$), 532.2177.

EXAMPLE 722

[3-(3-BENZYL-8-CHLOROQUINOLIN-4-YL)
PHENYL][3-(MORPHOLIN-4-YLCARBONYL)
PHENYL]AMINE

This compound was prepared via the procedure in Example 713 using morpholine in place of ammonium hydroxide. HRMS: calcd for C33H28ClN3O2+H+, 534.19428; found (ESI, [M+H]+), 534.196.

EXAMPLE 723

3-[3-(3-BENZYL-8-CHLOROQUINOLIN-4-YL)
PHENOXY]-5-BROMOBENZONITRILE 3-(3-benzyl-8-chloroquinolin-4-yl)phenol (0.100 g, 0.289 mmol) was taken into NMP (1 mL) and to this was added NaH (0.0127 g, 0.318 mmol, 60% dispersion in oil) and stirred for 15 minutes. 3-Bromo-5-fluorobenzonitrile (0.116 g, 0.578 mmol) was added and the reaction was heated at 160° C. overnight. The reaction was cooled and quenched with water followed by extraction with ether. After drying and concentration the product was purified via Prep HPLC using 10-100% v acetonitrile in water as the eluent to yield 0.028 g of product. MS (ESI) m/z 526 ([M+H])$^+$.

EXAMPLE 724

3-BENZYL-4-{3-[3-BROMO-5-(TRIFLUOROM-
ETHYL)PHENOXY]PHENYL}-8-CHLORO-
QUINOLINE

This compound was prepared via the procedure in Example 723 using 1-bromo-3-fluoro-5-trifluoromethylbenzene in place of 3-Bromo-5-fluorobenzonitrile. MS (ESI) m/z 569 ([M+H])$^+$.

EXAMPLE 725

3-[3-(3-BENZYL-8-CHLOROQUINOLIN-4-YL)
PHENOXY]-5-FLUOROBENZONITRILE

This compound was prepared via the procedure in Example 723 using 3,5-difluorobenzonitrile in place of 3-bromo-5-fluorobenzonitrile. MS (ESI) m/z 465 ([M+H])$^+$.

EXAMPLE 726

3-BENZYL-4-[3-(3-BROMO-5-CHLOROPHE-
NOXY)PHENYL]-8-CHLOROQUINOLINE

This compound was prepared via the procedure in Example 723 using 1-bromo-3-chloro-5-fluorobenzene in place of 3-bromo-5-fluorobenzonitrile. MS (ESI) m/z 536 ([M+H])$^+$.

EXAMPLE 727

N-{3-[3-BENZOYL-8-(TRIFLUOROMETHYL)
QUINOLIN-4-YL]PHENYL}-1H-IMIDAZOLE-1-
CARBOXIMIDAMIDE

To imidazole (65 mg, 9.760 mmol) in CH$_2$Cl$_2$ (10 ml) at room temperature under nitrogen atmosphere bromonitrile (500 mg, 4.71 mmol) was added. The resulting mixture was heated at reflux for 1 hr. Cooling to room temperature, filtration and concentration in vacuo to a volume of approximately 10 ml. The resulting pale liquor was let stand at 0° C. for 15 hrs. Filtration afforded a pale white powder for C-(di-imidazol-1-yl)-methyleneamine (210 mg, 28% yield). To [4-(3-amino-phenyl)-8-trifluoromethyl-quinolin-3-yl]-phenyl-methanone (132 mg, 3.389 mmol), aniline (213 mg, 2.347 mmol) and C-(di-imidazol-1-yl)-methyleneamine (420 mg, 2.608 mmol) in THF (20 mg) was heated at reflux for 2.5 hrs. Concentration in vacuo and RP-HPLC (gradient water:acetonitrile) afforded the title compound as a yellow powder (20 mg, 14% yield). MS (ESI) m/z 486.

EXAMPLE 728

4-[({3-[3-BENZYL-8-(TRIFLUOROMETHYL)
QUINOLIN-4-YL]PHENYL}AMINO)METHYL]
BENZOIC ACID

This compound was prepared according to the procedure of Example 66 from 3-(3-benzyl-8-trifluoromethyl-quinolin-4-yl)-phenylamine and 4-formyl-benzoic acid methyl ester MS (ESI) m/z 511.

EXAMPLE 729

METHYL N-{4-[({3-[3-BENZYL-8-(TRIFLUO-
ROMETHYL)QUINOLIN-4-YL]
PHENYL}AMINO)METHYL]
BENZOYL}GLYCINATE

To 4-{[3-(3-benzyl-8-trifluoromethyl-quinolin-4-yl)-phenylamino]-methyl}-benzoic acid (130 mg, 0.254 nmol), glycine methyl ester (35 mg, 0.279 mmol) morpholine (102 mg, 1.014 mmol), EDCI (58 mg, 0.304 mmol), and HOBT (41 mg, 0.304 mmol) in CH$_2$Cl$_2$ (15 ml) were combined at room temperature under a nitrogen atmosphere. The resulting mixture was stirred at room temperature under a nitrogen atmosphere for 15 hrs. Quenching with brine (15 ml), separation, drying MgSO$_4$ of the organics and concentration in vacuo. RP-HPLC (gradient water:acetonitrile) afforded the ester as an off white powder (88 mg, 61% Yield). MS (ESI) m/z 582.

EXAMPLE 730

METHYL N-{4-[({3-[3-BENZYL-8-(TRIFLUO-
ROMETHYL)QUINOLIN-4-YL]
PHENYL}AMINO)METHYL]BENZOYL}-D-
LEUCINATE

This compound was prepared according to Example 729, substituting D-leucine methyl ester. MS (ESI) m/z 638.

EXAMPLE 731

ETHYL N-{4-[({3-[3-BENZYL-8-(TRIFLUOROM-
ETHYL)QUINOLIN-4-YL]PHENYL}AMINO)
METHYL]BENZOYL}-D-PHENYLALANINATE

This compound was prepared according to Example 729, substituting D-phenyl alanine ethyl ester. MS (ESI) m/z 686.

EXAMPLE 732

N-{4-[({3-[3-BENZYL-8-(TRIFLUOROMETHYL)
QUINOLIN-4-YL]PHENYL}AMINO)METHYL]
BENZOYL}-D-LEUCINE

This compound was prepared according to the Example 729, substituting methyl N-{4-[({3-[3-benzyl-8-(trifluoromethyl)quinolin-4-yl]phenyl}amino)methyl]benzoyl}-D-leucinate. MS (ESI) m/z 624.

EXAMPLE 733

N-{4-[({3-[3-BENZYL-8-(TRIFLUOROMETHYL)
QUINOLIN-4-YL]PHENYL}AMINO)METHYL]
BENZOYL}GLYCINE

This compound was prepared according to the procedure of example 66, substituting methyl N-{4-[({3-[3-benzyl-8-(trifluoromethyl)quinolin-4yl]phenyl}amino)methyl]benzoyl}-glycine. MS (ESI) m/z 568.

EXAMPLE 734

N-{4-[({3-[3-BENZYL-8-(TRIFLUOROMETHYL)
QUINOLIN-4-YL]PHENYL}AMINO)METHYL]
BENZOYL}-D-PHENYLALANINE

This compound was prepared according to the procedure of example 66, substituting methyl N-{4-[({3-[3-benzyl-8-(trifluoromethyl)quinolin-4yl]phenyl}amino)methyl]benzoyl}-D-phenylalanine. MS (ESI) m/z 658.

EXAMPLE 735

3-{3-[({3-[3-CYANO-8-(TRIFLUOROMETHYL)
QUINOLIN-4-YL]PHENYL}AMINO)METHYL]
PHENYL}PROPANOIC ACID

This compound was prepared according to the procedure of example 66, substituting 3-(3-{[3-(3-cyano-8-trifluoromethyl-quinolin-4-yl)-phenylamino]-methyl}-phenyl)-propionic acid ethyl ester. MS (ESI) m/z 476.

EXAMPLE 736

ETHYL 3-{3-[({3-[3-CYANO-8-(TRIFLUOROM-ETHYL)QUINOLIN-4-YL]PHENYL}AMINO)METHYL]PHENYL}PROPANOATE

This compound was prepared according to the procedure of example 66, substituting 4-(3-amino-phenyl)-8-trifluoromethyl-quinoline-3-carbonitrile and 3-(3-formyl-phenyl)-propionic acid methyl ester. MS (ESI) m/z 503.9.

EXAMPLE 737

{4'-[({3-[3-BENZYL-8-(TRIFLUOROMETHYL)QUINOLIN-4-YL]PHENYL}AMINO)METHYL]-1,1'-BIPHENYL-3-YL}ACETIC ACID

This compound was prepared according to the procedure of example 66, substituting 3-(3-benzyl-8-trifluoromethyl-quinolin-4-yl)-phenylamine and (4'-formyl-biphenyl-3-yl)-acetic acid methyl ester. MS (ESI) m/z 601.

EXAMPLE 738

{4'-[({3-[3-BENZOYL-8-(TRIFLUOROMETHYL)QUINOLIN-4-YL]PHENYL}AMINO)METHYL]-1,1'-BIPHENYL-3-YL}ACETIC ACID

This compound was prepared according to the procedure of example 66, substituting [4-(3-amino-phenyl)-8-trifluoromethyl-quinolin-3-yl]-phenyl-methanone and (4'-formyl-biphenyl-3-yl)-acetic acid methyl ester. MS (ESI) m/z 615.

EXAMPLE 739

4-{4-[2-({3-[3-BENZYL-8-(TRIFLUOROMETHYL)QUINOLIN-4-YL]PHENYL}AMINO)ETHYL]PIPERIDIN-1-YL}BENZOIC ACID

This compound was prepared according to the procedure of example 66, substituting 3-(3-benzyl-8-trifluoromethyl-quinolin-4-yl)-phenylamine and 4-[4-(2-oxo-ethyl)-piperidin-1-yl]-benzoic acid methyl ester. MS (ESI) m/z 610.

EXAMPLE 740

(4-{[3-(8-CHLORO-3-PHENYLQUINOLIN-4-YL)PHENOXY]METHYL}PHENYL)ACETIC ACID

This compound was prepared according to the procedure of example 41, substituting (4-{[3-(8-Chloro-3-phenylquinolin-4-yl)phenoxy]methyl}phenyl)acetic acid methyl ester. MS (ESI) m/z 480.

EXAMPLE 741

(4-{[3-(8-CHLORO-3-METHYLQUINOLIN-4-YL)PHENOXY]METHYL}PHENYL)ACETIC ACID

This compound was prepared according to the procedure of example 41, substituting (4-{[3-(8-chloro-3-methylquinolin-4-yl)phenoxy]methyl}phenyl)acetic acid methyl ester. MS (ESI) m/z 418.

EXAMPLE 742

(4-{[3-(3-BENZYL-8-CHLOROQUINOLIN-4-YL)PHENOXY]METHYL}PHENYL)ACETIC ACID

This compound was prepared according to the procedure of example 66, substituting (4-{[3-(3-benzyl-8-chloroquinolin-4-yl)phenoxy]methyl}phenyl)acetic acid methyl ester. MS (ESI) m/z 494.

EXAMPLE 743

METHYL 2-(4-{[3-(8-CHLORO-3-PHENYLQUINOLIN-4-YL)PHENOXY]METHYL}PHENYL)-2-METHYLPROPANOATE

This compound was prepared according to the procedure of example 41, substituting 3-(8-chloro-3-phenyl-quinolin-4-yl)-phenylamine and 2-(4-bromomethyl-phenyl)-2-methyl-propionic acid methyl ester. MS (ESI) m/z 522.

EXAMPLE 744

METHYL 2-(4-{[3-(3-BENZYL-8-CHLOROQUINOLIN-4-YL)PHENOXY]METHYL}PHENYL)-2 METHYLPROPANOATE

This compound was prepared according to the procedure of example 41, substituting 3-(8-chloro-3-bennzyl-quinolin-4-yl)-phenylamine and 2-(4-bromomethyl-phenyl)-2-methyl-propionic acid methyl ester. MS (ESI) m/z 536.

EXAMPLE 745

2-(4-{[3-(8-CHLORO-3-PHENYLQUINOLIN-4-YL)PHENOXY]METHYL}PHENYL)-2-METHYLPROPANOIC ACID

This compound was prepared according to the procedure of example 41, substituting 2-(4-{[3-(8-chloro-3-phenylquinolin-4-yl)phenoxy]methyl}phenyl)-2-methylpropanoic acid methyl ester. MS (ESI) m/z 506.

EXAMPLE 746

2-(4-{[3-(3-BENZYL-8-CHLOROQUINOLIN-4-YL)PHENOXY]METHYL}PHENYL)-2-METHYLPROPANOIC ACID

This compound was prepared according to the procedure of example 41, substituting 2-(4-{[3-(3-benzyl-8-chloro-quinolin-4-yl)phenoxy]methyl}phenyl)-2-methylpropanoic acid methyl ester. MS (ESI) m/z 520.

EXAMPLE 747

{3-[3-BENZYL-8-(TRIFLUOROMETHYL)QUINOLIN-4-YL]PHENYL}(2,5-DIMETHYLBENZYL)AMINE

This compound was prepared according to the procedure of example 66, substituting 3-(3-benzyl-8-trifluoromethyl-quinolin-4-yl)-phenylamine and 2,5-dimethyl-benzaldehyde. MS (ESI) m/z 497.

EXAMPLE 748

{3-[3-BENZYL-8-(TRIFLUOROMETHYL)
QUINOLIN-4-YL]PHENYL}(2,3-DIMETHYL-
BENZYL)AMINE

This compound was prepared according to the procedure of example 66, substituting 3-(3-benzyl-8-trifluoromethyl-quinolin-4-yl)-phenylamine and 2,3-dimethyl benzaldehyde. MS (ESI) m/z 497.

EXAMPLE 749

{3-[3-BENZYL-8-(TRIFLUOROMETHYL)
QUINOLIN-4-YL]PHENYL}(2,6-DIMETHYL-
BENZYL)AMINE

This compound was prepared according to the procedure of example 66, substituting 3-(3-benzyl-8-trifluoromethyl-quinolin-4-yl)-phenylamine and 2,6-dimethyl benzaldehyde. MS (ESI) m/z 497.

EXAMPLE 750

{3-[3-BENZYL-8-(TRIFLUOROMETHYL)
QUINOLIN-4-YL]PHENYL}(1H-IMIDAZOL-2-
YLMETHYL)AMINE

This compound was prepared according to the procedure of example 66, substituting 3-(3-benzyl-8-trifluoromethyl-quinolin-4-yl)-phenylamine and 1H-imidazole-2 carbaldehyde. MS (ESI) m/z 457.

EXAMPLE 751

{3-[3-BENZYL-8-(TRIFLUOROMETHYL)
QUINOLIN-4-YL]PHENYL}{3-[3-(TRIFLUO-
ROMETHYL)PHENOXY]BENZYL}AMINE

This compound was prepared according to the procedure of example 66, substituting 3-(3-benzyl-8-trifluoromethyl-quinolin-4-yl)-phenylamine and 3-(3-trifluoromethyl phenoxy)-benzaldehyde. MS (ESI) m/z 629.

EXAMPLE 752

{3-[3-BENZYL-8-(TRIFLUOROMETHYL)
QUINOLIN-4-YL]PHENYL}(2,6-DIMETHOXY-
BENZYL)AMINE

This compound was prepared according to the procedure of example 66, substituting 3-(3-benzyl-8-trifluoromethyl-quinolin-4-yl)-phenylamine and 2,6 dimethoxybenzaldehyde. MS (ESI) m/z 529.

EXAMPLE 753

{3-[3-BENZYL-8-(TRIFLUOROMETHYL)
QUINOLIN-4-YL]PHENYL}[3,5-BIS(BENZY-
LOXY)BENZYL]AMINE

This compound was prepared according to the procedure of example 66, substituting 3-(3-benzyl-8-trifluoromethyl-quinolin-4-yl)-phenylamine and 3,5-bis-benzyloxy benzaldehyde. MS (ESI) m/z 681.

EXAMPLE 754

{3-[3-BENZYL-8-(TRIFLUOROMETHYL)
QUINOLIN-4-YL]PHENYL}(2-METHOXYBEN-
ZYL)AMINE

This compound was prepared according to the procedure of example 66, substituting 3-(3-benzyl-8-trifluoromethyl-quinolin-4-yl)-phenylamine and 2 methoxybenzaldehyde. MS (ESI) m/z 499.

EXAMPLE 755

{3-[3-BENZYL-8-(TRIFLUOROMETHYL)
QUINOLIN-4-YL]PHENYL}(4-METHYLBEN-
ZYL)AMINE

This compound was prepared according to the procedure of example 66, substituting 3-(3-benzyl-8-trifluoromethyl-quinolin-4-yl)-phenylamine and 4-methylbenzaldehyde. MS (ESI) m/z 483.

EXAMPLE 756

{3-[3-BENZYL-8-(TRIFLUOROMETHYL)
QUINOLIN-4-YL]PHENYL}[(1-OXIDOPYRIDIN-
4-YL)METHYL]AMINE

This compound was prepared according to the procedure of example 66, substituting 3-(3-benzyl-8-trifluoromethyl-quinolin-4-yl)-phenylamine and 1-oxidopyridin-4-yl benzaldehyde. MS (ESI) m/z 484.

EXAMPLE 757

{3-[3-BENZYL-8-(TRIFLUOROMETHYL)
QUINOLIN-4-YL]PHENYL}[(4,5-DIMETHYL-2-
FURYL)METHYL]AMINE

This compound was prepared according to the procedure of example 66, substituting 3-(3-benzyl-8-trifluoromethyl-quinolin-4-yl)-phenylamine and 3,4-dimethylfuraldehyde. MS (ESI) m/z 487.

EXAMPLE 758

{3-[3-BENZYL-8-(TRIFLUOROMETHYL)
QUINOLIN-4-YL]PHENYL}(1-NAPHTHYLM-
ETHYL)AMINE

This compound was prepared according to the procedure of example 66, substituting 3-(3-benzyl-8-trifluoromethyl-quinolin-4-yl)-phenylamine and naphthalene-1 carbaldehyde. MS (ESI) m/z 519.

EXAMPLE 759

{3-[3-BENZYL-8-(TRIFLUOROMETHYL)
QUINOLIN-4-YL]PHENYL}(3,5-DIMETHOXY-
BENZYL)AMINE

This compound was prepared according to the procedure of example 66, substituting 3-(3-benzyl-8-trifluoromethyl-quinolin-4-yl)-phenylamine and 3,5 dimethoxylbenzaldehyde. MS (ESI) m/z 522.

EXAMPLE 760

{3-[3-BENZYL-8-(TRIFLUOROMETHYL) QUINOLIN-4-YL]PHENYL}(2,4-DIMETHOXY-BENZYL)AMINE

This compound was prepared according to the procedure of example 66, substituting 3-(3-benzyl-8-trifluoromethyl-quinolin-4-yl)-phenylamine and 2,4 dimethoxylbenzaldehyde. MS (ESI) m/z 529.

EXAMPLE 761

{3-[3-BENZYL-8-(TRIFLUOROMETHYL) QUINOLIN-4-YL]PHENYL}(2-NAPHTHYLMETHYL)AMINE

This compound was prepared according to the procedure of example 66, substituting 3-(3-benzyl-8-trifluoromethyl-quinolin-4-yl)-phenylamine and naphthalene-2 carbaldehyde. MS (ESI) m/z 519.

EXAMPLE 762

{3-[3-BENZYL-8-(TRIFLUOROMETHYL) QUINOLIN-4-YL]PHENYL}[4-(DIPHENYLAMINO)BENZYL]AMINE

This compound was prepared according to the procedure of example 66, substituting 3-(3-benzyl-8-trifluoromethyl-quinolin-4-yl)-phenylamine and 4-diphenylamino-benzaldehyde. MS (ESI) m/z 636.

EXAMPLE 763

{3-[3-BENZYL-8-(TRIFLUOROMETHYL) QUINOLIN-4-YL]PHENYL}(4-ISOPROPYLBENZYL)AMINE

This compound was prepared according to the procedure of example 66, substituting 3-(3-benzyl-8-trifluoromethyl-quinolin-4-yl)-phenylamine and 4 isopropylbenzaldehyde. MS (ESI) m/z 511.

EXAMPLE 764

{3-[3-BENZYL-8-(TRIFLUOROMETHYL) QUINOLIN-4-YL]PHENYL}(2-NITROBENZYL)AMINE

This compound was prepared according to the procedure of example 66, substituting 3-(3-benzyl-8-trifluoromethyl-quinolin-4-yl)-phenylamine and 2-nitrobenzaldehyde. MS (ESI) m/z 512.

EXAMPLE 765

{3-[3-BENZYL-8-(TRIFLUOROMETHYL) QUINOLIN-4-YL]PHENYL}(3-NITROBENZYL)AMINE

This compound was prepared according to the procedure of example 66, substituting 3-(3-benzyl-8-trifluoromethyl-quinolin-4-yl)-phenylamine and 3-nitrobenzaldehyde. MS (ESI) m/z 512.

EXAMPLE 766

METHYL 2-(4-{[3-(8-CHLORO-3-METHYLQUINOLIN-4-YL)PHENOXY]METHYL}PHENYL)-2 METHYLPROPANOATE

This compound was prepared according to the procedure of example 41, substituting 3-(8-chloro-3-methyl-quinolin-4-yl)-phenol and 3-(4-bromomethyl-phenyl)-3-methyl-butyric acid methyl ester. MS (ESI) m/z 460.

EXAMPLE 767

2-(4-{[3-(8-CHLORO-3-METHYLQUINOLIN-4-YL)PHENOXY]METHYL}PHENYL)-2-METHYL PROPANOIC ACID

This compound was prepared according to the procedure of example 41, substituting methyl 2-(4-{[3-(8-chloro-3-methylquinolin-4-yl)phenoxy]methyl}phenyl)-2 methylpropanoate. MS (ESI) m/z 446.

EXAMPLE 768

5-[({3-[3-BENZYL-8-(TRIFLUOROMETHYL) QUINOLIN-4-YL]PHENYL}AMINO)METHYL]-2-METHOXYPHENOL

This compound was prepared according to the procedure of example 66, substituting 3-(3-benzyl-8-trifluoromethyl-quinolin-4-yl)-phenylamine and 3-hydroxy-4-methoxy-benzaldehyde. MS (ESI) m/z 515.

EXAMPLE 769

4-[({3-[3-BENZYL-8-(TRIFLUOROMETHYL) QUINOLIN-4-YL]PHENYL}AMINO)METHYL]-2-METHOXYPHENOL

This compound was prepared according to the procedure of example 66, substituting 3-(3-benzyl-8-trifluoromethyl-quinolin-4-yl)-phenylamine and 4-hydroxy-3-methoxy-benzaldehyde. MS (ESI) m/z 515.

EXAMPLE 770

2-[({3-[3-BENZYL-8-(TRIFLUOROMETHYL) QUINOLIN-4-YL]PHENYL}AMINO)METHYL] BENZENE-1,4-DIOL

This compound was prepared according to the procedure of example 66, substituting 3-(3-benzyl-8-trifluoromethyl-quinolin-4-yl)-phenylamine and 2,5 dihydroxybenzaldehyde. MS (ESI) m/z 501.

EXAMPLE 771

{3-[3-BENZYL-8-(TRIFLUOROMETHYL) QUINOLIN-4-YL]PHENYL}(2-FLUORO-5-NITROBENZYL)AMINE

This compound was prepared according to the procedure of example 66, substituting 3-(3-benzyl-8-trifluoromethyl-quinolin-4-yl)-phenylamine and 2-fluoro-5 nitrobenzaldehyde. MS (ESI) m/z 532.

EXAMPLE 772

{3-[3-BENZYL-8-(TRIFLUOROMETHYL) QUINOLIN-4-YL]PHENYL}(5-BROMO-2-ETHOXYBENZYL) AMINE

This compound was prepared according to the procedure of example 66, substituting 3-(3-benzyl-8-trifluoromethyl-quinolin-4-yl)-phenylamine and 5-bromo-2-ethoxy benzaldehyde. MS (ESI) m/z 591.

EXAMPLE 773

{3-[3-BENZYL-8-(TRIFLUOROMETHYL) QUINOLIN-4-YL]PHENYL}(3-ETHOXY-4-METHOXYBENZYL)AMINE

This compound was prepared according to the procedure of example 66, substituting 3-(3-benzyl-8-trifluoromethyl-quinolin-4-yl)-phenylamine and 3-ethoxy-4-methoxy benzaldehyde. MS (ESI) m/z 591.

EXAMPLE 774

{3-[3-BENZYL-8-(TRIFLUOROMETHYL) QUINOLIN-4-YL]PHENYL}(2,5-DIFLUOROBENZYL)AMINE

This compound was prepared according to the procedure of example 66, substituting 3-(3-benzyl-8-trifluoromethyl-quinolin-4-yl)-phenylamine and 2,5 difluorobenzaldehyde. MS (ESI) m/z 505.

EXAMPLE 775

{3-[3-BENZYL-8-(TRIFLUOROMETHYL) QUINOLIN-4-YL]PHENYL}(3,4-DIFLUOROBENZYL)AMINE

This compound was prepared according to the procedure of example 66, substituting 3-(3-benzyl-8-trifluoromethyl-quinolin-4-yl)-phenylamine and 3,4 difluorobenzaldehyde. MS (ESI) m/z 505.

EXAMPLE 776

{3-[3-BENZYL-8-(TRIFLUOROMETHYL) QUINOLIN-4-YL]PHENYL}(5-BROMO-2-METHOXYBENZYL) AMINE

This compound was prepared according to the procedure of example 66, substituting 3-(3-benzyl-8-trifluoromethyl-quinolin-4-yl)-phenylamine and 5-bromo-2 methoxybenzaldehyde. MS (ESI) m/z 577.

EXAMPLE 777

{3-[3-BENZYL-8-(TRIFLUOROMETHYL) QUINOLIN-4-YL]PHENYL}(5-BROMO-2-FLUOROBENZYL) AMINE

This compound was prepared according to the procedure of example 66, substituting 3-(3-benzyl-8-trifluoromethyl-quinolin-4-yl)-phenylamine and 5-bromo-2-fluorobenz aldehyde. MS (ESI) m/z 565.

EXAMPLE 778

{3-[3-BENZYL-8-(TRIFLUOROMETHYL) QUINOLIN-4-YL]PHENYL}[2-FLUORO-3-(TRIFLUOROMETHYL)BENZYL]AMINE

This compound was prepared according to the procedure of example 66, substituting 3-(3-benzyl-8-trifluoromethyl-quinolin-4-yl)-phenylamine and 2-fluoro-3-trifluoromethyl benzaldehyde. MS (ESI) m/z 555.

EXAMPLE 779

{3-[3-BENZYL-8-(TRIFLUOROMETHYL) QUINOLIN-4-YL]PHENYL}(2-FLUORO-5-METHOXYBENZYL)AMINE

This compound was prepared according to the procedure of example 66, substituting 3-(3-benzyl-8-trifluoromethyl-quinolin-4-yl)-phenylamine and 2-fluoro-5-methoxy benzaldehyde. MS (ESI) m/z 517.

EXAMPLE 780

{3-[3-BENZYL-8-(TRIFLUOROMETHYL) QUINOLIN-4-YL]PHENYL}[2,5-BIS(TRIFLUOROMETHYL) BENZYL]AMINE

This compound was prepared according to the procedure of example 66, substituting 3-(3-benzyl-8-trifluoromethyl-quinolin-4-yl)-phenylamine and 2,5-bistrifluoromethyl benzaldehyde. MS (ESI) m/z 605.

EXAMPLE 781

{3-[3-BENZYL-8-(TRIFLUOROMETHYL) QUINOLIN-4-YL]PHENYL}(2-METHYLBENZYL)AMINE

This compound was prepared according to the procedure of example 66, substituting 3-(3-benzyl-8-trifluoromethyl-quinolin-4-yl)-phenylamine and 2-methylbenzaldehyde. MS (ESI) m/z 483.

EXAMPLE 782

{3-[3-BENZYL-8-(TRIFLUOROMETHYL) QUINOLIN-4-YL]PHENYL}(2,4,6-TRIFLUOROBENZYL)AMINE

This compound was prepared according to the procedure of example 66, substituting 3-(3-benzyl-8-trifluoromethyl-quinolin-4-yl)-phenylamine and 2,4,6 trifluorobenzaldehyde. MS (ESI) m/z 523.

EXAMPLE 783

{3-[3-BENZYL-8-(TRIFLUOROMETHYL) QUINOLIN-4-YL]PHENYL}(3-FLUORO-4-METHOXYBENZYL)AMINE

This compound was prepared according to the procedure of example 66, substituting 3-(3-benzyl-8-trifluoromethyl-quinolin-4-yl)-phenylamine and 3-fluoro-4-methoxybenz aldehyde. MS (ESI) m/z 517.

EXAMPLE 784

{3-[3-BENZYL-8-(TRIFLUOROMETHYL) QUINOLIN-4-YL]PHENYL}(CYCLOPROPYLM-ETHYL)AMINE

This compound was prepared according to the procedure of example 66, substituting 3-(3-benzyl-8-trifluoromethyl-quinolin-4-yl)-phenylamine and cyclopropanecarbaldehyde. MS (ESI) m/z 433.

EXAMPLE 785

{3-[3-BENZYL-8-(TRIFLUOROMETHYL) QUINOLIN-4-YL]PHENYL}[(2-METHYL-1H-IMIDAZOL-5-YL)METHYL]AMINE

This compound was prepared according to the procedure of example 66, substituting 3-(3-benzyl-8-trifluoromethyl-quinolin-4-yl)-phenylamine and 2-methyl-3H-imidazole-4-carbaldehyde. MS (ESI) m/z 473.

EXAMPLE 786

{3-[3-BENZYL-8-(TRIFLUOROMETHYL) QUINOLIN-4-YL] PHENYL}(PYRIDIN-3-YLM-ETHYL)AMINE

This compound was prepared according to the procedure of example 66, substituting 3-(3-benzyl-8-trifluoromethyl-quinolin-4-yl)-phenylamine and pyridine-3 carbaldehyde. MS (ESI) m/z 470.

EXAMPLE 787

{3-[3-BENZYL-8-(TRIFLUOROMETHYL) QUINOLIN-4-YL]PHENYL}(PYRIDIN-4-YLM-ETHYL)AMINE

This compound was prepared according to the procedure of example 66, substituting 3-(3-benzyl-8-trifluoromethyl-quinolin-4-yl)-phenylamine and pyridine-4 carbaldehyde. MS (ESI) m/z 470.

EXAMPLE 788

1-[4-({3-[3-BENZYL-8-(TRIFLUOROMETHYL) QUINOLIN-4-YL]BENZYL}OXY)PHENYL] ETHANE-1,2-DIOL

This compound was prepared according to the procedure of example 34, substituting {4-[3-(3-benzyl-8-trifluorom-ethyl-quinolin-4-yl)-benzyloxy]-phenyl}-oxo-acetic acid ethyl ester. MS (ESI) m/z 570.

EXAMPLE 789

ETHYL [4-({3-[3-BENZYL-8-(TRIFLUOROM-ETHYL)QUINOLIN-4-YL]BENZYL}OXY)PHE-NYL](OXO) ACETATE

This compound was prepared according to the procedure of example 69, substituting [3-(3-benzyl-8-trifluoromethyl-quinolin-4-yl)-phenyl]-methanol. MS (ESI) m/z 530.

EXAMPLE 790

{3-[3-BENZYL-8-(TRIFLUOROMETHYL) QUINOLIN-4-YL]PHENYL}(3-THIENYLM-ETHYL)AMINE

This compound was prepared according to the procedure of example 66, substituting 3-(3-benzyl-8-trifluoromethyl-quinolin-4-yl)-phenylamine and thiophene-3 carbaldehyde. MS (ESI) m/z 475.

EXAMPLE 791

{3-[3-BENZYL-8-(TRIFLUOROMETHYL) QUINOLIN-4-YL]PHENYL}(3-FURYLMETHYL) AMINE

This compound was prepared according to the procedure of example 66, substituting 3-(3-benzyl-8-trifluoromethyl-quinolin-4-yl)-phenylamine and furan-3-carbaldehyde. MS (ESI) m/z 459.

EXAMPLE 792

{3-[3-BENZYL-8-(TRIFLUOROMETHYL) QUINOLIN-4-YL]PHENYL}[2-(TRIFLUO-ROMETHOXY)BENZYL]AMINE

This compound was prepared according to the procedure of example 66, substituting 3-(3-benzyl-8-trifluoromethyl-quinolin-4-yl)-phenylamine and 2-trifluoromethoxy benzal-dehyde. MS (ESI) m/z 553.

EXAMPLE 793

{3-[3-BENZYL-8-(TRIFLUOROMETHYL) QUINOLIN-4-YL]PHENYL}[3-CHLORO-2-FLUORO-6-(TRIFLUOROMETHYL)BENZYL] AMINE

This compound was prepared according to the procedure of example 66, substituting 3-(3-benzyl-8-trifluoromethyl-quinolin-4-yl)-phenylamine and 3-chloro-2-fluoro-6-trif-luoro methyl-benzaldehyde. MS (ESI) m/z 587.

EXAMPLE 794

{3-[3-BENZYL-8-(TRIFLUOROMETHYL) QUINOLIN-4-YL]PHENYL}(PYRIDIN-2-YLM-ETHYL)AMINE

This compound was prepared according to the procedure of example 66, substituting 3-(3-benzyl-8-trifluoromethyl-quinolin-4-yl)-phenylamine and pyridine-2-carbaldehyde. MS (ESI) m/z 470.

EXAMPLE 795

{3-[3-BENZYL-8-(TRIFLUOROMETHYL) QUINOLIN-4-YL]PHENYL}[4-(TRIFLUO-ROMETHOXY)BENZYL]AMINE

This compound was prepared according to the procedure of example 66, substituting 3-(3-benzyl-8-trifluoromethyl-quinolin-4-yl)-phenylamine and 4-trifluoromethoxy-benz aldehyde. MS (ESI) m/z 551.

EXAMPLE 796

{3-[3-BENZYL-8-(TRIFLUOROMETHYL)
QUINOLIN-4-YL]PHENYL}(4-CHLORO-3-
FLUOROBENZYL)AMINE

This compound was prepared according to the procedure of example 66, substituting 3-(3-benzyl-8-trifluoromethyl-quinolin-4-yl)-phenylamine and 4-chloro-3-fluoro benzaldehyde. MS (ESI) m/z 519.

EXAMPLE 797

{3-[3-BENZYL-8-(TRIFLUOROMETHYL)
QUINOLIN-4-YL]PHENYL}[2-FLUORO-5-(TRIF-
LUOROMETHYL)

This compound was prepared according to the procedure of example 66, substituting 3-(3-benzyl-8-trifluoromethyl-quinolin-4-yl)-phenylamine and 2-fluoro-5 trifluoromethyl-benzaldehyde. MS (ESI) m/z 553.

EXAMPLE 798

{3-[3-BENZYL-8-(TRIFLUOROMETHYL)
QUINOLIN-4-YL]PHENYL}[3-(TRIFLUO-
ROMETHOXY)BENZYL]AMINE

This compound was prepared according to the procedure of example 66, substituting 3-(3-benzyl-8-trifluoromethyl-quinolin-4-yl)-phenylamine and 3-trifluoromethoxy-benzaldehyde. MS (ESI) m/z 553.

EXAMPLE 799

N-(1-BENZOFURAN-2-YLMETHYL)-3-[3-BEN-
ZYL-8-(TRIFLUOROMETHYL)QUINOLIN-4-YL]
ANILINE

This compound was prepared according to the procedure of example 66, substituting 3-(3-benzyl-8-trifluoromethyl-quinolin-4-yl)-phenylamine and benzofuran-2 carbaldehyde. MS (ESI) m/z 509.

EXAMPLE 800

{3-[3-BENZYL-8-(TRIFLUOROMETHYL)
QUINOLIN-4-YL]PHENYL}(QUINOLIN-3-YLM-
ETHYL)AMINE

This compound was prepared according to the procedure of example 66, substituting 3-(3-benzyl-8-trifluoromethyl-quinolin-4-yl)-phenylamine and quinoline-3 carbaldehyde. MS (ESI) m/z 518.

EXAMPLE 801

{3-[3-BENZYL-8-(TRIFLUOROMETHYL)
QUINOLIN-4-YL]PHENYL}(2,4-DIETHOXY-
BENZYL)AMINE

This compound was prepared according to the procedure of example 66, substituting 3-(3-benzyl-8-trifluoromethyl-quinolin-4-yl)-phenylamine and 2,4-diethoxybenzaldehyde. MS (ESI) m/z 557.

EXAMPLE 802

3,3'-(3-PHENYLQUINOLINE-4,8-DIYL)DIPHENOL

This compound was prepared according to the procedure of example 1, substituting 4-bromo-8-chloro-3-phenyl-quinoline and 3-hydroxybenzeneboronic acid MS (ESI) m/z 390.

EXAMPLE 803

2-(4-{[3-(8-CHLORO-3-METHYLQUINOLIN-4-
YL)PHENOXY]METHYL}PHENYL)PROPANOIC
ACID

This compound was prepared according to the procedure of example 41, substituting 3-(8-chloro-3-methyl-quinolin-4-yl)-phenol and 2-(4-bromomethyl-phenyl)-propionic acid methyl ester. MS (ESI) m/z 432.

EXAMPLE 804

3-BENZYL-4-{3-[(5-BROMO-2-METHOXYBEN-
ZYL)OXY]PHENYL}-8-(TRIFLUOROMETHYL)
QUINOLINE

This compound was prepared according to the procedure of example 41, substituting 3-(3-benzyl-8-chloro-quinolin-4-yl)-phenol and 1-bromo-2-bromomethyl-4-methoxy-benzene. MS (ESI) m/z 578.

EXAMPLE 805

3-BENZYL-4-{3-[(2,3-DIMETHYLBENZYL)
OXY]PHENYL}-8-(TRIFLUOROMETHYL)
QUINOLINE

This compound was prepared according to the procedure of example 69, substituting 3-(3-benzyl-8-chloro-quinolin-4-yl)-phenol and (2,3-dimethyl-phenyl)-methanol. MS (ESI) m/z 498.

EXAMPLE 806

3-BENZYL-4-{3-[(2-METHOXYBENZYL)OXY]
PHENYL}-8-(TRIFLUOROMETHYL)QUINO-
LINE

This compound was prepared according to the procedure of example 69, substituting 3-(3-benzyl-8-chloro-quinolin-4-yl)-phenol and (2-methoxyphenyl)-methanol. MS (ESI) m/z 500.

EXAMPEL 807

(2R)-2-(4-{[3-(8-CHLORO-3-METHYLQUINO-
LIN-4-YL)PHENOXY]METHYL}PHENYL)PRO-
PANOIC ACID

This compound was prepared according to the procedure of example 41, substituting 3-(8-chloro-3-methyl-quinolin-4-yl)-phenol and 2-(4-bromomethyl-phenyl)-propionic acid methyl ester. Purification by supercritical fluid chromatography (MeOH/CO$_2$). Electronic circular dichroism CD $\lambda_{max}$=+6 mdeg @ 226 nm (EtOH). MS (ESI) m/z 432.

EXAMPLE 808

(2S)-2-(4-{[3-(8-CHLORO-3-METHYLQUINO-
LIN-4-YL)PHENOXY]METHYL}PHENYL)PRO-
PANOIC ACID

This compound was prepared according to the procedure of example 41, substituting 3-(8-chloro-3-methyl-quinolin-4-yl)-phenol and 2-(4-bromomethyl-phenyl)-propionic acid methyl ester. Purification by supercritical fluid chromatography (MeOH/CO₂). Electronic circular dichroism CD λ_max=−4 mdeg @ 225 nm (EtOH). MS (ESI) m/z 432.

EXAMPLE 809

{3-[3-BENZYL-8-(TRIFLUOROMETHYL) QUINOLIN-4-YL]PHENYL}[(2-METHOXY-1-NAPHTHYL) METHYL]AMINE

This compound was prepared according to the procedure of example 66, substituting 3-(3-benzyl-8-trifluoromethyl-quinolin-4-yl)-phenylamine and 2-methoxy-naphthalene-1-carbaldehyde. MS (ESI) m/z 379.

EXAMPLE 810

{3-[3-BENZYL-8-(TRIFLUOROMETHYL) QUINOLIN-4-YL]PHENYL}(2-CHLOROBENZYL)AMINE

This compound was prepared according to the procedure of example 66, substituting 3-(3-benzyl-8-trifluoromethyl-quinolin-4-yl)-phenylamine and 1-bromomethyl-2-chlorobenzene. MS (ESI) m/z 503.

EXAMPLE 811

{3-[3-BENZYL-8-(TRIFLUOROMETHYL) QUINOLIN-4-YL]PHENYL}[(6-BROMO-1,3-BENZODIOXOL-5-YL)METHYL]AMINE

This compound was prepared according to the procedure of example 66, substituting 3-(3-benzyl-8-trifluoromethyl-quinolin-4-yl)-phenylamine and 6-bromo benzo[1,3]dioxole-5-carbaldehyde. MS (ESI) m/z 591.

EXAMPLE 812

{3-[3-BENZYL-8-(TRIFLUOROMETHYL) QUINOLIN-4-YL]PHENYL}BIS(2-CHLOROBENZYL)AMINE

This compound was prepared according to the procedure of example 41, substituting 3-(3-benzyl-8-trifluoromethyl-quinolin-4-yl)-phenylamine and 1-bromomethyl-2-chlorobenzene MS (ESI) m/z 627.

EXAMPLE 813

{3-[3-BENZYL-8-(TRIFLUOROMETHYL) QUINOLIN-4-YL]PHENYL}[(6-METHOXY-2-NAPHTHYL) METHYL]AMINE

This compound was prepared according to the procedure of example 66, substituting 3-(3-benzyl-8-trifluoromethyl-quinolin-4-yl)-phenylamine and 6-methoxy-naphthalene-2-carbaldehyde. MS (ESI) m/z 549.

EXAMPLE 814

N-(9-ANTHRYLMETHYL)-3-[3-BENZYL-8-(TRIFLUOROMETHYL)QUINOLIN-4-YL]Aniline

This compound was prepared according to the procedure of example 66, substituting 3-(3-benzyl-8-trifluoromethyl-quinolin-4-yl)-phenylamine and anthracene-9-carbaldehyde. MS (ESI) m/z 569.

EXAMPLE 815

{3-[3-BENZYL-8-(TRIFLUOROMETHYL) QUINOLIN-4-YL]PHENYL}(2-ISOPROPOXY-BENZYL)AMINE

This compound was prepared according to the procedure of example 66, substituting 3-(3-benzyl-8-trifluoromethyl-quinolin-4-yl)-phenylamine and 2-isopropoxy-benzaldehyde. MS (ESI) m/z 527.

EXAMPLE 816

3-BENZYL-4-(3-{[2-(DIFLUOROMETHOXY) BENZYL]OXY}PHENYL)-8-(TRIFLUOROMETHYL)QUINOLINE

This compound was prepared according to the procedure of example 69, substituting 3-(3-benzyl-8-trifluoromethyl-quinolin-4-yl)-phenol and (2-difluoromethoxy-phenyl)-methanol. MS (ESI) m/z 535.

EXAMPLE 817

{3-[3-BENZYL-8-(TRIFLUOROMETHYL) QUINOLIN-4-YL]PHENYL}[2,4-BIS(TRIFLUOROMETHYL)BENZYL]AMINE

This compound was prepared according to the procedure of example 66, substituting 3-(3-benzyl-8-trifluoromethyl-quinolin-4-yl)-phenylamine and 2,4-bis-trifluoromethyl-benzaldehyde. MS (ESI) m/z 602.

EXAMPLE 818

{3-[3-BENZYL-8-(TRIFLUOROMETHYL) QUINOLIN-4-YL]PHENYL}[4-FLUORO-2-(TRIFLUOROMETHYL) BENZYL]AMINE

This compound was prepared according to the procedure of example 66, substituting 3-(3-benzyl-8-trifluoromethyl-quinolin-4-yl)-phenylamine and 4-fluoro-2 trifluoromethyl-benzaldehyde. MS (ESI) m/z 552.

EXAMPLE 819

{3-[3-BENZYL-8-(TRIFLUOROMETHYL) QUINOLIN-4-YL]PHENYL}[2-CHLORO-3-(TRIFLUOROMETHYL) BENZYL]AMINE

This compound was prepared according to the procedure of example 66, substituting 3-(3-benzyl-8-trifluoromethyl-quinolin-4-yl)-phenylamine and 2-chloro-3 trifluoromethyl-benzaldehyde. MS (ESI) m/z 552.

EXAMPLE 820

{3-[3-BENZYL-8-(TRIFLUOROMETHYL) QUINOLIN-4-YL]PHENYL}[(2,6-DICHLOROPYRIDIN-4-YL)METHYL]AMINE

This compound was prepared according to the procedure of example 66, substituting 3-(3-benzyl-8-trifluoromethyl-quinolin-4-yl)-phenylamine and 2,6-dichloro-pyridine-4-carbaldehyde. MS (ESI) m/z 535.

EXAMPLE 821

{3-[3-BENZYL-8-(TRIFLUOROMETHYL)
QUINOLIN-4-YL]PHENYL}[(3-BROMO-5-IODO-
4-METHYL-2-THIENYL)METHYL]AMINE

This compound was prepared according to the procedure of example 66, substituting 3-(3-benzyl-8-trifluoromethyl-quinolin-4-yl)-phenylamine and 3-bromo-5-iodo-4-methyl-thiophene-2-carbaldehyde. MS (ESI) m/z 693.

EXAMPLE 822

{3-[3-BENZYL-8-(TRIFLUOROMETHYL)
QUINOLIN-4-YL]PHENYL}[(3-METHYL-1-BEN-
ZOTHIEN-2-YL)METHYL]AMINE

This compound was prepared according to the procedure of example 66, substituting 3-(3-benzyl-8-trifluoromethyl-quinolin-4-yl)-phenylamine and 3-methyl benzo[b]thiophene-2-carbaldehyde. MS (ESI) m/z 539.

EXAMPLE 823

N-(1-BENZOTHIEN-3-YLMETHYL)-3-[3-BEN-
ZYL-8-(TRIFLUOROMETHYL)QUINOLIN-4-YL]
ANILINE

This compound was prepared according to the procedure of example 66, substituting 3-(3-benzyl-8-trifluoromethyl-quinolin-4-yl)-phenylamine and benzo[b]thiophene-3-carbaldehyde. MS (ESI) m/z 525.

EXAMPLE 824

{3-[3-BENZYL-8-(TRIFLUOROMETHYL)
QUINOLIN-4-YL]PHENYL}[(5-BROMO-2-THIE-
NYL)METHYL]AMINE

This compound was prepared according to the procedure of example 66, substituting 3-(3-benzyl-8-trifluoromethyl-quinolin-4-yl)-phenylamine and 5-bromo-thiophene-2-carbaldehyde. MS (ESI) m/z 553.

EXAMPLE 825

{3-[3-BENZYL-8-(TRIFLUOROMETHYL)
QUINOLIN-4-YL]PHENYL}[(5-METHYL-2-
THIENYL)METHYL]AMINE

This compound was prepared according to the procedure of example 66, substituting 3-(3-benzyl-8-trifluoromethyl-quinolin-4-yl)-phenylamine and 5-methyl-thiophene-2-carbaldehyde. MS (ESI) m/z 489.

EXAMPLE 826

{3-[3-BENZYL-8-(TRIFLUOROMETHYL)
QUINOLIN-4-YL]PHENYL}[2-(DIFLUO-
ROMETHOXY)BENZYL]AMINE

This compound was prepared according to the procedure of example 66, substituting 3-(3-benzyl-8-trifluoromethyl-quinolin-4-yl)-phenylamine and 2-difluoromethoxy-benzaldehyde. MS (ESI) m/z 535.

EXAMPLE 827

3-BENZYL-4-(3-{[2-(TRIFLUOROMETHOXY)
BENZYL]OXY}PHENYL)-8-(TRIFLUOROM-
ETHYL)QUINOLINE

This compound was prepared according to the procedure of example 69, substituting 3-(3-benzyl-8-trifluoromethyl-quinolin-4-yl)-phenol and (2-trifluoromethoxy-phenyl)-methanol. MS (ESI) m/z 554.

EXAMPLE 828

3-BENZYL-4-[3-(1,2,3,4-TETRAHYDRONAPH-
THALEN-1-YLMETHOXY)PHENYL]-8-(TRIF-
LUOROMETHYL)QUINOLINE

This compound was prepared according to the procedure of example 69, substituting 3-(3-benzyl-8-trifluoromethyl-quinolin-4-yl)-phenol and (1,2,3,4-tetrahydro naphthalen-1-yl)-methanol. MS (ESI) m/z 524.

EXAMPLE 829

3-BENZYL-4-[3-(2,3-DIHYDRO-1H-INDEN-1-
YLMETHOXY)PHENYL]-8-(TRIFLUOROM-
ETHYL)QUINOLINE

This compound was prepared according to the procedure of example 69, substituting 3-(3-benzyl-8-trifluoromethyl-quinolin-4-yl)-phenol and indan-1-yl-methanol. MS (ESI) m/z 510.

EXAMPLE 830

3-BENZYL-4-[3-(1-PHENYLETHOXY)PHENYL]-
8-(TRIFLUOROMETHYL)QUINOLINE

This compound was prepared according to the procedure of example 69, substituting 3-(3-benzyl-8-trifluoromethyl-quinolin-4-yl)-phenol and 1-phenyl-ethanol. MS (ESI) m/z 484.

EXAMPLE 831

3-BENZYL-4-{3-[1-(2-CHLOROPHENYL)
ETHOXY]PHENYL}-8-(TRIFLUOROMETHYL)
QUINOLINE

This compound was prepared according to the procedure of example 69, substituting 3-(3-benzyl-8-trifluoromethyl-quinolin-4-yl)-phenol and 1-(2-chloro-phenyl)-ethanol. MS (ESI) m/z 519.

EXAMPLE 832

3-BENZYL-4-{3-[1-(2,5-DICHLOROPHENYL)
ETHOXY]PHENYL}-8-(TRIFLUOROMETHYL)
QUINOLINE

This compound was prepared according to the procedure of example 69, substituting 3-(3-benzyl-8-trifluoromethyl-quinolin-4-yl)-phenol and 1-(2,5-dichloro-phenyl) ethanol. MS (ESI) m/z 553.

EXAMPLE 833

3-(3-BENZYL-8-CHLOROQUINOLIN-4-YL)PHENOL

The title compound was prepared from 4-bromo-8-chloro-3-methyl-quinoline and 3-hydroxyphenyl boronic acid according to the procedure of Example 1. MS (ES) m/z 343.9.

EXAMPLE 834

3-(8-CHLORO-3-METHYLQUINOLIN-4-YL) PHENOL

The title compound was prepared from 3-benzyl-4-bromo-8-chloro-quinoline and 3-hydroxyphenyl boronic acid according to the procedure of Example 1. MS (ES) m/z 267.9.

EXAMPLE 835

{3-[3-BENZYL-8-(TRIFLUOROMETHYL) QUINOLIN-4-YL]PHENYL}[4-(TRIFLUOROMETHYL)BENZYL]AMINE

The title compound was prepared from {3-[3-benzyl-8-(trifluoromethyl)quinolin-4-yl]phenyl}amine and 4-trifluorobenzaldehyde according to the procedure of step 1, Example 66. MS (ESI) m/z 537;

EXAMPLE 836

ETHYL2-[4-({3-[3-BENZYL-8-(TRIFLUOROMETHYL)QUINOLIN-4-YL]PHENOXY}METHYL) PHENYL]PROPANOATE

The title compound was prepared from 3-[3-benzyl-8-(trifluoromethyl)quinolin-4-yl]phenol and 2-(4-Bromomethylphenyl)-propionic acid propyl ester as in the procedure of Example 43. MS m/z 570;

EXAMPLE 837

METHYL 2-[4-({3-[3-BENZYL-8-(TRIFLUOROMETHYL)QUINOLIN-4-YL] PHENOXY}METHYL)PHENYL]-2-METHYL-PROPANOATE

The title compound was prepared from 3-[3-benzyl-8-(trifluoromethyl)quinolin-4-yl]phenol and 2-(4-Bromomethylphenyl)-2-methyl-propionic acid ethyl ester as in the procedure of Example 43. MS m/z 570;

EXAMPLE 838

{3-[3-(2-METHYLPHENYL)-8-(TRIFLUOROMETHYL)QUINOLIN-4-YL]PHENYL}AMINE

This compound was prepared according to the procedure of Example 1 step 5, using 4-Bromo-3-o-tolyl-8-trifluoromethyl-quinoline and substituting 3-aminophenyl boronic acid for phenyl boronic acid. mp 148-151° C., MS(ES)m/z 378.9;

EXAMPLE 839

(3-{8-(TRIFLUOROMETHYL)-3-[2-(TRIFLUOROMETHYL)PHENYL]QUINOLIN-4-YL}PHENYL)AMINE

This compound was prepared according to the procedure of Example 1 step 5, using 4-Bromo-3-o-trifluoromethylphenyl-8-trifluoromethyl-quinoline and substituting 3-aminophenyl boronic acid for phenyl boronic acid.

EXAMPLE 840

ETHYL[4-({3-[3-BENZYL-8-(TRIFLUOROMETHYL)QUINOLIN-4-YL]PHENOXY}METHYL) PHENYL]ACETATE

The title compound was prepared from 3-[3-benzyl-8-(trifluoromethyl)quinolin-4-yl]phenol and (4-Bromomethylphenyl)-acetic acid propyl ester as in the procedure of Example 43. MS (ESI) m/z 556;

EXAMPLE 841

[4-((1S)-1-{3-[3-BENZYL-8-(TRIFLUOROMETHYL)QUINOLIN-4-YL]PHENOXY}ETHYL) PHENYL]ACETIC ACID

The title compound was prepared using the procedure of example 69 using 3-[3-benzyl-8-(trifluoromethyl)quinolin-4-yl]phenol as the phenol and [4-(1-Hydroxy-ethyl)-phenyl]-acetic acid ethyl ester as the alcohol .MS (ESI) m/z 540;

EXAMPLE 842

{3-[3-BENZYL-8-(TRIFLUOROMETHYL) QUINOLIN-4-YL]PHENYL}(2,3,5-TRICHLOROBENZYL)AMINE

The title compound was prepared from {3-[3-benzyl-8-(trifluoromethyl)quinolin-4-yl]phenyl}amine and 2,3,5-trichlorobenzaldehyde according to the procedure of step 1, Example 66. MS (ESI) m/z 571.

EXAMPLE 843

{3-[3-BENZYL-8-(TRIFLUOROMETHYL) QUINOLIN-4-YL]PHENYL}[(1-METHYL-1 H-INDOL-6-YL)METHYL]AMINE

The title compound was prepared from {3-[3-benzyl-8-(trifluoromethyl)quinolin-4-yl]phenyl}amine and 6-formyl-1-methylindole to the procedure of step 1, Example 66. MS (ESI) m/z 522.

By procedures similar to those in the preceding examples, the following Examples 844 to 1203 were prepared.

| Example | Name | MS | HRMS | Example Number of Similar Procedure |
|---|---|---|---|---|
| Example 844 | methyl 4-(4-{3-[3-benzyl-8-(trifluoromethyl)quinolin-4-yl]phenoxy}phenoxy)butanoate | MS (ES) m/z 572.0; | HRMS: calcd for $C_{34}H_{28}F_3NO_4$ + H+, 572.20432; found (ESI, [M + H]+), 572.2064; | 478 |

-continued

| Example | Name | MS | HRMS | Example Number of Similar Procedure |
|---|---|---|---|---|
| Example 845 | methyl 5-(4-{3-[3-benzyl-8-(trifluoromethyl)quinolin-4-yl]phenoxy}phenoxy)pentanoate | MS (ESI) m/z 586; | HRMS: calcd for $C_{35}H_{30}F_3NO_4$ + H+, 586.21997; found (ESI, [M + H]+), 586.2192; | 478 |
| Example 846 | 4-(4-{3-[3-benzyl-8-(trifluoromethyl)quinolin-4-yl]phenoxy}phenoxy)butanoic acid | MS (ES) m/z 556.0; | | 66 |
| Example 847 | 5-(4-{3-[3-benzyl-8-(trifluoromethyl)quinolin-4-yl]phenoxy}phenoxy)pentanoic acid | MS (ES) m/z 570.0; | HRMS: calcd for $C_{34}H_{28}F_3NO_4$ + H+, 572.20432; found (ESI, [M + H]+), 572.2042; | 66 |
| Example 848 | 3-[3-(4-chlorobenzyl)-8-(trifluoromethyl)quinolin-4-yl]phenol | MS (ESI) m/z 414; | HRMS: calcd for $C_{23}H_{15}ClF_3NO$ + H+, 414.08670; found (ESI, [M + H]+), 414.0859; | 457 |
| Example 849 | methyl {[4-({3-[3-(4-chlorobenzyl)-8-(trifluoromethyl)quinolin-4-yl]phenoxy}methyl)benzyl]oxy}acetate | MS (ES) m/z 605.9; | | 44 |
| Example 850 | methyl 3-[4-({3-[3-methyl-8-(trifluoromethyl)quinolin-4-yl]phenoxy}methyl)phenyl]propanoate | | HRMS: calcd for $C_{28}H_{24}F_3NO_3$ + H+, 480.17810; found (ESI, [M + H]+), 480.1776; | 365 |
| Example 851 | 3-[(4-{3-[3-benzyl-8-(trifluoromethyl)quinolin-4-yl]phenoxy}phenoxy)methyl]benzoic acid | MS (ES) m/z 603.9; | HRMS: calcd for $C_{37}H_{26}F_3NO_4$ + H+, 606.18867; found (ESI, [M + H]+), 606.1906; | 66 |
| Example 852 | 3-[4-({3-[3-methyl-8-(trifluoromethyl)quinolin-4-yl]phenoxy}methyl)phenyl]propanoic acid | | HRMS: calcd for $C_{27}H_{22}F_3NO_3$ + H+, 466.16245; found (ESI, [M + H]+), 466.1631; | 216 |
| Example 853 | 3-[3-(2-phenylethyl)-8-(trifluoromethyl)quinolin-4-yl]phenol | MS (ESI) m/z 394.4 (M + H)+, 392.3 (M − H)+ | | 457 |
| Example 854 | 3-[3-(2,4,6-trifluorobenzyl)-8-(trifluoromethyl)quinolin-4-yl]phenol | MS (ESI) m/z 433.7 (M + H)+, 431.9 (M − H)+ | | 457 |
| Example 855 | 3-[3-(3-phenylpropyl)-8-(trifluoromethyl)quinolin-4-yl]phenol | MS (ES) m/z 406.0; | | 457 |
| Example 856 | 3-[3-(4-phenylbutyl)-8-(trifluoromethyl)quinolin-4-yl]phenol | MS (ES) m/z 420.0; | | 457 |
| Example 857 | 3-[3-(5-phenylpentyl)-8-(trifluoromethyl)quinolin-4-yl]phenol | MS (ESI) m/z 436; | | 457 |
| Example 858 | 3-[3-(diphenylmethyl)-8-(trifluoromethyl)quinolin-4-yl]phenol | MS (ESI) m/z 456; | | 457 |
| Example 859 | [4-({3-[3-(2,4,6-trifluorobenzyl)-8-(trifluoromethyl)quinolin-4-yl]phenoxy}methyl)phenyl]acetic acid | MS (ESI) m/z 582; | | 66 |

| Example | Name | MS | HRMS | Example Number of Similar Procedure |
|---|---|---|---|---|
| Example 860 | [4-({3-[3-(2-methylphenyl)-8-(trifluoromethyl)quinolin-4-yl]phenoxy}methyl)phenyl]acetic acid | MS (ESI) m/z 528.2 (M + H)+, 526.2 (M − H)+ | | 66 |
| Example 861 | 3-[4-({3-[3-(2-methylphenyl)-8-(trifluoromethyl)quinolin-4-yl]phenoxy}methyl)phenyl]propanoic acid | MS (ESI) m/z 542.1 (M + H)+, 540.2 (M − H)+ | | 66 |
| Example 862 | 3-[4-({3-[3-(2,4,6-trifluorobenzyl)-8-(trifluoromethyl)quinolin-4-yl]phenoxy}methyl)phenyl]propanoic acid | MS (ESI) m/z 596.1 (M + H)+, 594.0 (M − H)+ | | 66 |
| Example 863 | 3-[4-({3-[3-benzyl-8-(trifluoromethyl)quinolin-4-yl]phenoxy}methyl)phenyl]propanoic acid | MS (ESI) m/z 542.0 (M + H)+, 439.8 (M − H)+ | | 66 |
| Example 864 | 3-{4-[(3-{8-(trifluoromethyl)-3-[2-(trifluoromethyl)phenyl]quinolin-4-yl}phenoxy)methyl]phenyl}propanoic acid | MS (ESI) m/z 595.9 (M + H)+, 593.8 (M − H)+ | | 66 |
| Example 865 | 3-[4-({3-[3-methyl-8-(trifluoromethyl)quinolin-4-yl]phenoxy}methyl)phenyl]propanamide | | HRMS: calcd for $C_{27}H_{23}F_3N_2O_2$ + H+, 465.17844; found (ESI, [M + H]+), 465.1777; | 713 |
| Example 866 | 4-{3-[(4-fluorobenzyl)oxy]phenyl}-3-methyl-8-(trifluoromethyl)quinoline | | HRMS: calcd for $C_{24}H_{17}F_4NO$ + H+, 412.13190; found (ESI, [M + H]+), 412.1331; | 365 |
| Example 867 | 4-{3-[(2-chlorobenzyl)oxy]phenyl}-3-methyl-8-(trifluoromethyl)quinoline | | HRMS: calcd for $C_{24}H_{17}ClF_3NO$ + H+, 428.10235; found (ESI, [M + H]+), 428.104; | 365 |
| Example 868 | [4-({3-[3-methyl-8-(trifluoromethyl)quinolin-4-yl]phenoxy}methyl)phenoxy]acetonitrile | | HRMS: calcd for $C_{26}H_{19}F_3N_2O_2$ + H+, 449.14714; found (ESI, [M + H]+), 449.1494; | 365 |
| Example 869 | 2-{2-[4-({3-[3-methyl-8-(trifluoromethyl)quinolin-4-yl]phenoxy}methyl)phenoxy]ethyl}-1H-isoindole-1,3(2H)-dione | | HRMS: calcd for $C_{34}H_{25}F_3N_2O_4$ + H+, 583.18392; found (ESI, [M + H]+), 583.1832; | 365 |
| Example 870 | methyl [4-({3-[3-methyl-8-(trifluoromethyl)quinolin-4-yl]phenoxy}methyl)phenoxy]acetate | | HRMS: calcd for $C_{27}H_{22}F_3NO_4$ + H+, 482.15737; found (ESI, [M + H]+), 482.1578; | 365 |
| Example 871 | methyl [3-({3-[3-methyl-8-(trifluoromethyl)quinolin-4-yl]phenoxy}methyl)phenoxy]acetate | | HRMS: calcd for $C_{27}H_{22}F_3NO_4$ + H+, 482.15737; found (ESI, [M + H]+), 482.1553; | 365 |

-continued

| Example | Name | MS | HRMS | Example Number of Similar Procedure |
|---|---|---|---|---|
| Example 872 | 3-[4-({3-[3-phenyl-8-(trifluoromethyl)quinolin-4-yl]phenoxy}methyl)phenyl]propanoic acid | MS (ESI) m/z 528; | | 41 |
| Example 873 | methyl 3-[4-({3-[3-methyl-8-(trifluoromethyl)quinolin-4-yl]phenoxy}methyl)phenyl]prop-2-ynoate | | HRMS: calcd for $C_{28}H_{20}F_3NO_3$ + H+, 476.14680; found (ESI, [M + H]+), 476.1452; | 365 |
| Example 874 | methyl {[4-({3-[3-methyl-8-(trifluoromethyl)quinolin-4-yl]phenoxy}methyl)benzyl]oxy}acetate | | HRMS: calcd for $C_{28}H_{24}F_3NO_4$ + H+, 496.17302; found (ESI, [M + H]+) 496.1765 | 365 |
| Example 875 | methyl {[3-({3-[3-methyl-8-(trifluoromethyl)quinolin-4-yl]phenoxy}methyl)benzyl]oxy}acetate | | HRMS: calcd for $C_{28}H_{24}F_3NO_4$ + H+, 496.17302; found (ESI, [M + H]+), 496.1756; | 365 |
| Example 876 | 3-[8-(trifluoromethyl)quinolin-4-yl]phenol | MS (ESI) m/z 290; | | 42 |
| Example 877 | 3-[3-(2-ethylphenyl)-8-(trifluoromethyl)quinolin-4-yl]phenol | MS (ES) m/z 391.9; | HRMS: calcd for $C_{24}H_{18}F_3NO$ + H+, 394.14132; found (ESI, [M + H]+), 394.1398; | 457 |
| Example 878 | 3-[3-(2-isopropylphenyl)-8-(trifluoromethyl)quinolin-4-yl]phenol | MS (ES) m/z 405.9; | HRMS: calcd for $C_{25}H_{20}F_3NO$ + H+, 408.15697; found (ESI, [M + H]+), 408.1552; | 457 |
| Example 879 | [4-({3-[3-methyl-8-(trifluoromethyl)quinolin-4-yl]phenoxy}methyl)phenoxy]acetic acid | | HRMS: calcd for $C_{26}H_{20}F_3NO_4$ + H+, 468.14172; found (ESI, [M + H]+), 468.1411; | 216 |
| Example 880 | [3-({3-[3-methyl-8-(trifluoromethyl)quinolin-4-yl]phenoxy}methyl)phenoxy]acetic acid | | HRMS: calcd for $C_{26}H_{20}F_3NO_4$ + H+, 468.14172; found (ESI, [M + H]+), 468.1413; | 216 |
| Example 881 | 3-[4-({3-[3-methyl-8-(trifluoromethyl)quinolin-4-yl]phenoxy}methyl)phenyl]prop-2-ynoic acid | $^1$H NMR (CDCl$_3$): d 04-1429-INH; CONSISTENT | HRMS: calcd for $C_{27}H_{18}F_3NO_3$ + H+, 462.13115; found (ESI, [M + H ]+), 462.1307; | 216 |
| Example 882 | (2E)-3-[4-({3-[3-methyl-8-(trifluoromethyl)quinolin-4-yl]phenoxy}methyl)phenyl]acrylic acid | | HRMS: calcd for $C_{27}H_{20}F_3NO_3$ + H+, 464.14680; found (ESI, [M + H]+), 464.1449; | 216 |

| Example | Name | MS | HRMS | Example Number of Similar Procedure |
|---|---|---|---|---|
| Example 883 | {[4-({3-[3-methyl-8-(trifluoromethyl)quinolin-4-yl]phenoxy}methyl)benzyl]oxy}acetic acid | | HRMS: calcd for $C_{27}H_{22}F_3NO_4$ + H+, 482.15737; found (ESI, [M + H]+), 482.1563; | 216 |
| Example 884 | {[3-({3-[3-methyl-8-(trifluoromethyl)quinolin-4-yl]phenoxy}methyl)benzyl]oxy}acetic acid | | HRMS: calcd for $C_{27}H_{22}F_3NO_4$ + H+, 482.15737; found (ESI, [M + H]+), 482.1559; | 216 |
| Example 885 | methyl {[3-({3-[3-(4-chlorobenzyl)-8-(trifluoromethyl)quinolin-4-yl]phenoxy}methyl)benzyl]oxy}acetate | MS (ESI) m/z 606; | HRMS: calcd for $C_{34}H_{27}ClF_3NO_4$ + H+, 606.16535; found (ESI, [M + H]+), 606.1656; | 44 |
| Example 886 | methyl 3-[4-({3-[3-(4-chlorobenzyl)-8-(trifluoromethyl)quinolin-4-yl]phenoxy}methyl)phenyl]propanoate | MS (ES) m/z 590.0; | HRMS: calcd for $C_{34}H_{27}ClF_3NO_3$ + H+, 590.17043; found (ESI, [M + H]+), 590.17; | 44 |
| Example 887 | methyl [4-({3-[3-(4-chlorobenzyl)-8-(trifluoromethyl)quinolin-4-yl]phenoxy}methyl)phenoxy]acetate | MS (ESI) m/z 592; | HRMS: calcd for $C_{33}H_{25}ClF_3NO_4$ + H+, 592.14970; found (ESI, [M + H]+), 592.1487; | 44 |
| Example 888 | methyl [3-({3-[3-(4-chlorobenzyl)-8-(trifluoromethyl)quinolin-4-yl]phenoxy}methyl)phenoxy]acetate | MS (ESI) m/z 592; | HRMS: calcd for $C_{33}H_{25}ClF_3NO_4$ + H+, 592.14970; found (ESI, [M + H]+), 592.1516; | 44 |
| Example 889 | methyl 3-[4-({3-[3-(2-ethylphenyl)-8-(trifluoromethyl)quinolin-4-yl]phenoxy}methyl)phenyl]propanoate | MS (ESI) m/z 570; | HRMS: calcd for $C_{35}H_{30}F_3NO_3$ + H+, 570.22505; found (ESI, [M + H]+), 570.2228; | 478 |
| Example 890 | methyl 3-[4-({3-[3-(2-isopropylphenyl)-8-(trifluoromethyl)quinolin-4-yl]phenoxy}methyl)phenyl]propanoate | MS (ESI) m/z 584; | HRMS: calcd for $C_{36}H_{32}F_3NO_3$ + H+, 584.24070; found (ESI, [M + H]+), 584.2404; | 478 |
| Example 891 | [4-({3-[8-(trifluoromethyl)quinolin-4-yl]phenoxy}methyl)phenyl]acetic acid | MS (ESI) m/z 438; | | 41 |
| Example 892 | [4-({4-fluoro-3-[phenyl-8-(trifluoromethyl)quinolin-4-yl]phenoxy}methyl)phenyl]acetic acid | MS (ESI) m/z 532; | | 41 |
| Example 893 | 3-[4-({3-[3-(2-ethylphenyl)-8-(trifluoromethyl)quinolin-4-yl]phenoxy}methyl)phenyl]propanoic acid | MS (ESI) m/z 556; | HRMS: calcd for $C_{34}H_{28}F_3NO_3$ + H+, 556.20940; found (ESI, [M + H]+), 556.2069; | 66 |

-continued

| Example | Name | MS | HRMS | Example Number of Similar Procedure |
|---|---|---|---|---|
| Example 894 | 3-[4-({3-[3-(2-isopropylphenyl)-8-(trifluoromethyl)quinolin-4-yl]phenoxy}methyl)phenyl]propanoic acid | MS (ESI) m/z 570; | HRMS: calcd for $C_{35}H_{30}F_3NO_3$ + H+, 570.22505; found (ESI, [M + H]+), 570.2247; | 66 |
| Example 895 | {4-[(4-{3-[3-benzyl-8-(trifluoromethyl)quinolin-4-yl]phenoxy}phenoxy)methyl]phenyl}acetic acid | MS (ESI) m/z 620; | | 66 |
| Example 896 | {[4-({3-[3-(4-chlorobenzyl)-8-(trifluoromethyl)quinolin-4-yl]phenoxy}methyl)benzyl]oxy}acetic acid | | HRMS: calcd for $C_{33}H_{25}ClF_3NO_4$ + H+, 592.14970; found (ESI, [M + H]+), 592.1481; | 66 |
| Example 897 | {[3-({3-[3-(4-chlorobenzyl)-8-(trifluoromethyl)quinolin-4-yl]phenoxy}methyl)benzyl]oxy}acetic acid | MS (ESI) m/z 592; | HRMS: calcd for $C_{33}H_{25}ClF_3NO_4$ + H+, 592.14970; found (ESI, [M + H]+), 592.148; | 66 |
| Example 898 | 3-[4-({3-[3-(4-chlorobenzyl)-8-(trifluoromethyl)quinolin-4-yl]phenoxy}methyl)phenyl]propanoic acid | MS (ESI) m/z 576; | HRMS: calcd for $C_{33}H_{25}ClF_3NO_3$ + H+, 576.15478; found (ESI, [M + H]+), 576.1572; | 66 |
| Example 899 | [4-({3-[3-(4-chlorobenzyl)-8-(trifluoromethyl)quinolin-4-yl]phenoxy}methyl)phenoxy]acetic acid | MS (ESI) m/z 578; | HRMS: calcd for $C_{32}H_{23}ClF_3NO_4$ + H+, 578.13405; found (ESI, [M + H]+), 578.1355; | 66 |
| Example 900 | [3-({3-[3-(4-chlorobenzyl)-8-(trifluoromethyl)quinolin-4-yl]phenoxy}methyl)phenoxy]acetic acid | MS (ESI) m/z 578; | HRMS: calcd for $C_{32}H_{23}ClF_3NO_4$ + H+, 578.13405; found (ESI, [M + H]+), 578.1315; | 66 |
| Example 901 | methyl 4-({3-[3-(4-chlorobenzyl)-8-(trifluoromethyl)quinolin-4-yl]phenoxy}methyl)benzoate | MS (ESI) m/z 562; | HRMS: calcd for $C_{32}H_{23}ClF_3NO_3$ + H+, 562.13913; found (ESI, [M + H]+), 562.1404; | 44 |
| Example 902 | methyl 3-[3-({3-[3-methyl-8-(trifluoromethyl)quinolin-4-yl]phenoxy}methyl)phenyl]propanoate | | HRMS: calcd for $C_{28}H_{24}F_3NO_3$ + H+, 480.17810; found (ESI, [M + H]+), 480.1792; | 365 |
| Example 903 | {3-[3-methyl-8-(trifluoromethyl)quinolin-4-yl]phenyl}amine | | HRMS: calcd for $C_{17}H_{13}F_3N_2$ + H+, 303.11036; found (ESI, [M + H]+), 303.11; | 390 |
| Example 904 | 3-[3-({3-[3-methyl-8-(trifluoromethyl)quinolin-4-yl]phenoxy}methyl)phenyl]propanoic acid | | HRMS: calcd for $C_{27}H_{22}F_3NO_3$ + H+, 466.16245; found (ESI, [M + H]+), 466.1609; | 216 |

| Example | Name | MS | HRMS | Example Number of Similar Procedure |
|---|---|---|---|---|
| Example 905 | 2-[4-({3-[3-methyl-8-(trifluoromethyl)quinolin-4-yl]phenoxy}methyl)phenyl]propanoic acid | | HRMS: calcd for $C_{27}H_{22}F_3NO_3$ + H+, 466.16245; found (ESI, [M + H]+), 466.1612; | 365 |
| Example 906 | 3-(4-chlorobenzyl)-4-{3-[(2,5-dimethylbenzyl)oxy]phenyl}-8-(trifluoromethyl)quinoline | MS (ESI) m/z 532; | HRMS: calcd for $C_{32}H_{25}ClF_3NO$ + H+, 532.16495; found (ESI, [M + H]+), 532.163; | 44 |
| Example 907 | 4-({3-[3-(4-chlorobenzyl)-8-(trifluoromethyl)quinolin-4-yl]phenoxy}methyl)benzoic acid | MS (ESI) m/z 548; | HRMS: calcd for $C_{31}H_{21}ClF_3NO_3$ + H+, 548.12348; found (ESI, [M + H]+), 548.1227; | 66 |
| Example 908 | methyl 2-[4-({3-[3-methyl-8-(trifluoromethyl)quinolin-4-yl]phenoxy}methyl)phenyl]propanoate | | HRMS: calcd for $C_{28}H_{24}F_3NO_3$ + H+, 480.17810; found (ESI, [M + H]+), 480.1771; | 365 |
| Example 909 | 4-(3-methoxyphenyl)-3-methyl-8-(trifluoromethyl)quinoline | MS (ES) m/z 318.2; | HRMS: calcd for $C_{18}H_{14}F_3NO$ + H+, 318.11002; found (ESI, [M + H]+), 318.1092; | 43 |
| Example 910 | 4-{3-[(2,5-dimethylbenzyl)oxy]phenyl}-3-methyl-8-(trifluoromethyl)quinoline | | HRMS: calcd for $C_{26}H_{22}F_3NO$ + H+, 422.17262; found (ESI, [M + H]+), 422.1711; | 43 |
| Example 911 | 4-{3-[(2,6-dimethylbenzyl)oxy]phenyl}-3-methyl-8-(trifluoromethyl)quinoline | | HRMS: calcd for $C_{26}H_{22}F_3NO$ + H+, 422.17262; found (ESI, [M + H]+), 422.173; | 43 |
| Example 912 | methyl 3-[3-({3-[3-(2-ethylphenyl)-8-(trifluoromethyl)quinolin-4-yl]phenoxy}methyl)phenyl]propanoate | MS (ESI) m/z 570; | | 478 |
| Example 913 | methyl 3-[3-({3-[3-(2-isopropylphenyl)-8-(trifluoromethyl)quinolin-4-yl]phenoxy}methyl)phenyl]propanoate | MS (ESI) m/z 584; | | 478 |
| Example 914 | [4-({3-[3-(2-ethylphenyl)-8-(trifluoromethyl)quinolin-4-yl]phenoxy}methyl)phenyl]acetic acid | MS (ESI) m/z 542; | | 66 |
| Example 915 | 3-[3-({3-[3-(2-ethylphenyl)-8-(trifluoromethyl)quinolin-4-yl]phenoxy}methyl)phenyl]propanoic acid | MS (ESI) m/z 556; | HRMS: calcd for $C_{34}H_{28}F_3NO_3$ + H+, 556.20940; found (ESI, [M + H]+), 556.2094; | 66 |

-continued

| Example | Name | MS | HRMS | Example Number of Similar Procedure |
|---|---|---|---|---|
| Example 916 | 3-[3-({3-[3-(2-isopropylphenyl)-8-(trifluoromethyl)quinolin-4-yl]phenoxy}methyl)phenyl]propanoic acid | MS (ESI) m/z 570; | HRMS: calcd for $C_{35}H_{30}F_3NO_3$ + H+, 570.22505; found (ESI, [M + H]+), 570.2226; | 66 |
| Example 917 | methyl 2-methyl-2-[4-({3-[3-methyl-8-(trifluoromethyl)quinolin-4-yl]phenoxy}methyl)phenyl]propanoate | | HRMS: calcd for $C_{29}H_{26}F_3NO_3$ + H+, 494.19375; found (ESI, [M + H]+), 494.193; | 365 |
| Example 918 | 3-[3-(2-methylbenzyl)-8-(trifluoromethyl)quinolin-4-yl]phenol | | HRMS: calcd for $C_{24}H_{18}F_3NO$ + H+, 394.14132; found (ESI, [M + H]+), 394.1409; | 457 |
| Example 919 | 2-methyl-2-[4-({3-[3-methyl-8-(trifluoromethyl)quinolin-4-yl]phenoxy}methyl)phenyl]propanoic acid | | HRMS: calcd for $C_{28}H_{24}F_3NO_3$ + H+, 480.17810; found (ESI, [M + H]+), 480.176; | 66 |
| Example 920 | ethyl [3-({3-[3-(2-ethylphenyl)-8-(trifluoromethyl)quinolin-4-yl]phenoxy}methyl)phenyl]acetate | MS (ESI) m/z 570; | HRMS: calcd for $C_{35}H_{30}F_3NO_3$ + H+, 570.22505; found (ESI, [M + H]+), 570.2226; | 478 |
| Example 921 | 4-{3-[(2,5-dimethylbenzyl)oxy]phenyl}-8-(trifluoromethyl)quinoline | MS (ESI) m/z 408; | HRMS: calcd for $C_{25}H_{20}F_3NO$ + H+, 408.15697; found (ESI, [M + H]+), 408.1563; | 44 |
| Example 922 | 4-{3-[(2-chlorobenzyl)oxy]phenyl}-8-(trifluoromethyl)quinoline | MS (ESI) m/z 414; | HRMS: calcd for $C_{23}H_{15}ClF_3NO$, 413.07943; found (ESI, [H + M]+), 414.0868 | 44 |
| Example 923 | 4-{3-[(3,4-dimethylbenzyl)oxy]phenyl}-8-(trifluoromethyl)quinoline | MS (ES) m/z 408.0; | HRMS: calcd for $C_{25}H_{20}F_3NO$ + H+, 408.15697; found (ESI, [M + H]+), 408.1574; | 44 |
| Example 924 | 4-{3-[(2,5-dimethylbenzyl)oxy]phenyl}-3-(2-methylbenzyl)-8-(trifluoromethyl)quinoline | | HRMS: calcd for $C_{33}H_{28}F_3NO$ + H+, 512.21957; found (ESI, [M + H]+), 512.2179; | 43 |
| Example 925 | 4-{3-[(2,6-dimethylbenzyl)oxy]phenyl}-3-(2-methylbenzyl)-8-(trifluoromethyl)quinoline | | HRMS: calcd for $C_{33}H_{28}F_3NO$, 511.21230; found (ESI, [H + M]+), 512.2217 | 43 |

-continued

| Example | Name | MS | HRMS | Example Number of Similar Procedure |
|---|---|---|---|---|
| Example 926 | [4-({3-[3-(2-methylbenzyl)-8-(trifluoromethyl)quinolin-4-yl]phenoxy}methyl)phenyl]acetic acid | | HRMS: calcd for $C_{33}H_{26}F_3NO_3$, 541.18648; found (ESI, [H + M]+), 542.1927 | 366 |
| Example 927 | 4-{3-[(2,6-dimethylbenzyl)oxy]phenyl}-8-(trifluoromethyl)quinoline | MS (ES) m/z 408.1; | HRMS: calcd for $C_{25}H_{20}F_3NO + H+$, 408.15697; found (ESI, [M + H]+), 408.1596 | 44 |
| Example 928 | 4-{3-[(3-fluorobenzyl)oxy]phenyl}-8-(trifluoromethyl)quinoline | MS (ESI) m/z 398; | HRMS: calcd for $C_{23}H_{15}F_4NO + H+$, 398.11625; found (ESI, [M + H]+), 398.1173; | 44 |
| Example 929 | 2-[4-({3-[3-(2-methylbenzyl)-8-(trifluoromethyl)quinolin-4-yl]phenoxy}methyl)phenyl]ethanol | | HRMS: calcd for $C_{33}H_{28}F_3NO_2$, 527.20721; found (ESI, [H + M]+), 528.2133 | 365 |
| Example 930 | ethyl [3-({3-[3-(2-methylbenzyl)-8-(trifluoromethyl)quinolin-4-yl]phenoxy}methyl)phenyl]acetate | | HRMS: calcd for $C_{35}H_{30}F_3NO_3 + H+$, 570.22505; found (ESI, [M + H]+), 570.223; | 365 |
| Example 931 | [4-({3-[3-(2-methylbenzyl)-8-(trifluoromethyl)quinolin-4-yl]phenoxy}methyl)phenoxy]acetonitrile | | HRMS: calcd for $C_{33}H_{25}F_3N_2O_2 + H+$, 539.19409; found (ESI, [M + H]+), 539.1935; | 365 |
| Example 932 | methyl [4-({3-[3-(2-methylbenzyl)-8-(trifluoromethyl)quinolin-4-yl]phenoxy}methyl)phenoxy]acetate | | HRMS: calcd for $C_{34}H_{28}F_3NO_4 + H+$, 572.20432; found (ESI, [M + H]+), 572.2025; | 365 |
| Example 933 | [3-({3-[3-(2-ethylphenyl)-8-(trifluoromethyl)quinolin-4-yl]phenoxy}methyl)phenyl]acetic acid | MS (ES) m/z 539.9; | HRMS: calcd for $C_{33}H_{26}F_3NO_3 + H+$, 542.19375; found (ESI, [M + H]+), 542.1921; | 66 |
| Example 934 | methyl [3-({3-[3-(2-methylbenzyl)-8-(trifluoromethyl)quinolin-4-yl]phenoxy}methyl)phenoxy]acetate | | HRMS: calcd for $C_{34}H_{28}F_3NO_4 + H+$, 572.20432; found (ESI, [M + H]+), 572.2052; | 365 |
| Example 935 | methyl 3-[4-({3-[3-(2-methylbenzyl)-8-(trifluoromethyl)quinolin-4-yl]phenoxy}methyl)phenyl]propanoate | | HRMS: calcd for $C_{35}H_{30}F_3NO_3 + H+$, 570.22505; found (ESI, [M + H]+), 570.2228; | 365 |

| Example | Name | MS | HRMS | Example Number of Similar Procedure |
|---|---|---|---|---|
| Example 936 | methyl 3-[3-({3-[3-(2-methylbenzyl)-8-(trifluoromethyl)quinolin-4-yl]phenoxy}methyl)phenyl]propanoate | | HRMS: calcd for $C_{35}H_{30}F_3NO_3$ + H+, 570.22505; found (ESI, [M + H]+), 570.2238; | 365 |
| Example 937 | methyl 3-[4-({3-[3-(2-methylbenzyl)-8-(trifluoromethyl)quinolin-4-yl]phenoxy}methyl)phenyl]prop-2-ynoate | | HRMS: calcd for $C_{35}H_{26}F_3NO_3$ + H+, 566.19375; found (ESI, [M + H]+), 566.1946; | 365 |
| Example 938 | 4-{3-[(2,6-dichlorobenzyl)oxy]phenyl}-8-(trifluoromethyl)quinoline | MS (ESI) m/z 448; | HRMS: calcd for $C_{23}H_{14}Cl_2F_3NO$ + H+, 448.04773; found (ESI, [M + H]+), 448.0496; | 44 |
| Example 939 | 4-{3-[(2,6-difluorobenzyl)oxy]phenyl}-8-(trifluoromethyl)quinoline | MS (ESI) m/z 416; | HRMS: calcd for $C_{23}H_{14}F_5NO$ + H+, 416.10683; found (ESI, [M + H]+), 416.1065; | 44 |
| Example 940 | methyl [3-({3-[8-(trifluoromethyl)quinolin-4-yl]phenoxy}methyl)phenoxy]acetate | MS (ESI) m/z 468; | HRMS: calcd for $C_{26}H_{20}F_3NO_4$ + H+, 468.14172; found (ESI, [M + H]+), 468.141; | 44 |
| Example 941 | methyl [4-({3-[8-(trifluoromethyl)quinolin-4-yl]phenoxy}methyl)phenoxy]acetate | MS (ES) m/z 468.0; | HRMS: calcd for $C_{26}H_{20}F_3NO_4$ + H+, 468.14172; found (ESI, [M + H]+), 468.144; | 44 |
| Example 942 | methyl {[3-({3-[8-(trifluoromethyl)quinolin-4-yl]phenoxy}methyl)benzyl]oxy}acetate | MS (ES) m/z 482.0; | HRMS: calcd for $C_{27}H_{22}F_3NO_4$ + H+, 482.15737; found (ESI, [M + H]+), 482.1556; | 44 |
| Example 943 | methyl (2E)-3-[4-({3-[3-(2-methylbenzyl)-8-(trifluoromethyl)quinolin-4-yl]phenoxy}methyl)phenyl]acrylate | | HRMS: calcd for $C_{35}H_{28}F_3NO_3$ + H+, 568.20940; found (ESI, [M + H]+), 568.2104; | 365 |
| Example 944 | methyl 2-methyl-2-[4-({3-[3-(2-methylbenzyl)-8-(trifluoromethyl)quinolin-4-yl]phenoxy}methyl)phenyl]propanoate | | HRMS: calcd for $C_{36}H_{32}F_3NO_3$ + H+, 584.24070; found (ESI, [M + H]+), 584.2426; | 365 |
| Example 945 | 4-{3-[(2,5-dimethylbenzyl)oxy]phenyl}-3-(2-methylbenzyl)-8-(trifluoromethyl)quinoline | MS (ES) m/z 498.1; | HRMS: calcd for $C_{32}H_{26}F_3NO$ + H+, 498.20392; found (ESI, [M + H]+), 498.2034; | 478 |

-continued

| Example | Name | MS | HRMS | Example Number of Similar Procedure |
|---|---|---|---|---|
| Example 946 | 4-{3-[(2-fluorobenzyl)oxy]phenyl}-3-(2-methylphenyl)-8-(trifluoromethyl)quinoline | MS (ES) m/z 488.0; | HRMS: calcd for $C_{30}H_{21}F_4NO$ + H+, 488.16320; found (ESI, [M + H]+), 488.1666 | 478 |
| Example 947 | 4-{3-[(2,6-dimethylbenzyl)oxy]phenyl}-3-(2-methylbenzyl)-8-(trifluoromethyl)quinoline | MS (ES) m/z 498.1; | HRMS: calcd for $C_{32}H_{26}F_3NO$ + H+, 498.20392; found (ESI, [M + H]+), 498.2038; | 478 |
| Example 948 | 4-{3-[(2-fluoro-5-nitrobenzyl)oxy]phenyl}-3-(2-methylphenyl)-8-(trifluoromethyl)quinoline | MS (ES) m/z 533.0; | HRMS: calcd for $C_{30}H_{20}F_4N_2O_3$ + H+, 533.14828; found (ESI, [M + H]+), 533.1472; | 478 |
| Example 949 | ethyl [4-({3-[3-(2-ethylphenyl)-8-(trifluoromethyl)quinolin-4-yl]phenoxy}methyl)phenyl]acetate | MS (ES) m/z 570.1; | | 478 |
| Example 950 | methyl {[3-({3-[3-(2-methylbenzyl)-8-(trifluoromethyl)quinolin-4-yl]phenoxy}methyl)benzyl]oxy}acetate | | HRMS: calcd for $C_{35}H_{30}F_3NO_4$ + H+, 586.21997; found (ESI, [M + H]+), 586.2219; | 365 |
| Example 951 | methyl {4-[({3-[3-phenyl-8-(trifluoromethyl)quinolin-4-yl]phenyl}amino)methyl]phenyl}acetate | MS (ES) m/z 527.0; | HRMS: calcd for $C_{32}H_{25}F_3N_2O_2$ + H+, 527.19409; found (ESI, [M + H]+), 527.1966; | 66 |
| Example 952 | methyl {[4-({3-[8-(trifluoromethyl)quinolin-4-yl]phenoxy}methyl)benzyl]oxy}acetate | MS (ES) m/z 482.0; | HRMS: calcd for $C_{27}H_{22}F_3NO_4$ + H+, 482.15737; found (ESI, [M + H]+), 482.1574; | 44 |
| Example 953 | methyl 3-[4-({3-[8-(trifluoromethyl)quinolin-4-yl]phenoxy}methyl)phenyl]propanoate | MS (ES) m/z 466.0; | HRMS: calcd for $C_{27}H_{22}F_3NO_3$ + H+, 466.16245; found (ESI, [M + H]+), 466.1628; | 44 |
| Example 954 | methyl 3-[3-({3-[8-(trifluoromethyl)quinolin-4-yl]phenoxy}methyl)phenyl]propanoate | MS (ES) m/z 466.0; | HRMS: calcd for $C_{27}H_{22}F_3NO_3$ + H+, 466.16245; found (ESI, [M + H]+), 466.1627; | 44 |
| Example 955 | 4-{3-[(2,5-difluorobenzyl)oxy]phenyl}-8-(trifluoromethyl)quinoline | MS (ES) m/z 416.0; | HRMS: calcd for $C_{23}H_{14}F_5NO$ + H+, 416.10683; found (ESI, [M + H]+), 416.1063; | 44 |
| Example 956 | [4-({3-[8-(trifluoromethyl)quinolin-4-yl]phenoxy}methyl)phenoxy]acetonitrile | MS (ES) m/z 435.0; | HRMS: calcd for $C_{25}H_{17}F_3N_2O_2$ + H+, 435.13149; found (ESI, [M + H]+), 435.1329; | 44 |

| Example | Name | MS | HRMS | Example Number of Similar Procedure |
|---|---|---|---|---|
| Example 957 | 4-{3-[(2,4-difluorobenzyl)oxy]phenyl}-8-(trifluoromethyl)quinoline | MS (ES) m/z 416.0; | HRMS: calcd for $C_{23}H_{14}F_5NO + H+$, 416.10683; found (ESI, $[M + H]^+$), 416.1065; | 44 |
| Example 958 | 4-{3-[(2,5-dichlorobenzyl)oxy]phenyl}-8-(trifluoromethyl)quinoline | MS (ES) m/z 447.9; | HRMS: calcd for $C_{23}H_{14}Cl_2F_3NO + H+$, 448.04773; found (ESI, $[M + H]^+$), 448.0461; | 44 |
| Example 959 | [3-({3-[3-(2-methylbenzyl)-8-(trifluoromethyl)quinolin-4-yl]phenoxy}methyl)phenyl]acetic acid | | HRMS: calcd for $C_{33}H_{26}F_3NO_3 + H+$, 542.19375; found (ESI, $[M + H]^+$), 542.1937; | 216 |
| Example 960 | [4-({3-[3-(2-methylbenzyl)-8-(trifluoromethyl)quinolin-4-yl]phenoxy}methyl)phenoxy]acetic acid | | HRMS: calcd for $C_{33}H_{26}F_3NO_4 + H+$, 558.18867; found (ESI, $[M + H]^+$), 558.1889; | 216 |
| Example 961 | [3-({3-[3-(2-methylbenzyl)-8-(trifluoromethyl)quinolin-4-yl]phenoxy}methyl)phenoxy]acetic acid | | HRMS: calcd for $C_{33}H_{26}F_3NO_4 + H+$, 558.18867; found (ESI, $[M + H]^+$), 558.189; | 216 |
| Example 962 | ethyl [4-({3-[3-(2-isopropylphenyl)-8-(trifluoromethyl)quinolin-4-yl]phenoxy}methyl)phenyl]acetate | MS (ES) m/z 584.1; | | 478 |
| Example 963 | 3-[4-({3-[3-(2-methylbenzyl)-8-(trifluoromethyl)quinolin-4-yl]phenoxy}methyl)phenyl]propanoic acid | | HRMS: calcd for $C_{34}H_{28}F_3NO_3 + H+$, 556.20940; found (ESI, $[M + H]^+$), 556.2083; | 216 |
| Example 964 | 3-[3-({3-[3-(2-methylbenzyl)-8-(trifluoromethyl)quinolin-4-yl]phenoxy}methyl)phenyl]propanoic acid | | HRMS: calcd for $C_{34}H_{28}F_3NO_3 + H+$, 556.20940; found (ESI, $[M + H]^+$), 556.2083; | 216 |
| Example 965 | 3-[4-({3-[3-(2-methylbenzyl)-8-(trifluoromethyl)quinolin-4-yl]phenoxy}methyl)phenyl]prop-2-ynoic acid | | HRMS: calcd for $C_{34}H_{24}F_3NO_3 + H+$, 552.17810; found (ESI, $[M + H]^+$), 552.1771; | 216 |
| Example 966 | (2E)-3-[4-({3-[3-(2-methylbenzyl)-8-(trifluoromethyl)quinolin-4-yl]phenoxy}methyl)phenyl]acrylic acid | | HRMS: calcd for $C_{34}H_{26}F_3NO_3 + H+$, 554.19375; found (ESI, $[M + H]^+$), 554.193; | 216 |
| Example 967 | 2-methyl-2-[4-({3-[3-(2-methylbenzyl)-8-(trifluoromethyl)quinolin-4-yl]phenoxy}methyl)phenyl]propanoic acid | | HRMS: calcd for $C_{35}H_{30}F_3NO_3 + H+$, 570.22505; found (ESI, $[M + H]^+$), 570.2244; | 66 |

| Example | Name | MS | HRMS | Example Number of Similar Procedure |
|---|---|---|---|---|
| Example 968 | {[3-({3-[3-(2-methylbenzyl)-8-(trifluoromethyl)quinolin-4-yl]phenoxy}methyl)benzyl]oxy}acetic acid | | HRMS: calcd for $C_{34}H_{28}F_3NO_4$ + H+, 572.20432; found (ESI, [M + H]+), 572.2034; | 216 |
| Example 969 | 4-[3-(2-{1-[2-(1H-indol-3-yl)ethyl]-1H-indol-3-yl}ethoxy)phenyl]-8-(trifluoromethyl)quinoline | MS (ES) m/z 574.1; | HRMS: calcd for $C_{36}H_{28}F_3N_3O$ + H+, 576.22572; found (ESI, [M + H]+), 576.2236; | 44 |
| Example 970 | [3-({3-[8-(trifluoromethyl)quinolin-4-yl]phenoxy}methyl)phenoxy]acetic acid | MS (ESI) m/z 454; | HRMS: calcd for $C_{25}H_{18}F_3NO_4$ + H+, 454.12607; found (ESI, [M + H]+), 454.1244; | 41 |
| Example 971 | [4-({3-[8-(trifluoromethyl)quinolin-4-yl]phenoxy}methyl)phenoxy]acetic acid | MS (ESI) m/z 454; | HRMS: calcd for $C_{25}H_{18}F_3NO_4$ + H+, 454.12607; found (ESI, [M + H]+), 454.1265; | 41 |
| Example 972 | methyl 4-({3-[8-(trifluoromethyl)quinolin-4-yl]phenoxy}methyl)benzoate | MS (ES) m/z 438.0; | HRMS: calcd for $C_{25}H_{18}F_3NO_3$ + H+, 438.13115; found (ESI, [M + H]+), 438.13; | 44 |
| Example 973 | methyl 4-({3-[3-phenyl-8-(trifluoromethyl)quinolin-4-yl]phenoxy}methyl)benzoate | MS (ES) m/z 514.1; | HRMS: calcd for $C_{31}H_{22}F_3NO_3$ + H+, 514.16245; found (ESI, [M + H]+), 514.1653 | 44 |
| Example 974 | methyl 4-({3-[3-methyl-8-(trifluoromethyl)quinolin-4-yl]phenoxy}methyl)benzoate | | HRMS: calcd for $C_{26}H_{20}F_3NO_3$ + H+, 452.14680; found (ESI, [M + H]+), 452.146; | 365 |
| Example 975 | methyl 3-({3-[3-methyl-8-(trifluoromethyl)quinolin-4-yl]phenoxy}methyl)benzoate | | HRMS: calcd for $C_{26}H_{20}F_3NO_3$ + H+, 452.14680; found (ESI, [M + H]+), 452.1488; | 365 |
| Example 976 | ethyl [3-({3-[3-methyl-8-(trifluoromethyl)quinolin-4-yl]phenoxy}methyl)phenyl]acetate | | HRMS: calcd for $C_{28}H_{24}F_3NO_3$ + H+, 480.17810; found (ESI, [M + H]+), 480.178; | 365 |
| Example 977 | 4-({3-[3-methyl-8-(trifluoromethyl)quinolin-4-yl]phenoxy}methyl)benzoic acid | | HRMS: calcd for $C_{25}H_{18}F_3NO_3$ + H+, 438.13115; found (ESI, [M + H]+), 438.1335; | 216 |

| Example | Name | MS | HRMS | Example Number of Similar Procedure |
|---|---|---|---|---|
| Example 978 | 3-({3-[3-methyl-8-(trifluoromethyl)quinolin-4-yl]phenoxy}methyl)benzoic acid | | HRMS: calcd for $C_{25}H_{18}F_3NO_3$ + H+, 438.13115; found (ESI, [M + H]+), 438.132; | 216 |
| Example 979 | [3-({3-[3-methyl-8-(trifluoromethyl)quinolin-4-yl]phenoxy}methyl)phenyl]acetic | | HRMS: calcd for $C_{26}H_{20}F_3NO_3$ + H+, 452.14680; found (ESI, [M + H]+), 452.1457; | 216 |
| Example 980 | {[3-({3-[8-(trifluoromethyl)quinolin-4-yl]phenoxy}methyl)benzyl]oxy}acetic acid | MS (ESI) m/z 468; | HRMS: calcd for $C_{26}H_{20}F_3NO_4$ + H+, 468.14172; found (ESI, [M + H]+), 468.1441; | 41 |
| Example 981 | {[4-({3-[8-(trifluoromethyl)quinolin-4-yl]phenoxy}methyl)benzyl]oxy}acetic acid | MS (ESI) m/z 468; | HRMS: calcd for $C_{26}H_{20}F_3NO_4$ + H+, 468.14172; found (ESI, [M + H]+), 468.1436; | 41 |
| Example 982 | 3-[4-({3-[8-(trifluoromethyl)quinolin-4-yl]phenoxy}methyl)phenyl]propanoic acid | MS (ESI) m/z 452; | HRMS: calcd for $C_{26}H_{20}F_3NO_3$ + H+, 452.14680; found (ESI, [M + H]+), 452.1461; | 41 |
| Example 983 | 3-[3-({3-[8-(trifluoromethyl)quinolin-4-yl]phenoxy}methyl)phenyl]propanoic acid | MS (ESI) m/z 452; | HRMS: calcd for $C_{26}H_{20}F_3NO_3$ + H+, 452.14680; found (ESI, [M + H]+), 452.1474; | 41 |
| Example 984 | 4-{3-[2-(1H-indol-3-yl)ethoxy]phenyl}-8-(trifluoromethyl)quinoline | MS (ESI) m/z 433; | HRMS: calcd for $C_{26}H_{19}F_3N_2O$ + H+, 433.15222; found (ESI, [M + H]+), 433.1506; | 44 |
| Example 985 | 4-({3-[8-(trifluoromethyl)quinolin-4-yl]phenoxy}methyl)benzoic acid | MS (ESI) m/z 424; | HRMS: calcd for $C_{24}H_{16}F_3NO_3$ + H+, 424.11550; found (ESI, [M + H]+), 424.116; | 41 |
| Example 986 | 3-{3-[3-methyl-8-(trifluoromethyl)quinolin-4-yl]phenoxy}benzoic acid | MS (ES) m/z 422.0; | HRMS: calcd for $C_{24}H_{16}F_3NO_3$ + H+, 424.11550; found (ESI, [M + H]+), 424.115; | 66 |
| Example 987 | methyl 3-{3-[3-methyl-8-(trifluoromethyl)quinolin-4-yl]phenoxy}benzoate | MS (ESI) m/z 438; | HRMS: calcd for $C_{25}H_{18}F_3NO_3$ + H+, 438.13115; found (ESI, [M + H]+), 438.1339 | 709 |

| Example | Name | MS | HRMS | Example Number of Similar Procedure |
|---|---|---|---|---|
| Example 988 | methyl 4-{3-[3-methyl-8-(trifluoromethyl)quinolin-4-yl]phenoxy}benzoate | MS (ESI) m/z 438; | HRMS: calcd for $C_{25}H_{18}F_3NO_3$ + H+, 438.13115; found (ESI, [M + H]+), 438.1331; | 709 |
| Example 989 | 4-{3-[3-methyl-8-(trifluoromethyl)quinolin-4-yl]phenoxy}benzoic acid | MS m/z 04-1790-IMN; | HRMS: calcd for $C_{24}H_{16}F_3NO_3$ + H+, 424.11550; found (ESI, [M + H]+), 424.1153; | 66 |
| Example 990 | 4-{3-[(2-methoxybenzyl)oxy]phenyl}-3-methyl-8-(trifluoromethyl)quinoline | | HRMS: calcd for $C_{25}H_{20}F_3NO_2$ + H+, 424.15189; found (ESI, [M + H]+), 424.1512; | 43 |
| Example 991 | 3-methyl-4-{3-[(2-nitrobenzyl)oxy]phenyl}-8-(trifluoromethyl)quinoline | | HRMS: calcd for $C_{24}H_{17}F_3N_2O_3$ + H+, 439.12640; found (ESI, [M + H]+), 439.1255; | 43 |
| Example 992 | 4-{3-[(3-fluorobenzyl)oxy]phenyl}-3-methyl-8-(trifluoromethyl)quinoline | | HRMS: calcd for $C_{24}H_{17}F_4NO$ + H+, 412.13190; found (ESI, [M + H]+), 412.1335; | 43 |
| Example 993 | 4-{3-[(3-bromobenzyl)oxy]phenyl}-3-methyl-8-(trifluoromethyl)quinoline | | HRMS: calcd for $C_{24}H_{17}BrF_3NO$ + H+, 472.05183; found (ESI, [M + H]+), 472.0543; | 43 |
| Example 994 | 3-({3-[3-methyl-8-(trifluoromethyl)quinolin-4-yl]phenoxy}methyl)benzonitrile | | HRMS: calcd for $C_{25}H_{17}F_3N_2O$ + H+, 419.13657; found (ESI, [M + H]+), 419.1354; | 43 |
| Example 995 | 4-{3-[(3-methoxybenzyl)oxy]phenyl}-3-methyl-8-(trifluoromethyl)quinoline | | HRMS: calcd for $C_{25}H_{20}F_3NO_2$ + H+, 424.15189; found (ESI, [M + H]+), 424.1498; | 43 |
| Example 996 | 3-methyl-4-{3-[(3-nitrobenzyl)oxy]phenyl}-8-(trifluoromethyl)quinoline | | HRMS: calcd for $C_{24}H_{17}F_3N_2O_3$ + H+, 439.12640; found (ESI, [M + H]+), 439.1243; | 43 |
| Example 997 | 4-{3-[(4-methoxybenzyl)oxy]phenyl}-3-methyl-8-(trifluoromethyl)quinoline | | HRMS: calcd for $C_{25}H_{20}F_3NO_2$ + H+, 424.15189; found (ESI, [M + H]+), 424.1516; | 43 |

-continued

| Example | Name | MS | HRMS | Example Number of Similar Procedure |
|---|---|---|---|---|
| Example 998 | 4-{3-[(2,5-dichlorobenzyl)oxy]phenyl}-3-methyl-8-(trifluoromethyl)quinoline | | HRMS: calcd for $C_{24}H_{16}Cl_2F_3NO$ + H+, 462.06338; found (ESI, [M + H]+), 462.0624; | 43 |
| Example 999 | 4-{3-[(2,5-difluorobenzyl)oxy]phenyl}-3-methyl-8-(trifluoromethyl)quinoline | | HRMS: calcd for $C_{24}H_{16}F_5NO$ + H+, 430.12248; found (ESI, [M + H]+), 430.1225; | 43 |
| Example 1000 | 4-{3-[(2,6-dichlorobenzyl)oxy]phenyl}-3-methyl-8-(trifluoromethyl)quinoline | | HRMS: calcd for $C_{24}H_{16}Cl_2F_3NO$ + H+, 462.06338; found (ESI, [M + H]+), 462.0636; | 43 |
| Example 1001 | 4-{3-[(2,6-difluorobenzyl)oxy]phenyl}-3-methyl-8-(trifluoromethyl)quinoline | | HRMS: calcd for $C_{24}H_{16}F_5NO$ + H+, 430.12248; found (ESI, [M + H]+), 430.1212; | 43 |
| Example 1002 | 3-methyl-4-[3-(2-naphthylmethoxy)phenyl]-8-(trifluoromethyl)quinoline | | HRMS: calcd for $C_{28}H_{20}F_3NO$ + H+, 444.15697; found (ESI, [M + H]+), 444.1574; | 43 |
| Example 1003 | 3-methyl-4-[3-(pyridin-3-ylmethoxy)phenyl]-8-(trifluoromethyl)quinoline | | HRMS: calcd for $C_{23}H_{17}F_3N_2O$ + H+, 395.13657; found (ESI, [M + H]+), 395.1363; | 43 |
| Example 1004 | 3-methyl-4-[3-(quinolin-2-ylmethoxy)phenyl]-8-(trifluoromethyl)quinoline | | HRMS: calcd for $C_{27}H_{19}F_3N_2O$ + H+, 445.15222; found (ESI, [M + H]+), 445.1517; | 43 |
| Example 1005 | 4-{3-[(3-chlorobenzyl)oxy]phenyl}-3-methyl-8-(trifluoromethyl)quinoline | | HRMS: calcd for $C_{24}H_{17}ClF_3NO$ + H+, 428.10235; found (ESI, [M + H]+), 428.1038; | 43 |
| Example 1006 | 3-methyl-4-{3-[(3-methylbenzyl)oxy]phenyl}-8-(trifluoromethyl)quinoline | | HRMS: calcd for $C_{25}H_{20}F_3NO$ + H+, 408.15697; found (ESI, [M + H]+), 408.1566; | 43 |
| Example 1007 | 4-{3-[(3-ethoxybenzyl)oxy]phenyl}-3-methyl-8-(trifluoromethyl)quinoline | | HRMS: calcd for $C_{26}H_{22}F_3NO_2$ + H+, 438.16754; found (ESI, [M + H]+), 438.1671; | 43 |

| Example | Name | MS | HRMS | Example Number of Similar Procedure |
|---|---|---|---|---|
| Example 1008 | 3-methyl-4-{3-[(3-propoxybenzyl)oxy]phenyl}-8-(trifluoromethyl)quinoline | | HRMS: calcd for $C_{27}H_{24}F_3NO_2$ + H+, 452.18319; found (ESI, [M + H]+), 452.1818; | 43 |
| Example 1009 | 4-{3-[(3-isobutoxybenzyl)oxy]phenyl}-3-methyl-8-(trifluoromethyl)quinoline | | HRMS: calcd for $C_{28}H_{26}F_3NO_2$ + H+, 466.19884; found (ESI, [M + H]+), 466.198; | 43 |
| Example 1010 | 4-{3-[(2,5-difluorobenzyl)oxy]phenyl}-3-(2-methylphenyl)-8-(trifluoromethyl)quinoline | MS (ESI) m/z 506; | HRMS: calcd for $C_{30}H_{20}F_5NO$ + H+, 506.15378; found (ESI, [M + H]+), 506.1565; | 478 |
| Example 1011 | 4-(3-{[2,5-bis(trifluoromethyl)benzyl]oxy}phenyl)-3-(2-methylphenyl)-8-(trifluoromethyl)quinoline | MS (ESI) m/z 606; | HRMS: calcd for $C_{32}H_{20}F_9NO$ + H+, 606.14739; found (ESI, [M + H]+), 606.1492; | 478 |
| Example 1012 | 4-{3-[(2-bromo-5-methoxybenzyl)oxy]phenyl}-3-(2-methylphenyl)-8-(trifluoromethyl)quinoline | MS (ESI) m/z 578; | HRMS: calcd for $C_{31}H_{23}BrF_3NO_2$ + H+, 578.09370; found (ESI, [M + H]+), 578.0931; | 478 |
| Example 1013 | 4-{3-[(2-chloro-5-fluorobenzyl)oxy]phenyl}-3-(2-methylphenyl)-8-(trifluoromethyl)quinoline | MS (ESI) m/z 522; | | 478 |
| Example 1014 | 4-{3-[(5-bromo-2-methoxybenzyl)oxy]phenyl}-3-(2-methylphenyl)-8-(trifluoromethyl)quinoline | MS (ESI) m/z 578; | HRMS: calcd for $C_{31}H_{23}BrF_3NO_2$ + H+, 578.09370; found (ESI, [M +H]+), 578.095; | 478 |
| Example 1015 | 4-{3-[(5-bromo-2-fluorobenzyl)oxy]phenyl}-3-(2-methylphenyl)-8-(trifluoromethyl)quinoline | MS (ESI) m/z 566; | HRMS: calcd for $C_{30}H_{20}BrF_4NO$ + H+, 566.07371; found (ESI, [M + H]+), 566.0758; | 478 |
| Example 1016 | 4-{3-[(2-methoxy-5-nitrobenzyl)oxy]phenyl}-3-(2-methylphenyl)-8-(trifluoromethyl)quinoline | MS (ESI) m/z 545; | HRMS: calcd for $C_{31}H_{23}F_3N_2O_4$ + H+, 545.16827; found (ESI, [M + H]+), 545.1661; | 478 |
| Example 1017 | 4-{3-[(2,6-dichlorobenzyl)oxy]phenyl}-3-(2-methylphenyl)-8-(trifluoromethyl)quinoline | MS (ESI) m/z 538; | HRMS: calcd for $C_{30}H_{20}Cl_2F_3NO$ + H+, 538.09468; found (ESI, [M + H]+), 538.0931; | 478 |
| Example 1018 | 4-{3-[(2,6-difluorobenzyl)oxy]phenyl}-3-(2-methylphenyl)-8-(trifluoromethyl)quinoline | MS (ESI) m/z 506; | HRMS: calcd for $C_{30}H_{20}F_5NO$ + H+, 506.15378; found (ESI, [M + H]+), 506.1525; | 478 |

| Example | Name | MS | HRMS | Example Number of Similar Procedure |
|---|---|---|---|---|
| Example 1019 | 4-[3-(benzyloxy)phenyl]-3-phenyl-8-(trifluoromethyl)quinoline | MS (ESI) m/z 456; | HRMS: calcd for $C_{29}H_{20}F_3NO + H+$, 456.15697; found (ESI, $[M + H]^+$), 456.1571; | 44 |
| Example 1020 | 4-{3-[(2,5-dimethylbenzyl)oxy]phenyl}-3-phenyl-8-(trifluoromethyl)quinoline | MS (ESI) m/z 484; | HRMS: calcd for $C_{31}H_{24}F_3NO + H+$, 484.18827; found (ESI, $[M + H]^+$), 484.1889; | 44 |
| Example 1021 | 4-{3-[(2,5-difluorobenzyl)oxy]phenyl}-3-phenyl-8-(trifluoromethyl)quinoline | MS (ESI) m/z 492; | HRMS: calcd for $C_{29}H_{18}F_5NO + H+$, 492.13813; found (ESI, $[M + H]^+$), 492.1399; | 44 |
| Example 1022 | 4-{3-[(2,5-dichlorobenzyl)oxy]phenyl}-3-phenyl-8-(trifluoromethyl)quinoline | MS (ESI) m/z 524; | HRMS: calcd for $C_{29}H_{18}Cl_2F_3NO + H+$, 524.07903; found (ESI, $[M + H]^+$), 524.1779 | 44 |
| Example 1023 | 4-{3-[(4-fluoro-3-nitrobenzyl)oxy]phenyl}-3-(2-methylphenyl)-8-(trifluoromethyl)quinoline | MS (ESI) m/z 533; | HRMS: calcd for $C_{30}H_{20}F_4N_2O_3 + H+$, 533.14828; found (ESI, $[M + H]^+$), 533.1483; | 478 |
| Example 1024 | 3-(2-methylphenyl)-4-{3-[(4-nitrobenzyl)oxy]phenyl}-8-(trifluoromethyl)quinoline | MS (ESI) m/z 515; | HRMS: calcd for $C_{30}H_{21}F_3N_2O_3 + H+$, 515.15770; found (ESI, $[M + H]^+$), 515.16; | 478 |
| Example 1025 | 4-{3-[(5-chloro-2-fluorobenzyl)oxy]phenyl}-3-(2-methylphenyl)-8-(trifluoromethyl)quinoline | MS (ESI) m/z 522; | HRMS: calcd for $C_{30}H_{20}ClF_4NO + H+$, 522.12423; found (ESI, $[M + H]^+$), 522.1249; | 478 |
| Example 1026 | 4-{3-[(3-methoxybenzyl)oxy]phenyl}-3-phenyl-8-(trifluoromethyl)quinoline | MS (ESI) m/z 486; | HRMS: calcd for $C_{30}H_{22}F_3NO_2 + H+$, 486.16754; found (ESI, $[M + H]^+$), 486.1667; | 44 |
| Example 1027 | 4-{3-[(4-isopropylbenzyl)oxy]phenyl}-3-phenyl-8-(trifluoromethyl)quinoline | MS (ESI) m/z 498; | HRMS: calcd for $C_{32}H_{26}F_3NO + H+$, 498.20392; found (ESI, $[M + H]^+$), 498.2076 | 44 |
| Example 1028 | 4-{3-[(3,4-dimethylbenzyl)oxy]phenyl}-3-phenyl-8-(trifluoromethyl)quinoline | MS (ESI) m/z 484; | HRMS: calcd for $C_{31}H_{24}F_3NO + H+$, 484.18827; found (ESI, $[M + H]^+$), 484.1859; | 44 |

-continued

| Example | Name | MS | HRMS | Example Number of Similar Procedure |
|---|---|---|---|---|
| Example 1029 | 4-{3-[(2,6-dimethylbenzyl)oxy]phenyl}-3-phenyl-8-(trifluoromethyl)quinoline | MS (ESI) m/z 484; | HRMS: calcd for $C_{31}H_{24}F_3NO$ + H+, 484.18827; found (ESI, [M + H]+), 484.1871; | 44 |
| Example 1030 | 4-{3-[(2-chloro-4-fluorobenzyl)oxy]phenyl}-3-phenyl-8-(trifluoromethyl)quinoline | MS (ESI) m/z 508; | HRMS: calcd for $C_{29}H_{18}ClF_4NO$ + H+, 508.10858; found (ESI, [M+H]+), 508.1072; | 44 |
| Example 1031 | 4-(3-{[2,5-bis(trifluoromethyl)benzyl]oxy}phenyl)-3-phenyl-8-(trifluoromethyl)quinoline | MS (ESI) m/z 592; | HRMS: calcd for $C_{31}H_{18}F_9NO$ + H+, 592.13174; found (ESI, [M+H]+), 592.1306; | 44 |
| Example 1032 | 4-(3-{[2-chloro-3-(trifluoromethyl)benzyl]oxy}phenyl)-3-phenyl-8-(trifluoromethyl)quinoline | MS (ESI) m/z 558; | HRMS: calcd for $C_{30}H_{18}ClF_6NO$ + H+, 558.10538; found (ESI, [M+H]+), 558.1071; | 44 |
| Example 1033 | 4-{3-[(2-chloro-5-fluorobenzyl)oxy]phenyl}-3-phenyl-8-(trifluoromethyl)quinoline | MS (ESI) m/z 508; | HRMS: calcd for $C_{29}H_{18}ClF_4NO$ + H+, 508.10858; found (ESI, [M+H]+), 508.1062; | 44 |
| Example 1034 | 4-{3-[(3,4-dichlorobenzyl)oxy]phenyl}-3-phenyl-8-(trifluoromethyl)quinoline | MS (ESI) m/z 524; | HRMS: calcd for $C_{29}H_{18}Cl_2F_3NO$ + H+, 524.07903; found (ESI, [M+H]+), 524.0778; | 44 |
| Example 1035 | 4-{3-[(2,6-dichlorobenzyl)oxy]phenyl}-3-phenyl-8-(trifluoromethyl)quinoline | MS (ESI) m/z 524; | HRMS: calcd for $C_{29}H_{18}Cl_2F_3NO$ + H+, 524.07903; found (ESI, [M+H]+), 524.0815; | 44 |
| Example 1036 | 4-{3-[(2,6-difluorobenzyl)oxy]phenyl}-3-phenyl-8-(trifluoromethyl)quinoline | MS (ESI) m/z 492; | | 44 |
| Example 1037 | 4-{3-[(2,4-difluorobenzyl)oxy]phenyl}-3-phenyl-8-(trifluoromethyl)quinoline | MS (ESI) m/z 492; | HRMS: calcd for $C_{29}H_{18}F_5NO$ + H+, 492.13813; found (ESI, [M + H]+), 492.1371; | 44 |
| Example 1038 | 3-[3-(2-ethynylphenyl)-8-(trifluoromethyl)quinolin-4-yl]phenol | MS (ESI) m/z 390; | | 676 |
| Example 1039 | 4-{3-[(2,3-difluorobenzyl)oxy]phenyl}-3-phenyl-8-(trifluoromethyl)quinoline | MS (ES) m/z 492.1; | HRMS: calcd for $C_{29}H_{18}F_5NO$ + H+, 492.13813; found (ESI, [M + H]+), 492.1367; | 44 |

| Example | Name | MS | HRMS | Example Number of Similar Procedure |
|---|---|---|---|---|
| Example 1040 | N-[(5-methyl-2-thienyl)methyl]-3-[3-methyl-8-(trifluoromethyl)quinolin-4-yl]aniline | | HRMS: calcd for $C_{23}H_{19}F_3N_2S + H+$, 413.12938; found (ESI, [M + H]$^+$), 413.1292; | 66 |
| Example 1041 | N-[(5-ethyl-2-furyl)methyl]-3-[3-methyl-8-(trifluoromethyl)quinolin-4-yl]aniline | | HRMS: calcd for $C_{24}H_{21}F_3N_2O + H+$, 411.16787; found (ESI, [M + H]$^+$), 411.169; | 66 |
| Example 1042 | N-[(4,5-dimethyl-2-furyl)methyl]-3-[3-methyl-8-(trifluoromethyl)quinolin-4-yl]aniline | | HRMS: calcd for $C_{24}H_{21}F_3N_2O + H+$, 411.16787; found (ESI, [M + H]$^+$), 411.169; | 66 |
| Example 1043 | N-(2-fluoro-5-methoxybenzyl)-3-[3-methyl-8-(trifluoromethyl)quinolin-4-yl]aniline | | HRMS: calcd for $C_{25}H_{20}F_4N_2O + H+$, 441.15845; found (ESI, [M + H]$^+$), 441.1581; | 66 |
| Example 1044 | N-(2-bromo-5-methoxybenzyl)-3-[3-methyl-8-(trifluoromethyl)quinolin-4-yl]aniline | | HRMS: calcd for $C_{25}H_{20}BrF_3N_2O + H+$, 501.07838; found (ESI, [M + H]$^+$), 501.0788; | 66 |
| Example 1045 | N-(2,3-dimethoxybenzyl)-3-[3-methyl-8-(trifluoromethyl)quinolin-4-yl]aniline | | HRMS: calcd for $C_{26}H_{23}F_3N_2O_2 + H+$, 453.17844; found (ESI, [M + H]$^+$), 453.1808; | 66 |
| Example 1046 | N-(2,4-dimethoxybenzyl)-3-[3-methyl-8-(trifluoromethyl)quinolin-4-yl]aniline | | HRMS: calcd for $C_{26}H_{23}F_3N_2O_2 + H+$, 453.17844; found (ESI, [M + H]$^+$), 453.1787; | 66 |
| Example 1047 | N-(3,4-dimethoxybenzyl)-3-[3-methyl-8-(trifluoromethyl)quinolin-4-yl]aniline | | HRMS: calcd for $C_{26}H_{23}F_3N_2O_2 + H+$, 453.17844; found (ESI, [M + H]$^+$), 453.1808; | 66 |
| Example 1048 | N-(3,5-dimethoxybenzyl)-3-[3-methyl-8-(trifluoromethyl)quinolin-4-yl]aniline | | HRMS: calcd for $C_{26}H_{23}F_3N_2O_2 + H+$, 453.17844; found (ESI, [M + H]$^+$), 453.1792; | 66 |
| Example 1049 | N-(2,3-dimethylbenzyl)-3-[3-methyl-8-(trifluoromethyl)quinolin-4-yl]aniline | | HRMS: calcd for $C_{26}H_{23}F_3N_2 + H+$, 421.18861; found (ESI, [M + H]$^+$), 421.1896; | 66 |

-continued

| Example | Name | MS | HRMS | Example Number of Similar Procedure |
|---|---|---|---|---|
| Example 1050 | N-(4-isopropylbenzyl)-3-[3-methyl-8-(trifluoromethyl)quinolin-4-yl]aniline | | HRMS: calcd for $C_{27}H_{25}F_3N_2$ + H+, 435.20426; found (ESI, [M + H]+), 435.2059; | 66 |
| Example 1051 | {3-[3-methyl-8-(trifluoromethyl)quinolin-4-yl]phenyl}(1-naphthylmethyl)amine | | HRMS: calcd for $C_{28}H_{21}F_3N_2$ + H+, 443.17296; found (ESI, [M + H]+), 443.1733; | 66 |
| Example 1052 | {3-[3-methyl-8-(trifluoromethyl)quinolin-4-yl]phenyl}(2-naphthylmethyl)amine | | HRMS: calcd for $C_{28}H_{21}F_3N_2$ + H+, 443.17296; found (ESI, [M + H]+), 443.1754; | 66 |
| Example 1053 | {3-[3-methyl-8-(trifluoromethyl)quinolin-4-yl]phenyl}(quinolin-3-ylmethyl)amine | | HRMS: calcd for $C_{27}H_{20}F_3N_3$ + H+, 444.16821; found (ESI, [M + H]+), 444.1686; | 66 |
| Example 1054 | N-(1-benzofuran-2-ylmethyl)-3-[3-methyl-8-(trifluoromethyl)quinolin-4-yl]aniline | | HRMS: calcd for $C_{26}H_{19}F_3N_2O$ + H+, 433.15222; found (ESI, [M + H]+), 433.1536; | 66 |
| Example 1055 | N-[(5-methyl-2-furyl)methyl]-3-[3-methyl-8-(trifluoromethyl)quinolin-4-yl]aniline | | HRMS: calcd for $C_{23}H_{19}F_3N_2O$ + H+, 397.15222; found (ESI, [M + H]+), 397.1528; | 66 |
| Example 1056 | methyl {4-[({3-[3-methyl-8-(trifluoromethyl)quinolin-4-yl]phenyl}amino)methyl]phenyl}acetate | | HRMS: calcd for $C_{27}H_{23}F_3N_2O_2$ + H+, 465.17844; found (ESI, [M + H]+), 465.1797; | 66 |
| Example 1057 | methyl 2-{4-[({3-[3-methyl-8-(trifluoromethyl)quinolin-4-yl]phenyl}amino)methyl]phenyl}propanoate | | HRMS: calcd for $C_{28}H_{25}F_3N_2O_2$ + H+, 479.19409; found (ESI, [M + H]+), 479.1933; | 66 |
| Example 1058 | methyl 2-methyl-2-{4-[({3-[3-methyl-8-(trifluoromethyl)quinolin-4-yl]phenyl}amino)methyl]phenyl}propanoate | | HRMS: calcd for $C_{29}H_{27}F_3N_2O_2$ + H+, 493.20974; found (ESI, [M + H]+), 493.2089; | 66 |
| Example 1059 | 4-{3-[(4-fluorobenzyl)oxy]phenyl}-3-(2-methylphenyl)-8-(trifluoromethyl)quinoline | MS (ESI) m/z 488; | HRMS: calcd for $C_{30}H_{21}F_4NO$ + H+, 488.16320; found (ESI, [M + H]+), 488.1635; | 478 |
| Example 1060 | 4-(3-{[5-fluoro-2-(trifluoromethyl)benzyl]oxy}phenyl)-3-(2-methylphenyl)-8-(trifluoromethyl)quinoline | MS (ESI) m/z 556; | HRMS: calcd for $C_{31}H_{20}F_7NO$ + H+, 556.15059; found (ESI, [M + H]+), 556.1496; | 478 |

-continued

| Example | Name | MS | HRMS | Example Number of Similar Procedure |
|---|---|---|---|---|
| Example 1061 | 4-(3-{[2-chloro-5-(trifluoromethyl)benzyl]oxy}phenyl)-3-(2-methylphenyl)-8-(trifluoromethyl)quinoline | MS (ESI) m/z 572; | HRMS: calcd for $C_{31}H_{20}ClF_6NO + H+$, 572.12104; found (ESI, [M + H]+), 572.1196; | 478 |
| Example 1062 | 4-{3-[(2-chloro-4-fluorobenzyl)oxy]phenyl}-3-(2-methylphenyl)-8-(trifluoromethyl)quinoline | MS (ESI) m/z 522; | HRMS: calcd for $C_{30}H_{20}ClF_4NO + H+$, 522.12423; found (ESI, [M + H]+), 522.1254; | 478 |
| Example 1063 | 4-{3-[(2-chlorobenzyl)oxy]phenyl}-3-(2-methylphenyl)-8-(trifluoromethyl)quinoline | MS (ESI) m/z 504; | HRMS: calcd for $C_{30}H_{21}ClF_3NO + H+$, 504.13365; found (ESI, [M + H]+), 504.1335; | 478 |
| Example 1064 | 4-(3-{[2-chloro-3-(trifluoromethyl)benzyl]oxy}phenyl)-3-(2-methylphenyl)-8-(trifluoromethyl)quinoline | MS (ESI) m/z 572; | HRMS: calcd for $C_{31}H_{20}ClF_6NO + H+$, 572.12104; found (ESI, [M + H]+), 572.119; | 478 |
| Example 1065 | 4-(3-{[5-chloro-2-(trifluoromethyl)benzyl]oxy}phenyl)-3-(2-methylphenyl)-8-(trifluoromethyl)quinoline | MS (ESI) m/z 572; | HRMS: calcd for $C_{31}H_{20}ClF_6NO + H+$, 572.12104; found (ESI, [M + H]+), 572.1216; | 478 |
| Example 1066 | 4-{3-[(2-fluoro-4-nitrobenzyl)oxy]phenyl}-3-(2-methylphenyl)-8-(trifluoromethyl)quinoline | MS (ESI) m/z 533; | HRMS: calcd for $C_{30}H_{20}F_4N_2O_3 + H+$, 533.14828; found (ESI, [M + H]+), 533.1478; | 478 |
| Example 1067 | 4-[3-(1-naphthylmethoxy)phenyl]-3-phenyl-8-(trifluoromethyl)quinoline | MS (ESI) m/z 506; | HRMS: calcd for $C_{33}H_{22}F_3NO + H+$, 506.17262; found (ESI, [M + H]+), 506.1727; | 44 |
| Example 1068 | 4-{3-[(2-methoxybenzyl)oxy]phenyl}-3-phenyl-8-(trifluoromethyl)quinoline | MS (ESI) m/z 486; | HRMS: calcd for $C_{30}H_{22}F_3NO_2 + H+$, 486.16754; found (ESI, [M + H]+), 486.1673; | 44 |
| Example 1069 | 4-{3-[(2,3-dimethylbenzyl)oxy]phenyl}-3-phenyl-8-(trifluoromethyl)quinoline | MS (ESI) m/z 484; | HRMS: calcd for $C_{31}H_{24}F_3NO + H+$, 484.18827; found (ESI, [M + H]+), 484.19; | 44 |
| Example 1070 | 4-{3-[(3,5-dimethoxybenzyl)oxy]phenyl}-3-phenyl-8-(trifluoromethyl)quinoline | MS (ESI) m/z 516; | | 44 |
| Example 1071 | methyl [4-({3-[3-phenyl-8-(trifluoromethyl)quinolin-4-yl]phenoxy}methyl)phenoxy]acetate | MS (ESI) m/z 544; | HRMS: calcd for $C_{32}H_{24}F_3NO_4 + H+$, 544.17302; found (ESI, [M + H]+), 544.1744; | 44 |

-continued

| Example | Name | MS | HRMS | Example Number of Similar Procedure |
|---|---|---|---|---|
| Example 1072 | 4-{3-[(2,3-dimethoxybenzyl)oxy]phenyl}-3-phenyl-8-(trifluoromethyl)quinoline | MS (ESI) m/z 516; | HRMS: calcd for $C_{31}H_{24}F_3NO_3$ + H+, 516.17810; found (ESI, [M + H]+), 516.1794; | 44 |
| Example 1073 | 4-(3-{[5-chloro-2-(trifluoromethyl)benzyl]oxy}phenyl)-3-phenyl-8-(trifluoromethyl)quinoline | MS (ESI) m/z 558; | HRMS: calcd for $C_{30}H_{18}ClF_6NO$ + H+, 558.10538; found (ESI, [M + H]+), 558.106; | 44 |
| Example 1074 | 4-{3-[(4-bromo-2-nitrobenzyl)oxy]phenyl}-3-(2-methylphenyl)-8-(trifluoromethyl)quinoline | MS (ESI) m/z 593; | | 478 |
| Example 1075 | {4-[({3-[3-methyl-8-(trifluoromethyl)quinolin-4-yl]phenyl}amino)methyl]phenyl}acetic acid | | HRMS: calcd for $C_{26}H_{21}F_3N_2O_2$ + H+, 451.16279; found (ESI, [M + H]+), 451.1609; | 66 |
| Example 1076 | 2-{4-[({3-[3-methyl-8-(trifluoromethyl)quinolin-4-yl]phenyl}amino)methyl]phenyl}propanoic acid | | HRMS: calcd for $C_{27}H_{23}F_3N_2O_2$ + H+, 465.17844; found (ESI, [M + H]+), 465.177; | 66 |
| Example 1077 | 2-methyl-2-{4-[({3-[3-methyl-8-(trifluoromethyl)quinolin-4-yl]phenyl}amino)methyl]phenyl}propanoic acid | | HRMS: calcd for $C_{28}H_{25}F_3N_2O_2$ + H+, 479.19409; found (ESI, [M + H]+), 479.1932; | 66 |
| Example 1078 | (2R)-2-[4-({3-[3-methyl-8-(trifluoromethyl)quinolin-4-yl]phenoxy}methyl)phenyl]propanoic acid | | HRMS: calcd for $C_{27}H_{22}F_3NO_3$ + H+, 466.16245; found (ESI, [M + H]+), 466.1634; | 366 |
| Example 1079 | (2S)-2-[4-({3-[3-methyl-8-(trifluoromethyl)quinolin-4-yl]phenoxy}methyl)phenyl]propanoic acid | | HRMS: calcd for $C_{27}H_{22}F_3NO_3$ + H+, 466.16245; found (ESI, [M + H]+), 466.1631; | 366 |
| Example 1080 | 3-benzyl-4-{3-[(2-chlorobenzyl)oxy]phenyl}-8-(trifluoromethyl)quinoline | MS (ESI) m/z 504; | | 478 |
| Example 1081 | 3-benzyl-4-{3-[(2-fluorobenzyl)oxy]phenyl}-8-(trifluoromethyl)quinoline | MS (ESI) m/z 488; | | 478 |
| Example 1082 | 3-benzyl-4-{3-[(4-fluorobenzyl)oxy]phenyl}-8-(trifluoromethyl)quinoline | MS (ESI) m/z 488; | | 478 |
| Example 1083 | 3-benzyl-4-{3-[(4-nitrobenzyl)oxy]phenyl}-8-(trifluoromethyl)quinoline | MS (ESI) m/z 515; | | 478 |
| Example 1084 | 3-benzyl-4-[3-(3-chloro-4-fluorophenoxy)phenyl]-8-(trifluoromethyl)quinoline | MS (ESI) m/z 508; | HRMS: calcd for $C_{29}H_{18}ClF_4NO$ + H+, 508.10858; found (ESI, [M + H]+), 508.1096; | 519 |

-continued

| Example | Name | MS | HRMS | Example Number of Similar Procedure |
|---|---|---|---|---|
| Example 1085 | 3-benzyl-4-[3-(3-methylphenoxy)phenyl]-8-(trifluoromethyl)quinoline | MS (ESI) m/z 470; | HRMS: calcd for $C_{30}H_{22}F_3NO$ + H+, 470.17262; found (ESI, [M + H]+), 470.1759 | 519 |
| Example 1086 | 3-benzyl-8-(trifluoromethyl)-4-{3-[3-(trifluoromethyl)phenoxy]phenyl}quinoline | MS (ESI) m/z 524; | HRMS: calcd for $C_{30}H_{19}F_6NO$ + H+, 524.14436; found (ESI, [M + H]+), 524.1441; | 519 |
| Example 1087 | 3-benzyl-4-[3-(3-chlorophenoxy)phenyl]-8-(trifluoromethyl)quinoline | MS (ESI) m/z 490; | HRMS: calcd for $C_{29}H_{19}ClF_3NO$ + H+, 490.11800; found (ESI, [M + H]+), 490.1157; | 519 |
| Example 1088 | 3-benzyl-4-[3-(3,5-dimethylphenoxy)phenyl]-8-(trifluoromethyl)quinoline | MS (ESI) m/z 484; | HRMS: calcd for $C_{31}H_{24}F_3NO$ + H+, 484.18827; found (ESI, [M + H]+), 484.1869; | 519 |
| Example 1089 | 3-benzyl-4-[3-(4-fluorophenoxy)phenyl]-8-(trifluoromethyl)quinoline | MS (ESI) m/z 474; | HRMS: calcd for $C_{29}H_{19}F_4NO$ + H+, 474.14755; found (ESI, [M + H]+), 474.1492; | 519 |
| Example 1090 | 3-benzyl-4-[3-(2-naphthyloxy)phenyl]-8-(trifluoromethyl)quinoline | MS (ESI) m/z 506; | HRMS: calcd for $C_{33}H_{22}F_3NO$ + H+, 506.17262; found (ESI, [M + H]+), 506.1752; | 519 |
| Example 1091 | 3-benzyl-4-[3-(3,5-difluorophenoxy)phenyl]-8-(trifluoromethyl)quinoline | MS (ESI) m/z 492; | HRMS: calcd for $C_{29}H_{18}F_5NO$ + H+, 492.13813; found (ESI, [M + H]+), 492.1386; | 519 |
| Example 1092 | (3-{3-[3-methyl-8-(trifluoromethyl)quinolin-4-yl]phenoxy}phenyl)methanol | MS (ESI) m/z 410; | HRMS: calcd for $C_{24}H_{18}F_3NO_2$ + H+, 410.13624; found (ESI, [M + H]+), 410.1362; | 415 |
| Example 1093 | (4-{3-[3-methyl-8-(trifluoromethyl)quinolin-4-yl]phenoxy}phenyl)methanol | MS (ESI) m/z 410; | HRMS: calcd for $C_{24}H_{18}F_3NO_2$ + H+, 410.13624; found (ESI, [M + H]+), 410.1342; | 415 |
| Example 1094 | 3-benzyl-4-[3-(3,5-dichlorophenoxy)phenyl]-8-(trifluoromethyl)quinoline | MS (ESI) m/z 524; | HRMS: calcd for $C_{29}H_{18}Cl_{12}F_3NO$ + H+, 524.07903; found (ESI, [M + H]+), 524.0775; | 519 |

-continued

| Example | Name | MS | HRMS | Example Number of Similar Procedure |
|---|---|---|---|---|
| Example 1095 | N-(2,5-dimethylbenzyl)-3-[3-methyl-8-(trifluoromethyl)quinolin-4-yl]aniline | | HRMS: calcd for $C_{26}H_{23}F_3N_2$ + H+, 421.18861; found (ESI, [M + H]+), 421.1897; | 66 |
| Example 1096 | N-(5-fluoro-2-methoxybenzyl)-3-[3-methyl-8-(trifluoromethyl)quinolin-4-yl]aniline | | HRMS: calcd for $C_{25}H_{20}F_4N_2O$ + H+, 441.15845; found (ESI, [M + H]+), 441.1575; | 66 |
| Example 1097 | N-[5-fluoro-2-(trifluoromethyl)benzyl]-3-[3-methyl-8-(trifluoromethyl)quinolin-4-yl]aniline | | HRMS: calcd for $C_{25}H_{17}F_7N_2$ + H+, 479.13527; found (ESI, [M + H]+), 479.1375; | 66 |
| Example 1098 | N-[2-fluoro-5-(trifluoromethyl)benzyl]-3-[3-methyl-8-(trifluoromethyl)quinolin-4-yl]aniline | | HRMS: calcd for $C_{25}H_{17}F_7N_2$ + H+, 479.13527; found (ESI, [M + H]+), 479.1344; | 66 |
| Example 1099 | N-(5-ethoxy-2-fluorobenzyl)-3-[3-methyl-8-(trifluoromethyl)quinolin-4-yl]aniline | | HRMS: calcd for $C_{26}H_{22}F_4N_2O$ + H+, 455.17410; found (ESI-FTMS, [M + H]$^{1+}$), 455.17452; | 66 |
| Example 1100 | N-(2-fluoro-5-propoxybenzyl)-3-[3-methyl-8-(trifluoromethyl)quinolin-4-yl]aniline | | HRMS: calcd for $C_{27}H_{24}F_4N_2O$ + H+, 469.18975; found (ESI-FTMS, [M + H]$^{1+}$), 469.1899; | 66 |
| Example 1101 | N-(2-bromo-5-ethoxybenzyl)-3-[3-methyl-8-(trifluoromethyl)quinolin-4-yl]aniline | | HRMS: calcd for $C_{26}H_{22}BrF_3N_2O$ + H+, 515.09403; found (ESI-FTMS, [M + H]$^{1+}$), 515.09489; | 66 |
| Example 1102 | N-(2,6-dimethylbenzyl)-3-[3-methyl-8-(trifluoromethyl)quinolin-4-yl]aniline | | HRMS: calcd for $C_{26}H_{23}F_3N_2$ + H+, 421.18861; found (ESI-FTMS, [M + H]$^{1+}$), 421.18907; | 66 |
| Example 1103 | {3-[3-methyl-8-(trifluoromethyl)quinolin-4-yl]phenyl}[2-(trifluoromethoxy)benzyl]amine | | HRMS: calcd for $C_{25}H_{18}F_6N_2O$ + H+, 477.13961; found (ESI-FTMS, [M + H]$^{1+}$), 477.13955; | 66 |
| Example 1104 | {3-[3-methyl-8-(trifluoromethyl)quinolin-4-yl]phenyl}[3-(trifluoromethoxy)benzyl]amine | | HRMS: calcd for $C_{25}H_{18}F_6N_2O$ + H+, 477.13961; found (ESI-FTMS, [M + H]$^{1+}$), 477.13957; | 66 |

-continued

| Example | Name | MS | HRMS | Example Number of Similar Procedure |
|---|---|---|---|---|
| Example 1105 | N-(2-fluoro-6-methoxybenzyl)-3-[3-methyl-8-(trifluoromethyl)quinolin-4-yl]aniline | | HRMS: calcd for $C_{25}H_{20}F_4N_2O$ + H+, 441.15845; found (ESI-FTMS, $[M + H]^{1+}$), 441.15891; | 66 |
| Example 1106 | N-(3-fluoro-4-methoxybenzyl)-3-[3-methyl-8-(trifluoromethyl)quinolin-4-yl]aniline | | HRMS: calcd for $C_{25}H_{20}F_4N_2O$ + H+, 441.15845; found (ESI-FTMS, $[M + H]^{1+}$), 441.15917; | 66 |
| Example 1107 | N-(2-ethoxy-3-methoxybenzyl)-3-[3-methyl-8-(trifluoromethyl)quinolin-4-yl]aniline | MS (ESI) m/z 467 ($[M + H]$)+ | | 66 |
| Example 1108 | N-(2,3-dihydro-1,4-benzodioxin-6-ylmethyl)-3-[3-methyl-8-(trifluoromethyl)quinolin-4-yl]aniline | | HRMS: calcd for $C_{26}H_{21}F_3N_2O_2$+ H+, 451.16279; found (ESI-FTMS, $[M + H]^{1+}$), 451.16329; | 66 |
| Example 1109 | N-(1H-indol-5-ylmethyl)-3-[3-methyl-8-(trifluoromethyl)quinolin-4-yl]aniline | | HRMS: calcd for $C_{26}H_{20}F_3N_3$ + H+, 432.16821; found (ESI-FTMS, $[M + H]^{1+}$), 432.16886; | 66 |
| Example 1110 | 3-(2-methylphenyl)-8-(trifluoromethyl)-4-{3-[(3,4,5-trimethoxybenzyl)oxy]phenyl}quinoline | MS m/z 560; | | 478 |
| Example 1111 | 3-benzyl-4-{3-[(5-bromo-2-fluorobenzyl)oxy]phenyl}-8-(trifluoromethyl)quinoline | MS m/z 566; | | 478 |
| Example 1112 | [4-({3-[3-phenyl-8-(trifluoromethyl)quinolin-4-yl]phenoxy}methyl)phenoxy]acetic acid | MS (ESI) m/z 530; | HRMS: calcd for $C_{31}H_{22}F_3NO_4$ + H+, 530.15737; found (ESI-FTMS, $[M + H]^{1+}$), 530.1573; | 41 |
| Example 1113 | 3-({3-[3-benzyl-8-(trifluoromethyl)quinolin-4-yl]phenoxy}methyl)-4-fluorobenzonitrile | MS (ESI) m/z 513; | | 478 |
| Example 1114 | N-[2-chloro-3-(trifluoromethyl)benzyl]-3-[3-phenyl-8-(trifluoromethyl)quinolin-4-yl]aniline | MS (ESI) m/z 557; | HRMS: calcd for $C_{30}H_{19}ClF_6N_2$ + H+, 557.12137; found (ESI-FTMS, $[M + H]^{1+}$), 557.12108; | 66 |
| Example 1115 | N-(1H-indol-5-ylmethyl)-3-[3-phenyl-8-(trifluoromethyl)quinolin-4-yl]aniline | MS (ESI) m/z 492; | | 66 |
| Example 1116 | 4-fluoro-3-({3-[3-(2-methylphenyl)-8-(trifluoromethyl)quinolin-4-yl]phenoxy}methyl)benzonitrile | MS (ESI) m/z 513.2 (M + H)+ | | 478 |

-continued

| Example | Name | MS | HRMS | Example Number of Similar Procedure |
|---|---|---|---|---|
| Example 1117 | 3-benzyl-8-fluoro-4-(3-methoxyphenyl)quinoline | MS (ESI) m/z 344; | HRMS: calcd for $C_{23}H_{18}FNO$ + H+, 344.14452; found (ESI, [M + H]+), 344.1457; | 457 |
| Example 1118 | N-(2,3-dihydro-1,4-benzodioxin-6-ylmethyl)-3-[3-phenyl-8-(trifluoromethyl)quinolin-4-yl]aniline | MS (ES) m/z 513.2; | HRMS: calcd for $C_{31}H_{23}F_3N_2O_2$ + H+, 513.17844; found (ESI-FT/MS, [M + H]$^{1+}$), 513.1789; | 66 |
| Example 1119 | N-(1H-indol-6-ylmethyl)-3-[3-phenyl-8-(trifluoromethyl)quinolin-4-yl]aniline | MS (ES) m/z 492.1; | HRMS: calcd for $C_{31}H_{22}F_3N_3$ + H+, 494.18386; found (ESI-FT/MS, [M + H]$^{1+}$), 494.1837; | 66 |
| Example 1120 | N-(1-naphthylmethyl)-3-[3-phenyl-8-(trifluoromethyl)quinolin-4-yl]aniline | MS (ES) m/z 505.2; | HRMS: calcd for $C_{33}H_{23}F_3N_2$ + H+, 505.18861; found (ESI-FT/MS, [M + H]$^{1+}$), 505.1879; | 66 |
| Example 1121 | {3-[3-phenyl-8-(trifluoromethyl)quinolin-4-yl]phenyl}[2-(trifluoromethoxy)benzyl]amine | MS (ES) m/z 539.1; | HRMS: calcd for $C_{30}H_{20}F_6N_2O$ + H+, 539.15526; found (ESI-FT/MS, [M + H]$^{1+}$), 539.1563; | 66 |
| Example 1122 | N-[2-fluoro-5-(trifluoromethyl)benzyl]-3-[3-phenyl-8-(trifluoromethyl)quinolin-4-yl]aniline | MS (ES) m/z 539.1; | HRMS: calcd for $C_{30}H_{19}F_7N_2$ + H+, 541.15092; found (ESI-FT/MS, [M + H]$^{1+}$), 541.1504; | 66 |
| Example 1123 | N-(2,3-dimethylbenzyl)-3-[3-phenyl-8-(trifluoromethyl)quinolin-4-yl]aniline | MS (ES) m/z 483.2; | HRMS: calcd for $C_{31}H_{25}F_3N_2$ + H+, 483.20426; found (ESI-FT/MS, [M + H]$^{1+}$), 483.2046; | 66 |
| Example 1124 | N-(2,3-dimethoxybenzyl)-3-[3-phenyl-8-(trifluoromethyl)quinolin-4-yl]aniline | MS (ES) m/z 515.1; | HRMS: calcd for $C_{31}H_{25}F_3N_2O_2$ + H+, 515.19409; found (ESI-FT/MS, [M + H]$^{1+}$), 515.194; | 66 |
| Example 1125 | 3-[({3-[3-phenyl-8-(trifluoromethyl)quinolin-4-yl]phenyl}amino)methyl]benzonitrile | MS (ES) m/z 478.1; | HRMS: calcd for $C_{30}H_{20}F_3N_3$ + H+, 480.16821; found (ESI-FT/MS, [M + H]$^{1+}$), 480.1677; | 66 |
| Example 1126 | N-[(1-methyl-1H-indol-2-yl)methyl]-3-[3-phenyl-8-(trifluoromethyl)quinolin-4-yl]aniline | MS (ES) m/z 508.2; | HRMS: calcd for $C_{32}H_{24}F_3N_3$ + H+, 508.19951; found (ESI-FT/MS, [M + H]$^{1+}$), 508.2; | 66 |

-continued

| Example | Name | MS | HRMS | Example Number of Similar Procedure |
|---|---|---|---|---|
| Example 1127 | N-[(1-acetyl-1H-indol-3-yl)methyl]-3-[3-phenyl-8-(trifluoromethyl)quinolin-4-yl]aniline | MS (ES) m/z 536.1; | HRMS: calcd for $C_{33}H_{24}F_3N_3O$ + H+, 536.19442; found (ESI-FT/MS, [M + H]$^{1+}$), 536.195; | 66 |
| Example 1128 | 4-{3-[(5-ethynyl-2-fluorobenzyl)oxy]phenyl}-3-(2-methylphenyl)-8-(trifluoromethyl)quinoline | MS (ES) m/z 512.1; | | 676 |
| Example 1129 | 3-benzyl-8-chloro-4-(3-nitrophenyl)quinoline | | HRMS: calcd for $C_{22}H_{15}ClN_2O_2$ + H+, 375.08948; found (ESI-FT/MS, [M + H]$^{1+}$), 375.0901; | 457 |
| Example 1130 | 3-benzyl-8-chloro-4-(4-nitrophenyl)quinoline | MS (ES) m/z 375.1; | HRMS: calcd for $C_{22}H_{15}ClN_2O_2$ + H+, 375.08948; found (ESI-FT/MS, [M + H]$^{1+}$), 375.0901; | 457 |
| Example 1131 | 3-benzyl-4-{3-[(5-ethynyl-2-fluorobenzyl)oxy]phenyl}-8-(trifluoromethyl)quinoline | MS (ES) m/z 512.1; | | 676 |
| Example 1132 | [4-(3-benzyl-8-chloroquinolin-4-yl)phenyl]amine | MS (ESI) m/z 345; | HRMS: calcd for $C_{22}H_{17}ClN_2$ + H+, 345.11530; found (ESI-FT/MS, [M + H]$^{1+}$), 345.1151; | 457 |
| Example 1133 | (3-{3-[3-phenyl-8-(trifluoromethyl)quinolin-4-yl]phenoxy}phenyl)methanol | MS (ESI) m/z 472; | HRMS: calcd for $C_{29}H_{20}F_3NO_2$ + H+, 472.15189; found (ESI-FT/MS, [M + H]$^{1+}$), 472.1517; | 519 |
| Example 1134 | (4-{3-[3-phenyl-8-(trifluoromethyl)quinolin-4-yl]phenoxy}phenyl)methanol | MS (ESI) m/z 472; | HRMS: calcd for $C_{29}H_{20}F_3NO_2$ + H+, 472.15189; found (ESI-FT/MS, [M + H]$^{1+}$), 472.1513; | 519 |
| Example 1135 | 4-{3-[(5-ethyl-2-fluorobenzyl)oxy]phenyl}-3-(2-methylphenyl)-8-(trifluoromethyl)quinoline | MS (ESI) m/z 516; | | 678 |
| Example 1136 | 4-{3-[(2-fluoro-5-vinylbenzyl)oxy]phenyl}-3-(2-methylphenyl)-8-(trifluoromethyl)quinoline | MS (ES) m/z 514.2; | | 676 |
| Example 1137 | ethyl 3-({3-[3-methyl-8-(trifluoromethyl)quinolin-4-yl]phenyl}amino)benzoate | | HRMS: calcd for $C_{26}H_{21}F_3N_2O_2$ + H+, 451.16279; found (ESI, [M + H]$^+$), 451.1638; | 110 |

| Example | Name | MS | HRMS | Example Number of Similar Procedure |
|---|---|---|---|---|
| Example 1138 | [3-(3-benzyl-8-chloroquinolin-4-yl)phenyl]amine | | HRMS: calcd for $C_{22}H_{17}ClN_2$ + H+, 345.11530; found (ESI, [M + H]+), 345.1171; | 60 |
| Example 1139 | 3-benzyl-4-{3-[(2-fluoro-5-vinylbenzyl)oxy]phenyl}-8-(trifluoromethyl)quinoline | MS (ES) m/z 514.2; | | 676 |
| Example 1140 | 3-benzyl-4-(3-{[2-chloro-3-(trifluoromethyl)benzyl]oxy}phenyl)-8-(trifluoromethyl)quinoline | MS (ES) m/z 572.1; | | 478 |
| Example 1141 | 3-benzyl-4-{3-[(3-bromobenzyl)oxy]phenyl}-8-(trifluoromethyl)quinoline | MS (ES) m/z 548.1; | | 478 |
| Example 1142 | 3-[3,8-bis(trifluoromethyl)quinolin-4-yl]phenol | MS (ES) m/z 356.1; | | 457 |
| Example 1143 | [4-({3-[3,8-bis(trifluoromethyl)quinolin-4-yl]phenoxy}methyl)phenyl]acetic acid | MS (ES) m/z 504.1; | | 66 |
| Example 1144 | methyl 2-[4-({3-[3,8-bis(trifluoromethyl)quinolin-4-yl]phenoxy}methyl)phenyl]-2-methylpropanoate | MS (ES) m/z 548.2; | | 478 |
| Example 1145 | 2-[4-({3-[3,8-bis(trifluoromethyl)quinolin-4-yl]phenoxy}methyl)phenyl]-2-methylpropanoic acid | MS (ES) m/z 532.1; | | 66 |
| Example 1146 | 4-(3-{[2-chloro-3-(trifluoromethyl)benzyl]oxy}phenyl)-3-(2,4,6-trifluorobenzyl)-8-(trifluoromethyl)quinoline | MS (ES) m/z 626.2; | | 478 |
| Example 1147 | ethyl 3-{[3-(3-benzyl-8-chloroquinolin-4-yl)phenyl]amino}benzoate | | HRMS: calcd for $C_{31}H_{25}ClN_2O_2$ + H+, 493.16773; found (ESI, [M + H]+), 493.1676; | 110 |
| Example 1148 | [3-({3-[3-methyl-8-(trifluoromethyl)quinolin-4-yl]phenyl}amino)phenyl]methanol | | HRMS: calcd for $C_{24}H_{19}F_3N_2O$ + H+, 409.15222; found (ESI, [M + H]+), 409.1528; | 415 |
| Example 1149 | (3-{[3-(3-benzyl-8-chloroquinolin-4-yl)phenyl]amino}phenyl)methanol | | HRMS: calcd for $C_{29}H_{23}ClN_2O$ + H+, 451.15717; found (ESI, [M + H]+), 451.1592; | 415 |
| Example 1150 | 4-(3-bromophenyl)-8-chloro-3-methylquinoline | MS (ES) m/z 332.1; | HRMS: calcd for $C_{16}H_{11}BrClN$ + H+, 331.98361; found (ESI, [M + H]+), 331.9853; | 457 |
| Example 1151 | 3-benzyl-4-(3-bromophenyl)-8-chloroquinoline | MS (ES) m/z 408.1; | HRMS: calcd for $C_{22}H_{15}BrClN$ + H+, 408.01491; found (ESI, [M + H]+), 408.0145; | 457 |
| Example 1152 | 2-methyl-2-[4-({3-[3-(2,4,6-trifluorobenzyl)-8-(trifluoromethyl)quinolin-4-yl]phenoxy}methyl)phenyl]propanoic acid | MS m/z 04-2798-IMN; | | 66 |

| Example | Name | MS | HRMS | Example Number of Similar Procedure |
|---|---|---|---|---|
| Example 1153 | 2-(3-{[3-(3-benzyl-8-chloroquinolin-4-yl)phenyl]amino}phenyl)propan-2-ol | | HRMS: calcd for $C_{31}H_{27}ClN_2O$ + H+, 479.18847; found (ESI, [M + H]+), 479.189; | 710 |
| Example 1154 | 3-{[3-(3-benzyl-8-chloroquinolin-4-yl)phenyl]amino}benzoic acid | | HRMS: calcd for $C_{29}H_{21}ClN_2O_2$ + H+, 465.13643; found (ESI, [M + H]+), 465.1355; | 110 |
| Example 1155 | (3-{3-[3-benzyl-8-(trifluoromethyl)quinolin-4-yl]phenoxy}phenyl)methanol | MS (ES) m/z 486.2; | HRMS: calcd for $C_{30}H_{22}F_3NO_2$ + H+, 486.16754; found (ESI, [M + H]+), 486.1691; | 415 |
| Example 1156 | methyl 3-[3-(8-chloro-3-methylquinolin-4-yl)phenoxy]benzoate | MS (ES) m/z 404.2; | HRMS: calcd for $C_{24}H_{18}ClNO_3$ + H+, 404.10480; found (ESI, [M + H]+), 404.1063; | 709 |
| Example 1157 | 4-(3-methoxyphenyl)-3-(2,4,6-trifluorobenzyl)-8-(trifluoromethyl)quinoline | MS (ES) m/z 448.1; | | 457 |
| Example 1158 | methyl 3-bromo-2,6-dimethoxy-4-({3-[3-phenyl-8-(trifluoromethyl)quinolin-4-yl]phenoxy}methyl)benzoate | MS (ES) m/z 652.1; | HRMS: calcd for $C_{33}H_{25}BrF_3NO_5$ + H+, 652.09410; found (ESI, [M + H]+), 652.0978; | 44 |
| Example 1159 | [4-({3-[3-phenyl-8-(trifluoromethyl)quinolin-4-yl]phenoxy}methyl)phenyl]methanol | MS (ES) m/z 486.2; | HRMS: calcd for $C_{30}H_{22}F_3NO_2$ + H+, 486.16754; found (ESI, [M + H]+), 486.169; | 519 |
| Example 1160 | {3-[3-(8-chloro-3-methylquinolin-4-yl)phenoxy]phenyl}methanol | MS (ES) m/z 376.1; | HRMS: calcd for $C_{23}H_{18}ClNO_2$ + H+, 376.10988; found (ESI, [M + H]+), 376.109; | 415 |
| Example 1161 | 2-{3-[3-(8-chloro-3-methylquinolin-4-yl)phenoxy]phenyl}propan-2-ol | MS (ES) m/z 404.2; | HRMS: calcd for $C_{25}H_{22}ClNO_2$ + H+, 404.14118; found (ESI, [M + H]+), 404.1414; | 710 |
| Example 1162 | 8-chloro-4-(3-{[2-chloro-3-(trifluoromethyl)benzyl]oxy}phenyl)-3-phenylquinoline | MS (ES) m/z 524.1; | HRMS: calcd for $C_{29}H_{18}Cl_2F_3NO$ + H+, 524.07903; found (ESI, [M + H]+), 524.0784; | 44 |
| Example 1163 | [3-({3-[3-phenyl-8-(trifluoromethyl)quinolin-4-yl]phenoxy}methyl)phenyl]methanol | MS (ES) m/z 486.2; | HRMS: calcd for $C_{30}H_{22}F_3NO_2$ + H+, 486.16754; found (ESI, [M + H]+), 486.1684; | 44 |

-continued

| Example | Name | MS | HRMS | Example Number of Similar Procedure |
|---|---|---|---|---|
| Example 1164 | 3-benzyl-4-(3-{[2-fluoro-3-(trifluoromethyl)benzyl]oxy}phenyl)-8-(trifluoromethyl)quinoline | MS (ES) m/z 556.1; | | 478 |
| Example 1165 | 3-benzyl-4-{3-[(3-ethynylbenzyl)oxy]phenyl}-8-(trifluoromethyl)quinoline | MS (ES) m/z 494.2; | | 676 |
| Example 1166 | methyl 3-{[3-(3-benzyl-8-chloroquinolin-4-yl)phenyl]amino}benzoate | | HRMS: calcd for $C_{30}H_{23}ClN_2O_2$ + H+, 479.15208; found (ESI, [M + H]+), 479.1502; | 110 |
| Example 1167 | N-[3-(3-benzyl-8-chloroquinolin-4-yl)phenyl]-3,5-dimethylaniline | | HRMS: calcd for $C_{30}H_{25}ClN_2$ + H+, 449.17790; found (ESI, [M + H]+), 449.1782; | 119 |
| Example 1168 | 3-{[3-(3-benzyl-8-chloroquinolin-4-yl)phenyl]amino}-N-propylbenzamide | | HRMS: calcd for $C_{32}H_{28}ClN_3O$ + H+, 506.19937; found (ESI, [M + H]+), 506.1993; | 708 |
| Example 1169 | 3-benzyl-4-{3-[(4-bromo-2-fluorobenzyl)oxy]phenyl}-8-(trifluoromethyl)quinoline | MS (ESI) m/z 566; | | 478 |
| Example 1170 | 4-(3-methoxyphenyl)-3-(2-methylphenyl)-8-(trifluoromethyl)quinoline | MS (ES) m/z 394.2; | | 457 |
| Example 1171 | 3-[3-(2-chloro-6-fluorophenyl)-8-(trifluoromethyl)quinolin-4-yl]phenol | MS m/z 418; | | 457 |
| Example 1172 | 3-bromo-2,6-dimethoxy-4-({3-[3-phenyl-8-(trifluoromethyl)quinolin-4-yl]phenoxy}methyl)benzoic acid | MS (ES) m/z 638.0; | HRMS: calcd for $C_{32}H_{23}BrF_3NO_5$ + H+, 638.07844; found (ESI, [M + H]+), 638.0815; | 41 |
| Example 1173 | 3-[3-(8-chloro-3-methylquinolin-4-yl)phenoxy]-N-methylbenzamide | MS (ES) m/z 403.2; | HRMS: calcd for $C_{24}H_{19}ClN_2O_2$ + H+, 403.12078; found (ESI, [M + H]+), 403.123 | 708 |
| Example 1174 | N-[3-(3-benzyl-8-chloroquinolin-4-yl)phenyl]-3,5-difluoroaniline | | HRMS: calcd for $C_{28}H_{19}ClF_2N_2$ + H+, 457.12776; found (ESI, [M + H]+), 457.1273; | 110 |
| Example 1175 | N-[3-(3-benzyl-8-chloroquinolin-4-yl)phenyl]-3,5-dichloroaniline | | HRMS: calcd for $C_{28}H_{19}Cl_3N_2$ + H+, 489.06866; found (ESI, [M + H]+), 489.0213 | 110 |
| Example 1176 | N-[3-(3-benzyl-8-chloroquinolin-4-yl)phenyl]-3,5-dibromoaniline | | HRMS: calcd for $C_{28}H_{19}Br_2ClN_2$ + H+, 576.96762; found (ESI, [M + H]+), 576.9662; | 110 |

-continued

| Example | Name | MS | HRMS | Example Number of Similar Procedure |
|---|---|---|---|---|
| Example 1177 | {4-[3-(8-chloro-3-phenylquinolin-4-yl)phenoxy]phenyl}methanol | MS (ES) m/z 438.2; | HRMS: calcd for $C_{28}H_{20}ClNO_2$ + H+, 438.12553; found (ESI, [M + H]$^+$), 438.1239; | 519 |
| Example 1178 | methyl 3-[3-(3-benzyl-8-chloroquinolin-4-yl)phenoxy]benzoate | MS (ES) m/z 480.2; | HRMS: calcd for $C_{30}H_{22}ClNO_3$ + H+, 480.13610; found (ESI, [M + H]$^+$), 480.1376; | 519 |
| Example 1179 | methyl 4-{3-[3-phenyl-8-(trifluoromethyl)quinolin-4-yl]phenoxy}benzoate | MS (ES) m/z 499.9; | HRMS: calcd for $C_{30}H_{20}F_3NO_3$ + H+, 500.14680; found (ESI, [M + H]$^+$), 500.1456; | 519 |
| Example 1180 | 3-[3-(2-prop-1-yn-1-ylphenyl)-8-(trifluoromethyl)quinolin-4-yl]phenol | MS (ESI) m/z 404; | | 676 |
| Example 1181 | 2-[4-(3-hydroxyphenyl)-8-(trifluoromethyl)quinolin-3-yl]benzonitrile | MS (ESI) m/z 391; | | 676 |
| Example 1182 | 3-benzyl-8-(trifluoromethyl)-4-(3-vinylphenyl)quinoline | MS (ESI) m/z 390; | | 676 |
| Example 1183 | 3-[8-(trifluoromethyl)-3-(2-vinylphenyl)quinolin-4-yl]phenol | MS (ESI) m/z 392; | | 676 |
| Example 1184 | 2,6-dimethoxy-4-({3-[3-phenyl-8-(trifluoromethyl)quinolin-4-yl]phenoxy}methyl)benzoic acid | MS (ESI) m/z 560; | | 41 |
| Example 1185 | 3-[3-(2-prop-1-en-1-ylphenyl)-8-(trifluoromethyl)quinolin-4-yl]phenol | MS (ESI) m/z 405.97 (M + H)+, 404.0 (M − H)+ | | 676 |
| Example 1186 | 3-benzyl-4-{3-[(2-fluoro-4-vinylbenzyl)oxy]phenyl}-8-(trifluoromethyl)quinoline | ESI (M + H)+ = 514. | | 676 |
| Example 1187 | 3-benzyl-8-chloro-4-[3-(3,5-difluorophenoxy)phenyl]quinoline | MS (ESI) 458 m/z ([M + H])+ | | 519 |
| Example 1188 | 3-benzyl-8-chloro-4-[3-(3,5-dimethylphenoxy)phenyl]quinoline | MS (ESI) 450 m/z ([M + H])+ | | 519 |
| Example 1189 | 3-{3-[3-benzyl-8-(trifluoromethyl)quinolin-4-yl]phenoxy}-N-propylbenzamide | MS (ESI) m/z 541; | HRMS: calcd for $C_{33}H_{27}F_3N_2O_2$ + H+, 541.20974; found (ESI, [M + H]$^+$), 541.21; | 708 |
| Example 1190 | 3-{3-[3-benzyl-8-(trifluoromethyl)quinolin-4-yl]phenoxy}-N-isopropylbenzamide | MS (ESI) m/z 541; | HRMS: calcd for $C_{33}H_{27}F_3N_2O_2$ + H+, 541.20974; found (ESI, [M + H]$^+$), 541.2088; | 708 |
| Example 1191 | 3-{3-[3-benzyl-8-(trifluoromethyl)quinolin-4-yl]phenoxy}-N,N-diethylbenzamide | MS (ESI) m/z 555; | | 708 |

-continued

| Example | Name | MS | HRMS | Example Number of Similar Procedure |
|---|---|---|---|---|
| Example 1192 | 3-benzyl-4-{3-[3-(pyrrolidin-1-ylcarbonyl)phenoxy]phenyl}-8-(trifluoromethyl)quinoline | MS (ESI) m/z 553; | HRMS: calcd for $C_{34}H_{27}F_3N_2O_2$ + H+, 553.20974; found (ESI, [M + H]+), 553.2108; | 708 |
| Example 1193 | 3-benzyl-4-{3-[3-(piperidin-1-ylcarbonyl)phenoxy]phenyl}-8-(trifluoromethyl)quinoline | MS (ESI) m/z 567; | HRMS: calcd for $C_{35}H_{29}F_3N_2O_2$ + H+, 567.22539; found (ESI, [M + H]+), 567.2275; | 708 |
| Example 1194 | 3-benzyl-4-{3-[3-(morpholin-4-ylcarbonyl)phenoxy]phenyl}-8-(trifluoromethyl)quinoline | MS (ESI) m/z 569; |  | 708 |
| Example 1195 | 3-[3-(8-chloro-3-methylquinolin-4-yl)phenoxy]-N-propylbenzamide | MS (ESI) m/z 431; | HRMS: calcd for $C_{26}H_{23}ClN_2O_2$ + H+, 431.15208; found (ESI, [M + H]+), 431.1519; | 708 |
| Example 1196 | 3-[3-(8-chloro-3-methylquinolin-4-yl)phenoxy]-N-isopropylbenzamide | MS (ESI) m/z 431; | HRMS: calcd for $C_{26}H_{23}ClN_2O_2$ + H+, 431.15208; found (ESI, [M + H]+), 431.1501; | 708 |
| Example 1197 | 3-[3-(8-chloro-3-methylquinolin-4-yl)phenoxy]-N,N-diethylbenzamide | MS (ESI) m/z 445; | HRMS: calcd for $C_{27}H_{25}ClN_2O_2$ + H+, 445.16773; found (ESI, [M + H]+), 445.1694; | 708 |
| Example 1198 | 8-chloro-3-methyl-4-{3-[3-(pyrrolidin-1-ylcarbonyl)phenoxy]phenyl}quinoline | MS (ESI) m/z 443; |  | 708 |
| Example 1199 | 8-chloro-3-methyl-4-{3-[3-(piperidin-1-ylcarbonyl)phenoxy]phenyl}quinoline | MS (ESI) m/z 457; | HRMS: calcd for $C_{28}H_{25}ClN_2O_2$ + H+, 457.16773; found (ESI, [M + H]+), 457.1673; | 708 |
| Example 1200 | 8-chloro-3-methyl-4-{3-[3-(morpholin-4-ylcarbonyl)phenoxy]phenyl}quinoline | MS (ESI) m/z 459; |  | 708 |
| Example 1201 | 3-[3-(8-chloro-3-methylquinolin-4-yl)phenoxy]-N-(3-methoxyphenyl)benzamide | MS (ESI) m/z 495; |  | 708 |
| Example 1202 | 3-benzyl-4-{3-[(2-fluoro-5-prop-1-yn-1-ylbenzyl)oxy]phenyl}-8-(trifluoromethyl)quinoline | MS (ESI) m/z 526; |  | 676 |
| Example 1203 | N-[3-(3-benzyl-8-chloroquinolin-4-yl)phenyl]-N,3,5-trimethylaniline | MS (ESI) m/z 464 ([M + H])+; |  | 43 |

It is intended that each of the patents, applications, and printed publications including books mentioned in this patent document be hereby incorporated by reference in their entirety.

As those skilled in the art will appreciate, numerous changes and modifications may be made to the preferred embodiments of the invention without departing from the spirit of the invention. It is intended that all such variations fall within the scope of the invention.

What is claimed is:

1. A compound of formula I having the structure:

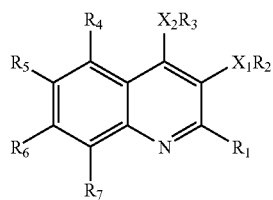

(I)

wherein:

$R_1$ is —H;

$X_1$ is a bond, $C_1$ to $C_5$ alkyl, —C(O)—, —C(=$CR_8R_9$)—, —O—, —S(O)$_t$—, —$NR_8$—, —$CR_8R_9$—, —$CHR_{23}$—, —$CR_8(CR_9)$—, —C($CR_8$)$_2$—, —$CR_8$(OC(O)$R_9$)—, —C=$NOR_9$—, —C(O)$NR_8$—, —$CH_2$O—, —$CH_2$S—, —$CH_2NR_8$—, —$OCH_2$—, —$SCH_2$—, —$NR_8CH_2$—, or

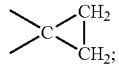

$R_2$ is H, $C_1$ to $C_6$ alkyl, $C_2$ to $C_6$ alkenyl, $C_2$ to $C_6$ alkynyl, $C_3$ to $C_6$ cycloalkyl, —$CH_2$OH, $C_7$ to $C_{11}$ arylalkyl, phenyl, naphthyl, $C_1$ to $C_3$ perfluoroalkyl, CN, C(O)$NH_2$, $CO_2R_{12}$ or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR_8R_9$, —CN, —OH, and $C_1$ to $C_3$ alkyl substituted with 1 to 5 fluorines, or $R_2$ is a heterocycle selected from the group consisting of pyridine, thiophene, benzisoxazole, benzothiophene, oxadiazole, pyrrole, pyrazole, imidazole and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —$NO_2$, —$NR_8R_9$, —CN, and $C_1$ to $C_3$ alkyl substituted with 1 to 5 fluorines;

$X_2$ is a bond or —$CH_2$—;

$R_3$ is phenyl, naphthyl, or phenyl or naphthyl substituted independently by one to four groups independently selected from $C_1$ to $C_3$ alkyl, hydroxy, phenyl, acyl, halogen, —$NH_2$, —CN, —$NO_2$, $C_1$ to $C_3$ alkoxy, $C_1$ to $C_3$ perfluoroalkyl, $C_1$ to $C_3$ alkyl substituted with 1 to 5 fluorines, $NR_{14}R_{15}$, —C(O)$R_{10}$, —C(O)$NR_{10}R_{11}$, —C(O)$NR_{11}$A, —C≡$CR_8$, —CH=$CHR_8$, —WA, —C≡CA, —CH=CHA, —WYA, —$WYNR_{11}$-A, —$WYR_{10}$, —WY($CH_2$)$_j$A, —$WCHR_{11}$($CH_2$)$_j$A, —W($CH_2$)$_j$A, —W($CH_2$)$_j$$R_{10}$, —$CHR_{11}$W($CH_2$)$_j$$R_{10}$, —$CHR_{11}$W($CH_2$)$_j$A, —$CHR_{11}NR_{12}$YA, —$CHR_{11}NR_{12}YR_{10}$, pyrrole, —W($CH_2$)$_j$A($CH_2$)$_k$D($CH_2$)$_p$Z, —W($CR_{18}R_{19}$)A($CH_2$)$_k$D($CH_2$)$_p$Z, —(C$H_2$)$_j$WA($CH_2$)$_k$D($CH_2$)$_p$Z, —CH=CHA($CH_2$)$_k$D($CH_2$)$_p$Z, —C≡CA($CH_2$)$_k$D($CH_2$)$_p$Z, —W(C$H_2$)$_j$C≡CA($CH_2$)$_k$D($CH_2$)$_p$Z, and —W($CH_2$)$_j$Z, or $R_3$ is a heterocycle selected from pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$ alkyl, $C_1$ to $C_3$ alkoxy, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R_{10}$, —C(O)$NR_{10}R_{11}$, —C(O)$NR_{11}$A, —C≡$CR_8$, —CH=$CHR_8$, —WA, —C≡CA, —CH=CHA, —WYA, —$WYR_{10}$, —WY($CH_2$)$_j$A, —W($CH_2$)$_j$A, —W($CH_2$)$_j$$R_{10}$, —$CHR_{11}$W($CH_2$)$_j$$R_{10}$, —$CHR_{11}$W($CH_2$)$_j$A, —$CHR_{11}NR_{12}$YA, —$CHR_{11}NR_{12}YR_{10}$, —$WCHR_{11}$($CH_2$)$_j$A, —W($CH_2$)$_j$A($CH_2$)$_k$D($CH_2$)$_p$Z, —W($CR_{18}R_{19}$)A($CH_2$)$_k$D($CH_2$)$_p$Z, —($CH_2$)$_j$WA(C$H_2$)$_k$D($CH_2$)$_p$Z, —CH=CHA($CH_2$)$_k$D($CH_2$)$_p$Z, —C≡CA($CH_2$)$_k$D($CH_2$)$_p$Z, —W($CH_2$)$_j$C≡CA(C$H_2$)$_k$D($CH_2$)$_p$Z, and —W($CH_2$)$_j$Z;

W is a bond, —O—, —S—, —S(O)—, —S(O)$_2$—, —$NR_{11}$—, or —N(COR$_{12}$)—;

Y is —CO—, —S(O)$_2$—, —$CONR_{13}$—, —$CONR_{13}$CO—, —$CONR_{13}SO_2$—, —C(NCN)—, —$CSNR_{13}$, —C(NH)$NR_{13}$, or —C(O)O—;

j is 0 to 3;

k is 0 to 3;

t is 0 to 2;

D is a bond, —CH=CH—, —C≡C—, —C=, —C(O)—, phenyl, —O—, —NH—, —S—, —$CHR_{14}$—, —$CR_{14}R_{15}$—, —$OCHR_{14}$, —$OCR_{14}R_{15}$—, or —CH(OH)CH(OH)—;

p is 0 to 3;

Z is —$CO_2R_{11}$, —$CONR_{10}R_{11}$, —C($NR_{10}$)$NR_{11}R_{12}$, —$CONH_2NH_2$, —CN, —$CH_2$OH, —$NR_{16}R_{17}$, phenyl, CONHCH(R$_{20}$)COR$_{12}$, phthalimide, pyrrolidine-2,5-dione, thiazolidine-2,4-dione, tetrazolyl, pyrrole, indole, oxazole, 2-thioxo-1,3-thiazolinin-4-one, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —$CO_2CH_3$, —$CO_2$H, —$COCH_3$, —$CONH_2$ and —CN; wherein said $C_1$ to $C_7$ amines are optionally substituted with one to two substituents independently selected from the group consisting of —OH, halogen, —$OCH_3$, and —C≡CH; wherein said phenyl is optionally substituted with $CO_2R_{11}$, and wherein said $C_3$ to $C_7$ cyclic amines are optionally substituted with one or two substituents independently selected from the group consisting of —OH —$CH_2$OH, $C_1$ to $C_3$ alkyl, —$CH_2OCH_3$, —$CO_2CH_3$, and —$CONH_2$, and wherein said oxazole is optionally substituted with $CH_2CO_2R_{11}$;

A is phenyl, naphthyl, tetrahydronaphthyl, indan or biphenyl, each of which may be optionally substituted by one to four groups independently selected from halogen, $C_1$ to $C_3$ alkyl, $C_2$ to $C_4$ alkenyl, $C_2$ to $C_4$ alkynyl, acyl, hydroxy, halogen, —CN, —$NO_2$, —$CO_2R_{11}$, —$CH_2CO_2R_{11}$, phenyl, $C_1$ to $C_3$ perfluoroalkoxy, $C_1$ to $C_3$ perfluoroalkyl, —$NR_{10}R_{11}$, —$CH_2NR_{10}R_{11}$, —$SR_{11}$, $C_1$ to $C_6$ alkyl substituted with 1 to 5 fluorines, $C_1$ to $C_3$ alkyl substituted with 1 to 2 —OH groups, $C_1$ to $C_6$ alkoxy optionally substituted with 1 to 5 fluorines, or phenoxy optionally substituted with 1 to 2 $CF_3$ groups; or A is a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole, benzo[1,2,5]-oxadiazole, isochromen-1-one, benzothiophene, benzofuran, 2,3-dihydrobenzo[1,4]-dioxine, bitheinyl, quinazolin-2,4-91,3H]dione, and 3-H—isobenzofuran-1-one, each of which may be optionally substituted by one to three groups independently selected from halogen, $C_1$ to $C_3$ alkyl, acyl, hydroxy, —CN, —$NO_2$, $C_1$ to $C_3$ perfluoroalkyl, —$NR_{10}R_{11}$, —$CH_2NR_{10}R_{11}$, —$SR_{11}$, $C_1$ to $C_3$ alkyl substituted with 1 to 5 fluorines, and $C_1$ to $C_3$ alkoxy optionally substituted with 1 to 5 fluorines;

$R_4$, $R_5$, and $R_6$ are each, independently, —H or —F;

$R_7$ is $C_1$ to $C_4$ alkyl, $C_1$ to $C_4$ perfluoroalkyl, halogen, —$NO_2$, —CN, phenyl or phenyl substituted with one or two groups independently selected from halogen, $C_1$ to $C_2$ alkyl and OH;

provided that if $X_1R_2$ forms hydrogen, then $R_3$ is selected from:

(a) phenyl substituted by —$W(CH_2)_jA(CH_2)_kD(CH_2)_pZ$, —$W(CR_{18}R_{19})A(CH_2)_kD(CH_2)_pZ$, —$(CH_2)_jWA(CH_2)_kD(CH_2)_pZ$, —$CH$=$CHA(CH_2)_kD(CH_2)_pZ$, —$C$≡$CA(CH_2)_kD(CH_2)_pZ$, or —$W(CH_2)_jC$=$CA(CH_2)_kD(CH_2)_pZ$, wherein the phenyl moiety is further optionally substituted with one or two groups independently selected from $C_1$ to $C_2$ alkyl, $C_1$ to $C_2$ perfluoroalkyl, halogen, and CN; and (b) a heterocycle selected from pyrimidine, thiophene, and furan, each of which is substituted by one of —$W(CH_2)_jA(CH_2)_kD(CH_2)_pZ$, —$W(CR_{18}R_{19})A(CH_2)_kD(CH_2)_pZ$, —$(CH_2)_jWA(CH_2)_kD(CH_2)_pZ$, —$CH$=$CHA(CH_2)_kD(CH_2)_pZ$, —$C$≡$CA(CH_2)_kD(CH_2)_pZ$, or —$W(CH_2)_jC$=$CA(CH_2)_kD(CH_2)_pZ$;

each $R_8$ is independently —H, or $C_1$ to $C_3$ alkyl;

each $R_9$ is independently —H, or $C_1$ to $C_3$ alkyl;

each $R_{10}$ is independently —H, —CH, $C_1$ to $C_3$ alkoxy, $C_1$ to $C_7$ alkyl, $C_3$ to $C_7$ alkenyl, $C_3$ to $C_7$ alkynyl, $C_3$ to $C_7$ cycloalkyl, —$CH_2CH_2OCH_3$, 2-methyl-tetrahydro-furan, 2-methyl-tetrahydro-pyran, 4-methyl-piperidine, morpholine, pyrrolidine, or phenyl optionally substituted with one or two $C_1$ to $C_3$ alkoxy groups, wherein said $C_1$ to $C_7$ alkyl is optionally substituted with 1, 2 or 3 groups independently selected from $C_1$ to $C_3$ alkoxy, $C_1$ to $C_3$ thioalkoxy and CN;

each $R_{11}$ is independently —H, $C_1$ to $C_3$ alkyl or $R_{22}$;

or $R_{10}$ and $R_{11}$, when attached to the same atom, together with said atom form:

a 5 to 7 membered saturated ring, optionally substituted by 1 to 2 groups independently selected from $C_1$ to $C_3$ alkyl, OH and $C_1$—$C_3$ alkoxy; or a 5 to 7 membered ring containing 1 or 2 heteroatoms, optionally substituted by 1 to 2 groups independently selected from $C_1$ to $C_3$ alkyl, OH and $C_1$—$C_3$ alkoxy;

each $R_{12}$ is independently —H, or $C_1$ to $C_3$ alkyl;

each $R_{13}$ is independently —H, or $C_1$ to $C_3$ alkyl;

each $R_{14}$ and $R_{15}$ is, independently, $C_1$ to $C_7$ alkyl, $C_3$ to $C_8$ cycloalkyl, $C_2$ to $C_7$ alkenyl, $C_2$ to $C_7$ alkynyl, —CH, —F, $C_7$ to $C_{14}$ arylalkyl, where said arylalkyl is optionally substituted with 1 to 3 groups independently selected from $NO_2$, $C_1$ to $C_6$ alkyl, $C_1$ to $C_3$ perhaloalkyl, halogen, $CH_2CO_2R_{11}$, phenyl and $C_1$ to $C_3$ alkoxy, or $R_{14}$ and $R_{15}$ together with the atom to which they are attached can form a 3 to 7 membered saturated ring;

each $R_{16}$ and $R_{17}$ is, independently, hydrogen, $C_1$ to $C_3$ alkyl, $C_1$ to $C_3$ alkenyl, $C_1$ to $C_3$ alkynyl, phenyl, benzyl or $C_3$ to $C_8$ cycloalkyl, wherein said $C_1$ to $C_3$ alkyl is optionally substituted with one OH group, and wherein said benzyl is optionally substituted with 1 to 3 groups selected from $C_1$ to $C_3$ alkyl and $C_1$ to $C_3$ alkoxy; or $R_{16}$ and $R_{17}$, together with the atom to which they are attached, can form a 3 to 8 membered heterocycle which is optionally substituted with one or two substituents independently selected from the group consisting of $C_1$ to $C_3$ alkyl, —OH, $CH_2OH$, —$CH_2OCH_3$, —$CO_2CH_3$, and —$CONH_2$;

each $R_{18}$ and $R_{19}$ is, independently, $C_1$ to $C_3$ alkyl;

each $R20$ is independently H, phenyl, or the side chain of a naturally occurring alpha amino acid;

each $R_{22}$ is independently arylalkyl optionally substituted with $CH_2COOH$; and each $R_{23}$ is phenyl;

or a pharmaceutically acceptable salt thereof.

2. A compound according to claim 1, wherein $X_1$ is a bond, —C(O)—, —O—, —S(O)$_t$—, —$NR_8$—, or —$CR_8R_9$—;

$R_2$ is $C_1$ to $C_6$ alkyl, phenyl, or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR_8R_9$, —CN, —OH, and $C_1$ to $C_3$ alkyl substituted with 1 to 5 fluorines, or $R_2$ is a heterocycle selected from the group consisting of pyridine, thiophene, benzisoxazole, benzothiophene, oxadiazole, pyrrole, pyrazole, imidazole and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —$NO_2$, —$NR_8R_9$, —CN, and $C_1$ to $C_3$ alkyl substituted with 1 to 5 fluorines;

$X_2$ is a bond or —$CH_2$—;

$R_3$ is phenyl, naphthyl, or phenyl or naphthyl substituted independently by one to four groups independently selected from $C_1$ to $C_3$ alkyl, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R_{10}$, —C(O)$NR_{10}R_{11}$, —C(O)$NR_{11}A$, —C≡$CR_8$, —CH=$CHR_8$, —WA, —C≡CA, —CH=CHA, —WYA, —$WYR_{10}$, —$WY(CH_2)_jA$, —$WCHR_{11}(CH_2)_jA$, —$W(CH_2)_jA$, —$W(CH_2)_jR_{10}$, —$CHR_{11}W(CH_2)_jR_{10}$, —$CHR_{11}W(CH_2)_jA$, —$CHR_{11}NR_{12}YA$, —$CHR_{11}NR_{12}YR_{10}$, and pyrrole, or $R_3$ is a heterocycle selected from pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$ alkyl, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R_{10}$, —C(O)$NR_{10}R_{11}$, —C(O)$NR_{11}A$, —C≡$CR_8$, —CH=$CHR_8$, —WA, —C≡CA, —CH=CHA, —WYA, —$WYR_{10}$, —$WY(CH_2)_jA$, —$W(CH_2)_jA$, —$W(CH_2)_jR_{10}$, —$CHR_{11}W(CH_2)_jR_{10}$, —$CHR_{11}W(CH_2)_jA$, —$CHR_{11}NR_{12}YA$, and —$CHR_{11}NR_{12}YR_{10}$;

W is a bond, —O—, —S—, —S(O)—, —S(O)$_2$—, —$NR_{11}$—, or N(COR$_{12}$)—;

Y is —CO—, —S(O)$_2$—, —$CONR_{13}$, —$CONR_{13}CO$—, —$CONR_{13}SO_2$—, —C(NCN)—, —$CSNR_{13}$, —C(NH)$NR_{13}$, or —C(O)O—;

j is 0 to 3;

t is 0 to 2;

A is phenyl, naphthyl, tetrahydronaphthyl, or phenyl substituted by one to four groups independently selected from halogen, $C_1$ to $C_3$ alkyl, $C_2$ to $C_4$ alkenyl, $C_2$ to $C_4$ alkynyl, acyl, $C_1$ to $C_3$ alkoxy, hydroxy, halogen, —CN, —NO$_2$, —CO$_2$R$_{11}$, CH$_2$CO$_2$R$_{11}$, phenyl, phenoxy, $C_1$ to $C_3$ perfluoroalkoxy, $C_1$ to $C_3$ perfluoroalkyl, —NR$_{10}$R$_{11}$, —CH$_2$NR$_{10}$R$_{11}$, —SR$_{11}$, $C_1$ to $C_3$ alkyl substituted with 1 to 5 fluorines, $C_1$ to $C_6$ alkyl substituted with 1 to 2 —OH groups, and $C_1$ to $C_6$ alkoxy optionally substituted with 1 to 5 fluorines; or A is a heterocycle selected from pyrrole, pyridine, pyrimidine, thiophene, furan, quinoline, oxazole, thiazole, imidazole, isoxazole, indole, benzo[1,3]-dioxole, benzo[1,2,5]-oxadiazole, isochromen-1-one, and 3—H-isobenzofuran-1-one, each of which may be optionally substituted by one to three groups independently selected from halogen, $C_1$ to $C_3$ alkyl, acyl, $C_1$ to $C_3$ alkoxy, hydroxy, halogen, CN, NO$_2$, $C_1$ to $C_3$ perfluoroalkyl, —NR$_{10}$R$_{11}$, —CH$_2$NR$_{10}$R$_{11}$, —SR$_{11}$, $C_1$ to $C_6$ alkyl substituted with 1 to 5 fluorines, and $C_1$ to $C_6$ alkoxy optionally substituted with 1 to 5 fluorines;

R$_4$, R$_5$, R$_6$ are each, independently, —H;

R$_7$ is $C_1$ to $C_4$ alkyl, $C_1$ to $C_4$ perfluoroalkyl, or halogen;

each R$_8$ is independently —H, or $C_1$ to $C_2$ alkyl;

each R$_9$ is independently —H, or $C_1$ to $C_2$ alkyl;

each R$_{10}$ is independently —H, $C_1$ to $C_7$ alkyl, $C_2$ to $C_7$ alkenyl, or $C_3$ to $C_7$ cycloalkyl;

each R$_{11}$ is independently —H, or $C_1$ to $C_3$ alkyl;

each R$_{12}$ is independently —H, or $C_1$ to $C_3$ alkyl;

or a pharmaceutically acceptable salt thereof.

3. A compound according to claim 2, wherein

X$_1$ is a bond, —C(O)—, or —OR$_8$R$_9$—;

R$_2$ is phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —NO$_2$, —NR$_8$R$_9$, —CN, —OH, and $C_1$ to $C_3$ alkyl substituted with 1 to $_5$ fluorines, or R$_2$ is a heterocycle selected from the group consisting of pyridine, thiophene, and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —NO$_2$, —NR$_8$R$_9$, CN, and $C_1$ to $C_3$ alkyl substituted with 1 to 5 fluorines, X$_2$ is a bond;

R$_3$ is phenyl substituted independently by one to four groups independently selected from hydroxy, halogen, $C_1$ to $C_3$ perfluoroalkyl, $C_1$ to $C_3$ alkyl substituted with 1 to 5 fluorines, —C≡CR$_8$, —CH═CHR$_8$, —WA, —C≡CA, —WYA, —WY(CH$_2$)$_j$A, —W(CH$_2$)$_j$A, —WCHR$_{11}$(CH$_2$)$_j$A, and —CHR$_{11}$W(CH$_2$)$_j$A;

or a pharmaceutically acceptable salt thereof.

4. A compound according to claim 1, wherein

X$_1$ is a bond, —C(O)—, —O—, —S(O)$_t$—, —NR$_8$—, —CR$_8$R$_9$—, or —CR$_8$(OR$_9$)—;

R$_2$ is $C_1$ to $C_6$ alkyl, $C_2$ to $C_6$ alkenyl, $C_2$ to $C_6$ alkynyl, $C_3$ to $C_8$ cycloalkyl, —CH$_2$OH, CF$_3$, CN, phenyl, or phenyl substituted by one to four groups independently selected from $C_1$ to $C_3$ alkyl, $C_1$ to $C_3$ alkoxy, $C_1$ to $C_2$ perfluoroalkyl, halogen, —NO$_2$, —NR$_8$R$_9$, —CN, and $C_1$ to $C_2$ alkyl substituted with 1 to 3 fluorines, or R$_2$ is a heterocycle selected from pyridine, thiophene, and furan, each of which may be optionally substituted with one to three groups independently selected from $C_1$ to $C_3$ alkyl, $C_1$ to $C_3$ alkoxy, $C_1$ to $C_2$ perfluoroalkyl, halogen, —NO$_2$, —NR$_8$R$_9$, —CN, and $C_1$ to $C_2$ alkyl substituted with 1 to 3 fluorines;

X$_2$ is a bond or —CH$_2$—;

R$_3$ is phenyl substituted by —W(CH$_2$)$_j$A(CH$_2$)$_k$D(CH$_2$)$_p$Z, —W(CR$_{18}$R$_{19}$)A(CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or W(CH$_2$)$_j$C≡CA(CH$_2$)$_k$D(CH$_2$)$_p$Z, and further optionally substituted with one or two groups independently selected from $C_1$ to $C_2$ alkyl, $C_1$ to $C_2$ perfluoroalkyl, halogen, and —CN, or R$_3$ is a heterocycle selected from pyrimidine, thiophene, and furan, each of which is optionally substituted by —W(CH$_2$)$_j$A(CH$_2$)$_k$D(CH$_2$)$_p$Z, —W(CR$_{18}$R$_{19}$)A(CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z;

W is a bond, —O—, —S—, —S(O)—, —S(O)$_2$—, —NR$_{11}$—, or —N(COR$_{12}$)—;

j is 0 to 3;

k is 0 to 3;

t is 0 to 2;

D is a bond, —CH═CH—, —C≡C—, phenyl, —O—, —NH—, —S—, —CHR$_{14}$—, —CR$_{14}$R$_{15}$—, —OCHR$_{14}$—, —OCR$_{14}$R$_{15}$—, Or —CH(CH)CH(CH)—;

p is 0 to 3,

Z is —CO$_2$R$_{11}$, —CONR$_{10}$R$_{11}$, —C(═NR$_{10}$)NR$_{11}$R$_{12}$, —CONH$_2$NH$_2$, —CN, —CH$_2$OH, —NR$_{16}$R$_{17}$, CONHCH(R$_{20}$)CO$_{12}$, phthalimide, pyrrolidine-2,5-dione, thiazolidine-2,4-dione, tetrazolyl, pyrrole, $C_1$ to $C_7$ amines, $C_3$ to $C_7$ cyclic amines, or $C_1$ to $C_3$ alkyl substituted with one to two OH groups; wherein said pyrrole is optionally substituted with one or two substituents independently selected from the group consisting of —CO$_2$CH$_3$, —CO$_2$H, —COCH$_3$, and —CN; wherein said $C_1$ to $C_7$ amines are optionally substituted with one to two substituents independently selected from the group consisting of —OH, halogen, —OCH$_3$, and —C≡CH; and wherein said $C_3$ to $C_7$ cyclic amines are optionally substituted with one or two substituents independently selected from the group consisting of —OH—CH$_2$OH, —CH$_2$OCH$_3$, —CO$_2$OH$_3$, and —CONH$_2$;

A is phenyl, or phenyl substituted by one to four groups independently selected from halogen, acyl, $C_1$ to $C_3$ alkyl, $C_1$ to $C_3$ alkoxy, hydroxy, halogen, —CN, —NO$_2$, $C_1$ to $C_3$ perfluoroalkyl, —NR$_{10}$R$_{11}$, —CH$_2$NR$_{10}$R$_{11}$, —SR$_{11}$, and $C_1$ to $C_2$ alkyl substituted with 1 to 3 fluorines; or A is a heterocycle selected from pyrrole, pyridine, pyrimidine, thiophene, indole, oxazole, and furan, which may be optionally substituted by one to three groups independently selected from halogen, acyl, $C_1$ to $C_3$ alkyl, $C_1$ to $C_3$ alkoxy, hydroxy, —CN, —NO$_2$, $C_1$ to $C_3$ perfluoroalkyl, —NR$_{10}$R$_{11}$, —CH$_2$NR$_{10}$R$_{11}$, —SR$_{11}$, and $C_1$ to $C_2$ alkyl substituted with 1 to 3 fluorines;

R$_4$, R$_5$, R$_6$ are —H;

R$_7$ is $C_1$ to $C_4$ alkyl, $C_1$ to $C_4$ perfluoroalkyl, or halogen;

each R$_8$ is independently —H, or $C_1$ to $C_2$ alkyl;

each R$_9$ is independently —H, or $C_1$ to $C_2$ alkyl;

each R$_{10}$ is independently —H, or $C_1$ to $C_3$ alkyl;

each R$_{11}$ is independently —H, or $C_1$ to $C_3$ alkyl;

or R$_{10}$ and R$_{11}$, when attached to the same atom, together with said atom form:

a 5 to 7 membered saturated ring, optionally substituted by 1 to 2 groups independently selected from $C_1$ to $C_3$ alkyl, OH and $C_1$—$C_3$ alkoxy, or a 5 to 7 membered ring containing 1 or 2 Heteroatoms, optionally substituted by 1 to 2 groups independently selected from $C_1$ to $C_3$ alkyl, CH and $C_1$—$C_3$ alkoxy;

each $R_{12}$ is independently —H, or $C_1$ to $C_3$ alkyl;

each $R_{14}$, and $R_{15}$ is, independently, $C_1$ to $C_7$ alkyl, $C_3$ to $C_8$ cycloalkyl, $C_2$ to $C_7$ alkenyl, $C_2$ to $C_7$ alkynyl, —CH, —F, $C_7$ to $C_{14}$ arylalkyl, where said arylalkyl is optionally substituted with 1 to $_3$ groups independently selected from $NO_2$, $C_1$ to $C_6$ alkyl, $C_1$ to $C_3$ perhaloalkyl, halogen and $C_1$ to $C_3$ alkoxy, or $R_{14}$ and $R_{15}$ together with the atom to which they are attached can form a 3 to 7 membered saturated ring;

each $R_{16}$ and $R_{17}$ is, independently, hydrogen, $C_1$ to $C_3$ alkyl, $C_1$ to $C_3$ alkenyl, $C_1$ to $C_3$ alkynyl, or $C_3$ to $C_8$ cycloalkyl, wherein said $C_1$ to $C_3$ alkyl is optionally substituted with one OH group; or $R_{16}$ and $R_{17}$, together with the atom to which they are attached, can form a 3 to 8 membered heterocycle which is optionally substituted with one or two substituents independently selected from the group consisting of $C_1$ to $C_3$ alkyl, —OH, $CH_2OH$, —$CH_2OCH_3$, —$CO_2CH_3$, and —$CONH_2$;

each $R_{18}$ and $R_{19}$ is, independently $C_1$ to $C_3$ alkyl;

or a pharmaceutically acceptable salt thereof.

5. A compound according to claim 4, wherein
$X_1$ is a bond, —C(O)—, or —$CR_8R_9$—;

$R_2$ is $C_1$ to $C_6$ alkyl, $CF_3$, CN, phenyl, or phenyl substituted by one to four groups independently selected from $C_1$ to $C_2$ perfluoroalkyl, halogen, and $C_1$ to $C_2$ alkyl substituted with 1 to 3 fluorines, or $R_2$ is a heterocycle selected from thiophene, and furan, which may be optionally substituted with one to three groups independently selected from $C_1$ to $C_2$ perfluoroalkyl, halogen, and $C_1$ to $C_2$ alkyl substituted with 1 to 3 fluorines;

$X_2$ is a bond;

$R_3$ is phenyl substituted by —W($CH_2$)$_j$A($CH_2$)$_k$D($CH_2$)$_p$Z, —W($CR_{18}R_{19}$)A($CH_2$)$_k$D($CH_2$)$_p$Z, —C≡CA($CH_2$)$_k$D($CH_2$)$_p$Z, or —($CH_2$)$_j$WA($CH_2$)$_k$D($CH_2$)$_p$Z, and further optionally substituted with one or two groups independently selected from $C_1$ to $C_2$ perfluoroalkyl, halogen, and —CN, or $R_3$ is a heterocycle selected from pyrimidine, thiophene, and furan which is substituted by —W($CH_2$)$_j$A($CH_2$)$_k$D($CH_2$)$_p$Z, —W($CR_{18}R_{19}$)A($CH_2$)$_k$D($CH_2$)$_p$Z, or —($CH_2$)$_j$WA($CH_2$)$_k$D($CH_2$)$_p$Z;

D is a bond, —O—, —NH—, —S—, —$CHR_{14}$—, —$CR_{14}R_{15}$—, —$OCHR_{14}$—, or —$OCR_{14}R_{15}$—;

Z is —$CO_2R_{11}$, —$CONR_{10}R_{11}$, —CN, —$CH_2OH$, or —$NR_{16}R_{17}$;

A is phenyl, or phenyl substituted by one to four groups independently selected from halogen, —CN, $C_1$ to $C_3$ perfluoroalkyl, and $C_1$ to $C_2$ alkyl substituted with 1 to 3 fluorines, or A is a heterocycle selected from pyrrole, pyridine, pyrimidine, and thiophene, each of which may be optionally substituted by one to three groups independently selected from halogen, —CN, $C_1$ to $C_3$ perfluoroalkyl, and $C_1$ to $C_2$ alkyl substituted with 1 to 3 fluorines;

or a pharmaceutically acceptable salt thereof.

6. The compound according to claim 1, which is:
a) [4-(4-methoxyphenyl)-8-(trifluoromethyl)quinolin-3-yl](phenyl)methanone;
b) [4-(4-hydroxyphenyl)-8-(trifluoromethyl)quinolin-3-yl](phenyl)methanone;
c) [4-(4-methylphenyl)-8-(trifluoromethyl)quinolin-3-yl](phenyl)methanone;
d) [4-(4-methylphenyl)-8-(trifluoromethyl)quinolin-3-yl](pyridin-2-yl)methanone;
e) [4-(3,4-dimethoxyphenyl)-8-(trifluoromethyl)quinolin-3-yl](phenyl)methanone;
f) [4-(2,6-dimethoxyphenyl)-8-(trifluoromethyl)quinolin-3-yl](phenyl)methanone;
g) 1-{2-[3-benzoyl-8-(trifluoromethyl)quinolin-4-yl]phenyl}ethanone;
h) [4-phenyl-8-(trifluoromethyl)quinolin-3-yl](pyridin-2-yl)methanone;
i) [4-(1,1'-biphenyl-4-yl)-8-(trifluoromethyl)quinolin-3-yl](pyridin-2-yl)methanone;
j) pyridin-2-yl{8-(trifluoromethyl)-4-[3-(trifluoromethyl)phenyl]quinolin-3-yl}methanone;
k) [4-(4-chlorophenyl)-8-(trifluoromethyl)quinolin-3-yl](pyridin-2-yl)methanone;
l) phenyl[4-phenyl-8-(trifluoromethyl)quinolin-3-yl]methanone;
m) phenyl{8-(trifluoromethyl)-4-[3-(trifluoromethyl)phenyl]quinolin-3-yl}methanone;
n) [4-(3,4-dichlorophenyl)-8-(trifluoromethyl)quinolin-3-yl](pyridin-2-yl)methanone;
o) [4-(4-tert-butylphenyl)-8-(trifluoromethyl)quinolin-3-yl](pyridin-2-yl)methanone;
p) 3-benzyl-4-(4-methoxyphenyl)-8-(trifluoromethyl)quinoline;
q) 3-benzyl-4-phenyl-8-(trifluoromethyl)quinoline;
r) [4-(3-hydroxyphenyl)-8-(trifluoromethyl)quinolin-3-yl](phenyl)methanone;
s) (3-methylphenyl)[4-phenyl-8-(trifluoromethyl)quinolin-3-yl]methanone;
t) [4-(3-methoxyphenyl)-8-(trifluoromethyl)quinolin-3-yl](phenyl)methanone;
u) (2-methoxyphenyl)[4-phenyl-8-(trifluoromethyl)quinolin-3-yl]methanone;
v) (2-methylphenyl)[4-phenyl-8-(trifluoromethyl)quinolin-3-yl]methanone;
w) [4-phenyl-8-(trifluoromethyl)quinolin-3-yl](pyridin-3-yl)methanone;
x) (4-methylphenyl)[4-phenyl-8-(trifluoromethyl)quinolin-3-yl]methanone;
aa) (3-ethylphenyl)[4-phenyl-8-(trifluoromethyl)quinolin-3-yl]methanone;
ab) (2,4-dimethylphenyl)[4-phenyl-8-(trifluoromethyl)quinolin-3-yl]methanone;
ac) [4-phenyl-8-(trifluoromethyl)quinolin-3-yl](3-propylphenyl)methanone;
ad) 3-methoxyphenyl)[4-phenyl-8-(trifluoromethyl)quinolin-3-yl]methanone;
ae) [4-phenyl-8-(trifluoromethyl)quinolin-3-yl](thien-2-yl)methanone;
af) phenyl[4-phenyl-8-(trifluoromethyl)quinolin-3-yl]methanol;
ag) 1-phenyl-1-[4-phenyl-8-(trifluoromethyl)quinolin-3-yl]ethanol;
ah) 3-[methoxy(phenyl)methyl]-4-phenyl-8-(trifluoromethyl)quinoline;
ai) phenyl[4-phenyl-8-(trifluoromethyl)quinolin-3-yl]methyl acetate;
aj) (E)-phenyl[4-phenyl-8-(trifluoromethyl)quinolin-3-yl]methanone oxime;
ak) 3-(1-methoxy-1-phenylethyl)-4-phenyl-8-(trifluoromethyl)quinoline;
al) [4-[3-(benzyloxy)phenyl]-8-(trifluoromethyl)quinolin-3-yl](phenyl)methanone;
am) [4-{3-[(2-chlorobenzyl)oxy]phenyl}-8-(trifluoromethyl)quinolin-3-yl](phenyl)methanone;

an) phenyl[4-[3-(2-phenylethoxy)phenyl]-8-(trifluoromethyl)quinolin-3-yl]methanone;
ao) (E)-phenyl[4-phenyl-8-(trifluoromethyl)quinolin-3-yl]methanone oxime;
ap) [4-{3-[(2-chloro-6-fluorobenzyl)oxy]phenyl}-8-(trifluoromethyl)quinolin-3-yl](phenyl)methanone;
aq) [4-{3-[(4-chlorobenzyl)oxy]phenyl}-8-(trifluoromethyl)quinolin-3-yl](phenyl) methanone;
ar) [4-{3-[(2-fluorobenzyl)oxy]phenyl}-8-(trifluoromethyl)quinolin-3-yl](phenyl) methanone;
as) [4-{3-[(4-fluorobenzyl)oxy]phenyl}-8-(trifluoromethyl)quinolin-3-yl](phenyl) methanone;
at) [4-{3-[(2-chloro-4-fluorobenzyl)oxy]phenyl}-8-(trifluoromethyl)quinolin-3-yl](phenyl)methanone;
au) phenyl[4-{3-[(2,4,6-trifluorobenzyl)oxy]phenyl}-8-(trifluoromethyl)quinolin-3-yl]methanone;
av) [4-{3-[(2,4-difluorobenzyl)oxy]phenyl}-8-(trifluoromethyl)quinolin-3-yl](phenyl) methanone;
aw) [4-{3-[(3,4-difluorobenzyl)oxy]phenyl}-8-(trifluoromethyl)quinolin-3-yl](phenyl) methanone;
ax) (E)-phenyl[4-phenyl-8-(trifluoromethyl)quinolin-3-yl]methanone O-methyloxime;
ay) [4-(3-aminophenyl)-8-(trifluoromethyl)quinolin-3-yl](phenyl)methanone;
az) [4-phenyl-8-(trifluoromethyl)quinolin-3-yl](thien-3-yl)methanone;
ba) 4-[({3-[3-benzoyl-8-(trifluoromethyl)quinolin-4-yl]phenyl}amino)sulfonyl]benzoic acid;
bb) N-[3-(3-Benzoyl-8-trifluoromethyl-quinolin-4-yl)-phenyl]-4-trifluoromethyl-benzenesulfonamide;
bc) N-{3-[3-benzoyl-8-(trifluoromethyl)quinolin-4-yl]phenyl}benzenesulfonamide;
bd) 1-[3-(3-Benzoyl-8-trifluoromethyl-quinolin-4-yl)-phenyl]-3-phenyl-urea;
be) N-[3-(3-Benzoyl-8-trifluoromethyl-quinolin-4-yl)-phenyl]-benzamide;
bf) (6—Fluoro-4-phenyl-8-trifluoromethyl-quinolin-3-yl)-phenyl-methanone;
bg) ([4-(3—Hydroxymethyl-phenyl)-8-trifluoromethyl-quinolin-3-yl]-phenyl-methanone);
bh) 1-{2-[3-(Pyridin-2-ylcarbonyl)-8-(trifluoromethyl)quinolin-4-yl]phenyl}ethanone;
bi) 4-({3-[3-benzoyl-8-(trifluoromethyl)quinolin-4-yl]phenoxy}methyl)benzoic acid;
bj) 3-({3-[3-benzoyl-8-(trifluoromethyl)quinolin-4-yl]phenoxy}methyl)benzoic acid;
bk) [4-({3-[3-benzoyl-8-(trifluoromethyl)quinolin-4-yl]phenoxy}methyl)phenyl]acetic acid;
bl) 4-({4-[3-benzoyl-8-(trifluoromethyl)quinolin-4-yl]phenoxy}methyl)benzoic acid;
bm) {4-[({3-[3-Benzoyl-8-(trifluoromethyl)quinolinyl]phenyl}amino)methyl]phenyl}acetic acid;
bn) (4-{[{3-[3-Benzoyl-8-(trifluoromethyl)quinolin-4-yl]phenyl}(methyl)amino]methyl}phenyl)acetic acid;
bo) ([4-({3-[3-benzoyl-8-(trifluoromethyl)quinolin-4-yl]benzyl}oxy)phenyl]acetic acid);
bp) ([4-({3-[3-benzoyl-8-(trifluoromethyl)quinolin-4-yl]phenoxy}methyl)phenyl]acetonitrile);
bq) (Phenyl[4-(3-{[4-(1H-tetrazol-5-yl methyl)benzyl]oxy}phenyl)-8-(trifluoromethyl)quinolin-$_3$-yl]methanone);
br) {4-[({3-[3-benzoyl-8-(trifluoromethyl)quinolin-4-yl]phenyl}amino)sulfonyl]phenyl}acetic acid;
bs) phenyl[4-[3-(1H-pyrrol-1-yl)phenyl]-8-(trifluoromethyl)quinolin-3-yl]methanone;
bt) (4-{[{3-[3-benzoyl-8-(trifluoromethyl)quinolin-4-yl]phenyl}(formyl)amino]methyl}phenyl)acetic acid;
bu) [4-(3-anilinophenyl)-8-(trifluoromethyl)quinolin-3-yl]
by) {3-[3-benzoyl-8-(trifluoromethyl)quinolin-4-yl]phenyl}amine;
bw) [4-[3-(benzylamino)phenyl]-8-(trifluoromethyl)quinolin-3-yl](phenyl)methanone;
bx) 2-{4-[({3-[3-benzoyl-8-(trifluoromethyl)quinolin-4-yl]phenyl}amino)methyl]phenyl}acetamide;
by) {4-[({3-[3-benzoyl-8-(trifluoromethyl)quinolin-4-yl]phenyl}amino)methyl]phenyl}acetic acid;
bz) 3-[3-benzoyl-8-(trifluoromethyl)quinolin-4-yl]benzaldehyde;
ca) [4-({3-[3-benzoyl-8-(trifluoromethyl)quinolin-4-yl]benzyl}amino)phenyl]acetic acid;
cb) C$_3$-[4-({3-[3-benzoyl-8-(trifluoromethyl)quinolin-4-yl]benzyl}oxy)phenyl]propanoic acid;
cc) 4-({3-[3-benzoyl-8-(trifluoromethyl)quinolin-4-yl]benzyl}amino)benzoic acid;
cd) 4-[({3-[3-benzoyl-8-(trifluoromethyl)quinolin-4-yl]benzyl}amino)methyl]benzoic acid;
ce) [3-({3-[3-benzoyl-8-(trifluoromethyl)quinolin-4-yl]benzyl}amino)phenyl]acetic acid;
cf) methyl (4-{[{3-[3-benzoyl-8-(trifluoromethyl)quinolin-4-yl]phenyl}(methyl)amino]methyl}phenyl)acetate;
cg) 4-[({3-[3-benzoyl-8-(trifluoromethyl)quinolin-4-yl]phenyl}amino)methyl]benzoic acid;
ch) 3-[({3-[3-benzoyl-8-(trifluoromethyl)quinolin-4-yl]phenyl}amino)methyl]-1H-indole-6-carboxylic acid;
ci) [4-({[3-(3-benzoyl-8-methylquinolin-4-yl)phenyl]amino}methyl)phenyl]acetic acid;
cj) [4-(4-aminophenyl)-8-(trifluoromethyl)quinolin-3-yl](phenyl)methanone;
ck) {4-[({4-[3-benzoyl-8-(trifluoromethyl)quinolin-4-yl]phenyl}amino)methyl]phenyl}acetic acid;
cl) 2-{4-[({3-[3-benzoyl-8-(trifluoromethyl)quinolin-4-yl]phenyl}amino)methyl]phenyl}acetohydrazide;
cm) [4-[3-({4-[(dimethylamino)methyl]benzyl}oxy)phenyl]-8-(trifluoromethyl)quinolin-3-yl](phenyl)methanone;
cn) N-{3-[3-benzoyl-8-(trifluoromethyl)quinolin-4-yl]phenyl}-N'-(2,4-difluorophenyl) urea;
co) N-{3-[3-benzoyl-8-(trifluoromethyl)quinolin-4-yl]phenyl}-N'-cyclohexylurea;
cp) N-{3-[3-benzoyl-8-(trifluoromethyl)quinolin-4-yl]phenyl}-N'-(2-fluorophenyl)urea;
cq) N-{3-[3-benzoyl-8-(trifluoromethyl)quinolin-4-yl]phenyl}-N'-(4-fluorophenyl)urea;
cr) N-{3-[3-benzoyl-8-(trifluoromethyl)quinolin-4-yl]phenyl}-N'-(4-cyanophenyl)urea;
cs) N-{3-[3-benzoyl-8-(trifluoromethyl)quinolin-4-yl]phenyl}-N'-[4-(methylthio) phenyl]urea;
ct) N-[({3-[3-benzoyl-8-(trifluoromethyl)quinolin-4-yl]phenyl}amino)carbonyl]benzamide;
cu) N-[({3-[3-benzoyl-8-(trifluoromethyl)quinolin-4-yl]phenyl}amino)carbonyl]benzenesulfonamide;
cv) N-{3-[3-benzoyl-8-(trifluoromethyl)quinolin-4-yl]phenyl}-N'-(3-fluorophenyl)urea;
cw) N-(3-acetylphenyl)-N'-{3-[3-benzoyl-8-(trifluoromethyl)quinolin-4-yl]phenyl}urea;
cx) N-{3-[3-benzoyl-8-(trifluoromethyl)quinolin-4-yl]phenyl}-N'-(3-methoxyphenyl)urea;
dy) N-{3-[3-benzoyl-8-(trifluoromethyl)quinolin-4-yl]phenyl}-N'-(2,6-dichlorophenyl)urea;
dz) N-{3-[3-benzoyl-8-(trifluoromethyl)quinolin-4-yl]phenyl}-N'-(2-methylphenyl)urea;

da) N-{3-[3-benzoyl-8-(trifluoromethyl)quinolin-4-yl]phenyl}-N'-(2,6-dimethyl phenyl)urea;
db) N-{3-[3-benzoyl-8-(trifluoromethyl)quinolin-4-yl]phenyl}-N'-(4-phenoxyphenyl)urea;
dc) N-{3-[3-benzoyl-8-(trifluoromethyl)quinolin-4-yl]phenyl}-N'-(4-nitrophenyl)urea;
dd) N-{3-[3-benzoyl-8-(trifluoromethyl)quinolin-4-yl]phenyl}-N'-[4-(dimethylamino) phenyl]urea;
de) N-{3-[3-benzoyl-8-(trifluoromethyl)quinolin-4-yl]phenyl}-N'-butylurea;
df) N-{3-[3-benzoyl-8-(trifluoromethyl)quinolin-4-yl]phenyl}-N'-benzylurea;
dg) N-aIIyl-N'-{3-[3-benzoyl-8-(trifluoromethyl)quinolin-4-yl]phenyl}urea;
dh) N-{3-[3-benzoyl-8-(trifluoromethyl)quinolin-4-yl]phenyl}-N'-(4-fluorophenyl) thiourea;
dk) (4-{[({3-[3-benzoyl-8-(trifluoromethyl)quinolin-4-yl]phenyl}amino)carbonyl]amino}phenyl)acetic acid;
dl) [4-({3-[3-benzyl-8-(trifluoromethyl)quinolin-4-yl]phenoxy}methyl)phenyl]acetic acid;
dm) {4-[3-(dimethylamino)phenyl]-8-methylquinolin-3-yl}(phenyl)methanone;
dn) (4-{[[3-(3-benzoyl-8-methylquinolin-4-yl)phenyl](methyl)amino]methyl}phenyl) acetic acid;
do) [4-({[3-(3-benzoyl-8-methylquinolin-4-yl)phenyl]amino}methyl)phenyl]acetic acid
dp) (4-{[{3-[3-benzyl-8-(trifluoromethyl)quinolin-4-yl]phenyl}(methyl)amino]methyl}phenyl)acetic acid;
dq) phenyl[4-(3-{[(2-phenylethyl)amino]methyl}phenyl)-8-(trifluoromethyl)quinolin-3-yl]methanone;
dr) [4-(3{[(2-methylphenyl)amino[methyl]phenyl)-8-(trifluoromethyl)quinolin-3-yl](phenyl)methanone;
ds) phenyl[4-(3-}[(tetrahydrofuran-2-ylmethyl)amino]methyl}phenyl)-8-(trifluoromethyl)quinolin-3-yl]methanone;
dt) phenyl[4-(3-}[(pyridin-4-ylmethyl)amino]methyl]phenyl)-8-(trifluoromethyl) quinolin-3-yl]methanone;
du) [4-(3-((2-methoxybenzyl)amino]methyl}phenyl)-8-(trifluoromethyl)quinolin-3-yl](phenyl)methanone;
dv) [4-]3-({[2-(methylthio)benzyl]amino)methyl)phenyl-8-(trifluoromethyl)quinolin-3-yl](phenyl)methanone;
dw) [4-(3-{[(methoxybenzyl)amino]methyl}phenyl-8-(trifluoromethyl)quinolin-3-yl](phenyl)methanone;
dx) [4-{[(2-methoxyethyl)amino]methy}phenyl(trifluoromethyl)quinolin-3-yl](phenyl)methanone
dy) pheny[4-(3-{[2-pyridin-2-ylethyl)amino]methy}phenyl)-8-(trifluoromethyl) quinolin-3-yl]methanone;
dz) 5-[({3-[3-benzoyl-8-(trifluoromethyl)quinolin-4-yl]phenyl}amino)methyl]-2-hydroxybenzoic acid;
ea) phenyl[4-(3-{[4-(pyrrolidin-1-ylmethyl)benzyl]oxy}phenyl)-8-(trifluoromethyl) quinolin-3-yl]methanone;
eb) phenyl[4-(3-{[4-(piperidin-1-ylmethyl)benzyl]oxy}phenyl)-8-(trifluoromethyl) quinolin-3-yl]methanone;
ec) [4-3-[(4-{[ethyl(methyl)amino]methyl}benzyl)oxy]phenyl})-8-(trifluoromethyl)quinolin-3-yl]phenyl)methanone
ed) [4-3-({4-[-(methylamino)methyl]benzyfloxy)phenyfl-8-trifluoromethyl)quinolin-3-yl](phenyl)methanone;
ee) [4-[3-({4-[(3-hydroxypiperidin-1-yl)methyl]benzyl}oxy)phenyl]-8-(trifluoromethyl) quinolin-3-yl](phenyl)methanone;
ef) [4-[3-({4-[(diethylamino)methyl]benzyl}oxy)phenyl]-8-(trifluoromethyl)quinolin-3-yl](phenyl)methanone;
eg) [4-{3-[(4-{[(2-hydroxyethyl)(methyl)amino]methyl]benzylbenzyl)oxy]phenyl }-8-(trifluoromethyl)quinolin-3-yl](phenyl)methanone;
eh) [4-{3-[(4-{[methyl(prop-2-ynyl)amino]methyl}benzyl)oxy]phenyl}-8-(trifluoromethyl)quinolin-3-yl](phenyl)methanone;
ei) [4-[3-({4-[(4-methylpiperazin-1-yl)methyl]benzyl}oxy)phenyl]-8-(trifluoromethyl)quinolin-3-yl](phenyl)methanone;
ej) [4-[3-({4-[(3-hydroxypyrrolidin-1-yl)methyl]benzyl}oxy)phenyl]-8-(trifluoromethyl)quinolin-3-yl](phenyl)methanone;
ek) [4-{3-[(4-{[2-(methoxymethyl)pyrrolidin-1-yl]methyl}benzyl)oxy]phenyl}-8-(trifluoromethyl)quinolin-3-yl](phenyl)methanone;
el) [4-{3-[(4-{[2-(hydroxymethyl)pyrrolidin-1-yl]methyl}benzyl)oxy]phenyl}-8-(trifluoromethyl)quinolin-3-yl](phenyl)methanone;
em) methyl-1-[4-({3-[3-benzoyl-8-(trifluoromethyl)quinolin-4-yl]phenoxy}methyl)benzyl]prolinate;
en)1-[4-({3-[3-benzoyl-8-(trifluoromethyl)quinolin-4-yl]phenoxy}methyl)benzyl]prolinamide;
eo) 1-{1-[4-({3-[3-benzoyl-8-(trifluoromethyl)quinolin-4-yl]phenoxy}methyl)benzyl]-1H-pyrrole-2-yl]ethanone;
ep) methyl1-[4-({3-[3-benzoyl-8-(trifluoromethyl)quinolin-4-yl]phenoxy}methyl) benzyl]-1H-pyrrole-2-carboxylate;
eq) 1-[4-({3-[3-benzoyl-8-(trifluoromethyl)quinolin-4-yl]phenoxy}methyl)benzyl]-1H-pyrrole-2-carboxylic acid;
er) 1-[4-({3-[3-benzoyl-8-(trifluoromethyl)quinolin-4-yl]phenoxy}methyl)benzyl]pyrrolidine-$_{2,5}$-dione;
es) 1-[4-({3-[3-benzoyl-8-(trifluoromethyl)quinolin-4-yl]phenoxy}methyl)benzyl]-1H-pyrrole-2-carbonitrile;
et) [4-({3-[3-[hydroxy(phenyl)methyl]-8-(trifluoromethyl)quinolin-4-yl]phenoxy}methyl)phenyl]acetic acid
eu) [3-({3-[3-benzoyl-8-(trifluoromethyl)quinolin-4-yl]phenoxy}methyl)phenyl]acetic acid
ev) N-{4-[3-benzoyl-8-(trifluoromethyl)quinolin-4-yl]phenyl}-N'-phenylurea
ew) {3-[3-benzyl-8-(trifluoromethyl)quinolin-4-yl]phenyl}methanol
ex) phenyl[4-3-(prop-2-ynyloxy)phenyl]-8-(trifluoromethyl)quinolin-3-yl]methanone
ey) 4-(3-{3-[3-benzoyl-8-(trifluoromethyl)quinolin-4-yl]phenoxy}prop-1-ynyl)benzoic acid
ez) 3-(3-{3-[3-benzoyl-8-(trifluoromethyl)quinolin-4-yl]phenoxy}prop-1-ynyl)benzoic acid
fa) 3-[3-benzoyl-8-(trifluoromethyl)quinolin-4-yl]phenyl phenylcarbamate;
fb) N-phenyl-N'-{3-[3-phenyl-8-(trifluoromethyl)quinolin-4-yl]phenyl}urea;
fc) N-(2-chlorophenyl)-N'-{3-[3-phenyl-8-(trifluoromethyl)quinolin-4-yl]phenyl}urea;
fd) N-(2-fluorophenyl)-N'-{3-[3-phenyl-8-(trifluoromethyl)quinolin-4-yl]phenyl}urea;
fe) phenyl[4-thien-2-yl-8-(trifluoromethyl)quinolin-3-yl]methanone;
ff) phenyl[4-thien-3-yl-8-(trifluoromethyl)quinolin-3-yl]methanone;
fg) [4-(3-chloro-4-fluorophenyl)-8-(trifluoromethyl)quinolin-3-yl](phenyl)methanone;
fh) [4-(3-fluorophenyl)-8-(trifluoromethyl)quinolin-3-yl](phenyl)methanone;

fi) [4-(4-ethylphenyl)-8-(trifluoromethyl)quinolin-3-yl](phenyl)methanone;
fj) 1-{3-[3-benzoyl-8-(trifluoromethyl)quinolin-4-yl]phenyl}ethanone;
fk) [4-[4-(dimethylamino)phenyl]-8-(trifluoromethyl)quinolin-3-yl](phenyl) methanone;
fl) [4-(3-methylphenyl)-8-(trifluoromethyl)quinolin-3-yl](phenyl)methanone;
fm) [4-[3-(dimethylamino)phenyl]-8-(trifluoromethyl)quinolin-3-yl](phenyl) methanone;
fn) [4-(3-nitrophenyl)-8-(trifluoromethyl)quinolin-3-yl](phenyl)methanone;
fo) [4-(3,4-difluorophenyl)-8-(trifluoromethyl)quinolin-3-yl](phenyl)methanone;
fp) [4-(3,5-difluorophenyl)-8-(trifluoromethyl)quinolin-3-yl](phenyl)methanone;
fq) 3-[3-benzoyl-8-(trifluoromethyl)quinolin-4-yl]benzonitrile;
fr) phenyl[4-(3-{[(piperidin-4-ylmethyl)amino]methyl}phenyl)-8-(trifluoromethyl) quinolin-3-yl]methanone;
fs) {3-[({3-[3-benzoyl-8-(trifluoromethyl)quinolin-4-yl]phenyl}amino)methyl]phenoxy}acetic acid;
ft) {4-[({3-[3-benzoyl-8-(trifluoromethyl)quinolin-4-yl]phenyl}amino)methyl]phenoxy}acetic acid;
fu) (2E)-3-{4-[({3-[3-benzoyl-8-(trifluoromethyl)quinolin-4-yl]phenyl}amino)methyl]phenyl}acrylic acid;
fv) {4-[({3-[3-[hydroxy(phenyl)methyl]-8-(trifluoromethyl)quinolin-4-yl]phenyl}amino) methyl]phenyl}acetic acid;
fw) ethyl {4-[({3-[3-benzoyl-8-(trifluoromethyl)quinolin-4-yl]phenyl}amino)methyl]phenyl}(hydroxy)acetate;
fx) {4-[({3-[3-benzoyl-8-(trifluoromethyl)quinolin-4-yl]phenyl}amino)methyl]phenyl}(hydroxy)acetic acid;
fy) ethyl {4-[({3-[3-benzoyl-8-(trifluoromethyl)quinolin-4-yl]phenyl}amino)methyl]phenyl}(difluoro)acetate;
fz) {4-[({3-[3-benzoyl-8-(trifluoromethyl)quinolin-4-yl]phenyl}amino)methyl]phenyl}(difluoro)acetic acid;
ga) [4-({[3-(3-benzoyl-8-chloroquinolin-4-yl)phenyl]amino}methyl)phenyl]acetic acid;
gb) [3-({[3-(3-benzoyl-8-chloroquinolin-4-yl)phenyl]amino}methyl)phenyl]acetic acid;
gc) (3-{[(3-{8-chloro-3-[hydroxy(phenyl)methyl]quinolin-4-yl}phenyl)amino]methyl}phenyl)acetic acid;
gd) {3-[({3-[3-benzyl-8-(trifluoromethyl)quinolin-4-yl]phenyl}amino)methyl]phenyl}acetic acid;
ge) (4-{[(3-{3-[hydroxy(phenyl)methyl]-8-methylquinolin-4-yl}phenyl)amino]methyl}phenyl)acetic acid;
gf) [4-({[3-(3-benzoyl-8-chloroquinolin-4-yl)phenyl]amino}methyl)phenyl]acetic acid;
gg) 2-{4-[({3-[3-benzoyl-8-(trifluoromethyl)quinolin-4-yl]phenyl}amino)methyl]phenyl}-2-methylpropanoic acid;
gh) 2-{4-[({3-[3-benzyl-8-(trifluoromethyl)quinolin-4-yl]phenyl}amino)methyl]phenyl}-2-methylpropanoic acid;
gi) 2-{4-[({3-[3-benzoyl-8-(trifluoromethyl)quinolin-4-yl]phenyl}amino)methyl]phenyl}propanoic acid;
gj) 2-{4-[({3-[3-benzyl-8-(trifluoromethyl)quinolin-4-yl]phenyl}amino)methyl]phenyl}propanoic acid;
gk) N-[({3-[3-benzoyl-8-(trifluoromethyl)quinolin-4-yl]phenyl}amino)carbonyl]-4-methylbenzenesulfonamide;
gl) N-[({3-[3-benzoyl-8-(trifluoromethyl)quinolin-4-yl]phenyl}amino)carbonyl]-2-chlorobenzenesulfonamide;
gm) N-[({3-[3-benzoyl-8-(trifluoromethyl)quinolin-4-yl]phenyl}amino)carbonyl]-4-chlorobenzenesulfonamide;
gn) N-[({3-[3-benzoyl-8-(trifluoromethyl)quinolin-4-yl]phenyl}amino)carbonyl]-4-fluorobenzenesulfonamide;
go) N-{3-[3-benzoyl-8-(trifluoromethyl)quinolin-4-yl]phenyl}-N'-(2-chlorophenyl)urea;
gp) N-{3-[3-benzoyl-8-(trifluoromethyl)quinolin-4-yl]phenyl}-N-methyl-N'-phenylurea;
gq) N'-{3-[3-benzoyl-8-(trifluoromethyl)quinolin-4-yl]phenyl}-N-methyl-N-phenylurea;
gr) 3-[4-({3-[3-benzoyl-8-(trifluoromethyl)quinolin-4-yl]benzyl}amino)phenyl]propanoic acid;
gs) 4-[4-({3-[3-benzoyl-8-(trifluoromethyl)quinolin-4-yl]benzyl}amino)phenyl]butanoic acid;
gt) 4'-[({3-[3-benzoyl-8-(trifluoromethyl)quinolin-4-yl]phenyl}amino)methyl]-1,1'-biphenyl-2-carboxylic acid;
gu) {4'-[({3-[3-benzoyl-8-(trifluoromethyl)quinolin-4-yl]phenyl}amino)methyl]-1,1'-biphenyl-4-yl}acetic acid;
gv) 4'-[({3-[3-benzoyl-8-(trifluoromethyl)quinolin-4-yl]phenyl}amino)methyl]-1,1'-biphenyl-4-carboxylic acid;
gw) 4'-[({3-[3-benzoyl-8-(trifluoromethyl)quinolin-4-yl]phenyl}amino)methyl]-1,1'-biphenyl-3-carboxylic acid;
gx) [4-{3-[(1,1'-biphenyl-4-ylmethyl)amino]phenyl}-8-(trifluoromethyl)quinolin-3-yl](phenyl)methanone;
gy) N-{3-[3-benzoyl-8-(trifluoromethyl)quinolin-4-yl]phenyl}pyrrolidne-1-carboxamide;
gz) N'-{3-[3-benzoyl-8-(trifluoromethyl)quinolin-4-yl]phenyl}-N,N-diethylurea;
ha) N-{3-[3-benzoyl-8-(trifluoromethyl)quinolin-4-yl]phenyl}morpholine-4-carboxamide;
hb) N-{3-[3-benzoyl-8-(trifluoromethyl)quinolin-4-yl]phenyl}-N,N'-dimethyl-N'-phenylurea;
hc) 4-{4-[({3-[3-benzoyl-8-(trifluoromethyl)quinolin-4-yl]phenyl}amino)methyl]-3-methoxyphenoxy}butanoic acid;
hd) N-[4-({3-[3-benzoyl-8-(trifluoromethyl)quinolin-4-yl]benzyl}amino)benzoyl]-beta-alanine;
he) phenyl[({3-[3-benzoyl-8-(trifluoromethyl)quinolin-4-yl]phenyl}amino)carbonyl]carbamate;
hf) 3-[3-({3-[3-benzoyl-8-(trifluoromethyl)quinolin-4-yl]benzyl}amino)phenyl]propanoic acid;
hg) N-{3-[3-benzoyl-8-(trifluoromethyl)quinolin-4-yl]phenyl}-N'-(2-methoxyphenyl) urea;
hh) N-{3-[3-benzoyl-8-(trifluoromethyl)quinolin-4-yl]phenyl}-N'-5,6,7,8-tetrahydronaphthalen-1-ylurea;
hk) (2S, 3S)-3-{4-[({3-[3-benzoyl-8-(trifluoromethyl)quinolin-4-yl]phenyl}amino) methyl]phenyl}-3-hydroxy-2-methylpropanoic acid;
hi) N-{3-[3-benzoyl-8-(trifluoromethyl)quinolin-4-yl]phenyl}-N'-(2-ethyl phenyl)urea;
hm) N-{3-[3-benzoyl-8-(trifluoromethyl)quinolin-4-yl]phenyl}-N'-(2,3-dichlorophenyl)urea;
hn) N-{3-[3-benzoyl-8-(trifluoromethyl)quinolin-4-yl]phenyl}-N'-[2-(trifluoromethyl) phenyl]urea;
ho) N-{3-[3-benzoyl-8-(trifluoromethyl)quinolin-4-yl]phenyl}-N'-[2-(trifluoromethoxy) phenyl]urea;
hp) N-{3-[3-benzoyl-8-(trifluoromethyl)quinolin-4-yl]phenyl}-N'-(2-isopropylphenyl) urea;
hq) 3-[3-({3-[3-benzyl-8-(trifluoromethyl)quinolin-4-yl]benzyl}oxy)phenyl]propanoic acid;
hr) 3-[4-({3-[3-benzyl-8-(trifluoromethyl)quinolin-4-yl]benzyl}oxy)phenyl]prop-2-ynoic acid;

hs) N-{3-[3-benzoyl-8-(trifluoromethyl)quinolin-4-yl]phenyl}-N'-[2-fluoro-3-(trifluoromethyl)phenyl]urea;
ht) (5Z)-5-{4-[({3-[3-benzoyl-8-(trifluoromethyl)quinolin-4-yl]phenyl}amino) methyl]benzylidene}-1,3-thiazolidine-2,4-dione;
hu) 2-[4-({[3-(3-benzoyl-8-methylquinolin-4-yl)phenyl]amino}methyl)phenyl]-3-phenylpropanoic acid;
hv) N-{3-[3-benzyl-8-(trifluoromethyl)quinolin-4-yl]phenyl}-N'-(2-fluorophenyl)urea;
hw) N-{3-[3-benzyl-8-(trifluoromethyl)quinolin-4-yl]phenyl}-N'-(2-chlorophenyl)urea;
hx) N-{3-[3-benzoyl-8-(trifluoromethyl)quinolin-4-yl]phenyl}-N'-(2-bromophenyl)urea;
hy) N-{3-[3-benzoyl-8-(trifluoromethyl)quinolin-4-yl]phenyl}-N'-(2-iodophenyl)urea;
hz) N-{3-[3-benzoyl-8-(trifluoromethyl)quinolin-4-yl]phenyl}-2-phenylacetamide
ia) N-{3-[3-benzoyl-8-(trifluoromethyl)quinolin-4-yl]phenyl}-2-(2-fluorophenyl)acetamide;
ib) N-{3-[3-benzoyl-8-(trifluoromethyl)quinolin-4-yl]phenyl}-2-(2-chlorophenyl)acetamide;
ic) ethyl 4-{[({3-[3-benzoyl-8-(trifluoromethyl)quinolin-4-yl]phenyl}amino)carbonyl]amino}benzoate;
id) 4-{[({3-[3-benzoyl-8-(trifluoromethyl)quinolin-4-yl]phenyl}amino)carbonyl]amino}benzoic acid;
ie) N-{3-[3-benzoyl-8-(trifluoromethyl)quinolin-4-yl]phenyl}urea;
if) N-{3-[3-benzoyl-8-(trifluoromethyl)quinolin-4-yl]phenyl}-N'-(2,6-difluorophenyl)urea;
ig) 5-{4-[({3-[3-benzoyl-8-(trifluoromethyl)quinolin-4-yl]phenyl}amino)methyl]benzylidene}-2-thioxo-1,3-thiazolidin-4-one;
ih) 3-allyl-5-{4-[({3-[3-benzoyl-8-(trifluoromethyl)quinolin-4-yl]phenyl}amino) methyl]benzylidene}-2-thioxo-1,3-thiazolidin-4-one;
ii) 5-{4-[({3-[3-benzoyl-8-(trifluoromethyl)quinolin-4-yl]phenyl}amino)methyl]benzylidene}-3-methyl-2-thioxo-1 3-thiazolidin-4-one;
ij) N-{3-[3-benzoyl-8-(trifluoromethyl)quinolin-4-yl]phenyl}-N'-(2-nitrophenyl)urea;
ik) N-(2-aminophenyl)-N'-{3-[3-benzoyl-8-(trifluoromethyl)quinolin-4-yl]phenyl}urea;
il) N-{3-[3-benzoyl-8-(trifluoromethyl)quinolin-4-yl]phenyl}-N'-(2-chlorophenyl)thiourea;
im) N-{3-[3-benzoyl-8-(trifluoromethyl)quinolin-4-yl]phenyl}-N'-(2-chlorophenyl)guanidine;
in) phenyl N-{3-[3-benzoyl-8-(trifluoromethyl)quinolin-4-yl]phenyl}-N'-cyanoimidocarbamate;
io) N-(2-aminophenyl)-N'-{3-[3-[hydroxy(phenyl)methyl]-8-(trifluoromethyl)quinolin-4-yl]phenyl}urea;
ip) 2-furyl[4-phenyl-8-(trifluoromethyl)quinolin-3-yl]methanone;
iq) 3-furyl[4-phenyl-8-(trifluoromethyl)quinolin-3-yl]methanone;
ir) (4-bromo-2-furyl)[4-phenyl-8-(trifluoromethyl)quinolin-3-yl]methanone;
is) (3-bromo-2-furyl)[4-phenyl-8-(trifluoromethyl)quinolin-3-yl]methanone;
it) (4-ethylphenyl)[4-phenyl-8-(trifluoromethyl)quinolin-3-yl]methanone;
iu) [4-(2-furyl)-8-(trifluoromethyl)quinolin-3-yl](phenyl)methanone;
iv) (3-methylthien-2-yl)[4-phenyl-8-(trifluoromethyl)quinolin-3-yl]methanone;
iw) 4-[3-benzoyl-8-(trifluoromethyl)quinolin-4-yl]benzonitrile;
ix) [4-(1-naphthyl)-8-(trifluoromethyl)quinolin-3-yl](phenyl)methanone;
iy) [4-[3-(ethylsulfonyl)phenyl]-8-(trifluoromethyl)quinolin-3-yl](phenyl)methanone;
jb) phenyl[4-pyrimidin-5-yl-8-(trifluoromethyl)quinolin-3-yl]methanone;
jc) (4-fluorophenyl)[4-phenyl-8-(trifluoromethyl)quinolin-3-yl]methanone;
jd) (4-chlorophenyl)[4-phenyl-8-(trifluoromethyl)quinolin-3-yl]methanone;
je) bis(4-chlorophenyl)[4-phenyl-8-(trifluoromethyl)quinolin-3-yl]methanol;
jf) (4-aminophenyl)[4-phenyl-8-(trifluoromethyl)quinolin-3-yl]methanone;
ig) (4-nitrophenyl)[4-phenyl-8-(trifluoromethyl)quinolin-3-yl]methanone;
jh) phenyl[4-{3-[(thien-3-yl methyl)amino]phenyl}-8-(trifluoromethyl)quinolin-3-yl]methanone;
ji) phenyl[4-{3-[(pyridin-3-ylmethyl)amino]phenyl}-8-(trifluoromethyl)quinolin-3-yl]methanone;
ii) [4-(3-aminophenyl)-8-methylquinolin-3-yl](phenyl)methanone;
jk) (4-bromophenyl)[4-phenyl-8-(trifluoromethyl)quinolin-3-yl]methanone;
jl) [4-phenyl-8-(trifluoromethyl)quinolin-3-yl][4-(trifluoromethyl)phenyl]methanone;
jm) (4-methoxyphenyl)[4-phenyl-8-(trifluoromethyl)quinolin-3-yl]methanone;
jn) phenyl[4-{3-[(pyridin-2-ylmethyl)amino]phenyl}-8-(trifluoromethyl)quinolin-3-yl]methanone;
jo) phenyl[4-{3-[(pyridin-4-ylmethyl)amino]phenyl}-8-(trifluoromethyl)quinolin-3-yl]methanone;
jp) [4-{3-[(2,5-difluorobenzyl)amino]phenyl}-8-(trifluoromethyl)quinolin-3-yl](phenyl) methanone;
jq) [4-{3-[(2-fluorobenzyl)amino]phenyl}-8-(trifluoromethyl)quinolin-3-yl](phenyl) methanone;
jr) [4-{3-[(2-furylmethyl)amino]phenyl}-8-(trifluoromethyl)quinolin-3-yl](phenyl)methanone;
js) [4-{3-[(3-fluorobenzyl)amino]phenyl}-8-(trifluoromethyl)quinolin-3-yl](phenyl) methanone;
jt) [4-{3-[(2-chlorobenzyl)amino]phenyl}-8-(trifluoromethyl)quinolin-3-yl](phenyl) methanone;
ju) phenyl[4-{3-[(1,3-thiazol-2-ylmethyl)amino]phenyl}-8-(trifluoromethyl)quinolin-3-yl]methanone;
jv) [4-(3-amino-4-methylphenyl)-8-(trifluoromethyl)quinolin-3-yl](phenyl) methanone;
jw) [4-{3-[(2-furylmethyl)(3-furylmethyl)amino]phenyl}-8-(trifluoromethyl)quinolin-3-yl](phenyl)methanone;
jx) [4-[3-(ethylamino)phenyl]-8-(trifluoromethyl)quinolin-3-yl](phenyl)methanone;
jy) phenyl [4-{3-[(2-phenylethyl)amino]phenyl}-8-(trifluoromethyl)quinolin-3-yl]methanone;
jz) [4-{3-[(4-isopropylbenzyl)amino]phenyl}-8-(trifluoromethyl)quinolin-3-yl](phenyl)methanone;
ka) [4-(3-{[(5-chlorothien-2-yl)methyl]amino}phenyl)-8-(trifluoromethyl)quinolin-3-yl](phenyl)methanone;
kb) phenyl[4-{3-[(3-phenylpropyl)amino]phenyl}-8-(trifluoromethyl)quinolin-3-yl]methanone;
kc) [4-{3-[(1H-imidazol-2-ylmethyl)amino]phenyl}-8-(trifluoromethyl)quinolin-3-yl](phenyl)methanone;
kd) [4-{3-[(2,4-dichlorobenzyl)amino]phenyl}-8-(trifluoromethyl)quinolin-3-yl](phenyl)methanone;
ke) phenyl[4-{3-[(thien-2-ylmethyl)amino]phenyl}-8-(trifluoromethyl)quinolin-3-yl]methanone;

kf) [4-(3-{[(4-methyl-1H-imidazol-5-yl)methyl]amino}phenyl)-8-(trifluoromethyl)quinolin-3-yl](phenyl)methanone;
kg) [4-(3-{[(4,5-dimethyl-2-furyl)methyl]amino}phenyl)-8-(trifluoromethyl)quinolin-3-yl](phenyl)methanone;
kh) ethyl {3-[({3-[3-benzoyl-8-(trifluoromethyl)quinolin-4-yl]phenyl}amino)methyl]phenyl}acetate;
ki) {3-[({3-[3-benzoyl-8-(trifluoromethyl)quinolin-4-yl]phenyl}amino)methyl]phenyl}acetic acid;
kj) [4-{3-[(3-methylbenzyl)amino]phenyl}-8-(trifluoromethyl)quinolin-3-yl](phenyl)methanone;
kk) [4-{3-[(3-nitrobenzyl)amino]phenyl}-8-(trifluoromethyl)quinolin-3-yl](phenyl) methanone;
kl) 3-{4-[({3-[3-benzoyl-8-(trifluoromethyl)quinolin-4-yl]phenyl}amino)methyl]phenyl}propanoic acid;
km) [4-(3-aminophenyl)-8-chloroquinolin-3-yl](phenyl)methanone;
kn) 3-[({3-[3-benzoyl-8-(trifluoromethyl)quinolin-4-yl]phenyl}amino)methyl]benzonitrile;
ko) [4-{3-[(3-chlorobenzyl)amino]phenyl}-8-(trifluoromethyl)quinolin-3-yl](phenyl)methanone;
kp) [4-{3-[(3-methoxybenzyl)amino]phenyl}-8-(trifluoromethyl)quinolin-3-yl](phenyl)methanone;
kq) phenyl[8-(trifluoromethyl)-4-(3-{[3-(trifluoromethyl)benzyl]amino}phenyl) quinolin-3-yl]methanone;
kr) phenyl(8-(trifluoromethyl)-4-{3-[(3-vinylbenzyl)amino]phenyl}quinolin-3-yl)methanone;
ks) [4-(3-aminophenyl)-8-fluoroquinolin-3-yl](phenyl)methanone;
kt) [4-(3-{[4-(2-hydroxyethyl)benzyl]amino}phenyl)-8-(trifluoromethyl)quinolin-3-yl](phenyl)methanone;
ku) [4-({[3-(3-benzoyl-8-fluoroquinolin-4-yl)phenyl]amino}methyl)phenyl]acetic acid;
kw) [4-{3-[(4-hydroxybenzyl)amino]phenyl}-8-(trifluoromethyl)quinolin-3-yl](phenyl) methanone;
kx) [4-(3-{[4-(hydroxymethyl)benzyl]amino}phenyl)-8-(trifluoromethyl)quinolin-3-yl](phenyl)methanone;
ky) N-[3-(3-benzoyl-8-chloroquinolin-4-yl)phenyl]-N'-phenylurea;
kz) N-[3-(3-benzoyl-8-chloroquinolin-4-yl)phenyl]-N'-(2,6-dichlorophenyl)urea;
la) N-[3-(3-benzoyl-8-chloroquinolin-4-yl)phenyl]-N'-(2,6-dimethylphenyl)urea;
lb) N-{3-[3-benzyl-8-(trifluoromethyl)quinolin-4-yl]phenyl}-N'-phenyl urea;
lc) N-{3-[3-benzyl-8-(trifluoromethyl)quinolin-4-yl]phenyl}-N'-(2,6-dimethylphenyl)urea;
ld) N-{3-[3-benzyl-8-(trifluoromethyl)quinolin-4-yl]phenyl}-N'-(2,6-dichlorophenyl)urea;
le) 2-methoxyphenyl {3-[3-benzoyl-8-(trifluoromethyl)quinolin-4-yl]phenyl}carbamate;
lf) 4-methoxyphenyl {3-[3-benzoyl-8-(trifluoromethyl)quinolin-4-yl]phenyl}carbamate;
lg) 4-methylphenyl {3-[3-benzoyl-8-(trifluoromethyl)quinolin-4-yl]phenyl}carbamate;
lh) 3-(trifluoromethyl)phenyl {3-[3-benzoyl-8-(trifluoromethyl)quinolin-4-yl]phenyl}carbamate;
li) N-{3-[3-benzoyl-8-(trifluoromethyl)quinolin-4-yl]phenyl}-N'-(3-chloro-4-fluorophenyl)urea;
lj) N-{3-[3-benzoyl-8-(trifluoromethyl)quinolin-4-yl]phenyl}-N'-(3,4-difluorophenyl)urea;
lk) N-{3-[3-benzoyl-8-(trifluoromethyl)quinolin-4-yl]phenyl}-N'-(3,4,5-trimethoxyphenyl)urea;
ll) N-{3-[3-benzoyl-8-(trifluoromethyl)quinolin-4-yl]phenyl}-N'-(2-phenylethyl)urea;
lm) [8-chloro-4-(3-hydroxyphenyl)quinolin-3-yl](phenyl)methanone;
ln) (8-chloro-4-{3-[(2-fluorobenzyl)oxy]phenyl}quinolin-3-yl)(phenyl)methanone;
lo) (8-chloro-4-{3-[(4-fluorobenzyl)oxy]phenyl}quinolin-3-yl)(phenyl)methanone;
lp) N-{3-[3-benzoyl-8-(trifluoromethyl)quinolin-4-yl]phenyl}-N'-(2-thien-2-ylethyl)urea;
lr) N-{3-[3-benzoyl-8-(trifluoromethyl)quinolin-4-yl]phenyl}-N'-(5-phenylthien-2-yl)urea;
ls) N-{3-[3-benzoyl-8-(trifluoromethyl)quinolin-4-yl]phenyl}-N'-thien-3-ylurea;
lt) N-{3-[3-benzoyl-8-(trifluoromethyl)quinolin-4-yl]phenyl}-N'-thien-2-ylurea;
lu) N-{3-[3-benzoyl-8-(trifluoromethyl)quinolin-4-yl]phenyl}-N'-(3,5-dimethylisoxazol-4-yl)urea;
lv) N-{3-[3-benzoyl-8-(trifluoromethyl)quinolin-4-yl]phenyl}-N'-(5-methyl-3-phenylisoxazol-4-yl)urea;
lw) N-2,1,3-benzothiadiazol-4-yl-N'-{3-[3-benzoyl-8-(trifluoromethyl)quinolin-4-yl]phenyl}urea;
lx) phenyl {3-[3-benzoyl-8-(trifluoromethyl)quinolin-4-yl]phenyl}carbamate;
ly) {4-[({3-[3-benzoyl-8-(trifluoromethyl)quinolin-4-yl]benzyl}amino)methyl]phenyl}acetic acid;
lz) 4-{[3-(3-benzoyl-8-chloroquinolin-4-yl)phenoxy]methyl}benzoic acid;
ma) [4-[(3-hydroxybenzyl)amino]-8-(trifluoromethyl)quinolin-3-yl](phenyl)methanone;
mb) 3-{4-[({3-[3-benzyl-8-(trifluoromethyl)quinolin-4-yl]phenyl}amino)methyl]phenyl}propanoic acid;
mc) 3-{3-[({3-[3-benzoyl-8-(trifluoromethyl)quinolin-4-yl]phenyl}amino)methyl]phenyl}propanoic acid;
md) N, 4-diphenyl-8-(trifluoromethyl)quinoline-3-carboxamide;
me) N-methyl-N, 4-diphenyl-8-(trifluoromethyl)quinoline-3-carboxamide;
mf) 3,4-diphenyl-8-(trifluoromethyl)quinoline;
mg) 3-[dimethoxy(phenyl)methyl]-4-phenyl-8-(trifluoromethyl)quinoline;
mh) 4-phenyl-3-(1-phenylvinyl)-8-(trifluoromethyl)quinoline;
mi) 4-phenyl-3-(1-phenylethyl)-8-(trifluoromethyl)quinoline;
mj) 3-[3-phenyl-8-(trifluoromethyl)quinolin-4-yl]phenol;
mk) (4-hydroxyphenyl)[4-phenyl-8-(trifluoromethyl)quinolin-3-yl]methanone;
ml) [4-phenyl-8-(trifluoromethyl)quinolin-3-yl](4-vinylphenyl)methanone;
mm) (2-hydroxyphenyl)[4-phenyl-8-(trifluoromethyl)quinolin-3-yl]methanone;
mn) 1-[4-phenyl-8-(trifluoromethyl)quinolin-3-yl]pentan-1-one;
mo) 1-[4-phenyl-8-(trifluoromethyl)quinolin-3-yl]hexan-1-one;
mp) cyclopropyl[4-phenyl-8-(trifluoromethyl)quinolin-3-yl]methanone;
mq) cyclopentyl[4-phenyl-8-(trifluoromethyl)quinolin-3-yl]methanone
mr) (3-fluorophenyl)[4-phenyl-8-(trifluoromethyl)quinolin-3-yl]methanone;
ms) (3-chlorophenyl)[4-phenyl-8-(trifluoromethyl)quinolin-3-yl]methanone;
mt) (4-chloro-3-fluorophenyl)[4-phenyl-8-(trifluoromethyl)quinolin-3-yl]methanone;
mu) (3,4-dichlorophenyl)[4-phenyl-8-(trifluoromethyl)quinolin-3-yl]methanone;
mv) (4-chloro-2-methylphenyl)[4-phenyl-8-(trifluoromethyl)quinolin-3-yl]methanone;

mw) (3-fluoro-2-methylphenyl)[4-phenyl-8-(trifluoromethyl)quinolin-3-yl]methanone;
mx) (3-fluoro-4-methylphenyl)[4-phenyl-8-(trifluoromethyl)quinolin-3-yl]methanone;
my) (Z)-(2-hydroxyphenyl)[4-phenyl-8-(trifluoromethyl)quinolin-3-yl]methanone hydrazone;
mz) 3-(1,2-benzisoxazol-3-yl)-4-phenyl-8-(trifluoromethyl)quinoline;
na) N-(3-methylphenyl)-4-phenyl-8-(trifluoromethyl)quinoline-3-carboxamide;
nb) N-(4-methylphenyl)-4-phenyl-8-(trifluoromethyl)quinoline-3-carboxamide;
nc) 4-phenyl-8-(trifluoromethyl)-N-[3-(trifluoromethyl)phenyl]quinoline-3-carboxamide;
nd) N-(4-chlorophenyl)-4-phenyl-8-(trifluoromethyl)quinoline-3-carboxamide;
ne) N-(3-chlorophenyl)-4-phenyl-8-(trifluoromethyl)quinoline-3-carboxamide;
nf) N-(2-chlorophenyl)-4-phenyl-8-(trifluoromethyl)quinoline-3-carboxamide;
ng) N-(3-methoxyphenyl)-4-phenyl-8-(trifluoromethyl)quinoline-3-carboxamide;
nh) N-(4-fluorophenyl)-4-phenyl-8-(trifluoromethyl)quinoline-3-carboxamide;
ni) N-(3-fluorophenyl)-4-phenyl-8-(trifluoromethyl)quinoline-3-carboxamide;
nj) N-methyl-N-(3-methylphenyl)-4-phenyl-8-(trifluoromethyl)quinoline-3-carboxamide;
nk) N-methyl-N-(4-methylphenyl)-4-phenyl-8-(trifluoromethyl)quinoline-3-carboxamide;
nl) N-methyl-4-phenyl-8-(trifluoromethyl)-N-[3-(trifluoromethyl)phenyl]quinoline-3-carboxamide;
nm) N-(4-chlorophenyl)-N-methyl-4-phenyl-8-(trifluoromethyl)quinoline-3-carboxamide;
nn) N-(3-chlorophenyl)-N-methyl-4-phenyl-8-(trifluoromethyl)quinoline-3-carboxamide;
no) N-(4-ethylphenyl)-N-methyl-4-phenyl-8-(trifluoromethyl)quinoline-3-carboxamide;
np) N-(3-ethylphenyl)-N-methyl-4-phenyl-8-(trifluoromethyl)quinoline-3-carboxamide;
nq) N-(4-fluorophenyl)-N-methyl-4-phenyl-8-(trifluoromethyl)quinoline-3-carboxamide;
nr) N-methyl-N-(2-methylphenyl)-4-phenyl-8-(trifluoromethyl)quinoline-3-carboxamide;
ns) N-(2-methoxyphenyl)-N-methyl-4-phenyl-8-(trifluoromethyl)quinoline-3-carboxamide;
nt) N-(3-fluorophenyl)-N-methyl-4-phenyl-8-(trifluoromethyl)quinoline-3-carboxamide;
nu) 3-(1-methyl-1-phenylethyl)-4-phenyl-8-(trifluoromethyl)quinoline;
nv) 4-phenyl-3-(1-phenylcyclopropyl)-8-(trifluoromethyl)quinoline;
nw) (2-fluorophenyl)[4-phenyl-8-(trifluoromethyl)quinolin-3-yl]methanone;
nx) (2-bromophenyl)[4-phenyl-8-(trifluoromethyl)quinolin-3-yl]methanone;
ny) (2-chlorophenyl)[4-phenyl-8-(trifluoromethyl)quinolin-3-yl]methanone;
nz) [4-({3-[3-methyl-8-(trifluoromethyl)quinolin-4-yl]phenoxy}methyl)phenyl]acetic acid;
oa) 2-[4-({3-[3-methyl-8-(trifluoromethyl)quinolin-4-yl]phenoxy}methyl)phenyl]ethanol;
ob) [4-({3-[3-(hydroxymethyl)-8-(trifluoromethyl)quinolin-4-yl]phenoxy}methyl)phenyl]acetic acid;
oc) 2-chloro-5-[3-phenyl-8-(trifluoromethyl)quinolin-4-yl]phenol;
od) 3-phenoxy-4-phenyl-8-(trifluoromethyl)quinoline;
oe) 4-phenyl-3-(phenylsulfonyl)-8-(trifluoromethyl)quinoline;
of) 4-phenyl-3-(phenylthio)-8-(trifluoromethyl)quinoline;
og) {3-[3-phenyl-8-(trifluoromethyl)quinolin-4-yl]phenyl}amine;
oh) ethyl [4-({3-[3-phenyl-8-(trifluoromethyl)quinolin-4-yl]phenoxy}methyl)phenyl]acetate;
oi) [4-({3-[3-phenyl-8-(trifluoromethyl)quinolin-4-yl]phenoxy}methyl)phenyl]acetic acid;
oj) 3-[(4-chlorophenoxy)methyl]-4-phenyl-8-(trifluoromethyl)quinoline;
ol) 3-[(4-methylphenoxy)methyl]-4-phenyl-8-(trifluoromethyl)quinoline;
ok) 3-[(2,4-dimethylphenoxy)methyl]-4-phenyl-8-(trifluoromethyl)quinoline;
om) 3-[(1-naphthyloxy)methyl]-4-phenyl-8-(trifluoromethyl)quinoline;
on) 3-{[4-phenyl-8-(trifluoromethyl)quinolin-3-yl]methoxy}benzonitrile;
oo) 3-[(4-methoxyphenoxy)methyl]-4-phenyl-8-(trifluoromethyl)quinoline;
op) 3-(4-methoxybenzyl)-4-phenyl-8-(trifluoromethyl)quinoline;
oq) 3-[3-benzyl-8-(trifluoromethyl)quinolin-4-yl]phenol;
or) 3-(4-chlorobenzyl)-4-phenyl-8-(trifluoromethyl)quinoline;
os) 3-(3-chlorobenzyl)-4-phenyl-8-(trifluoromethyl)quinoline;
ot) 3-(4-fluorobenzyl)-4-phenyl-8-(trifluoromethyl)quinoline;
ou) 3-(3-fluorobenzyl)-4-phenyl-8-(trifluoromethyl)quinoline;
ov) 3-(2-fluorobenzyl)-4-phenyl-8-(trifluoromethyl)quinoline;
ow) 3-(3,5-difluorobenzyl)-4-phenyl-8-(trifluoromethyl)quinoline
ox) 4-{[4-phenyl-8-(trifluoromethyl)quinolin-3-yl]methyl}benzonitrile;
oy) 3-{[4-phenyl-8-(trifluoromethyl)quinolin-3-yl]methyl}phenol;
oz) 4-phenyl-3-(thien-3-ylmethyl)-8-(trifluoromethyl)quinoline;
pa) 3-(2-naphthylmethyl)-4-phenyl-8-(trifluoromethyl)quinoline;
pb) 3-(1-benzathien-2-ylmethyl)-4-phenyl-8-(trifluoromethyl)quinoline;
pc) 4-phenyl-3-(3-phenyl-1,2,4-oxadiaxol-5-yl)-8-(trifluoromethyl)quinoline;
pd) {4-[({3-[3-phenyl-8-(trifluoromethyl)quinolin-4-yl]phenyl}amino)methyl]phenyl}acetic acid;
pe) 3-(3-methyl-1,2,4-oxadiaxol-5-yl)-4-phenyl-8-(trifluoromethyl)quinoline;
pf) 3-(4-methylbenzyl)-4-phenyl-8-(trifluoromethyl)quinoline;
pg) 3-(2-methylbenzyl)-4-phenyl-8-(trifluoromethyl)quinoline;
ph) 4-phenyl-8-(trifluoromethyl)-3-[4-(trifluoromethyl)benzyl]quinoline;
pi) 3-(2-methoxybenzyl)-4-phenyl-8-(trifluoromethyl)quinoline;
pj) 3-(2-chlorobenzyl)-4-phenyl-8-(trifluoromethyl)quinoline;
pk) 3-(2,4-difluorobenzyl)-4-phenyl-8-(trifluoromethyl)quinoline;
pl) 3-[3-phenoxy-8-(trifluoromethyl)quinolin-4-yl]phenol;

pm) 4-phenyl-3-(1H-pyrazol-1-ylmethyl)-8-(trifluoromethyl)quinoline;
pn) 3-(1H-imidazol-1-ylmethyl)-4-phenyl-8-(trifluoromethyl)quinoline;
po) 4-phenyl-3-(1H-pyrrol-1-ylmethyl)-8-(trifluoromethyl)quinoline;
pp) methyl [4-({3-[3-phenyl-8-(trifluoromethyl)quinolin-4-yl]phenoxy}methyl)phenyl]acetate;
pq) 3-[(cyclobutyloxy)methyl]-4-phenyl-8-(trifluoromethyl)quinoline;
pr) 3-[(cyclopentyloxy)methyl]-4-phenyl-8-(trifluoromethyl)quinoline;
ps) 4-phenyl-3-[(2-phenylethoxy)methyl]-8-(trifluoromethyl)quinoline;
pt) 3-[(allyloxy)methyl]-4-phenyl-8-(trifluoromethyl)quinoline;
pu) 3-(ethoxymethyl)-4-phenyl-8-(trifluoromethyl)quinoline;
pv) 3-[(cyclohexyloxy)methyl]-4-phenyl-8-(trifluoromethyl)quinoline;
pw) 3-(sec-butoxymethyl)-4-phenyl-8-(trifluoromethyl)quinoline;
px) 3-{[(2-chlorobenzyl)oxy]methyl}-4-phenyl-8-(trifluoromethyl)quinoline;
py) 3-(isobutoxymethyl)-4-phenyl-8-(trifluoromethyl)quinoline;
pz) 3-(isapropoxymethyl)-4-phenyl-8-(trifluoromethyl)quinoline;
qa) 3-(methoxymethyl)-4-phenyl-8-(trifluoromethyl)quinoline;
qb) 3-(phenoxymethyl)-4-phenyl-8-(trifluoromethyl)quinoline;
qc) 4-(4-chloro-3-methoxyphenyl)-3-phenyl-8-(trifluoromethyl)quinoline;
qd) [4-({2-chloro-5-[3-phenyl-8-(trifluoromethyl)quinolin-4-yl]phenoxy}methyl)phenyl]acetic acid;
qe) ethyl [4-({3-[3-phenoxy-8-(trifluoromethyl)quinolin-4-yl]phenoxy}methyl)phenyl]acetate;
qf) [4-({3-[3-phenoxy-8-(trifluoromethyl)quinolin-4-yl]phenoxy}methyl)phenyl]acetic acid;
qg) methyl (2E)-3-[4-({3-[3-phenyl-8-(trifluoromethyl)quinolin-4-yl]phenoxy}methyl) phenyl]acrylate;
qh) (2E)-3-[4-({2-chloro-5-[3-phenyl-8-(trifluoromethyl)quinolin-4-yl]phenoxy}methyl) phenyl]acrylic acid;
qi) 4-(2-fluoro-5-methoxyphenyl)-3-phenyl-8-(trifluoromethyl)quinoline;
qj) ethyl [4-({4-fluoro-3-[3-phenyl-8-(trifluoromethyl)quinolin-4-yl]phenoxy}methyl) phenyl]acetate;
qk) [4-({4-fluoro-3-[3-phenyl-8-(trifluoromethyl)quinolin-4-yl]phenoxy}methyl)phenyl]acetic acid;
ql) [4-(3-phenoxyphenyl)-8-(trifluoromethyl)quinolin-3-yl](phenyl)methanone;
qm) [4-{3-[(2-nitrobenzyl)oxy]phenyl}-8-(trifluoromethyl)quinolin-3-yl](phenyl) methanone;
qn) [4-{3-[(3-nitrobenzyl)oxy]phenyl}-8-(trifluoromethyl)quinolin-3-yl](phenyl)methanone;
qo) [4-{3-[(4-nitrobenzyl)oxy]phenyl}-8-(trifluoromethyl)quinolin-3-yl](phenyl)methanone;
qp) [4-{3-[(2-methylbenzyl)oxy]phenyl}-8-(trifluoromethyl)quinolin-3-yl](phenyl)methanone;
qq) [4-{3-[(3-methylbenzyl)oxy]phenyl}-8-(trifluoromethyl)quinolin-3-yl](phenyl)methanone;
qr) [4-{3-[(4-methylbenzyl)oxy]phenyl}-8-(trifluoromethyl)quinolin-3-yl](phenyl)methanone;
qs) [4-{3-[(2-methoxybenzyl)oxy]phenyl}-8-(trifluoromethyl)quinolin-3-yl](phenyl) methanone;
qt) [4-{3-[(3-methoxybenzyl)oxy]phenyl}-8-(trifluoromethyl)quinolin-3-yl](phenyl) methanone;
qu) [4-{3-[(4-methoxybenzyl)oxy]phenyl}-8-(trifluoromethyl)quinolin-3-yl](phenyl) methanone;
qv) phenyl[8-(trifluoromethyl)-4-(3-{[2-(trifluoromethyl)benzyl]oxy}phenyl)quinolin-3-yl]methanone;
qw) phenyl[8-(trifluoromethyl)-4-(3-{[3-(trifluoromethyl)benzyl]oxy}phenyl)quinolin-3-yl]methanone;
qx) [4-{3-[(4-tert-butylbenzyl)oxy]phenyl}-8-(trifluoromethyl)quinolin-3-yl](phenyl) methanone;
qy) [4-{3-[(4-isopropylbenzyl)oxy]phenyl}-8-(trifluoromethyl)quinolin-3-yl](phenyl) methanone;
qz) [4-{3-[(4-chloro-2-fluorobenzyl)oxy]phenyl}-8-(trifluoromethyl)quinolin-3-yl](phenyl)methanone;
ra) [4-[3-(2-naphthyl methoxy)phenyl]-8-(trifluoromethyl)quinolin-3-yl](phenyl)methanone;
rb) phenyl[4-[3-(pyridin-2-yl methoxy)phenyl]-8-(trifluoromethyl)quinolin-3-yl]methanone;
rc) phenyl[4-[3-(pyridin-4-yl methoxy)phenyl]-8-(trifluoromethyl)quinolin-3-yl]methanone;
rd) [2-methyl-4-phenyl-8-(trifluoromethyl)quinolin-3-yl](phenyl)methanone;
re) [4-[3-( 1,3-benzodioxol-5-ylmethoxy)phenyl]-8-(trifluoromethyl)quinolin-3-yl](phenyl)methanone;
rf) phenyl[4-[3-(tetrahydro-2H-pyran-2-yl methoxy)phenyl]-8-(trifluoromethyl)quinolin-3-yl]methanone;
rg) [4-[3-(2,1,3-benzoxadiazol-5-ylmethoxy)phenyl]-8-(trifluoromethyl)quinolin-3-yl](phenyl)methanone;
rh) 4-({3-[3-benzoyl-8-(trifluoromethyl)quinolin-4-yl]phenoxy}methyl)-1H-isochromen-1-one;
ri) 3-{3-[3-benzoyl-8-(trifluoromethyl)quinolin-4-yl]phenoxy}-2-benzofuran-1(3H)-one;
rj) [4-(3-isopropoxyphenyl)-8-(trifluoromethyl)quinolin-3-yl](phenyl)methanone;
rk) [4-{3-[(4-methylpent-3-enyl)oxy]phenyl}-8-(trifluoromethyl)quinolin-3-yl](phenyl)methanone;
rl) [4-{3-[(2,6-dichlorobenzyl)oxy]phenyl}-8-(trifluoromethyl)quinolin-3-yl](phenyl)methanone;
rm) [4-{3-[(4-methylpentyl)oxy]phenyl}-8-(trifluoromethyl)quinolin-3-yl](phenyl)methanone; in) [4-[3-(cyclohexylmethoxy)phenyl]-8-(trifluoromethyl)quinolin-3-yl](phenyl)methanone;
ro) [4-{3-[(6-chloropyridin-3-yl)methoxy]phenyl}-8-(trifluoromethyl)quinolin-3-yl](phenyl)methanone;
rp) phenyl[4-[3-(quinolin-2-ylmethoxy)phenyl]-8-(trifluoromethyl)quinolin-3-yl]methanone;
rq) [4-{3-[(5-nitro-2-furyl)methoxy]phenyl}-8-(trifluoromethyl)quinolin-3-yl](phenyl)methanone;
rr) 4-{3-[3-benzoyl-8-(trifluoromethyl)quinolin-4-yl]phenoxy}benzoic acid;
rs) 3-{3-[3-benzoyl-8-(trifluoromethyl)quinolin-4-yl]phenoxy}benzoic acid;
rt) [4-{3-[(2,6-difluorobenzyl)oxy]phenyl}-8-(trifluoromethyl)quinolin-3-yl](phenyl)methanone;
ru) [4-{3-[(6-methoxypyridin-3-yl)oxy]phenyl}-8-(trifluoromethyl)quinolin-3-yl](phenyl)methanone;
rv) [4-[3-( 1H-indol-5-yloxy)phenyl]-8-(trifluoromethyl)quinolin-3-yl](phenyl)methanone;
rw) [4-[3-(1 3-benzodioxol-5-yloxy)phenyl]-8-(trifluoromethyl)quinolin-3-yl](phenyl)methanone;
rx) 3-[3-methyl-8-(trifluoromethyl)quinolin-4-yl]phenol;
ry) 3-[3-(2-fluorophenyl)-8-(trifluoromethyl)quinolin-4-yl]phenol;
rz) [4-{3-[(4-bromo-2-methoxybenzyl)oxy]phenyl}-8-(trifluoromethyl)quinolin-3-yl](phenyl)methanone;
sa) 4-({3-[3-phenyl-8-(trifluoromethyl)quinolin-4-yl]phenoxy}methyl)benzoic acid;

sb) 3-[3-(3-fluorophenyl)-8-(trifluoromethyl)quinolin-4-yl]phenol;
so) 3-benzyl-4-[3-(4-methylphenoxy)phenyl]-8-(trifluoromethyl)quinoline;
sd) 3-[3-(4-fluorophenyl)-8-(trifluoromethyl)quinolin-4-yl]phenol;
se) [4-{3-[(2,6-dimethylbenzyl)oxy]phenyl}-8-(trifluoromethyl)quinolin-3-yl](phenyl)methanone;
sf) 3-[3-(2-methoxyphenyl)-8-(trifluoromethyl)quinolin-4-yl]phenol;
sg) 3-[3-(3-methoxyphenyl)-8-(trifluoromethyl)quinolin-4-yl]phenol;
sh) 3-[3-(4-methoxyphenyl)-8-(trifluoromethyl)quinolin-4-yl]phenol;
si) 3-[3-(2-methyl phenyl)-8-(trifluoromethyl)quinolin-4-yl]phenol;
sj) 3-[3-(3-methyl phenyl)-8-(trifluoromethyl)quinolin-4-yl]phenol;
sk) 3-[3-(4-methyl phenyl)-8-(trifluoromethyl)quinolin-4-yl]phenol;
sl) 3-[3-(2,5-dimethylphenyl)-8-(trifluoromethyl)quinolin-4-yl]phenol;
sm) 3-[3-mesityl-8-(trifluoromethyl)quinolin-4-yl]phenol;
sn) 3-benzyl-4-[3-(4-methoxyphenoxy)phenyl]-8-(trifluoromethyl)quinoline;
so) 3-{8-(trifluoromethyl)-3-[2-(trifluoromethyl)phenyl]quinolin-4-yl}phenol;
sp) 3-benzyl-4-(3-bromophenyl)-8-(trifluoromethyl)quinoline;
sq) 3-benzyl-4-{3-[(2,6-dimethylbenzyl)oxy]phenyl}-8-(trifluoromethyl)quinoline;
sr) 4-({3-[3-benzyl-8-(trifluoromethyl)quinolin-4-yl]phenoxy}methyl)-3-fluorobenzoic acid;
ss) 3-{3'-[3-benzyl-8-(trifluoromethyl)quinolin-4-yl]-1,1'-biphenyl-4-yl}propanoic acid;
st) 3-{8-(trifluoromethyl)-3-[3-(trifluoromethyl)phenyl]quinolin-4-yl}phenol;
su) 3-[3-(2-bromophenyl)-8-(trifluoromethyl)quinolin-4-yl]phenol;
sv) 3-[3-(2-chlorophenyl)-8-(trifluoromethyl)quinolin-4-yl]phenol;
sw) 3-[3-(3-bromophenyl)-8-(trifluoromethyl)quinolin-4-yl]phenol;
sx) 3-[3-(3-chlorophenyl)-8-(trifluoromethyl)quinolin-4-yl]phenol;
sy) 3-[3-(2,6-dichlorophenyl)-8-(trifluoromethyl)quinolin-4-yl]phenol;
sz) 4-{3-[3-benzyl-8-(trifluoromethyl)quinolin-4-yl]phenoxy}phenol;
ta) methyl 4-({3-[3-benzoyl-8-(trifluoromethyl)quinolin-4-yl]phenoxy}methyl)-3-methoxybenzoate;
tb) 4-({3-[3-benzoyl-8-(trifluoromethyl)quinolin-4-yl]phenoxy}methyl)-3-methoxybenzoic acid;
tc) methyl (4-{3-[3-benzyl-8-(trifluoromethyl)quinolin-4-yl]phenoxy}phenoxy) acetate;
td) (4-{3-[3-benzyl-8-(trifluoromethyl)quinolin-4-yl]phenoxy}phenoxy)acetic acid;
te) methyl 4-[(4-{3-[3-benzyl-8-(trifluoromethyl)quinolin-4-yl]phenoxy}phenoxy) methyl]benzoate;
tf) 4-[(4-{3-[3-benzyl-8-(trifluoromethyl)quinolin-4-yl]phenoxy}phenoxy)methyl]benzoic acid;
tg) 4-(2—Fluoro-5-hydroxyphenyl)-3-phenyl-8-(trifluoromethyl)quinoline;
th) Ethyl[4-({4-fluoro-3-[3-phenyl-8-(trifluoromethyl)quinolin-4-yl]phenoxy}methyl) phenyl]acetate;
ti) Methyl(2E)-3-[4-({2-chloro-5-[3-phenyl-8-(trifluoromethyl)quinolin-4-yl]phenoxy}methyl)phenyl]acrylate;
tj) 4-({4-Fluoro-3-[3-phenyl-8-(trifluoromethyl)quinolin-4-yl]phenoxy}methyl)phenyl]acetic acid;
tk) [3-(3-Benzoyl-8-(trifluoromethyl)quinolin-4-yl)phenoxy]acetic acid;
tl) [4-(1,1'-Biphenyl-4-yl)-8-(trifluoromethyl)quinolin-3-yl](phenyl)methanone;
tm) [4-(3,4-Dimethoxyphenyl)-8-(trifluoromethyl)quinolin-3-yl](pyridine-2-yl)methanone;
tn) [4-(4-Chlorophenyl)-8-(trifluoromethyl)quinolin-3-yl](phenyl)methanone;
to) [4-{3-[(2-Methoxybenzyl)oxy]phenyl}-8-(trifluoromethyl)quinolin-3-yl](phenyl)methanone;
tp) (2E)-3-[4-({3-[3-Phenyl-8-(trifluoromethyl)quinolin-4-yl]phenoxy}methyl)phenyl]acrylic acid;
tq) ethyl 4-(3-hydroxyphenyl)-8-(trifluoromethyl)quinoline-3-carboxylate;
tr) ethyl [4-({3-[3-benzyl-8-(trifluoromethyl)quinolin-4-yl]phenoxy}methyl)phenyl]acetate;
ts) N-{3-[3-benzoyl-8-(trifluoromethyl)quinolin-4-yl]phenyl}-N'-(2-fluorophenyl)guanidine;
tt) N-{3-[3-benzoyl-8-(trifluoromethyl)quinolin-4-yl]benzyl}-N'-(2-fluorophenyl)urea;
tu) [4-({3-[3-phenyl-8-(trifluoromethyl)quinolin-4-yl]phenoxy}methyl)phenyl]methanol;
tv) N-{3-[3-benzoyl-8-(trifluoromethyl)quinolin-4-yl]phenyl}-1H-imidazole-1-carboximidamide;
tw) 2-chlorophenyl {3-[3-benzoyl-8-(trifluoromethyl)quinolin-4-yl]phenyl}carbamate;
tx) 2-[4-({3-[3-phenoxy-8-(trifluoromethyl)quinolin-4-yl]phenoxy}methyl)phenyl]ethanol;
ty) N-{3-[3-benzoyl-8-(trifluoromethyl)quinolin-4-yl]phenyl}-N'-(2-chlorophenyl)-N''-cyanoguanidine;
tz) {3-[3-(2-methylphenyl)-8-(trifluoromethyl)quinolin-4-yl]phenyl}amine;
ua) N-{3-[3-(2-methylphenyl)-8-(trifluoromethyl)quinolin-4-yl]phenyl}-N'-phenylurea;
ub) methyl 4-(4-{3-[3-benzyl-8-(trifluoromethyl)quinolin-4-yl]phenoxy}phenoxy)butanoate;
uc) N-{3-[3-benzoyl-8-(trifluoromethyl)quinolin-4-yl]phenyl}-N'-(2-fluorophenyl)thiourea;
ud) N-(2-chlorophenyl)-N'-{3-[3-(2-methylphenyl)-8-(trifluoromethyl)quinolin-4-yl]phenyl}urea;
ue) methyl 5-(4-{3-[3-benzyl-8-(trifluoromethyl)quinolin-4-yl]phenoxy}phenoxy)pentanoate;
uf) 3-[3-(4-chlorobenzyl)-8-(trifluoromethyl)quinolin-4-yl]phenol;
ug) N-{3-[3-benzoyl-8-(trifluoromethyl)quinolin-4-yl]phenyl}-N''-cyano-N'-(2-fluorophenyl)guanidine;
uh) N-(2-fluorophenyl)-N'-{3-[3-(2-methyl phenyl)-8-(trifluoromethyl)quinolin-4-yl]phenyl}urea;
ui) N-{3-[3-benzoyl-8-(trifluoromethyl)quinolin-4-yl]phenyl}-N'-phenylthiourea;
uj) N-{3-[3-benzoyl-8-(trifluoromethyl)quinolin-4-yl]phenyl}-N''-cyano-N'-phenylguanidine;
uk) 5-(4-{3-[3-benzyl-8-(trifluoromethyl)quinolin-4-yl]phenoxy}phenoxy)pentanoic acid;
ul) 4-(4-{3-[3-benzyl-8-(trifluoromethyl)quinolin-4-yl]phenoxy}phenoxy)butanoic acid;
um) 4-[({3-[3-benzyl-8-(trifluoromethyl)quinolin-4-yl]phenyl}amino)methyl]benzoic acid;
un) [4-({3-[3-benzyl-8-(trifluoromethyl)quinolin-4-yl]benzyl}oxy)phenyl]-1 3-oxazol-4-yl}acetic acid;

uo) methyl N-{4-[({3-[3-benzyl-8-(trifluoromethyl)quinolin-4-yl]phenyl}amino)methyl]benzoyl}glycinate;
up) N-{4-[({3-[3-benzyl-8-(trifluoromethyl)quinolin-4-yl]phenyl}amino)methyl]benzoyl}glycine;
uq) methyl N-{4-[({3-[3-benzyl-8-(trifluoromethyl)quinolin-4-yl]phenyl}amino)methyl]benzoyl}-D-leucinate;
ur) N-{4-[({3-[3-benzyl-8-(trifluoromethyl)quinolin-4-yl]phenyl}amino)methyl]benzoyl}-D-leucine;
us) N-{4-[({3-[3-benzyl-8-(trifluoromethyl)quinolin-4-yl]phenyl}amino)methyl]benzoyl}-D-phenylalanine;
ut) 4-(3-{[3-cyano-8-(trifluoromethyl)quinolin-4-yl]amino}phenyl)-8-(trifluoromethyl)quinoline-3-carbonitrile;
uu) {4-[({3-[3-cyano-8-(trifluoromethyl)quinolin-4-yl]phenyl}amino)methyl]phenyl}acetic acid;
uv) (3-{8-(trifluoromethyl)-3-[2-(trifluoromethyl)phenyl]quinolin-4-yl}phenyl)amine;
uw) ethyl N-{4-[({3-[3-benzyl-8-(trifluoromethyl)quinolin-4-yl]phenyl}amino)methyl]benzoyl}D-phenylalaninate;
ux) N-(2-chlorophenyl)-N'-(3-{8-(trifluoromethyl)-3-[2-(trifluoromethyl)phenyl]quinolin-4-yl}phenyl)urea;
uy) 4-(3-aminophenyl)-8-(trifluoromethyl)quinoline-3-carbonitrile;
uz) methyl {[4-({3-[3-(4-chlorobenzyl)-8-(trifluoromethyl)quinolin-4-yl]phenoxy}methyl)benzyl]oxy}acetate;
va) 3-{3-[({3-[3-cyano-8-(trifluoromethyl)quinolin-4-yl]phenyl}amino)methyl]phenyl}propanoic acid;
vb) ethyl 3-{3-[({3-[3-cyano-8-(trifluoromethyl)quinolin-4-yl]phenyl}amino)methyl]phenyl}propanoate;
vc) 4-(3-hydroxyphenyl)-8-(trifluoromethyl)quinoline-3-carbonitrile;
vd) N-(2-chlorophenyl)-N'-{3-[3-cyano-8-(trifluoromethyl)quinolin-4-yl]phenyl}urea;
ve) [4-({3-[3-cyano-8-(trifluoromethyl)quinolin-4-yl]phenoxy}methyl)phenyl]acetic acid;
vf) {4-[({[4-({3-[3-cyano-8-(trifluoromethyl)quinolin-4-yl]phenoxy}methyl)phenyl]acetyl}oxy)methyl]phenyl}acetic acid;
vg) methyl 3-[4-({3-[3-methyl-8-(trifluoromethyl)quinolin-4-yl]phenoxy}methyl)phenyl]propanoate;
vh) methyl 2-{[({3-[3-benzoyl-8-(trifluoromethyl)quinolin-4-yl]phenyl}amino)carbonyl]amino}benzoate;
vi) 3-{3-[3-benzoyl-8-(trifluoromethyl)quinolin-4-yl]phenyl}quinazoline-2,4(1H, 3H)-dione;
vj) 4-{4-[2-({3-[3-benzyl-8-(trifluoromethyl)quinolin-4-yl]phenyl}amino)ethyl]piperidin-i-yl}benzoic acid;
vk) 3-{[({3-[3-benzoyl-8-(trifluoromethyl)quinolin-4-yl]phenyl}amino)carbonyl]amino}benzoic acid;
vl) ethyl 3-{[({3-[3-benzoyl-8-(trifluoromethyl)quinolin-4-yl]phenyl}amino)carbonyl]amino}benzoate;
vm) 3-[(4-{3-[3-benzyl-8-(trifluoromethyl)quinolin-4-yl]phenoxy}phenoxy)methyl]benzoic acid;
vn) 3-[4-({3-[3-methyl-8-(trifluoromethyl)quinolin-4-yl]phenoxy}methyl)phenyl]propanoic acid;
vo) 3-[3-(2-phenylethyl)-8-(trifluoromethyl)quinolin-4-yl]phenol;
vp) 3-[3-(3-phenylpropyl)-8-(trifluoromethyl)quinolin-4-yl]phenol;
vq) 3-[3-(2,4,6-trifluorobenzyl)-8-(trifluoromethyl)quinolin-4-yl]phenol;
vr) 2-[4-({3-[3-phenyl-8-(trifluoromethyl)quinolin-4-yl]phenoxy}methyl)phenyl]ethanol;
vs) 3-[4-({3-[3-methyl-8-(trifluoromethyl)quinolin-4-yl]phenoxy}methyl)phenyl]propanamide;
vt) 3-[3-(4-phenylbutyl)-8-(trifluoromethyl)quinolin-4-yl]phenol;
vu) [4-[3-(benzylthio)phenyl]-8-(trifluoromethyl)quinolin-3-yl](phenyl)methanone;
vv) 3-[4-({3-[3-phenyl-8-(trifluoromethyl)quinolin-4-yl]phenoxy}methyl)phenyl]propanoic acid;
vw) 3-[3-(5-phenylpentyl)-8-(trifluoromethyl)quinolin-4-yl]phenol;
vx) 3-[3-(diphenylmethyl)-8-(trifluoromethyl)quinolin-4-yl]phenol;
vy) 4-{3-[(4-fluorobenzyl)oxy]phenyl}-3-methyl-8-(trifluoromethyl)quinoline;
vz) 4-{3-[(2-chlorobenzyl)oxy]phenyl}-3-methyl-8-(trifluoromethyl)quinoline;
wa) [4-({3-[3-methyl-8-(trifluoromethyl)quinolin-4-yl]phenoxy}methyl)phenoxy]acetonitrile;
wb) 2-{2-[4-({3-[3-methyl-8-(trifluoromethyl)quinolin-4-yl]phenoxy}methyl)phenoxy]ethyl}-$_1$H-isoindole-1,3(2H)-dione;
wc) methyl [4-({3-[3-methyl-8-(trifluoromethyl)quinolin-4-yl]phenoxy}methyl)phenoxy]acetate;
wd) methyl [3-({3-[3-methyl-8-(trifluoromethyl)quinolin-4-yl]phenoxy}methyl)phenoxy]acetate;
we) 3-[4-({3-[3-(2,4,6-trifluorobenzyl)-8-(trifluoromethyl)quinolin-4-yl]phenoxy}methyl)phenyl]propanoic acid;
wf) [4-({3-[3-(2,4,6-trifluorobenzyl)-8-(trifluoromethyl)quinolin-4-yl]phenoxy}methyl)phenyl]acetic acid;
wg) 3-[4-({3-[3-(2-methylphenyl)-8-(trifluoromethyl)quinolin-4-yl]phenoxy}methyl)phenyl]propanoic acid;
wh) 3-{4-[(3-{8-(trifluoromethyl)-3-[2-(trifluoromethyl)phenyl]quinolin-4-yl}phenoxy)methyl]phenyl}propanoic acid;
wi) 3-[4-({3-[3-benzyl-8-(trifluoromethyl)quinolin-4-yl]phenoxy}methyl)phenyl]propanoic acid;
wj) [4-({3-[3-(2-methyl phenyl)-8-(trifluoromethyl)quinolin-4-yl]phenoxy}methyl)phenyl]acetic acid;
wk) [4-({3-[3-(aminocarbonyl)-8-(trifluoromethyl)quinolin-4-yl]phenoxy}methyl)phenyl]acetic acid;
wl) {4-[({[4-({3-[3-(aminocarbonyl)-8-(trifluoromethyl)quinolin-4-yl]phenoxy}methyl)phenyl]acetyl}oxy)methyl]phenyl}acetic acid;
wm) 3-[8-(trifluoromethyl)quinolin-4-yl]phenol;
wn) [4-({3-[8-(trifluoromethyl)quinolin-4-yl]phenoxy}methyl)phenyl]acetic acid;
wo) 4-(3-aminophenyl)-8-(trifluoromethyl)quinoline-3-carboxamide;
wp) methyl 3-[4-({3-[3-methyl-8-(trifluoromethyl)quinolin-4-yl]phenoxy}methyl)phenyl]prop-$_2$-ynoate;
wq) methyl {[4-({3-[3-methyl-8-(trifluoromethyl)quinolin-4-yl]phenoxy}methyl)benzyl]oxy}acetate;
wr) methyl {[3-({3-[3-methyl-8-(trifluoromethyl)quinolin-4-yl]phenoxy}methyl)benzyl]oxy}acetate;
ws) {4-[({3-[3-(aminocarbonyl)-8-(trifluoromethyl)quinolin-4-yl]phenyl}amino)methyl]phenyl}acetic acid;
wt) {4'-[({3-[3-benzoyl-8-(trifluoromethyl)quinolin-4-yl]phenyl}amino)methyl]-1,1'-biphenyl-3-yl}acetic acid;
wu) {4'-[({3-[3-benzyl-8-(trifluoromethyl)quinolin-4-yl]phenyl}amino)methyl]-1,1'-biphenyl-3-yl}acetic acid;
wv) 3-[3-(2-ethyl phenyl)-8-(trifluoromethyl)quinolin-4-yl]phenol;
ww) 3-[3-(2-isapropylphenyl)-8-(trifluoromethyl)quinolin-4-yl]phenol;

wx) ethyl 4-(3-aminophenyl)-8-(trifluoromethyl)quinoline-3-carboxylate;
wy) methyl {[3-({3-[3-(4-chlorobenzyl)-8-(trifluoromethyl)quinolin-4-yl]phenoxy}methyl)benzyl]oxy}acetate;
wz) methyl 3-[4-({3-[3-(4-chlorobenzyl)-8-(trifluoromethyl)quinolin-4-yl]phenoxy}methyl)phenyl]propanoate;
xa) methyl [4-({3-[3-(4-chlorobenzyl)-8-(trifluoromethyl)quinolin-4-yl]phenoxy}methyl)phenoxy]acetate;
xb) methyl [3-({3-[3-(4-chlorobenzyl)-8-(trifluoromethyl)quinolin-4-yl]phenoxy}methyl)phenoxy]acetate;
xc) 3-[4-({3-[3-methyl-8-(trifluoromethyl)quinolin-4-yl]phenoxy}methyl)phenyl]prop-2-ynoic acid;
xd) {[4-({3-[3-methyl-8-(trifluoromethyl)quinolin-4-yl]phenoxy}methyl)benzyl]oxy}acetic acid;
xe) ethyl 4-[3-({[(2-chlorophenyl)amino]carbonyl}amino)phenyl]-8-(trifluoromethyl)quinoline-3-carboxylate;
xf) 4-[3-({[(2-chlorophenyl)amino]carbonyl}amino)phenyl]-8-(trifluoromethyl)quinoline-3-carboxylic acid;
xg) 4-{3-[(2-fluorobenzyl)oxy]phenyl}-8-(trifluoromethyl)quinoline-3-carboxylic acid;
xh) [4-({3-[3-methyl-8-(trifluoromethyl)quinolin-4-yl]phenoxy}methyl)phenoxy]acetic acid;
xi) [3-({3-[3-methyl-8-(trifluoromethyl)quinolin-4-yl]phenoxy}methyl)phenoxy]acetic acid;
xj) (2E)-3-[4-({3-[3-methyl-8-(trifluoromethyl)quinolin-4-yl]phenoxy}methyl)phenyl]acrylic acid;
xk) {[3-({3-[3-methyl-8-(trifluoromethyl)quinolin-4-yl]phenoxy}methyl)benzyl]oxy}acetic acid;
xl) [4-({4-fluoro-3-[3-phenyl-8-(trifluoromethyl)quinolin-4-yl]phenoxy}methyl)phenyl]acetic acid;
xm) methyl 3-[4-({3-[3-(2-ethylphenyl)-8-(trifluoromethyl)quinolin-4-yl]phenoxy}methyl)phenyl]propanoate;
xn) methyl 3-[4-({3-[3-(2-isopropylphenyl)-8-(trifluoromethyl)quinolin-4-yl]phenoxy}methyl)phenyl]propanoate;
xo) 3-[4-({3-[3-(2-ethylphenyl)-8-(trifluoromethyl)quinolin-4-yl]phenoxy}methyl)phenyl]propanoic acid;
xp) 3-[4-({3-[3-(2-isopropylphenyl)-8-(trifluoromethyl)quinolin-4-yl]phenoxy}methyl)phenyl]propanoic acid;
xq) 3-(8-chloro-3-methylquinolin-4-yl)phenol;
xr) [4-({3-[3-(4-chlorobenzyl)-8-(trifluoromethyl)quinolin-4-yl]phenoxy}methyl)phenoxy]acetic acid;
xs) [3-({3-[3-(4-chlorobenzyl)-8-(trifluoromethyl)quinolin-4-yl]phenoxy}methyl)phenoxy]acetic acid;
xt) 3-[4-({3-[3-(4-chlorobenzyl)-8-(trifluoromethyl)quinolin-4-yl]phenoxy}methyl)phenyl]propanoic acid;
xu) {[3-({3-[3-(4-chlorobenzyl)-8-(trifluoromethyl)quinolin-4-yl]phenoxy}methyl)benzyl]oxy}acetic acid;
xv) {4-[(4-{3-[3-benzyl-8-(trifluoromethyl)quinolin-4-yl]phenoxy}phenoxy)methyl]phenyl}acetic acid;
xw) 5-({3-[3-benzyl-8-(trifluoromethyl)quinolin-4-yl]benzyl}oxy)-1H-indole-2-carboxylic acid;
xx) {[4-({3-[3-(4-chlorobenzyl)-8-(trifluoromethyl)quinolin-4-yl]phenoxy}methyl)benzyl]oxy}acetic acid;
xy) methyl 2-[4-({3-[3-benzoyl-8-(trifluoromethyl)quinolin-4-yl]phenoxy}methyl)phenyl]-3-[4-(2-methoxy-2-oxoethyl)phenyl]propanoate;
xz) 2-[4-({3-[3-benzoyl-8-(trifluoromethyl)quinolin-4-yl]phenoxy}methyl)phenyl]-3-[4-(carboxymethyl)phenyl]propanoic acid;
ya) 2-[4-({3-[3-benzoyl-8-(trifluoromethyl)quinolin-4-yl]phenoxy}methyl)phenyl]-3-phenylpropanoic acid;
yb) 2-[4-({3-[3-benzoyl-8-(trifluoromethyl)quinolin-4-yl]phenoxy}methyl)phenyl]-3-(4-tert-butylphenyl)propanoic acid;
yc) 3-benzyl-4-(3-ethynylphenyl)-8-(trifluoromethyl)quinoline;
yd) 2-[4-({3-[3-benzoyl-8-(trifluoromethyl)quinolin-4-yl]phenoxy}methyl)phenyl]-3-biphenyl-4-ylpropanoic acid;
ye) 2-[4-({3-[3-benzoyl-8-(trifluoromethyl)quinolin-4-yl]phenoxy}methyl)phenyl]-3-(4-nitrophenyl)propanoic acid;
yf) methyl 4-({3-[3-(4-chlorobenzyl)-8-(trifluoromethyl)quinolin-4-yl]phenoxy}methyl)benzoate;
yg) 4-({3-[3-(4-chlorobenzyl)-8-(trifluoromethyl)quinolin-4-yl]phenoxy}methyl)benzoic acid;
yh) methyl 3-[3-({3-[3-methyl-8-(trifluoromethyl)quinolin-4-yl]phenoxy}methyl)phenyl]propanoate;
yi) 2-[4-({3-[3-benzoyl-8-(trifluoromethyl)quinolin-4-yl]phenoxy}methyl)phenyl]-3,3-diphenylpropanoic acid;
yj) {3-[3-methyl-8-(trifluoromethyl)quinolin-4-yl]phenyl}amine;
yk) 2-[4-({3-[3-benzoyl-8-(trifluoromethyl)quinolin-4-yl]phenoxy}methyl)phenyl]-2-prop-2-yn-1-ylpent-4-ynoic acid;
yl) 3-[3-({3-[3-methyl-8-(trifluoromethyl)quinolin-4-yl]phenoxy}methyl)phenyl]propanoic acid;
ym) 3-(3-benzyl-8-chloroquinolin-4-yl)phenol;
yn) 3-(4-chlorobenzyl)-4-{3-[(2,5-dimethylbenzyl)oxy]phenyl}-8-(trifluoromethyl)quinoline;
yo) 2-[4-({3-[3-methyl-8-(trifluoromethyl)quinolin-4-yl]phenoxy}methyl)phenyl]propanoic acid;
yp) ethyl 2-[4-({3-[3-benzyl-8-(trifluoromethyl)quinolin-4-yl]phenoxy}methyl)phenyl]propanoate;
yq) 2-[4-({3-[3-benzyl-8-(trifluoromethyl)quinolin-4-yl]phenoxy}methyl)phenyl]propanoic acid;
yr) methyl 2-[4-({3-[3-methyl-8-(trifluoromethyl)quinolin-4-yl]phenoxy}methyl)phenyl]propanoate;
ys) (4-{[3-(8-chloro-3-phenylquinolin-4-yl)phenoxy]methyl}phenyl)acetic acid;
yt) (4-{[3-(8-chloro-3-methylquinolin-4-yl)phenoxy]methyl}phenyl)acetic acid;
yu) (4-{[3-(3-benzyl-8-chloroquinolin-4-yl)phenoxy]methyl}phenyl)acetic acid;
yv) 4-(3-methoxyphenyl)-3-methyl-8-(trifluoromethyl)quinoline;
yw) methyl 3-[3-({3-[3-(2-isopropylphenyl)-8-(trifluoromethyl)quinolin-4-yl]phenoxy}methyl)phenyl]propanoate;
yx) methyl 3-[3-({3-[3-(2-ethylphenyl)-8-(trifluoromethyl)quinolin-4-yl]phenoxy}methyl)phenyl]propanoate;
yy) [4-({3-[3-(2-ethyl phenyl)-8-(trifluoromethyl)quinolin-4-yl]phenoxy}methyl)phenyl]acetic acid;
yz) 4-{3-[(2,5-dimethylbenzyl)oxy]phenyl}-8-(trifluoromethyl)quinoline;
za) {4-[({3-[3-benzyl-8-(trifluoromethyl)quinolin-4-yl]phenyl}thio)methyl]phenyl}acetic acid;
zb) {4-[({3-[3-benzyl-8-(trifluoromethyl)quinolin-4-yl]phenyl}sulfonyl)methyl]phenyl}acetic acid;
zc) 4-{3-[(2-chlorobenzyl)oxy]phenyl}-8-(trifluoromethyl)quinoline;
zd) methyl {4-[({3-[3-phenyl-8-(trifluoromethyl)quinolin-4-yl]phenyl}amino)methyl]phenyl}acetate;
ze) 4-{3-[(2,5-dimethylbenzyl)oxy]phenyl}-3-methyl-8-(trifluoromethyl)quinoline;

zf) 4-{3-[(2,6-dimethylbenzyl)oxy]phenyl}-3-methyl-8-(trifluoromethyl)quinoline;
zg) 3-[3-({3-[3-(2-ethylphenyl)-8-(trifluoromethyl)quinolin-4-yl]phenoxy}methyl)phenyl]propanoic acid;
zh) 3-[3-({3-[3-(2-isopropylphenyl)-8-(trifluoromethyl)quinolin-4-yl]phenoxy}methyl)phenyl]propanoic acid;
zi) methyl 2-methyl-2-[4-({3-[3-methyl-8-(trifluoromethyl)quinolin-4-yl]phenoxy}methyl)phenyl]propanoate;
zj) 3-[3-(2-methylbenzyl)-8-(trifluoromethyl)quinolin-4-yl]phenol;
zk) methyl 2-(4-{[3-(8-chloro-3-phenylquinolin-4-yl)phenoxy]methyl}phenyl)-2-methylpropanoate;
zl) methyl 2-(4-{[3-(3-benzyl-8-chloroquinolin-4-yl)phenoxy]methyl}phenyl)-2-methylpropanoate;
zm) methyl 2-[4-({3-[3-benzyl-8-(trifluoromethyl)quinolin-4-yl]phenoxy}methyl)phenyl]-2-methylpropanoate;
zn) 2-[4-({3-[3-benzyl-8-(trifluoromethyl)quinolin-4-yl]phenoxy}methyl)phenyl]-2-methylpropanoic acid;
zo) 4-{3-[(3,4-dimethylbenzyl)oxy]phenyl}-8-(trifluoromethyl)quinoline;
zp) 4-{3-[(2,6-dimethylbenzyl)oxy]phenyl}-8-(trifluoromethyl)quinoline;
zq) 4-{3-[(3-fluorobenzyl)oxy]phenyl}-8-(trifluoromethyl)quinoline;
zr) 2-methyl-2-[4-({3-[3-methyl-8-(trifluoromethyl)quinolin-4-yl]phenoxy}methyl)phenyl]propanoic acid;
zs) 4-{3-[(2,6-dichlorobenzyl)oxy]phenyl}-8-(trifluoromethyl)quinoline;
zt) 4-{3-[(2,6-difluorobenzyl)oxy]phenyl}-8-(trifluoromethyl)quinoline;
zu) ethyl [3-({3-[3-(2-ethylphenyl)-8-(trifluoromethyl)quinolin-4-yl]phenoxy}methyl)phenyl]acetate;
zv) methyl [3-({3-[8-(trifluoromethyl)quinolin-4-yl]phenoxy}methyl)phenoxy]acetate;
zw) {3-[3-benzyl-8-(trifluoromethyl)quinolin-4-yl]phenyl}(2,5-dichlorobenzyl)amine;
zx) {3-[3-benzyl-8-(trifluoromethyl)quinolin-4-yl]phenyl}(2,3-dimethoxybenzyl)amine;
zy) {3-[3-benzyl-8-(trifluoromethyl)quinolin-4-yl]phenyl}(2,5-dimethylbenzyl)amine;
zz) {3-[3-benzyl-8-(trifluoromethyl)quinolin-4-yl]phenyl}(2,3-dimethylbenzyl)amine;
aaa) {3-[3-benzyl-8-(trifluoromethyl)quinolin-4-yl]phenyl}(2,6-dimethylbenzyl)amine;
aab) {3-[3-benzyl-8-(trifluoromethyl)quinolin-4-yl]phenyl}(1H-imidazol-2-ylmethyl)amine;
aac) {3-[3-benzyl-8-(trifluoromethyl)quinolin-4-yl]phenyl}{3-[3-(trifluoromethyl)phenoxy]benzyl}amine;
aad) {3-[3-benzyl-8-(trifluoromethyl)quinolin-4-yl]phenyl}(2,6-dimethoxybenzyl)amine;
aae) {3-[3-benzyl-8-(trifluoromethyl)quinolin-4-yl]phenyl}(3-methoxybenzyl)amine;
aaf) {3-[3-benzyl-8-(trifluoromethyl)quinolin-4-yl]phenyl}(2-methoxybenzyl)amine;
aag) {3-[3-benzyl-8-(trifluoromethyl)quinolin-4-yl]phenyl}(4-methylbenzyl)amine;
aah) {3-[3-benzyl-8-(trifluoromethyl)quinolin-4-yl]phenyl}(pyridin-4-ylmethyl)amine;
aai) {3-[3-benzyl-8-(trifluoromethyl)quinolin-4-yl]phenyl}[(4,5-dimethyl-2-furyl)methyl]amine;
aaj) {3-[3-benzyl-8-(trifluoromethyl)quinolin-4-yl]phenyl}(1-naphthylmethyl)amine;
aak) {3-[3-benzyl-8-(trifluoromethyl)quinolin-4-yl]phenyl}(2,4-dimethylbenzyl)amine;
aal) {3-[3-benzyl-8-(trifluoromethyl)quinolin-4-yl]phenyl}(2-naphthylmethyl)amine;
aam) {3-[3-benzyl-8-(trifluoromethyl)quinolin-4-yl]phenyl}[4-(diphenylamino)benzyl]amine;
aan) {3-[3-benzyl-8-(trifluoromethyl)quinolin-4-yl]phenyl}(4-isopropylbenzyl)amine;
aao) [4-({3-[3-(2-methylbenzyl)-8-(trifluoromethyl)quinolin-4-yl]phenoxy}methyl)phenyl]acetic acid;
aap) 4-{3-[(2,5-dimethylbenzyl)oxy]phenyl}-3-(2-methylbenzyl)-8-(trifluoromethyl)quinoline;
aaq) 4-{3-[(2,6-dimethylbenzyl)oxy]phenyl}-3-(2-methylbenzyl)-8-(trifluoromethyl)quinoline;
aar) [3-({3-[3-(2-ethyl phenyl)-8-(trifluoromethyl)quinolin-4-yl]phenoxy}methyl)phenyl]acetic acid;
aas) 2-[4-({3-[3-(2-methylbenzyl)-8-(trifluoromethyl)quinolin-4-yl]phenoxy}methyl)phenyl]ethanol;
aat) ethyl [3-({3-[3-(2-methylbenzyl)-8-(trifluoromethyl)quinolin-4-yl]phenoxy}methyl)phenyl]acetate;
aau) [4-({3-[3-(2-methylbenzyl)-8-(trifluoromethyl)quinolin-4-yl]phenoxy}methyl)phenoxy]acetonitrile;
aav) methyl [4-({3-[3-(2-methylbenzyl)-8-(trifluoromethyl)quinolin-4-yl]phenoxy}methyl)phenoxy]acetate;
aaw) methyl [4-({3-[8-(trifluoromethyl)quinolin-4-yl]phenoxy}methyl)phenoxy]acetate;
aax) methyl 3-[4-({3-[8-(trifluoromethyl)quinolin-4-yl]phenoxy}methyl)phenyl]propanoate;
aay) methyl 3-[3-({3-[8-(trifluoromethyl)quinolin-4-yl]phenoxy}methyl)phenyl]propanoate;
aaz) 2-(4-{[3-(8-chloro-3-phenylquinolin-4-yl)phenoxy]methyl}phenyl)-2-methylpropanoic acid;
aba) 2-(4-{[3-(3-benzyl-8-chloroquinolin-4-yl)phenoxy]methyl}phenyl)-2-methylpropanoic acid;
abb) 4-{3-[(2,5-difluorobenzyl)oxy]phenyl}-8-(trifluoromethyl)quinoline;
abc) {3-[3-benzyl-8-(trifluoromethyl)quinolin-4-yl]phenyl}[3,5-bis(benzyloxy)benzyl]amine;
abd) {3-[3-benzyl-8-(trifluoromethyl)quinolin-4-yl]phenyl}(3-methylbenzyl)amine;
abe) {3-[3-benzyl-8-(trifluoromethyl)quinolin-4-yl]phenyl}[(1-oxidopyridin-4-yl)methyl]amine;
abf) [4-({3-[8-(trifluoromethyl)quinolin-4-yl]phenoxy}methyl)phenoxy]acetonitrile;
abg) 4-{3-[(2,4-difluorobenzyl)oxy]phenyl}-8-(trifluoromethyl)quinoline;
abh) {3-[3-benzyl-8-(trifluoromethyl)quinolin-4-yl]phenyl}(3,5-dimethoxybenzyl)amine;
abi) {3-[3-benzyl-8-(trifluoromethyl)quinolin-4-yl]phenyl}(2,4-dimethoxybenzyl)amine;
abj) 4-{3-[(2,5-dichlorobenzyl)oxy]phenyl}-8-(trifluoromethyl)quinoline;
abk) methyl {[3-({3-[8-(trifluoromethyl)quinolin-4-yl]phenoxy}methyl)benzyl]oxy}acetate;
abl) {3-[3-benzyl-8-(trifluoromethyl)quinolin-4-yl]phenyl}(2-nitrobenzyl)amine;
abm) methyl {[4-({3-[8-(trifluoromethyl)quinolin-4-yl]phenoxy}methyl)benzyl]oxy}acetate;
abn) {3-[3-benzyl-8-(trifluoromethyl)quinolin-4-yl]phenyl}(3-nitrobenzyl)amine;
abo) methyl [3-({3-[3-(2-methylbenzyl)-8-(trifluoromethyl)quinolin-4-yl]phenoxy}methyl)phenoxy]acetate;
abp) methyl 3-[4-({3-[3-(2-methylbenzyl)-8-(trifluoromethyl)quinolin-4-yl]phenoxy}methyl)phenyl]propanoate;
abq) methyl 3-[3-({3-[3-(2-methylbenzyl)-8-(trifluoromethyl)quinolin-4-yl]phenoxy}methyl)phenyl]propanoate;

abr) methyl 3-[4-({3-[3-(2-methylbenzyl)-8-(trifluoromethyl)quinolin-4-yl]phenoxy}methyl)phenyl]prop-2-ynoate;
abs) 2-[({3-[3-benzyl-8-(trifluoromethyl)quinolin-4-yl]phenyl}amino)methyl]-4-bromophenol;
abt) 2-[({3-[3-benzyl-8-(trifluoromethyl)quinolin-4-yl]phenyl}amino)methyl]-4-methoxyphenol;
abu) {3-[3-benzyl-8-(trifluoromethyl)quinolin-4-yl]phenyl}{[4-(dimethylamino)-1-naphthyl]methyl}amine;
abv) 2-[({3-[3-benzyl-8-(trifluoromethyl)quinolin-4-yl]phenyl}amino)methyl]-5-methoxyphenol;
abw) 4-[({3-[3-benzyl-8-(trifluoromethyl)quinolin-4-yl]phenyl}amino)methyl]benzene-1,2-diol;
abx) 3-[({3-[3-benzyl-8-(trifluoromethyl)quinolin-4-yl]phenyl}amino)methyl]-4-nitraphenol;
aby) {3-[3-benzyl-8-(trifluoromethyl)quinolin-4-yl]phenyl}(4,5-dimethoxy-2-nitrobenzyl)amine;
abz) 2-[({3-[3-benzyl-8-(trifluoromethyl)quinolin-4-yl]phenyl}amino)methyl]-4-chlorophenol;
aca) {3-[3-benzyl-8-(trifluoromethyl)quinolin-4-yl]phenyl}(3,4-dimethoxybenzyl)amine;
acb) {3-[3-benzyl-8-(trifluoromethyl)quinolin-4-yl]phenyl}(2,5-dimethoxybenzyl)amine;
acc) {3-[3-benzyl-8-(trifluoromethyl)quinolin-4-yl]phenyl}(3-phenoxybenzyl)amine;
acd) 4-{3-[(2,5-dimethylbenzyl)oxy]phenyl}-3-(2-methylphenyl)-8-(trifluoromethyl)quinoline;
ace) 4-{3-[(2-fluorobenzyl)oxy]phenyl}-3-(2-methyl phenyl)-8-(trifluoromethyl)quinoline;
acf) 4-{3-[(2,6-dimethylbenzyl)oxy]phenyl}-3-(2-methylphenyl)-8-(trifluoromethyl)quinoline;
acg) 4-{3-[(2-fluoro-5-nitrobenzyl)oxy]phenyl}-3-(2-methylphenyl)-8-(trifluoromethyl)quinoline;
ach) methyl (2E)-3-[4-({3-[3-(2-methylbenzyl)-8-(trifluoromethyl)quinolin-4-yl]phenoxy}methyl)phenyl]acrylate;
aci) methyl 2-methyl-2-[4-({3-[3-(2-methylbenzyl)-8-(trifluoromethyl)quinolin-4-yl]phenoxy}methyl)phenyl]propanoate;
acj) methyl {[3-({3-[3-(2-methylbenzyl)-8-(trifluoromethyl)quinolin-4-yl]phenoxy}methyl)benzyl]oxy}acetate;
ack) ethyl [4-({3-[3-(2-ethylphenyl)-8-(trifluoromethyl)quinolin-4-yl]phenoxy}methyl)phenyl]acetate;
acl) methyl 2-(4-{[3-(8-chloro-3-methylquinolin-4-yl)phenoxy]methyl}phenyl)-2-methylpropanoate;
acm) 2-(4-{[3-(8-chloro-3-methylquinolin-4-yl)phenoxy]methyl}phenyl)-2-methylpropanoic acid;
acn) ethyl [4-({3-[3-(2-isopropylphenyl)-8-(trifluoromethyl)quinolin-4-yl]phenoxy}methyl)phenyl]acetate;
aco) ethyl [4-({3-[3-benzyl-8-(trifluoromethyl)quinolin-4-yl]benzyl}oxy)phenyl](oxo)acetate;
acp) [3-({3-[3-(2-methylbenzyl)-8-(trifluoromethyl)quinolin-4-yl]phenoxy}methyl)phenyl]acetic acid;
acq) [4-({3-[3-(2-methylbenzyl)-8-(trifluoromethyl)quinolin-4-yl]phenoxy}methyl)phenoxy]acetic acid;
acr) [3-({3-[3-(2-methylbenzyl)-8-(trifluoromethyl)quinolin-4-yl]phenoxy}methyl)phenoxy]acetic acid;
acs) methyl 4-({3-[8-(trifluoromethyl)quinolin-4-yl]phenoxy}methyl)benzoate;
act) methyl 4-({3-[3-phenyl-8-(trifluoromethyl)quinolin-4-yl]phenoxy}methyl)benzoate;
acu) 4-[3-(2-{1-[2-(1H-indol-3-yl)ethyl]-1H-indol-3-yl}ethoxy)phenyl]-8-(trifluoromethyl)quinoline;
acv) 3-[4-({3-[3-(2-methylbenzyl)-8-(trifluoromethyl)quinolin-4-yl]phenoxy}methyl)phenyl]propanoic acid;
acw) 3-[3-({3-[3-(2-methylbenzyl)-8-(trifluoromethyl)quinolin-4-yl]phenoxy}methyl)phenyl]propanoic acid;
acx) 3-[4-({3-[3-(2-methylbenzyl)-8-(trifluoromethyl)quinolin-4-yl]phenoxy}methyl)phenyl]prop-2-ynoic acid;
acy) (2E)-3-[4-({3-[3-(2-methylbenzyl)-8-(trifluoromethyl)quinolin-4-yl]phenoxy}methyl)phenyl]acrylic acid;
acz) 2-methyl-2-[4-({3-[3-(2-methylbenzyl)-8-(trifluoromethyl)quinolin-4-yl]phenoxy}methyl)phenyl]propanoic acid;
ada) {[3-({3-[3-(2-methylbenzyl)-8-(trifluoromethyl)quinolin-4-yl]phenoxy}methyl)benzyl]oxy}acetic acid;
adb) 2-[4-({3-[3-benzoyl-8-(trifluoromethyl)quinolin-4-yl]phenoxy}methyl)phenyl]pent-4-enoic acid;
adc) [3-({3-[8-(trifluoromethyl)quinolin-4-yl]phenoxy}methyl)phenoxy]acetic acid;
add) 2-[4-({3-[3-benzoyl-8-(trifluoromethyl)quinolin-4-yl]phenoxy}methyl)phenyl]hept-4-ynoic acid;
ade) [4-({3-[8-(trifluoromethyl)quinolin-4-yl]phenoxy}methyl)phenoxy]acetic acid;
adf) {[3-({3-[8-(trifluoromethyl)quinolin-4-yl]phenoxy}methyl)benzyl]oxy}acetic acid;
adg) 2-[4-({3-[3-benzoyl-8-(trifluoromethyl)quinolin-4-yl]phenoxy}methyl)phenyl]hex-4-ynoic acid;
adh) {[4-({3-[8-(trifluoromethyl)quinolin-4-yl]phenoxy}methyl)benzyl]oxy}acetic acid;
adi) 3-[4-({3-[8-(trifluoromethyl)quinolin-4-yl]phenoxy}methyl)phenyl]propanoic acid;
adj) 3-[3-({3-[8-(trifluoromethyl)quinolin-4-yl]phenoxy}methyl)phenyl]propanoic acid;
adk) 4-{3-[2-(1H-indol-3-yl)ethoxy]phenyl}-8-(trifluoromethyl)quinoline;
adl) methyl 4-({3-[3-methyl-8-(trifluoromethyl)quinolin-4-yl]phenoxy}methyl)benzoate;
adm) methyl 3-({3-[3-methyl-8-(trifluoromethyl)quinolin-4-yl]phenoxy}methyl)benzoate;
adn) ethyl [3-({3-[3-methyl-8-(trifluoromethyl)quinolin-4-yl]phenoxy}methyl)phenyl]acetate;
ado) 4-({3-[3-methyl-8-(trifluoromethyl)quinolin-4-yl]phenoxy}methyl)benzoic acid;
adp) 3-({3-[3-methyl-8-(trifluoromethyl)quinolin-4-yl]phenoxy}methyl)benzoic acid;
adq) [3-({3-[3-methyl-8-(trifluoromethyl)quinolin-4-yl]phenoxy}methyl)phenyl]acetic acid;
adr) 4-({3-[8-(trifluoromethyl)quinolin-4-yl]phenoxy}methyl)benzoic acid;
ads) {3-[3-benzyl-8-(trifluoromethyl)quinolin-4-yl]phenyl}(2-fluoro-5-nitrobenzyl)amine;
adt) 2-[({3-[3-benzyl-8-(trifluoromethyl)quinolin-4-yl]phenyl}amino)methyl]benzene-1,4-diol;
adu) 5-[({3-[3-benzyl-8-(trifluoromethyl)quinolin-4-yl]phenyl}amino)methyl]-2-methoxyphenol;
adv) 4-[({3-[3-benzyl-8-(trifluoromethyl)quinolin-4-yl]phenyl}amino)methyl]-2-methoxyphenol;
adw) {3-[3-benzyl-8-(trifluoromethyl)quinolin-4-yl]phenyl}(5-bromo-2-ethoxybenzyl)amine;
adx) {3-[3-benzyl-8-(trifluoromethyl)quinolin-4-yl]phenyl}(3-ethoxy-4-methoxybenzyl)amine;
ady) {3-[3-benzyl-8-(trifluoromethyl)quinolin-4-yl]phenyl}(2,5-difluorobenzyl)amine;
adz) {3-[3-benzyl-8-(trifluoromethyl)quinolin-4-yl]phenyl}(3,4-difluorobenzyl)amine;
aea) {3-[3-benzyl-8-(trifluoromethyl)quinolin-4-yl]phenyl}(2-fluoro-5-methoxybenzyl)amine;

aeb) {3-[3-benzyl-8-(trifluoromethyl)quinolin-4-yl]phenyl}(5-bromo-2-methoxybenzyl)amine;
aec) {3-[3-benzyl-8-(trifluoromethyl)quinolin-4-yl]phenyl}(5-bromo-2-fluorobenzyl)amine;
aed) {3-[3-benzyl-8-(trifluoromethyl)quinolin-4-yl]phenyl}[2-fluoro-3-(trifluoromethyl)benzyl]amine;
aee) {3-[3-benzyl-8-(trifluoromethyl)quinolin-4-yl]phenyl}[4-(trifluoromethyl)benzyl]amine;
aef) 2-[4-({3-[3-benzoyl-8-(trifluoromethyl)quinolin-4-yl]phenoxy}methyl)phenyl]-2-pent-2-yn-1-ylhept-4-ynoic acid;
aeg) methyl 3-{3-[3-methyl-8-(trifluoromethyl)quinolin-4-yl]phenoxy}benzoate;
aeh) methyl 4-{3-[3-methyl-8-(trifluoromethyl)quinolin-4-yl]phenoxy}benzoate;
aei) 3-{3-[3-methyl-8-(trifluoromethyl)quinolin-4-yl]phenoxy}benzoic acid;
aej) {3-[3-benzyl-8-(trifluoromethyl)quinolin-4-yl]phenyl}[2,5-bis(trifluoromethyl)benzyl]amine;
aek) {3-[3-benzyl-8-(trifluoromethyl)quinolin-4-yl]phenyl}(2-methylbenzyl)amine;
ael) {3-[3-benzyl-8-(trifluoromethyl)quinolin-4-yl]phenyl}(2,4,6-trifluorobenzyl)amine;
aem) {3-[3-benzyl-8-(trifluoromethyl)quinolin-4-yl]phenyl}(3-fluoro-4-methoxybenzyl)amine;
aen) {3-[3-benzyl-8-(trifluoromethyl)quinolin-4-yl]phenyl}(cyclopropylmethyl)amine;
aeo) {3-[3-benzyl-8-(trifluoromethyl)quinolin-4-yl]phenyl}[(2-methyl-1H-imidazol-5-yl)methyl]amine;
aep) {3-[3-benzyl-8-(trifluoromethyl)quinolin-4-yl]phenyl}(pyridin-3-ylmethyl)amine;
aeq) 4-{3-[3-methyl-8-(trifluoromethyl)quinolin-4-yl]phenoxy}benzoic acid;
aer) {3-[3-benzyl-8-(trifluoromethyl)quinolin-4-yl]phenyl}(2-ethoxy-3-methoxybenzyl)amine;
aes) {3-[3-benzyl-8-(trifluoromethyl)quinolin-4-yl]phenyl}(5-fluoro-2-methoxybenzyl)amine;
aet) {3-[3-benzyl-8-(trifluoromethyl)quinolin-4-yl]phenyl}(3-chloro-4-methoxybenzyl)amine;
aeu) 2-[({3-[3-benzyl-8-(trifluoromethyl)quinolin-4-yl]phenyl}amino)methyl]-6-fluorophenol;
aev) {3-[3-benzyl-8-(trifluoromethyl)quinolin-4-yl]phenyl}(2-fluoro-6-methoxybenzyl)amine;
aew) 2-[({3-[3-benzyl-8-(trifluoromethyl)quinolin-4-yl]phenyl}amino)methyl]-4-iodophenol;
aex) {3-[3-benzyl-8-(trifluoromethyl)quinolin-4-yl]phenyl}(3-chloro-4-fluorobenzyl)amine;
aey) {3-[3-benzyl-8-(trifluoromethyl)quinolin-4-yl]phenyl}(3-chloro-2-fluorobenzyl)amine;
aez) 3-[({3-[3-benzyl-8-(trifluoromethyl)quinolin-4-yl]phenyl}amino)methyl]benzene-1,2-diol;
afa) {3-[3-benzyl-8-(trifluoromethyl)quinolin-4-yl]phenyl}(3,4-diethoxybenzyl)amine;
afb) 2-[({3-[3-benzyl-8-(trifluoromethyl)quinolin-4-yl]phenyl}amino)methyl]-4-fluorophenol;
afc) 4-[({3-[3-benzyl-8-(trifluoromethyl)quinolin-4-yl]phenyl}amino)methyl]-2-ethoxyphenol;
afd) N-[2-(benzyloxy)-3-methoxybenzyl]-3-[3-benzyl-8-(trifluoromethyl)quinolin-4-yl]aniline;
afe) {3-[3-benzyl-8-(trifluoromethyl)quinolin-4-yl]phenyl}(2,3-dihydro-1,4-benzodioxin-6-ylmethyl)amine;
aff) N-[4-(benzyloxy)-3-methoxybenzyl]-3-[3-benzyl-8-(trifluoromethyl)quinolin-4-yl]aniline;
afg) {3-[3-benzyl-8-(trifluoromethyl)quinolin-4-yl]phenyl}(2-fluoro-3-methoxybenzyl)amine;
afh) 2-[({3-[3-benzyl-8-(trifluoromethyl)quinolin-4-yl]phenyl}amino)methyl]-6-ethoxyphenol;
afi) 4-{3-[(2-methoxybenzyl)oxy]phenyl}-3-methyl-8-(trifluoromethyl)quinoline;
afj) 3-methyl-4-{3-[(2-nitrobenzyl)oxy]phenyl}-8-(trifluoromethyl)quinoline;
afk) 4-{3-[(3-fluorobenzyl)oxy]phenyl}-3-methyl-8-(trifluoromethyl)quinoline;
afl) 4-{3-[(3-bromobenzyl)oxy]phenyl}-3-methyl-8-(trifluoromethyl)quinoline;
afm) 3-({3-[3-methyl-8-(trifluoromethyl)quinolin-4-yl]phenoxy}methyl)benzonitrile;
afn) 4-{3-[(3-methoxybenzyl)oxy]phenyl}-3-methyl-8-(trifluoromethyl)quinoline;
afo) 3-methyl-4-{3-[(3-nitrobenzyl)oxy]phenyl}-8-(trifluoromethyl)quinoline;
afp) 4-{3-[(4-methoxybenzyl)oxy]phenyl}-3-methyl-8-(trifluoromethyl)quinoline;
afq) 4-{3-[(2,5-dichlorobenzyl)oxy]phenyl}-3-methyl-8-(trifluoromethyl)quinoline;
afr) 4-{3-[(2,5-difluorobenzyl)oxy]phenyl}-3-methyl-8-(trifluoromethyl)quinoline;
afs) 4-{3-[(2,6-dichlorobenzyl)oxy]phenyl}-3-methyl-8-(trifluoromethyl)quinoline;
aft) 4-{3-[(2,6-difluorobenzyl)oxy]phenyl}-3-methyl-8-(trifluoromethyl)quinoline;
afu) 3-methyl-4-[3-(2-naphthylmethoxy)phenyl]-8-(trifluoromethyl)quinoline;
afv) 3-methyl-4-[3-(pyridin-3-ylmethoxy)phenyl]-8-(trifluoromethyl)quinoline;
afw) 3-methyl-4-[3-(quinolin-2-ylmethoxy)phenyl]-8-(trifluoromethyl)quinoline;
afx) 4-{3-[(3-chlorobenzyl)oxy]phenyl}-3-methyl-8-(trifluoromethyl)quinoline;
afy) 3-methyl-4-{3-[(3-methylbenzyl)oxy]phenyl}-8-(trifluoromethyl)quinoline;
afz) 4-{3-[(2,5-difluorobenzyl)oxy]phenyl}-3-(2-methylphenyl)-8-(trifluoromethyl)quinoline;
aga) 4-(3-{[2,5-bis(trifluoromethyl)benzyl]oxy}phenyl)-3-(2-methylphenyl)-8-(trifluoromethyl)quinoline;
agb) 4-{3-[(2-bromo-5-methoxybenzyl)oxy]phenyl}-3-(2-methylphenyl)-8-(trifluoromethyl)quinoline;
agc) {3-[3-benzyl-8-(trifluoromethyl)quinolin-4-yl]phenyl}(3-thienylmethyl)amine;
agd) {3-[3-benzyl-8-(trifluoromethyl)quinolin-4-yl]phenyl}(3-furylmethyl)amine;
age) {3-[3-benzyl-8-(trifluoromethyl)quinolin-4-yl]phenyl}[3-(trifluoromethoxy)benzyl]amine;
agf) {3-[3-benzyl-8-(trifluoromethyl)quinolin-4-yl]phenyl}[3-chloro-2-fluoro-6-(trifluoromethyl)benzyl]amine;
agg) {3-[3-benzyl-8-(trifluoromethyl)quinolin-4-yl]phenyl}(pyridin-2-ylmethyl)amine;
agh) {3-[3-benzyl-8-(trifluoromethyl)quinolin-4-yl]phenyl}[4-(trifluoromethoxy)benzyl]amine;
agi) {3-[3-benzyl-8-(trifluoromethyl)quinolin-4-yl]phenyl}(4-chloro-3-fluorobenzyl)amine;
agj) {3-[3-benzyl-8-(trifluoromethyl)quinolin-4-yl]phenyl}[2-fluoro-5-(trifluoromethyl)benzyl]amine;
agk) {3-[3-benzyl-8-(trifluoromethyl)quinolin-4-yl]phenyl}[2-(trifluoromethoxy)benzyl]amine;
agl) N-(1-benzofuran-2-ylmethyl)-3-[3-benzyl-8-(trifluoromethyl)quinolin-4-yl]aniline;
agm) {3-[3-benzyl-8-(trifluoromethyl)quinolin-4-yl]phenyl}(quinolin-3-ylmethyl)amine;
agn) {3-[3-benzyl-8-(trifluoromethyl)quinolin-4-yl]phenyl}(2,4-diethoxybenzyl)amine;
ago) 4-{3-[(2-chloro-5-fluorobenzyl)oxy]phenyl}-3-(2-methylphenyl)-8-(trifluoromethyl)quinoline;

agp) 4-{3-[(5-bromo-2-methoxybenzyl)oxy]phenyl}-3-(2-methyl phenyl)-8-(trifluoromethyl)quinoline;
agq) 4-{3-[(5-bromo-2-fluorobenzyl)oxy]phenyl}-3-(2-methylphenyl)-8-(trifluoromethyl)quinoline;
agr) 4-{3-[(2-methoxy-5-nitrobenzyl)oxy]phenyl}-3-(2-methylphenyl)-8-(trifluoromethyl)quinoline;
ags) 4-{3-[(2,6-dichlorobenzyl)oxy]phenyl}-3-(2-methylphenyl)-8-(trifluoromethyl)quinoline;
agt) 4-{3-[(2,6-difluorobenzyl)oxy]phenyl}-3-(2-methylphenyl)-8-(trifluoromethyl)quinoline;
agu) 1-[4-({3-[3-benzyl-8-(trifluoromethyl)quinolin-4-yl]benzyl}oxy)phenyl]ethone-1,2-diol;
agv) {3-[3-benzyl-8-(trifluoromethyl)quinolin-4-yl]phenyl}(2,3-dichlorobenzyl)amine;
agw) {3-[3-benzyl-8-(trifluoromethyl)quinolin-4-yl]phenyl}(2,6-dichlorobenzyl)amine;
agx) {3-[3-benzyl-8-(trifluoromethyl)quinolin-4-yl]phenyl}(5-chloro-2-nitrobenzyl)amine;
agy) {3-[3-benzyl-8-(trifluoromethyl)quinolin-4-yl]phenyl}(2,6-difluorobenzyl)amine;
agz) {3-[3-benzyl-8-(trifluoromethyl)quinolin-4-yl]phenyl}(3,5-difluorobenzyl)amine;
aha) {3-[3-benzyl-8-(trifluoromethyl)quinolin-4-yl]phenyl}(3,4-dichlorobenzyl)amine;
ahb) {3-[3-benzyl-8-(trifluoromethyl)quinolin-4-yl]phenyl}[(4-bromo-2-thienyl)methyl]amine;
ahc) {3-[3-benzyl-8-(trifluoromethyl)quinolin-4-yl]phenyl}(2,3,5-trichlorobenzyl)amine;
ahd) {3-[3-benzyl-8-(trifluoromethyl)quinolin-4-yl]phenyl}(2,4-dichlorobenzyl)amine;
ahe) {3-[3-benzyl-8-(trifluoromethyl)quinolin-4-yl]phenyl}(2-fluorobenzyl)amine;
ahf) {3-[3-benzyl-8-(trifluoromethyl)quinolin-4-yl]phenyl}(2,3-difluorobenzyl)amine;
ahg) {3-[3-benzyl-8-(trifluoromethyl)quinolin-4-yl]phenyl}(2,3,6-trichlorobenzyl)amine;
ahh) [4-({3-[3-benzyl-8-(trifluoromethyl)quinolin-4-yl]phenyl}ethynyl)phenyl]acetic acid;
ahi) 4-{3-[(3-ethoxybenzyl)oxy]phenyl}-3-methyl-8-(trifluoromethyl)quinoline;
ahj) 3-methyl-4-{3-[(3-propoxybenzyl)oxy]phenyl}-8-(trifluoromethyl)quinoline;
ahk) 4-{3-[(3-isobutoxybenzyl)oxy]phenyl}-3-methyl-8-(trifluoromethyl)quinoline;
ahl) N-benzyl-3-[3-benzyl-8-(trifluoromethyl)quinolin-4-yl]aniline;
ahm) N,N-dibenzyl-3-[3-benzyl-8-(trifluoromethyl)quinolin-4-yl]aniline;
ahn) {3-[3-benzyl-8-(trifluoromethyl)quinolin-4-yl]phenyl}bis(3-methylbenzyl)amine;
aho) 4-[3-(benzyloxy)phenyl]-3-phenyl-8-(trifluoromethyl)quinoline;
ahp) 4-{3-[(2,5-dimethylbenzyl)oxy]phenyl}-3-phenyl-8-(trifluoromethyl)quinoline;
ahq) 4-{3-[(2,5-difluorobenzyl)oxy]phenyl}-3-phenyl-8-(trifluoromethyl)quinoline;
ahr) 4-{3-[(2,5-dichlorobenzyl)oxy]phenyl}-3-phenyl-8-(trifluoromethyl)quinoline;
ahs) {3-[3-benzyl-8-(trifluoromethyl)quinolin-4-yl]phenyl}(4-methoxybenzyl)amine;
aht) 2-[({3-[3-benzyl-8-(trifluoromethyl)quinolin-4-yl]phenyl}amino)methyl]-4-(trifluoromethoxy)phenol;
ahu) {3-[3-benzyl-8-(trifluoromethyl)quinolin-4-yl]phenyl}bis(2-ethoxy-3-methoxybenzyl)amine;
ahv) 4-{3-[(3-methoxybenzyl)oxy]phenyl}-3-phenyl-8-(trifluoromethyl)quinoline;
ahw) {3-[3-benzyl-8-(trifluoromethyl)quinolin-4-yl]phenyl}[3-(trifluoromethyl)benzyl]amine;
ahx) 4-{3-[(4-isopropylbenzyl)oxy]phenyl}-3-phenyl-8-(trifluoromethyl)quinoline;
ahy) 4-{3-[(3,4-dimethylbenzyl)oxy]phenyl}-3-phenyl-8-(trifluoromethyl)quinoline;
ahz) 4-{3-[(2,6-dimethylbenzyl)oxy]phenyl}-3-phenyl-8-(trifluoromethyl)quinoline;
aia) 4-{3-[(3,4-dichlorobenzyl)oxy]phenyl}-3-phenyl-8-(trifluoromethyl)quinoline;
aib) 4-{3-[(2,6-dichlorobenzyl)oxy]phenyl}-3-phenyl-8-(trifluoromethyl)quinoline;
aic) 4-{3-[(2,6-difluorobenzyl)oxy]phenyl}-3-phenyl-8-(trifluoromethyl)quinoline;
aid) 4-{3-[(2,4-difluorobenzyl)oxy]phenyl}-3-phenyl-8-(trifluoromethyl)quinoline;
aie) 4-{3-[(2-chloro-4-fluorobenzyl)oxy]phenyl}-3-phenyl-8-(trifluoromethyl)quinoline;
aif) 4-(3-{[2,5-bis(trifluoromethyl)benzyl]oxy}phenyl)-3-phenyl-8-(trifluoromethyl)quinoline;
aig) 4-(3-{[2-chloro-3-(trifluoromethyl)benzyl]oxy}phenyl)-3-phenyl-8-(trifluoromethyl)quinoline;
aih) 4-{3-[(2-chloro-5-fluorobenzyl)oxy]phenyl}-3-phenyl-8-(trifluoromethyl)quinoline;
aii) 4-{3-[(4-fluoro-3-nitrobenzyl)oxy]phenyl}-3-(2-methylphenyl)-8-(trifluoromethyl)quinoline;
aij) 3-(2-methylphenyl)-4-{3-[(4-nitrobenzyl)oxy]phenyl}-8-(trifluoromethyl)quinoline;
aik) 4-{3-[(5-chloro-2-fluorobenzyl)oxy]phenyl}-3-(2-methylphenyl)-8-(trifluoromethyl)quinoline;
ail) 4-{3-[(2,3-difluorobenzyl)oxy]phenyl}-3-phenyl-8-(trifluoromethyl)quinoline;
aim) 4-{3-[(2,3-dimethoxybenzyl)oxy]phenyl}-3-phenyl-8-(trifluoromethyl)quinoline;
ain) 4-(3-{[5-chloro-2-(trifluoromethyl)benzyl]oxy}phenyl)-3-phenyl-8-(trifluoromethyl)quinoline;
aio) 2-(4-{[3-(8-chloro-3-methylquinolin-4-yl)phenoxy]methyl}phenyl)propanoic acid;
aip) 3,3'-(3-phenylquinoline-4,8-diyl)diphenol;
aiq) 3-[3-(2-ethynylphenyl)-8-(trifluoromethyl)quinolin-4-yl]phenol;
air) {3-[3-benzyl-8-(trifluoromethyl)quinolin-4-yl]phenyl}[(1-methyl-1H-indol-2-yl)methyl]amine;
ais) {3-[3-benzyl-8-(trifluoromethyl)quinolin-4-yl]phenyl}[(6-bromopyridin-3-yl)methyl]amine;
ait) {3-[3-benzyl-8-(trifluoromethyl)quinolin-4-yl]phenyl}[(2-chloroquinolin-3-yl)methyl]amine;
aiu) {3-[3-benzyl-8-(trifluoromethyl)quinolin-4-yl]phenyl}[(6-methoxypyridin-3-yl)methyl]amine;
aiv) {3-[3-benzyl-8-(trifluoromethyl)quinolin-4-yl]phenyl}[(6-chloropyridin-3-yl)methyl]amine;
aiw) {3-[3-benzyl-8-(trifluoromethyl)quinolin-4-yl]phenyl}(2,3,4-trimethoxybenzyl)amine;
aix) {3-[3-benzyl-8-(trifluoromethyl)quinolin-4-yl]phenyl}(1H-indol-5-ylmethyl)amine;
aiy) N-[(5-methyl-2-thienyl)methyl]-3-[3-methyl-8-(trifluoromethyl)quinolin-4-yl]aniline;
aiz) N-[(5-ethyl-2-furyl)methyl]-3-[3-methyl-8-(trifluoromethyl)quinolin-4-yl]aniline;
aja) N-[(4,5-dimethyl-2-furyl)methyl]-3-[3-methyl-8-(trifluoromethyl)quinolin-4-yl]aniline;
ajb) N-(2-fluoro-5-methoxybenzyl)-3-[3-methyl-8-(trifluoromethyl)quinolin-4-yl]aniline;
ajc) N-(2-bromo-5-methoxybenzyl)-3-[3-methyl-8-(trifluoromethyl)quinolin-4-yl]aniline;
ajd) N-(2,3-dimethoxybenzyl)-3-[3-methyl-8-(trifluoromethyl)quinolin-4-yl]aniline;

aje) N-(2,4-dimethoxybenzyl)-3-[3-methyl-8-(trifluoromethyl)quinolin-4-yl]aniline;
ajf) N-(3,4-dimethoxybenzyl)-3-[3-methyl-8-(trifluoromethyl)quinolin-4-yl]aniline;
ajg) N-(3,5-dimethoxybenzyl)-3-[3-methyl-8-(trifluoromethyl)quinolin-4-yl]aniline;
ajh) N-(2,3-dimethylbenzyl)-3-[3-methyl-8-(trifluoromethyl)quinolin-4-yl]anime;
aji) N-(4-isopropylbenzyl)-3-[3-methyl-8-(trifluoromethyl)quinolin-4-yl]aniline;
ajj) {3-[3-methyl-8-(trifluoromethyl)quinolin-4-yl]phenyl}(1-naphthylmethyl)amine;
ajk) {3-[3-methyl-8-(trifluoromethyl)quinolin-4-yl]phenyl}(2-naphthylmethyl)amine;
ajl) {3-[3-methyl-8-(trifluoromethyl)quinolin-4-yl]phenyl}(quinolin-3-ylmethyl)amine;
ajm) N-(1-benzofuran-2-ylmethyl)-3-[3-methyl-8-(trifluoromethyl)quinolin-4-yl]aniline;
ajn) N-[(5-methyl-2-furyl)methyl]-3-[3-methyl-8-(trifluoromethyl)quinolin-4-yl]aniline;
ajo) methyl {4-[({3-[3-methyl-8-(trifluoromethyl)quinolin-4-yl]phenyl}amino)methyl]phenyl}acetate;
ajp) methyl 2-{4-[({3-[3-methyl-8-(trifluoromethyl)quinolin-4-yl]phenyl}amino)methyl]phenyl}propanoate;
ajq) methyl 2-methyl-2-{4-[({3-[3-methyl-8-(trifluoromethyl)quinolin-4-yl]phenyl}amino)methyl]phenyl}propanoate;
ajr) 4-{3-[(2,3-dimethylbenzyl)oxy]phenyl}-3-phenyl-8-(trifluoromethyl)quinoline;
ajs) {3-[3-benzyl-8-(trifluoromethyl)quinolin-4-yl]phenyl}[5-chloro-2-(trifluoromethyl)benzyl]amine;
ajt) methyl [4-({3-[3-phenyl-8-(trifluoromethyl)quinolin-4-yl]phenoxy}methyl)phenoxy]acetate;
aju) 4-{3-[(2-methoxybenzyl)oxy]phenyl}-3-phenyl-8-(trifluoromethyl)quinoline;
ajv) 4-{3-[(3,5-dimethoxybenzyl)oxy]phenyl}-3-phenyl-8-(trifluoromethyl)quinoline;
ajw) 4-[3-(1-naphthylmethoxy)phenyl]-3-phenyl-8-(trifluoromethyl)quinoline;
ajx) 4-{3-[(4-fluorobenzyl)oxy]phenyl}-3-(2-methyl phenyl)-8-(trifluoromethyl)quinoline;
ajy) 4-(3-{[5-fluoro-2-(trifluoromethyl)benzyl]oxy}phenyl)-3-(2-methylphenyl)-8-(trifluoromethyl)quinoline;
ajz) 4-(3-{[2-chloro-5-(trifluoromethyl)benzyl]oxy}phenyl)-3-(2-methylphenyl)-8-(trifluoromethyl)quinoline;
aka) 4-{3-[(2-chloro-4-fluorobenzyl)oxy]phenyl}-3-(2-methylphenyl)-8-(trifluoromethyl)quinoline;
akb) 4-{3-[(2-chlorobenzyl)oxy]phenyl}-3-(2-methylphenyl)-8-(trifluoromethyl)quinoline;
akc) 4-(3-{[2-chloro-3-(trifluoromethyl)benzyl]oxy}phenyl)-3-(2-methylphenyl)-8-(trifluoromethyl)quinoline;
akd) 4-(3-{[5-chloro-2-(trifluoromethyl)benzyl]oxy}phenyl)-3-(2-methylphenyl)-8-(trifluoromethyl)quinoline;
ake) 4-{3-[(2-fluoro-4-nitrobenzyl)oxy]phenyl}-3-(2-methylphenyl)-8-(trifluoromethyl)quinoline;
akf) (2R)-2-[4-({3-[3-methyl-8-(trifluoromethyl)quinolin-4-yl]phenoxy}methyl)phenyl]propanoic acid;
akg) (2S)-2-[4-({3-[3-methyl-8-(trifluoromethyl)quinolin-4-yl]phenoxy}methyl)phenyl]propanoic acid;
akh) 3-benzyl-4-(3-{[5-chloro-2-(trifluoromethyl)benzyl]oxy}phenyl)-8-(trifluoromethyl)quinoline;
aki) 3-benzyl-4-(3-{[5-fluoro-2-(trifluoromethyl)benzyl]oxy}phenyl)-8-(trifluoromethyl)quinoline;
akj) 4-{3-[(4-bromo-2-nitrobenzyl)oxy]phenyl}-3-(2-methyl phenyl)-8-(trifluoromethyl)quinoline;
akk) {4-[({3-[3-methyl-8-(trifluoromethyl)quinolin-4-yl]phenyl}amino)methyl]phenyl}acetic acid;
akl) 2-{4-[({3-[3-methyl-8-(trifluoromethyl)quinolin-4-yl]phenyl}amino)methyl]phenyl}propanoic acid;
akm) 2-methyl-2-{4-[({3-[3-methyl-8-(trifluoromethyl)quinolin-4-yl]phenyl}amino)methyl]phenyl}propanoic acid;
akn) 3-benzyl-4-[3-(3-chloro-4-fluorophenoxy)phenyl]-8-(trifluoromethyl)quinoline;
ako) 3-benzyl-4-[3-(3-methylphenoxy)phenyl]-8-(trifluoromethyl)quinoline;
akp) 3-benzyl-8-(trifluoromethyl)-4-{3-[3-(trifluoromethyl)phenoxy]phenyl}quinoline;
akq) 3-benzyl-4-[3-(3-chlorophenoxy)phenyl]-8-(trifluoromethyl)quinoline;
akr) 3-benzyl-4-[3-(3,5-dimethylphenoxy)phenyl]-8-(trifluoromethyl)quinoline;
aks) 3-benzyl-4-[3-(4-fluorophenoxy)phenyl]-8-(trifluoromethyl)quinoline;
akt) 3-benzyl-4-[3-(2-naphthyloxy)phenyl]-8-(trifluoromethyl)quinoline;
aku) 3-benzyl-4-[3-(3,5-difluorophenoxy)phenyl]-8-(trifluoromethyl)quinoline;
akv) 3-benzyl-4-[3-(3,5-dichlorophenoxy)phenyl]-8-(trifluoromethyl)quinoline;
akw) (3-{3-[3-benzyl-8-(trifluoromethyl)quinolin-4-yl]phenoxy}phenyl)methanol;
akx) (3-{3-[3-methyl-8-(trifluoromethyl)quinolin-4-yl]phenoxy}phenyl)methanol;
aky) (4-{3-[3-methyl-8-(trifluoromethyl)quinolin-4-yl]phenoxy}phenyl)methanol;
akz) 3-benzyl-4-{3-[(2-chlorobenzyl)oxy]phenyl}-8-(trifluoromethyl)quinoline;
ala) 3-benzyl-4-{3-[(2-fluorobenzyl)oxy]phenyl}-8-(trifluoromethyl)quinoline;
alb) 3-benzyl-4-{3-[(4-fluorobenzyl)oxy]phenyl}-8-(trifluoromethyl)quinoline;
alc) 3-benzyl-4-{3-[(4-nitrobenzyl)oxy]phenyl}-8-(trifluoromethyl)quinoline;
ald) 3-(2-methylphenyl)-8-(trifluoromethyl)-4-{3-[(3,4,5-trimethoxybenzyl)oxy]phenyl}quinoline;
ale) 3-[3-(2-chloro-6-fluorophenyl)-8-(trifluoromethyl)quinolin-4-yl]phenol;
alf) 3-benzyl-4-{3-[(5-bromo-2-fluorobenzyl)oxy]phenyl}-8-(trifluoromethyl)quinoline;
alg) 2-({3-[3-benzyl-8-(trifluoromethyl)quinolin-4-yl]phenoxy}methyl)terephthalonitrile;
alh) N-(2,5-dimethylbenzyl)-3-[3-methyl-8-(trifluoromethyl)quinolin-4-yl]anime;
ali) N-(5-fluoro-2-methoxybenzyl)-3-[3-methyl-8-(trifluoromethyl)quinolin-4-yl]aniline;
alj) N-[5-fluoro-2-(trifluoromethyl)benzyl]-3-[3-methyl-8-(trifluoromethyl)quinolin-4-yl]aniline;
alk) N-[2-fluoro-5-(trifluoromethyl)benzyl]-3-[3-methyl-8-(trifluoromethyl)quinolin-4-yl]aniline;
all) N-(5-ethoxy-2-fluorobenzyl)-3-[3-methyl-8-(trifluoromethyl)quinolin-4-yl]aniline;
alm) N-(2-fluoro-5-propoxybenzyl)-3-[3-methyl-8-(trifluoromethyl)quinolin-4-yl]aniline;
aln) N-(2-bromo-5-ethoxybenzyl)-3-[3-methyl-8-(trifluoromethyl)quinolin-4-yl]aniline;
alo) N-(2,6-dimethylbenzyl)-3-[3-methyl-8-(trifluoromethyl)quinolin-4-yl]anime;

alp) {3-[3-methyl-8-(trifluoromethyl)quinolin-4-yl]phenyl}[2-(trifluoromethoxy)benzyl]amine;
alq) {3-[3-methyl-8-(trifluoromethyl)quinolin-4-yl]phenyl}[3-(trifluoromethoxy)benzyl]amine;
alr) N-(2-fluoro-6-methoxybenzyl)-3-[3-methyl-8-(trifluoromethyl)quinolin-4-yl]anime;
als) N-(3-fluoro-4-methoxybenzyl)-3-[3-methyl-8-(trifluoromethyl)quinolin-4-yl]anime;
alt) N-(2-ethoxy-3-methoxybenzyl)-3-[3-methyl-8-(trifluoromethyl)quinolin-4-yl]anime;
alu) N-(2,3-dihydro-1,4-benzodioxin-6-ylmethyl)-3-[3-methyl-8-(trifluoromethyl)quinolin-4-yl]amine;
alv) N-(1H-indol-5-ylmethyl)-3-[3-methyl-8-(trifluoromethyl)quinolin-4-yl]amine;
alw) {3-[3-benzyl-8-(trifluoromethyl)quinolin-4-yl]phenyl}(1H-indol-6-ylmethyl)amine;
alx) {3-[3-benzyl-8-(trifluoromethyl)quinolin-4-yl]phenyl}[(1-methyl-1H-indol-6-yl)methyl]amine;
aly) [4-({3-[3-phenyl-8-(trifluoromethyl)quinolin-4-yl]phenoxy}methyl)phenoxy]acetic acid;
alz) 3-[4-({3-[3-benzyl-8-(trifluoromethyl)quinolin-4-yl]phenyl}amino)phenyl]propanoic acid;
ama) 3-({3-[3-benzyl-8-(trifluoromethyl)quinolin-4-yl]phenoxy}methyl)-4-fluorobenzonitrile;
amb) N-[2-chloro-3-(trifluoromethyl)benzyl]-3-[3-phenyl-8-(trifluoromethyl)quinolin-4-yl]aniline;
amc) N-(1H-indol-5-ylmethyl)-3-[3-phenyl-8-(trifluoromethyl)quinolin-4-yl]aniline;
amd) 3-benzyl-8-fluoro-4-(3-methoxyphenyl)quinoline;
ame) {3-[3-benzyl-8-(trifluoromethyl)quinolin-4-yl]phenyl}[(1-ethyl-1H-indol-6-yl)methyl]amine;
amf) 4-fluoro-3-({3-[3-(2-methyl phenyl)-8-(trifluoromethyl)quinolin-4-yl]phenoxy}methyl)benzonitrile;
amg) N-(2,3-dihydro-1,4-benzodioxin-6-ylmethyl)-3-[3-phenyl-8-(trifluoromethyl)quinolin-4-yl]aniline;
amh) N-(1H-indol-6-ylmethyl)-3-[3-phenyl-8-(trifluoromethyl)quinolin-4-yl]aniline;
ami) N-(1-naphthylmethyl)-3-[3-phenyl-8-(trifluoromethyl)quinolin-4-yl]aniline;
amj) {3-[3-phenyl-8-(trifluoromethyl)quinolin-4-yl]phenyl}[2-(trifluoromethoxy)benzyl]amine;
amk) N-[2-fluoro-5-(trifluoromethyl)benzyl]-3-[3-phenyl-8-(trifluoromethyl)quinolin-4-yl]aniline;
aml) N-(2,3-dimethylbenzyl)-3-[3-phenyl-8-(trifluoromethyl)quinolin-4-yl]anime;
amm) N-(2,3-dimethoxybenzyl)-3-[3-phenyl-8-(trifluoromethyl)quinolin-4-yl]aniline;
amn) N-[(i -acetyl-1H-indal-3-yl)methyl]-3-[3-phenyl-8-(trifluoromethyl)quinolin-4-yl]aniline;
ama) 3-[({3-[3-phenyl-8-(trifluoromethyl)quinolin-4-yl]phenyl}amino)methyl]benzonitrile;
amp) N-[(1-methyl-1H-indal-2-yl)methyl]-3-[3-phenyl-8-(trifluoromethyl)quinolin-4-yl]an ii ne;
amq) 4-{3-[(5-ethynyl-2-fluorobenzyl)oxy]phenyl}-3-(2-methyl phenyl)-8-(trifluoromethyl)quinoline;
amr) 3-benzyl-8-chloro-4-(4-nitraphenyl)quinoline;
ams) 3-benzyl-8-chloro-4-(3-nitraphenyl)quinoline;
amt) (3-{3-[3-phenyl-8-(trifluoromethyl)quinolin-4-yl]phenoxy}phenyl)methanol;
amu) (4-{3-[3-phenyl-8-(trifluoromethyl)quinolin-4-yl]phenoxy}phenyl)methanol;
amv) 3-[3,8-bis(trifluoromethyl)quinolin-4-yl]phenol;
amw)₃-benzyl-4-{3-[(5-ethynyl-2-fluorobenzyl)oxy]phenyl}-8-(trifluoromethyl)quinoline;
amx) 3-benzyl-4-{3-[(1-methyl-1H-pyrrole-2-yl)methoxy]phenyl}-8-(trifluoromethyl)quinoline;
amy) [4-(3-benzyl-8-chloroquinolin-4-yl)phenyl]amine;
amz) 4-{3-[(5-ethyl-2-fluorobenzyl)oxy]phenyl}-3-(2-methylphenyl)-8-(trifluoromethyl)quinoline;
ana) methyl [5-({4-[3-benzyl-8-(trifluoromethyl)quinolin-4-yl]phenoxy}methyl)-1-methyl-1H-pyrrol-2-yl]acetate;
anb) [4-(1-{3-[3-benzyl-8-(trifluoromethyl)quinolin-4-yl]phenoxy}ethyl)phenyl]acetic acid;
anc) methyl 3-{3-[3-benzyl-8-(trifluoromethyl)quinolin-4-yl]phenoxy}benzoate;
and) 4-{3-[(2-fluoro-5-vinylbenzyl)oxy]phenyl}-3-(2-methyl phenyl)-8-(trifluoromethyl)quinoline;
ane) [4-({3-[3,8-bis(trifluoromethyl)quinolin-4-yl]phenoxy}methyl)phenyl]acetic acid;
anf) ethyl 3-({3-[3-methyl-8-(trifluoromethyl)quinolin-4-yl]phenyl}amino)benzoate;
ang) [3-(3-benzyl-8-chloroquinolin-4-yl)phenyl]amine;
anh) (2R)-2-(4-{[3-(8-chloro-3-methylquinolin-4-yl)phenoxy]methyl}phenyl)propanoic acid;
ani) (2S)-2-(4-{[3-(8-chloro-3-methylquinolin-4-yl)phenoxy]methyl}phenyl)propanoic acid;
anj) methyl 2-[4-({3-[3,8-bis(trifluoromethyl)quinolin-4-yl]phenoxy}methyl)phenyl]-2-methylpropanoate;
ank) 2-[4-({3-[3,8-bis(trifluoromethyl)quinolin-4-yl]phenoxy}methyl)phenyl]-2-methylpropanoic acid;
anl) 4-(3-{[2-chloro-3-(trifluoromethyl)benzyl]oxy}phenyl)-3-(2,4,6-trifluorobenzyl)-8-(trifluoromethyl)quinoline;
anm) 3-benzyl-4-{3-[(2-fluoro-5-vinylbenzyl)oxy]phenyl}-8-(trifluoromethyl)quinoline;
ann) 3-benzyl-4-{3-[(2,5-dimethylphenoxy)methyl]phenyl}-8-(trifluoromethyl)quinoline;
ano) 3-benzyl-4-(3-{[2-fluoro-3-(trifluoromethyl)phenoxy]methyl}phenyl)-8-(trifluoromethyl)quinoline;
anp) 3-benzyl-4-{3-[(2,3-dimethylphenoxy)methyl]phenyl}-8-(trifluoromethyl)quinoline;
anq) 3-benzyl-4-(3-{[2-chloro-3-(trifluoromethyl)phenoxy]methyl}phenyl)-8-(trifluoromethyl)quinoline;
anr) 3-benzyl-4-{3-[(2-methoxybenzyl)oxy]phenyl}-8-(trifluoromethyl)quinoline;
ans) 3-benzyl-4-{3-[(2,3-dimethylbenzyl)oxy]phenyl}-8-(trifluoromethyl)quinoline;
ant) 3-benzyl-4-{3-[(3-bromobenzyl)oxy]phenyl}-8-(trifluoromethyl)quinoline;
anu) 3-benzyl-4-(3-{[2-chloro-3-(trifluoromethyl)benzyl]oxy}phenyl)-8-(trifluoromethyl)quinoline;
anv) {5-[({3-[3-benzyl-8-(trifluoromethyl)quinolin-4-yl]phenyl}amino)methyl]-2-thienyl}acetic acid;
anw) 3-benzyl-4-{3-[(5-bromo-2-methoxybenzyl)oxy]phenyl}-8-(trifluoromethyl)quinoline;
anx) {3-[3-benzyl-8-(trifluoromethyl)quinolin-4-yl]phenyl}[2-chloro-3-(trifluoromethyl)benzyl]amine;
any) ethyl 3-{[3-(3-benzyl-8-chloroquinolin-4-yl)phenyl]amino}benzoate;
anz) 3-{[3-benzyl-8-(trifluoromethyl)quinolin-4-yl]methyl}phenol;
aoa) {3-[3-benzyl-8-(trifluoromethyl)quinolin-4-yl]phenyl}[(6-bromo-1,3-benzodioxol-5-yl)methyl]amine;
aob) N-(9-anthrylmethyl)-3-[3-benzyl-8-(trifluoromethyl)quinolin-4-yl]aniline;
aoc) {3-[3-benzyl-8-(trifluoromethyl)quinolin-4-yl]phenyl}[(2-methoxy-1-naphthyl)methyl]amine;
aod) {3-[3-benzyl-8-(trifluoromethyl)quinolin-4-yl]phenyl}[(6-methoxy-2-naphthyl)methyl]amine;
aoe) {3-[3-benzyl-8-(trifluoromethyl)quinolin-4-yl]phenyl}(2-isopropoxybenzyl)amine;
aof) {3-[3-benzyl-8-(trifluoromethyl)quinolin-4-yl]phenyl}[2,4-bis(trifluoromethyl)benzyl]amine;

aog) {3-[3-benzyl-8-(trifluoromethyl)quinolin-4-yl]phenyl}[4-fluoro-2-(trifluoromethyl)benzyl]amine;
aoh) {3-[3-benzyl-8-(trifluoromethyl)quinolin-4-yl]phenyl}[(2,6-dichloropyridin-4-yl)methyl]amine;
aoi) {3-[3-benzyl-8-(trifluoromethyl)quinolin-4-yl]phenyl}(2-thienylmethyl)amine;
aoj) {2-[({3-[3-benzyl-8-(trifluoromethyl)quinolin-4-yl]phenyl}amino)methyl]-3-thienyl}acetic acid;
aok) [3-({3-[3-methyl-8-(trifluoromethyl)quinolin-4-yl]phenyl}amino)phenyl]methanol;
aol) (3-{[3-(3-benzyl-8-chloroquinolin-4-yl)phenyl]amino}phenyl)methanol;
aom) 4-(3-bromophenyl)-8-chloro-3-methylquinoline;
aon) 3-benzyl-4-(3-bromophenyl)-8-chloroquinoline;
aoo) 2-(3-{3-[3-benzyl-8-(trifluoromethyl)quinolin-4-yl]phenoxy}phenyl)propan-2-ol;
aop) {3-[3-benzyl-8-(trifluoromethyl)quinolin-4-yl]phenyl}[(1-methyl-1H-indol-5-yl)methyl]amine;
aoq) 3-benzyl-4-[3-(phenylethynyl)phenyl]-8-(trifluoromethyl)quinoline;
aor) (5Z)-5-{4-[({3-[3-benzyl-8-(trifluoromethyl)quinolin-4-yl]phenyl}amino)methyl]benzylidene}-1,3-thiazolidine-2,4-dione;
aos) (5Z)-5-{4-[({3-[3-benzyl-8-(trifluoromethyl)quinolin-4-yl]phenyl}amino)methyl]benzylidene}-2-thioxo-1,3-thiazolidin-4-one;
aot) 2-(3-{[3-(3-benzyl-8-chloroquinolin-4-yl)phenyl]amino}phenyl)propan-2-ol;
aou) 3-{[3-(3-benzyl-8-chloroquinolin-4-yl)phenyl]amino}benzoic acid;
aov) 2-methyl-2-[4-({3-[3-(2,4,6-trifluorobenzyl)-8-(trifluoromethyl)quinolin-4-yl]phenoxy}methyl)phenyl]propanoic acid;
aow) ethyl 3-({3-[3-benzyl-8-(trifluoromethyl)quinolin-4-yl]phenyl}ethynyl)benzoate;
aox) 3-{[3-(3-benzyl-8-chloroquinolin-4-yl)phenyl]amino}benzamide;
aoy) 3-{[3-(3-benzyl-8-chloroquinolin-4-yl)phenyl]amino}—N-(2-hydroxyethyl)benzamide;
aoz) 3-{[3-(3-benzyl-8-chloroquinolin-4-yl)phenyl]amino}—N-methylbenzamide;
apa) 3-{[3-(3-benzyl-8-chloroquinolin-4-yl)phenyl]amino}—N-ethylbenzamide;
apb) 3-{[3-(3-benzyl-8-chloroquinolin-4-yl)phenyl]amino}—N-cyclopropylbenzamide;
apc) methyl 3-[3-(8-chloro-3-methylquinolin-4-yl)phenoxy]benzoate;
apd) 3-({3-[3-benzyl-8-(trifluoromethyl)quinolin-4-yl]phenyl}ethynyl)benzoic acid;
ape) methyl 4-({3-[3-benzyl-8-(trifluoromethyl)quinolin-4-yl]phenyl}ethynyl)benzoate;
apf) 5-{4-[({3-[3-benzyl-8-(trifluoromethyl)quinolin-4-yl]phenyl}amino)methyl]benzyl}-2-thioxo-1,3-thiazolidin-4-one;
apg) 5-{4-[({3-[3-benzyl-8-(trifluoromethyl)quinolin-4-yl]phenyl}amino)methyl]benzyl}-1 3-thiazolidine-2,4-dione;
aph) 4-({3-[3-benzyl-8-(trifluoromethyl)quinolin-4-yl]phenyl}ethynyl)benzoic acid;
api) methyl 3-bromo-2,6-dimethoxy-4-({3-[3-phenyl-8-(trifluoromethyl)quinolin-4-yl]phenoxy}methyl)benzoate;
apj) 3-{[3-(3-benzyl-8-chloroquinolin-4-yl)phenyl]amino}-N-isopropylbenzamide;
apk) 3-{[3-(3-benzyl-8-chloroquinolin-4-yl)phenyl]amino}-N,N-diethylbenzamide;
apl) [3-(3-benzyl-8-chloroquinolin-4-yl)phenyl][3-(pyrrolidin-1-ylcarbonyl)phenyl]amine;
apm) [3-(3-benzyl-8-chloroquinolin-4-yl)phenyl][3-(piperidin-1-ylcarbonyl)phenyl]amine;
apn) [3-(3-benzyl-8-chloroquinolin-4-yl)phenyl][3-(morpholin-4-ylcarbonyl)phenyl]amine;
apo) {3-[3-(8-chloro-3-methylquinolin-4-yl)phenoxy]phenyl}methanol;
app) 2-{3-[3-(8-chloro-3-methylquinolin-4-yl)phenoxy]phenyl}propan-2-ol;
apq) 3-[3-(8-chloro-3-methylquinolin-4-yl)phenoxy]-N-ethylbenzamide;
apr) 3-[3-(8-chloro-3-methylquinolin-4-yl)phenoxy]-N-methylbenzamide;
aps) 3-[4-({3-[3-benzyl-8-(trifluoromethyl)quinolin-4-yl]phenyl}ethynyl)phenyl]propanoic acid;
apt) methyl 3-[4-({3-[3-benzyl-8-(trifluoromethyl)quinolin-4-yl]phenyl}ethynyl)phenyl]propanoate;
apu) methyl 3-[3-({3-[3-benzyl-8-(trifluoromethyl)quinolin-4-yl]phenyl}ethynyl)phenyl]propanoate;
apv) 3-[3-({3-[3-benzyl-8-(trifluoromethyl)quinolin-4-yl]phenyl}ethynyl)phenyl]propanoic acid;
apw) [3-({3-[3-benzyl-8-(trifluoromethyl)quinolin-4-yl]phenyl}ethynyl)phenyl]acetic acid;
apx) 4-(3-methoxyphenyl)-3-(2,4,6-trifluorobenzyl)-8-(trifluoromethyl)quinoline;
apy) methyl 3-{[3-(3-benzyl-8-chloroquinolin-4-yl)phenyl]amino}benzoate;
apz) [3-({3-[3-phenyl-8-(trifluoromethyl)quinolin-4-yl]phenoxy}methyl)phenyl]methanol;
aqa) 8-chloro-4-(3-{[2-chloro-3-(trifluoromethyl)benzyl]oxy}phenyl)-3-phenylquinoline;
aqb) 3-benzyl-4-(3-{[2-fluoro-3-(trifluoromethyl)benzyl]oxy}phenyl)-8-(trifluoromethyl)quinoline;
aqc) 3-benzyl-4-{3-[(3-ethynyl benzyl)oxy]phenyl}-8-(trifluoromethyl)quinoline;
aqd) {3-[3-benzyl-8-(trifluoromethyl)quinolin-4-yl]phenyl}[(1-methyl-1H-indol-7-yl)methyl]amine;
aqe) {3-[3-benzyl-8-(trifluoromethyl)quinolin-4-yl]phenyl}(1H-indol-7-ylmethyl)amine;
aqf) 3-bromo-2,6-dimethoxy-4-({3-[3-phenyl-8-(trifluoromethyl)quinolin-4-yl]phenoxy}methyl)benzoic acid;
aqg) 3-benzyl-4-{3-[(4-bromo-2-fluorobenzyl)oxy]phenyl}-8-(trifluoromethyl)quinoline;
aqh) N-[3-(3-benzyl-8-chloroquinolin-4-yl)phenyl]-3,5-dimethylaniline;
aqi) 3-{[3-(3-benzyl-8-chloroquinolin-4-yl)phenyl]amino}-N-propylbenzamide;
aqj) {3-[3-benzyl-8-(trifluoromethyl)quinolin-4-yl]phenyl}(2-chlorobenzyl)amine;
aqk) {3-[3-benzyl-8-(trifluoromethyl)quinolin-4-yl]phenyl}bis(2-chlorobenzyl)amine;
aql) {3-[3-benzyl-8-(trifluoromethyl)quinolin-4-yl]phenyl}[2-(difluoromethoxy)benzyl]amine;
aqm) 3-benzyl-4-(3-{[2-(difluoromethoxy)benzyl]oxy}phenyl)-8-(trifluoromethyl)quinoline;
aqn) 3-benzyl-4-(3-{[2-(trifluoromethoxy)benzyl]oxy}phenyl)-8-(trifluoromethyl)quinoline;
aqo) 4-(3-methoxyphenyl)-3-(2-methylphenyl)-8-(trifluoromethyl)quinoline;
aqp) [4-(2-{3-[3-benzyl-8-(trifluoromethyl)quinolin-4-yl]phenyl}ethyl)phenyl]acetic acid;
aqq) [4-((1 R)-1-{3-[3-benzyl-8-(trifluoromethyl)quinolin-4-yl]phenoxy}ethyl)phenyl]acetic acid;
aqr) [4-((1 S)-1-{3-[3-benzyl-8-(trifluoromethyl)quinolin-4-yl]phenoxy}ethyl)phenyl]acetic acid;

aqs) {4-[3-(8-chloro-3-phenylquinolin-4-yl)phenoxy]phenyl}methanol;
aqt) methyl 3-[3-(3-benzyl-8-chloroquinolin-4-yl)phenoxy]benzoate;
aqu) methyl 4-{3-[3-phenyl-8-(trifluoromethyl)quinolin-4-yl]phenoxy}benzoate;
aqv) N-[3-(3-benzyl-8-chloroquinolin-4-yl)phenyl]-3,5-difluoroaniline;
aqw) N-[3-(3-benzyl-8-chloroquinolin-4-yl)phenyl]-3,5-dichloroaniline;
aqx) N-[3-(3-benzyl-8-chloroquinolin-4-yl)phenyl]-3,5-dibromoaniline;
aqy) 3-{3-[3-benzyl-8-(trifluoromethyl)quinolin-4-yl]phenoxy}-N-propylbenzamide;
aqz) 3-[3-(8-chloro-3-methylquinolin-4-yl)phenoxy]-N-propylbenzamide;
ara) 3-[3-(8-chloro-3-methylquinolin-4-yl)phenoxy]-N-isopropylbenzamide;
arb) 3-[3-(8-chloro-3-methylquinolin-4-yl)phenoxy]-N,N-diethylbenzamide;
arc) 8-chloro-3-methyl-4-{3-[3-(pyrrolidin-1-ylcarbonyl)phenoxy]phenyl}quinoline;
ard) 8-chloro-3-methyl-4-{3-[3-(piperidin-1-ylcarbonyl)phenoxy]phenyl}quinoline;
are) 8-chloro-3-methyl-4-{3-[3-(morpholin-4-ylcarbonyl)phenoxy]phenyl}quinoline;
arf) 3-[3-(8-chloro-3-methylquinolin-4-yl)phenoxy]-N-(3-methoxyphenyl)benzamide;
arg) 3-{3-[3-benzyl-8-(trifluoromethyl)quinolin-4-yl]phenoxy}-N-isopropylbenzamide;
arh) 3-{3-[3-benzyl-8-(trifluoromethyl)quinolin-4-yl]phenoxy}-N,N-diethylbenzamide;
ari) 3-benzyl-4-{3-[3-(pyrrolidin-1-ylcarbonyl)phenoxy]phenyl}-8-(trifluoromethyl)quinoline;
arj) 3-benzyl-4-{3-[3-(piperidin-1-ylcarbonyl)phenoxy]phenyl}-8-(trifluoromethyl)quinoline;
ark) 3-benzyl-4-{3-[3-(morpholin-4-ylcarbonyl)phenoxy]phenyl}-8-(trifluoromethyl)quinoline;
arl) 3-benzyl-4-{3-[(2-fluorophenyl)ethynyl]phenyl}-8-(trifluoromethyl)quinoline;
arm) 3-benzyl-4-{3-[(2-chlorophenyl)ethynyl]phenyl}-8-(trifluoromethyl)quinoline;
arn) 3-benzyl-4-{3-[(4-bromophenyl)ethynyl]phenyl}-8-(trifluoromethyl)quinoline;
aro) 3-benzyl-4-{3-[(2,4-dichlorophenyl)ethynyl]phenyl}-8-(trifluoromethyl)quinoline;
arp) 2-[4-(3-hydroxyphenyl)-8-(trifluoromethyl)quinolin-3-yl]benzonitrile;
arq) 3-benzyl-4-{3-[(2,5-dichlorophenyl)ethynyl]phenyl}-8-(trifluoromethyl)quinoline;
arr) 3-benzyl-4-{3-[(3,4-dichlorophenyl)ethynyl]phenyl}-8-(trifluoromethyl)quinoline;
ars) 3-benzyl-8-(trifluoromethyl)-4-(3-vinylphenyl)quinoline;
art) {3-[3-benzyl-8-(trifluoromethyl)quinolin-4-yl]phenyl}[(3-bromo-5-iodo-4-methyl-2-thienyl)methyl]amine;
aru) {3-[3-benzyl-8-(trifluoromethyl)quinolin-4-yl]phenyl}[(3-methyl-1-benzothien-2-yl)methyl]amine;
arv) N-(1-benzothien-3-ylmethyl)-3-[3-benzyl-8-(trifluoromethyl)quinolin-4-yl]aniline;
arw) {3-[3-benzyl-8-(trifluoromethyl)quinolin-4-yl]phenyl}[(5-bromo-2-thienyl)methyl]amine;
arx) {3-[3-benzyl-8-(trifluoromethyl)quinolin-4-yl]phenyl}[(5-methyl-2-thienyl)methyl]amine;
ary) 3-[3-(2-prop-1-yn-1-ylphenyl)-8-(trifluoromethyl)quinolin-4-yl]phenol;
arz) 3-[8-(trifluoromethyl)-3-(2-vinylphenyl)quinolin-4-yl]phenol;
asa) 3-[3-(2-prop-1-en-1-ylphenyl)-8-(trifluoromethyl)quinolin-4-yl]phenol;
asb) {3-[3-benzyl-8-(trifluoromethyl)quinolin-4-yl]phenyl}(1H-indol-4-ylmethyl)amine;
asc) 2,6-dimethoxy-4-({3-[3-phenyl-8-(trifluoromethyl)quinolin-4-yl]phenoxy}methyl)benzoic acid;
asd) 3-benzyl-4-{3-[(2-fluoro-4-vinylbenzyl)oxy]phenyl}-8-(trifluoromethyl)quinoline;
ase) 3-benzyl-8-chloro-4-[3-(3,5-difluorophenoxy)phenyl]quinoline;
asf) 3-benzyl-8-chloro-4-[3-(3,5-dimethylphenoxy)phenyl]quinoline;
asg) 3-benzyl-4-{3-[(2-fluoro-5-prop-1-yn-1-ylbenzyl)oxy]phenyl}-8-(trifluoromethyl)quinoline;
ash) 3'-[({3-[3-benzyl-8-(trifluoromethyl)quinolin-4-yl]phenyl}amino)methyl]-4'-fluorobiphenyl-4-ol;
asi) {3-[3-benzyl-8-(trifluoromethyl)quinolin-4-yl]phenyl}[(3-fluoro-4'-methoxybiphenyl-4-yl)methyl]amine;
asj) methyl 3-[(3-{[3-benzyl-8-(trifluoromethyl)quinolin-4-yl]methyl}phenoxy)methyl]benzoate;
ask) methyl 4-[(3-{[3-benzyl-8-(trifluoromethyl)quinolin-4-yl]methyl}phenoxy)methyl]benzoate;
asl) ethyl {3-[(3-{[3-benzyl-8-(trifluoromethyl)quinolin-4-yl]methyl}phenoxy)methyl]phenyl}acetate;
asm) methyl 3-{3-[(3-{[3-benzyl-8-(trifluoromethyl)quinolin-4-yl]methyl}phenoxy)methyl]phenyl}propanoate;
asn) methyl {3-[(3-{[3-benzyl-8-(trifluoromethyl)quinolin-4-yl]methyl}phenoxy)methyl]phenoxy}acetate;
aso) methyl {4-[(3-{[3-benzyl-8-(trifluoromethyl)quinolin-4-yl]methyl}phenoxy)methyl]phenoxy}acetate;
asp) {3-[3-benzyl-8-(trifluoromethyl)quinolin-4-yl]phenyl}(2,2'-bithien-5-ylmethyl)amine;
asq) {3-[3-benzyl-8-(trifluoromethyl)quinolin-4-yl]phenyl}[(4-fluorobiphenyl-3-yl)methyl]amine;
asr) N-[3-(3-benzyl-8-chloroquinolin-4-yl)phenyl]-N,3,5-trimethylaniline;
ass) 3-[(3-{[3-benzyl-8-(trifluoromethyl)quinolin-4-yl]methyl}phenoxy)methyl]benzoic acid;
ast) 4-[(3-{[3-benzyl-8-(trifluoromethyl)quinolin-4-yl]methyl}phenoxy)methyl]benzoic acid;
asu) {3-[(3-{[3-benzyl-8-(trifluoromethyl)quinolin-4-yl]methyl}phenoxy)methyl]phenyl}acetic acid;
asv) 3-{3-[(3-{[3-benzyl-8-(trifluoromethyl)quinolin-4-yl]methyl}phenoxy)methyl]phenyl}propanoic acid;
asw) {3-[(3-{[3-benzyl-8-(trifluoromethyl)quinolin-4-yl]methyl}phenoxy)methyl]phenoxy}acetic acid;
asx) {4-[(3-{[3-benzyl-8-(trifluoromethyl)quinolin-4-yl]methyl}phenoxy)methyl]phenoxy}acetic acid;
asy) 3-benzyl-4-[3-(1,2,3,4-tetrahydronaphthalen-1-ylmethoxy)phenyl]-8-(trifluoromethyl)quinoline;
asz) 3-benzyl-4-[3-(2,3-dihydro-1H-inden-1-yl methoxy)phenyl]-8-(trifluoromethyl)quinoline;
ata) 3-benzyl-4-[3-(1-phenylethoxy)phenyl]-8-(trifluoromethyl)quinoline;
atb) 3-benzyl-4-{3-[1-(2-chlorophenyl)ethoxy]phenyl}-8-(trifluoromethyl)quinoline;
atc) 3-benzyl-4-{3-[1-(2,5-dichlorophenyl)ethoxy]phenyl}-8-(trifluoromethyl)quinoline;
atd) 3-[3-(3-benzyl-8-chloroquinolin-4-yl)phenoxy]-5-bromobenzonitrile;
ate) 3-benzyl-4-{3-[3-bromo-5-(trifluoromethyl)phenoxy]phenyl}-8-chloroquinoline;

atf) 3-[3-(3-benzyl-8-chloroquinolin-4-yl)phenoxy]-5-fluorobenzonitrile;
atg) 3-benzyl-4-[3-(3-bromo-5-chlorophenoxy)phenyl]-8-chloroquinoline;
ath) N-[(1-acetyl-1H-indol-3-yl)methyl]-3-[3-benzyl-8-(trifluoromethyl)quinolin-4-yl]aniline;
ati) N,N-bis[(1-acetyl-1H-indol-3-yl)methyl]-3-[3-benzyl-8-(trifluoromethyl)quinolin-4-yl]aniline;
atj) 3-benzyl-4-{3-[( 1-methyl-1H-indol-3-yl)methoxy]phenyl}-8-(trifluoromethyl)quinoline;
atk) {3-[3-benzyl-8-(trifluoromethyl)quinolin-4-yl]phenyl}[2-fluoro-5-(1H-pyrrol-2-yl)benzyl]amine or
atl) 3-benzyl-4-{3-[( 1-methyl-1H-indol-7-yl)methoxy]phenyl}-8-(trifluoromethyl)quinoline. or a pharmaceutically acceptable salt thereof.

7. A pharmaceutical composition which comprises a compound of claim 1 and a pharmaceutically acceptable carrier.

8. The compound of claim 1, wherein the compound is a compound of formula II having the structure

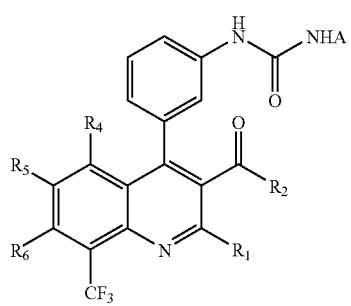

(II)

wherein
$R_1$ is —H;
$R_2$ is phenyl, or phenyl substituted independently by one or more of the groups independently selected from $C_1$ to $C_3$ alkyl, $C_1$ to $C_3$ alkoxy, $C_1$ to $C_3$ perfluoroalkyl, $C_1$ to $C_3$ alkyl substituted with 1 to 5 fluorines, halogen, —$NO_2$, —$NR_8R_9$, and —CN, or
A is phenyl, or phenyl substituted by one to four groups independently selected from halogen, C1 to C3 alkyl, acyl, $C_1$ to $C_3$ alkoxy, hydroxy, halogen, —CN, —$NO_2$, $C_1$ to $C_3$ perfluoroalkyl, and $C_1$ to $C_3$ alkyl substituted with 1 to 5 fluorines, or
$R_8$ is —H, or $C_1$ to $C_3$ alkyl;
$R_9$ is —H, or $C_1$ to $C_3$ alkyl;
$R_4$, $R_5$, and $R_6$ are each independently —H or —F;
or a pharmaceutically acceptable salt thereof.

9. A process for preparing a compound of formula I having the structure:

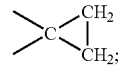

(I)

wherein:
$R_1$ is —H;
$X_1$ is a bond, $C_1$ to $C_5$ alkyl, —C(O)—, —C(=$CR_8R_9$)—, —O—, —S(O)$_t$—, —$NR_8$—, —$CR_8R_9$—, —$CHR_{23}$,
—$CR_8(OR_9)$—, —C($OR_8$)$_2$—, —$CR_8(OC(O)R_9)$—, —C=$NOR_9$—, —C(O)$NR_8$—, —$CH_2O$—, —$CH_2S$—, —$CH_2NR_8$—, —$OCH_2$—, —$SCH_2$—, —$NR_8CH_2$—, or

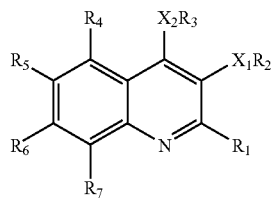

$R_2$ is H, $C_1$ to $C_6$ alkyl, $C_2$ to $C_6$ alkenyl, $C_2$ to $C_6$ alkynyl, $C_3$ to $C_6$ cycloalkyl, —$CH_2OH$, $C_7$ to $C_{11}$ arylalkyl, phenyl, naphthyl, $C_1$ to $C_3$ perfluoroalkyl, CN, C(O)$NH_2$, $CO_2R_{12}$ or phenyl substituted independently by one or more of the groups independently selected from $C_1$ to $C_3$ alkyl, $C_2$ to $C_4$ alkenyl, $C_2$ to $C_4$ alkynyl, $C_1$ to $C_3$ alkoxy, $C_1$ to $C_3$ perfluoroalkyl, halogen, —$NO_2$, —$NR_8R_9$, —CN, —OH, and $C_1$ to $C_3$ alkyl substituted with 1 to 5 fluorines, or
$R_2$ is a heterocycle selected from the group consisting of pyridine, thiophene, benzisoxazole, benzothiophene, oxadiazole, pyrrole, pyrazole, imidazole and furan, each of which may be optionally substituted with one to three groups independently selected from $C_1$ to $C_3$ alkyl, $C_1$ to $C_3$ alkoxy, $C_1$ to $C_3$ perfluoroalkyl, halogen, —$NO_2$, —$NR_8R_9$, —CN, and $C_1$ to $C_3$ alkyl substituted with 1 to 5 fluorines;
$X_2$ is a bond or —$CH_2$—;
$R_3$ is phenyl, naphthyl, or phenyl or naphthyl substituted independently by one to four groups independently selected from $C_1$ to $C_3$ alkyl, hydroxy, phenyl, acyl, halogen, —$NH_2$, —CN, —$NO_2$, $C_1$ to $C_3$alkoxy, $C_1$ to $C_3$ perfluoroalkyl, $C_1$ to $C_3$ alkyl substituted with 1 to 5 fluorines, $NR_{14}R_{15}$, —C(O)$R_{10}$, —C(O)$NR_{10}R_{11}$, —C(O)$NR_{11}$A, —C≡$CR_8$, —CH=$CHR_8$, —WA, —C≡CA, —CH=CHA, —WYA, —WY$NR_{11}$-A, —WY$R_{10}$, —WY($CH_2$)$_j$A, —WC$HR_{11}$($CH_2$)$_j$A, —W($CH_2$)$_j$A, —W($CH_2$)$_j R_{10}$, —C$HR_{11}$W($CH_2$)$_j R_{10}$, —C$HR_{11}$W($CH_2$)$_j$A, —C$HR_{11}NR_{12}$YA, —C$HR_{11}NR_{12}YR_{10}$, pyrrole, —W($CH_2$)$_j$A($CH_2$)$_k$D($CH_2$)$_p$Z, —W($CR_{18}R_{19}$)A($CH_2$)$_k$D($CH_2$)$_p$Z, —(C$H_2$)$_j$WA($CH_2$)$_k$D($CH_2$)$_p$Z, —CH=CHA($CH_2$)$_k$D($CH_2$)$_p$Z, —C≡CA($CH_2$)$_k$D($CH_2$)$_p$Z, —W(C$H_2$)$_j$C≡CA($CH_2$)$_k$D($CH_2$)$_p$Z, and —W($CH_2$)$_j$Z, or
$R_3$ is a heterocycle selected from pyrimidine, thiophene, furan, benzothiophene, indole, benzofuran, benzimidazole, benzothiazole, benzoxazole, and quinoline, each of which may be optionally substituted with one to three groups independently selected from $C_1$ to $C_3$ alkyl, $C_1$ to $C_3$ alkoxy, hydroxy, phenyl, acyl, halogen, —$NH_2$, —CN, —$NO_2$, $C_1$ to $C_3$ perfluoroalkyl, $C_1$ to $C_3$ alkyl substituted with 1 to 5 fluorines, —C(O)$R_{10}$, —C(O)$NR_{10}R_{11}$, —C(O)$NR_{11}$A, —C≡$CR_8$, —CH=$CHR_8$, —WA, —C≡CA, —CH=CHA, —WYA, —WY$R_{10}$, —WY($CH_2$)$_j$A, —W($CH_2$)$_j$A, —W($CH_2$)$_j R_{10}$, —C$HR_{11}$W($CH_2$)$_j R_{10}$, —C$HR_{11}$W($CH_2$)$_j$A, —C$HR_{11}NR_{12}$YA, —C$HR_{11}NR_{12}YR_{10}$, —WC$HR_{11}$($CH_2$)$_j$A, —W($CH_2$)$_j$A($CH_2$)$_k$D($CH_2$)$_p$Z, —W($CR_{18}R_{19}$)A($CH_2$)$_k$D($CH_2$)$_p$Z, —($CH_2$)$_j$WA(C$H_2$)$_k$D($CH_2$)$_p$Z, —CH=CHA($CH_2$)$_k$D($CH_2$)$_p$Z, —C≡CA($CH_2$)$_k$D($CH_2$)$_p$Z, —W($CH_2$)$_j$C≡CA(C$H_2$)$_k$D($CH_2$)$_p$Z, and —W($CH_2$)$_j$Z;
W is a bond, —O—, —S—, —S(O)—, —S(O)$_2$—, —$NR_{11}$—, or N(COR$_{12}$)—;
Y is —CO—, —S(O)$_2$—, —CONR$_{13}$, —CONR$_{13}$CO—, —CONR$_{13}SO_2$—, —C(NCN)—, —CS$NR_{13}$, —C(NH)$NR_{13}$, or —C(O)O—;

j is 0 to 3;
k is 0 to 3;
t is 0 to 2;
D is a bond, —CH═CH—, —C≡C—, —C═, —C(O)—, phenyl, —O—, —NH—, —S—, —CHR$_{14}$—, —CR$_{14}$R$_{15}$—, —OCHR$_{14}$—, —OCR$_{14}$R$_{15}$—, or —CH(OH)CH(OH)—;
p is 0 to 3;
Z is —CO$_2$R$_{11}$, —CONR$_{10}$R$_{11}$, —C(═NR$_{10}$)NR$_{11}$R$_{12}$, —CONH$_2$NH$_2$, —CN, —CH$_2$OH, —NR$_{16}$R$_{17}$, phenyl, CONHCH(R$_{20}$)COR$_{12}$, phthalimide, pyrrolidine-2,5-dione, thiazolidine-2,4-dione, tetrazolyl, pyrrole, indole, oxazole, 2-thioxo-1,3-thiazolinin-4-one, C$_1$ to C$_7$ amines, C$_3$ to C$_7$ cyclic amines, or C$_1$ to C$_3$ alkyl substituted with one to two OH groups; wherein said pyrrole is optionally substituted with one or two substituents independently selected from the group consisting of —CO$_2$CH$_3$, —CO$_2$H, —COCH$_3$, —CONH$_2$ and —CN; wherein said C$_1$ to C$_7$ amines are optionally substituted with one to two substituents independently selected from the group consisting of —OH, halogen, —COH$_3$, and —C≡CH; wherein said phenyl is optionally substituted with CO$_2$R$_{11}$, and wherein said C$_3$ to C$_7$ cyclic amines are optionally substituted with one or two substituents independently selected from the group consisting of —OH —CH$_2$OH, C$_1$ to C$_3$ alkyl, —CH$_2$OCH$_3$, —CO$_2$CH$_3$, and —CONH$_2$, and wherein said oxazole is optionally substituted with CH$_2$CO$_2$R$_{11}$;
A is phenyl, naphthyl, tetrahydronaphthyl, indan or biphenyl, each of which may be optionally substituted by one to four groups independently selected from halogen, C$_1$ to C$_3$ alkyl, C$_2$ to C$_4$ alkenyl, C$_2$ to C$_4$ alkynyl, acyl, hydroxy, halogen, —CN, —NO$_2$, —CO$_2$R$_{11}$, —CH$_2$CO$_2$R$_{11}$, phenyl, C$_1$ to C$_3$ perfluoroalkoxy, C$_1$ to C$_3$ perfluoroalkyl, —NR$_{10}$R$_{11}$, —CH$_2$NR$_{10}$R$_{11}$, —SR$_{11}$, C$_1$ to C$_6$ alkyl substituted with 1 to 5 fluorines, C$_1$ to C$_3$ alkyl substituted with 1 to 2 —OH groups, C$_1$ to C$_6$ alkoxy optionally substituted with 1 to 5 fluorines, or phenoxy optionally substituted with 1 to 2 CF$_3$ groups; or
A is a heterocycle selected from pyrrole, pyridine, pyridine-N-oxide, pyrimidine, pyrazole, thiophene, furan, quinoline, oxazole, thiazole, imidazole, isoxazole, indole, benzo[1,3]-dioxole, benzo[1,2,5]-oxadiazole, isochromen-1-one, benzothiophene, benzofuran, 2,3-dihydrobenzo[1,4]-dioxine, bitheinyl, quinazolin-2,4-91, 3H]dione, and 3—H-isobenzofuran-1-one, each of which may be optionally substituted by one to three groups independently selected from halogen, C$_1$ to C$_3$ alkyl, acyl, hydroxy, —CN, —NO$_2$, C$_1$ to C$_3$ perfluoroalkyl, —NR$_{10}$R$_{11}$, —CH$_2$NR$_{10}$R$_{11}$, —SR$_{11}$, C$_1$ to C$_3$ alkyl substituted with 1 to 5 fluorines, and C$_1$ to C$_3$ alkoxy optionally substituted with 1 to 5 fluorines;
R$_4$, R$_5$, and R$_6$ are each, independently, —H or —F;
R$_7$ is C$_1$ to C$_4$ alkyl, C$_1$ to C$_4$ perfluoroalkyl, halogen, —NO$_2$, —CN, phenyl or phenyl substituted with one or two groups independently selected from halogen, C$_1$ to C$_2$ alkyl and OH; provided that if X$_1$R$_2$ forms hydrogen, then R$_3$ is selected from:
(a) phenyl substituted by —W(CH$_2$)$_j$A(CH$_2$)$_k$D(CH$_2$)$_p$Z, —W(CR$_{18}$R$_{19}$)A(CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or —W(CH$_2$)$_j$C═CA(CH$_2$)$_k$D(CH$_2$)$_p$Z, wherein the phenyl moiety is further optionally substituted with one or two groups independently selected from C$_1$ to C$_2$ alkyl, C$_1$ to C$_2$ perfluoroalkyl, halogen, and CN; and
(b) a heterocycle selected from, pyrimidine, thiophene, and furan, each of which is substituted by one of —W(CH$_2$)$_j$A(CH$_2$)$_k$D(CH$_2$)$_p$Z, —W(CR$_{18}$R$_{19}$)A (CH$_2$)$_k$D(CH$_2$)$_p$Z, —(CH$_2$)$_j$WA(CH$_2$)$_k$D(CH$_2$)$_p$Z, —CH═CHA(CH$_2$)$_k$D(CH$_2$)$_p$Z, —C≡CA(CH$_2$)$_k$D(CH$_2$)$_p$Z, or —W(CH$_2$)$_j$C≡CA(CH$_2$)$_k$D(CH$_2$)$_p$Z;

each R$_8$ is independently —H, or C$_1$ to C$_3$ alkyl;
each R$_9$ is independently —H, or C$_1$ to C$_3$ alkyl;
each R$_{10}$ is independently —H, —OH, C$_1$ to C$_3$ alkoxy, C$_1$ to C$_7$ alkyl, C$_3$ to C$_7$ alkenyl, C$_3$ to C$_7$ alkynyl, C$_3$ to C$_7$cycloalkyl, —CH$_2$CH$_2$OCH$_3$, 2-methyl-tetrahydrofuran, 2-methyl-tetrahydro-pyran, 4-methyl-piperidine, morpholine, pyrrolidine, or phenyl optionally substituted with one or two C$_1$ to C$_3$ alkoxy groups, wherein said C$_1$ to C$_7$ alkyl is optionally substituted with 1, 2 or 3 groups independently selected from C$_1$ to C$_3$ alkoxy, C$_1$ to C$_3$ thioalkoxy and CN;
each R$_{11}$ is independently —H, C$_1$ to C$_3$ alkyl or R$_{22}$;
or R$_{10}$ and R$_{11}$, when attached to the same atom, together with said atom form:
a 5 to 7 membered saturated ring, optionally substituted by 1 to 2 groups independently selected from C$_1$ to C$_3$ alkyl, OH and C$_1$-C$_3$ alkoxy; or
a 5 to 7 membered ring containing 1 or 2 heteroatoms, optionally substituted by 1 to 2 groups independently selected from C$_1$ to C$_3$ alkyl, OH and C$_1$-C$_3$ alkoxy;
each R$_{12}$ is independently —H, or C$_1$ to C$_3$ alkyl;
each R$_{13}$ is independently —H, or C$_1$ to C$_3$ alkyl;
each R$_{14}$ and R$_{15}$ is, independently, C$_1$ to C$_7$ alkyl, C$_3$ to C$_8$ cycloalkyl, C$_2$ to C$_7$ alkenyl, C$_2$ to C$_7$ alkynyl, —CH, —F, C$_7$ to C$_{14}$ arylalkyl, where said arylalkyl is optionally substituted with 1 to 3 groups independently selected from NO$_2$, C$_1$ to C$_6$ alkyl, C$_1$ to C$_3$ perhaloalkyl, halogen, CH$_2$CO$_2$R$_{11}$, phenyl and C$_1$ to C$_3$ alkoxy, or R$_{14}$ and R$_{15}$ together with the atom to which they are attached can form a 3 to 7 membered saturated ring;
each R$_{16}$ and R$_{17}$ is, independently, hydrogen, C$_1$ to C$_3$ alkyl, C$_1$ to C$_3$ alkenyl, C$_1$ to C$_3$ alkynyl, phenyl, benzyl or C$_3$ to C$_8$ cycloalkyl, wherein said C$_1$ to C$_3$ alkyl is optionally substituted with one OH group, and wherein said benzyl is optionally substituted with 1 to 3 groups selected from C$_1$ to C$_3$ alkyl and C$_1$ to C$_3$ alkoxy; or
R$_{16}$ and R$_{17}$, together with the atom to which they are attached, can form a 3 to 8 membered heterocycle which is optionally substituted with one or two substituents independently selected from the group consisting of C$_1$ to C$_3$ alkyl, —OH, CH$_2$OH, —CH$_2$OCH$_3$, —CO$_2$CH$_3$, and —CONH$_2$;
each R$_{18}$ and R$_{19}$ is, independently, C$_1$ to C$_3$ alkyl;
each R20 is independently H, phenyl, or the side chain of a naturally occurring alpha amino acid;
each R$_{22}$ is independently arylalkyl optionally substituted with CH$_2$COOH; and
each R$_{23}$ is phenyl;
or a pharmaceutically acceptable salt thereof;
which comprises one of the following:
a) reacting a compound of formula IA

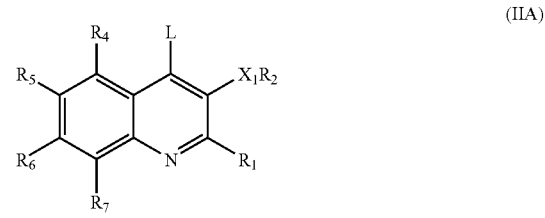

(IIA)

wherein L is Cl or triflate, $R_1$, $R_2$ and $R_{4-7}$ are as defined above, and $X_1$ is —CO—, with a boronic acid derivative of formula:

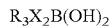

wherein $R_3$ and $X_2$ are as defined above, to give a compound of formula I wherein $X_1$ is —CO—; or b) reacting a compound of formula

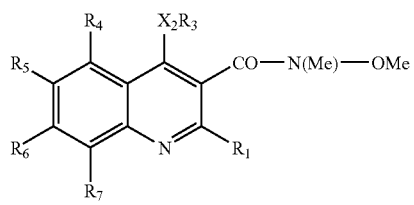

wherein $R_1$, $R_{3-7}$ and $X_2$ are as defined above, with a Grignard of formula:

wherein $R_2$ is as defined above, to give a corresponding compound of formula (I) wherein $X_1$ is —CO—;

or c) cyclocondensing a compound of formula IV

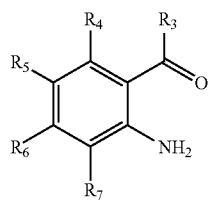

wherein $R_{3-7}$ are as defined above, with a compound of formula

wherein $R_2$ and $X_1$ are as defined above, to give a corresponding compound of formula

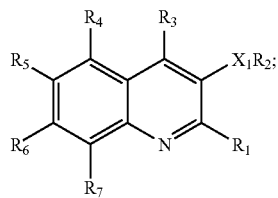

or d) reacting a compound of formula V

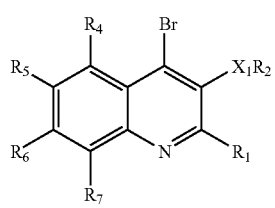

wherein $R_1$ and $R_{4-7}$ are as defined above, and $X_1$ is a bond, —S— or —O—, with a boronic acid derivative of formula:

$R_3B(OH)_2$ wherein $R_3$ is as defined above, to give a corresponding compound of formula I wherein $X_2$ is a bond.

or e) reacting a compound of formula

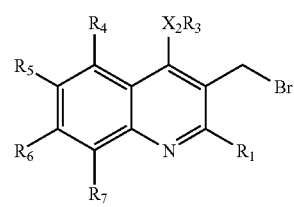

wherein $X_2$, $R_1$ and $R_{3-7}$ are as defined above, with a boronic acid derivative of formula $R_2B(OH)_2$ wherein $R_2$ is as defined herein, to give a corresponding compound of formula I wherein $X_1$ is —CH$_2$—;

or f) reacting a compound VI as defined above with pyrrole, pyrazole or imidazole to give a corresponding compound of formula I wherein $R_2$ is pyrrole, pyrazole or imidazole and $X_1$ is —CH$_2$—;

or g) reacting a compound of formula VI as defined above with an alcohol or phenol of formula $R_2O$ to give a corresponding compound of formula I wherein $X_1$ is —CH$_2$O—;

or h) cyclising a compound of formula

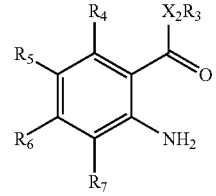

wherein $X_2$ and $R_{3-7}$ are as defined above, with a compound of formula

wherein $R_2$ is as defined above, to give a corresponding compound of formula I wherein $R_1$ is H, $X_1$ is $SO_2$;

or i) reacting a compound of formula

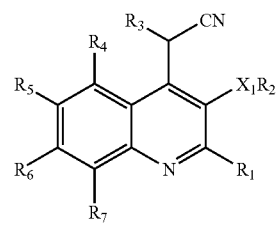

wherein $R_{17}$ and X, are as defined above, with HBr to give a corresponding compound of formula I wherein $X_2$ is —$CH_2$—;

j) converting a compound of formula I having a reactive substituent group or site to a different compound of formula I;

k) converting a basic compound of formula I to a pharmaceutically acid addition acceptable salt thereof or vice versa.

* * * * *

UNITED STATES PATENT AND TRADEMARK OFFICE
CERTIFICATE OF CORRECTION

PATENT NO. : 7,576,215 B2 Page 1 of 1
APPLICATION NO. : 11/010236
DATED : August 18, 2009
INVENTOR(S) : Collini et al.

It is certified that error appears in the above-identified patent and that said Letters Patent is hereby corrected as shown below:

On the cover page,

[*] Notice: Subject to any disclaimer, the term of this patent is extended or adjusted under 35 USC 154(b) by 535 days Delete the phrase "by 535 days" and insert -- by 996 days --

Signed and Sealed this

Thirteenth Day of April, 2010

David J. Kappos
*Director of the United States Patent and Trademark Office*